(12) United States Patent
Cassayre et al.

(10) Patent No.: US 8,895,587 B2
(45) Date of Patent: Nov. 25, 2014

(54) INSECTICIDAL COMPOUNDS BASED ON ARYLTHIOACETAMIDE DERIVATIVES

(75) Inventors: Jerome Yves Cassayre, Stein (CH); Myriem El Qacemi, Stein (CH); Torsten Luksch, Stein (CH); Peter Renold, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/118,037

(22) PCT Filed: May 15, 2012

(86) PCT No.: PCT/EP2012/059014
§ 371 (c)(1),
(2), (4) Date: Nov. 21, 2013

(87) PCT Pub. No.: WO2012/156400
PCT Pub. Date: Nov. 22, 2012

(65) Prior Publication Data
US 2014/0107161 A1    Apr. 17, 2014

(30) Foreign Application Priority Data
May 18, 2011    (EP) .................................... 11166535

(51) Int. Cl.
| | | |
|---|---|---|
| *C07D 307/28* | (2006.01) |
| *A01N 43/10* | (2006.01) |
| *A01N 43/36* | (2006.01) |
| *A01N 43/40* | (2006.01) |
| *A01N 43/78* | (2006.01) |
| *A01N 43/80* | (2006.01) |
| *C07D 207/20* | (2006.01) |
| *C07D 261/04* | (2006.01) |
| *C07D 405/12* | (2006.01) |
| *C07D 407/12* | (2006.01) |
| *C07D 409/12* | (2006.01) |
| *C07D 413/04* | (2006.01) |
| *C07D 413/12* | (2006.01) |
| *C07D 417/12* | (2006.01) |
| *A01N 43/08* | (2006.01) |

(52) U.S. Cl.
CPC ............ *C07D 307/28* (2013.01); *C07D 409/12* (2013.01); *C07D 413/12* (2013.01); *A01N 43/36* (2013.01); *C07D 207/20* (2013.01); *C07D 261/04* (2013.01); *C07D 417/12* (2013.01); *A01N 43/10* (2013.01); *A01N 43/08* (2013.01); *A01N 43/40* (2013.01); *C07D 405/12* (2013.01); *C07D 407/12* (2013.01); *A01N 43/80* (2013.01); *A01N 43/78* (2013.01); *C07D 413/04* (2013.01)
USPC ........... 514/340; 514/336; 514/371; 514/378; 514/429; 514/430; 514/471; 514/472; 546/283.4; 548/195; 548/240; 548/565; 549/88; 549/473; 549/496

(58) Field of Classification Search
None
See application file for complete search history.

(56) References Cited

U.S. PATENT DOCUMENTS

| | | |
|---|---|---|
| 3,296,308 A | 1/1967 | Walker et al. |
| 5,079,381 A | 1/1992 | Gregory |
| 2005/0032009 A1 | 2/2005 | Goswami |

FOREIGN PATENT DOCUMENTS

| | | |
|---|---|---|
| EP | 1731512 | 12/2006 |
| EP | 2172448 | 12/2006 |
| EP | 2151437 | 2/2010 |
| EP | 2199287 | 6/2010 |
| JP | 2003670 | 1/1990 |
| JP | 2007106756 | 4/2007 |
| NL | 6506045 | 11/1965 |
| WO | 2007003960 | 1/2007 |
| WO | 200819760 | 2/2008 |
| WO | 2008122375 | 10/2008 |

*Primary Examiner* — Janet L Andres
*Assistant Examiner* — Timothy R Rozof
(74) *Attorney, Agent, or Firm* — R. Kody Jones

(57) ABSTRACT

The present invention provides compounds of formula (I) wherein $R^1$, $R^2$, $R^3$, $R^4$, $G^1$, n, $A^1$, $A^2$, $A^3$, $A^4$, $Y^1$, $Y^2$, and $Y^3$ are as defined in the claims. The invention also relates to processes and intermediates for preparing these compounds, to insecticidal, acaricidal, nematicidal and molluscicidal compositions comprising these compounds and to methods of using these compounds to control insect, acarine, nematode and mollusc pests.

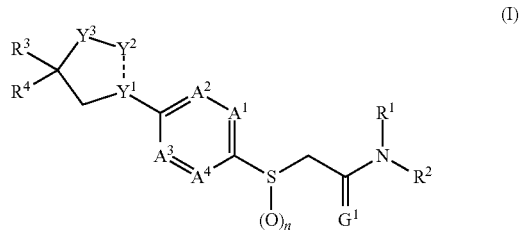

16 Claims, No Drawings

INSECTICIDAL COMPOUNDS BASED ON ARYLTHIOACETAMIDE DERIVATIVES

RELATED APPLICATION INFORMATION

This application claims priority under 35 U.S.C. §371 from PCT Application No. PCT/EP2012/059014, filed 15 May 2012, which claims the benefit of European Patent Application 11166535.2, filed 18 May 2011, the disclosures of which are incorporated by reference herein.

The present invention relates to certain arylthioacetamides and derivatives thereof, to processes and intermediates for preparing these compounds, to insecticidal, acaricidal, nematicidal and molluscicidal compositions comprising these compounds and to methods of using these compounds to control insect, acarine, nematode and mollusc pests.

Certain compounds with insecticidal properties are disclosed, for example, in JP2007106756. It has now surprisingly been found that certain orthosubstituted arylthioacetamides have significantly improved insecticidal properties compared to otherwise structurally similar compounds that lack the ortho substituent and thioacetamide side chain.

Accordingly in a first aspect the invention provides compounds of formula I

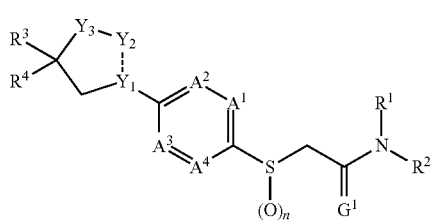

wherein
$A^1$ is C—$R^{5b}$;
$A^2$, $A^3$ and $A^4$ are independently of one another C—H, C—$R^{5a}$ or nitrogen;
$G^1$ is oxygen or sulfur;
$Y_1$—$Y_2$—$Y_3$ is —C=N—O—, —C=N—$CH_2$—, —C=CH—O— or —N—$CH_2$—$CH_2$—;
n is 0, 1 or 2;
$R^1$ is hydrogen, $C_1$-$C_8$alkyl, $C_1$-$C_8$alkyl substituted by one to five $R^6$, $C_1$-$C_8$alkoxy, $C_1$-$C_8$alkylcarbonyl or $C_1$-$C_8$alkoxycarbonyl;
$R^2$ is $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, $C_3$-$C_{10}$cycloalkyl-$C_1$-$C_4$alkylene or $C_3$-$C_{10}$cycloalkyl-$C_1$-$C_4$alkylene substituted by one to five $R^7$, aryl-$C_1$-$C_4$alkylene or aryl-$C_1$-$C_4$alkylene wherein the aryl moiety is substituted by one to five $R^8$, heterocyclyl-$C_1$-$C_4$alkylene or heterocyclyl-$C_1$-$C_4$alkylene wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$alkylene, $C_1$-$C_8$haloalkylaminocarbonyl-$C_1$-$C_4$alkylene, $C_3$-$C_8$cycloalkyl-aminocarbonyl-$C_1$-$C_4$alkylene, $C_1$-$C_6$alkyl-O—N=CH— or $C_1$-$C_6$haloalkyl-O—N=CH—, $C_1$-$C_6$alkyl-O—N=CH—$C_1$-$C_4$alkylene or $C_1$-$C_6$haloalkyl-O—N=CH—$C_1$-$C_4$alkylene, cyano, or $C_1$-$C_8$alkylsulfonyl;
$R^3$ is $C_1$-$C_8$haloalkyl;
$R^4$ is aryl or aryl substituted by one to five $R^9$, or heteroaryl or heteroaryl substituted by one to five $R^9$;
each $R^{5a}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl-, $C_1$-$C_8$haloalkylsulfinyl-, $C_1$-$C_8$alkylsulfonyl- or $C_1$-$C_8$haloalkylsulfonyl-;
$R^{5b}$ is halogen, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl or $C_3$-$C_{10}$cycloalkyl substituted by one to five $R^7$,
or $R^{5a}$ and $R^{5b}$, together form a —CH=CH—CH=CH— bridge or a —N=CH—CH=CH— bridge;
each $R^6$ is independently halogen, cyano, nitro, hydroxy, $C_3$-$C_{10}$cycloalkyl, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl;
each $R^7$ is independently halogen, cyano, $C_1$-$C_8$alkyl or $C_1$-$C_8$haloalkyl;
each $R^8$ and $R^9$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{10}$ or heterocyclyl or heterocyclyl substituted by one to five $R^{10}$;
each $R^{10}$ is independently halogen, cyano, nitro, $C_1$-$C_4$alkyl, $C_1$-$C_4$haloalkyl, $C_1$-$C_4$alkoxy or $C_1$-$C_4$haloalkoxy;
or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, for example, in the —$CR^3R^4$— group and may exist as enantiomers (or as pairs of diastereoisomers) or as mixtures of such. Further, where any group is SO, the compounds of the invention are sulfoxides, which can also exist in two enantiomeric forms.

Alkyl groups (either alone or as part of a larger group, such as alkoxy, alkylthio, alkylsulfinyl, alkylsulfonyl, alkylcarbonyl or alkoxycarbonyl) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Alkylene groups can be in the form of a straight or branched chain and are, for example, —$CH_2$—, —$CH_2$—$CH_2$—, —$CH(CH_3)$—, —$CH_2$—$CH_2$—$CH_2$—, —$CH(CH_3)$—$CH_2$— or —$CH(CH_2CH_3)$—. The alkylene groups are preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy, haloalkylthio, haloalkylsulfinyl or haloalkylsulfonyl) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups or carbocyclic rings can be in mono- or bi-cyclic form and are, for example, cyclopropyl, cyclobutyl, cyclohexyl and bicyclo[2.2.1]heptan-2-yl. The cycloalkyl groups are preferably $C_3$-$C_8$, more preferably $C_3$-$C_6$ cycloalkyl groups. Where a cycloalkyl moiety is said to be substituted, the cycloalkyl moiety is preferably substituted by one to four substituents, most preferably by one to three substituents.

Aryl groups (either alone or as part of a larger group, such as aryl-alkylene) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as heteroaryl-alkylene) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. 1.2.4 triazoyl), furanyl, thiophenyl, oxazolyl, isoxazolyl, oxadiazolyl, thiazolyl, isothiazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkylene) are defined to include heteroaryl groups and in addition their unsaturated or partially unsaturated analogues. Examples of monocyclic groups include isoxazolyl, thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents.

Preferred values of $A^1$, $A^2$, $A^3$, $A^4$, $G^1$, n, $R^1$, $R^2$, $R^3$, $R^4$, $Y^1$, $Y^2$, $Y^3$, $R^{5a}$, $R^{5b}$, $R^6$, $R^7$, $R^8$, $R^9$, $R^{10}$, $R^{11}$ and $R^{12}$ are, in any combination, as set out below.

Preferably no more than two of $A^2$, $A^3$ and $A^4$ are nitrogen.

Preferably $A^2$ is C—H, C—$R^{5a}$ or N, more preferably $A^2$ is C—H or C—$R^{5a}$, most preferably $A^2$ is C—H.

Preferably $A^3$ is C—H or N, most preferably $A^3$ is C—H.

Preferably $A^4$ is C—H or N, most preferably $A^4$ is C—H.

In one group of compounds $A^2$, $A^3$ and $A^4$ are C—H or N, wherein no more than two of $A^2$, $A^3$ and $A^4$ are N and wherein $A^3$ and $A^4$ are not both N. Preferably $A^2$ is C—H and $A^3$ and $A^4$ are C—H or one of $A^3$ and $A^4$ is N. More preferably $A^2$, $A^3$ and $A^4$ are C—H.

Preferably $G^1$ is oxygen.

Preferably $R^1$ is hydrogen, methyl, ethyl, methylcarbonyl or methoxycarbonyl, more preferably hydrogen, methyl or ethyl, even more preferably hydrogen or methyl, most preferably hydrogen.

Preferably, $R^2$ is $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, $C_3$-$C_{10}$cycloalkyl-$C_1$-$C_4$alkylene or $C_3$-$C_{10}$cycloalkyl-$C_1$-$C_4$alkylene substituted by one to five $R^7$, aryl-$C_1$-$C_4$alkylene or aryl-$C_1$-$C_4$alkylene wherein the aryl moiety is substituted by one to five $R^8$, heterocyclyl-$C_1$-$C_4$alkylene or heterocyclyl-$C_1$-$C_4$alkylene wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$alkylene, $C_1$-$C_8$haloalkylaminocarbonyl-$C_1$-$C_4$alkylene, $C_3$-$C_8$cycloalkyl-aminocarbonyl-$C_1$-$C_4$alkylene, wherein each aryl group is a phenyl group and each heterocyclyl group is independently selected from pyridyl, pyridazinyl, pyrimidinyl, pyrazinyl, pyrrolyl, pyrazolyl, imidazolyl, triazolyl, tetrahydrothiophenyl, tetrazolyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, oxetanyl, thietanyl, oxo-thietanyl, dioxo-thietanyl, pyrrolidinyl, tetrahydrofuranyl, [1,3]dioxolanyl, piperidinyl, piperazinyl, [1,4]dioxanyl, and morpholinyl, 2,3-dihydro-benzofuranyl, benzo[1,3]dioxolanyl, and 2,3-dihydro-benzo[1,4]dioxinyl.

More preferably $R^2$ is $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, $C_3$-$C_{10}$cycloalkyl-$C_1$-$C_4$alkylene or $C_3$-$C_{10}$cycloalkyl-$C_1$-$C_4$alkylene substituted by one to five $R^7$, phenyl-$C_1$-$C_4$alkylene or phenyl-$C_1$-$C_4$alkylene wherein the phenyl moiety is substituted by one to five $R^8$, pyridyl-$C_1$-$C_4$alkylene or pyridyl-$C_1$-$C_4$alkylene wherein the pyridyl moiety is substituted by one to four $R^8$, oxetanyl or oxetanyl substituted by one to five $R^8$, thietanyl-$C_1$-$C_4$alkylene or thietanyl-$C_1$-$C_4$alkylene wherein the thietanyl moiety is substituted by one to five $R^8$, oxo-thietanyl-$C_1$-$C_4$alkylene or oxo-thietanyl-$C_1$-$C_4$alkylene wherein the oxo-thietanyl moiety is substituted by one to five $R^8$, dioxo-thietanyl-$C_1$-$C_4$alkylene or dioxo-thietanyl-$C_1$-$C_4$alkylene wherein the dioxo-thietanyl moiety is substituted by one to five $R^8$, thietanyl or thietanyl substituted by one to five $R^8$, oxo-thietanyl or oxo-thietanyl substituted by one to five $R^8$, dioxo-thietanyl or dioxo-thietanyl substituted by one to five $R^8$, $C_1$-$C_8$alkylaminocarbonyl-$C_1$-$C_4$alkylene, $C_1$-$C_8$haloalkylaminocarbonyl-$C_1$-$C_4$alkylene or $C_3$-$C_8$cycloalkyl-aminocarbonyl-$C_1$-$C_4$alkylene, Even more preferably $R^2$ is $C_1$-$C_4$alkyl or $C_1$-$C_4$alkyl substituted by one to five $R^6$, $C_2$-$C_4$alkenyl or $C_2$-$C_4$alkenyl substituted by one to five $R^6$, $C_2$-$C_4$alkynyl or $C_2$-$C_4$alkynyl substituted by one to five $R^6$, $C_3$-$C_6$cycloalkyl or $C_3$-$C_6$cycloalkyl substituted by one to five $R^7$, $C_3$-$C_6$cycloalkyl-methylene or $C_3$-$C_6$cycloalkyl-methylene substituted by one to five $R^7$, phenyl-$C_1$-$C_2$alkylene or phenyl-$C_1$-$C_2$alkylene wherein the phenyl moiety is substituted by one to five $R^8$, pyridyl-$C_1$-$C_2$alkylene or pyridyl-$C_1$-$C_2$alkylene wherein the pyridyl moiety is substituted by one to four $R^8$, thietanyl or thietanyl substituted by one to five $R^8$, oxo-thietanyl or oxo-thietanyl substituted by one to five $R^8$, dioxo-thietanyl or dioxo-thietanyl substituted by one to five $R^8$.

Most preferably $R^2$ is $C_1$-$C_4$alkyl or $C_1$-$C_4$alkyl substituted by one to five halogen, $C_3$-$C_6$cyclo-alkyl or $C_3$-$C_6$cycloalkyl substituted by one to five groups independently selected from halogen, methyl and halomethyl, $C_3$-$C_6$cycloalkyl-methylene or $C_3$-$C_6$cycloalkyl-methylene substituted by one to five-groups independently selected from halogen, methyl and halomethyl, $C_2$-$C_4$alkenyl or $C_2$-$C_4$alkenyl substituted by one to five halogen, $C_2$-$C_4$alkynyl or $C_2$-$C_4$alkynyl substituted by one to five halogen. Examples of specific groups include ethyl, propyl, butyl, fluoroethyl, fluoropropyl, fluorobutyl, difluoroethyl, difluoropropyl, difluorobutyl, trifluoroethyl, trifluoropropyl, trifluorobutyl, cyclopropyl, cyclobutyl, cyclopropylmethylene, cyclobutylmethylene, allyl, propargyl.

Preferably $R^3$ is chlorodifluoromethyl or trifluoromethyl, most preferably trifluoromethyl.

Preferably $R^4$ is aryl or aryl substituted by one to three $R^9$, more preferably $R^4$ is phenyl or phenyl substituted by one to three $R^9$, even more preferably $R^4$ is phenyl substituted by one to three $R^9$, more preferably $R^4$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, more preferably 3,5-dichlorophenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds $R^4$ is group A1

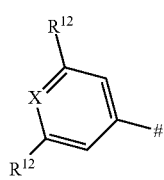

(A1)

wherein X is C—$R^{12}$ or nitrogen (preferably C—$R^{12}$) and each $R^{12}$ is independently hydrogen, halogen or trihalomethyl, wherein at least two $R^{12}$ are not hydrogen.

Preferably each $R^{5a}$ is independently halogen, cyano, nitro, $C_1$-$C_8$alkyl, $C_3$-$C_8$cycloalkyl, $C_1$-$C_8$haloalkyl, $C_2$-$C_8$alkenyl, more preferably halogen, cyano, nitro, $C_1$-$C_8$alkyl, $C_2$-$C_8$alkenyl, $C_3$-$C_8$cycloalkyl, $C_1$-$C_8$haloalkyl, even more preferably bromo, chloro, fluoro, cyano, nitro, methyl, ethyl, trifluoromethyl, cyclopropyl, vinyl, most preferably bromo, chloro, fluoro, cyclopropyl, trifluoromethyl, vinyl or methyl.

Preferably $R^{5b}$ is halogen, $C_1$-$C_8$alkyl, $C_3$-$C_8$cycloalkyl, $C_1$-$C_8$haloalkyl, $C_2$-$C_8$alkenyl, more preferably bromo, chloro, fluoro, cyano, nitro, methyl, ethyl, trifluoromethyl, cyclopropyl, vinyl, even more preferably bromo, chloro, fluoro, cyclopropyl, trifluoromethyl, vinyl or methyl, most preferably bromo, chloro, or methyl, most preferably chloro, bromo or methyl. In one group of compounds $R^{5b}$ is bromo. In one group of compounds $R^{5b}$ is chloro. In one group of compounds $R^{5b}$ is methyl. In one group of compounds $R^{5b}$ is chloro or bromo.

Preferably each $R^6$ is independently halogen, nitro, cyano, $C_1$-$C_4$alkyl, $C_1$-$C_4$haloalkyl, $C_1$-$C_4$alkoxy, $C_1$-$C_4$haloalkoxy, more preferably bromo, chloro, fluoro, cyano, nitro, methyl, ethyl, trifluoromethyl, methoxy, difluoromethoxy, trifluoromethoxy, even more preferably chloro, fluoro, cyano, nitro, methyl, ethyl, trifluoromethyl, methoxy or trifluoromethoxy, most preferably bromo, chloro, fluoro, or trifluoromethyl.

Preferably each $R^7$ is independently chloro, fluoro, cyano, or methyl or trifluoromethyl, most preferably fluoro, cyano, or methyl.

Preferably each $R^8$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{10}$ or heterocyclyl or heterocyclyl substituted by one to five $R^{10}$, more preferably each $R^8$ is independently halogen, cyano, nitro, $C_1$-$C_8$alkyl, $C_1$-$C_8$haloalkyl, $C_1$-$C_8$alkoxy, $C_1$-$C_8$haloalkoxy, more preferably bromo, chloro, fluoro, cyano, nitro, methyl, ethyl, trifluoromethyl, methoxy, difluoromethoxy or trifluoromethoxy, most preferably bromo, chloro, fluoro, cyano or methyl.

Preferably each $R^9$ is independently halogen, $C_1$-$C_8$alkyl, $C_1$-$C_8$haloalkyl, $C_1$-$C_8$alkoxy, $C_1$-$C_8$haloalkoxy, $C_1$-$C_8$alkylthio or $C_1$-$C_8$haloalkylthio, more preferably bromo, chloro, fluoro, trifluoromethyl, methoxy or methylthio, most preferably trifluoromethyl, bromo or chloro.

Preferably each $R^{10}$ is independently bromo, chloro, fluoro, cyano, nitro, methyl, ethyl, trifluoromethyl, methoxy, difluoromethoxy or trifluoromethoxy, more preferably bromo, chloro, fluoro, nitro or methyl, most preferably chloro, fluoro or methyl.

In one group of compounds n is 0. In another group of compounds n is 1. In another group of compounds n is 2. Preferably n is 0.

In one group of compounds $Y_1$—$Y_2$—$Y_3$ is —C=N—O—. In another group of compounds $Y_1$—$Y_2$—$Y_3$ is —C=N—$CH_2$—. In another group of compounds $Y_1$—$Y_2$—$Y_3$ is —C=CH—O—. In another group of compounds $Y_1$—$Y_2$—$Y_3$ is —N—$CH_2$—$CH_2$—.

In one group of compounds $R^{5a}$ and $R^{5b}$ on adjacent carbon atoms together form a —CH=CH—CH=CH— bridge or a —N=CH—CH=CH— bridge. In another group of compounds $R^{5a}$ and $R^{5b}$ on adjacent carbon atoms do not together form a —CH=CH—CH=CH— bridge or a —N=CH—CH=CH— bridge.

In one group of compounds the invention relates to compounds of formula IAa wherein $Y_1$—$Y_2$—$Y_3$ is —C=N—O—, and wherein the definitions of the other substituents and preferred definitions thereof are as defined above. A particularly preferred embodiment within this group of compounds is represented by compounds of formula IAb

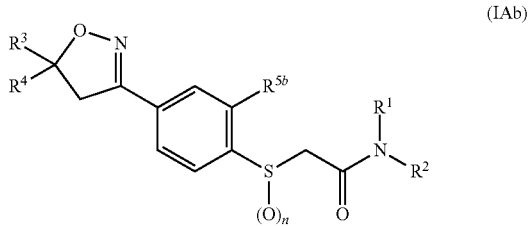

(IAb)

wherein $R^3$, $R^4$, $R^{5b}$, n, $R^1$ and $R^2$, including preferred definitions thereof, are as defined for compounds of formula I. Preferably $R^{5b}$ is bromo, chloro, or methyl. In one group of compounds of formula IAb $R^{5b}$ is bromo or chloro.

In one group of compounds the invention relates to compounds of formula IBa wherein $Y_1$—$Y_2$—$Y_3$ is —C=N—$CH_2$—, and wherein the definitions of the other substituents and preferred definitions thereof are as defined above. A particularly preferred embodiment within this group of compounds is represented by compounds of formula IBb

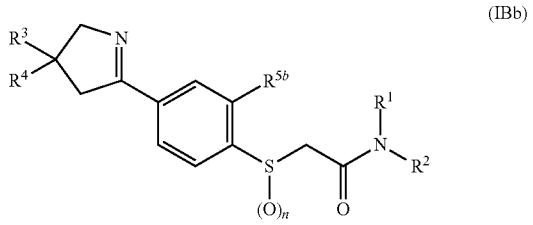

(IBb)

wherein $R^3$, $R^4$, $R^{5b}$, n, $R^1$ and $R^2$, including preferred definitions thereof, are as defined for compounds of formula I. Preferably $R^{5b}$ is bromo, chloro, or methyl. In one group of compounds of formula IBb $R^{5b}$ is bromo or chloro.

In one group of compounds the invention relates to compounds of formula ICa wherein $Y_1$—$Y_2$—$Y_3$ is —C=CH—O—, and wherein the definitions of the other substituents and preferred definitions thereof are as defined above. A particularly preferred embodiment within this group of compounds is represented by compounds of formula ICb

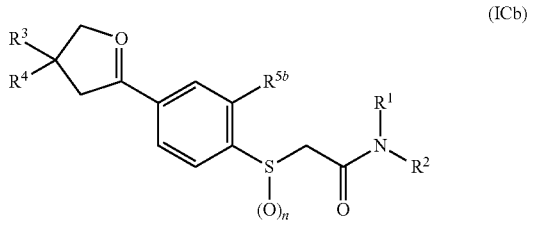

(ICb)

wherein $R^3$, $R^4$, $R^{5b}$, n, $R^1$ and $R^2$, including preferred definitions thereof, are as defined for compounds of formula I.

Preferably $R^{5b}$ is bromo, chloro, or methyl. In one group of compounds of formula ICb $R^{5b}$ is bromo or chloro.

In one group of compounds the invention relates to compounds of formula IDa wherein $Y_1$—$Y_2$—$Y_3$ is —N—$CH_2$—$CH_2$—, and wherein the definitions of the other substituents and preferred definitions thereof are as defined above. A particularly preferred embodiment within this group of compounds is represented by compounds of formula IDb

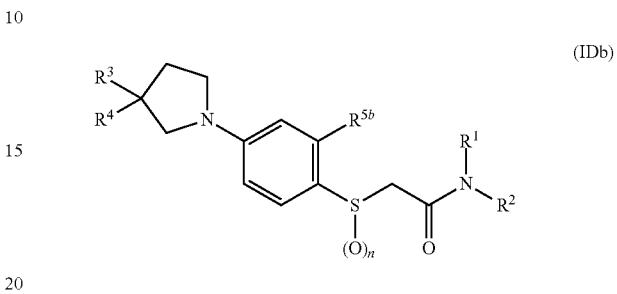

(IDb)

wherein $R^3$, $R^4$, $R^{5b}$, n, $R^1$ and $R^2$, including preferred definitions thereof, are as defined for compounds of formula I. Preferably $R^{5b}$ is bromo, chloro, or methyl. In one group of compounds of formula IDb $R^{5b}$ is bromo or chloro.

In one group of compounds $A^2$ is C—H and $A^3$ and $A^4$ are C—H or one of $A^3$ and $A^4$ is N; $G^1$ is O, $R^3$ is chlorodifluoromethyl or trifluoromethyl; $R^4$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, in particular 3,5-dibromo-phenyl, 3,5-dichloro-phenyl, 3,5-bis-(trifluoromethyl)-phenyl, 4-bromo-3,5-dichlorophenyl or 3,4,5-trichloro-phenyl.

In one group of compounds $A^2$ is C—H and $A^3$ and $A^4$ are C—H or one of $A^3$ and $A^4$ is N; $G^1$ is O, $R^1$ is H, $R^3$ is chlorodifluoromethyl or trifluoromethyl; $R^4$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, in particular 3,5-dibromo-phenyl, 3,5-dichloro-phenyl, 3,5-bis-(trifluoromethyl)-phenyl, 4-bromo-3,5-dichlorophenyl or 3,4,5-trichloro-phenyl.

In one group of compounds $A^2$, $A^3$ and $A^4$ are C—H; $G^1$ is O, $R^1$ is H, $R^3$ is chlorodifluoromethyl or trifluoromethyl; $R^4$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, in particular 3,5-dibromo-phenyl, 3,5- dichloro-phenyl, 3,5-bis-(trifluoromethyl)-phenyl, 4-bromo-3,5-dichlorophenyl or 3,4,5-trichloro-phenyl.

In one group of compounds $A^2$, $A^3$ and $A^4$ are C—H; $G^1$ is O, $R^1$ is H, $R^3$ is chlorodifluoromethyl or trifluoromethyl; $R^4$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, in particular 3,5-dibromo-phenyl, 3,5-dichloro-phenyl, 3,5-bis-(trifluoromethyl)-phenyl, 4-bromo-3,5-dichlorophenyl or 3,4,5-trichloro-phenyl; $R^{5b}$ is bromo, chloro, or methyl.

In one group of compounds $A^1$ is C—$R^{5b}$; $A^2$, $A^3$ and $A^4$ are C—H; $G^1$ is O; $Y_1$—$Y_2$—$Y_3$ is —C=N—O—, —C=N—CH$_2$—, —C=CH—O— or —N—CH$_2$—CH$_2$—; $R^1$ is hydrogen; $R^2$ is $C_1$-$C_4$alkyl or $C_1$-$C_4$alkyl substituted by one to five halogen, $C_3$-$C_6$cycloalkyl or $C_3$-$C_6$cycloalkyl substituted by one to five groups independently selected from halogen, methyl and halomethyl, $C_3$-$C_6$cycloalkyl-methylene or $C_3$-$C_6$cycloalkyl-methylene substituted by one to five groups independently selected from halogen, methyl and halomethyl, $C_2$-$C_4$alkenyl or $C_2$-$C_4$alkenyl substituted by one to five halogen, $C_2$-$C_4$alkynyl or $C_2$-$C_4$alkynyl substituted by one to five halogen; $R^3$ is chlorodifluoromethyl or trifluoromethyl; $R^4$ is group A1

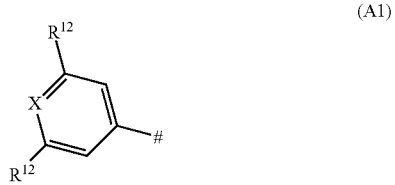

(A1)

wherein X is C—$R^{12}$ or nitrogen (preferably C—$R^{12}$) and each $R^{12}$ is independently hydrogen, halogen or trihalomethyl, wherein at least two $R^{12}$ are not hydrogen; $R^{5b}$ is chloro, bromo or methyl.

In one group of compounds $A^1$ is C—$R^{5b}$; $A^2$, $A^3$ and $A^4$ are C—H; $G^1$ is O; $Y_1$—$Y_2$—$Y_3$ is —C=N—O; $R^1$ is hydrogen; $R^2$ is $C_1$-$C_4$alkyl or $C_1$-$C_4$alkyl substituted by one to five halogen, $C_3$-$C_6$cycloalkyl or $C_3$-$C_6$cycloalkyl substituted by one to five groups independently selected from halogen, methyl and halomethyl, $C_3$-$C_6$cycloalkyl-methylene or $C_3$-$C_6$cycloalkyl-methylene substituted by one to five groups independently selected from halogen, methyl and halomethyl, $C_2$-$C_4$alkenyl or $C_2$-$C_4$alkenyl substituted by one to five halogen, $C_2$-$C_4$alkynyl or $C_2$-$C_4$alkynyl substituted by one to five halogen; $R^3$ is trifluoromethyl; $R^4$ is group A1 wherein X is C—$R^{12}$ or nitrogen (preferably C—$R^{12}$) and each $R^{12}$ is independently hydrogen, halogen or trihalomethyl, wherein at least two $R^{12}$ are not hydrogen; $R^{5b}$ is chloro, bromo or methyl.

In one group of compounds $A^1$ is C—$R^{5b}$; $A^2$, $A^3$ and $A^4$ are C—H; $G^1$ is oxygen; $Y_1$—$Y_2$—$Y_3$ is —C=N—O—, —C=N—CH$_2$—, —C=CH—O— or —N—CH$_2$—CH$_2$—; $R^1$ is hydrogen; $R^2$ is ethyl, propyl, butyl, fluoroethyl, fluoropropyl, fluorobutyl, difluoroethyl, difluoropropyl, difluorobutyl, trifluoroethyl, trifluoropropyl, trifluorobutyl, cyclopropyl, cyclobutyl, cyclopropylmethylene, cyclobutylmethylene, allyl or propargyl; $R^3$ is chlorodifluoromethyl or trifluoromethyl; $R^4$ is group A1, wherein X is C—$R^{12}$ and each $R^{12}$ is independently hydrogen, halogen or trihalomethyl, wherein at least two $R^{12}$ are not hydrogen; $R^{5b}$ is chloro, bromo or methyl.

In one group of compounds $A^1$ is C—$R^{5b}$; $A^2$, $A^3$ and $A^4$ are C—H; $G^1$ is O; $Y_1$—$Y_2$—$Y_3$ is —C=N—O—; $R^1$ is hydrogen; $R^2$ is $C_1$-$C_4$alkyl or $C_1$-$C_4$alkyl substituted by one to five halogen; $R^3$ is trifluoromethyl; $R^4$ is group A1 wherein X is C—$R^{12}$ or nitrogen (preferably C—$R^{12}$) and each $R^{12}$ is independently hydrogen, halogen or trihalomethyl, wherein at least two $R^{12}$ are not hydrogen; $R^{5b}$ is chloro, bromo or methyl.

In one group of compounds the invention provides compounds of formula I wherein
$A^1$ is C—$R^{5b}$;
$A^2$, $A^3$ and $A^4$ are independently of one another C—H, C—$R^{5a}$ or nitrogen;
$G^1$ is oxygen or sulfur;
$Y_1$—$Y_2$—$Y_3$ is —C=N—O—, —C=N—CH$_2$—, —C=CH—O— or —N—CH$_2$—CH$_2$—;
n is 0, 1 or 2;
$R^1$ is hydrogen, $C_1$-$C_8$alkyl, $C_1$-$C_8$alkoxy, $C_1$-$C_8$alkylcarbonyl or $C_1$-$C_8$alkoxycarbonyl;
$R^2$ is $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, aryl-$C_1$-$C_4$alkylene or aryl-$C_1$-$C_4$alkylene wherein the aryl moiety is substituted by one to five $R^8$, heterocyclyl-$C_1$-$C_4$alkylene or heterocyclyl-$C_1$-$C_4$alkylene wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-$C_4$alkylene, $C_1$-$C_8$haloalkylaminocarbonyl-$C_1$-$C_4$alkylene, $C_3$-$C_8$cycloalkyl-aminocarbonyl-$C_1$-$C_4$alkylene, $C_1$-$C_6$alkyl-O—N=CH— or $C_1$-$C_6$haloalkyl-O—N=CH—;
$R^3$ is $C_1$-$C_8$haloalkyl;
$R^4$ is aryl or aryl substituted by one to five $R^9$ or heteroaryl or heteroaryl substituted by one to five $R^9$;
each $R^{5a}$ and $R^{5b}$ are independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl-, $C_1$-$C_8$haloalkylsulfinyl-, $C_1$-$C_8$alkylsulfonyl- or $C_1$-$C_8$haloalkylsulfonyl-;
each $R^6$ is independently halogen, cyano, nitro, hydroxy, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl;
each $R^7$ is independently halogen or $C_1$-$C_8$alkyl;
each $R^8$ and $R^9$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{10}$ or heterocyclyl or heterocyclyl substituted by one to five $R^{10}$;
each $R^{10}$ is independently halogen, cyano, nitro, $C_1$-$C_4$alkyl, $C_1$-$C_4$haloalkyl, $C_1$-$C_4$alkoxy or $C_1$-$C_4$haloalkoxy.

In one group of compounds $A^2$, $A^3$ and $A^4$ are C—H; $G^1$ is O, $R^1$ is H; $R^2$ is $C_1$-$C_4$alkyl or $C_1$-$C_4$alkyl substituted by one to five $R^6$, $C_4$-$C_6$cycloalkyl or $C_4$-$C_6$cycloalkyl substituted by one to five $R^7$, phenyl-$C_1$-$C_2$alkylene or phenyl-$C_1$-$C_2$alkylene wherein the phenyl moiety is substituted by one to five $R^8$, pyridyl-$C_1$-$C_2$alkylene or pyridyl-$C_1$-$C_2$alkylene wherein the pyridyl moiety is substituted by one to four $R^8$, thietanyl or thietanyl substituted by one to five $R^8$, oxo-thietanyl or oxo-thietanyl substituted by one to five $R^8$, dioxo-thietanyl or dioxo-thietanyl substituted by one to five $R^8$; $R^3$ is chlorodifluoromethyl or trifluoromethyl; $R^4$ is 3,5-dibromo-phenyl, 3,5-dichloro-phenyl, 3,5-bis-(trifluoromethyl)-phenyl, 4-bromo-3,5-dichlorophenyl or 3,4,5-trichloro-phenyl; $R^{5b}$ is bromo, chloro or methyl; each $R^6$ is independently halogen, cyano, nitro, hydroxy, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl; each $R^7$ is independently halogen or $C_1$-$C_8$alkyl; each $R^8$ and $R^9$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{10}$ or heterocyclyl or heterocyclyl substituted by one to five $R^{10}$; each $R^{10}$ is independently halogen, cyano, nitro, $C_1$-$C_4$alkyl, $C_1$-$C_4$haloalkyl, $C_1$-$C_4$alkoxy or $C_1$-$C_4$haloalkoxy.

The earlier described preferred substituent values are applicable to the groups of compounds described above, where feasible.

Certain intermediates are novel and are also included as further aspects of the invention.

In a further aspect the invention provides compounds of formula Int-I

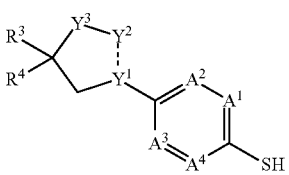

Int-I wherein $Y_1$—$Y_2$—$Y_3$ is —C=N—$CH_2$—, —C=CH—O— or —N—$CH_2$—$CH_2$— and $A^1$, $A^2$, $A^3$, $A^4$, $R^3$ and $R^4$ are as defined for the compound of formula I or a salt or N-oxide thereof. Preferred definitions of $A^1$, $A^2$, $A^3$, $A^4$, $R^3$ and $R^4$ are as defined for compounds of formula I. In one group of compounds of formula Int-I $Y_1$—$Y_2$—$Y_3$ is —C=N—$CH_2$. In another group of compounds of formula Int-I $Y_1$—$Y_2$—$Y_3$ is —C=CH—O—. In another group of formula Int-I $Y_1$—$Y_2$—$Y_3$ is —N—$CH_2$—$CH_2$—.

In a further aspect the invention provides compounds of formula Int-II

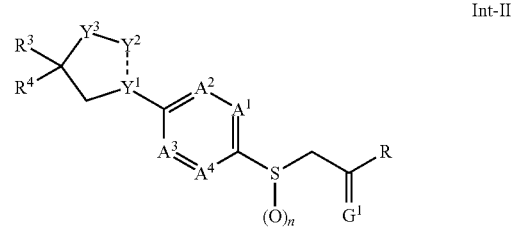

Int-II wherein $Y_1$—$Y_2$—$Y_3$ is —C=N—O—, —C=N—$CH_2$—, —C=CH—O— or —N—$CH_2$—$CH_2$— and $A^1$, $A^2$, $A^3$, $A^4$, $R^3$, $R^4$, $G^1$ and n are as defined for the compound of formula I, and R is OH, $C_1$-$C_6$alkoxy, Cl, F or Br or a salt or N-oxide thereof. Preferred definitions of $A^1$, $A^2$, $A^3$, $A^4$, $R^3$, $R^4$, $G^1$, and n are as defined for compounds of formula I. In one group of compounds of formula Int-II $Y_1$—$Y_2$—$Y_3$ is —C=N—O—. In another group of compounds of formula Int-II $Y_1$—$Y_2$—$Y_3$ is —C=N—$CH_2$. In another group of compounds of formula Int-II $Y_1$—$Y_2$—$Y_3$ is —C=CH—O—. In another group of compounds of formula Int-II $Y_1$—$Y_2$—$Y_3$ is —N—$CH_2$—$CH_2$—.

In a further aspect the invention provides compounds of formula Int-III

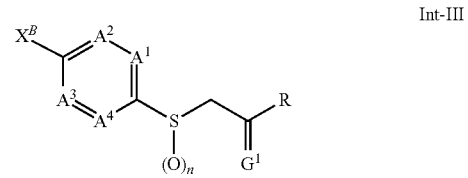

Int-III wherein $A^1$, $A^2$, $A^3$, $A^4$, $G^1$ and n are as defined for the compound of formula I, R is OH, $C_1$-$C_6$alkoxy, Cl, F or Br and $X^B$ is a leaving group, e.g. halogen, such as bromo or $X^B$ is cyano or C(O)$R^x$ wherein $R^x$ is H, OH or $C_1$-$C_{15}$alkoxy, preferably $X^B$ is cyano, formyl or acetyl, or a salt or N-oxide thereof. Preferred definitions of $A^1$, $A^2$, $A^3$, $A^4$, $G^1$ and n are as defined for compounds of formula I.

In a further aspect the invention provides compounds of formula Int-IV

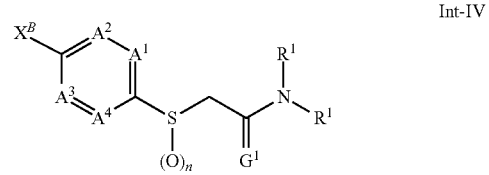

Int-IV wherein $A^1$, $A^2$, $A^3$, $A^4$, $R^1$, $R^2$, $G^1$ and n are as defined for the compound of formula I, and $X^B$ is a leaving group, e.g. halogen, such as bromo or $X^B$ is cyano or C(O)$R^x$ wherein $R^x$ is H, OH or $C_1$-$C_{15}$alkoxy, preferably $X^B$ is cyano, formyl or acetyl, or a salt or N-oxide thereof. Preferred definitions of $A^1$, $A^2$, $A^3$, $A^4$, $R^1$, $R^2$, $G^1$ and n are as defined for compounds of formula I.

An example of a compound of formula Int-III is a compound of formula Int-V

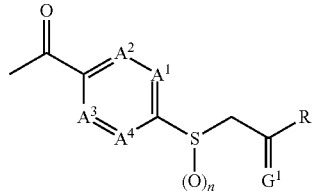

Int-V wherein $A^1$, $A^2$, $A^3$, $A^4$, $G^1$ and n are as defined for the compound of formula I, R is OH, $C_1$-$C_6$alkoxy, Cl, F or Br or a salt or N-oxide thereof. Preferred definitions of $A^1$, $A^2$, $A^3$, $A^4$, $G^1$ and n are as defined for compounds of formula I.

An example of a compound of formula Int-IV is a compound of formula Int-VI

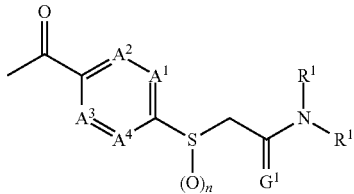

Int-VI wherein $A^1$, $A^2$, $A^3$, $A^4$, $R^1$, $R^2$, $G^1$ and n are as defined for the compound of formula I or a salt or N-oxide thereof. Preferred definitions of $A^1$, $A^2$, $A^3$, $A^4$, $R^1$, $R^2$, $G^1$ and n are as defined for compounds of formula I.

In a further aspect the invention provides compounds of formula Int-VII

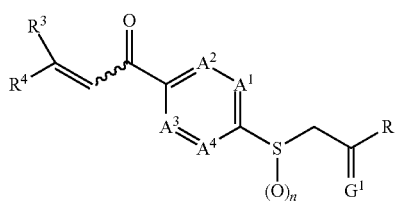

Int-VII wherein $A^1$, $A^2$, $A^3$, $A^4$, $R^3$, $R^4$, $G^1$ and n are as defined for the compound of formula I, R is OH, $C_1$-$C_6$alkoxy, Cl, F or Br or a salt or N-oxide thereof. Preferred definitions of $A^1$, $A^2$, $A^3$, $A^4$, $R^3$, $R^4$, $G^1$ and n are as defined for compounds of formula I.

In a further aspect the invention provides compounds of formula Int-VIII

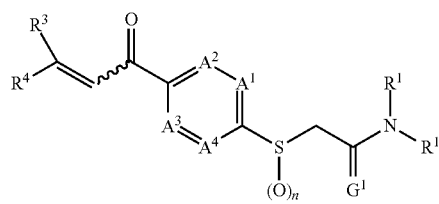

Int-VIII wherein $A^1$, $A^2$, $A^3$, $A^4$, $R^1$, $R^2$, $R^3$, $R^4$, $G^1$ and n are as defined for the compound of formula I or a salt or N-oxide thereof. Preferred definitions of $A^1$, $A^2$, $A^3$, $A^4$, $R^1$, $R^2$, $G^1$ and n are as defined for compounds of formula I.

In a further aspect the invention provides compounds of formula Int-IX

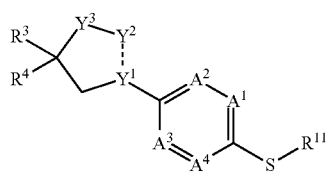

Int-IX wherein $Y_1$—$Y_2$—$Y_3$ is —C=N—O—, —C=N—$CH_2$—, —C=CH—O— or —N—$CH_2$—$CH_2$— and $A^1$, $A^2$, $A^3$, $A^4$, $R^3$ and $R^4$ are as defined for the compound of formula I, $R^{11}$ is $C_1$-$C_6$alkyl or $C_1$-$C_6$alkyl optionally substituted by aryl or a salt or N-oxide thereof, optionally with the proviso that when $Y_1$—$Y_2$—$Y_3$ is —C=N—O—, then $R^4$ is not 3,5-dichloro-phenyl. Preferred definitions of $A^1$, $A^2$, $A^3$, $A^4$, $R^3$ and $R^4$ are as defined for compounds of formula I. Aryl is e.g. phenyl or phenyl optionally substituted by one to three groups selected from cyano, halogen, $C_1$-$C_4$alkyl, $C_1$-$C_4$haloalkyl, $C_1$-$C_4$methoxy or $C_1$-$C_4$halomethoxy. In one group of compounds of formula Int-IX, $Y_1$—$Y_2$—$Y_3$ is —C=N—O—. In another group of compounds of formula Int-IX $Y_1$—$Y_2$—$Y_3$ is —C=N—$CH_2$. In another group of compounds of formula Int-IX $Y_1$—$Y_2$—$Y_3$ is —C=CH—O—. In another group of compounds of formula Int-IX $Y_1$—$Y_2$—$Y_3$ is —N—$CH_2$—$CH_2$—.

In a further aspect the invention provides compounds of formula Int-X

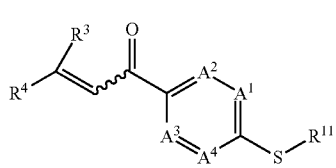

Int-X wherein $A^1$, $A^2$, $A^3$, $A^4$, $R^3$ and $R^4$ are as defined for the compound of formula I, and $R^{11}$ is $C_1$-$C_6$alkyl or $C_1$-$C_6$alkyl optionally substituted by aryl or a salt or N-oxide thereof. Preferred definitions of $A^1$, $A^2$, $A^3$, $A^4$, $R^3$ and $R^4$ are as defined for compounds of formula I. Aryl is e.g. phenyl or phenyl optionally substituted by one to three groups selected from cyano, halogen, $C_1$-$C_4$alkyl, $C_1$-$C_4$haloalkyl, $C_1$-$C_4$methoxy or $C_1$-$C_4$halomethoxy.

A leaving group as referred to herein may be for example a halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. —$N_2^+Cl^-$, —$N_2^+BF_4^-$, —$N_2^+Br^-$, —$N_2^+PF_6^-$), phosphonate esters (e.g. —OP(O)(OR)$_2$, wherein R is methyl or ethyl), preferably bromo, iodo, chloro, trifluoromethylsulfoxy, p-toluenesulfoxy, diazonium chloride.

Tables 1 to 672 below illustrate compounds of the invention.

TABLE Y

| | R5b | n | R2 |
|---|---|---|---|
| Y.1 | F | 0 | (1,1-dioxothietan-2-yl)methyl- |
| Y.2 | F | 0 | (1-oxothietan-2-yl)methyl- |
| Y.3 | F | 0 | (2-methoxy-phenyl)-methyl- |
| Y.4 | F | 0 | (3-fluoro-phenyl)-methyl- |
| Y.5 | F | 0 | (4,4-dimethyl-4,5-dihydrothiazol-2-yl)-methyl- |
| Y.6 | F | 0 | (4,5-dihydrothiazol-2-yl)-methyl- |
| Y.7 | F | 0 | (4,5-dimethyl-4,5-dihydrothiazol-2-yl)-methyl- |
| Y.8 | F | 0 | (4-fluoro-phenyl)-methyl- |
| Y.9 | F | 0 | (4-methyl-4,5-dihydrothiazol-2-yl)-methyl- |
| Y.10 | F | 0 | (5-methyl-4,5-dihydrothiazol-2-yl)-methyl- |
| Y.11 | F | 0 | (pyrid-3-yl)-methyl- |
| Y.12 | F | 0 | (pyrid-4-yl)-methyl- |
| Y.13 | F | 0 | (tetrahydrothiophene-2-yl)-methyl- |
| Y.14 | F | 0 | (tetrahydrothiophene-3-yl)-methyl- |
| Y.15 | F | 0 | (thiazol-2-yl)-methyl- |
| Y.16 | F | 0 | (thiazol-2-yl)-methylmethyl- |
| Y.17 | F | 0 | (thiazol-4-yl)-methyl- |
| Y.18 | F | 0 | (thiazol-5-yl)-methyl- |
| Y.19 | F | 0 | 1,1-dioxo-thietan-3-ylmethyl- |
| Y.20 | F | 0 | 1-cyanocyclobutyl- |
| Y.21 | F | 0 | 1-cyanocyclopentyl- |
| Y.22 | F | 0 | 1-cyanocyclopropyl- |
| Y.23 | F | 0 | 1-fluoroprop-2-yl- |
| Y.24 | F | 0 | 1-methylallyl- |
| Y.25 | F | 0 | 1-methylsulfanyl-prop-2-yl- |
| Y.26 | F | 0 | 2-(1,1-dioxothietan-3-yl)ethanyl- |
| Y.27 | F | 0 | 2-(1-oxothietan-3-yl)ethanyl- |
| Y.28 | F | 0 | 2-(thietan-3-yl)ethanyl- |
| Y.29 | F | 0 | 2-(trifluoromethoxy)phenyl- |
| Y.30 | F | 0 | 2,2-dimethyl-1,1-dioxo-thietan-3-yl- |
| Y.31 | F | 0 | 2,2-dimethyl-1-oxo-thietan-3-yl- |
| Y.32 | F | 0 | 2,2-dimethylthietan-3-yl- |
| Y.33 | F | 0 | 2,3-dichlorophenyl- |
| Y.34 | F | 0 | 2,3-difluoro-phenyl- |
| Y.35 | F | 0 | 2,4-dichlorophenyl- |
| Y.36 | F | 0 | 2,4-difluoro-phenyl- |
| Y.37 | F | 0 | 2,4-dimethylphenyl- |
| Y.38 | F | 0 | 2,5-dichlorophenyl- |
| Y.39 | F | 0 | 2,5-difluoro-phenyl- |
| Y.40 | F | 0 | 2,6-dichlorophenyl- |
| Y.41 | F | 0 | 2,6-difluoro-phenyl- |
| Y.42 | F | 0 | 2,6-diisopropylphenyl- |
| Y.43 | F | 0 | 2-bromo-4-fluorophenyl- |
| Y.44 | F | 0 | 2-bromoallyl- |
| Y.45 | F | 0 | 2-bromophenyl- |
| Y.46 | F | 0 | 2-butenyl- |
| Y.47 | F | 0 | 2-chloroallyl- |
| Y.48 | F | 0 | 2-chlorophenyl- |
| Y.49 | F | 0 | 2-chloropyrid-2-yl- |
| Y.50 | F | 0 | 2-chloropyrid-3-yl- |
| Y.51 | F | 0 | 2-cyanocyclopropyl- |
| Y.52 | F | 0 | 2-cyanoethyl- |
| Y.53 | F | 0 | 2-ethylphenyl- |
| Y.54 | F | 0 | 2-fluoroethyl- |
| Y.55 | F | 0 | 2-fluoro-phenyl- |
| Y.56 | F | 0 | 2-fluoropropyl- |
| Y.57 | F | 0 | 2-furylmethyl- |
| Y.58 | F | 0 | 2-hydroxyphenyl- |
| Y.59 | F | 0 | 2-methoxy-ethyl- |
| Y.60 | F | 0 | 2-methoxyphenyl- |
| Y.61 | F | 0 | 2-methoxy-prop-3-yl- |
| Y.62 | F | 0 | 2-methylallyl- |
| Y.63 | F | 0 | 2-methyl-but-1-yl- |
| Y.64 | F | 0 | 2-methyl-but-2-yl- |
| Y.65 | F | 0 | 2-methylbut-3-yn-2-yl- |
| Y.66 | F | 0 | 2-methylphenyl- |
| Y.67 | F | 0 | 2-methyl-prop-1-yl- |
| Y.68 | F | 0 | 2-methylsulfanyl-ethyl- |
| Y.69 | F | 0 | 2-methylsulfanyl-prop-3-yl- |
| Y.70 | F | 0 | 2-methyl-thiazol-4-yl- |
| Y.71 | F | 0 | 2-nitrophenyl- |
| Y.72 | F | 0 | 2-propyl- |
| Y.73 | F | 0 | 2-pyridyl- |
| Y.74 | F | 0 | 2-trifluoromethoxy-ethyl- |
| Y.75 | F | 0 | 3-(trifluoromethoxy)phenyl- |
| Y.76 | F | 0 | 3,3,3-trifluoro-2,2-difluoropropyl- |
| Y.77 | F | 0 | 3,3,3-trifluoro-butyl- |
| Y.78 | F | 0 | 3,3-dibromoallyl- |
| Y.79 | F | 0 | 3,3-dichloroallyl- |
| Y.80 | F | 0 | 3,4-dichlorophenyl- |
| Y.81 | F | 0 | 3,4-difluoro-phenyl- |
| Y.82 | F | 0 | 3,5-dichlorophenyl- |
| Y.83 | F | 0 | 3,5-difluoro-phenyl- |
| Y.84 | F | 0 | 3,6-difluoro-phenyl- |
| Y.85 | F | 0 | 3-bromoallyl- |
| Y.86 | F | 0 | 3-bromophenyl- |
| Y.87 | F | 0 | 3-butenyl- |
| Y.88 | F | 0 | 3-chloroallyl- |
| Y.89 | F | 0 | 3-chlorophenyl- |
| Y.90 | F | 0 | 3-chloropyrid-2-yl- |
| Y.91 | F | 0 | 3-cyanopropyl- |
| Y.92 | F | 0 | 3-ethylphenyl- |
| Y.93 | F | 0 | 3-hydroxyphenyl- |
| Y.94 | F | 0 | 3-methyl-1,1-dioxo-thietan-3-yl- |
| Y.95 | F | 0 | 3-methyl-1-oxo-thietan-3-yl- |
| Y.96 | F | 0 | 3-methyl-but-1-yl- |
| Y.97 | F | 0 | 3-methyl-but-2-yl- |
| Y.98 | F | 0 | 3-methylphenyl- |
| Y.99 | F | 0 | 3-nitrophenyl- |
| Y.100 | F | 0 | 3-pyridyl- |
| Y.101 | F | 0 | 4-(trifluoromethoxy)phenyl- |
| Y.102 | F | 0 | 4,5-dihydrothiazol-2-yl- |
| Y.103 | F | 0 | 4,5-dimethyl-4,5-dihydrothiazol-2-yl- |
| Y.104 | F | 0 | 4,5-dimethyl-thiazol-2-yl- |
| Y.105 | F | 0 | 4-bromophenyl- |
| Y.106 | F | 0 | 4-chlorophenyl- |
| Y.107 | F | 0 | 4-ethylphenyl- |
| Y.108 | F | 0 | 4-fluoro-phenyl- |
| Y.109 | F | 0 | 4H-1,2,4-triazol-3-yl- |
| Y.110 | F | 0 | 4-methoxyphenyl- |
| Y.111 | F | 0 | 4-methyl-4,5-dihydrothiazol-2-yl- |
| Y.112 | F | 0 | 4-methylphenyl- |
| Y.113 | F | 0 | 4-methylpyrid-2-yl |
| Y.114 | F | 0 | 4-nitrophenyl- |
| Y.115 | F | 0 | 4-pyridyl- |
| Y.116 | F | 0 | 5-methyl-4,5-dihydrothiazol-2-yl- |
| Y.117 | F | 0 | 5-methyl-thiazol-2-yl- |
| Y.118 | F | 0 | 6-methylpyrid-2-yl- |
| Y.119 | F | 0 | allyl- |
| Y.120 | F | 0 | but-2-ynyl- |
| Y.121 | F | 0 | but-3-ynyl- |
| Y.122 | F | 0 | cis-1-oxo-thietan-3-yl- |
| Y.123 | F | 0 | cis-1-oxo-thietan-3-ylmethyl- |
| Y.124 | F | 0 | cyanodimethylmethyl- |
| Y.125 | F | 0 | cyanoethyl- |
| Y.126 | F | 0 | cyanomethyl- |
| Y.127 | F | 0 | cyclopentyl- |
| Y.128 | F | 0 | cyclopropyl-methyl- |
| Y.129 | F | 0 | methylpropargyl- |
| Y.130 | F | 0 | oxetan-3-yl- |
| Y.131 | F | 0 | pent-3-yl- |
| Y.132 | F | 0 | phenyl-methyl-methyl- |
| Y.133 | F | 0 | propargyl- |
| Y.134 | F | 0 | tert-butyl- |
| Y.135 | F | 0 | tetrazolyl- |
| Y.136 | F | 0 | thiazol-2-yl- |
| Y.137 | F | 0 | thiazol-4-yl- |
| Y.138 | F | 0 | thietan-2-ylmethyl- |
| Y.139 | F | 0 | thietan-3-ylmethyl- |
| Y.140 | F | 0 | ethyl- |
| Y.141 | F | 0 | 3,3,3-trifluoro-propyl- |
| Y.142 | F | 0 | but-2-yl- |
| Y.143 | F | 0 | (tetrahydrofuran-2-yl)-methyl- |
| Y.144 | F | 0 | benzyl- |
| Y.145 | F | 0 | (2-fluoro-phenyl)-methyl- |
| Y.146 | F | 0 | 1-phenyl-eth-1-yl- |
| Y.147 | F | 0 | (4-methoxy-phenyl)-methyl- |
| Y.148 | F | 0 | 1,1-dioxo-thietan-3-yl- |
| Y.149 | F | 0 | (2-chloro-pyrid-5-yl)-methyl- |

TABLE Y-continued

| | R5b | n | R2 |
|---|---|---|---|
| Y.150 | F | 0 | 3-fluoro-phenyl- |
| Y.151 | F | 0 | n-butyl- |
| Y.152 | F | 0 | (pyrid-2-yl)-methyl- |
| Y.153 | F | 0 | 1,3-dimethyl-1H-pyrazol-5-yl- |
| Y.154 | F | 0 | 4-methyl-thiazol-2-yl- |
| Y.155 | F | 0 | 3-methyl-thietan-3-yl- |
| Y.156 | F | 0 | 1,1-dimethyl-2-methylsulfanyl-ethyl |
| Y.157 | F | 0 | 1-oxo-thietan-3-yl- |
| Y.158 | F | 0 | thietan-3-yl- |
| Y.159 | F | 0 | bicyclo[2.2.1]hept-2-yl- |
| Y.160 | F | 0 | cyclobutyl- |
| Y.161 | F | 0 | methyl- |
| Y.162 | F | 0 | cyclopropyl- |
| Y.163 | F | 0 | n-propyl- |
| Y.164 | F | 0 | 2,2-difluoroethyl- |
| Y.165 | F | 0 | 1-methoxy-prop-2-yl- |
| Y.166 | F | 0 | N-(2,2,2-trifluoro-ethyl)-acetamide-2-yl |
| Y.167 | F | 0 | 2,2,2-trifluoro-ethyl- |
| Y.168 | F | 1 | (1,1-dioxothietan-2-yl)methyl- |
| Y.169 | F | 1 | (1-oxothietan-2-yl)methyl- |
| Y.170 | F | 1 | (2-methoxy-phenyl)-methyl- |
| Y.171 | F | 1 | (3-fluoro-phenyl)-methyl- |
| Y.172 | F | 1 | (4,4-dimethyl-4,5-dihydrothiazol-2-yl)-methyl- |
| Y.173 | F | 1 | (4,5-dihydrothiazol-2-yl)-methyl- |
| Y.174 | F | 1 | (4,5-dimethyl-4,5-dihydrothiazol-2-yl)-methyl- |
| Y.175 | F | 1 | (4-fluoro-phenyl)-methyl- |
| Y.176 | F | 1 | (4-methyl-4,5-dihydrothiazol-2-yl)-methyl- |
| Y.177 | F | 1 | (5-methyl-4,5-dihydrothiazol-2-yl)-methyl- |
| Y.178 | F | 1 | (pyrid-3-yl)-methyl- |
| Y.179 | F | 1 | (pyrid-4-yl)-methyl- |
| Y.180 | F | 1 | (tetrahydrothiophene-2-yl)-methyl- |
| Y.181 | F | 1 | (tetrahydrothiophene-3-yl)-methyl- |
| Y.182 | F | 1 | (thiazol-2-yl)-methyl- |
| Y.183 | F | 1 | (thiazol-2-yl)-methylmethyl- |
| Y.184 | F | 1 | (thiazol-4-yl)-methyl- |
| Y.185 | F | 1 | (thiazol-5-yl)-methyl- |
| Y.186 | F | 1 | 1,1-dioxo-thietan-3-ylmethyl- |
| Y.187 | F | 1 | 1-cyanocyclobutyl- |
| Y.188 | F | 1 | 1-cyanocyclopentyl- |
| Y.189 | F | 1 | 1-cyanocyclopropyl- |
| Y.190 | F | 1 | 1-fluoroprop-2-yl- |
| Y.191 | F | 1 | 1-methylallyl- |
| Y.192 | F | 1 | 1-methylsulfanyl-prop-2-yl- |
| Y.193 | F | 1 | 2-(1,1-dioxothietan-3-yl)ethanyl- |
| Y.194 | F | 1 | 2-(1-oxothietan-3-yl)ethanyl- |
| Y.195 | F | 1 | 2-(thietan-3-yl)ethanyl- |
| Y.196 | F | 1 | 2-(trifluoromethoxy)phenyl- |
| Y.197 | F | 1 | 2,2-dimethyl-1,1-dioxo-thietan-3-yl- |
| Y.198 | F | 1 | 2,2-dimethyl-1-oxo-thietan-3-yl- |
| Y.199 | F | 1 | 2,2-dimethylthietan-3-yl- |
| Y.200 | F | 1 | 2,3-dichlorophenyl- |
| Y.201 | F | 1 | 2,3-difluoro-phenyl- |
| Y.202 | F | 1 | 2,4-dichlorophenyl- |
| Y.203 | F | 1 | 2,4-difluoro-phenyl- |
| Y.204 | F | 1 | 2,4-dimethylphenyl- |
| Y.205 | F | 1 | 2,5-dichlorophenyl- |
| Y.206 | F | 1 | 2,5-difluoro-phenyl- |
| Y.207 | F | 1 | 2,6-dichlorophenyl- |
| Y.208 | F | 1 | 2,6-difluoro-phenyl- |
| Y.209 | F | 1 | 2,6-diisopropylphenyl- |
| Y.210 | F | 1 | 2-bromo-4-fluorophenyl- |
| Y.211 | F | 1 | 2-bromoallyl- |
| Y.212 | F | 1 | 2-bromophenyl- |
| Y.213 | F | 1 | 2-butenyl- |
| Y.214 | F | 1 | 2-chloroallyl- |
| Y.215 | F | 1 | 2-chlorophenyl- |
| Y.216 | F | 1 | 2-chloropyrid-2-yl- |
| Y.217 | F | 1 | 2-chloropyrid-3-yl- |
| Y.218 | F | 1 | 2-cyanocyclopropyl- |
| Y.219 | F | 1 | 2-cyanoethyl- |
| Y.220 | F | 1 | 2-ethylphenyl- |
| Y.221 | F | 1 | 2-fluoroethyl- |
| Y.222 | F | 1 | 2-fluoro-phenyl- |
| Y.223 | F | 1 | 2-fluoropropyl- |
| Y.224 | F | 1 | 2-furylmethyl- |
| Y.225 | F | 1 | 2-hydroxyphenyl- |
| Y.226 | F | 1 | 2-methoxy-ethyl- |
| Y.227 | F | 1 | 2-methoxyphenyl- |
| Y.228 | F | 1 | 2-methoxy-prop-3-yl- |
| Y.229 | F | 1 | 2-methylallyl- |
| Y.230 | F | 1 | 2-methyl-but-1-yl- |
| Y.231 | F | 1 | 2-methyl-but-2-yl- |
| Y.232 | F | 1 | 2-methylbut-3-yn-2-yl- |
| Y.233 | F | 1 | 2-methylphenyl- |
| Y.234 | F | 1 | 2-methyl-prop-1-yl- |
| Y.235 | F | 1 | 2-methylsulfanyl-ethyl- |
| Y.236 | F | 1 | 2-methylsulfanyl-prop-3-yl- |
| Y.237 | F | 1 | 2-methyl-thiazol-4-yl- |
| Y.238 | F | 1 | 2-nitrophenyl- |
| Y.239 | F | 1 | 2-propyl- |
| Y.240 | F | 1 | 2-pyridyl- |
| Y.241 | F | 1 | 2-trifluoromethoxy-ethyl- |
| Y.242 | F | 1 | 3-(trifluoromethoxy)phenyl- |
| Y.243 | F | 1 | 3,3,3-trifluoro-2,2-difluoropropyl- |
| Y.244 | F | 1 | 3,3,3-trifluoro-butyl- |
| Y.245 | F | 1 | 3,3-dibromoallyl- |
| Y.246 | F | 1 | 3,3-dichloroallyl- |
| Y.247 | F | 1 | 3,4-dichlorophenyl- |
| Y.248 | F | 1 | 3,4-difluoro-phenyl- |
| Y.249 | F | 1 | 3,5-dichlorophenyl- |
| Y.250 | F | 1 | 3,5-difluoro-phenyl- |
| Y.251 | F | 1 | 3,6-difluoro-phenyl- |
| Y.252 | F | 1 | 3-bromoallyl- |
| Y.253 | F | 1 | 3-bromophenyl- |
| Y.254 | F | 1 | 3-butenyl- |
| Y.255 | F | 1 | 3-chloroallyl- |
| Y.256 | F | 1 | 3-chlorophenyl- |
| Y.257 | F | 1 | 3-chloropyrid-2-yl- |
| Y.258 | F | 1 | 3-cyanopropyl- |
| Y.259 | F | 1 | 3-ethylphenyl- |
| Y.260 | F | 1 | 3-hydroxyphenyl- |
| Y.261 | F | 1 | 3-methyl-1,1-dioxo-thietan-3-yl- |
| Y.262 | F | 1 | 3-methyl-1-oxo-thietan-3-yl- |
| Y.263 | F | 1 | 3-methyl-but-1-yl- |
| Y.264 | F | 1 | 3-methyl-but-2-yl- |
| Y.265 | F | 1 | 3-methylphenyl- |
| Y.266 | F | 1 | 3-nitrophenyl- |
| Y.267 | F | 1 | 3-pyridyl- |
| Y.268 | F | 1 | 4-(trifluoromethoxy)phenyl- |
| Y.269 | F | 1 | 4,5-dihydrothiazol-2-yl- |
| Y.270 | F | 1 | 4,5-dimethyl-4,5-dihydrothiazol-2-yl- |
| Y.271 | F | 1 | 4,5-dimethyl-thiazol-2-yl- |
| Y.272 | F | 1 | 4-bromophenyl- |
| Y.273 | F | 1 | 4-chlorophenyl- |
| Y.274 | F | 1 | 4-ethylphenyl- |
| Y.275 | F | 1 | 4-fluoro-phenyl- |
| Y.276 | F | 1 | 4H-1,2,4-triazol-3-yl- |
| Y.277 | F | 1 | 4-methoxyphenyl- |
| Y.278 | F | 1 | 4-methyl-4,5-dihydrothiazol-2-yl- |
| Y.279 | F | 1 | 4-methylphenyl- |
| Y.280 | F | 1 | 4-methylpyrid-2-yl |
| Y.281 | F | 1 | 4-nitrophenyl- |
| Y.282 | F | 1 | 4-pyridyl- |
| Y.283 | F | 1 | 5-methyl-4,5-dihydrothiazol-2-yl- |
| Y.284 | F | 1 | 5-methyl-thiazol-2-yl- |
| Y.285 | F | 1 | 6-methylpyrid-2-yl- |
| Y.286 | F | 1 | allyl- |
| Y.287 | F | 1 | but-2-ynyl- |
| Y.288 | F | 1 | but-3-ynyl- |
| Y.289 | F | 1 | cis-1-oxo-thietan-3-yl- |
| Y.290 | F | 1 | cis-1-oxo-thietan-3-ylmethyl- |
| Y.291 | F | 1 | cyanodimethylmethyl- |
| Y.292 | F | 1 | cyanoethyl- |
| Y.293 | F | 1 | cyanomethyl- |
| Y.294 | F | 1 | cyclopentyl- |
| Y.295 | F | 1 | cyclopropyl-methyl- |
| Y.296 | F | 1 | methylpropargyl- |
| Y.297 | F | 1 | oxetan-3-yl- |
| Y.298 | F | 1 | pent-3-yl- |
| Y.299 | F | 1 | phenyl-methyl-methyl- |
| Y.300 | F | 1 | propargyl- |
| Y.301 | F | 1 | tert-butyl- |

TABLE Y-continued

| | R5b | n | R2 |
|---|---|---|---|
| Y.302 | F | 1 | tetrazolyl- |
| Y.303 | F | 1 | thiazol-2-yl- |
| Y.304 | F | 1 | thiazol-4-yl- |
| Y.305 | F | 1 | thietan-2-ylmethyl- |
| Y.306 | F | 1 | thietan-3-ylmethyl- |
| Y.307 | F | 1 | ethyl- |
| Y.308 | F | 1 | 3,3,3-trifluoro-propyl- |
| Y.309 | F | 1 | but-2-yl- |
| Y.310 | F | 1 | (tetrahydrofuran-2-yl)-methyl- |
| Y.311 | F | 1 | benzyl- |
| Y.312 | F | 1 | (2-fluoro-phenyl)-methyl- |
| Y.313 | F | 1 | 1-phenyl-eth-1-yl- |
| Y.314 | F | 1 | (4-methoxy-phenyl)-methyl- |
| Y.315 | F | 1 | 1,1-dioxo-thietan-3-yl- |
| Y.316 | F | 1 | (2-chloro-pyrid-5-yl)-methyl- |
| Y.317 | F | 1 | 3-fluoro-phenyl- |
| Y.318 | F | 1 | n-butyl- |
| Y.319 | F | 1 | (pyrid-2-yl)-methyl- |
| Y.320 | F | 1 | 1,3-dimethyl-1H-pyrazol-5-yl- |
| Y.321 | F | 1 | 4-methyl-thiazol-2-yl- |
| Y.322 | F | 1 | 3-methyl-thietan-3-yl- |
| Y.323 | F | 1 | 1,1-dimethyl-2-methylsulfanyl-ethyl |
| Y.324 | F | 1 | 1-oxo-thietan-3-yl- |
| Y.325 | F | 1 | thietan-3-yl- |
| Y.326 | F | 1 | bicyclo[2.2.1]hept-2-yl- |
| Y.327 | F | 1 | cyclobutyl- |
| Y.328 | F | 1 | methyl- |
| Y.329 | F | 1 | cyclopropyl- |
| Y.330 | F | 1 | n-propyl- |
| Y.331 | F | 1 | 2,2-difluoroethyl- |
| Y.332 | F | 1 | 1-methoxy-prop-2-yl- |
| Y.333 | F | 1 | N-(2,2,2-trifluoro-ethyl)-acetamide-2-yl |
| Y.334 | F | 1 | 2,2,2-trifluoro-ethyl- |
| Y.335 | F | 2 | (1,1-dioxothietan-2-yl)methyl- |
| Y.336 | F | 2 | (1-oxothietan-2-yl)methyl- |
| Y.337 | F | 2 | (2-methoxy-phenyl)-methyl- |
| Y.338 | F | 2 | (3-fluoro-phenyl)-methyl- |
| Y.339 | F | 2 | (4,4-dimethyl-4,5-dihydrothiazol-2-yl)-methyl- |
| Y.340 | F | 2 | (4,5-dihydrothiazol-2-yl)-methyl- |
| Y.341 | F | 2 | (4,5-dimethyl-4,5-dihydrothiazol-2-yl)-methyl- |
| Y.342 | F | 2 | (4-fluoro-phenyl)-methyl- |
| Y.343 | F | 2 | (4-methyl-4,5-dihydrothiazol-2-yl)-methyl- |
| Y.344 | F | 2 | (5-methyl-4,5-dihydrothiazol-2-yl)-methyl- |
| Y.345 | F | 2 | (pyrid-3-yl)-methyl- |
| Y.346 | F | 2 | (pyrid-4-yl)-methyl- |
| Y.347 | F | 2 | (tetrahydrothiophene-2-yl)-methyl- |
| Y.348 | F | 2 | (tetrahydrothiophene-3-yl)-methyl- |
| Y.349 | F | 2 | (thiazol-2-yl)-methyl- |
| Y.350 | F | 2 | (thiazol-2-yl)-methylmethyl- |
| Y.351 | F | 2 | (thiazol-4-yl)-methyl- |
| Y.352 | F | 2 | (thiazol-5-yl)-methyl- |
| Y.353 | F | 2 | 1,1-dioxo-thietan-3-ylmethyl- |
| Y.354 | F | 2 | 1-cyanocyclobutyl- |
| Y.355 | F | 2 | 1-cyanocyclopentyl- |
| Y.356 | F | 2 | 1-cyanocyclopropyl- |
| Y.357 | F | 2 | 1-fluoroprop-2-yl- |
| Y.358 | F | 2 | 1-methylallyl- |
| Y.359 | F | 2 | 1-methylsulfanyl-prop-2-yl- |
| Y.360 | F | 2 | 2-(1,1-dioxothietan-3-yl)ethanyl- |
| Y.361 | F | 2 | 2-(1-oxothietan-3-yl)ethanyl- |
| Y.362 | F | 2 | 2-(thietan-3-yl)ethanyl- |
| Y.363 | F | 2 | 2-(trifluoromethoxy)phenyl- |
| Y.364 | F | 2 | 2,2-dimethyl-1,1-dioxo-thietan-3-yl- |
| Y.365 | F | 2 | 2,2-dimethyl-1-oxo-thietan-3-yl- |
| Y.366 | F | 2 | 2,2-dimethylthietan-3-yl- |
| Y.367 | F | 2 | 2,3-dichlorophenyl- |
| Y.368 | F | 2 | 2,3-difluoro-phenyl- |
| Y.369 | F | 2 | 2,4-dichlorophenyl- |
| Y.370 | F | 2 | 2,4-difluoro-phenyl- |
| Y.371 | F | 2 | 2,4-dimethylphenyl- |
| Y.372 | F | 2 | 2,5-dichlorophenyl- |
| Y.373 | F | 2 | 2,5-difluoro-phenyl- |
| Y.374 | F | 2 | 2,6-dichlorophenyl- |
| Y.375 | F | 2 | 2,6-difluoro-phenyl- |
| Y.376 | F | 2 | 2,6-diisopropylphenyl- |
| Y.377 | F | 2 | 2-bromo-4-fluorophenyl- |
| Y.378 | F | 2 | 2-bromoallyl- |
| Y.379 | F | 2 | 2-bromophenyl- |
| Y.380 | F | 2 | 2-butenyl- |
| Y.381 | F | 2 | 2-chloroallyl- |
| Y.382 | F | 2 | 2-chlorophenyl- |
| Y.383 | F | 2 | 2-chloropyrid-2-yl- |
| Y.384 | F | 2 | 2-chloropyrid-3-yl- |
| Y.385 | F | 2 | 2-cyanocyclopropyl- |
| Y.386 | F | 2 | 2-cyanoethyl- |
| Y.387 | F | 2 | 2-ethylphenyl- |
| Y.388 | F | 2 | 2-fluoroethyl- |
| Y.389 | F | 2 | 2-fluoro-phenyl- |
| Y.390 | F | 2 | 2-fluoropropyl- |
| Y.391 | F | 2 | 2-furylmethyl- |
| Y.392 | F | 2 | 2-hydroxyphenyl- |
| Y.393 | F | 2 | 2-methoxy-ethyl- |
| Y.394 | F | 2 | 2-methoxyphenyl- |
| Y.395 | F | 2 | 2-methoxy-prop-3-yl- |
| Y.396 | F | 2 | 2-methylallyl- |
| Y.397 | F | 2 | 2-methyl-but-1-yl- |
| Y.398 | F | 2 | 2-methyl-but-2-yl- |
| Y.399 | F | 2 | 2-methylbut-3-yn-2-yl- |
| Y.400 | F | 2 | 2-methylphenyl- |
| Y.401 | F | 2 | 2-methyl-prop-1-yl- |
| Y.402 | F | 2 | 2-methylsulfanyl-ethyl- |
| Y.403 | F | 2 | 2-methylsulfanyl-prop-3-yl- |
| Y.404 | F | 2 | 2-methyl-thiazol-4-yl- |
| Y.405 | F | 2 | 2-nitrophenyl- |
| Y.406 | F | 2 | 2-propyl- |
| Y.407 | F | 2 | 2-pyridyl- |
| Y.408 | F | 2 | 2-trifluoromethoxy-ethyl- |
| Y.409 | F | 2 | 3-(trifluoromethoxy)phenyl- |
| Y.410 | F | 2 | 3,3,3-trifluoro-2,2-difluoropropyl- |
| Y.411 | F | 2 | 3,3,3-trifluoro-butyl- |
| Y.412 | F | 2 | 3,3-dibromoallyl- |
| Y.413 | F | 2 | 3,3-dichloroallyl- |
| Y.414 | F | 2 | 3,4-dichlorophenyl- |
| Y.415 | F | 2 | 3,4-difluoro-phenyl- |
| Y.416 | F | 2 | 3,5-dichlorophenyl- |
| Y.417 | F | 2 | 3,5-difluoro-phenyl- |
| Y.418 | F | 2 | 3,6-difluoro-phenyl- |
| Y.419 | F | 2 | 3-bromoallyl- |
| Y.420 | F | 2 | 3-bromophenyl- |
| Y.421 | F | 2 | 3-butenyl- |
| Y.422 | F | 2 | 3-chloroallyl- |
| Y.423 | F | 2 | 3-chlorophenyl- |
| Y.424 | F | 2 | 3-chloropyrid-2-yl- |
| Y.425 | F | 2 | 3-cyanopropyl- |
| Y.426 | F | 2 | 3-ethylphenyl- |
| Y.427 | F | 2 | 3-hydroxyphenyl- |
| Y.428 | F | 2 | 3-methyl-1,1-dioxo-thietan-3-yl- |
| Y.429 | F | 2 | 3-methyl-1-oxo-thietan-3-yl- |
| Y.430 | F | 2 | 3-methyl-but-1-yl- |
| Y.431 | F | 2 | 3-methyl-but-2-yl- |
| Y.432 | F | 2 | 3-methylphenyl- |
| Y.433 | F | 2 | 3-nitrophenyl- |
| Y.434 | F | 2 | 3-pyridyl- |
| Y.435 | F | 2 | 4-(trifluoromethoxy)phenyl- |
| Y.436 | F | 2 | 4,5-dihydrothiazol-2-yl- |
| Y.437 | F | 2 | 4,5-dimethyl-4,5-dihydrothiazol-2-yl- |
| Y.438 | F | 2 | 4,5-dimethyl-thiazol-2-yl- |
| Y.439 | F | 2 | 4-bromophenyl- |
| Y.440 | F | 2 | 4-chlorophenyl- |
| Y.441 | F | 2 | 4-ethylphenyl- |
| Y.442 | F | 2 | 4-fluoro-phenyl- |
| Y.443 | F | 2 | 4H-1,2,4-triazol-3-yl- |
| Y.444 | F | 2 | 4-methoxyphenyl- |
| Y.445 | F | 2 | 4-methyl-4,5-dihydrothiazol-2-yl- |
| Y.446 | F | 2 | 4-methylphenyl- |
| Y.447 | F | 2 | 4-methylpyrid-2-yl |
| Y.448 | F | 2 | 4-nitrophenyl- |
| Y.449 | F | 2 | 4-pyridyl- |
| Y.450 | F | 2 | 5-methyl-4,5-dihydrothiazol-2-yl- |
| Y.451 | F | 2 | 5-methyl-thiazol-2-yl- |
| Y.452 | F | 2 | 6-methylpyrid-2-yl- |
| Y.453 | F | 2 | allyl- |

TABLE Y-continued

| | R5b | n | R2 |
|---|---|---|---|
| Y.454 | F | 2 | but-2-ynyl- |
| Y.455 | F | 2 | but-3-ynyl- |
| Y.456 | F | 2 | cis-1-oxo-thietan-3-yl- |
| Y.457 | F | 2 | cis-1-oxo-thietan-3-ylmethyl- |
| Y.458 | F | 2 | cyanodimethylmethyl- |
| Y.459 | F | 2 | cyanoethyl- |
| Y.460 | F | 2 | cyanomethyl- |
| Y.461 | F | 2 | cyclopentyl- |
| Y.462 | F | 2 | cyclopropyl-methyl- |
| Y.463 | F | 2 | methylpropargyl- |
| Y.464 | F | 2 | oxetan-3-yl- |
| Y.465 | F | 2 | pent-3-yl- |
| Y.466 | F | 2 | phenyl-methyl-methyl- |
| Y.467 | F | 2 | propargyl- |
| Y.468 | F | 2 | tert-butyl- |
| Y.469 | F | 2 | tetrazolyl- |
| Y.470 | F | 2 | thiazol-2-yl- |
| Y.471 | F | 2 | thiazol-4-yl- |
| Y.472 | F | 2 | thietan-2-ylmethyl- |
| Y.473 | F | 2 | thietan-3-ylmethyl- |
| Y.474 | F | 2 | ethyl- |
| Y.475 | F | 2 | 3,3,3-trifluoro-propyl- |
| Y.476 | F | 2 | but-2-yl- |
| Y.477 | F | 2 | (tetrahydrofuran-2-yl)-methyl- |
| Y.478 | F | 2 | benzyl- |
| Y.479 | F | 2 | (2-fluoro-phenyl)-methyl- |
| Y.480 | F | 2 | 1-phenyl-eth-1-yl- |
| Y.481 | F | 2 | (4-methoxy-phenyl)-methyl- |
| Y.482 | F | 2 | 1,1-dioxo-thietan-3-yl- |
| Y.483 | F | 2 | (2-chloro-pyrid-5-yl)-methyl- |
| Y.484 | F | 2 | 3-fluoro-phenyl- |
| Y.485 | F | 2 | n-butyl- |
| Y.486 | F | 2 | (pyrid-2-yl)-methyl- |
| Y.487 | F | 2 | 1,3-dimethyl-1H-pyrazol-5-yl- |
| Y.488 | F | 2 | 4-methyl-thiazol-2-yl- |
| Y.489 | F | 2 | 3-methyl-thietan-3-yl- |
| Y.490 | F | 2 | 1,1-dimethyl-2-methylsulfanyl-ethyl |
| Y.491 | F | 2 | 1-oxo-thietan-3-yl- |
| Y.492 | F | 2 | thietan-3-yl- |
| Y.493 | F | 2 | bicyclo[2.2.1]hept-2-yl- |
| Y.494 | F | 2 | cyclobutyl- |
| Y.495 | F | 2 | methyl- |
| Y.496 | F | 2 | cyclopropyl- |
| Y.497 | F | 2 | n-propyl- |
| Y.498 | F | 2 | 2,2-difluoroethyl- |
| Y.499 | F | 2 | 1-methoxy-prop-2-yl- |
| Y.500 | F | 2 | N-(2,2,2-trifluoro-ethyl)-acetamide-2-yl |
| Y.501 | F | 2 | 2,2,2-trifluoro-ethyl- |
| Y.502 | Cl | 0 | (1,1-dioxothietan-2-yl)methyl- |
| Y.503 | Cl | 0 | (1-oxothietan-2-yl)methyl- |
| Y.504 | Cl | 0 | (2-methoxy-phenyl)-methyl- |
| Y.505 | Cl | 0 | (3-fluoro-phenyl)-methyl- |
| Y.506 | Cl | 0 | (4,4-dimethyl-4,5-dihydrothiazol-2-yl)-methyl- |
| Y.507 | Cl | 0 | (4,5-dihydrothiazol-2-yl)-methyl- |
| Y.508 | Cl | 0 | (4,5-dimethyl-4,5-dihydrothiazol-2-yl)-methyl- |
| Y.509 | Cl | 0 | (4-fluoro-phenyl)-methyl- |
| Y.510 | Cl | 0 | (4-methyl-4,5-dihydrothiazol-2-yl)-methyl- |
| Y.511 | Cl | 0 | (5-methyl-4,5-dihydrothiazol-2-yl)-methyl- |
| Y.512 | Cl | 0 | (pyrid-3-yl)-methyl- |
| Y.513 | Cl | 0 | (pyrid-4-yl)-methyl- |
| Y.514 | Cl | 0 | (tetrahydrothiophene-2-yl)-methyl- |
| Y.515 | Cl | 0 | (tetrahydrothiophene-3-yl)-methyl- |
| Y.516 | Cl | 0 | (thiazol-2-yl)-methyl- |
| Y.517 | Cl | 0 | (thiazol-2-yl)-methylmethyl- |
| Y.518 | Cl | 0 | (thiazol-4-yl)-methyl- |
| Y.519 | Cl | 0 | (thiazol-5-yl)-methyl- |
| Y.520 | Cl | 0 | 1,1-dioxo-thietan-3-ylmethyl- |
| Y.521 | Cl | 0 | 1-cyanocyclobutyl- |
| Y.522 | Cl | 0 | 1-cyanocyclopentyl- |
| Y.523 | Cl | 0 | 1-cyanocyclopropyl- |
| Y.524 | Cl | 0 | 1-fluoroprop-2-yl- |
| Y.525 | Cl | 0 | 1-methylallyl- |
| Y.526 | Cl | 0 | 1-methylsulfanyl-prop-2-yl- |
| Y.527 | Cl | 0 | 2-(1,1-dioxothietan-3-yl)ethanyl- |
| Y.528 | Cl | 0 | 2-(1-oxothietan-3-yl)ethanyl- |
| Y.529 | Cl | 0 | 2-(thietan-3-yl)ethanyl- |
| Y.530 | Cl | 0 | 2-(trifluoromethoxy)phenyl- |
| Y.531 | Cl | 0 | 2,2-dimethyl-1,1-dioxo-thietan-3-yl- |
| Y.532 | Cl | 0 | 2,2-dimethyl-1-oxo-thietan-3-yl- |
| Y.533 | Cl | 0 | 2,2-dimethylthietan-3-yl- |
| Y.534 | Cl | 0 | 2,3-dichlorophenyl- |
| Y.535 | Cl | 0 | 2,3-difluoro-phenyl- |
| Y.536 | Cl | 0 | 2,4-dichlorophenyl- |
| Y.537 | Cl | 0 | 2,4-difluoro-phenyl- |
| Y.538 | Cl | 0 | 2,4-dimethylphenyl- |
| Y.539 | Cl | 0 | 2,5-dichlorophenyl- |
| Y.540 | Cl | 0 | 2,5-difluoro-phenyl- |
| Y.541 | Cl | 0 | 2,6-dichlorophenyl- |
| Y.542 | Cl | 0 | 2,6-difluoro-phenyl- |
| Y.543 | Cl | 0 | 2,6-diisopropylphenyl- |
| Y.544 | Cl | 0 | 2-bromo-4-fluorophenyl- |
| Y.545 | Cl | 0 | 2-bromoallyl- |
| Y.546 | Cl | 0 | 2-bromophenyl- |
| Y.547 | Cl | 0 | 2-butenyl- |
| Y.548 | Cl | 0 | 2-chloroallyl- |
| Y.549 | Cl | 0 | 2-chlorophenyl- |
| Y.550 | Cl | 0 | 2-chloropyrid-2-yl- |
| Y.551 | Cl | 0 | 2-chloropyrid-3-yl- |
| Y.552 | Cl | 0 | 2-cyanocyclopropyl- |
| Y.553 | Cl | 0 | 2-cyanoethyl- |
| Y.554 | Cl | 0 | 2-ethylphenyl- |
| Y.555 | Cl | 0 | 2-fluoroethyl- |
| Y.556 | Cl | 0 | 2-fluoro-phenyl- |
| Y.557 | Cl | 0 | 2-fluoropropyl- |
| Y.558 | Cl | 0 | 2-furylmethyl- |
| Y.559 | Cl | 0 | 2-hydroxyphenyl- |
| Y.560 | Cl | 0 | 2-methoxy-ethyl- |
| Y.561 | Cl | 0 | 2-methoxyphenyl- |
| Y.562 | Cl | 0 | 2-methoxy-prop-3-yl- |
| Y.563 | Cl | 0 | 2-methylallyl- |
| Y.564 | Cl | 0 | 2-methyl-but-1-yl- |
| Y.565 | Cl | 0 | 2-methyl-but-2-yl- |
| Y.566 | Cl | 0 | 2-methylbut-3-yn-2-yl- |
| Y.567 | Cl | 0 | 2-methylphenyl- |
| Y.568 | Cl | 0 | 2-methyl-prop-1-yl- |
| Y.569 | Cl | 0 | 2-methylsulfanyl-ethyl- |
| Y.570 | Cl | 0 | 2-methylsulfanyl-prop-3-yl- |
| Y.571 | Cl | 0 | 2-methyl-thiazol-4-yl- |
| Y.572 | Cl | 0 | 2-nitrophenyl- |
| Y.573 | Cl | 0 | 2-propyl- |
| Y.574 | Cl | 0 | 2-pyridyl- |
| Y.575 | Cl | 0 | 2-trifluoromethoxy-ethyl- |
| Y.576 | Cl | 0 | 3-(trifluoromethoxy)phenyl- |
| Y.577 | Cl | 0 | 3,3,3-trifluoro-2,2-difluoropropyl- |
| Y.578 | Cl | 0 | 3,3,3-trifluoro-butyl- |
| Y.579 | Cl | 0 | 3,3-dibromoallyl- |
| Y.580 | Cl | 0 | 3,3-dichloroallyl- |
| Y.581 | Cl | 0 | 3,4-dichlorophenyl- |
| Y.582 | Cl | 0 | 3,4-difluoro-phenyl- |
| Y.583 | Cl | 0 | 3,5-dichlorophenyl- |
| Y.584 | Cl | 0 | 3,5-difluoro-phenyl- |
| Y.585 | Cl | 0 | 3,6-difluoro-phenyl- |
| Y.586 | Cl | 0 | 3-bromoallyl- |
| Y.587 | Cl | 0 | 3-bromophenyl- |
| Y.588 | Cl | 0 | 3-butenyl- |
| Y.589 | Cl | 0 | 3-chloroallyl- |
| Y.590 | Cl | 0 | 3-chlorophenyl- |
| Y.591 | Cl | 0 | 3-chloropyrid-2-yl- |
| Y.592 | Cl | 0 | 3-cyanopropyl- |
| Y.593 | Cl | 0 | 3-ethylphenyl- |
| Y.594 | Cl | 0 | 3-hydroxyphenyl- |
| Y.595 | Cl | 0 | 3-methyl-1,1-dioxo-thietan-3-yl- |
| Y.596 | Cl | 0 | 3-methyl-1-oxo-thietan-3-yl- |
| Y.597 | Cl | 0 | 3-methyl-but-1-yl- |
| Y.598 | Cl | 0 | 3-methyl-but-2-yl- |
| Y.599 | Cl | 0 | 3-methylphenyl- |
| Y.600 | Cl | 0 | 3-nitrophenyl- |
| Y.601 | Cl | 0 | 3-pyridyl- |
| Y.602 | Cl | 0 | 4-(trifluoromethoxy)phenyl- |
| Y.603 | Cl | 0 | 4,5-dihydrothiazol-2-yl- |
| Y.604 | Cl | 0 | 4,5-dimethyl-4,5-dihydrothiazol-2-yl- |
| Y.605 | Cl | 0 | 4,5-dimethyl-thiazol-2-yl- |

TABLE Y-continued

| | R5b | n | R2 |
|---|---|---|---|
| Y.606 | Cl | 0 | 4-bromophenyl- |
| Y.607 | Cl | 0 | 4-chlorophenyl- |
| Y.608 | Cl | 0 | 4-ethylphenyl- |
| Y.609 | Cl | 0 | 4-fluoro-phenyl- |
| Y.610 | Cl | 0 | 4H-1,2,4-triazol-3-yl- |
| Y.611 | Cl | 0 | 4-methoxyphenyl- |
| Y.612 | Cl | 0 | 4-methyl-4,5-dihydrothiazol-2-yl- |
| Y.613 | Cl | 0 | 4-methylphenyl- |
| Y.614 | Cl | 0 | 4-methylpyrid-2-yl |
| Y.615 | Cl | 0 | 4-nitrophenyl- |
| Y.616 | Cl | 0 | 4-pyridyl- |
| Y.617 | Cl | 0 | 5-methyl-4,5-dihydrothiazol-2-yl- |
| Y.618 | Cl | 0 | 5-methyl-thiazol-2-yl- |
| Y.619 | Cl | 0 | 6-methylpyrid-2-yl- |
| Y.620 | Cl | 0 | allyl- |
| Y.621 | Cl | 0 | but-2-ynyl- |
| Y.622 | Cl | 0 | but-3-ynyl- |
| Y.623 | Cl | 0 | cis-1-oxo-thietan-3-yl- |
| Y.624 | Cl | 0 | cis-1-oxo-thietan-3-ylmethyl- |
| Y.625 | Cl | 0 | cyanodimethylmethyl- |
| Y.626 | Cl | 0 | cyanoethyl- |
| Y.627 | Cl | 0 | cyanomethyl- |
| Y.628 | Cl | 0 | cyclopentyl- |
| Y.629 | Cl | 0 | cyclopropyl-methyl- |
| Y.630 | Cl | 0 | methylpropargyl- |
| Y.631 | Cl | 0 | oxetan-3-yl- |
| Y.632 | Cl | 0 | pent-3-yl- |
| Y.633 | Cl | 0 | phenyl-methyl-methyl- |
| Y.634 | Cl | 0 | propargyl- |
| Y.635 | Cl | 0 | tert-butyl- |
| Y.636 | Cl | 0 | tetrazolyl- |
| Y.637 | Cl | 0 | thiazol-2-yl- |
| Y.638 | Cl | 0 | thiazol-4-yl- |
| Y.639 | Cl | 0 | thietan-2-ylmethyl- |
| Y.640 | Cl | 0 | thietan-3-ylmethyl- |
| Y.641 | Cl | 0 | ethyl- |
| Y.642 | Cl | 0 | 3,3,3-trifluoro-propyl- |
| Y.643 | Cl | 0 | but-2-yl- |
| Y.644 | Cl | 0 | (tetrahydrofuran-2-yl)-methyl- |
| Y.645 | Cl | 0 | benzyl- |
| Y.646 | Cl | 0 | (2-fluoro-phenyl)-methyl- |
| Y.647 | Cl | 0 | 1-phenyl-eth-1-yl- |
| Y.648 | Cl | 0 | (4-methoxy-phenyl)-methyl- |
| Y.649 | Cl | 0 | 1,1-dioxo-thietan-3-yl- |
| Y.650 | Cl | 0 | (2-chloro-pyrid-5-yl)-methyl- |
| Y.651 | Cl | 0 | 3-fluoro-phenyl- |
| Y.652 | Cl | 0 | n-butyl- |
| Y.653 | Cl | 0 | (pyrid-2-yl)-methyl- |
| Y.654 | Cl | 0 | 1,3-dimethyl-1H-pyrazol-5-yl- |
| Y.655 | Cl | 0 | 4-methyl-thiazol-2-yl- |
| Y.656 | Cl | 0 | 3-methyl-thietan-3-yl- |
| Y.657 | Cl | 0 | 1,1-dimethyl-2-methylsulfanyl-ethyl |
| Y.658 | Cl | 0 | 1-oxo-thietan-3-yl- |
| Y.659 | Cl | 0 | thietan-3-yl- |
| Y.660 | Cl | 0 | bicyclo[2.2.1]hept-2-yl- |
| Y.661 | Cl | 0 | cyclobutyl- |
| Y.662 | Cl | 0 | methyl- |
| Y.663 | Cl | 0 | cyclopropyl- |
| Y.664 | Cl | 0 | n-propyl- |
| Y.665 | Cl | 0 | 2,2-difluoroethyl- |
| Y.666 | Cl | 0 | 1-methoxy-prop-2-yl- |
| Y.667 | Cl | 0 | N-(2,2,2-trifluoro-ethyl)-acetamide-2-yl |
| Y.668 | Cl | 0 | 2,2,2-trifluoro-ethyl- |
| Y.669 | Cl | 1 | (1,1-dioxothietan-2-yl)methyl- |
| Y.670 | Cl | 1 | (1-oxothietan-2-yl)methyl- |
| Y.671 | Cl | 1 | (2-methoxy-phenyl)-methyl- |
| Y.672 | Cl | 1 | (3-fluoro-phenyl)-methyl- |
| Y.673 | Cl | 1 | (4,4-dimethyl-4,5-dihydrothiazol-2-yl)-methyl- |
| Y.674 | Cl | 1 | (4,5-dihydrothiazol-2-yl)-methyl- |
| Y.675 | Cl | 1 | (4,5-dimethyl-4,5-dihydrothiazol-2-yl)-methyl- |
| Y.676 | Cl | 1 | (4-fluoro-phenyl)-methyl- |
| Y.677 | Cl | 1 | (4-methyl-4,5-dihydrothiazol-2-yl)-methyl- |
| Y.678 | Cl | 1 | (5-methyl-4,5-dihydrothiazol-2-yl)-methyl- |
| Y.679 | Cl | 1 | (pyrid-3-yl)-methyl- |
| Y.680 | Cl | 1 | (pyrid-4-yl)-methyl- |
| Y.681 | Cl | 1 | (tetrahydrothiophene-2-yl)-methyl- |
| Y.682 | Cl | 1 | (tetrahydrothiophene-3-yl)-methyl- |
| Y.683 | Cl | 1 | (thiazol-2-yl)-methyl- |
| Y.684 | Cl | 1 | (thiazol-2-yl)-methylmethyl- |
| Y.685 | Cl | 1 | (thiazol-4-yl)-methyl- |
| Y.686 | Cl | 1 | (thiazol-5-yl)-methyl- |
| Y.687 | Cl | 1 | 1,1-dioxo-thietan-3-ylmethyl- |
| Y.688 | Cl | 1 | 1-cyanocyclobutyl- |
| Y.689 | Cl | 1 | 1-cyanocyclopentyl- |
| Y.690 | Cl | 1 | 1-cyanocyclopropyl- |
| Y.691 | Cl | 1 | 1-fluoroprop-2-yl- |
| Y.692 | Cl | 1 | 1-methylallyl- |
| Y.693 | Cl | 1 | 1-methylsulfanyl-prop-2-yl- |
| Y.694 | Cl | 1 | 2-(1,1-dioxothietan-3-yl)ethanyl- |
| Y.695 | Cl | 1 | 2-(1-oxothietan-3-yl)ethanyl- |
| Y.696 | Cl | 1 | 2-(thietan-3-yl)ethanyl- |
| Y.697 | Cl | 1 | 2-(trifluoromethoxy)phenyl- |
| Y.698 | Cl | 1 | 2,2-dimethyl-1,1-dioxo-thietan-3-yl- |
| Y.699 | Cl | 1 | 2,2-dimethyl-1-oxo-thietan-3-yl- |
| Y.700 | Cl | 1 | 2,2-dimethylthietan-3-yl- |
| Y.701 | Cl | 1 | 2,3-dichlorophenyl- |
| Y.702 | Cl | 1 | 2,3-difluoro-phenyl- |
| Y.703 | Cl | 1 | 2,4-dichlorophenyl- |
| Y.704 | Cl | 1 | 2,4-difluoro-phenyl- |
| Y.705 | Cl | 1 | 2,4-dimethylphenyl- |
| Y.706 | Cl | 1 | 2,5-dichlorophenyl- |
| Y.707 | Cl | 1 | 2,5-difluoro-phenyl- |
| Y.708 | Cl | 1 | 2,6-dichlorophenyl- |
| Y.709 | Cl | 1 | 2,6-difluoro-phenyl- |
| Y.710 | Cl | 1 | 2,6-diisopropylphenyl- |
| Y.711 | Cl | 1 | 2-bromo-4-fluorophenyl- |
| Y.712 | Cl | 1 | 2-bromoallyl- |
| Y.713 | Cl | 1 | 2-bromophenyl- |
| Y.714 | Cl | 1 | 2-butenyl- |
| Y.715 | Cl | 1 | 2-chloroallyl- |
| Y.716 | Cl | 1 | 2-chlorophenyl- |
| Y.717 | Cl | 1 | 2-chloropyrid-2-yl- |
| Y.718 | Cl | 1 | 2-chloropyrid-3-yl- |
| Y.719 | Cl | 1 | 2-cyanocyclopropyl- |
| Y.720 | Cl | 1 | 2-cyanoethyl- |
| Y.721 | Cl | 1 | 2-ethylphenyl- |
| Y.722 | Cl | 1 | 2-fluoroethyl- |
| Y.723 | Cl | 1 | 2-fluoro-phenyl- |
| Y.724 | Cl | 1 | 2-fluoropropyl- |
| Y.725 | Cl | 1 | 2-furylmethyl- |
| Y.726 | Cl | 1 | 2-hydroxyphenyl- |
| Y.727 | Cl | 1 | 2-methoxy-ethyl- |
| Y.728 | Cl | 1 | 2-methoxyphenyl- |
| Y.729 | Cl | 1 | 2-methoxy-prop-3-yl- |
| Y.730 | Cl | 1 | 2-methylallyl- |
| Y.731 | Cl | 1 | 2-methyl-but-1-yl- |
| Y.732 | Cl | 1 | 2-methyl-but-2-yl- |
| Y.733 | Cl | 1 | 2-methylbut-3-yn-2-yl- |
| Y.734 | Cl | 1 | 2-methylphenyl- |
| Y.735 | Cl | 1 | 2-methyl-prop-1-yl- |
| Y.736 | Cl | 1 | 2-methylsulfanyl-ethyl- |
| Y.737 | Cl | 1 | 2-methylsulfanyl-prop-3-yl- |
| Y.738 | Cl | 1 | 2-methyl-thiazol-4-yl- |
| Y.739 | Cl | 1 | 2-nitrophenyl- |
| Y.740 | Cl | 1 | 2-propyl- |
| Y.741 | Cl | 1 | 2-pyridyl- |
| Y.742 | Cl | 1 | 2-trifluoromethoxy-ethyl- |
| Y.743 | Cl | 1 | 3-(trifluoromethoxy)phenyl- |
| Y.744 | Cl | 1 | 3,3,3-trifluoro-2,2-difluoropropyl- |
| Y.745 | Cl | 1 | 3,3,3-trifluoro-butyl- |
| Y.746 | Cl | 1 | 3,3-dibromoallyl- |
| Y.747 | Cl | 1 | 3,3-dichloroallyl- |
| Y.748 | Cl | 1 | 3,4-dichlorophenyl- |
| Y.749 | Cl | 1 | 3,4-difluoro-phenyl- |
| Y.750 | Cl | 1 | 3,5-dichlorophenyl- |
| Y.751 | Cl | 1 | 3,5-difluoro-phenyl- |
| Y.752 | Cl | 1 | 3,6-difluoro-phenyl- |
| Y.753 | Cl | 1 | 3-bromoallyl- |
| Y.754 | Cl | 1 | 3-bromophenyl- |
| Y.755 | Cl | 1 | 3-butenyl- |
| Y.756 | Cl | 1 | 3-chloroallyl- |
| Y.757 | Cl | 1 | 3-chlorophenyl- |

TABLE Y-continued

| | R5b | n | R2 |
|---|---|---|---|
| Y.758 | Cl | 1 | 3-chloropyrid-2-yl- |
| Y.759 | Cl | 1 | 3-cyanopropyl- |
| Y.760 | Cl | 1 | 3-ethylphenyl- |
| Y.761 | Cl | 1 | 3-hydroxyphenyl- |
| Y.762 | Cl | 1 | 3-methyl-1,1-dioxo-thietan-3-yl- |
| Y.763 | Cl | 1 | 3-methyl-1-oxo-thietan-3-yl- |
| Y.764 | Cl | 1 | 3-methyl-but-1-yl- |
| Y.765 | Cl | 1 | 3-methyl-but-2-yl- |
| Y.766 | Cl | 1 | 3-methylphenyl- |
| Y.767 | Cl | 1 | 3-nitrophenyl- |
| Y.768 | Cl | 1 | 3-pyridyl- |
| Y.769 | Cl | 1 | 4-(trifluoromethoxy)phenyl- |
| Y.770 | Cl | 1 | 4,5-dihydrothiazol-2-yl- |
| Y.771 | Cl | 1 | 4,5-dimethyl-4,5-dihydrothiazol-2-yl- |
| Y.772 | Cl | 1 | 4,5-dimethyl-thiazol-2-yl- |
| Y.773 | Cl | 1 | 4-bromophenyl- |
| Y.774 | Cl | 1 | 4-chlorophenyl- |
| Y.775 | Cl | 1 | 4-ethylphenyl- |
| Y.776 | Cl | 1 | 4-fluoro-phenyl- |
| Y.777 | Cl | 1 | 4H-1,2,4-triazol-3-yl- |
| Y.778 | Cl | 1 | 4-methoxyphenyl- |
| Y.779 | Cl | 1 | 4-methyl-4,5-dihydrothiazol-2-yl- |
| Y.780 | Cl | 1 | 4-methylphenyl- |
| Y.781 | Cl | 1 | 4-methylpyrid-2-yl |
| Y.782 | Cl | 1 | 4-nitrophenyl- |
| Y.783 | Cl | 1 | 4-pyridyl- |
| Y.784 | Cl | 1 | 5-methyl-4,5-dihydrothiazol-2-yl- |
| Y.785 | Cl | 1 | 5-methyl-thiazol-2-yl- |
| Y.786 | Cl | 1 | 6-methylpyrid-2-yl- |
| Y.787 | Cl | 1 | allyl- |
| Y.788 | Cl | 1 | but-2-ynyl- |
| Y.789 | Cl | 1 | but-3-ynyl- |
| Y.790 | Cl | 1 | cis-1-oxo-thietan-3-yl- |
| Y.791 | Cl | 1 | cis-1-oxo-thietan-3-ylmethyl- |
| Y.792 | Cl | 1 | cyanodimethylmethyl- |
| Y.793 | Cl | 1 | cyanoethyl- |
| Y.794 | Cl | 1 | cyanomethyl- |
| Y.795 | Cl | 1 | cyclopentyl- |
| Y.796 | Cl | 1 | cyclopropyl-methyl- |
| Y.797 | Cl | 1 | methylpropargyl- |
| Y.798 | Cl | 1 | oxetan-3-yl- |
| Y.799 | Cl | 1 | pent-3-yl- |
| Y.800 | Cl | 1 | phenyl-methyl-methyl- |
| Y.801 | Cl | 1 | propargyl- |
| Y.802 | Cl | 1 | tert-butyl- |
| Y.803 | Cl | 1 | tetrazolyl- |
| Y.804 | Cl | 1 | thiazol-2-yl- |
| Y.805 | Cl | 1 | thiazol-4-yl- |
| Y.806 | Cl | 1 | thietan-2-ylmethyl- |
| Y.807 | Cl | 1 | thietan-3-ylmethyl- |
| Y.808 | Cl | 1 | ethyl- |
| Y.809 | Cl | 1 | 3,3,3-trifluoro-propyl- |
| Y.810 | Cl | 1 | but-2-yl- |
| Y.811 | Cl | 1 | (tetrahydrofuran-2-yl)-methyl- |
| Y.812 | Cl | 1 | benzyl- |
| Y.813 | Cl | 1 | (2-fluoro-phenyl)-methyl- |
| Y.814 | Cl | 1 | 1-phenyl-eth-1-yl- |
| Y.815 | Cl | 1 | (4-methoxy-phenyl)-methyl- |
| Y.816 | Cl | 1 | 1,1-dioxo-thietan-3-yl- |
| Y.817 | Cl | 1 | (2-chloro-pyrid-5-yl)-methyl- |
| Y.818 | Cl | 1 | 3-fluoro-phenyl- |
| Y.819 | Cl | 1 | n-butyl- |
| Y.820 | Cl | 1 | (pyrid-2-yl)-methyl- |
| Y.821 | Cl | 1 | 1,3-dimethyl-1H-pyrazol-5-yl- |
| Y.822 | Cl | 1 | 4-methyl-thiazol-2-yl- |
| Y.823 | Cl | 1 | 3-methyl-thietan-3-yl- |
| Y.824 | Cl | 1 | 1,1-dimethyl-2-methylsulfanyl-ethyl |
| Y.825 | Cl | 1 | 1-oxo-thietan-3-yl- |
| Y.826 | Cl | 1 | thietan-3-yl- |
| Y.827 | Cl | 1 | bicyclo[2.2.1]hept-2-yl- |
| Y.828 | Cl | 1 | cyclobutyl- |
| Y.829 | Cl | 1 | methyl- |
| Y.830 | Cl | 1 | cyclopropyl- |
| Y.831 | Cl | 1 | n-propyl- |
| Y.832 | Cl | 1 | 2,2-difluoroethyl- |
| Y.833 | Cl | 1 | 1-methoxy-prop-2-yl- |
| Y.834 | Cl | 1 | N-(2,2,2-trifluoro-ethyl)-acetamide-2-yl |
| Y.835 | Cl | 1 | 2,2,2-trifluoro-ethyl- |
| Y.836 | Cl | 2 | (1,1-dioxothietan-2-yl)methyl- |
| Y.837 | Cl | 2 | (1-oxothietan-2-yl)methyl- |
| Y.838 | Cl | 2 | (2-methoxy-phenyl)-methyl- |
| Y.839 | Cl | 2 | (3-fluoro-phenyl)-methyl- |
| Y.840 | Cl | 2 | (4,4-dimethyl-4,5-dihydrothiazol-2-yl)-methyl- |
| Y.841 | Cl | 2 | (4,5-dihydrothiazol-2-yl)-methyl- |
| Y.842 | Cl | 2 | (4,5-dimethyl-4,5-dihydrothiazol-2-yl)-methyl- |
| Y.843 | Cl | 2 | (4-fluoro-phenyl)-methyl- |
| Y.844 | Cl | 2 | (4-methyl-4,5-dihydrothiazol-2-yl)-methyl- |
| Y.845 | Cl | 2 | (5-methyl-4,5-dihydrothiazol-2-yl)-methyl- |
| Y.846 | Cl | 2 | (pyrid-3-yl)-methyl- |
| Y.847 | Cl | 2 | (pyrid-4-yl)-methyl- |
| Y.848 | Cl | 2 | (tetrahydrothiophene-2-yl)-methyl- |
| Y.849 | Cl | 2 | (tetrahydrothiophene-3-yl)-methyl- |
| Y.850 | Cl | 2 | (thiazol-2-yl)-methyl- |
| Y.851 | Cl | 2 | (thiazol-2-yl)-methylmethyl- |
| Y.852 | Cl | 2 | (thiazol-4-yl)-methyl- |
| Y.853 | Cl | 2 | (thiazol-5-yl)-methyl- |
| Y.854 | Cl | 2 | 1,1-dioxo-thietan-3-ylmethyl- |
| Y.855 | Cl | 2 | 1-cyanocyclobutyl- |
| Y.856 | Cl | 2 | 1-cyanocyclopentyl- |
| Y.857 | Cl | 2 | 1-cyanocyclopropyl- |
| Y.858 | Cl | 2 | 1-fluoroprop-2-yl- |
| Y.859 | Cl | 2 | 1-methylallyl- |
| Y.860 | Cl | 2 | 1-methylsulfanyl-prop-2-yl- |
| Y.861 | Cl | 2 | 2-(1,1-dioxothietan-3-yl)ethanyl- |
| Y.862 | Cl | 2 | 2-(1-oxothietan-3-yl)ethanyl- |
| Y.863 | Cl | 2 | 2-(thietan-3-yl)ethanyl- |
| Y.864 | Cl | 2 | 2-(trifluoromethoxy)phenyl- |
| Y.865 | Cl | 2 | 2,2-dimethyl-1,1-dioxo-thietan-3-yl- |
| Y.866 | Cl | 2 | 2,2-dimethyl-1-oxo-thietan-3-yl- |
| Y.867 | Cl | 2 | 2,2-dimethylthietan-3-yl- |
| Y.868 | Cl | 2 | 2,3-dichlorophenyl- |
| Y.869 | Cl | 2 | 2,3-difluoro-phenyl- |
| Y.870 | Cl | 2 | 2,4-dichlorophenyl- |
| Y.871 | Cl | 2 | 2,4-difluoro-phenyl- |
| Y.872 | Cl | 2 | 2,4-dimethylphenyl- |
| Y.873 | Cl | 2 | 2,5-dichlorophenyl- |
| Y.874 | Cl | 2 | 2,5-difluoro-phenyl- |
| Y.875 | Cl | 2 | 2,6-dichlorophenyl- |
| Y.876 | Cl | 2 | 2,6-difluoro-phenyl- |
| Y.877 | Cl | 2 | 2,6-diisopropylphenyl- |
| Y.878 | Cl | 2 | 2-bromo-4-fluorophenyl- |
| Y.879 | Cl | 2 | 2-bromoallyl- |
| Y.880 | Cl | 2 | 2-bromophenyl- |
| Y.881 | Cl | 2 | 2-butenyl- |
| Y.882 | Cl | 2 | 2-chloroallyl- |
| Y.883 | Cl | 2 | 2-chlorophenyl- |
| Y.884 | Cl | 2 | 2-chloropyrid-2-yl- |
| Y.885 | Cl | 2 | 2-chloropyrid-3-yl- |
| Y.886 | Cl | 2 | 2-cyanocyclopropyl- |
| Y.887 | Cl | 2 | 2-cyanoethyl- |
| Y.888 | Cl | 2 | 2-ethylphenyl- |
| Y.889 | Cl | 2 | 2-fluoroethyl- |
| Y.890 | Cl | 2 | 2-fluoro-phenyl- |
| Y.891 | Cl | 2 | 2-fluoropropyl- |
| Y.892 | Cl | 2 | 2-furylmethyl- |
| Y.893 | Cl | 2 | 2-hydroxyphenyl- |
| Y.894 | Cl | 2 | 2-methoxy-ethyl- |
| Y.895 | Cl | 2 | 2-methoxyphenyl- |
| Y.896 | Cl | 2 | 2-methoxy-prop-3-yl- |
| Y.897 | Cl | 2 | 2-methylallyl- |
| Y.898 | Cl | 2 | 2-methyl-but-1-yl- |
| Y.899 | Cl | 2 | 2-methyl-but-2-yl- |
| Y.900 | Cl | 2 | 2-methylbut-3-yn-2-yl- |
| Y.901 | Cl | 2 | 2-methylphenyl- |
| Y.902 | Cl | 2 | 2-methyl-prop-1-yl- |
| Y.903 | Cl | 2 | 2-methylsulfanyl-ethyl- |
| Y.904 | Cl | 2 | 2-methylsulfanyl-prop-3-yl- |
| Y.905 | Cl | 2 | 2-methyl-thiazol-4-yl- |
| Y.906 | Cl | 2 | 2-nitrophenyl- |
| Y.907 | Cl | 2 | 2-propyl- |
| Y.908 | Cl | 2 | 2-pyridyl- |
| Y.909 | Cl | 2 | 2-trifluoromethoxy-ethyl- |

TABLE Y-continued

| | R5b | n | R2 |
|---|---|---|---|
| Y.910 | Cl | 2 | 3-(trifluoromethoxy)phenyl- |
| Y.911 | Cl | 2 | 3,3,3-trifluoro-2,2-difluoropropyl- |
| Y.912 | Cl | 2 | 3,3,3-trifluoro-butyl- |
| Y.913 | Cl | 2 | 3,3-dibromoallyl- |
| Y.914 | Cl | 2 | 3,3-dichloroallyl- |
| Y.915 | Cl | 2 | 3,4-dichlorophenyl- |
| Y.916 | Cl | 2 | 3,4-difluoro-phenyl- |
| Y.917 | Cl | 2 | 3,5-dichlorophenyl- |
| Y.918 | Cl | 2 | 3,5-difluoro-phenyl- |
| Y.919 | Cl | 2 | 3,6-difluoro-phenyl- |
| Y.920 | Cl | 2 | 3-bromoallyl- |
| Y.921 | Cl | 2 | 3-bromophenyl- |
| Y.922 | Cl | 2 | 3-butenyl- |
| Y.923 | Cl | 2 | 3-chloroallyl- |
| Y.924 | Cl | 2 | 3-chlorophenyl- |
| Y.925 | Cl | 2 | 3-chloropyrid-2-yl- |
| Y.926 | Cl | 2 | 3-cyanopropyl- |
| Y.927 | Cl | 2 | 3-ethylphenyl- |
| Y.928 | Cl | 2 | 3-hydroxyphenyl- |
| Y.929 | Cl | 2 | 3-methyl-1,1-dioxo-thietan-3-yl- |
| Y.930 | Cl | 2 | 3-methyl-1-oxo-thietan-3-yl- |
| Y.931 | Cl | 2 | 3-methyl-but-1-yl- |
| Y.932 | Cl | 2 | 3-methyl-but-2-yl- |
| Y.933 | Cl | 2 | 3-methylphenyl- |
| Y.934 | Cl | 2 | 3-nitrophenyl- |
| Y.935 | Cl | 2 | 3-pyridyl- |
| Y.936 | Cl | 2 | 4-(trifluoromethoxy)phenyl- |
| Y.937 | Cl | 2 | 4,5-dihydrothiazol-2-yl- |
| Y.938 | Cl | 2 | 4,5-dimethyl-4,5-dihydrothiazol-2-yl- |
| Y.939 | Cl | 2 | 4,5-dimethyl-thiazol-2-yl- |
| Y.940 | Cl | 2 | 4-bromphenyl- |
| Y.941 | Cl | 2 | 4-chlorophenyl- |
| Y.942 | Cl | 2 | 4-ethylphenyl- |
| Y.943 | Cl | 2 | 4-fluoro-phenyl- |
| Y.944 | Cl | 2 | 4H-1,2,4-triazol-3-yl- |
| Y.945 | Cl | 2 | 4-methoxyphenyl- |
| Y.946 | Cl | 2 | 4-methyl-4,5-dihydrothiazol-2-yl- |
| Y.947 | Cl | 2 | 4-methylphenyl- |
| Y.948 | Cl | 2 | 4-methylpyrid-2-yl |
| Y.949 | Cl | 2 | 4-nitrophenyl- |
| Y.950 | Cl | 2 | 4-pyridyl- |
| Y.951 | Cl | 2 | 5-methyl-4,5-dihydrothiazol-2-yl- |
| Y.952 | Cl | 2 | 5-methyl-thiazol-2-yl- |
| Y.953 | Cl | 2 | 6-methylpyrid-2-yl- |
| Y.954 | Cl | 2 | allyl- |
| Y.955 | Cl | 2 | but-2-ynyl- |
| Y.956 | Cl | 2 | but-3-ynyl- |
| Y.957 | Cl | 2 | cis-1-oxo-thietan-3-yl- |
| Y.958 | Cl | 2 | cis-1-oxo-thietan-3-ylmethyl- |
| Y.959 | Cl | 2 | cyanodimethylmethyl- |
| Y.960 | Cl | 2 | cyanoethyl- |
| Y.961 | Cl | 2 | cyanomethyl- |
| Y.962 | Cl | 2 | cyclopentyl- |
| Y.963 | Cl | 2 | cyclopropyl-methyl- |
| Y.964 | Cl | 2 | methylpropargyl- |
| Y.965 | Cl | 2 | oxetan-3-yl- |
| Y.966 | Cl | 2 | pent-3-yl- |
| Y.967 | Cl | 2 | phenyl-methyl-methyl- |
| Y.968 | Cl | 2 | propargyl- |
| Y.969 | Cl | 2 | tert-butyl- |
| Y.970 | Cl | 2 | tetrazolyl- |
| Y.971 | Cl | 2 | thiazol-2-yl- |
| Y.972 | Cl | 2 | thiazol-4-yl- |
| Y.973 | Cl | 2 | thietan-2-ylmethyl- |
| Y.974 | Cl | 2 | thietan-3-ylmethyl- |
| Y.975 | Cl | 2 | ethyl- |
| Y.976 | Cl | 2 | 3,3,3-trifluoro-propyl- |
| Y.977 | Cl | 2 | but-2-yl- |
| Y.978 | Cl | 2 | (tetrahydrofuran-2-yl)-methyl- |
| Y.979 | Cl | 2 | benzyl- |
| Y.980 | Cl | 2 | (2-fluoro-phenyl)-methyl- |
| Y.981 | Cl | 2 | 1-phenyl-eth-1-yl- |
| Y.982 | Cl | 2 | (4-methoxy-phenyl)-methyl- |
| Y.983 | Cl | 2 | 1,1-dioxo-thietan-3-yl- |
| Y.984 | Cl | 2 | (2-chloro-pyrid-5-yl)-methyl- |
| Y.985 | Cl | 2 | 3-fluoro-phenyl- |
| Y.986 | Cl | 2 | n-butyl- |
| Y.987 | Cl | 2 | (pyrid-2-yl)-methyl- |
| Y.988 | Cl | 2 | 1,3-dimethyl-1H-pyrazol-5-yl- |
| Y.989 | Cl | 2 | 4-methyl-thiazol-2-yl- |
| Y.990 | Cl | 2 | 3-methyl-thietan-3-yl- |
| Y.991 | Cl | 2 | 1,1-dimethyl-2-methylsulfanyl-ethyl |
| Y.992 | Cl | 2 | 1-oxo-thietan-3-yl- |
| Y.993 | Cl | 2 | thietan-3-yl- |
| Y.994 | Cl | 2 | bicyclo[2.2.1]hept-2-yl- |
| Y.995 | Cl | 2 | cyclobutyl- |
| Y.996 | Cl | 2 | methyl- |
| Y.997 | Cl | 2 | cyclopropyl- |
| Y.998 | Cl | 2 | n-propyl- |
| Y.999 | Cl | 2 | 2,2-difluoroethyl- |
| Y.1000 | Cl | 2 | 1-methoxy-prop-2-yl- |
| Y.1001 | Cl | 2 | N-(2,2,2-trifluoro-ethyl)-acetamide-2-yl |
| Y.1002 | Cl | 2 | 2,2,2-trifluoro-ethyl- |
| Y.1003 | Br | 0 | (1,1-dioxothietan-2-yl)methyl- |
| Y.1004 | Br | 0 | (1-oxothietan-2-yl)methyl- |
| Y.1005 | Br | 0 | (2-methoxy-phenyl)-methyl- |
| Y.1006 | Br | 0 | (3-fluoro-phenyl)-methyl- |
| Y.1007 | Br | 0 | (4,4-dimethyl-4,5-dihydrothiazol-2-yl)-methyl- |
| Y.1008 | Br | 0 | (4,5-dihydrothiazol-2-yl)-methyl- |
| Y.1009 | Br | 0 | (4,5-dimethyl-4,5-dihydrothiazol-2-yl)-methyl- |
| Y.1010 | Br | 0 | (4-fluoro-phenyl)-methyl- |
| Y.1011 | Br | 0 | (4-methyl-4,5-dihydrothiazol-2-yl)-methyl- |
| Y.1012 | Br | 0 | (5-methyl-4,5-dihydrothiazol-2-yl)-methyl- |
| Y.1013 | Br | 0 | (pyrid-3-yl)-methyl- |
| Y.1014 | Br | 0 | (pyrid-4-yl)-methyl- |
| Y.1015 | Br | 0 | (tetrahydrothiophene-2-yl)-methyl- |
| Y.1016 | Br | 0 | (tetrahydrothiophene-3-yl)-methyl- |
| Y.1017 | Br | 0 | (thiazol-2-yl)-methyl- |
| Y.1018 | Br | 0 | (thiazol-2-yl)-methylmethyl- |
| Y.1019 | Br | 0 | (thiazol-4-yl)-methyl- |
| Y.1020 | Br | 0 | (thiazol-5-yl)-methyl- |
| Y.1021 | Br | 0 | 1,1-dioxo-thietan-3-ylmethyl- |
| Y.1022 | Br | 0 | 1-cyanocyclobutyl- |
| Y.1023 | Br | 0 | 1-cyanocyclopentyl- |
| Y.1024 | Br | 0 | 1-cyanocyclopropyl- |
| Y.1025 | Br | 0 | 1-fluoroprop-2-yl- |
| Y.1026 | Br | 0 | 1-methylallyl- |
| Y.1027 | Br | 0 | 1-methylsulfanyl-prop-2-yl- |
| Y.1028 | Br | 0 | 2-(1,1-dioxothietan-3-yl)ethanyl- |
| Y.1029 | Br | 0 | 2-(1-oxothietan-3-yl)ethanyl- |
| Y.1030 | Br | 0 | 2-(thietan-3-yl)ethanyl- |
| Y.1031 | Br | 0 | 2-(trifluoromethoxy)phenyl- |
| Y.1032 | Br | 0 | 2,2-dimethyl-1,1-dioxo-thietan-3-yl- |
| Y.1033 | Br | 0 | 2,2-dimethyl-1-oxo-thietan-3-yl- |
| Y.1034 | Br | 0 | 2,2-dimethylthietan-3-yl- |
| Y.1035 | Br | 0 | 2,3-dichlorophenyl- |
| Y.1036 | Br | 0 | 2,3-difluoro-phenyl- |
| Y.1037 | Br | 0 | 2,4-dichlorophenyl- |
| Y.1038 | Br | 0 | 2,4-difluoro-phenyl- |
| Y.1039 | Br | 0 | 2,4-dimethylphenyl- |
| Y.1040 | Br | 0 | 2,5-dichlorophenyl- |
| Y.1041 | Br | 0 | 2,5-difluoro-phenyl- |
| Y.1042 | Br | 0 | 2,6-dichlorophenyl- |
| Y.1043 | Br | 0 | 2,6-difluoro-phenyl- |
| Y.1044 | Br | 0 | 2,6-diisopropylphenyl- |
| Y.1045 | Br | 0 | 2-bromo-4-fluorophenyl- |
| Y.1046 | Br | 0 | 2-bromoallyl- |
| Y.1047 | Br | 0 | 2-bromophenyl- |
| Y.1048 | Br | 0 | 2-butenyl- |
| Y.1049 | Br | 0 | 2-chloroallyl- |
| Y.1050 | Br | 0 | 2-chlorophenyl- |
| Y.1051 | Br | 0 | 2-chloropyrid-2-yl- |
| Y.1052 | Br | 0 | 2-chloropyrid-3-yl- |
| Y.1053 | Br | 0 | 2-cyanocyclopropyl- |
| Y.1054 | Br | 0 | 2-cyanoethyl- |
| Y.1055 | Br | 0 | 2-ethylphenyl- |
| Y.1056 | Br | 0 | 2-fluoroethyl- |
| Y.1057 | Br | 0 | 2-fluoro-phenyl- |
| Y.1058 | Br | 0 | 2-fluoropropyl- |
| Y.1059 | Br | 0 | 2-furylmethyl- |
| Y.1060 | Br | 0 | 2-hydroxyphenyl- |
| Y.1061 | Br | 0 | 2-methoxy-ethyl- |

TABLE Y-continued

| | R5b | n | R2 |
|---|---|---|---|
| Y.1062 | Br | 0 | 2-methoxyphenyl- |
| Y.1063 | Br | 0 | 2-methoxy-prop-3-yl- |
| Y.1064 | Br | 0 | 2-methylallyl- |
| Y.1065 | Br | 0 | 2-methyl-but-1-yl- |
| Y.1066 | Br | 0 | 2-methyl-but-2-yl- |
| Y.1067 | Br | 0 | 2-methylbut-3-yn-2-yl- |
| Y.1068 | Br | 0 | 2-methylphenyl- |
| Y.1069 | Br | 0 | 2-methyl-prop-1-yl- |
| Y.1070 | Br | 0 | 2-methylsulfanyl-ethyl- |
| Y.1071 | Br | 0 | 2-methylsulfanyl-prop-3-yl- |
| Y.1072 | Br | 0 | 2-methyl-thiazol-4-yl- |
| Y.1073 | Br | 0 | 2-nitrophenyl- |
| Y.1074 | Br | 0 | 2-propyl- |
| Y.1075 | Br | 0 | 2-pyridyl- |
| Y.1076 | Br | 0 | 2-trifluoromethoxy-ethyl- |
| Y.1077 | Br | 0 | 3-(trifluoromethoxy)phenyl- |
| Y.1078 | Br | 0 | 3,3,3-trifluoro-2,2-difluoropropyl- |
| Y.1079 | Br | 0 | 3,3,3-trifluoro-butyl- |
| Y.1080 | Br | 0 | 3,3-dibromoallyl- |
| Y.1081 | Br | 0 | 3,3-dichloroallyl- |
| Y.1082 | Br | 0 | 3,4-dichlorophenyl- |
| Y.1083 | Br | 0 | 3,4-difluoro-phenyl- |
| Y.1084 | Br | 0 | 3,5-dichlorophenyl- |
| Y.1085 | Br | 0 | 3,5-difluoro-phenyl- |
| Y.1086 | Br | 0 | 3,6-difluoro-phenyl- |
| Y.1087 | Br | 0 | 3-bromoallyl- |
| Y.1088 | Br | 0 | 3-bromophenyl- |
| Y.1089 | Br | 0 | 3-butenyl- |
| Y.1090 | Br | 0 | 3-chloroallyl- |
| Y.1091 | Br | 0 | 3-chlorophenyl- |
| Y.1092 | Br | 0 | 3-chloropyrid-2-yl- |
| Y.1093 | Br | 0 | 3-cyanopropyl- |
| Y.1094 | Br | 0 | 3-ethylphenyl- |
| Y.1095 | Br | 0 | 3-hydroxyphenyl- |
| Y.1096 | Br | 0 | 3-methyl-1,1-dioxo-thietan-3-yl- |
| Y.1097 | Br | 0 | 3-methyl-1-oxo-thietan-3-yl- |
| Y.1098 | Br | 0 | 3-methyl-but-1-yl- |
| Y.1099 | Br | 0 | 3-methyl-but-2-yl- |
| Y.1100 | Br | 0 | 3-methylphenyl- |
| Y.1101 | Br | 0 | 3-nitrophenyl- |
| Y.1102 | Br | 0 | 3-pyridyl- |
| Y.1103 | Br | 0 | 4-(trifluoromethoxy)phenyl- |
| Y.1104 | Br | 0 | 4,5-dihydrothiazol-2-yl- |
| Y.1105 | Br | 0 | 4,5-dimethyl-4,5-dihydrothiazol-2-yl- |
| Y.1106 | Br | 0 | 4,5-dimethyl-thiazol-2-yl- |
| Y.1107 | Br | 0 | 4-bromophenyl- |
| Y.1108 | Br | 0 | 4-chlorophenyl- |
| Y.1109 | Br | 0 | 4-ethylphenyl- |
| Y.1110 | Br | 0 | 4-fluoro-phenyl- |
| Y.1111 | Br | 0 | 4H-1,2,4-triazol-3-yl- |
| Y.1112 | Br | 0 | 4-methoxyphenyl- |
| Y.1113 | Br | 0 | 4-methyl-4,5-dihydrothiazol-2-yl- |
| Y.1114 | Br | 0 | 4-methylphenyl- |
| Y.1115 | Br | 0 | 4-methylpyrid-2-yl |
| Y.1116 | Br | 0 | 4-nitrophenyl- |
| Y.1117 | Br | 0 | 4-pyridyl- |
| Y.1118 | Br | 0 | 5-methyl-4,5-dihydrothiazol-2-yl- |
| Y.1119 | Br | 0 | 5-methyl-thiazol-2-yl- |
| Y.1120 | Br | 0 | 6-methylpyrid-2-yl- |
| Y.1121 | Br | 0 | allyl- |
| Y.1122 | Br | 0 | but-2-ynyl- |
| Y.1123 | Br | 0 | but-3-ynyl- |
| Y.1124 | Br | 0 | cis-1-oxo-thietan-3-yl- |
| Y.1125 | Br | 0 | cis-1-oxo-thietan-3-ylmethyl- |
| Y.1126 | Br | 0 | cyanodimethylmethyl- |
| Y.1127 | Br | 0 | cyanoethyl- |
| Y.1128 | Br | 0 | cyanomethyl- |
| Y.1129 | Br | 0 | cyclopentyl- |
| Y.1130 | Br | 0 | cyclopropyl-methyl- |
| Y.1131 | Br | 0 | methylpropargyl- |
| Y.1132 | Br | 0 | oxetan-3-yl- |
| Y.1133 | Br | 0 | pent-3-yl- |
| Y.1134 | Br | 0 | phenyl-methyl-methyl- |
| Y.1135 | Br | 0 | propargyl- |
| Y.1136 | Br | 0 | tert-butyl- |
| Y.1137 | Br | 0 | tetrazolyl- |
| Y.1138 | Br | 0 | thiazol-2-yl- |
| Y.1139 | Br | 0 | thiazol-4-yl- |
| Y.1140 | Br | 0 | thietan-2-ylmethyl- |
| Y.1141 | Br | 0 | thietan-3-ylmethyl- |
| Y.1142 | Br | 0 | ethyl- |
| Y.1143 | Br | 0 | 3,3,3-trifluoro-propyl- |
| Y.1144 | Br | 0 | but-2-yl- |
| Y.1145 | Br | 0 | (tetrahydrofuran-2-yl)-methyl- |
| Y.1146 | Br | 0 | benzyl- |
| Y.1147 | Br | 0 | (2-fluoro-phenyl)-methyl- |
| Y.1148 | Br | 0 | 1-phenyl-eth-1-yl- |
| Y.1149 | Br | 0 | (4-methoxy-phenyl)-methyl- |
| Y.1150 | Br | 0 | 1,1-dioxo-thietan-3-yl- |
| Y.1151 | Br | 0 | (2-chloro-pyrid-5-yl)-methyl- |
| Y.1152 | Br | 0 | 3-fluoro-phenyl- |
| Y.1153 | Br | 0 | n-butyl- |
| Y.1154 | Br | 0 | (pyrid-2-yl)-methyl- |
| Y.1155 | Br | 0 | 1,3-dimethyl-1H-pyrazol-5-yl- |
| Y.1156 | Br | 0 | 4-methyl-thiazol-2-yl- |
| Y.1157 | Br | 0 | 3-methyl-thietan-3-yl- |
| Y.1158 | Br | 0 | 1,1-dimethyl-2-methylsulfanyl-ethyl |
| Y.1159 | Br | 0 | 1-oxo-thietan-3-yl- |
| Y.1160 | Br | 0 | thietan-3-yl- |
| Y.1161 | Br | 0 | bicyclo[2.2.1]hept-2-yl- |
| Y.1162 | Br | 0 | cyclobutyl- |
| Y.1163 | Br | 0 | methyl- |
| Y.1164 | Br | 0 | cyclopropyl- |
| Y.1165 | Br | 0 | n-propyl- |
| Y.1166 | Br | 0 | 2,2-difluoroethyl- |
| Y.1167 | Br | 0 | 1-methoxy-prop-2-yl- |
| Y.1168 | Br | 0 | N-(2,2,2-trifluoro-ethyl)-acetamide-2-yl |
| Y.1169 | Br | 0 | 2,2,2-trifluoro-ethyl- |
| Y.1170 | Br | 1 | (1,1-dioxothietan-2-yl)methyl- |
| Y.1171 | Br | 1 | (1-oxothietan-2-yl)methyl- |
| Y.1172 | Br | 1 | (2-methoxy-phenyl)-methyl- |
| Y.1173 | Br | 1 | (3-fluoro-phenyl)-methyl- |
| Y.1174 | Br | 1 | (4,4-dimethyl-4,5-dihydrothiazol-2-yl)-methyl- |
| Y.1175 | Br | 1 | (4,5-dihydrothiazol-2-yl)-methyl- |
| Y.1176 | Br | 1 | (4,5-dimethyl-4,5-dihydrothiazol-2-yl)-methyl- |
| Y.1177 | Br | 1 | (4-fluoro-phenyl)-methyl- |
| Y.1178 | Br | 1 | (4-methyl-4,5-dihydrothiazol-2-yl)-methyl- |
| Y.1179 | Br | 1 | (5-methyl-4,5-dihydrothiazol-2-yl)-methyl- |
| Y.1180 | Br | 1 | (pyrid-3-yl)-methyl- |
| Y.1181 | Br | 1 | (pyrid-4-yl)-methyl- |
| Y.1182 | Br | 1 | (tetrahydrothiophene-2-yl)-methyl- |
| Y.1183 | Br | 1 | (tetrahydrothiophene-3-yl)-methyl- |
| Y.1184 | Br | 1 | (thiazol-2-yl)-methyl- |
| Y.1185 | Br | 1 | (thiazol-2-yl)-methylmethyl- |
| Y.1186 | Br | 1 | (thiazol-4-yl)-methyl- |
| Y.1187 | Br | 1 | (thiazol-5-yl)-methyl- |
| Y.1188 | Br | 1 | 1,1-dioxo-thietan-3-ylmethyl- |
| Y.1189 | Br | 1 | 1-cyanocyclobutyl- |
| Y.1190 | Br | 1 | 1-cyanocyclopentyl- |
| Y.1191 | Br | 1 | 1-cyanocyclopropyl- |
| Y.1192 | Br | 1 | 1-fluoroprop-2-yl- |
| Y.1193 | Br | 1 | 1-methylallyl- |
| Y.1194 | Br | 1 | 1-methylsulfanyl-prop-2-yl- |
| Y.1195 | Br | 1 | 2-(1,1-dioxothietan-3-yl)ethanyl- |
| Y.1196 | Br | 1 | 2-(1-oxothietan-3-yl)ethanyl- |
| Y.1197 | Br | 1 | 2-(thietan-3-yl)ethanyl- |
| Y.1198 | Br | 1 | 2-(trifluoromethoxy)phenyl- |
| Y.1199 | Br | 1 | 2,2-dimethyl-1,1-dioxo-thietan-3-yl- |
| Y.1200 | Br | 1 | 2,2-dimethyl-1-oxo-thietan-3-yl- |
| Y.1201 | Br | 1 | 2,2-dimethylthietan-3-yl- |
| Y.1202 | Br | 1 | 2,3-dichlorophenyl- |
| Y.1203 | Br | 1 | 2,3-difluoro-phenyl- |
| Y.1204 | Br | 1 | 2,4-dichlorophenyl- |
| Y.1205 | Br | 1 | 2,4-difluoro-phenyl- |
| Y.1206 | Br | 1 | 2,4-dimethylphenyl- |
| Y.1207 | Br | 1 | 2,5-dichlorophenyl- |
| Y.1208 | Br | 1 | 2,5-difluoro-phenyl- |
| Y.1209 | Br | 1 | 2,6-dichlorophenyl- |
| Y.1210 | Br | 1 | 2,6-difluoro-phenyl- |
| Y.1211 | Br | 1 | 2,6-diisopropylphenyl- |
| Y.1212 | Br | 1 | 2-bromo-4-fluorophenyl- |
| Y.1213 | Br | 1 | 2-bromoallyl- |

TABLE Y-continued

| | R5b | n | R2 |
|---|---|---|---|
| Y.1214 | Br | 1 | 2-bromophenyl- |
| Y.1215 | Br | 1 | 2-butenyl- |
| Y.1216 | Br | 1 | 2-chloroallyl- |
| Y.1217 | Br | 1 | 2-chlorophenyl- |
| Y.1218 | Br | 1 | 2-chloropyrid-2-yl- |
| Y.1219 | Br | 1 | 2-chloropyrid-3-yl- |
| Y.1220 | Br | 1 | 2-cyanocyclopropyl- |
| Y.1221 | Br | 1 | 2-cyanoethyl- |
| Y.1222 | Br | 1 | 2-ethylphenyl- |
| Y.1223 | Br | 1 | 2-fluoroethyl- |
| Y.1224 | Br | 1 | 2-fluoro-phenyl- |
| Y.1225 | Br | 1 | 2-fluoropropyl- |
| Y.1226 | Br | 1 | 2-furylmethyl- |
| Y.1227 | Br | 1 | 2-hydroxyphenyl- |
| Y.1228 | Br | 1 | 2-methoxy-ethyl- |
| Y.1229 | Br | 1 | 2-methoxyphenyl- |
| Y.1230 | Br | 1 | 2-methoxy-prop-3-yl- |
| Y.1231 | Br | 1 | 2-methylallyl- |
| Y.1232 | Br | 1 | 2-methyl-but-1-yl- |
| Y.1233 | Br | 1 | 2-methyl-but-2-yl- |
| Y.1234 | Br | 1 | 2-methylbut-3-yn-2-yl- |
| Y.1235 | Br | 1 | 2-methylphenyl- |
| Y.1236 | Br | 1 | 2-methyl-prop-1-yl- |
| Y.1237 | Br | 1 | 2-methylsulfanyl-ethyl- |
| Y.1238 | Br | 1 | 2-methylsulfanyl-prop-3-yl- |
| Y.1239 | Br | 1 | 2-methyl-thiazol-4-yl- |
| Y.1240 | Br | 1 | 2-nitrophenyl- |
| Y.1241 | Br | 1 | 2-propyl- |
| Y.1242 | Br | 1 | 2-pyridyl- |
| Y.1243 | Br | 1 | 2-trifluoromethoxy-ethyl- |
| Y.1244 | Br | 1 | 3-(trifluoromethoxy)phenyl- |
| Y.1245 | Br | 1 | 3,3,3-trifluoro-2,2-difluoropropyl- |
| Y.1246 | Br | 1 | 3,3,3-trifluoro-butyl- |
| Y.1247 | Br | 1 | 3,3-dibromoallyl- |
| Y.1248 | Br | 1 | 3,3-dichloroallyl- |
| Y.1249 | Br | 1 | 3,4-dichlorophenyl- |
| Y.1250 | Br | 1 | 3,4-difluoro-phenyl- |
| Y.1251 | Br | 1 | 3,5-dichlorphenyl- |
| Y.1252 | Br | 1 | 3,5-difluoro-phenyl- |
| Y.1253 | Br | 1 | 3,6-difluoro-phenyl- |
| Y.1254 | Br | 1 | 3-bromoallyl- |
| Y.1255 | Br | 1 | 3-bromophenyl- |
| Y.1256 | Br | 1 | 3-butenyl- |
| Y.1257 | Br | 1 | 3-chloroallyl- |
| Y.1258 | Br | 1 | 3-chlorophenyl- |
| Y.1259 | Br | 1 | 3-chloropyrid-2-yl- |
| Y.1260 | Br | 1 | 3-cyanopropyl- |
| Y.1261 | Br | 1 | 3-ethylphenyl- |
| Y.1262 | Br | 1 | 3-hydroxyphenyl- |
| Y.1263 | Br | 1 | 3-methyl-1,1-dioxo-thietan-3-yl- |
| Y.1264 | Br | 1 | 3-methyl-1-oxo-thietan-3-yl- |
| Y.1265 | Br | 1 | 3-methyl-but-1-yl- |
| Y.1266 | Br | 1 | 3-methyl-but-2-yl- |
| Y.1267 | Br | 1 | 3-methylphenyl- |
| Y.1268 | Br | 1 | 3-nitrophenyl- |
| Y.1269 | Br | 1 | 3-pyridyl- |
| Y.1270 | Br | 1 | 4-(trifluoromethoxy)phenyl- |
| Y.1271 | Br | 1 | 4,5-dihydrothiazol-2-yl- |
| Y.1272 | Br | 1 | 4,5-dimethyl-4,5-dihydrothiazol-2-yl- |
| Y.1273 | Br | 1 | 4,5-dimethyl-thiazol-2-yl- |
| Y.1274 | Br | 1 | 4-bromophenyl- |
| Y.1275 | Br | 1 | 4-chlorophenyl- |
| Y.1276 | Br | 1 | 4-ethylphenyl- |
| Y.1277 | Br | 1 | 4-fluoro-phenyl- |
| Y.1278 | Br | 1 | 4H-1,2,4-triazol-3-yl |
| Y.1279 | Br | 1 | 4-methoxyphenyl- |
| Y.1280 | Br | 1 | 4-methyl-4,5-dihydrothiazol-2-yl- |
| Y.1281 | Br | 1 | 4-methylphenyl- |
| Y.1282 | Br | 1 | 4-methylpyrid-2-yl |
| Y.1283 | Br | 1 | 4-nitrophenyl- |
| Y.1284 | Br | 1 | 4-pyridyl- |
| Y.1285 | Br | 1 | 5-methyl-4,5-dihydrothiazol-2-yl- |
| Y.1286 | Br | 1 | 5-methyl-thiazol-2-yl- |
| Y.1287 | Br | 1 | 6-methylpyrid-2-yl- |
| Y.1288 | Br | 1 | allyl- |
| Y.1289 | Br | 1 | but-2-ynyl- |
| Y.1290 | Br | 1 | but-3-ynyl- |
| Y.1291 | Br | 1 | cis-1-oxo-thietan-3-yl- |
| Y.1292 | Br | 1 | cis-1-oxo-thietan-3-ylmethyl- |
| Y.1293 | Br | 1 | cyanodimethylmethyl- |
| Y.1294 | Br | 1 | cyanoethyl- |
| Y.1295 | Br | 1 | cyanomethyl- |
| Y.1296 | Br | 1 | cyclopentyl- |
| Y.1297 | Br | 1 | cyclopropyl-methyl- |
| Y.1298 | Br | 1 | methylpropargyl- |
| Y.1299 | Br | 1 | oxetan-3-yl- |
| Y.1300 | Br | 1 | pent-3-yl- |
| Y.1301 | Br | 1 | phenyl-methyl-methyl- |
| Y.1302 | Br | 1 | propargyl- |
| Y.1303 | Br | 1 | tert-butyl- |
| Y.1304 | Br | 1 | tetrazolyl- |
| Y.1305 | Br | 1 | thiazol-2-yl- |
| Y.1306 | Br | 1 | thiazol-4-yl- |
| Y.1307 | Br | 1 | thietan-2-ylmethyl- |
| Y.1308 | Br | 1 | thietan-3-ylmethyl- |
| Y.1309 | Br | 1 | ethyl- |
| Y.1310 | Br | 1 | 3,3,3-trifluoro-propyl- |
| Y.1311 | Br | 1 | but-2-yl- |
| Y.1312 | Br | 1 | (tetrahydrofuran-2-yl)-methyl- |
| Y.1313 | Br | 1 | benzyl- |
| Y.1314 | Br | 1 | (2-fluoro-phenyl)-methyl- |
| Y.1315 | Br | 1 | 1-phenyl-eth-1-yl- |
| Y.1316 | Br | 1 | (4-methoxy-phenyl)-methyl- |
| Y.1317 | Br | 1 | 1,1-dioxo-thietan-3-yl- |
| Y.1318 | Br | 1 | (2-chloro-pyrid-5-yl)-methyl- |
| Y.1319 | Br | 1 | 3-fluoro-phenyl- |
| Y.1320 | Br | 1 | n-butyl- |
| Y.1321 | Br | 1 | (pyrid-2-yl)-methyl- |
| Y.1322 | Br | 1 | 1,3-dimethyl-1H-pyrazol-5-yl- |
| Y.1323 | Br | 1 | 4-methyl-thiazol-2-yl- |
| Y.1324 | Br | 1 | 3-methyl-thietan-3-yl- |
| Y.1325 | Br | 1 | 1,1-dimethyl-2-methylsulfanyl-ethyl |
| Y.1326 | Br | 1 | 1-oxo-thietan-3-yl- |
| Y.1327 | Br | 1 | thietan-3-yl- |
| Y.1328 | Br | 1 | bicyclo[2.2.1]hept-2-yl- |
| Y.1329 | Br | 1 | cyclobutyl- |
| Y.1330 | Br | 1 | methyl- |
| Y.1331 | Br | 1 | cyclopropyl- |
| Y.1332 | Br | 1 | n-propyl- |
| Y.1333 | Br | 1 | 2,2-difluoroethyl- |
| Y.1334 | Br | 1 | 1-methoxy-prop-2-yl- |
| Y.1335 | Br | 1 | N-(2,2,2-trifluoro-ethyl)-acetamide-2-yl |
| Y.1336 | Br | 1 | 2,2,2-trifluoro-ethyl- |
| Y.1337 | Br | 2 | (1,1-dioxothietan-2-yl)methyl- |
| Y.1338 | Br | 2 | (1-oxothietan-2-yl)methyl- |
| Y.1339 | Br | 2 | (2-methoxy-phenyl)-methyl- |
| Y.1340 | Br | 2 | (3-fluoro-phenyl)-methyl- |
| Y.1341 | Br | 2 | (4,4-dimethyl-4,5-dihydrothiazol-2-yl)-methyl- |
| Y.1342 | Br | 2 | (4,5-dihydrothiazol-2-yl)-methyl- |
| Y.1343 | Br | 2 | (4,5-dimethyl-4,5-dihydrothiazol-2-yl)-methyl- |
| Y.1344 | Br | 2 | (4-fluoro-phenyl)-methyl- |
| Y.1345 | Br | 2 | (4-methyl-4,5-dihydrothiazol-2-yl)-methyl- |
| Y.1346 | Br | 2 | (5-methyl-4,5-dihydrothiazol-2-yl)-methyl- |
| Y.1347 | Br | 2 | (pyrid-3-yl)-methyl- |
| Y.1348 | Br | 2 | (pyrid-4-yl)-methyl- |
| Y.1349 | Br | 2 | (tetrahydrothiophene-2-yl)-methyl- |
| Y.1350 | Br | 2 | (tetrahydrothiophene-3-yl)-methyl- |
| Y.1351 | Br | 2 | (thiazol-2-yl)-methyl- |
| Y.1352 | Br | 2 | (thiazol-2-yl)-methylmethyl- |
| Y.1353 | Br | 2 | (thiazol-4-yl)-methyl- |
| Y.1354 | Br | 2 | (thiazol-5-yl)-methyl- |
| Y.1355 | Br | 2 | 1,1-dioxo-thietan-3-ylmethyl- |
| Y.1356 | Br | 2 | 1-cyanocyclobutyl- |
| Y.1357 | Br | 2 | 1-cyanocyclopentyl- |
| Y.1358 | Br | 2 | 1-cyanocyclopropyl- |
| Y.1359 | Br | 2 | 1-fluoroprop-2-yl- |
| Y.1360 | Br | 2 | 1-methylallyl- |
| Y.1361 | Br | 2 | 1-methylsulfanyl-prop-2-yl- |
| Y.1362 | Br | 2 | 2-(1,1-dioxothietan-3-yl)ethanyl- |
| Y.1363 | Br | 2 | 2-(1-oxothietan-3-yl)ethanyl- |
| Y.1364 | Br | 2 | 2-(thietan-3-yl)ethanyl- |
| Y.1365 | Br | 2 | 2-(trifluoromethoxy)phenyl- |

TABLE Y-continued

| R5b | n | R2 |
|---|---|---|
| Y.1366 | Br | 2 | 2,2-dimethyl-1,1-dioxo-thietan-3-yl- |
| Y.1367 | Br | 2 | 2,2-dimethyl-1-oxo-thietan-3-yl- |
| Y.1368 | Br | 2 | 2,2-dimethylthietan-3-yl- |
| Y.1369 | Br | 2 | 2,3-dichlorophenyl- |
| Y.1370 | Br | 2 | 2,3-difluoro-phenyl- |
| Y.1371 | Br | 2 | 2,4-dichlorophenyl- |
| Y.1372 | Br | 2 | 2,4-difluoro-phenyl- |
| Y.1373 | Br | 2 | 2,4-dimethylphenyl- |
| Y.1374 | Br | 2 | 2,5-dichlorophenyl- |
| Y.1375 | Br | 2 | 2,5-difluoro-phenyl- |
| Y.1376 | Br | 2 | 2,6-dichlorophenyl- |
| Y.1377 | Br | 2 | 2,6-difluoro-phenyl- |
| Y.1378 | Br | 2 | 2,6-diisopropylphenyl- |
| Y.1379 | Br | 2 | 2-bromo-4-fluorophenyl- |
| Y.1380 | Br | 2 | 2-bromoallyl- |
| Y.1381 | Br | 2 | 2-bromophenyl- |
| Y.1382 | Br | 2 | 2-butenyl- |
| Y.1383 | Br | 2 | 2-chloroallyl- |
| Y.1384 | Br | 2 | 2-chlorophenyl- |
| Y.1385 | Br | 2 | 2-chloropyrid-2-yl- |
| Y.1386 | Br | 2 | 2-chloropyrid-3-yl- |
| Y.1387 | Br | 2 | 2-cyanocyclopropyl- |
| Y.1388 | Br | 2 | 2-cyanoethyl- |
| Y.1389 | Br | 2 | 2-ethylphenyl- |
| Y.1390 | Br | 2 | 2-fluoroethyl- |
| Y.1391 | Br | 2 | 2-fluoro-phenyl- |
| Y.1392 | Br | 2 | 2-fluoropropyl- |
| Y.1393 | Br | 2 | 2-furylmethyl- |
| Y.1394 | Br | 2 | 2-hydroxyphenyl- |
| Y.1395 | Br | 2 | 2-methoxy-ethyl- |
| Y.1396 | Br | 2 | 2-methoxyphenyl- |
| Y.1397 | Br | 2 | 2-methoxy-prop-3-yl- |
| Y.1398 | Br | 2 | 2-methylallyl- |
| Y.1399 | Br | 2 | 2-methyl-but-1-yl- |
| Y.1400 | Br | 2 | 2-methyl-but-2-yl- |
| Y.1401 | Br | 2 | 2-methylbut-3-yn-2-yl- |
| Y.1402 | Br | 2 | 2-methylphenyl- |
| Y.1403 | Br | 2 | 2-methyl-prop-1-yl- |
| Y.1404 | Br | 2 | 2-methylsulfanyl-ethyl- |
| Y.1405 | Br | 2 | 2-methylsulfanyl-prop-3-yl- |
| Y.1406 | Br | 2 | 2-methyl-thiazol-4-yl- |
| Y.1407 | Br | 2 | 2-nitrophenyl- |
| Y.1408 | Br | 2 | 2-propyl- |
| Y.1409 | Br | 2 | 2-pyridyl- |
| Y.1410 | Br | 2 | 2-trifluoromethoxy-ethyl- |
| Y.1411 | Br | 2 | 3-(trifluoromethoxy)phenyl- |
| Y.1412 | Br | 2 | 3,3,3-trifluoro-2,2-difluoropropyl- |
| Y.1413 | Br | 2 | 3,3,3-trifluoro-butyl- |
| Y.1414 | Br | 2 | 3,3-dibromoallyl- |
| Y.1415 | Br | 2 | 3,3-dichloroallyl- |
| Y.1416 | Br | 2 | 3,4-dichlorophenyl- |
| Y.1417 | Br | 2 | 3,4-difluoro-phenyl- |
| Y.1418 | Br | 2 | 3,5-dichlorophenyl- |
| Y.1419 | Br | 2 | 3,5-difluoro-phenyl- |
| Y.1420 | Br | 2 | 3,6-difluoro-phenyl- |
| Y.1421 | Br | 2 | 3-bromoallyl- |
| Y.1422 | Br | 2 | 3-bromophenyl- |
| Y.1423 | Br | 2 | 3-butenyl- |
| Y.1424 | Br | 2 | 3-chloroallyl- |
| Y.1425 | Br | 2 | 3-chlorophenyl- |
| Y.1426 | Br | 2 | 3-chloropyrid-2-yl- |
| Y.1427 | Br | 2 | 3-cyanopropyl- |
| Y.1428 | Br | 2 | 3-ethylphenyl- |
| Y.1429 | Br | 2 | 3-hydroxyphenyl- |
| Y.1430 | Br | 2 | 3-methyl-1,1-dioxo-thietan-3-yl- |
| Y.1431 | Br | 2 | 3-methyl-1-oxo-thietan-3-yl- |
| Y.1432 | Br | 2 | 3-methyl-but-1-yl- |
| Y.1433 | Br | 2 | 3-methyl-but-2-yl- |
| Y.1434 | Br | 2 | 3-methylphenyl- |
| Y.1435 | Br | 2 | 3-nitrophenyl- |
| Y.1436 | Br | 2 | 3-pyridyl- |
| Y.1437 | Br | 2 | 4-(trifluoromethoxy)phenyl- |
| Y.1438 | Br | 2 | 4,5-dihydrothiazol-2-yl- |
| Y.1439 | Br | 2 | 4,5-dimethyl-4,5-dihydrothiazol-2-yl- |
| Y.1440 | Br | 2 | 4,5-dimethyl-thiazol-2-yl- |
| Y.1441 | Br | 2 | 4-bromophenyl- |
| Y.1442 | Br | 2 | 4-chlorophenyl- |
| Y.1443 | Br | 2 | 4-ethylphenyl- |
| Y.1444 | Br | 2 | 4-fluoro-phenyl- |
| Y.1445 | Br | 2 | 4H-1,2,4-triazol-3-yl- |
| Y.1446 | Br | 2 | 4-methoxyphenyl- |
| Y.1447 | Br | 2 | 4-methyl-4,5-dihydrothiazol-2-yl- |
| Y.1448 | Br | 2 | 4-methylphenyl- |
| Y.1449 | Br | 2 | 4-methylpyrid-2-yl |
| Y.1450 | Br | 2 | 4-nitrophenyl- |
| Y.1451 | Br | 2 | 4-pyridyl- |
| Y.1452 | Br | 2 | 5-methyl-4,5-dihydrothiazol-2-yl- |
| Y.1453 | Br | 2 | 5-methyl-thiazol-2-yl- |
| Y.1454 | Br | 2 | 6-methylpyrid-2-yl- |
| Y.1455 | Br | 2 | allyl- |
| Y.1456 | Br | 2 | but-2-ynyl- |
| Y.1457 | Br | 2 | but-3-ynyl- |
| Y.1458 | Br | 2 | cis-1-oxo-thietan-3-yl- |
| Y.1459 | Br | 2 | cis-1-oxo-thietan-3-ylmethyl- |
| Y.1460 | Br | 2 | cyanodimethylmethyl- |
| Y.1461 | Br | 2 | cyanoethyl- |
| Y.1462 | Br | 2 | cyanomethyl- |
| Y.1463 | Br | 2 | cyclopentyl- |
| Y.1464 | Br | 2 | cyclopropyl-methyl- |
| Y.1465 | Br | 2 | methylpropargyl- |
| Y.1466 | Br | 2 | oxetan-3-yl- |
| Y.1467 | Br | 2 | pent-3-yl- |
| Y.1468 | Br | 2 | phenyl-methyl-methyl- |
| Y.1469 | Br | 2 | propargyl- |
| Y.1470 | Br | 2 | tert-butyl- |
| Y.1471 | Br | 2 | tetrazolyl- |
| Y.1472 | Br | 2 | thiazol-2-yl- |
| Y.1473 | Br | 2 | thiazol-4-yl- |
| Y.1474 | Br | 2 | thietan-2-ylmethyl- |
| Y.1475 | Br | 2 | thietan-3-ylmethyl- |
| Y.1476 | Br | 2 | ethyl- |
| Y.1477 | Br | 2 | 3,3,3-trifluoro-propyl- |
| Y.1478 | Br | 2 | but-2-yl- |
| Y.1479 | Br | 2 | (tetrahydrofuran-2-yl)-methyl- |
| Y.1480 | Br | 2 | benzyl- |
| Y.1481 | Br | 2 | (2-fluoro-phenyl)-methyl- |
| Y.1482 | Br | 2 | 1-phenyl-eth-1-yl- |
| Y.1483 | Br | 2 | (4-methoxy-phenyl)-methyl- |
| Y.1484 | Br | 2 | 1,1-dioxo-thietan-3-yl- |
| Y.1485 | Br | 2 | (2-chloro-pyrid-5-yl)-methyl- |
| Y.1486 | Br | 2 | 3-fluoro-phenyl- |
| Y.1487 | Br | 2 | n-butyl- |
| Y.1488 | Br | 2 | (pyrid-2-yl)-methyl- |
| Y.1489 | Br | 2 | 1,3-dimethyl-1H-pyrazol-5-yl- |
| Y.1490 | Br | 2 | 4-methyl-thiazol-2-yl- |
| Y.1491 | Br | 2 | 3-methyl-thietan-3-yl- |
| Y.1492 | Br | 2 | 1,1-dimethyl-2-methylsulfanyl-ethyl- |
| Y.1493 | Br | 2 | 1-oxo-thietan-3-yl- |
| Y.1494 | Br | 2 | thietan-3-yl- |
| Y.1495 | Br | 2 | bicyclo[2.2.1]hept-2-yl- |
| Y.1496 | Br | 2 | cyclobutyl- |
| Y.1497 | Br | 2 | methyl- |
| Y.1498 | Br | 2 | cyclopropyl- |
| Y.1499 | Br | 2 | n-propyl- |
| Y.1500 | Br | 2 | 2,2-difluoroethyl- |
| Y.1501 | Br | 2 | 1-methoxy-prop-2-yl- |
| Y.1502 | Br | 2 | N-(2,2,2-trifluoro-ethyl)-acetamide-2-yl- |
| Y.1503 | Br | 2 | 2,2,2-trifluoro-ethyl- |
| Y.1504 | methyl | 0 | (1,1-dioxothietan-2-yl)methyl- |
| Y.1505 | methyl | 0 | (1-oxothietan-2-yl)methyl- |
| Y.1506 | methyl | 0 | (2-methoxy-phenyl)-methyl- |
| Y.1507 | methyl | 0 | (3-fluoro-phenyl)-methyl- |
| Y.1508 | methyl | 0 | (4,4-dimethyl-4,5-dihydrothiazol-2-yl)-methyl- |
| Y.1509 | methyl | 0 | (4,5-dihydrothiazol-2-yl)-methyl- |
| Y.1510 | methyl | 0 | (4,5-dimethyl-4,5-dihydrothiazol-2-yl)-methyl- |
| Y.1511 | methyl | 0 | (4-fluoro-phenyl)-methyl- |
| Y.1512 | methyl | 0 | (4-methyl-4,5-dihydrothiazol-2-yl)-methyl- |
| Y.1513 | methyl | 0 | (5-methyl-4,5-dihydrothiazol-2-yl)-methyl- |
| Y.1514 | methyl | 0 | (pyrid-3-yl)-methyl- |
| Y.1515 | methyl | 0 | (pyrid-4-yl)-methyl- |
| Y.1516 | methyl | 0 | (tetrahydrothiophene-2-yl)-methyl- |
| Y.1517 | methyl | 0 | (tetrahydrothiophene-3-yl)-methyl- |

TABLE Y-continued

| | R5b | n | R2 |
|---|---|---|---|
| Y.1518 | methyl | 0 | (thiazol-2-yl)-methyl- |
| Y.1519 | methyl | 0 | (thiazol-2-yl)-methylmethyl- |
| Y.1520 | methyl | 0 | (thiazol-4-yl)-methyl- |
| Y.1521 | methyl | 0 | (thiazol-5-yl)-methyl- |
| Y.1522 | methyl | 0 | 1,1-dioxo-thietan-3-ylmethyl- |
| Y.1523 | methyl | 0 | 1-cyanocyclobutyl- |
| Y.1524 | methyl | 0 | 1-cyanocyclopentyl- |
| Y.1525 | methyl | 0 | 1-cyanocyclopropyl- |
| Y.1526 | methyl | 0 | 1-fluoroprop-2-yl- |
| Y.1527 | methyl | 0 | 1-methylallyl- |
| Y.1528 | methyl | 0 | 1-methylsulfanyl-prop-2-yl- |
| Y.1529 | methyl | 0 | 2-(1,1-dioxothietan-3-yl)ethanyl- |
| Y.1530 | methyl | 0 | 2-(1-oxothietan-3-yl)ethanyl- |
| Y.1531 | methyl | 0 | 2-(thietan-3-yl)ethanyl- |
| Y.1532 | methyl | 0 | 2-(trifluoromethoxy)phenyl- |
| Y.1533 | methyl | 0 | 2,2-dimethyl-1,1-dioxo-thietan-3-yl- |
| Y.1534 | methyl | 0 | 2,2-dimethyl-1-oxo-thietan-3-yl- |
| Y.1535 | methyl | 0 | 2,2-dimethylthietan-3-yl- |
| Y.1536 | methyl | 0 | 2,3-dichlorophenyl- |
| Y.1537 | methyl | 0 | 2,3-difluoro-phenyl- |
| Y.1538 | methyl | 0 | 2,4-dichlorophenyl- |
| Y.1539 | methyl | 0 | 2,4-difluoro-phenyl- |
| Y.1540 | methyl | 0 | 2,4-dimethylphenyl- |
| Y.1541 | methyl | 0 | 2,5-dichlorophenyl- |
| Y.1542 | methyl | 0 | 2,5-difluoro-phenyl- |
| Y.1543 | methyl | 0 | 2,6-dichlorophenyl- |
| Y.1544 | methyl | 0 | 2,6-difluoro-phenyl- |
| Y.1545 | methyl | 0 | 2,6-diisopropylphenyl- |
| Y.1546 | methyl | 0 | 2-bromo-4-fluorophenyl- |
| Y.1547 | methyl | 0 | 2-bromoallyl- |
| Y.1548 | methyl | 0 | 2-bromophenyl- |
| Y.1549 | methyl | 0 | 2-butenyl- |
| Y.1550 | methyl | 0 | 2-chloroallyl- |
| Y.1551 | methyl | 0 | 2-chlorophenyl- |
| Y.1552 | methyl | 0 | 2-chloropyrid-2-yl- |
| Y.1553 | methyl | 0 | 2-chloropyrid-3-yl- |
| Y.1554 | methyl | 0 | 2-cyanocyclopropyl- |
| Y.1555 | methyl | 0 | 2-cyanoethyl- |
| Y.1556 | methyl | 0 | 2-ethylphenyl- |
| Y.1557 | methyl | 0 | 2-fluoroethyl- |
| Y.1558 | methyl | 0 | 2-fluoro-phenyl- |
| Y.1559 | methyl | 0 | 2-fluoropropyl- |
| Y.1560 | methyl | 0 | 2-furylmethyl- |
| Y.1561 | methyl | 0 | 2-hydroxyphenyl- |
| Y.1562 | methyl | 0 | 2-methoxy-ethyl- |
| Y.1563 | methyl | 0 | 2-methoxyphenyl- |
| Y.1564 | methyl | 0 | 2-methoxy-prop-3-yl- |
| Y.1565 | methyl | 0 | 2-methylallyl- |
| Y.1566 | methyl | 0 | 2-methyl-but-1-yl- |
| Y.1567 | methyl | 0 | 2-methyl-but-2-yl- |
| Y.1568 | methyl | 0 | 2-methylbut-3-yn-2-yl- |
| Y.1569 | methyl | 0 | 2-methylphenyl- |
| Y.1570 | methyl | 0 | 2-methyl-prop-1-yl- |
| Y.1571 | methyl | 0 | 2-methylsulfanyl-ethyl- |
| Y.1572 | methyl | 0 | 2-methylsulfanyl-prop-3-yl- |
| Y.1573 | methyl | 0 | 2-methyl-thiazol-4-yl- |
| Y.1574 | methyl | 0 | 2-nitrophenyl- |
| Y.1575 | methyl | 0 | 2-propyl- |
| Y.1576 | methyl | 0 | 2-pyridyl- |
| Y.1577 | methyl | 0 | 2-trifluoromethoxy-ethyl- |
| Y.1578 | methyl | 0 | 3-(trifluoromethoxy)phenyl- |
| Y.1579 | methyl | 0 | 3,3,3-trifluoro-2,2-difluoropropyl- |
| Y.1580 | methyl | 0 | 3,3,3-trifluoro-butyl- |
| Y.1581 | methyl | 0 | 3,3-dibromoallyl- |
| Y.1582 | methyl | 0 | 3,3-dichloroallyl- |
| Y.1583 | methyl | 0 | 3,4-dichlorophenyl- |
| Y.1584 | methyl | 0 | 3,4-difluorophenyl- |
| Y.1585 | methyl | 0 | 3,5-dichlorophenyl- |
| Y.1586 | methyl | 0 | 3,5-difluoro-phenyl- |
| Y.1587 | methyl | 0 | 3,6-difluoro-phenyl- |
| Y.1588 | methyl | 0 | 3-bromoallyl- |
| Y.1589 | methyl | 0 | 3-bromophenyl- |
| Y.1590 | methyl | 0 | 3-butenyl- |
| Y.1591 | methyl | 0 | 3-chloroallyl- |
| Y.1592 | methyl | 0 | 3-chlorophenyl- |
| Y.1593 | methyl | 0 | 3-chloropyrid-2-yl- |
| Y.1594 | methyl | 0 | 3-cyanopropyl- |
| Y.1595 | methyl | 0 | 3-ethylphenyl- |
| Y.1596 | methyl | 0 | 3-hydroxyphenyl- |
| Y.1597 | methyl | 0 | 3-methyl-1,1-dioxo-thietan-3-yl- |
| Y.1598 | methyl | 0 | 3-methyl-1-oxo-thietan-3-yl- |
| Y.1599 | methyl | 0 | 3-methyl-but-1-yl- |
| Y.1600 | methyl | 0 | 3-methyl-but-2-yl- |
| Y.1601 | methyl | 0 | 3-methylphenyl- |
| Y.1602 | methyl | 0 | 3-nitrophenyl- |
| Y.1603 | methyl | 0 | 3-pyridyl- |
| Y.1604 | methyl | 0 | 4-(trifluoromethoxy)phenyl- |
| Y.1605 | methyl | 0 | 4,5-dihydrothiazol-2-yl- |
| Y.1606 | methyl | 0 | 4,5-dimethyl-4,5-dihydrothiazol-2-yl- |
| Y.1607 | methyl | 0 | 4,5-dimethyl-thiazol-2-yl- |
| Y.1608 | methyl | 0 | 4-bromophenyl- |
| Y.1609 | methyl | 0 | 4-chlorophenyl- |
| Y.1610 | methyl | 0 | 4-ethylphenyl- |
| Y.1611 | methyl | 0 | 4-fluoro-phenyl- |
| Y.1612 | methyl | 0 | 4H-1,2,4-triazol-3-yl- |
| Y.1613 | methyl | 0 | 4-methoxyphenyl- |
| Y.1614 | methyl | 0 | 4-methyl-4,5-dihydrothiazol-2-yl- |
| Y.1615 | methyl | 0 | 4-methylphenyl- |
| Y.1616 | methyl | 0 | 4-methylpyrid-2-yl |
| Y.1617 | methyl | 0 | 4-nitrophenyl- |
| Y.1618 | methyl | 0 | 4-pyridyl- |
| Y.1619 | methyl | 0 | 5-methyl-4,5-dihydrothiazol-2-yl- |
| Y.1620 | methyl | 0 | 5-methyl-thiazol-2-yl- |
| Y.1621 | methyl | 0 | 6-methylpyrid-2-yl- |
| Y.1622 | methyl | 0 | allyl- |
| Y.1623 | methyl | 0 | but-2-ynyl- |
| Y.1624 | methyl | 0 | but-3-ynyl- |
| Y.1625 | methyl | 0 | cis-1-oxo-thietan-3-yl- |
| Y.1626 | methyl | 0 | cis-1-oxo-thietan-3-ylmethyl- |
| Y.1627 | methyl | 0 | cyanodimethylmethyl- |
| Y.1628 | methyl | 0 | cyanoethyl- |
| Y.1629 | methyl | 0 | cyanomethyl- |
| Y.1630 | methyl | 0 | cyclopentyl- |
| Y.1631 | methyl | 0 | cyclopropyl-methyl- |
| Y.1632 | methyl | 0 | methylpropargyl- |
| Y.1633 | methyl | 0 | oxetan-3-yl- |
| Y.1634 | methyl | 0 | pent-3-yl- |
| Y.1635 | methyl | 0 | phenyl-methyl-methyl- |
| Y.1636 | methyl | 0 | propargyl- |
| Y.1637 | methyl | 0 | tert-butyl- |
| Y.1638 | methyl | 0 | tetrazolyl- |
| Y.1639 | methyl | 0 | thiazol-2-yl- |
| Y.1640 | methyl | 0 | thiazol-4-yl- |
| Y.1641 | methyl | 0 | thietan-2-ylmethyl- |
| Y.1642 | methyl | 0 | thietan-3-ylmethyl- |
| Y.1643 | methyl | 0 | ethyl- |
| Y.1644 | methyl | 0 | 3,3,3-trifluoro-propyl- |
| Y.1645 | methyl | 0 | but-2-yl- |
| Y.1646 | methyl | 0 | (tetrahydrofuran-2-yl)-methyl- |
| Y.1647 | methyl | 0 | benzyl- |
| Y.1648 | methyl | 0 | (2-fluoro-phenyl)-methyl- |
| Y.1649 | methyl | 0 | 1-phenyl-eth-1-yl- |
| Y.1650 | methyl | 0 | (4-methoxy-phenyl)-methyl- |
| Y.1651 | methyl | 0 | 1,1-dioxo-thietan-3-yl- |
| Y.1652 | methyl | 0 | (2-chloro-pyrid-5-yl)-methyl- |
| Y.1653 | methyl | 0 | 3-fluoro-phenyl- |
| Y.1654 | methyl | 0 | n-butyl- |
| Y.1655 | methyl | 0 | (pyrid-2-yl)-methyl- |
| Y.1656 | methyl | 0 | 1,3-dimethyl-1H-pyrazol-5-yl- |
| Y.1657 | methyl | 0 | 4-methyl-thiazol-2-yl- |
| Y.1658 | methyl | 0 | 3-methyl-thietan-3-yl- |
| Y.1659 | methyl | 0 | 1,1-dimethyl-2-methylsulfanyl-ethyl |
| Y.1660 | methyl | 0 | 1-oxo-thietan-3-yl- |
| Y.1661 | methyl | 0 | thietan-3-yl- |
| Y.1662 | methyl | 0 | bicyclo[2.2.1]hept-2-yl- |
| Y.1663 | methyl | 0 | cyclobutyl- |
| Y.1664 | methyl | 0 | methyl- |
| Y.1665 | methyl | 0 | cyclopropyl- |
| Y.1666 | methyl | 0 | n-propyl- |
| Y.1667 | methyl | 0 | 2,2-difluoroethyl- |
| Y.1668 | methyl | 0 | 1-methoxy-prop-2-yl- |
| Y.1669 | methyl | 0 | N-(2,2,2-trifluoro-ethyl)-acetamide-2-yl |
| Y.1670 | methyl | 0 | 2,2,2-trifluoro-ethyl- |
| Y.1671 | methyl | 1 | (1,1-dioxothietan-2-yl)methyl- |
| Y.1672 | methyl | 1 | (1-oxothietan-2-yl)methyl- |
| Y.1673 | methyl | 1 | (2-methoxy-phenyl)-methyl- |

TABLE Y-continued

| | R5b | n | R2 |
|---|---|---|---|
| Y.1674 | methyl | 1 | (3-fluoro-phenyl)-methyl- |
| Y.1675 | methyl | 1 | (4,4-dimethyl-4,5-dihydrothiazol-2-yl)-methyl- |
| Y.1676 | methyl | 1 | (4,5-dihydrothiazol-2-yl)-methyl- |
| Y.1677 | methyl | 1 | (4,5-dimethyl-4,5-dihydrothiazol-2-yl)-methyl- |
| Y.1678 | methyl | 1 | (4-fluoro-phenyl)-methyl- |
| Y.1679 | methyl | 1 | (4-methyl-4,5-dihydrothiazol-2-yl)-methyl- |
| Y.1680 | methyl | 1 | (5-methyl-4,5-dihydrothiazol-2-yl)-methyl- |
| Y.1681 | methyl | 1 | (pyrid-3-yl)-methyl- |
| Y.1682 | methyl | 1 | (pyrid-4-yl)-methyl- |
| Y.1683 | methyl | 1 | (tetrahydrothiophene-2-yl)-methyl- |
| Y.1684 | methyl | 1 | (tetrahydrothiophene-3-yl)-methyl- |
| Y.1685 | methyl | 1 | (thiazol-2-yl)-methyl- |
| Y.1686 | methyl | 1 | (thiazol-2-yl)-methylmethyl- |
| Y.1687 | methyl | 1 | (thiazol-4-yl)-methyl- |
| Y.1688 | methyl | 1 | (thiazol-5-yl)-methyl- |
| Y.1689 | methyl | 1 | 1,1-dioxo-thietan-3-ylmethyl- |
| Y.1690 | methyl | 1 | 1-cyanocyclobutyl- |
| Y.1691 | methyl | 1 | 1-cyanocyclopentyl- |
| Y.1692 | methyl | 1 | 1-cyanocyclopropyl- |
| Y.1693 | methyl | 1 | 1-fluoroprop-2-yl- |
| Y.1694 | methyl | 1 | 1-methylallyl- |
| Y.1695 | methyl | 1 | 1-methylsulfanyl-prop-2-yl- |
| Y.1696 | methyl | 1 | 2-(1,1-dioxothietan-3-yl)ethanyl- |
| Y.1697 | methyl | 1 | 2-(1-oxothietan-3-yl)ethanyl- |
| Y.1698 | methyl | 1 | 2-(thietan-3-yl)ethanyl- |
| Y.1699 | methyl | 1 | 2-(trifluoromethoxy)phenyl- |
| Y.1700 | methyl | 1 | 2,2-dimethyl-1,1-dioxo-thietan-3-yl- |
| Y.1701 | methyl | 1 | 2,2-dimethyl-1-oxo-thietan-3-yl- |
| Y.1702 | methyl | 1 | 2,2-dimethylthietan-3-yl- |
| Y.1703 | methyl | 1 | 2,3-dichlorophenyl- |
| Y.1704 | methyl | 1 | 2,3-difluoro-phenyl- |
| Y.1705 | methyl | 1 | 2,4-dichlorophenyl- |
| Y.1706 | methyl | 1 | 2,4-difluoro-phenyl- |
| Y.1707 | methyl | 1 | 2,4-dimethylphenyl- |
| Y.1708 | methyl | 1 | 2,5-dichlorophenyl- |
| Y.1709 | methyl | 1 | 2,5-difluoro-phenyl- |
| Y.1710 | methyl | 1 | 2,6-dichlorophenyl- |
| Y.1711 | methyl | 1 | 2,6-difluoro-phenyl- |
| Y.1712 | methyl | 1 | 2,6-diisopropylphenyl- |
| Y.1713 | methyl | 1 | 2-bromo-4-fluorophenyl- |
| Y.1714 | methyl | 1 | 2-bromoallyl- |
| Y.1715 | methyl | 1 | 2-bromophenyl- |
| Y.1716 | methyl | 1 | 2-butenyl- |
| Y.1717 | methyl | 1 | 2-chloroallyl- |
| Y.1718 | methyl | 1 | 2-chlorophenyl- |
| Y.1719 | methyl | 1 | 2-chloropyrid-2-yl- |
| Y.1720 | methyl | 1 | 2-chloropyrid-3-yl- |
| Y.1721 | methyl | 1 | 2-cyanocyclopropyl- |
| Y.1722 | methyl | 1 | 2-cyanoethyl- |
| Y.1723 | methyl | 1 | 2-ethylphenyl- |
| Y.1724 | methyl | 1 | 2-fluoroethyl- |
| Y.1725 | methyl | 1 | 2-fluoro-phenyl- |
| Y.1726 | methyl | 1 | 2-fluoropropyl- |
| Y.1727 | methyl | 1 | 2-furylmethyl- |
| Y.1728 | methyl | 1 | 2-hydroxyphenyl- |
| Y.1729 | methyl | 1 | 2-methoxy-ethyl- |
| Y.1730 | methyl | 1 | 2-methoxyphenyl- |
| Y.1731 | methyl | 1 | 2-methoxy-prop-3-yl- |
| Y.1732 | methyl | 1 | 2-methylallyl- |
| Y.1733 | methyl | 1 | 2-methyl-but-1-yl- |
| Y.1734 | methyl | 1 | 2-methyl-but-2-yl- |
| Y.1735 | methyl | 1 | 2-methylbut-3-yn-2-yl- |
| Y.1736 | methyl | 1 | 2-methylphenyl- |
| Y.1737 | methyl | 1 | 2-methyl-prop-1-yl- |
| Y.1738 | methyl | 1 | 2-methylsulfanyl-ethyl- |
| Y.1739 | methyl | 1 | 2-methylsulfanyl-prop-3-yl- |
| Y.1740 | methyl | 1 | 2-methyl-thiazol-4-yl- |
| Y.1741 | methyl | 1 | 2-nitrophenyl- |
| Y.1742 | methyl | 1 | 2-propyl- |
| Y.1743 | methyl | 1 | 2-pyridyl- |
| Y.1744 | methyl | 1 | 2-trifluoromethoxy-ethyl- |
| Y.1745 | methyl | 1 | 3-(trifluoromethoxy)phenyl- |
| Y.1746 | methyl | 1 | 3,3,3-trifluoro-2,2-difluoropropyl- |
| Y.1747 | methyl | 1 | 3,3,3-trifluoro-butyl- |
| Y.1748 | methyl | 1 | 3,3-dibromoallyl- |
| Y.1749 | methyl | 1 | 3,3-dichloroallyl- |
| Y.1750 | methyl | 1 | 3,4-dichlorophenyl- |
| Y.1751 | methyl | 1 | 3,4-difluoro-phenyl- |
| Y.1752 | methyl | 1 | 3,5-dichlorophenyl- |
| Y.1753 | methyl | 1 | 3,5-difluoro-phenyl- |
| Y.1754 | methyl | 1 | 3,6-difluoro-phenyl- |
| Y.1755 | methyl | 1 | 3-bromoallyl- |
| Y.1756 | methyl | 1 | 3-bromophenyl- |
| Y.1757 | methyl | 1 | 3-butenyl- |
| Y.1758 | methyl | 1 | 3-chloroallyl- |
| Y.1759 | methyl | 1 | 3-chlorophenyl- |
| Y.1760 | methyl | 1 | 3-chloropyrid-2-yl- |
| Y.1761 | methyl | 1 | 3-cyanopropyl- |
| Y.1762 | methyl | 1 | 3-ethylphenyl- |
| Y.1763 | methyl | 1 | 3-hydroxyphenyl- |
| Y.1764 | methyl | 1 | 3-methyl-1,1-dioxo-thietan-3-yl- |
| Y.1765 | methyl | 1 | 3-methyl-1-oxo-thietan-3-yl- |
| Y.1766 | methyl | 1 | 3-methyl-but-1-yl- |
| Y.1767 | methyl | 1 | 3-methyl-but-2-yl- |
| Y.1768 | methyl | 1 | 3-methylphenyl- |
| Y.1769 | methyl | 1 | 3-nitrophenyl- |
| Y.1770 | methyl | 1 | 3-pyridyl- |
| Y.1771 | methyl | 1 | 4-(trifluoromethoxy)phenyl- |
| Y.1772 | methyl | 1 | 4,5-dihydrothiazol-2-yl- |
| Y.1773 | methyl | 1 | 4,5-dimethyl-4,5-dihydrothiazol-2-yl- |
| Y.1774 | methyl | 1 | 4,5-dimethyl-thiazol-2-yl- |
| Y.1775 | methyl | 1 | 4-bromophenyl- |
| Y.1776 | methyl | 1 | 4-chlorophenyl- |
| Y.1777 | methyl | 1 | 4-ethylphenyl- |
| Y.1778 | methyl | 1 | 4-fluoro-phenyl- |
| Y.1779 | methyl | 1 | 4H-1,2,4-triazol-3-yl- |
| Y.1780 | methyl | 1 | 4-methoxyphenyl- |
| Y.1781 | methyl | 1 | 4-methyl-4,5-dihydrothiazol-2-yl- |
| Y.1782 | methyl | 1 | 4-methylphenyl- |
| Y.1783 | methyl | 1 | 4-methylpyrid-2-yl |
| Y.1784 | methyl | 1 | 4-nitrophenyl- |
| Y.1785 | methyl | 1 | 4-pyridyl- |
| Y.1786 | methyl | 1 | 5-methyl-4,5-dihydrothiazol-2-yl- |
| Y.1787 | methyl | 1 | 5-methyl-thiazol-2-yl- |
| Y.1788 | methyl | 1 | 6-methylpyrid-2-yl- |
| Y.1789 | methyl | 1 | allyl- |
| Y.1790 | methyl | 1 | but-2-ynyl- |
| Y.1791 | methyl | 1 | but-3-ynyl- |
| Y.1792 | methyl | 1 | cis-1-oxo-thietan-3-yl- |
| Y.1793 | methyl | 1 | cis-1-oxo-thietan-3-ylmethyl- |
| Y.1794 | methyl | 1 | cyanodimethylmethyl- |
| Y.1795 | methyl | 1 | cyanoethyl- |
| Y.1796 | methyl | 1 | cyanomethyl- |
| Y.1797 | methyl | 1 | cyclopentyl- |
| Y.1798 | methyl | 1 | cyclopropyl-methyl- |
| Y.1799 | methyl | 1 | methylpropargyl- |
| Y.1800 | methyl | 1 | oxetan-3-yl- |
| Y.1801 | methyl | 1 | pent-3-yl- |
| Y.1802 | methyl | 1 | phenyl-methyl-methyl- |
| Y.1803 | methyl | 1 | propargyl- |
| Y.1804 | methyl | 1 | tert-butyl- |
| Y.1805 | methyl | 1 | tetrazolyl- |
| Y.1806 | methyl | 1 | thiazol-2-yl- |
| Y.1807 | methyl | 1 | thiazol-4-yl- |
| Y.1808 | methyl | 1 | thietan-2-ylmethyl- |
| Y.1809 | methyl | 1 | thietan-3-ylmethyl- |
| Y.1810 | methyl | 1 | ethyl- |
| Y.1811 | methyl | 1 | 3,3,3-trifluoro-propyl- |
| Y.1812 | methyl | 1 | but-2-yl- |
| Y.1813 | methyl | 1 | (tetrahydrofuran-2-yl)-methyl- |
| Y.1814 | methyl | 1 | benzyl- |
| Y.1815 | methyl | 1 | (2-fluoro-phenyl)-methyl- |
| Y.1816 | methyl | 1 | 1-phenyl-eth-1-yl- |
| Y.1817 | methyl | 1 | (4-methoxy-phenyl)-methyl- |
| Y.1818 | methyl | 1 | 1,1-dioxo-thietan-3-yl- |
| Y.1819 | methyl | 1 | (2-chloro-pyrid-5-yl)-methyl- |
| Y.1820 | methyl | 1 | 3-fluoro-phenyl- |
| Y.1821 | methyl | 1 | n-butyl- |
| Y.1822 | methyl | 1 | (pyrid-2-yl)-methyl- |
| Y.1823 | methyl | 1 | 1,3-dimethyl-1H-pyrazol-5-yl- |
| Y.1824 | methyl | 1 | 4-methyl-thiazol-2-yl- |
| Y.1825 | methyl | 1 | 3-methyl-thietan-3-yl- |

TABLE Y-continued

| | R5b | n | R2 |
|---|---|---|---|
| Y.1826 | methyl | 1 | 1,1-dimethyl-2-methylsulfanyl-ethyl |
| Y.1827 | methyl | 1 | 1-oxo-thietan-3-yl- |
| Y.1828 | methyl | 1 | thietan-3-yl- |
| Y.1829 | methyl | 1 | bicyclo[2.2.1]hept-2-yl- |
| Y.1830 | methyl | 1 | cyclobutyl- |
| Y.1831 | methyl | 1 | methyl- |
| Y.1832 | methyl | 1 | cyclopropyl- |
| Y.1833 | methyl | 1 | n-propyl- |
| Y.1834 | methyl | 1 | 2,2-difluoroethyl- |
| Y.1835 | methyl | 1 | 1-methoxy-prop-2-yl- |
| Y.1836 | methyl | 1 | N-(2,2,2-trifluoro-ethyl)-acetamide-2-yl |
| Y.1837 | methyl | 1 | 2,2,2-trifluoro-ethyl- |
| Y.1838 | methyl | 2 | (1,1-dioxothietan-2-yl)methyl- |
| Y.1839 | methyl | 2 | (1-oxothietan-2-yl)methyl- |
| Y.1840 | methyl | 2 | (2-methoxy-phenyl)-methyl- |
| Y.1841 | methyl | 2 | (3-fluoro-phenyl)-methyl- |
| Y.1842 | methyl | 2 | (4,4-dimethyl-4,5-dihydrothiazol-2-yl)-methyl- |
| Y.1843 | methyl | 2 | (4,5-dihydrothiazol-2-yl)-methyl- |
| Y.1844 | methyl | 2 | (4,5-dimethyl-4,5-dihydrothiazol-2-yl)-methyl- |
| Y.1845 | methyl | 2 | (4-fluoro-phenyl)-methyl- |
| Y.1846 | methyl | 2 | (4-methyl-4,5-dihydrothiazol-2-yl)-methyl- |
| Y.1847 | methyl | 2 | (5-methyl-4,5-dihydrothiazol-2-yl)-methyl- |
| Y.1848 | methyl | 2 | (pyrid-3-yl)-methyl- |
| Y.1849 | methyl | 2 | (pyrid-4-yl)-methyl- |
| Y.1850 | methyl | 2 | (tetrahydrothiophene-2-yl)-methyl- |
| Y.1851 | methyl | 2 | (tetrahydrothiophene-3-yl)-methyl- |
| Y.1852 | methyl | 2 | (thiazol-2-yl)-methyl- |
| Y.1853 | methyl | 2 | (thiazol-2-yl)-methylmethyl- |
| Y.1854 | methyl | 2 | (thiazol-4-yl)-methyl- |
| Y.1855 | methyl | 2 | (thiazol-5-yl)-methyl- |
| Y.1856 | methyl | 2 | 1,1-dioxo-thietan-3-ylmethyl- |
| Y.1857 | methyl | 2 | 1-cyanocyclobutyl- |
| Y.1858 | methyl | 2 | 1-cyanocyclopentyl- |
| Y.1859 | methyl | 2 | 1-cyanocyclopropyl- |
| Y.1860 | methyl | 2 | 1-fluoroprop-2-yl- |
| Y.1861 | methyl | 2 | 1-methylallyl- |
| Y.1862 | methyl | 2 | 1-methylsulfanyl-prop-2-yl- |
| Y.1863 | methyl | 2 | 2-(1,1-dioxothietan-3-yl)ethanyl- |
| Y.1864 | methyl | 2 | 2-(1-oxothietan-3-yl)ethanyl- |
| Y.1865 | methyl | 2 | 2-(thietan-3-yl)ethanyl- |
| Y.1866 | methyl | 2 | 2-(trifluoromethoxy)phenyl- |
| Y.1867 | methyl | 2 | 2,2-dimethyl-1,1-dioxo-thietan-3-yl- |
| Y.1868 | methyl | 2 | 2,2-dimethyl-1-oxo-thietan-3-yl- |
| Y.1869 | methyl | 2 | 2,2-dimethylthietan-3-yl- |
| Y.1870 | methyl | 2 | 2,3-dichlorophenyl- |
| Y.1871 | methyl | 2 | 2,3-difluoro-phenyl- |
| Y.1872 | methyl | 2 | 2,4-dichlorophenyl- |
| Y.1873 | methyl | 2 | 2,4-difluoro-phenyl- |
| Y.1874 | methyl | 2 | 2,4-dimethylphenyl- |
| Y.1875 | methyl | 2 | 2,5-dichlorophenyl- |
| Y.1876 | methyl | 2 | 2,5-difluoro-phenyl- |
| Y.1877 | methyl | 2 | 2,6-dichlorophenyl- |
| Y.1878 | methyl | 2 | 2,6-difluoro-phenyl- |
| Y.1879 | methyl | 2 | 2,6-diisopropylphenyl- |
| Y.1880 | methyl | 2 | 2-bromo-4-fluorophenyl- |
| Y.1881 | methyl | 2 | 2-bromoallyl- |
| Y.1882 | methyl | 2 | 2-bromophenyl- |
| Y.1883 | methyl | 2 | 2-butenyl- |
| Y.1884 | methyl | 2 | 2-chloroallyl- |
| Y.1885 | methyl | 2 | 2-chlorophenyl- |
| Y.1886 | methyl | 2 | 2-chloropyrid-2-yl- |
| Y.1887 | methyl | 2 | 2-chloropyrid-3-yl- |
| Y.1888 | methyl | 2 | 2-cyanocyclopropyl- |
| Y.1889 | methyl | 2 | 2-cyanoethyl- |
| Y.1890 | methyl | 2 | 2-ethylphenyl- |
| Y.1891 | methyl | 2 | 2-fluoroethyl- |
| Y.1892 | methyl | 2 | 2-fluoro-phenyl- |
| Y.1893 | methyl | 2 | 2-fluoropropyl- |
| Y.1894 | methyl | 2 | 2-furylmethyl- |
| Y.1895 | methyl | 2 | 2-hydroxyphenyl- |
| Y.1896 | methyl | 2 | 2-methoxy-ethyl- |
| Y.1897 | methyl | 2 | 2-methoxyphenyl- |
| Y.1898 | methyl | 2 | 2-methoxy-prop-3-yl- |
| Y.1899 | methyl | 2 | 2-methylallyl- |
| Y.1900 | methyl | 2 | 2-methyl-but-1-yl- |
| Y.1901 | methyl | 2 | 2-methyl-but-2-yl- |
| Y.1902 | methyl | 2 | 2-methylbut-3-yn-2-yl- |
| Y.1903 | methyl | 2 | 2-methylphenyl- |
| Y.1904 | methyl | 2 | 2-methyl-prop-1-yl- |
| Y.1905 | methyl | 2 | 2-methylsulfanyl-ethyl- |
| Y.1906 | methyl | 2 | 2-methylsulfanyl-prop-3-yl- |
| Y.1907 | methyl | 2 | 2-methyl-thiazol-4-yl- |
| Y.1908 | methyl | 2 | 2-nitrophenyl- |
| Y.1909 | methyl | 2 | 2-propyl- |
| Y.1910 | methyl | 2 | 2-pyridyl- |
| Y.1911 | methyl | 2 | 2-trifluoromethoxy-ethyl- |
| Y.1912 | methyl | 2 | 2-(trifluoromethoxy)phenyl- |
| Y.1913 | methyl | 2 | 3,3,3-trifluoro-2,2-difluoropropyl- |
| Y.1914 | methyl | 2 | 3,3,3-trifluoro-butyl- |
| Y.1915 | methyl | 2 | 3,3-dibromoallyl- |
| Y.1916 | methyl | 2 | 3,3-dichloroallyl- |
| Y.1917 | methyl | 2 | 3,4-dichlorophenyl- |
| Y.1918 | methyl | 2 | 3,4-difluoro-phenyl- |
| Y.1919 | methyl | 2 | 3,5-dichlorophenyl- |
| Y.1920 | methyl | 2 | 3,5-difluoro-phenyl- |
| Y.1921 | methyl | 2 | 3,6-difluoro-phenyl- |
| Y.1922 | methyl | 2 | 3-bromoallyl- |
| Y.1923 | methyl | 2 | 3-bromophenyl- |
| Y.1924 | methyl | 2 | 3-butenyl- |
| Y.1925 | methyl | 2 | 3-chloroallyl- |
| Y.1926 | methyl | 2 | 3-chlorophenyl- |
| Y.1927 | methyl | 2 | 3-chloropyrid-2-yl- |
| Y.1928 | methyl | 2 | 3-cyanopropyl- |
| Y.1929 | methyl | 2 | 3-ethylphenyl- |
| Y.1930 | methyl | 2 | 3-hydroxyphenyl- |
| Y.1931 | methyl | 2 | 3-methyl-1,1-dioxo-thietan-3-yl- |
| Y.1932 | methyl | 2 | 3-methyl-1-oxo-thietan-3-yl- |
| Y.1933 | methyl | 2 | 3-methyl-but-1-yl- |
| Y.1934 | methyl | 2 | 3-methyl-but-2-yl- |
| Y.1935 | methyl | 2 | 3-methylphenyl- |
| Y.1936 | methyl | 2 | 3-nitrophenyl- |
| Y.1937 | methyl | 2 | 3-pyridyl- |
| Y.1938 | methyl | 2 | 4-(trifluoromethoxy)phenyl- |
| Y.1939 | methyl | 2 | 4,5-dihydrothiazol-2-yl- |
| Y.1940 | methyl | 2 | 4,5-dimethyl-4,5-dihydrothiazol-2-yl- |
| Y.1941 | methyl | 2 | 4,5-dimethyl-thiazol-2-yl- |
| Y.1942 | methyl | 2 | 4-bromophenyl- |
| Y.1943 | methyl | 2 | 4-chlorophenyl- |
| Y.1944 | methyl | 2 | 4-ethylphenyl- |
| Y.1945 | methyl | 2 | 4-fluoro-phenyl- |
| Y.1946 | methyl | 2 | 4H-1,2,4-triazol-3-yl- |
| Y.1947 | methyl | 2 | 4-methoxyphenyl- |
| Y.1948 | methyl | 2 | 4-methyl-4,5-dihydrothiazol-2-yl- |
| Y.1949 | methyl | 2 | 4-methylphenyl- |
| Y.1950 | methyl | 2 | 4-methylpyrid-2-yl |
| Y.1951 | methyl | 2 | 4-nitrophenyl- |
| Y.1952 | methyl | 2 | 4-pyridyl- |
| Y.1953 | methyl | 2 | 5-methyl-4,5-dihydrothiazol-2-yl- |
| Y.1954 | methyl | 2 | 5-methyl-thiazol-2-yl- |
| Y.1955 | methyl | 2 | 6-methylpyrid-2-yl- |
| Y.1956 | methyl | 2 | allyl- |
| Y.1957 | methyl | 2 | but-2-ynyl- |
| Y.1958 | methyl | 2 | but-3-ynyl- |
| Y.1959 | methyl | 2 | cis-1-oxo-thietan-3-yl- |
| Y.1960 | methyl | 2 | cis-1-oxo-thietan-3-ylmethyl- |
| Y.1961 | methyl | 2 | cyanodimethylmethyl- |
| Y.1962 | methyl | 2 | cyanoethyl- |
| Y.1963 | methyl | 2 | cyanomethyl- |
| Y.1964 | methyl | 2 | cyclopentyl- |
| Y.1965 | methyl | 2 | cyclopropyl-methyl- |
| Y.1966 | methyl | 2 | methylpropargyl- |
| Y.1967 | methyl | 2 | oxetan-3-yl- |
| Y.1968 | methyl | 2 | pent-3-yl- |
| Y.1969 | methyl | 2 | phenyl-methyl-methyl- |
| Y.1970 | methyl | 2 | propargyl- |
| Y.1971 | methyl | 2 | tert-butyl- |
| Y.1972 | methyl | 2 | tetrazolyl- |
| Y.1973 | methyl | 2 | thiazol-2-yl- |
| Y.1974 | methyl | 2 | thiazol-4-yl- |
| Y.1975 | methyl | 2 | thietan-2-ylmethyl- |
| Y.1976 | methyl | 2 | thietan-3-ylmethyl- |
| Y.1977 | methyl | 2 | ethyl- |

TABLE Y-continued

| | R5b | n | R2 |
|---|---|---|---|
| Y.1978 | methyl | 2 | 3,3,3-trifluoro-propyl- |
| Y.1979 | methyl | 2 | but-2-yl- |
| Y.1980 | methyl | 2 | (tetrahydrofuran-2-yl)-methyl- |
| Y.1981 | methyl | 2 | benzyl- |
| Y.1982 | methyl | 2 | (2-fluoro-phenyl)-methyl- |
| Y.1983 | methyl | 2 | 1-phenyl-eth-1-yl- |
| Y.1984 | methyl | 2 | (4-methoxy-phenyl)-methyl- |
| Y.1985 | methyl | 2 | 1,1-dioxo-thietan-3-yl- |
| Y.1986 | methyl | 2 | (2-chloro-pyrid-5-yl)-methyl- |
| Y.1987 | methyl | 2 | 3-fluoro-phenyl- |
| Y.1988 | methyl | 2 | n-butyl- |
| Y.1989 | methyl | 2 | (pyrid-2-yl)-methyl- |
| Y.1990 | methyl | 2 | 1,3-dimethyl-1H-pyrazol-5-yl- |
| Y.1991 | methyl | 2 | 4-methyl-thiazol-2-yl- |
| Y.1992 | methyl | 2 | 3-methyl-thietan-3-yl- |
| Y.1993 | methyl | 2 | 1,1-dimethyl-2-methylsulfanyl-ethyl |
| Y.1994 | methyl | 2 | 1-oxo-thietan-3-yl- |
| Y.1995 | methyl | 2 | thietan-3-yl- |
| Y.1996 | methyl | 2 | bicyclo[2.2.1]hept-2-yl- |
| Y.1997 | methyl | 2 | cyclobutyl- |
| Y.1998 | methyl | 2 | methyl- |
| Y.1999 | methyl | 2 | cyclopropyl- |
| Y.2000 | methyl | 2 | n-propyl- |
| Y.2001 | methyl | 2 | 2,2-difluoroethyl- |
| Y.2002 | methyl | 2 | 1-methoxy-prop-2-yl- |
| Y.2003 | methyl | 2 | N-(2,2,2-trifluoro-ethyl)-acetamide-2-yl |
| Y.2004 | methyl | 2 | 2,2,2-trifluoro-ethyl- |
| Y.2005 | trifluoromethyl | 0 | (1,1-dioxothietan-2-yl)methyl- |
| Y.2006 | trifluoromethyl | 0 | (1-oxothietan-2-yl)methyl- |
| Y.2007 | trifluoromethyl | 0 | (2-methoxy-phenyl)-methyl- |
| Y.2008 | trifluoromethyl | 0 | (3-fluoro-phenyl)-methyl- |
| Y.2009 | trifluoromethyl | 0 | (4,4-dimethyl-4,5-dihydrothiazol-2-yl)-methyl- |
| Y.2010 | trifluoromethyl | 0 | (4,5-dihydrothiazol-2-yl)-methyl- |
| Y.2011 | trifluoromethyl | 0 | (4,5-dimethyl-4,5-dihydrothiazol-2-yl)-methyl- |
| Y.2012 | trifluoromethyl | 0 | (4-fluoro-phenyl)-methyl- |
| Y.2013 | trifluoromethyl | 0 | (4-methyl-4,5-dihydrothiazol-2-yl)-methyl- |
| Y.2014 | trifluoromethyl | 0 | (5-methyl-4,5-dihydrothiazol-2-yl)-methyl- |
| Y.2015 | trifluoromethyl | 0 | (pyrid-3-yl)-methyl- |
| Y.2016 | trifluoromethyl | 0 | (pyrid-4-yl)-methyl- |
| Y.2017 | trifluoromethyl | 0 | (tetrahydrothiophene-2-yl)-methyl- |
| Y.2018 | trifluoromethyl | 0 | (tetrahydrothiophene-3-yl)-methyl- |
| Y.2019 | trifluoromethyl | 0 | (thiazol-2-yl)-methyl- |
| Y.2020 | trifluoromethyl | 0 | (thiazol-2-yl)-methylmethyl- |
| Y.2021 | trifluoromethyl | 0 | (thiazol-4-yl)-methyl- |
| Y.2022 | trifluoromethyl | 0 | (thiazol-5-yl)-methyl- |
| Y.2023 | trifluoromethyl | 0 | 1,1-dioxo-thietan-3-ylmethyl- |
| Y.2024 | trifluoromethyl | 0 | 1-cyanocyclobutyl- |
| Y.2025 | trifluoromethyl | 0 | 1-cyanocyclopentyl- |
| Y.2026 | trifluoromethyl | 0 | 1-cyanocyclopropyl- |
| Y.2027 | trifluoromethyl | 0 | 1-fluoroprop-2-yl- |
| Y.2028 | trifluoromethyl | 0 | 1-methylallyl- |
| Y.2029 | trifluoromethyl | 0 | 1-methylsulfanyl-prop-2-yl- |
| Y.2030 | trifluoromethyl | 0 | 2-(1,1-dioxothietan-3-yl)ethanyl- |
| Y.2031 | trifluoromethyl | 0 | 2-(1-oxothietan-3-yl)ethanyl- |
| Y.2032 | trifluoromethyl | 0 | 2-(thietan-3-yl)ethanyl- |
| Y.2033 | trifluoromethyl | 0 | 2-(trifluoromethoxy)phenyl- |
| Y.2034 | trifluoromethyl | 0 | 2,2-dimethyl-1,1-dioxo-thietan-3-yl- |
| Y.2035 | trifluoromethyl | 0 | 2,2-dimethyl-1-oxo-thietan-3-yl- |
| Y.2036 | trifluoromethyl | 0 | 2,2-dimethylthietan-3-yl- |
| Y.2037 | trifluoromethyl | 0 | 2,3-dichlorophenyl- |
| Y.2038 | trifluoromethyl | 0 | 2,3-difluoro-phenyl- |
| Y.2039 | trifluoromethyl | 0 | 2,4-dichlorophenyl- |
| Y.2040 | trifluoromethyl | 0 | 2,4-difluoro-phenyl- |
| Y.2041 | trifluoromethyl | 0 | 2,4-dimethylphenyl- |
| Y.2042 | trifluoromethyl | 0 | 2,5-dichlorophenyl- |
| Y.2043 | trifluoromethyl | 0 | 2,5-difluoro-phenyl- |
| Y.2044 | trifluoromethyl | 0 | 2,6-dichlorophenyl- |
| Y.2045 | trifluoromethyl | 0 | 2,6-difluoro-phenyl- |
| Y.2046 | trifluoromethyl | 0 | 2,6-diisopropylphenyl- |
| Y.2047 | trifluoromethyl | 0 | 2-bromo-4-fluorophenyl- |
| Y.2048 | trifluoromethyl | 0 | 2-bromoallyl- |
| Y.2049 | trifluoromethyl | 0 | 2-bromophenyl- |
| Y.2050 | trifluoromethyl | 0 | 2-butenyl- |
| Y.2051 | trifluoromethyl | 0 | 2-chloroallyl- |
| Y.2052 | trifluoromethyl | 0 | 2-chlorophenyl- |
| Y.2053 | trifluoromethyl | 0 | 2-chloropyrid-2-yl- |
| Y.2054 | trifluoromethyl | 0 | 2-chloropyrid-3-yl- |
| Y.2055 | trifluoromethyl | 0 | 2-cyanocyclopropyl- |
| Y.2056 | trifluoromethyl | 0 | 2-cyanoethyl- |
| Y.2057 | trifluoromethyl | 0 | 2-ethylphenyl- |
| Y.2058 | trifluoromethyl | 0 | 2-fluoroethyl- |
| Y.2059 | trifluoromethyl | 0 | 2-fluoro-phenyl- |
| Y.2060 | trifluoromethyl | 0 | 2-fluoropropyl- |
| Y.2061 | trifluoromethyl | 0 | 2-furylmethyl- |
| Y.2062 | trifluoromethyl | 0 | 2-hydroxyphenyl- |
| Y.2063 | trifluoromethyl | 0 | 2-methoxy-ethyl- |
| Y.2064 | trifluoromethyl | 0 | 2-methoxyphenyl- |
| Y.2065 | trifluoromethyl | 0 | 2-methoxy-prop-3-yl- |
| Y.2066 | trifluoromethyl | 0 | 2-methylallyl- |
| Y.2067 | trifluoromethyl | 0 | 2-methyl-but-1-yl- |
| Y.2068 | trifluoromethyl | 0 | 2-methyl-but-2-yl- |
| Y.2069 | trifluoromethyl | 0 | 2-methylbut-3-yn-2-yl- |
| Y.2070 | trifluoromethyl | 0 | 2-methylphenyl- |
| Y.2071 | trifluoromethyl | 0 | 2-methyl-prop-1-yl- |
| Y.2072 | trifluoromethyl | 0 | 2-methylsulfanyl-ethyl- |
| Y.2073 | trifluoromethyl | 0 | 2-methylsulfanyl-prop-3-yl- |
| Y.2074 | trifluoromethyl | 0 | 2-methyl-thiazol-4-yl- |
| Y.2075 | trifluoromethyl | 0 | 2-nitrophenyl- |
| Y.2076 | trifluoromethyl | 0 | 2-propyl- |
| Y.2077 | trifluoromethyl | 0 | 2-pyridyl- |
| Y.2078 | trifluoromethyl | 0 | 2-trifluoromethoxy-ethyl- |
| Y.2079 | trifluoromethyl | 0 | 3-(trifluoromethoxy)phenyl- |
| Y.2080 | trifluoromethyl | 0 | 3,3,3-trifluoro-2,2-difluoropropyl- |
| Y.2081 | trifluoromethyl | 0 | 3,3,3-trifluoro-butyl- |
| Y.2082 | trifluoromethyl | 0 | 3,3-dibromoallyl- |
| Y.2083 | trifluoromethyl | 0 | 3,3-dichloroallyl- |
| Y.2084 | trifluoromethyl | 0 | 3,4-dichlorophenyl- |
| Y.2085 | trifluoromethyl | 0 | 3,4-difluoro-phenyl- |
| Y.2086 | trifluoromethyl | 0 | 3,5-dichlorophenyl- |
| Y.2087 | trifluoromethyl | 0 | 3,5-difluoro-phenyl- |
| Y.2088 | trifluoromethyl | 0 | 3,6-difluoro-phenyl- |
| Y.2089 | trifluoromethyl | 0 | 3-bromoallyl- |
| Y.2090 | trifluoromethyl | 0 | 3-bromophenyl- |
| Y.2091 | trifluoromethyl | 0 | 3-butenyl- |
| Y.2092 | trifluoromethyl | 0 | 3-chloroallyl- |
| Y.2093 | trifluoromethyl | 0 | 3-chlorophenyl- |
| Y.2094 | trifluoromethyl | 0 | 3-chloropyrid-2-yl- |
| Y.2095 | trifluoromethyl | 0 | 3-cyanopropyl- |
| Y.2096 | trifluoromethyl | 0 | 3-ethylphenyl- |
| Y.2097 | trifluoromethyl | 0 | 3-hydroxyphenyl- |
| Y.2098 | trifluoromethyl | 0 | 3-methyl-1,1-dioxo-thietan-3-yl- |
| Y.2099 | trifluoromethyl | 0 | 3-methyl-1-oxo-thietan-3-yl- |
| Y.2100 | trifluoromethyl | 0 | 3-methyl-but-1-yl- |
| Y.2101 | trifluoromethyl | 0 | 3-methyl-but-2-yl- |
| Y.2102 | trifluoromethyl | 0 | 3-methylphenyl- |
| Y.2103 | trifluoromethyl | 0 | 3-nitrophenyl- |
| Y.2104 | trifluoromethyl | 0 | 3-pyridyl- |
| Y.2105 | trifluoromethyl | 0 | 4-(trifluoromethoxy)phenyl- |
| Y.2106 | trifluoromethyl | 0 | 4,5-dihydrothiazol-2-yl- |
| Y.2107 | trifluoromethyl | 0 | 4,5-dimethyl-4,5-dihydrothiazol-2-yl- |
| Y.2108 | trifluoromethyl | 0 | 4,5-dimethyl-thiazol-2-yl- |
| Y.2109 | trifluoromethyl | 0 | 4-bromophenyl- |
| Y.2110 | trifluoromethyl | 0 | 4-chlorophenyl- |
| Y.2111 | trifluoromethyl | 0 | 4-ethylphenyl- |
| Y.2112 | trifluoromethyl | 0 | 4-fluoro-phenyl- |
| Y.2113 | trifluoromethyl | 0 | 4H-1,2,4-triazol-3-yl- |
| Y.2114 | trifluoromethyl | 0 | 4-methoxyphenyl- |
| Y.2115 | trifluoromethyl | 0 | 4-methyl-4,5-dihydrothiazol-2-yl- |
| Y.2116 | trifluoromethyl | 0 | 4-methylphenyl- |
| Y.2117 | trifluoromethyl | 0 | 4-methylpyrid-2-yl |
| Y.2118 | trifluoromethyl | 0 | 4-nitrophenyl- |
| Y.2119 | trifluoromethyl | 0 | 4-pyridyl- |
| Y.2120 | trifluoromethyl | 0 | 5-methyl-4,5-dihydrothiazol-2-yl- |
| Y.2121 | trifluoromethyl | 0 | 5-methyl-thiazol-2-yl- |
| Y.2122 | trifluoromethyl | 0 | 6-methylpyrid-2-yl- |
| Y.2123 | trifluoromethyl | 0 | allyl- |
| Y.2124 | trifluoromethyl | 0 | but-2-ynyl- |
| Y.2125 | trifluoromethyl | 0 | but-3-ynyl- |
| Y.2126 | trifluoromethyl | 0 | cis-1-oxo-thietan-3-yl- |
| Y.2127 | trifluoromethyl | 0 | cis-1-oxo-thietan-3-ylmethyl- |
| Y.2128 | trifluoromethyl | 0 | cyanodimethylmethyl- |
| Y.2129 | trifluoromethyl | 0 | cyanoethyl- |

TABLE Y-continued

| | R5b | n | R2 |
|---|---|---|---|
| Y.2130 | trifluoromethyl | 0 | cyanomethyl- |
| Y.2131 | trifluoromethyl | 0 | cyclopentyl- |
| Y.2132 | trifluoromethyl | 0 | cyclopropyl-methyl- |
| Y.2133 | trifluoromethyl | 0 | methylpropargyl- |
| Y.2134 | trifluoromethyl | 0 | oxetan-3-yl- |
| Y.2135 | trifluoromethyl | 0 | pent-3-yl- |
| Y.2136 | trifluoromethyl | 0 | phenyl-methyl-methyl- |
| Y.2137 | trifluoromethyl | 0 | propargyl- |
| Y.2138 | trifluoromethyl | 0 | tert-butyl- |
| Y.2139 | trifluoromethyl | 0 | tetrazolyl- |
| Y.2140 | trifluoromethyl | 0 | thiazol-2-yl- |
| Y.2141 | trifluoromethyl | 0 | thiazol-4-yl- |
| Y.2142 | trifluoromethyl | 0 | thietan-2-ylmethyl- |
| Y.2143 | trifluoromethyl | 0 | thietan-3-ylmethyl- |
| Y.2144 | trifluoromethyl | 0 | ethyl- |
| Y.2145 | trifluoromethyl | 0 | 3,3,3-trifluoro-propyl- |
| Y.2146 | trifluoromethyl | 0 | but-2-yl- |
| Y.2147 | trifluoromethyl | 0 | (tetrahydrofuran-2-yl)-methyl- |
| Y.2148 | trifluoromethyl | 0 | benzyl- |
| Y.2149 | trifluoromethyl | 0 | (2-fluoro-phenyl)-methyl- |
| Y.2150 | trifluoromethyl | 0 | 1-phenyl-eth-1-yl- |
| Y.2151 | trifluoromethyl | 0 | (4-methoxy-phenyl)-methyl- |
| Y.2152 | trifluoromethyl | 0 | 1,1-dioxo-thietan-3-yl- |
| Y.2153 | trifluoromethyl | 0 | (2-chloro-pyrid-5-yl)-methyl- |
| Y.2154 | trifluoromethyl | 0 | 3-fluoro-phenyl- |
| Y.2155 | trifluoromethyl | 0 | n-butyl- |
| Y.2156 | trifluoromethyl | 0 | (pyrid-2-yl)-methyl- |
| Y.2157 | trifluoromethyl | 0 | 1,3-dimethyl-1H-pyrazol-5-yl- |
| Y.2158 | trifluoromethyl | 0 | 4-methyl-thiazol-2-yl- |
| Y.2159 | trifluoromethyl | 0 | 3-methyl-thietan-3-yl- |
| Y.2160 | trifluoromethyl | 0 | 1,1-dimethyl-2-methylsulfanyl-ethyl |
| Y.2161 | trifluoromethyl | 0 | 1-oxo-thietan-3-yl- |
| Y.2162 | trifluoromethyl | 0 | thietan-3-yl- |
| Y.2163 | trifluoromethyl | 0 | bicyclo[2.2.1]hept-2-yl- |
| Y.2164 | trifluoromethyl | 0 | cyclobutyl- |
| Y.2165 | trifluoromethyl | 0 | methyl- |
| Y.2166 | trifluoromethyl | 0 | cyclopropyl- |
| Y.2167 | trifluoromethyl | 0 | n-propyl- |
| Y.2168 | trifluoromethyl | 0 | 2,2-difluoroethyl- |
| Y.2169 | trifluoromethyl | 0 | 1-methoxy-prop-2-yl- |
| Y.2170 | trifluoromethyl | 0 | N-(2,2,2-trifluoro-ethyl)-acetamide-2-yl |
| Y.2171 | trifluoromethyl | 0 | 2,2,2-trifluoro-ethyl- |
| Y.2172 | trifluoromethyl | 1 | (1,1-dioxothietan-2-yl)methyl- |
| Y.2173 | trifluoromethyl | 1 | (1-oxothietan-2-yl)methyl- |
| Y.2174 | trifluoromethyl | 1 | (2-methoxy-phenyl)-methyl- |
| Y.2175 | trifluoromethyl | 1 | (3-fluoro-phenyl)-methyl- |
| Y.2176 | trifluoromethyl | 1 | (4,4-dimethyl-4,5-dihydrothiazol-2-yl)-methyl- |
| Y.2177 | trifluoromethyl | 1 | (4,5-dihydrothiazol-2-yl)-methyl- |
| Y.2178 | trifluoromethyl | 1 | (4,5-dimethyl-4,5-dihydrothiazol-2-yl)-methyl- |
| Y.2179 | trifluoromethyl | 1 | (4-fluoro-phenyl)-methyl- |
| Y.2180 | trifluoromethyl | 1 | (4-methyl-4,5-dihydrothiazol-2-yl)-methyl- |
| Y.2181 | trifluoromethyl | 1 | (5-methyl-4,5-dihydrothiazol-2-yl)-methyl- |
| Y.2182 | trifluoromethyl | 1 | (pyrid-3-yl)-methyl- |
| Y.2183 | trifluoromethyl | 1 | (pyrid-4-yl)-methyl- |
| Y.2184 | trifluoromethyl | 1 | (tetrahydrothiophene-2-yl)-methyl- |
| Y.2185 | trifluoromethyl | 1 | (tetrahydrothiophene-3-yl)-methyl- |
| Y.2186 | trifluoromethyl | 1 | (thiazol-2-yl)-methyl- |
| Y.2187 | trifluoromethyl | 1 | (thiazol-2-yl)-methylmethyl- |
| Y.2188 | trifluoromethyl | 1 | (thiazol-4-yl)-methyl- |
| Y.2189 | trifluoromethyl | 1 | (thiazol-5-yl)-methyl- |
| Y.2190 | trifluoromethyl | 1 | 1,1-dioxo-thietan-3-ylmethyl- |
| Y.2191 | trifluoromethyl | 1 | 1-cyanocyclobutyl- |
| Y.2192 | trifluoromethyl | 1 | 1-cyanocyclopentyl- |
| Y.2193 | trifluoromethyl | 1 | 1-cyanocyclopropyl- |
| Y.2194 | trifluoromethyl | 1 | 1-fluoroprop-2-yl- |
| Y.2195 | trifluoromethyl | 1 | 1-methylallyl- |
| Y.2196 | trifluoromethyl | 1 | 1-methylsulfanyl-prop-2-yl- |
| Y.2197 | trifluoromethyl | 1 | 2-(1,1-dioxothietan-3-yl)ethanyl- |
| Y.2198 | trifluoromethyl | 1 | 2-(1-oxothietan-3-yl)ethanyl- |
| Y.2199 | trifluoromethyl | 1 | 2-(thietan-3-yl)ethanyl- |
| Y.2200 | trifluoromethyl | 1 | 2-(trifluoromethoxy)phenyl- |
| Y.2201 | trifluoromethyl | 1 | 2,2-dimethyl-1,1-dioxo-thietan-3-yl- |
| Y.2202 | trifluoromethyl | 1 | 2,2-dimethyl-1-oxo-thietan-3-yl- |
| Y.2203 | trifluoromethyl | 1 | 2,2-dimethylthietan-3-yl- |
| Y.2204 | trifluoromethyl | 1 | 2,3-dichlorophenyl- |
| Y.2205 | trifluoromethyl | 1 | 2,3-difluoro-phenyl- |
| Y.2206 | trifluoromethyl | 1 | 2,4-dichlorophenyl- |
| Y.2207 | trifluoromethyl | 1 | 2,4-difluoro-phenyl- |
| Y.2208 | trifluoromethyl | 1 | 2,4-dimethylphenyl- |
| Y.2209 | trifluoromethyl | 1 | 2,5-dichlorophenyl- |
| Y.2210 | trifluoromethyl | 1 | 2,5-difluoro-phenyl- |
| Y.2211 | trifluoromethyl | 1 | 2,6-dichlorophenyl- |
| Y.2212 | trifluoromethyl | 1 | 2,6-difluoro-phenyl- |
| Y.2213 | trifluoromethyl | 1 | 2,6-diisopropylphenyl- |
| Y.2214 | trifluoromethyl | 1 | 2-bromo-4-fluorophenyl- |
| Y.2215 | trifluoromethyl | 1 | 2-bromoallyl- |
| Y.2216 | trifluoromethyl | 1 | 2-bromophenyl- |
| Y.2217 | trifluoromethyl | 1 | 2-butenyl- |
| Y.2218 | trifluoromethyl | 1 | 2-chloroallyl- |
| Y.2219 | trifluoromethyl | 1 | 2-chlorophenyl- |
| Y.2220 | trifluoromethyl | 1 | 2-chloropyrid-2-yl- |
| Y.2221 | trifluoromethyl | 1 | 2-chloropyrid-3-yl- |
| Y.2222 | trifluoromethyl | 1 | 2-cyanocyclopropyl- |
| Y.2223 | trifluoromethyl | 1 | 2-cyanoethyl- |
| Y.2224 | trifluoromethyl | 1 | 2-ethylphenyl- |
| Y.2225 | trifluoromethyl | 1 | 2-fluoroethyl- |
| Y.2226 | trifluoromethyl | 1 | 2-fluoro-phenyl- |
| Y.2227 | trifluoromethyl | 1 | 2-fluoropropyl- |
| Y.2228 | trifluoromethyl | 1 | 2-furylmethyl- |
| Y.2229 | trifluoromethyl | 1 | 2-hydroxyphenyl- |
| Y.2230 | trifluoromethyl | 1 | 2-methoxy-ethyl- |
| Y.2231 | trifluoromethyl | 1 | 2-methoxyphenyl- |
| Y.2232 | trifluoromethyl | 1 | 2-methoxy-prop-3-yl- |
| Y.2233 | trifluoromethyl | 1 | 2-methylallyl- |
| Y.2234 | trifluoromethyl | 1 | 2-methyl-but-1-yl- |
| Y.2235 | trifluoromethyl | 1 | 2-methyl-but-2-yl- |
| Y.2236 | trifluoromethyl | 1 | 2-methylbut-3-yn-2-yl- |
| Y.2237 | trifluoromethyl | 1 | 2-methylphenyl- |
| Y.2238 | trifluoromethyl | 1 | 2-methyl-prop-1-yl- |
| Y.2239 | trifluoromethyl | 1 | 2-methylsulfanyl-ethyl- |
| Y.2240 | trifluoromethyl | 1 | 2-methylsulfanyl-prop-3-yl- |
| Y.2241 | trifluoromethyl | 1 | 2-methyl-thiazol-4-yl- |
| Y.2242 | trifluoromethyl | 1 | 2-nitrophenyl- |
| Y.2243 | trifluoromethyl | 1 | 2-propyl- |
| Y.2244 | trifluoromethyl | 1 | 2-pyridyl- |
| Y.2245 | trifluoromethyl | 1 | 2-trifluoromethoxy-ethyl- |
| Y.2246 | trifluoromethyl | 1 | 3-(trifluoromethoxy)phenyl- |
| Y.2247 | trifluoromethyl | 1 | 3,3,3-trifluoro-2,2-difluoropropyl- |
| Y.2248 | trifluoromethyl | 1 | 3,3,3-trifluoro-butyl- |
| Y.2249 | trifluoromethyl | 1 | 3,3-dibromoallyl- |
| Y.2250 | trifluoromethyl | 1 | 3,3-dichloroallyl- |
| Y.2251 | trifluoromethyl | 1 | 3,4-dichlorophenyl- |
| Y.2252 | trifluoromethyl | 1 | 3,4-difluoro-phenyl- |
| Y.2253 | trifluoromethyl | 1 | 3,5-dichlorophenyl- |
| Y.2254 | trifluoromethyl | 1 | 3,5-difluoro-phenyl- |
| Y.2255 | trifluoromethyl | 1 | 3,6-difluoro-phenyl- |
| Y.2256 | trifluoromethyl | 1 | 3-bromoallyl- |
| Y.2257 | trifluoromethyl | 1 | 3-bromophenyl- |
| Y.2258 | trifluoromethyl | 1 | 3-butenyl- |
| Y.2259 | trifluoromethyl | 1 | 3-chloroallyl- |
| Y.2260 | trifluoromethyl | 1 | 3-chlorophenyl- |
| Y.2261 | trifluoromethyl | 1 | 3-chloropyrid-2-yl- |
| Y.2262 | trifluoromethyl | 1 | 3-cyanopropyl- |
| Y.2263 | trifluoromethyl | 1 | 3-ethylphenyl- |
| Y.2264 | trifluoromethyl | 1 | 3-hydroxyphenyl- |
| Y.2265 | trifluoromethyl | 1 | 3-methyl-1,1-dioxo-thietan-3-yl- |
| Y.2266 | trifluoromethyl | 1 | 3-methyl-1-oxo-thietan-3-yl- |
| Y.2267 | trifluoromethyl | 1 | 3-methyl-but-1-yl- |
| Y.2268 | trifluoromethyl | 1 | 3-methyl-but-2-yl- |
| Y.2269 | trifluoromethyl | 1 | 3-methylphenyl- |
| Y.2270 | trifluoromethyl | 1 | 3-nitrophenyl- |
| Y.2271 | trifluoromethyl | 1 | 3-pyridyl- |
| Y.2272 | trifluoromethyl | 1 | 4-(trifluoromethoxy)phenyl- |
| Y.2273 | trifluoromethyl | 1 | 4,5-dihydrothiazol-2-yl- |
| Y.2274 | trifluoromethyl | 1 | 4,5-dimethyl-4,5-dihydrothiazol-2-yl- |
| Y.2275 | trifluoromethyl | 1 | 4,5-dimethyl-thiazol-2-yl- |
| Y.2276 | trifluoromethyl | 1 | 4-bromophenyl- |
| Y.2277 | trifluoromethyl | 1 | 4-chlorophenyl- |
| Y.2278 | trifluoromethyl | 1 | 4-ethylphenyl- |
| Y.2279 | trifluoromethyl | 1 | 4-fluoro-phenyl- |
| Y.2280 | trifluoromethyl | 1 | 4H-1,2,4-triazol-3-yl- |
| Y.2281 | trifluoromethyl | 1 | 4-methoxyphenyl- |

TABLE Y-continued

| | R5b | n | R2 |
|---|---|---|---|
| Y.2282 | trifluoromethyl | 1 | 4-methyl-4,5-dihydrothiazol-2-yl- |
| Y.2283 | trifluoromethyl | 1 | 4-methylphenyl- |
| Y.2284 | trifluoromethyl | 1 | 4-methylpyrid-2-yl |
| Y.2285 | trifluoromethyl | 1 | 4-nitrophenyl- |
| Y.2286 | trifluoromethyl | 1 | 4-pyridyl- |
| Y.2287 | trifluoromethyl | 1 | 5-methyl-4,5-dihydrothiazol-2-yl- |
| Y.2288 | trifluoromethyl | 1 | 5-methyl-thiazol-2-yl- |
| Y.2289 | trifluoromethyl | 1 | 6-methylpyrid-2-yl |
| Y.2290 | trifluoromethyl | 1 | allyl- |
| Y.2291 | trifluoromethyl | 1 | but-2-ynyl- |
| Y.2292 | trifluoromethyl | 1 | but-3-ynyl- |
| Y.2293 | trifluoromethyl | 1 | cis-1-oxo-thietan-3-yl- |
| Y.2294 | trifluoromethyl | 1 | cis-1-oxo-thietan-3-ylmethyl- |
| Y.2295 | trifluoromethyl | 1 | cyanodimethylmethyl- |
| Y.2296 | trifluoromethyl | 1 | cyanoethyl- |
| Y.2297 | trifluoromethyl | 1 | cyanomethyl- |
| Y.2298 | trifluoromethyl | 1 | cyclopentyl- |
| Y.2299 | trifluoromethyl | 1 | cyclopropyl-methyl- |
| Y.2300 | trifluoromethyl | 1 | methylpropargyl- |
| Y.2301 | trifluoromethyl | 1 | oxetan-3-yl- |
| Y.2302 | trifluoromethyl | 1 | pent-3-yl- |
| Y.2303 | trifluoromethyl | 1 | phenyl-methyl-methyl- |
| Y.2304 | trifluoromethyl | 1 | propargyl- |
| Y.2305 | trifluoromethyl | 1 | tert-butyl- |
| Y.2306 | trifluoromethyl | 1 | tetrazolyl- |
| Y.2307 | trifluoromethyl | 1 | thiazol-2-yl- |
| Y.2308 | trifluoromethyl | 1 | thiazol-4-yl- |
| Y.2309 | trifluoromethyl | 1 | thietan-2-ylmethyl- |
| Y.2310 | trifluoromethyl | 1 | thietan-3-ylmethyl- |
| Y.2311 | trifluoromethyl | 1 | ethyl- |
| Y.2312 | trifluoromethyl | 1 | 3,3,3-trifluoro-propyl- |
| Y.2313 | trifluoromethyl | 1 | but-2-yl- |
| Y.2314 | trifluoromethyl | 1 | (tetrahydrofuran-2-yl)-methyl- |
| Y.2315 | trifluoromethyl | 1 | benzyl- |
| Y.2316 | trifluoromethyl | 1 | (2-fluoro-phenyl)-methyl- |
| Y.2317 | trifluoromethyl | 1 | 1-phenyl-eth-1-yl- |
| Y.2318 | trifluoromethyl | 1 | (4-methoxy-phenyl)-methyl- |
| Y.2319 | trifluoromethyl | 1 | 1,1-dioxo-thietan-3-yl- |
| Y.2320 | trifluoromethyl | 1 | (2-chloro-pyrid-5-yl)-methyl- |
| Y.2321 | trifluoromethyl | 1 | 3-fluoro-phenyl- |
| Y.2322 | trifluoromethyl | 1 | n-butyl- |
| Y.2323 | trifluoromethyl | 1 | (pyrid-2-yl)-methyl- |
| Y.2324 | trifluoromethyl | 1 | 1,3-dimethyl-1H-pyrazol-5-yl- |
| Y.2325 | trifluoromethyl | 1 | 4-methyl-thiazol-2-yl- |
| Y.2326 | trifluoromethyl | 1 | 3-methyl-thietan-3-yl- |
| Y.2327 | trifluoromethyl | 1 | 1,1-dimethyl-2-methylsulfanyl-ethyl |
| Y.2328 | trifluoromethyl | 1 | 1-oxo-thietan-3-yl- |
| Y.2329 | trifluoromethyl | 1 | thietan-3-yl- |
| Y.2330 | trifluoromethyl | 1 | bicyclo[2.2.1]hept-2-yl- |
| Y.2331 | trifluoromethyl | 1 | cyclobutyl- |
| Y.2332 | trifluoromethyl | 1 | methyl- |
| Y.2333 | trifluoromethyl | 1 | cyclopropyl- |
| Y.2334 | trifluoromethyl | 1 | n-propyl- |
| Y.2335 | trifluoromethyl | 1 | 2,2-difluoroethyl- |
| Y.2336 | trifluoromethyl | 1 | 1-methoxy-prop-2-yl- |
| Y.2337 | trifluoromethyl | 1 | N-(2,2,2-trifluoro-ethyl)-acetamide-2-yl |
| Y.2338 | trifluoromethyl | 1 | 2,2,2-trifluoro-ethyl- |
| Y.2339 | trifluoromethyl | 2 | (1,1-dioxothietan-2-yl)methyl- |
| Y.2340 | trifluoromethyl | 2 | (1-oxothietan-2-yl)methyl- |
| Y.2341 | trifluoromethyl | 2 | (2-methoxy-phenyl)-methyl- |
| Y.2342 | trifluoromethyl | 2 | (3-fluoro-phenyl)-methyl- |
| Y.2343 | trifluoromethyl | 2 | (4,4-dimethyl-4,5-dihydrothiazol-2-yl)-methyl- |
| Y.2344 | trifluoromethyl | 2 | (4,5-dihydrothiazol-2-yl)-methyl- |
| Y.2345 | trifluoromethyl | 2 | (4,5-dimethyl-4,5-dihydrothiazol-2-yl)-methyl- |
| Y.2346 | trifluoromethyl | 2 | (4-fluoro-phenyl)-methyl- |
| Y.2347 | trifluoromethyl | 2 | (4-methyl-4,5-dihydrothiazol-2-yl)-methyl- |
| Y.2348 | trifluoromethyl | 2 | (5-methyl-4,5-dihydrothiazol-2-yl)-methyl- |
| Y.2349 | trifluoromethyl | 2 | (pyrid-3-yl)-methyl- |
| Y.2350 | trifluoromethyl | 2 | (pyrid-4-yl)-methyl- |
| Y.2351 | trifluoromethyl | 2 | (tetrahydrothiophene-2-yl)-methyl- |
| Y.2352 | trifluoromethyl | 2 | (tetrahydrothiophene-3-yl)-methyl- |
| Y.2353 | trifluoromethyl | 2 | (thiazol-2-yl)-methyl- |
| Y.2354 | trifluoromethyl | 2 | (thiazol-2-yl)-methylmethyl- |
| Y.2355 | trifluoromethyl | 2 | (thiazol-4-yl)-methyl- |
| Y.2356 | trifluoromethyl | 2 | (thiazol-5-yl)-methyl- |
| Y.2357 | trifluoromethyl | 2 | 1,1-dioxo-thietan-3-ylmethyl- |
| Y.2358 | trifluoromethyl | 2 | 1-cyanocyclobutyl- |
| Y.2359 | trifluoromethyl | 2 | 1-cyanocyclopentyl- |
| Y.2360 | trifluoromethyl | 2 | 1-cyanocyclopropyl- |
| Y.2361 | trifluoromethyl | 2 | 1-fluoroprop-2-yl- |
| Y.2362 | trifluoromethyl | 2 | 1-methylallyl- |
| Y.2363 | trifluoromethyl | 2 | 1-methylsulfanyl-prop-2-yl- |
| Y.2364 | trifluoromethyl | 2 | 2-(1,1-dioxothietan-3-yl)ethanyl- |
| Y.2365 | trifluoromethyl | 2 | 2-(1-oxothietan-3-yl)ethanyl- |
| Y.2366 | trifluoromethyl | 2 | 2-(thietan-3-yl)ethanyl- |
| Y.2367 | trifluoromethyl | 2 | 2-(trifluoromethoxy)phenyl- |
| Y.2368 | trifluoromethyl | 2 | 2,2-dimethyl-1,1-dioxo-thietan-3-yl- |
| Y.2369 | trifluoromethyl | 2 | 2,2-dimethyl-1-oxo-thietan-3-yl- |
| Y.2370 | trifluoromethyl | 2 | 2,2-dimethylthietan-3-yl- |
| Y.2371 | trifluoromethyl | 2 | 2,3-dichlorophenyl- |
| Y.2372 | trifluoromethyl | 2 | 2,3-difluoro-phenyl- |
| Y.2373 | trifluoromethyl | 2 | 2,4-dichlorophenyl- |
| Y.2374 | trifluoromethyl | 2 | 2,4-difluoro-phenyl- |
| Y.2375 | trifluoromethyl | 2 | 2,4-dimethylphenyl- |
| Y.2376 | trifluoromethyl | 2 | 2,5-dichlorophenyl- |
| Y.2377 | trifluoromethyl | 2 | 2,5-difluoro-phenyl- |
| Y.2378 | trifluoromethyl | 2 | 2,6-dichlorophenyl- |
| Y.2379 | trifluoromethyl | 2 | 2,6-difluoro-phenyl- |
| Y.2380 | trifluoromethyl | 2 | 2,6-diisopropylphenyl- |
| Y.2381 | trifluoromethyl | 2 | 2-bromo-4-fluorophenyl- |
| Y.2382 | trifluoromethyl | 2 | 2-bromoallyl- |
| Y.2383 | trifluoromethyl | 2 | 2-bromophenyl- |
| Y.2384 | trifluoromethyl | 2 | 2-butenyl- |
| Y.2385 | trifluoromethyl | 2 | 2-chloroallyl- |
| Y.2386 | trifluoromethyl | 2 | 2-chlorophenyl- |
| Y.2387 | trifluoromethyl | 2 | 2-chloropyrid-2-yl- |
| Y.2388 | trifluoromethyl | 2 | 2-chloropyrid-3-yl- |
| Y.2389 | trifluoromethyl | 2 | 2-cyanocyclopropyl- |
| Y.2390 | trifluoromethyl | 2 | 2-cyanoethyl- |
| Y.2391 | trifluoromethyl | 2 | 2-ethylphenyl- |
| Y.2392 | trifluoromethyl | 2 | 2-fluoroethyl- |
| Y.2393 | trifluoromethyl | 2 | 2-fluoro-phenyl- |
| Y.2394 | trifluoromethyl | 2 | 2-fluoropropyl- |
| Y.2395 | trifluoromethyl | 2 | 2-furylmethyl- |
| Y.2396 | trifluoromethyl | 2 | 2-hydroxyphenyl- |
| Y.2397 | trifluoromethyl | 2 | 2-methoxy-ethyl- |
| Y.2398 | trifluoromethyl | 2 | 2-methoxyphenyl- |
| Y.2399 | trifluoromethyl | 2 | 2-methoxy-prop-3-yl- |
| Y.2400 | trifluoromethyl | 2 | 2-methylallyl- |
| Y.2401 | trifluoromethyl | 2 | 2-methyl-but-1-yl- |
| Y.2402 | trifluoromethyl | 2 | 2-methyl-but-2-yl- |
| Y.2403 | trifluoromethyl | 2 | 2-methylbut-3-yn-2-yl- |
| Y.2404 | trifluoromethyl | 2 | 2-methylphenyl- |
| Y.2405 | trifluoromethyl | 2 | 2-methyl-prop-1-yl- |
| Y.2406 | trifluoromethyl | 2 | 2-methylsulfanyl-ethyl- |
| Y.2407 | trifluoromethyl | 2 | 2-methylsulfanyl-prop-3-yl- |
| Y.2408 | trifluoromethyl | 2 | 2-methyl-thiazol-4-yl- |
| Y.2409 | trifluoromethyl | 2 | 2-nitrophenyl- |
| Y.2410 | trifluoromethyl | 2 | 2-propyl- |
| Y.2411 | trifluoromethyl | 2 | 2-pyridyl- |
| Y.2412 | trifluoromethyl | 2 | 2-trifluoromethoxy-ethyl- |
| Y.2413 | trifluoromethyl | 2 | 3-(trifluoromethoxy)phenyl- |
| Y.2414 | trifluoromethyl | 2 | 3,3,3-trifluoro-2,2-difluoropropyl- |
| Y.2415 | trifluoromethyl | 2 | 3,3,3-trifluoro-butyl- |
| Y.2416 | trifluoromethyl | 2 | 3,3-dibromoallyl- |
| Y.2417 | trifluoromethyl | 2 | 3,3-dichloroallyl- |
| Y.2418 | trifluoromethyl | 2 | 3,4-dichlorophenyl- |
| Y.2419 | trifluoromethyl | 2 | 3,4-difluoro-phenyl- |
| Y.2420 | trifluoromethyl | 2 | 3,5-dichlorophenyl- |
| Y.2421 | trifluoromethyl | 2 | 3,5-difluoro-phenyl- |
| Y.2422 | trifluoromethyl | 2 | 3,6-difluoro-phenyl- |
| Y.2423 | trifluoromethyl | 2 | 3-bromoallyl- |
| Y.2424 | trifluoromethyl | 2 | 3-bromophenyl- |
| Y.2425 | trifluoromethyl | 2 | 3-butenyl- |
| Y.2426 | trifluoromethyl | 2 | 3-chloroallyl- |
| Y.2427 | trifluoromethyl | 2 | 3-chlorophenyl- |
| Y.2428 | trifluoromethyl | 2 | 3-chloropyrid-2-yl- |
| Y.2429 | trifluoromethyl | 2 | 3-cyanopropyl- |
| Y.2430 | trifluoromethyl | 2 | 3-ethylphenyl- |
| Y.2431 | trifluoromethyl | 2 | 3-hydroxyphenyl- |
| Y.2432 | trifluoromethyl | 2 | 3-methyl-1,1-dioxo-thietan-3-yl- |
| Y.2433 | trifluoromethyl | 2 | 3-methyl-1-oxo-thietan-3-yl- |

TABLE Y-continued

| | R5b | n | R2 |
|---|---|---|---|
| Y.2434 | trifluoromethyl | 2 | 3-methyl-but-1-yl- |
| Y.2435 | trifluoromethyl | 2 | 3-methyl-but-2-yl- |
| Y.2436 | trifluoromethyl | 2 | 3-methylphenyl- |
| Y.2437 | trifluoromethyl | 2 | 3-nitrophenyl- |
| Y.2438 | trifluoromethyl | 2 | 3-pyridyl- |
| Y.2439 | trifluoromethyl | 2 | 4-(trifluoromethoxy)phenyl- |
| Y.2440 | trifluoromethyl | 2 | 4,5-dihydrothiazol-2-yl- |
| Y.2441 | trifluoromethyl | 2 | 4,5-dimethyl-4,5-dihydrothiazol-2-yl- |
| Y.2442 | trifluoromethyl | 2 | 4,5-dimethyl-thiazol-2-yl- |
| Y.2443 | trifluoromethyl | 2 | 4-bromophenyl- |
| Y.2444 | trifluoromethyl | 2 | 4-chlorophenyl- |
| Y.2445 | trifluoromethyl | 2 | 4-ethylphenyl- |
| Y.2446 | trifluoromethyl | 2 | 4-fluoro-phenyl- |
| Y.2447 | trifluoromethyl | 2 | 4H-1,2,4-triazol-3-yl- |
| Y.2448 | trifluoromethyl | 2 | 4-methoxyphenyl- |
| Y.2449 | trifluoromethyl | 2 | 4-methyl-4,5-dihydrothiazol-2-yl- |
| Y.2450 | trifluoromethyl | 2 | 4-methylphenyl- |
| Y.2451 | trifluoromethyl | 2 | 4-methylpyrid-2-yl |
| Y.2452 | trifluoromethyl | 2 | 4-nitrophenyl- |
| Y.2453 | trifluoromethyl | 2 | 4-pyridyl- |
| Y.2454 | trifluoromethyl | 2 | 5-methyl-4,5-dihydrothiazol-2-yl- |
| Y.2455 | trifluoromethyl | 2 | 5-methyl-thiazol-2-yl- |
| Y.2456 | trifluoromethyl | 2 | 6-methylpyrid-2-yl- |
| Y.2457 | trifluoromethyl | 2 | allyl- |
| Y.2458 | trifluoromethyl | 2 | but-2-ynyl- |
| Y.2459 | trifluoromethyl | 2 | but-3-ynyl- |
| Y.2460 | trifluoromethyl | 2 | cis-1-oxo-thietan-3-yl- |
| Y.2461 | trifluoromethyl | 2 | cis-1-oxo-thietan-3-ylmethyl- |
| Y.2462 | trifluoromethyl | 2 | cyanodimethylmethyl- |
| Y.2463 | trifluoromethyl | 2 | cyanoethyl- |
| Y.2464 | trifluoromethyl | 2 | cyanomethyl- |
| Y.2465 | trifluoromethyl | 2 | cyclopentyl- |
| Y.2466 | trifluoromethyl | 2 | cyclopropyl-methyl- |
| Y.2467 | trifluoromethyl | 2 | methylpropargyl- |
| Y.2468 | trifluoromethyl | 2 | oxetan-3-yl- |
| Y.2469 | trifluoromethyl | 2 | pent-3-yl- |
| Y.2470 | trifluoromethyl | 2 | phenyl-methyl-methyl- |
| Y.2471 | trifluoromethyl | 2 | propargyl- |
| Y.2472 | trifluoromethyl | 2 | tert-butyl- |
| Y.2473 | trifluoromethyl | 2 | tetrazolyl- |
| Y.2474 | trifluoromethyl | 2 | thiazol-2-yl- |
| Y.2475 | trifluoromethyl | 2 | thiazol-4-yl- |
| Y.2476 | trifluoromethyl | 2 | thietan-2-ylmethyl- |
| Y.2477 | trifluoromethyl | 2 | thietan-3-ylmethyl- |
| Y.2478 | trifluoromethyl | 2 | ethyl- |
| Y.2479 | trifluoromethyl | 2 | 3,3,3-trifluoro-propyl- |
| Y.2480 | trifluoromethyl | 2 | but-2-yl- |
| Y.2481 | trifluoromethyl | 2 | (tetrahydrofuran-2-yl)-methyl- |
| Y.2482 | trifluoromethyl | 2 | benzyl- |
| Y.2483 | trifluoromethyl | 2 | (2-fluoro-phenyl)-methyl- |
| Y.2484 | trifluoromethyl | 2 | 1-phenyl-eth-1-yl- |
| Y.2485 | trifluoromethyl | 2 | (4-methoxy-phenyl)-methyl- |
| Y.2486 | trifluoromethyl | 2 | 1,1-dioxo-thietan-3-yl- |
| Y.2487 | trifluoromethyl | 2 | (2-chloro-pyrid-5-yl)-methyl- |
| Y.2488 | trifluoromethyl | 2 | 3-fluoro-phenyl- |
| Y.2489 | trifluoromethyl | 2 | n-butyl- |
| Y.2490 | trifluoromethyl | 2 | (pyrid-2-yl)-methyl- |
| Y.2491 | trifluoromethyl | 2 | 1,3-dimethyl-1H-pyrazol-5-yl- |
| Y.2492 | trifluoromethyl | 2 | 4-methyl-thiazol-2-yl- |
| Y.2493 | trifluoromethyl | 2 | 3-methyl-thietan-3-yl- |
| Y.2494 | trifluoromethyl | 2 | 1,1-dimethyl-2-methylsulfanyl-ethyl |
| Y.2495 | trifluoromethyl | 2 | 1-oxo-thietan-3-yl- |
| Y.2496 | trifluoromethyl | 2 | thietan-3-yl- |
| Y.2497 | trifluoromethyl | 2 | bicyclo[2.2.1]hept-2-yl- |
| Y.2498 | trifluoromethyl | 2 | cyclobutyl- |
| Y.2499 | trifluoromethyl | 2 | methyl- |
| Y.2500 | trifluoromethyl | 2 | cyclopropyl- |
| Y.2501 | trifluoromethyl | 2 | n-propyl- |
| Y.2502 | trifluoromethyl | 2 | 2,2-difluoroethyl- |
| Y.2503 | trifluoromethyl | 2 | 1-methoxy-prop-2-yl- |
| Y.2504 | trifluoromethyl | 2 | N-(2,2,2-trifluoro-ethyl)-acetamide-2-yl |
| Y.2505 | trifluoromethyl | 2 | 2,2,2-trifluoro-ethyl- |
| Y.2506 | ethyl | 0 | (1,1-dioxothietan-2-yl)methyl- |
| Y.2507 | ethyl | 0 | (1-oxothietan-2-yl)methyl- |
| Y.2508 | ethyl | 0 | (2-methoxy-phenyl)-methyl- |
| Y.2509 | ethyl | 0 | (3-fluoro-phenyl)-methyl- |
| Y.2510 | ethyl | 0 | (4,4-dimethyl-4,5-dihydrothiazol-2-yl)-methyl- |
| Y.2511 | ethyl | 0 | (4,5-dihydrothiazol-2-yl)-methyl- |
| Y.2512 | ethyl | 0 | (4,5-dimethyl-4,5-dihydrothiazol-2-yl)-methyl- |
| Y.2513 | ethyl | 0 | (4-fluoro-phenyl)-methyl- |
| Y.2514 | ethyl | 0 | (4-methyl-4,5-dihydrothiazol-2-yl)-methyl- |
| Y.2515 | ethyl | 0 | (5-methyl-4,5-dihydrothiazol-2-yl)-methyl- |
| Y.2516 | ethyl | 0 | (pyrid-3-yl)-methyl- |
| Y.2517 | ethyl | 0 | (pyrid-4-yl)-methyl- |
| Y.2518 | ethyl | 0 | (tetrahydrothiophene-2-yl)-methyl- |
| Y.2519 | ethyl | 0 | (tetrahydrothiophene-3-yl)-methyl- |
| Y.2520 | ethyl | 0 | (thiazol-2-yl)-methyl- |
| Y.2521 | ethyl | 0 | (thiazol-2-yl)-methylmethyl- |
| Y.2522 | ethyl | 0 | (thiazol-4-yl)-methyl- |
| Y.2523 | ethyl | 0 | (thiazol-5-yl)-methyl- |
| Y.2524 | ethyl | 0 | 1,1-dioxo-thietan-3-ylmethyl- |
| Y.2525 | ethyl | 0 | 1-cyanocyclobutyl- |
| Y.2526 | ethyl | 0 | 1-cyanocyclopentyl- |
| Y.2527 | ethyl | 0 | 1-cyanocyclopropyl- |
| Y.2528 | ethyl | 0 | 1-fluoroprop-2-yl- |
| Y.2529 | ethyl | 0 | 1-methylallyl- |
| Y.2530 | ethyl | 0 | 1-methylsulfanyl-prop-2-yl- |
| Y.2531 | ethyl | 0 | 2-(1,1-dioxothietan-3-yl)ethanyl- |
| Y.2532 | ethyl | 0 | 2-(1-oxothietan-3-yl)ethanyl- |
| Y.2533 | ethyl | 0 | 2-(thietan-3-yl)ethanyl- |
| Y.2534 | ethyl | 0 | 2-(trifluoromethoxy)phenyl- |
| Y.2535 | ethyl | 0 | 2,2-dimethyl-1,1-dioxo-thietan-3-yl- |
| Y.2536 | ethyl | 0 | 2,2-dimethyl-1-oxo-thietan-3-yl- |
| Y.2537 | ethyl | 0 | 2,2-dimethylthietan-3-yl- |
| Y.2538 | ethyl | 0 | 2,3-dichlorophenyl- |
| Y.2539 | ethyl | 0 | 2,3-difluoro-phenyl- |
| Y.2540 | ethyl | 0 | 2,4-dichlorophenyl- |
| Y.2541 | ethyl | 0 | 2,4-difluoro-phenyl- |
| Y.2542 | ethyl | 0 | 2,4-dimethylphenyl- |
| Y.2543 | ethyl | 0 | 2,5-dichlorophenyl- |
| Y.2544 | ethyl | 0 | 2,5-difluoro-phenyl- |
| Y.2545 | ethyl | 0 | 2,6-dichlorophenyl- |
| Y.2546 | ethyl | 0 | 2,6-difluoro-phenyl- |
| Y.2547 | ethyl | 0 | 2,6-diisopropylphenyl- |
| Y.2548 | ethyl | 0 | 2-bromo-4-fluorophenyl- |
| Y.2549 | ethyl | 0 | 2-bromoallyl- |
| Y.2550 | ethyl | 0 | 2-bromophenyl- |
| Y.2551 | ethyl | 0 | 2-butenyl- |
| Y.2552 | ethyl | 0 | 2-chloroallyl- |
| Y.2553 | ethyl | 0 | 2-chlorophenyl- |
| Y.2554 | ethyl | 0 | 2-chloropyrid-2-yl- |
| Y.2555 | ethyl | 0 | 2-chloropyrid-3-yl- |
| Y.2556 | ethyl | 0 | 2-cyanocyclopropyl- |
| Y.2557 | ethyl | 0 | 2-cyanoethyl- |
| Y.2558 | ethyl | 0 | 2-ethylphenyl- |
| Y.2559 | ethyl | 0 | 2-fluoroethyl- |
| Y.2560 | ethyl | 0 | 2-fluoro-phenyl- |
| Y.2561 | ethyl | 0 | 2-fluoropropyl- |
| Y.2562 | ethyl | 0 | 2-furylmethyl- |
| Y.2563 | ethyl | 0 | 2-hydroxyphenyl- |
| Y.2564 | ethyl | 0 | 2-methoxy-ethyl- |
| Y.2565 | ethyl | 0 | 2-methoxyphenyl- |
| Y.2566 | ethyl | 0 | 2-methoxy-prop-3-yl- |
| Y.2567 | ethyl | 0 | 2-methylallyl- |
| Y.2568 | ethyl | 0 | 2-methyl-but-1-yl- |
| Y.2569 | ethyl | 0 | 2-methyl-but-2-yl- |
| Y.2570 | ethyl | 0 | 2-methylbut-3-yn-2-yl- |
| Y.2571 | ethyl | 0 | 2-methylphenyl- |
| Y.2572 | ethyl | 0 | 2-methyl-prop-1-yl- |
| Y.2573 | ethyl | 0 | 2-methylsulfanyl-ethyl- |
| Y.2574 | ethyl | 0 | 2-methylsulfanyl-prop-3-yl- |
| Y.2575 | ethyl | 0 | 2-methyl-thiazol-4-yl- |
| Y.2576 | ethyl | 0 | 2-nitrophenyl- |
| Y.2577 | ethyl | 0 | 2-propyl- |
| Y.2578 | ethyl | 0 | 2-pyridyl- |
| Y.2579 | ethyl | 0 | 2-trifluoromethoxy-ethyl- |
| Y.2580 | ethyl | 0 | 3-(trifluoromethoxy)phenyl- |
| Y.2581 | ethyl | 0 | 3,3,3-trifluoro-2,2-difluoropropyl- |
| Y.2582 | ethyl | 0 | 3,3,3-trifluoro-butyl- |
| Y.2583 | ethyl | 0 | 3,3-dibromoallyl- |
| Y.2584 | ethyl | 0 | 3,3-dichloroallyl- |
| Y.2585 | ethyl | 0 | 3,4-dichlorophenyl- |

TABLE Y-continued

| | R5b | n | R2 |
|---|---|---|---|
| Y.2586 | ethyl | 0 | 3,4-difluoro-phenyl- |
| Y.2587 | ethyl | 0 | 3,5-dichlorophenyl- |
| Y.2588 | ethyl | 0 | 3,5-difluoro-phenyl- |
| Y.2589 | ethyl | 0 | 3,6-difluoro-phenyl- |
| Y.2590 | ethyl | 0 | 3-bromoallyl- |
| Y.2591 | ethyl | 0 | 3-bromophenyl- |
| Y.2592 | ethyl | 0 | 3-butenyl- |
| Y.2593 | ethyl | 0 | 3-chloroallyl- |
| Y.2594 | ethyl | 0 | 3-chlorophenyl- |
| Y.2595 | ethyl | 0 | 3-chloropyrid-2-yl- |
| Y.2596 | ethyl | 0 | 3-cyanopropyl- |
| Y.2597 | ethyl | 0 | 3-ethylphenyl- |
| Y.2598 | ethyl | 0 | 3-hydroxyphenyl- |
| Y.2599 | ethyl | 0 | 3-methyl-1,1-dioxo-thietan-3-yl- |
| Y.2600 | ethyl | 0 | 3-methyl-1-oxo-thietan-3-yl- |
| Y.2601 | ethyl | 0 | 3-methyl-but-1-yl- |
| Y.2602 | ethyl | 0 | 3-methyl-but-2-yl- |
| Y.2603 | ethyl | 0 | 3-methylphenyl- |
| Y.2604 | ethyl | 0 | 3-nitrophenyl- |
| Y.2605 | ethyl | 0 | 3-pyridyl- |
| Y.2606 | ethyl | 0 | 4-(trifluoromethoxy)phenyl- |
| Y.2607 | ethyl | 0 | 4,5-dihydrothiazol-2-yl- |
| Y.2608 | ethyl | 0 | 4,5-dimethyl-4,5-dihydrothiazol-2-yl- |
| Y.2609 | ethyl | 0 | 4,5-dimethyl-thiazol-2-yl- |
| Y.2610 | ethyl | 0 | 4-bromophenyl- |
| Y.2611 | ethyl | 0 | 4-chlorophenyl- |
| Y.2612 | ethyl | 0 | 4-ethylphenyl- |
| Y.2613 | ethyl | 0 | 4-fluoro-phenyl- |
| Y.2614 | ethyl | 0 | 4H-1,2,4-triazol-3-yl- |
| Y.2615 | ethyl | 0 | 4-methoxyphenyl- |
| Y.2616 | ethyl | 0 | 4-methyl-4,5-dihydrothiazol-2-yl- |
| Y.2617 | ethyl | 0 | 4-methylphenyl- |
| Y.2618 | ethyl | 0 | 4-methylpyrid-2-yl |
| Y.2619 | ethyl | 0 | 4-nitrophenyl- |
| Y.2620 | ethyl | 0 | 4-pyridyl- |
| Y.2621 | ethyl | 0 | 5-methyl-4,5-dihydrothiazol-2-yl- |
| Y.2622 | ethyl | 0 | 5-methyl-thiazol-2-yl- |
| Y.2623 | ethyl | 0 | 6-methylpyrid-2-yl- |
| Y.2624 | ethyl | 0 | allyl- |
| Y.2625 | ethyl | 0 | but-2-ynyl- |
| Y.2626 | ethyl | 0 | but-3-ynyl- |
| Y.2627 | ethyl | 0 | cis-1-oxo-thietan-3-yl- |
| Y.2628 | ethyl | 0 | cis-1-oxo-thietan-3-ylmethyl- |
| Y.2629 | ethyl | 0 | cyanodimethylmethyl- |
| Y.2630 | ethyl | 0 | cyanoethyl- |
| Y.2631 | ethyl | 0 | cyanomethyl- |
| Y.2632 | ethyl | 0 | cyclopentyl- |
| Y.2633 | ethyl | 0 | cyclopropyl-methyl- |
| Y.2634 | ethyl | 0 | methylpropargyl- |
| Y.2635 | ethyl | 0 | oxetan-3-yl- |
| Y.2636 | ethyl | 0 | pent-3-yl- |
| Y.2637 | ethyl | 0 | phenyl-methyl-methyl- |
| Y.2638 | ethyl | 0 | propargyl- |
| Y.2639 | ethyl | 0 | tert-butyl- |
| Y.2640 | ethyl | 0 | tetrazolyl- |
| Y.2641 | ethyl | 0 | thiazol-2-yl- |
| Y.2642 | ethyl | 0 | thiazol-4-yl- |
| Y.2643 | ethyl | 0 | thietan-2-ylmethyl- |
| Y.2644 | ethyl | 0 | thietan-3-ylmethyl- |
| Y.2645 | ethyl | 0 | ethyl- |
| Y.2646 | ethyl | 0 | 3,3,3-trifluoro-propyl- |
| Y.2647 | ethyl | 0 | but-2-yl- |
| Y.2648 | ethyl | 0 | (tetrahydrofuran-2-yl)-methyl- |
| Y.2649 | ethyl | 0 | benzyl- |
| Y.2650 | ethyl | 0 | (2-fluoro-phenyl)-methyl- |
| Y.2651 | ethyl | 0 | 1-phenyl-eth-1-yl- |
| Y.2652 | ethyl | 0 | (4-methoxy-phenyl)-methyl- |
| Y.2653 | ethyl | 0 | 1,1-dioxo-thietan-3-yl- |
| Y.2654 | ethyl | 0 | (2-chloro-pyrid-5-yl)-methyl- |
| Y.2655 | ethyl | 0 | 3-fluoro-phenyl- |
| Y.2656 | ethyl | 0 | n-butyl- |
| Y.2657 | ethyl | 0 | (pyrid-2-yl)-methyl- |
| Y.2658 | ethyl | 0 | 1,3-dimethyl-1H-pyrazol-5-yl- |
| Y.2659 | ethyl | 0 | 4-methyl-thiazol-2-yl- |
| Y.2660 | ethyl | 0 | 3-methyl-thietan-3-yl- |
| Y.2661 | ethyl | 0 | 1,1-dimethyl-2-methylsulfanyl-ethyl |
| Y.2662 | ethyl | 0 | 1-oxo-thietan-3-yl- |
| Y.2663 | ethyl | 0 | thietan-3-yl- |
| Y.2664 | ethyl | 0 | bicyclo[2.2.1]hept-2-yl- |
| Y.2665 | ethyl | 0 | cyclobutyl- |
| Y.2666 | ethyl | 0 | methyl- |
| Y.2667 | ethyl | 0 | cyclopropyl- |
| Y.2668 | ethyl | 0 | n-propyl- |
| Y.2669 | ethyl | 0 | 2,2-difluoroethyl- |
| Y.2670 | ethyl | 0 | 1-methoxy-prop-2-yl- |
| Y.2671 | ethyl | 0 | N-(2,2,2-trifluoro-ethyl)-acetamide-2-yl |
| Y.2672 | ethyl | 0 | 2,2,2-trifluoro-ethyl- |
| Y.2673 | ethyl | 1 | (1,1-dioxothietan-2-yl)methyl- |
| Y.2674 | ethyl | 1 | (1-oxothietan-2-yl)methyl- |
| Y.2675 | ethyl | 1 | (2-methoxy-phenyl)-methyl- |
| Y.2676 | ethyl | 1 | (3-fluoro-phenyl)-methyl- |
| Y.2677 | ethyl | 1 | (4,4-dimethyl-4,5-dihydrothiazol-2-yl)-methyl- |
| Y.2678 | ethyl | 1 | (4,5-dihydrothiazol-2-yl)-methyl- |
| Y.2679 | ethyl | 1 | (4,5-dimethyl-4,5-dihydrothiazol-2-yl)-methyl- |
| Y.2680 | ethyl | 1 | (4-fluoro-phenyl)-methyl- |
| Y.2681 | ethyl | 1 | (4-methyl-4,5-dihydrothiazol-2-yl)-methyl- |
| Y.2682 | ethyl | 1 | (5-methyl-4,5-dihydrothiazol-2-yl)-methyl- |
| Y.2683 | ethyl | 1 | (pyrid-3-yl)-methyl- |
| Y.2684 | ethyl | 1 | (pyrid-4-yl)-methyl- |
| Y.2685 | ethyl | 1 | (tetrahydrothiophene-2-yl)-methyl- |
| Y.2686 | ethyl | 1 | (tetrahydrothiophene-3-yl)-methyl- |
| Y.2687 | ethyl | 1 | (thiazol-2-yl)-methyl- |
| Y.2688 | ethyl | 1 | (thiazol-2-yl)-methylmethyl- |
| Y.2689 | ethyl | 1 | (thiazol-4-yl)-methyl- |
| Y.2690 | ethyl | 1 | (thiazol-5-yl)-methyl- |
| Y.2691 | ethyl | 1 | 1,1-dioxo-thietan-3-ylmethyl- |
| Y.2692 | ethyl | 1 | 1-cyanocyclobutyl- |
| Y.2693 | ethyl | 1 | 1-cyanocyclopentyl- |
| Y.2694 | ethyl | 1 | 1-cyanocyclopropyl- |
| Y.2695 | ethyl | 1 | 1-fluoroprop-2-yl- |
| Y.2696 | ethyl | 1 | 1-methylallyl- |
| Y.2697 | ethyl | 1 | 1-methylsulfanyl-prop-2-yl- |
| Y.2698 | ethyl | 1 | 2-(1,1-dioxothietan-3-yl)ethanyl- |
| Y.2699 | ethyl | 1 | 2-(1-oxothietan-3-yl)ethanyl- |
| Y.2700 | ethyl | 1 | 2-(thietan-3-yl)ethanyl- |
| Y.2701 | ethyl | 1 | 2-(trifluoromethoxy)phenyl- |
| Y.2702 | ethyl | 1 | 2,2-dimethyl-1,1-dioxo-thietan-3-yl- |
| Y.2703 | ethyl | 1 | 2,2-dimethyl-1-oxo-thietan-3-yl- |
| Y.2704 | ethyl | 1 | 2,2-dimethylthietan-3-yl- |
| Y.2705 | ethyl | 1 | 2,3-dichlorophenyl- |
| Y.2706 | ethyl | 1 | 2,3-difluoro-phenyl- |
| Y.2707 | ethyl | 1 | 2,4-dichlorophenyl- |
| Y.2708 | ethyl | 1 | 2,4-difluoro-phenyl- |
| Y.2709 | ethyl | 1 | 2,4-dimethylphenyl- |
| Y.2710 | ethyl | 1 | 2,5-dichlorophenyl- |
| Y.2711 | ethyl | 1 | 2,5-difluoro-phenyl- |
| Y.2712 | ethyl | 1 | 2,6-dichlorophenyl- |
| Y.2713 | ethyl | 1 | 2,6-difluoro-phenyl- |
| Y.2714 | ethyl | 1 | 2,6-diisopropylphenyl- |
| Y.2715 | ethyl | 1 | 2-bromo-4-fluorophenyl- |
| Y.2716 | ethyl | 1 | 2-bromoallyl- |
| Y.2717 | ethyl | 1 | 2-bromophenyl- |
| Y.2718 | ethyl | 1 | 2-butenyl- |
| Y.2719 | ethyl | 1 | 2-chloroallyl- |
| Y.2720 | ethyl | 1 | 2-chlorophenyl- |
| Y.2721 | ethyl | 1 | 2-chloropyrid-2-yl- |
| Y.2722 | ethyl | 1 | 2-chloropyrid-3-yl- |
| Y.2723 | ethyl | 1 | 2-cyanocyclopropyl- |
| Y.2724 | ethyl | 1 | 2-cyanoethyl- |
| Y.2725 | ethyl | 1 | 2-ethylphenyl- |
| Y.2726 | ethyl | 1 | 2-fluoroethyl- |
| Y.2727 | ethyl | 1 | 2-fluoro-phenyl- |
| Y.2728 | ethyl | 1 | 2-fluoropropyl- |
| Y.2729 | ethyl | 1 | 2-furylmethyl- |
| Y.2730 | ethyl | 1 | 2-hydroxyphenyl- |
| Y.2731 | ethyl | 1 | 2-methoxy-ethyl- |
| Y.2732 | ethyl | 1 | 2-methoxyphenyl- |
| Y.2733 | ethyl | 1 | 2-methoxy-prop-3-yl- |
| Y.2734 | ethyl | 1 | 2-methylallyl- |
| Y.2735 | ethyl | 1 | 2-methyl-but-1-yl- |
| Y.2736 | ethyl | 1 | 2-methyl-but-2-yl- |
| Y.2737 | ethyl | 1 | 2-methylbut-3-yn-2-yl- |

TABLE Y-continued

| | R5b | n | R2 |
|---|---|---|---|
| Y.2738 | ethyl | 1 | 2-methylphenyl- |
| Y.2739 | ethyl | 1 | 2-methyl-prop-1-yl- |
| Y.2740 | ethyl | 1 | 2-methylsulfanyl-ethyl- |
| Y.2741 | ethyl | 1 | 2-methylsulfanyl-prop-3-yl- |
| Y.2742 | ethyl | 1 | 2-methyl-thiazol-4-yl- |
| Y.2743 | ethyl | 1 | 2-nitrophenyl- |
| Y.2744 | ethyl | 1 | 2-propyl- |
| Y.2745 | ethyl | 1 | 2-pyridyl- |
| Y.2746 | ethyl | 1 | 2-trifluoromethoxy-ethyl- |
| Y.2747 | ethyl | 1 | 3-(trifluoromethoxy)phenyl- |
| Y.2748 | ethyl | 1 | 3,3,3-trifluoro-2,2-difluoropropyl- |
| Y.2749 | ethyl | 1 | 3,3,3-trifluoro-butyl- |
| Y.2750 | ethyl | 1 | 3,3-dibromoallyl- |
| Y.2751 | ethyl | 1 | 3,3-dichloroallyl- |
| Y.2752 | ethyl | 1 | 3,4-dichlorophenyl- |
| Y.2753 | ethyl | 1 | 3,4-difluoro-phenyl- |
| Y.2754 | ethyl | 1 | 3,5-dichlorophenyl- |
| Y.2755 | ethyl | 1 | 3,5-difluoro-phenyl- |
| Y.2756 | ethyl | 1 | 3,6-difluoro-phenyl- |
| Y.2757 | ethyl | 1 | 3-bromoallyl- |
| Y.2758 | ethyl | 1 | 3-bromophenyl- |
| Y.2759 | ethyl | 1 | 3-butenyl- |
| Y.2760 | ethyl | 1 | 3-chloroallyl- |
| Y.2761 | ethyl | 1 | 3-chlorophenyl- |
| Y.2762 | ethyl | 1 | 3-chloropyrid-2-yl- |
| Y.2763 | ethyl | 1 | 3-cyanopropyl- |
| Y.2764 | ethyl | 1 | 3-ethylphenyl- |
| Y.2765 | ethyl | 1 | 3-hydroxyphenyl- |
| Y.2766 | ethyl | 1 | 3-methyl-1,1-dioxo-thietan-3-yl- |
| Y.2767 | ethyl | 1 | 3-methyl-1-oxo-thietan-3-yl- |
| Y.2768 | ethyl | 1 | 3-methyl-but-1-yl- |
| Y.2769 | ethyl | 1 | 3-methyl-but-2-yl- |
| Y.2770 | ethyl | 1 | 3-methylphenyl- |
| Y.2771 | ethyl | 1 | 3-nitrophenyl- |
| Y.2772 | ethyl | 1 | 3-pyridyl- |
| Y.2773 | ethyl | 1 | 4-(trifluoromethoxy)phenyl- |
| Y.2774 | ethyl | 1 | 4,5-dihydrothiazol-2-yl- |
| Y.2775 | ethyl | 1 | 4,5-dimethyl-4,5-dihydrothiazol-2-yl- |
| Y.2776 | ethyl | 1 | 4,5-dimethyl-thiazol-2-yl- |
| Y.2777 | ethyl | 1 | 4-bromophenyl- |
| Y.2778 | ethyl | 1 | 4-chlorophenyl- |
| Y.2779 | ethyl | 1 | 4-ethylphenyl- |
| Y.2780 | ethyl | 1 | 4-fluoro-phenyl- |
| Y.2781 | ethyl | 1 | 4H-1,2,4-triazol-3-yl- |
| Y.2782 | ethyl | 1 | 4-methoxyphenyl- |
| Y.2783 | ethyl | 1 | 4-methyl-4,5-dihydrothiazol-2-yl- |
| Y.2784 | ethyl | 1 | 4-methylphenyl- |
| Y.2785 | ethyl | 1 | 4-methylpyrid-2-yl |
| Y.2786 | ethyl | 1 | 4-nitrophenyl- |
| Y.2787 | ethyl | 1 | 4-pyridyl- |
| Y.2788 | ethyl | 1 | 5-methyl-4,5-dihydrothiazol-2-yl- |
| Y.2789 | ethyl | 1 | 5-methyl-thiazol-2-yl- |
| Y.2790 | ethyl | 1 | 6-methylpyrid-2-yl- |
| Y.2791 | ethyl | 1 | allyl- |
| Y.2792 | ethyl | 1 | but-2-ynyl- |
| Y.2793 | ethyl | 1 | but-3-ynyl- |
| Y.2794 | ethyl | 1 | cis-1-oxo-thietan-3-yl- |
| Y.2795 | ethyl | 1 | cis-1-oxo-thietan-3-ylmethyl- |
| Y.2796 | ethyl | 1 | cyanodimethylmethyl- |
| Y.2797 | ethyl | 1 | cyanoethyl- |
| Y.2798 | ethyl | 1 | cyanomethyl- |
| Y.2799 | ethyl | 1 | cyclopentyl- |
| Y.2800 | ethyl | 1 | cyclopropyl-methyl- |
| Y.2801 | ethyl | 1 | methylpropargyl- |
| Y.2802 | ethyl | 1 | oxetan-3-yl- |
| Y.2803 | ethyl | 1 | pent-3-yl- |
| Y.2804 | ethyl | 1 | phenyl-methyl-methyl- |
| Y.2805 | ethyl | 1 | propargyl- |
| Y.2806 | ethyl | 1 | tert-butyl- |
| Y.2807 | ethyl | 1 | tetrazolyl- |
| Y.2808 | ethyl | 1 | thiazol-2-yl- |
| Y.2809 | ethyl | 1 | thiazol-4-yl- |
| Y.2810 | ethyl | 1 | thietan-2-ylmethyl- |
| Y.2811 | ethyl | 1 | thietan-3-ylmethyl- |
| Y.2812 | ethyl | 1 | ethyl- |
| Y.2813 | ethyl | 1 | 3,3,3-trifluoro-propyl- |
| Y.2814 | ethyl | 1 | but-2-yl- |
| Y.2815 | ethyl | 1 | (tetrahydrofuran-2-yl)-methyl- |
| Y.2816 | ethyl | 1 | benzyl- |
| Y.2817 | ethyl | 1 | (2-fluoro-phenyl)-methyl- |
| Y.2818 | ethyl | 1 | 1-phenyl-eth-1-yl- |
| Y.2819 | ethyl | 1 | (4-methoxy-phenyl)-methyl- |
| Y.2820 | ethyl | 1 | 1,1-dioxo-thietan-3-yl- |
| Y.2821 | ethyl | 1 | (2-chloro-pyrid-5-yl)-methyl- |
| Y.2822 | ethyl | 1 | 3-fluoro-phenyl- |
| Y.2823 | ethyl | 1 | n-butyl- |
| Y.2824 | ethyl | 1 | (pyrid-2-yl)-methyl- |
| Y.2825 | ethyl | 1 | 1,3-dimethyl-1H-pyrazol-5-yl- |
| Y.2826 | ethyl | 1 | 4-methyl-thiazol-2-yl- |
| Y.2827 | ethyl | 1 | 3-methyl-thietan-3-yl- |
| Y.2828 | ethyl | 1 | 1,1-dimethyl-2-methylsulfanyl-ethyl |
| Y.2829 | ethyl | 1 | 1-oxo-thietan-3-yl- |
| Y.2830 | ethyl | 1 | thietan-3-yl- |
| Y.2831 | ethyl | 1 | bicyclo[2.2.1]hept-2-yl- |
| Y.2832 | ethyl | 1 | cyclobutyl- |
| Y.2833 | ethyl | 1 | methyl- |
| Y.2834 | ethyl | 1 | cyclopropyl- |
| Y.2835 | ethyl | 1 | n-propyl- |
| Y.2836 | ethyl | 1 | 2,2-difluoroethyl- |
| Y.2837 | ethyl | 1 | 1-methoxy-prop-2-yl- |
| Y.2838 | ethyl | 1 | N-(2,2,2-trifluoro-ethyl)-acetamide-2-yl |
| Y.2839 | ethyl | 1 | 2,2,2-trifluoro-ethyl- |
| Y.2840 | ethyl | 2 | (1,1-dioxothietan-2-yl)methyl- |
| Y.2841 | ethyl | 2 | (1-oxothietan-2-yl)methyl- |
| Y.2842 | ethyl | 2 | (2-methoxy-phenyl)-methyl- |
| Y.2843 | ethyl | 2 | (3-fluoro-phenyl)-methyl- |
| Y.2844 | ethyl | 2 | (4,4-dimethyl-4,5-dihydrothiazol-2-yl)-methyl- |
| Y.2845 | ethyl | 2 | (4,5-dihydrothiazol-2-yl)-methyl- |
| Y.2846 | ethyl | 2 | (4,5-dimethyl-4,5-dihydrothiazol-2-yl)-methyl- |
| Y.2847 | ethyl | 2 | (4-fluoro-phenyl)-methyl- |
| Y.2848 | ethyl | 2 | (4-methyl-4,5-dihydrothiazol-2-yl)-methyl- |
| Y.2849 | ethyl | 2 | (5-methyl-4,5-dihydrothiazol-2-yl)-methyl- |
| Y.2850 | ethyl | 2 | (pyrid-3-yl)-methyl- |
| Y.2851 | ethyl | 2 | (pyrid-4-yl)-methyl- |
| Y.2852 | ethyl | 2 | (tetrahydrothiophene-2-yl)-methyl- |
| Y.2853 | ethyl | 2 | (tetrahydrothiophene-3-yl)-methyl- |
| Y.2854 | ethyl | 2 | (thiazol-2-yl)-methyl- |
| Y.2855 | ethyl | 2 | (thiazol-2-yl)-methylmethyl- |
| Y.2856 | ethyl | 2 | (thiazol-4-yl)-methyl- |
| Y.2857 | ethyl | 2 | (thiazol-5-yl)-methyl- |
| Y.2858 | ethyl | 2 | 1,1-dioxo-thietan-3-ylmethyl- |
| Y.2859 | ethyl | 2 | 1-cyanocyclobutyl- |
| Y.2860 | ethyl | 2 | 1-cyanocyclopentyl- |
| Y.2861 | ethyl | 2 | 1-cyanocyclopropyl- |
| Y.2862 | ethyl | 2 | 1-fluoroprop-2-yl- |
| Y.2863 | ethyl | 2 | 1-methylallyl- |
| Y.2864 | ethyl | 2 | 1-methylsulfanyl-prop-2-yl- |
| Y.2865 | ethyl | 2 | 2-(1,1-dioxothietan-3-yl)ethanyl- |
| Y.2866 | ethyl | 2 | 2-(1-oxothietan-3-yl)ethanyl- |
| Y.2867 | ethyl | 2 | 2-(thietan-3-yl)ethanyl- |
| Y.2868 | ethyl | 2 | 2-(trifluoromethoxy)phenyl- |
| Y.2869 | ethyl | 2 | 2,2-dimethyl-1,1-dioxo-thietan-3-yl- |
| Y.2870 | ethyl | 2 | 2,2-dimethyl-1-oxo-thietan-3-yl- |
| Y.2871 | ethyl | 2 | 2,2-dimethylthietan-3-yl- |
| Y.2872 | ethyl | 2 | 2,3-dichlorophenyl- |
| Y.2873 | ethyl | 2 | 2,3-difluoro-phenyl- |
| Y.2874 | ethyl | 2 | 2,4-dichlorophenyl- |
| Y.2875 | ethyl | 2 | 2,4-difluoro-phenyl- |
| Y.2876 | ethyl | 2 | 2,4-dimethylphenyl- |
| Y.2877 | ethyl | 2 | 2,5-dichlorophenyl- |
| Y.2878 | ethyl | 2 | 2,5-difluoro-phenyl- |
| Y.2879 | ethyl | 2 | 2,6-dichlorophenyl- |
| Y.2880 | ethyl | 2 | 2,6-difluoro-phenyl- |
| Y.2881 | ethyl | 2 | 2,6-diisopropylphenyl- |
| Y.2882 | ethyl | 2 | 2-bromo-4-fluorophenyl- |
| Y.2883 | ethyl | 2 | 2-bromoallyl- |
| Y.2884 | ethyl | 2 | 2-bromophenyl- |
| Y.2885 | ethyl | 2 | 2-butenyl- |
| Y.2886 | ethyl | 2 | 2-chloroallyl- |
| Y.2887 | ethyl | 2 | 2-chlorophenyl- |
| Y.2888 | ethyl | 2 | 2-chloropyrid-2-yl- |
| Y.2889 | ethyl | 2 | 2-chloropyrid-3-yl- |

TABLE Y-continued

| | R5b | n | R2 |
|---|---|---|---|
| Y.2890 | ethyl | 2 | 2-cyanocyclopropyl- |
| Y.2891 | ethyl | 2 | 2-cyanoethyl- |
| Y.2892 | ethyl | 2 | 2-ethylphenyl- |
| Y.2893 | ethyl | 2 | 2-fluoroethyl- |
| Y.2894 | ethyl | 2 | 2-fluoro-phenyl- |
| Y.2895 | ethyl | 2 | 2-fluoropropyl- |
| Y.2896 | ethyl | 2 | 2-furylmethyl- |
| Y.2897 | ethyl | 2 | 2-hydroxyphenyl- |
| Y.2898 | ethyl | 2 | 2-methoxy-ethyl- |
| Y.2899 | ethyl | 2 | 2-methoxyphenyl- |
| Y.2900 | ethyl | 2 | 2-methoxy-prop-3-yl- |
| Y.2901 | ethyl | 2 | 2-methylallyl- |
| Y.2902 | ethyl | 2 | 2-methyl-but-1-yl- |
| Y.2903 | ethyl | 2 | 2-methyl-but-2-yl- |
| Y.2904 | ethyl | 2 | 2-methylbut-3-yn-2-yl- |
| Y.2905 | ethyl | 2 | 2-methylphenyl- |
| Y.2906 | ethyl | 2 | 2-methyl-prop-1-yl- |
| Y.2907 | ethyl | 2 | 2-methylsulfanyl-ethyl- |
| Y.2908 | ethyl | 2 | 2-methylsulfanyl-prop-3-yl- |
| Y.2909 | ethyl | 2 | 2-methyl-thiazol-4-yl- |
| Y.2910 | ethyl | 2 | 2-nitrophenyl- |
| Y.2911 | ethyl | 2 | 2-propyl- |
| Y.2912 | ethyl | 2 | 2-pyridyl- |
| Y.2913 | ethyl | 2 | 2-trifluoromethoxy-ethyl- |
| Y.2914 | ethyl | 2 | 3-(trifluoromethoxy)phenyl- |
| Y.2915 | ethyl | 2 | 3,3,3-trifluoro-2,2-difluoropropyl- |
| Y.2916 | ethyl | 2 | 3,3,3-trifluoro-butyl- |
| Y.2917 | ethyl | 2 | 3,3-dibromoallyl- |
| Y.2918 | ethyl | 2 | 3,3-dichloroallyl- |
| Y.2919 | ethyl | 2 | 3,4-dichlorophenyl- |
| Y.2920 | ethyl | 2 | 3,4-difluoro-phenyl- |
| Y.2921 | ethyl | 2 | 3,5-dichlorophenyl- |
| Y.2922 | ethyl | 2 | 3,5-difluoro-phenyl- |
| Y.2923 | ethyl | 2 | 3,6-difluoro-phenyl- |
| Y.2924 | ethyl | 2 | 3-bromoallyl- |
| Y.2925 | ethyl | 2 | 3-bromophenyl- |
| Y.2926 | ethyl | 2 | 3-butenyl- |
| Y.2927 | ethyl | 2 | 3-chloroallyl- |
| Y.2928 | ethyl | 2 | 3-chlorophenyl- |
| Y.2929 | ethyl | 2 | 3-chloropyrid-2-yl- |
| Y.2930 | ethyl | 2 | 3-cyanopropyl- |
| Y.2931 | ethyl | 2 | 3-ethylphenyl- |
| Y.2932 | ethyl | 2 | 3-hydroxyphenyl- |
| Y.2933 | ethyl | 2 | 3-methyl-1,1-dioxo-thietan-3-yl- |
| Y.2934 | ethyl | 2 | 3-methyl-1-oxo-thietan-3-yl- |
| Y.2935 | ethyl | 2 | 3-methyl-but-1-yl- |
| Y.2936 | ethyl | 2 | 3-methyl-but-2-yl- |
| Y.2937 | ethyl | 2 | 3-methylphenyl- |
| Y.2938 | ethyl | 2 | 3-nitrophenyl- |
| Y.2939 | ethyl | 2 | 3-pyridyl- |
| Y.2940 | ethyl | 2 | 4-(trifluoromethoxy)phenyl- |
| Y.2941 | ethyl | 2 | 4,5-dihydrothiazol-2-yl- |
| Y.2942 | ethyl | 2 | 4,5-dimethyl-4,5-dihydrothiazol-2-yl- |
| Y.2943 | ethyl | 2 | 4,5-dimethyl-thiazol-2-yl- |
| Y.2944 | ethyl | 2 | 4-bromophenyl- |
| Y.2945 | ethyl | 2 | 4-chlorophenyl- |
| Y.2946 | ethyl | 2 | 4-ethylphenyl- |
| Y.2947 | ethyl | 2 | 4-fluoro-phenyl- |
| Y.2948 | ethyl | 2 | 4H-1,2,4-triazol-3-yl- |
| Y.2949 | ethyl | 2 | 4-methoxyphenyl- |
| Y.2950 | ethyl | 2 | 4-methyl-4,5-dihydrothiazol-2-yl- |
| Y.2951 | ethyl | 2 | 4-methylphenyl- |
| Y.2952 | ethyl | 2 | 4-methylpyrid-2-yl |
| Y.2953 | ethyl | 2 | 4-nitrophenyl- |
| Y.2954 | ethyl | 2 | 4-pyridyl- |
| Y.2955 | ethyl | 2 | 5-methyl-4,5-dihydrothiazol-2-yl- |
| Y.2956 | ethyl | 2 | 5-methyl-thiazol-2-yl- |
| Y.2957 | ethyl | 2 | 6-methylpyrid-2-yl- |
| Y.2958 | ethyl | 2 | allyl- |
| Y.2959 | ethyl | 2 | but-2-ynyl- |
| Y.2960 | ethyl | 2 | but-3-ynyl- |
| Y.2961 | ethyl | 2 | cis-1-oxo-thietan-3-yl- |
| Y.2962 | ethyl | 2 | cis-1,1-dioxo-thietan-3-ylmethyl- |
| Y.2963 | ethyl | 2 | cyanodimethylmethyl- |
| Y.2964 | ethyl | 2 | cyanoethyl- |
| Y.2965 | ethyl | 2 | cyanomethyl- |
| Y.2966 | ethyl | 2 | cyclopentyl- |
| Y.2967 | ethyl | 2 | cyclopropyl-methyl- |
| Y.2968 | ethyl | 2 | methylpropargyl- |
| Y.2969 | ethyl | 2 | oxetan-3-yl- |
| Y.2970 | ethyl | 2 | pent-3-yl- |
| Y.2971 | ethyl | 2 | phenyl-methyl-methyl- |
| Y.2972 | ethyl | 2 | propargyl- |
| Y.2973 | ethyl | 2 | tert-butyl- |
| Y.2974 | ethyl | 2 | tetrazolyl- |
| Y.2975 | ethyl | 2 | thiazol-2-yl- |
| Y.2976 | ethyl | 2 | thiazol-4-yl- |
| Y.2977 | ethyl | 2 | thietan-2-ylmethyl- |
| Y.2978 | ethyl | 2 | thietan-3-ylmethyl- |
| Y.2979 | ethyl | 2 | ethyl- |
| Y.2980 | ethyl | 2 | 3,3,3-trifluoro-propyl- |
| Y.2981 | ethyl | 2 | but-2-yl- |
| Y.2982 | ethyl | 2 | (tetrahydrofuran-2-yl)-methyl- |
| Y.2983 | ethyl | 2 | benzyl- |
| Y.2984 | ethyl | 2 | (2-fluoro-phenyl)-methyl- |
| Y.2985 | ethyl | 2 | 1-phenyl-eth-1-yl- |
| Y.2986 | ethyl | 2 | (4-methoxy-phenyl)-methyl- |
| Y.2987 | ethyl | 2 | 1,1-dioxo-thietan-3-yl- |
| Y.2988 | ethyl | 2 | (2-chloro-pyrid-5-yl)-methyl- |
| Y.2989 | ethyl | 2 | 3-fluoro-phenyl- |
| Y.2990 | ethyl | 2 | n-butyl- |
| Y.2991 | ethyl | 2 | (pyrid-2-yl)-methyl- |
| Y.2992 | ethyl | 2 | 1,3-dimethyl-1H-pyrazol-5-yl- |
| Y.2993 | ethyl | 2 | 4-methyl-thiazol-2-yl- |
| Y.2994 | ethyl | 2 | 3-methyl-thietan-3-yl- |
| Y.2995 | ethyl | 2 | 1,1-dimethyl-2-methylsulfanyl-ethyl |
| Y.2996 | ethyl | 2 | 1-oxo-thietan-3-yl- |
| Y.2997 | ethyl | 2 | thietan-3-yl- |
| Y.2998 | ethyl | 2 | bicyclo[2.2.1]hept-2-yl- |
| Y.2999 | ethyl | 2 | cyclobutyl- |
| Y.3000 | ethyl | 2 | methyl- |
| Y.3001 | ethyl | 2 | cyclopropyl- |
| Y.3002 | ethyl | 2 | n-propyl- |
| Y.3003 | ethyl | 2 | 2,2-difluoroethyl- |
| Y.3004 | ethyl | 2 | 1-methoxy-prop-2-yl- |
| Y.3005 | ethyl | 2 | N-(2,2,2-trifluoro-ethyl)-acetamide-2-yl |
| Y.3006 | ethyl | 2 | 2,2,2-trifluoro-ethyl- |
| Y.3007 | cyclopropyl | 0 | (1,1-dioxothietan-2-yl)methyl- |
| Y.3008 | cyclopropyl | 0 | (1-oxothietan-2-yl)methyl- |
| Y.3009 | cyclopropyl | 0 | (2-methoxy-phenyl)-methyl- |
| Y.3010 | cyclopropyl | 0 | (3-fluoro-phenyl)-methyl- |
| Y.3011 | cyclopropyl | 0 | (4,4-dimethyl-4,5-dihydrothiazol-2-yl)-methyl- |
| Y.3012 | cyclopropyl | 0 | (4,5-dihydrothiazol-2-yl)-methyl- |
| Y.3013 | cyclopropyl | 0 | (4,5-dimethyl-4,5-dihydrothiazol-2-yl)-methyl- |
| Y.3014 | cyclopropyl | 0 | (4-fluoro-phenyl)-methyl- |
| Y.3015 | cyclopropyl | 0 | (4-methyl-4,5-dihydrothiazol-2-yl)methyl- |
| Y.3016 | cyclopropyl | 0 | (5-methyl-4,5-dihydrothiazol-2-yl)-methyl- |
| Y.3017 | cyclopropyl | 0 | (pyrid-3-yl)-methyl- |
| Y.3018 | cyclopropyl | 0 | (pyrid-4-yl)-methyl- |
| Y.3019 | cyclopropyl | 0 | (tetrahydrothiophene-2-yl)-methyl- |
| Y.3020 | cyclopropyl | 0 | (tetrahydrothiophene-3-yl)-methyl- |
| Y.3021 | cyclopropyl | 0 | (thiazol-2-yl)-methyl- |
| Y.3022 | cyclopropyl | 0 | (thiazol-2-yl)-methylmethyl- |
| Y.3023 | cyclopropyl | 0 | (thiazol-4-yl)-methyl- |
| Y.3024 | cyclopropyl | 0 | (thiazol-5-yl)-methyl- |
| Y.3025 | cyclopropyl | 0 | 1,1-dioxo-thietan-3-ylmethyl- |
| Y.3026 | cyclopropyl | 0 | 1-cyanocyclobutyl- |
| Y.3027 | cyclopropyl | 0 | 1-cyanocyclopentyl- |
| Y.3028 | cyclopropyl | 0 | 1-cyanocyclopropyl- |
| Y.3029 | cyclopropyl | 0 | 1-fluoroprop-2-yl- |
| Y.3030 | cyclopropyl | 0 | 1-methylallyl- |
| Y.3031 | cyclopropyl | 0 | 1-methylsulfanyl-prop-2-yl- |
| Y.3032 | cyclopropyl | 0 | 2-(1,1-dioxothietan-3-yl)ethanyl- |
| Y.3033 | cyclopropyl | 0 | 2-(1-oxothietan-3-yl)ethanyl- |
| Y.3034 | cyclopropyl | 0 | 2-(thietan-3-yl)ethanyl- |
| Y.3035 | cyclopropyl | 0 | 2-(trifluoromethoxy)phenyl- |
| Y.3036 | cyclopropyl | 0 | 2,2-dimethyl-1,1-dioxo-thietan-3-yl- |
| Y.3037 | cyclopropyl | 0 | 2,2-dimethyl-1-oxo-thietan-3-yl- |
| Y.3038 | cyclopropyl | 0 | 2,2-dimethylthietan-3-yl- |
| Y.3039 | cyclopropyl | 0 | 2,3-dichlorophenyl- |
| Y.3040 | cyclopropyl | 0 | 2,3-difluoro-phenyl- |
| Y.3041 | cyclopropyl | 0 | 2,4-dichlorophenyl- |

TABLE Y-continued

| | R5b | n | R2 |
|---|---|---|---|
| Y.3042 | cyclopropyl | 0 | 2,4-difluoro-phenyl- |
| Y.3043 | cyclopropyl | 0 | 2,4-dimethylphenyl- |
| Y.3044 | cyclopropyl | 0 | 2,5-dichlorophenyl- |
| Y.3045 | cyclopropyl | 0 | 2,5-difluoro-phenyl- |
| Y.3046 | cyclopropyl | 0 | 2,6-dichlorophenyl- |
| Y.3047 | cyclopropyl | 0 | 2,6-difluoro-phenyl- |
| Y.3048 | cyclopropyl | 0 | 2,6-diisopropylphenyl- |
| Y.3049 | cyclopropyl | 0 | 2-bromo-4-fluorophenyl- |
| Y.3050 | cyclopropyl | 0 | 2-bromoallyl- |
| Y.3051 | cyclopropyl | 0 | 2-bromophenyl- |
| Y.3052 | cyclopropyl | 0 | 2-butenyl- |
| Y.3053 | cyclopropyl | 0 | 2-chloroallyl- |
| Y.3054 | cyclopropyl | 0 | 2-chlorophenyl- |
| Y.3055 | cyclopropyl | 0 | 2-chloropyrid-2-yl- |
| Y.3056 | cyclopropyl | 0 | 2-chloropyrid-3-yl- |
| Y.3057 | cyclopropyl | 0 | 2-cyanocyclopropyl- |
| Y.3058 | cyclopropyl | 0 | 2-cyanoethyl- |
| Y.3059 | cyclopropyl | 0 | 2-ethylphenyl- |
| Y.3060 | cyclopropyl | 0 | 2-fluoroethyl- |
| Y.3061 | cyclopropyl | 0 | 2-fluoro-phenyl- |
| Y.3062 | cyclopropyl | 0 | 2-fluoropropyl- |
| Y.3063 | cyclopropyl | 0 | 2-furylmethyl- |
| Y.3064 | cyclopropyl | 0 | 2-hydroxyphenyl- |
| Y.3065 | cyclopropyl | 0 | 2-methoxy-ethyl- |
| Y.3066 | cyclopropyl | 0 | 2-methoxyphenyl- |
| Y.3067 | cyclopropyl | 0 | 2-methoxy-prop-3-yl- |
| Y.3068 | cyclopropyl | 0 | 2-methylallyl- |
| Y.3069 | cyclopropyl | 0 | 2-methyl-but-1-yl- |
| Y.3070 | cyclopropyl | 0 | 2-methyl-but-2-yl- |
| Y.3071 | cyclopropyl | 0 | 2-methylbut-3-yn-2-yl- |
| Y.3072 | cyclopropyl | 0 | 2-methylphenyl- |
| Y.3073 | cyclopropyl | 0 | 2-methyl-prop-1-yl- |
| Y.3074 | cyclopropyl | 0 | 2-methylsulfanyl-ethyl- |
| Y.3075 | cyclopropyl | 0 | 2-methylsulfanyl-prop-3-yl- |
| Y.3076 | cyclopropyl | 0 | 2-methyl-thiazol-4-yl- |
| Y.3077 | cyclopropyl | 0 | 2-nitrophenyl- |
| Y.3078 | cyclopropyl | 0 | 2-propyl- |
| Y.3079 | cyclopropyl | 0 | 2-pyridyl- |
| Y.3080 | cyclopropyl | 0 | 2-trifluoromethoxy-ethyl- |
| Y.3081 | cyclopropyl | 0 | 3-(trifluoromethoxy)phenyl- |
| Y.3082 | cyclopropyl | 0 | 3,3,3-trifluoro-2,2-difluoropropyl- |
| Y.3083 | cyclopropyl | 0 | 3,3,3-trifluoro-butyl- |
| Y.3084 | cyclopropyl | 0 | 3,3-dibromoallyl- |
| Y.3085 | cyclopropyl | 0 | 3,3-dichloroallyl- |
| Y.3086 | cyclopropyl | 0 | 3,4-dichlorophenyl- |
| Y.3087 | cyclopropyl | 0 | 3,4-difluoro-phenyl- |
| Y.3088 | cyclopropyl | 0 | 3,5-dichlorophenyl- |
| Y.3089 | cyclopropyl | 0 | 3,5-difluoro-phenyl- |
| Y.3090 | cyclopropyl | 0 | 3,6-difluoro-phenyl- |
| Y.3091 | cyclopropyl | 0 | 3-bromoallyl- |
| Y.3092 | cyclopropyl | 0 | 3-bromophenyl- |
| Y.3093 | cyclopropyl | 0 | 3-butenyl- |
| Y.3094 | cyclopropyl | 0 | 3-chloroallyl- |
| Y.3095 | cyclopropyl | 0 | 3-chlorophenyl- |
| Y.3096 | cyclopropyl | 0 | 3-chloropyrid-2-yl- |
| Y.3097 | cyclopropyl | 0 | 3-cyanopropyl- |
| Y.3098 | cyclopropyl | 0 | 3-ethylphenyl- |
| Y.3099 | cyclopropyl | 0 | 3-hydroxyphenyl- |
| Y.3100 | cyclopropyl | 0 | 3-methyl-1,1-dioxo-thietan-3-yl- |
| Y.3101 | cyclopropyl | 0 | 3-methyl-1-oxo-thietan-3-yl- |
| Y.3102 | cyclopropyl | 0 | 3-methyl-but-1-yl- |
| Y.3103 | cyclopropyl | 0 | 3-methyl-but-2-yl- |
| Y.3104 | cyclopropyl | 0 | 3-methylphenyl- |
| Y.3105 | cyclopropyl | 0 | 3-nitrophenyl- |
| Y.3106 | cyclopropyl | 0 | 3-pyridyl- |
| Y.3107 | cyclopropyl | 0 | 4-(trifluoromethoxy)phenyl- |
| Y.3108 | cyclopropyl | 0 | 4,5-dihydrothiazol-2-yl- |
| Y.3109 | cyclopropyl | 0 | 4,5-dimethyl-4,5-dihydrothiazol-2-yl- |
| Y.3110 | cyclopropyl | 0 | 4,5-dimethyl-thiazol-2-yl- |
| Y.3111 | cyclopropyl | 0 | 4-bromophenyl- |
| Y.3112 | cyclopropyl | 0 | 4-chlorophenyl- |
| Y.3113 | cyclopropyl | 0 | 4-ethylphenyl- |
| Y.3114 | cyclopropyl | 0 | 4-fluoro-phenyl- |
| Y.3115 | cyclopropyl | 0 | 4H-1,2,4-triazol-3-yl- |
| Y.3116 | cyclopropyl | 0 | 4-methoxyphenyl- |
| Y.3117 | cyclopropyl | 0 | 4-methyl-4,5-dihydrothiazol-2-yl- |
| Y.3118 | cyclopropyl | 0 | 4-methylphenyl- |
| Y.3119 | cyclopropyl | 0 | 4-methylpyrid-2-yl |
| Y.3120 | cyclopropyl | 0 | 4-nitrophenyl- |
| Y.3121 | cyclopropyl | 0 | 4-pyridyl- |
| Y.3122 | cyclopropyl | 0 | 5-methyl-4,5-dihydrothiazol-2-yl- |
| Y.3123 | cyclopropyl | 0 | 5-methyl-thiazol-2-yl- |
| Y.3124 | cyclopropyl | 0 | 6-methylpyrid-2-yl- |
| Y.3125 | cyclopropyl | 0 | allyl- |
| Y.3126 | cyclopropyl | 0 | but-2-ynyl- |
| Y.3127 | cyclopropyl | 0 | but-3-ynyl- |
| Y.3128 | cyclopropyl | 0 | cis-1-oxo-thietan-3-yl- |
| Y.3129 | cyclopropyl | 0 | cis-1-oxo-thietan-3-ylmethyl- |
| Y.3130 | cyclopropyl | 0 | cyanodimethylmethyl- |
| Y.3131 | cyclopropyl | 0 | cyanoethyl- |
| Y.3132 | cyclopropyl | 0 | cyanomethyl- |
| Y.3133 | cyclopropyl | 0 | cyclopentyl- |
| Y.3134 | cyclopropyl | 0 | cyclopropyl-methyl- |
| Y.3135 | cyclopropyl | 0 | methylpropargyl- |
| Y.3136 | cyclopropyl | 0 | oxetan-3-yl- |
| Y.3137 | cyclopropyl | 0 | pent-3-yl- |
| Y.3138 | cyclopropyl | 0 | phenyl-methyl-methyl- |
| Y.3139 | cyclopropyl | 0 | propargyl- |
| Y.3140 | cyclopropyl | 0 | tert-butyl- |
| Y.3141 | cyclopropyl | 0 | tetrazolyl- |
| Y.3142 | cyclopropyl | 0 | thiazol-2-yl- |
| Y.3143 | cyclopropyl | 0 | thiazol-4-yl- |
| Y.3144 | cyclopropyl | 0 | thietan-2-ylmethyl- |
| Y.3145 | cyclopropyl | 0 | thietan-3-ylmethyl- |
| Y.3146 | cyclopropyl | 0 | ethyl- |
| Y.3147 | cyclopropyl | 0 | 3,3,3-trifluoro-propyl- |
| Y.3148 | cyclopropyl | 0 | but-2-yl- |
| Y.3149 | cyclopropyl | 0 | (tetrahydrofuran-2-yl)-methyl- |
| Y.3150 | cyclopropyl | 0 | benzyl- |
| Y.3151 | cyclopropyl | 0 | (2-fluoro-phenyl)-methyl- |
| Y.3152 | cyclopropyl | 0 | 1-phenyl-eth-1-yl- |
| Y.3153 | cyclopropyl | 0 | (4-methoxy-phenyl)-methyl- |
| Y.3154 | cyclopropyl | 0 | 1,1-dioxo-thietan-3-yl- |
| Y.3155 | cyclopropyl | 0 | (2-chloro-pyrid-5-yl)-methyl- |
| Y.3156 | cyclopropyl | 0 | 3-fluoro-phenyl- |
| Y.3157 | cyclopropyl | 0 | n-butyl- |
| Y.3158 | cyclopropyl | 0 | (pyrid-2-yl)-methyl- |
| Y.3159 | cyclopropyl | 0 | 1,3-dimethyl-1H-pyrazol-5-yl- |
| Y.3160 | cyclopropyl | 0 | 4-methyl-thiazol-2-yl- |
| Y.3161 | cyclopropyl | 0 | 3-methyl-thietan-3-yl- |
| Y.3162 | cyclopropyl | 0 | 1,1-dimethyl-2-methylsulfanyl-ethyl |
| Y.3163 | cyclopropyl | 0 | 1-oxo-thietan-3-yl- |
| Y.3164 | cyclopropyl | 0 | thietan-3-yl- |
| Y.3165 | cyclopropyl | 0 | bicyclo[2.2.1]hept-2-yl- |
| Y.3166 | cyclopropyl | 0 | cyclobutyl- |
| Y.3167 | cyclopropyl | 0 | methyl- |
| Y.3168 | cyclopropyl | 0 | cyclopropyl- |
| Y.3169 | cyclopropyl | 0 | n-propyl- |
| Y.3170 | cyclopropyl | 0 | 2,2-difluoroethyl- |
| Y.3171 | cyclopropyl | 0 | 1-methoxy-prop-2-yl- |
| Y.3172 | cyclopropyl | 0 | N-(2,2,2-trifluoro-ethyl)-acetamide-2-yl |
| Y.3173 | cyclopropyl | 0 | 2,2,2-trifluoro-ethyl- |
| Y.3174 | cyclopropyl | 1 | (1,1-dioxothietan-2-yl)methyl- |
| Y.3175 | cyclopropyl | 1 | (1-oxothietan-2-yl)methyl- |
| Y.3176 | cyclopropyl | 1 | (2-methoxy-phenyl)-methyl- |
| Y.3177 | cyclopropyl | 1 | (3-fluoro-phenyl)-methyl- |
| Y.3178 | cyclopropyl | 1 | (4,4-dimethyl-4,5-dihydrothiazol-2-yl)-methyl- |
| Y.3179 | cyclopropyl | 1 | (4,5-dihydrothiazol-2-yl)-methyl- |
| Y.3180 | cyclopropyl | 1 | (4,5-dimethyl-4,5-dihydrothiazol-2-yl)-methyl- |
| Y.3181 | cyclopropyl | 1 | (4-fluoro-phenyl)-methyl- |
| Y.3182 | cyclopropyl | 1 | (4-methyl-4,5-dihydrothiazol-2-yl)-methyl- |
| Y.3183 | cyclopropyl | 1 | (5-methyl-4,5-dihydrothiazol-2-yl)-methyl- |
| Y.3184 | cyclopropyl | 1 | (pyrid-3-yl)-methyl- |
| Y.3185 | cyclopropyl | 1 | (pyrid-4-yl)-methyl- |
| Y.3186 | cyclopropyl | 1 | (tetrahydrothiophene-2-yl)-methyl- |
| Y.3187 | cyclopropyl | 1 | (tetrahydrothiophene-3-yl)-methyl- |
| Y.3188 | cyclopropyl | 1 | (thiazol-2-yl)-methyl- |
| Y.3189 | cyclopropyl | 1 | (thiazol-2-yl)-methylmethyl- |
| Y.3190 | cyclopropyl | 1 | (thiazol-4-yl)-methyl- |
| Y.3191 | cyclopropyl | 1 | (thiazol-5-yl)-methyl- |
| Y.3192 | cyclopropyl | 1 | 1,1-dioxo-thietan-3-ylmethyl- |
| Y.3193 | cyclopropyl | 1 | 1-cyanocyclobutyl- |

TABLE Y-continued

| | R5b | n | R2 |
|---|---|---|---|
| Y.3194 | cyclopropyl | 1 | 1-cyanocyclopentyl- |
| Y.3195 | cyclopropyl | 1 | 1-cyanocyclopropyl- |
| Y.3196 | cyclopropyl | 1 | 1-fluoroprop-2-yl- |
| Y.3197 | cyclopropyl | 1 | 1-methylallyl- |
| Y.3198 | cyclopropyl | 1 | 1-methylsulfanyl-prop-2-yl- |
| Y.3199 | cyclopropyl | 1 | 2-(1,1-dioxothietan-3-yl)ethanyl- |
| Y.3200 | cyclopropyl | 1 | 2-(1-oxothietan-3-yl)ethanyl- |
| Y.3201 | cyclopropyl | 1 | 2-(thietan-3-yl)ethanyl- |
| Y.3202 | cyclopropyl | 1 | 2-(trifluoromethoxy)phenyl- |
| Y.3203 | cyclopropyl | 1 | 2,2-dimethyl-1,1-dioxo-thietan-3-yl- |
| Y.3204 | cyclopropyl | 1 | 2,2-dimethyl-1-oxo-thietan-3-yl- |
| Y.3205 | cyclopropyl | 1 | 2,2-dimethylthietan-3-yl- |
| Y.3206 | cyclopropyl | 1 | 2,3-dichlorophenyl- |
| Y.3207 | cyclopropyl | 1 | 2,3-difluoro-phenyl- |
| Y.3208 | cyclopropyl | 1 | 2,4-dichlorophenyl- |
| Y.3209 | cyclopropyl | 1 | 2,4-difluoro-phenyl- |
| Y.3210 | cyclopropyl | 1 | 2,4-dimethylphenyl- |
| Y.3211 | cyclopropyl | 1 | 2,5-dichlorophenyl- |
| Y.3212 | cyclopropyl | 1 | 2,5-difluoro-phenyl- |
| Y.3213 | cyclopropyl | 1 | 2,6-dichlorophenyl- |
| Y.3214 | cyclopropyl | 1 | 2,6-difluoro-phenyl- |
| Y.3215 | cyclopropyl | 1 | 2,6-diisopropylphenyl- |
| Y.3216 | cyclopropyl | 1 | 2-bromo-4-fluorophenyl- |
| Y.3217 | cyclopropyl | 1 | 2-bromoallyl- |
| Y.3218 | cyclopropyl | 1 | 2-bromophenyl- |
| Y.3219 | cyclopropyl | 1 | 2-butenyl- |
| Y.3220 | cyclopropyl | 1 | 2-chloroallyl- |
| Y.3221 | cyclopropyl | 1 | 2-chlorophenyl- |
| Y.3222 | cyclopropyl | 1 | 2-chloropyrid-2-yl- |
| Y.3223 | cyclopropyl | 1 | 2-chloropyrid-3-yl- |
| Y.3224 | cyclopropyl | 1 | 2-cyanocyclopropyl- |
| Y.3225 | cyclopropyl | 1 | 2-cyanoethyl- |
| Y.3226 | cyclopropyl | 1 | 2-ethylphenyl- |
| Y.3227 | cyclopropyl | 1 | 2-fluoroethyl- |
| Y.3228 | cyclopropyl | 1 | 2-fluoro-phenyl- |
| Y.3229 | cyclopropyl | 1 | 2-fluoropropyl- |
| Y.3230 | cyclopropyl | 1 | 2-furylmethyl- |
| Y.3231 | cyclopropyl | 1 | 2-hydroxyphenyl- |
| Y.3232 | cyclopropyl | 1 | 2-methoxy-ethyl- |
| Y.3233 | cyclopropyl | 1 | 2-methoxyphenyl- |
| Y.3234 | cyclopropyl | 1 | 2-methoxy-prop-3-yl- |
| Y.3235 | cyclopropyl | 1 | 2-methylallyl- |
| Y.3236 | cyclopropyl | 1 | 2-methyl-but-1-yl- |
| Y.3237 | cyclopropyl | 1 | 2-methyl-but-2-yl- |
| Y.3238 | cyclopropyl | 1 | 2-methylbut-3-yn-2-yl- |
| Y.3239 | cyclopropyl | 1 | 2-methylphenyl- |
| Y.3240 | cyclopropyl | 1 | 2-methyl-prop-1-yl- |
| Y.3241 | cyclopropyl | 1 | 2-methylsulfanyl-ethyl- |
| Y.3242 | cyclopropyl | 1 | 2-methylsulfanyl-prop-3-yl- |
| Y.3243 | cyclopropyl | 1 | 2-methyl-thiazol-4-yl- |
| Y.3244 | cyclopropyl | 1 | 2-nitrophenyl- |
| Y.3245 | cyclopropyl | 1 | 2-propyl- |
| Y.3246 | cyclopropyl | 1 | 2-pyridyl- |
| Y.3247 | cyclopropyl | 1 | 2-trifluoromethoxy-ethyl- |
| Y.3248 | cyclopropyl | 1 | 3-(trifluoromethoxy)phenyl- |
| Y.3249 | cyclopropyl | 1 | 3,3,3-trifluoro-2,2-difluoropropyl- |
| Y.3250 | cyclopropyl | 1 | 3,3,3-trifluoro-butyl- |
| Y.3251 | cyclopropyl | 1 | 3,3-dibromoallyl- |
| Y.3252 | cyclopropyl | 1 | 3,3-dichloroallyl- |
| Y.3253 | cyclopropyl | 1 | 3,4-dichlorophenyl- |
| Y.3254 | cyclopropyl | 1 | 3,4-difluoro-phenyl- |
| Y.3255 | cyclopropyl | 1 | 3,5-dichlorophenyl- |
| Y.3256 | cyclopropyl | 1 | 3,5-difluoro-phenyl- |
| Y.3257 | cyclopropyl | 1 | 3,6-difluoro-phenyl- |
| Y.3258 | cyclopropyl | 1 | 3-bromoallyl- |
| Y.3259 | cyclopropyl | 1 | 3-bromophenyl- |
| Y.3260 | cyclopropyl | 1 | 3-butenyl- |
| Y.3261 | cyclopropyl | 1 | 3-chloroallyl- |
| Y.3262 | cyclopropyl | 1 | 3-chlorophenyl- |
| Y.3263 | cyclopropyl | 1 | 3-chloropyrid-2-yl- |
| Y.3264 | cyclopropyl | 1 | 3-cyanopropyl- |
| Y.3265 | cyclopropyl | 1 | 3-ethylphenyl- |
| Y.3266 | cyclopropyl | 1 | 3-hydroxyphenyl- |
| Y.3267 | cyclopropyl | 1 | 3-methyl-1,1-dioxo-thietan-3-yl- |
| Y.3268 | cyclopropyl | 1 | 3-methyl-1-oxo-thietan-3-yl- |
| Y.3269 | cyclopropyl | 1 | 3-methyl-but-1-yl- |
| Y.3270 | cyclopropyl | 1 | 3-methyl-but-2-yl- |
| Y.3271 | cyclopropyl | 1 | 3-methylphenyl- |
| Y.3272 | cyclopropyl | 1 | 3-nitrophenyl- |
| Y.3273 | cyclopropyl | 1 | 3-pyridyl- |
| Y.3274 | cyclopropyl | 1 | 4-(trifluoromethoxy)phenyl- |
| Y.3275 | cyclopropyl | 1 | 4,5-dihydrothiazol-2-yl- |
| Y.3276 | cyclopropyl | 1 | 4,5-dimethyl-4,5-dihydrothiazol-2-yl- |
| Y.3277 | cyclopropyl | 1 | 4,5-dimethyl-thiazol-2-yl- |
| Y.3278 | cyclopropyl | 1 | 4-bromophenyl- |
| Y.3279 | cyclopropyl | 1 | 4-chlorophenyl- |
| Y.3280 | cyclopropyl | 1 | 4-ethylphenyl- |
| Y.3281 | cyclopropyl | 1 | 4-fluoro-phenyl- |
| Y.3282 | cyclopropyl | 1 | 4H-1,2,4-triazol-3-yl- |
| Y.3283 | cyclopropyl | 1 | 4-methoxyphenyl- |
| Y.3284 | cyclopropyl | 1 | 4-methyl-4,5-dihydrothiazol-2-yl- |
| Y.3285 | cyclopropyl | 1 | 4-methylphenyl- |
| Y.3286 | cyclopropyl | 1 | 4-methylpyrid-2-yl |
| Y.3287 | cyclopropyl | 1 | 4-nitrophenyl- |
| Y.3288 | cyclopropyl | 1 | 4-pyridyl- |
| Y.3289 | cyclopropyl | 1 | 5-methyl-4,5-dihydrothiazol-2-yl- |
| Y.3290 | cyclopropyl | 1 | 5-methyl-thiazol-2-yl- |
| Y.3291 | cyclopropyl | 1 | 6-methylpyrid-2-yl- |
| Y.3292 | cyclopropyl | 1 | allyl- |
| Y.3293 | cyclopropyl | 1 | but-2-ynyl- |
| Y.3294 | cyclopropyl | 1 | but-3-ynyl- |
| Y.3295 | cyclopropyl | 1 | cis-1-oxo-thietan-3-yl- |
| Y.3296 | cyclopropyl | 1 | cis-1-oxo-thietan-3-ylmethyl- |
| Y.3297 | cyclopropyl | 1 | cyanodimethylmethyl- |
| Y.3298 | cyclopropyl | 1 | cyanoethyl- |
| Y.3299 | cyclopropyl | 1 | cyanomethyl- |
| Y.3300 | cyclopropyl | 1 | cyclopentyl- |
| Y.3301 | cyclopropyl | 1 | cyclopropyl-methyl- |
| Y.3302 | cyclopropyl | 1 | methylpropargyl- |
| Y.3303 | cyclopropyl | 1 | oxetan-3-yl- |
| Y.3304 | cyclopropyl | 1 | pent-3-yl- |
| Y.3305 | cyclopropyl | 1 | phenyl-methyl-methyl- |
| Y.3306 | cyclopropyl | 1 | propargyl- |
| Y.3307 | cyclopropyl | 1 | tert-butyl- |
| Y.3308 | cyclopropyl | 1 | tetrazolyl- |
| Y.3309 | cyclopropyl | 1 | thiazol-2-yl- |
| Y.3310 | cyclopropyl | 1 | thiazol-4-yl- |
| Y.3311 | cyclopropyl | 1 | thietan-2-ylmethyl- |
| Y.3312 | cyclopropyl | 1 | thietan-3-ylmethyl- |
| Y.3313 | cyclopropyl | 1 | ethyl- |
| Y.3314 | cyclopropyl | 1 | 3,3,3-trifluoro-propyl- |
| Y.3315 | cyclopropyl | 1 | but-2-yl- |
| Y.3316 | cyclopropyl | 1 | (tetrahydrofuran-2-yl)-methyl- |
| Y.3317 | cyclopropyl | 1 | benzyl- |
| Y.3318 | cyclopropyl | 1 | (2-fluoro-phenyl)-methyl- |
| Y.3319 | cyclopropyl | 1 | 1-phenyl-eth-1-yl- |
| Y.3320 | cyclopropyl | 1 | (4-methoxy-phenyl)-methyl- |
| Y.3321 | cyclopropyl | 1 | 1,1-dioxo-thietan-3-yl- |
| Y.3322 | cyclopropyl | 1 | (2-chloro-pyrid-5-yl)-methyl- |
| Y.3323 | cyclopropyl | 1 | 3-fluoro-phenyl- |
| Y.3324 | cyclopropyl | 1 | n-butyl- |
| Y.3325 | cyclopropyl | 1 | (pyrid-2-yl)-methyl- |
| Y.3326 | cyclopropyl | 1 | 1,3-dimethyl-1H-pyrazol-5-yl- |
| Y.3327 | cyclopropyl | 1 | 4-methyl-thiazol-2-yl- |
| Y.3328 | cyclopropyl | 1 | 3-methyl-thietan-3-yl- |
| Y.3329 | cyclopropyl | 1 | 1,1-dimethyl-2-methylsulfanyl-ethyl |
| Y.3330 | cyclopropyl | 1 | 1-oxo-thietan-3-yl- |
| Y.3331 | cyclopropyl | 1 | thietan-3-yl- |
| Y.3332 | cyclopropyl | 1 | bicyclo[2.2.1]hept-2-yl- |
| Y.3333 | cyclopropyl | 1 | cyclobutyl- |
| Y.3334 | cyclopropyl | 1 | methyl- |
| Y.3335 | cyclopropyl | 1 | cyclopropyl- |
| Y.3336 | cyclopropyl | 1 | n-propyl- |
| Y.3337 | cyclopropyl | 1 | 2,2-difluoroethyl- |
| Y.3338 | cyclopropyl | 1 | 1-methoxy-prop-2-yl- |
| Y.3339 | cyclopropyl | 1 | N-(2,2,2-trifluoro-ethyl)-acetamide-2-yl |
| Y.3340 | cyclopropyl | 1 | 2,2,2-trifluoro-ethyl- |
| Y.3341 | cyclopropyl | 2 | (1,1-dioxothietan-2-yl)methyl- |
| Y.3342 | cyclopropyl | 2 | (1-oxothietan-2-yl)methyl- |
| Y.3343 | cyclopropyl | 2 | (2-methoxy-phenyl)-methyl- |
| Y.3344 | cyclopropyl | 2 | (3-fluoro-phenyl)-methyl- |
| Y.3345 | cyclopropyl | 2 | (4,4-dimethyl-4,5-dihydrothiazol-2-yl)-methyl- |
| Y.3346 | cyclopropyl | 2 | (4,5-dihydrothiazol-2-yl)-methyl- |
| Y.3347 | cyclopropyl | 2 | (4,5-dimethyl-4,5-dihydrothiazol-2-yl)-methyl- |

TABLE Y-continued

| | R5b | n | R2 |
|---|---|---|---|
| Y.3348 | cyclopropyl | 2 | (4-fluoro-phenyl)-methyl- |
| Y.3349 | cyclopropyl | 2 | (4-methyl-4,5-dihydrothiazol-2-yl)-methyl- |
| Y.3350 | cyclopropyl | 2 | (5-methyl-4,5-dihydrothiazol-2-yl)-methyl- |
| Y.3351 | cyclopropyl | 2 | (pyrid-3-yl)-methyl- |
| Y.3352 | cyclopropyl | 2 | (pyrid-4-yl)-methyl- |
| Y.3353 | cyclopropyl | 2 | (tetrahydrothiophene-2-yl)-methyl- |
| Y.3354 | cyclopropyl | 2 | (tetrahydrothiophene-3-yl)-methyl- |
| Y.3355 | cyclopropyl | 2 | (thiazol-2-yl)-methyl- |
| Y.3356 | cyclopropyl | 2 | (thiazol-2-yl)-methylmethyl- |
| Y.3357 | cyclopropyl | 2 | (thiazol-4-yl)-methyl- |
| Y.3358 | cyclopropyl | 2 | (thiazol-5-yl)-methyl- |
| Y.3359 | cyclopropyl | 2 | 1,1-dioxo-thietan-3-ylmethyl- |
| Y.3360 | cyclopropyl | 2 | 1-cyanocyclobutyl- |
| Y.3361 | cyclopropyl | 2 | 1-cyanocyclopentyl- |
| Y.3362 | cyclopropyl | 2 | 1-cyanocyclopropyl- |
| Y.3363 | cyclopropyl | 2 | 1-fluoroprop-2-yl- |
| Y.3364 | cyclopropyl | 2 | 1-methylallyl- |
| Y.3365 | cyclopropyl | 2 | 1-methylsulfanyl-prop-2-yl- |
| Y.3366 | cyclopropyl | 2 | 2-(1,1-dioxothietan-3-yl)ethanyl- |
| Y.3367 | cyclopropyl | 2 | 2-(1-oxothietan-3-yl)ethanyl- |
| Y.3368 | cyclopropyl | 2 | 2-(thietan-3-yl)ethanyl- |
| Y.3369 | cyclopropyl | 2 | 2-(trifluoromethoxy)phenyl- |
| Y.3370 | cyclopropyl | 2 | 2,2-dimethyl-1,1-dioxo-thietan-3-yl- |
| Y.3371 | cyclopropyl | 2 | 2,2-dimethyl-1-oxo-thietan-3-yl- |
| Y.3372 | cyclopropyl | 2 | 2,2-dimethylthietan-3-yl- |
| Y.3373 | cyclopropyl | 2 | 2,3-dichlorophenyl- |
| Y.3374 | cyclopropyl | 2 | 2,3-difluoro-phenyl- |
| Y.3375 | cyclopropyl | 2 | 2,4-dichlorophenyl- |
| Y.3376 | cyclopropyl | 2 | 2,4-difluoro-phenyl- |
| Y.3377 | cyclopropyl | 2 | 2,4-dimethylphenyl- |
| Y.3378 | cyclopropyl | 2 | 2,5-dichlorophenyl- |
| Y.3379 | cyclopropyl | 2 | 2,5-difluoro-phenyl- |
| Y.3380 | cyclopropyl | 2 | 2,6-dichlorophenyl- |
| Y.3381 | cyclopropyl | 2 | 2,6-difluoro-phenyl- |
| Y.3382 | cyclopropyl | 2 | 2,6-diisopropylphenyl- |
| Y.3383 | cyclopropyl | 2 | 2-bromo-4-fluorophenyl- |
| Y.3384 | cyclopropyl | 2 | 2-bromoallyl- |
| Y.3385 | cyclopropyl | 2 | 2-bromophenyl- |
| Y.3386 | cyclopropyl | 2 | 2-butenyl- |
| Y.3387 | cyclopropyl | 2 | 2-chloroallyl- |
| Y.3388 | cyclopropyl | 2 | 2-chlorophenyl- |
| Y.3389 | cyclopropyl | 2 | 2-chloropyrid-2-yl- |
| Y.3390 | cyclopropyl | 2 | 2-chloropyrid-3-yl- |
| Y.3391 | cyclopropyl | 2 | 2-cyanocyclopropyl- |
| Y.3392 | cyclopropyl | 2 | 2-cyanoethyl- |
| Y.3393 | cyclopropyl | 2 | 2-ethylphenyl- |
| Y.3394 | cyclopropyl | 2 | 2-fluoroethyl- |
| Y.3395 | cyclopropyl | 2 | 2-fluoro-phenyl- |
| Y.3396 | cyclopropyl | 2 | 2-fluoropropyl- |
| Y.3397 | cyclopropyl | 2 | 2-furylmethyl- |
| Y.3398 | cyclopropyl | 2 | 2-hydroxyphenyl- |
| Y.3399 | cyclopropyl | 2 | 2-methoxy-ethyl- |
| Y.3400 | cyclopropyl | 2 | 2-methoxyphenyl- |
| Y.3401 | cyclopropyl | 2 | 2-methoxy-prop-3-yl- |
| Y.3402 | cyclopropyl | 2 | 2-methylallyl- |
| Y.3403 | cyclopropyl | 2 | 2-methyl-but-1-yl- |
| Y.3404 | cyclopropyl | 2 | 2-methyl-but-2-yl- |
| Y.3405 | cyclopropyl | 2 | 2-methylbut-3-yn-2-yl- |
| Y.3406 | cyclopropyl | 2 | 2-methylphenyl- |
| Y.3407 | cyclopropyl | 2 | 2-methyl-prop-1-yl- |
| Y.3408 | cyclopropyl | 2 | 2-methylsulfanyl-ethyl- |
| Y.3409 | cyclopropyl | 2 | 2-methylsulfanyl-prop-3-yl- |
| Y.3410 | cyclopropyl | 2 | 2-methyl-thiazol-4-yl- |
| Y.3411 | cyclopropyl | 2 | 2-nitrophenyl- |
| Y.3412 | cyclopropyl | 2 | 2-propyl- |
| Y.3413 | cyclopropyl | 2 | 2-pyridyl- |
| Y.3414 | cyclopropyl | 2 | 2-trifluoromethoxy-ethyl- |
| Y.3415 | cyclopropyl | 2 | 3-(trifluoromethoxy)phenyl- |
| Y.3416 | cyclopropyl | 2 | 3,3,3-trifluoro-2,2-difluoropropyl- |
| Y.3417 | cyclopropyl | 2 | 3,3,3-trifluoro-butyl- |
| Y.3418 | cyclopropyl | 2 | 3,3-dibromoallyl- |
| Y.3419 | cyclopropyl | 2 | 3,3-dichloroallyl- |
| Y.3420 | cyclopropyl | 2 | 3,4-dichlorophenyl- |
| Y.3421 | cyclopropyl | 2 | 3,4-difluoro-phenyl- |
| Y.3422 | cyclopropyl | 2 | 3,5-dichlorophenyl- |
| Y.3423 | cyclopropyl | 2 | 3,5-difluoro-phenyl- |
| Y.3424 | cyclopropyl | 2 | 3,6-difluoro-phenyl- |
| Y.3425 | cyclopropyl | 2 | 3-bromoallyl- |
| Y.3426 | cyclopropyl | 2 | 3-bromophenyl- |
| Y.3427 | cyclopropyl | 2 | 3-butenyl- |
| Y.3428 | cyclopropyl | 2 | 3-chloroallyl- |
| Y.3429 | cyclopropyl | 2 | 3-chlorophenyl- |
| Y.3430 | cyclopropyl | 2 | 3-chloropyrid-2-yl- |
| Y.3431 | cyclopropyl | 2 | 3-cyanopropyl- |
| Y.3432 | cyclopropyl | 2 | 3-ethylphenyl- |
| Y.3433 | cyclopropyl | 2 | 3-hydroxyphenyl- |
| Y.3434 | cyclopropyl | 2 | 3-methyl-1,1-dioxo-thietan-3-yl- |
| Y.3435 | cyclopropyl | 2 | 3-methyl-1-oxo-thietan-3-yl- |
| Y.3436 | cyclopropyl | 2 | 3-methyl-but-1-yl- |
| Y.3437 | cyclopropyl | 2 | 3-methyl-but-2-yl- |
| Y.3438 | cyclopropyl | 2 | 3-methylphenyl- |
| Y.3439 | cyclopropyl | 2 | 3-nitrophenyl- |
| Y.3440 | cyclopropyl | 2 | 3-pyridyl- |
| Y.3441 | cyclopropyl | 2 | 4-(trifluoromethoxy)phenyl- |
| Y.3442 | cyclopropyl | 2 | 4,5-dihydrothiazol-2-yl- |
| Y.3443 | cyclopropyl | 2 | 4,5-dimethyl-4,5-dihydrothiazol-2-yl- |
| Y.3444 | cyclopropyl | 2 | 4,5-dimethyl-thiazol-2-yl- |
| Y.3445 | cyclopropyl | 2 | 4-bromophenyl- |
| Y.3446 | cyclopropyl | 2 | 4-chlorophenyl- |
| Y.3447 | cyclopropyl | 2 | 4-ethylphenyl- |
| Y.3448 | cyclopropyl | 2 | 4-fluoro-phenyl- |
| Y.3449 | cyclopropyl | 2 | 4H-1,2,4-triazol-3-yl- |
| Y.3450 | cyclopropyl | 2 | 4-methoxyphenyl- |
| Y.3451 | cyclopropyl | 2 | 4-methyl-4,5-dihydrothiazol-2-yl- |
| Y.3452 | cyclopropyl | 2 | 4-methylphenyl- |
| Y.3453 | cyclopropyl | 2 | 4-methylpyrid-2-yl |
| Y.3454 | cyclopropyl | 2 | 4-nitrophenyl- |
| Y.3455 | cyclopropyl | 2 | 4-pyridyl- |
| Y.3456 | cyclopropyl | 2 | 5-methyl-4,5-dihydrothiazol-2-yl- |
| Y.3457 | cyclopropyl | 2 | 5-methyl-thiazol-2-yl- |
| Y.3458 | cyclopropyl | 2 | 6-methylpyrid-2-yl- |
| Y.3459 | cyclopropyl | 2 | allyl- |
| Y.3460 | cyclopropyl | 2 | but-2-ynyl- |
| Y.3461 | cyclopropyl | 2 | but-3-ynyl- |
| Y.3462 | cyclopropyl | 2 | cis-1-oxo-thietan-3-yl- |
| Y.3463 | cyclopropyl | 2 | cis-1-oxo-thietan-3-ylmethyl- |
| Y.3464 | cyclopropyl | 2 | cyanodimethylmethyl- |
| Y.3465 | cyclopropyl | 2 | cyanoethyl- |
| Y.3466 | cyclopropyl | 2 | cyanomethyl- |
| Y.3467 | cyclopropyl | 2 | cyclopentyl- |
| Y.3468 | cyclopropyl | 2 | cyclopropyl-methyl- |
| Y.3469 | cyclopropyl | 2 | methylpropargyl- |
| Y.3470 | cyclopropyl | 2 | oxetan-3-yl- |
| Y.3471 | cyclopropyl | 2 | pent-3-yl- |
| Y.3472 | cyclopropyl | 2 | phenyl-methyl-methyl- |
| Y.3473 | cyclopropyl | 2 | propargyl- |
| Y.3474 | cyclopropyl | 2 | tert-butyl- |
| Y.3475 | cyclopropyl | 2 | tetrazolyl- |
| Y.3476 | cyclopropyl | 2 | thiazol-2-yl- |
| Y.3477 | cyclopropyl | 2 | thiazol-4-yl- |
| Y.3478 | cyclopropyl | 2 | thietan-2-ylmethyl- |
| Y.3479 | cyclopropyl | 2 | thietan-3-ylmethyl- |
| Y.3480 | cyclopropyl | 2 | ethyl- |
| Y.3481 | cyclopropyl | 2 | 3,3,3-trifluoro-propyl- |
| Y.3482 | cyclopropyl | 2 | but-2-yl- |
| Y.3483 | cyclopropyl | 2 | (tetrahydrofuran-2-yl)-methyl- |
| Y.3484 | cyclopropyl | 2 | benzyl- |
| Y.3485 | cyclopropyl | 2 | (2-fluoro-phenyl)-methyl- |
| Y.3486 | cyclopropyl | 2 | 1-phenyl-eth-1-yl- |
| Y.3487 | cyclopropyl | 2 | (4-methoxy-phenyl)-methyl- |
| Y.3488 | cyclopropyl | 2 | 1,1-dioxo-thietan-3-yl- |
| Y.3489 | cyclopropyl | 2 | (2-chloro-pyrid-5-yl)-methyl- |
| Y.3490 | cyclopropyl | 2 | 3-fluoro-phenyl- |
| Y.3491 | cyclopropyl | 2 | n-butyl- |
| Y.3492 | cyclopropyl | 2 | (pyrid-2-yl)-methyl- |
| Y.3493 | cyclopropyl | 2 | 1,3-dimethyl-1H-pyrazol-5-yl- |
| Y.3494 | cyclopropyl | 2 | 4-methyl-thiazol-2-yl- |
| Y.3495 | cyclopropyl | 2 | 3-methyl-thietan-3-yl- |
| Y.3496 | cyclopropyl | 2 | 1,1-dimethyl-2-methylsulfanyl-ethyl |
| Y.3497 | cyclopropyl | 2 | 1-oxo-thietan-3-yl- |
| Y.3498 | cyclopropyl | 2 | thietan-3-yl- |
| Y.3499 | cyclopropyl | 2 | bicyclo[2.2.1]hept-2-yl- |
| Y.3500 | cyclopropyl | 2 | cyclobutyl- |
| Y.3501 | cyclopropyl | 2 | methyl- |

TABLE Y-continued

| | R5b | n | R2 |
|---|---|---|---|
| Y.3502 | cyclopropyl | 2 | cyclopropyl- |
| Y.3503 | cyclopropyl | 2 | n-propyl- |
| Y.3504 | cyclopropyl | 2 | 2,2-difluoroethyl- |
| Y.3505 | cyclopropyl | 2 | 1-methoxy-prop-2-yl- |
| Y.3506 | cyclopropyl | 2 | N-(2,2,2-trifluoro-ethyl)-acetamide-2-yl |
| Y.3507 | cyclopropyl | 2 | 2,2,2-trifluoro-ethyl- |

(I-A)

Table 1
Table 1 provides 3507 compounds of formula (I-A) wherein R3 is trifluoromethyl-, R4 is 3,5-dichlorophenyl-, Y1-Y2-Y3 is —C=N—O—, A2 is CH, A3 is CH, A4 is CH, R5b, n and R2 have the values listed in the Table Y.

Table 2
Table 2 provides 3507 compounds of formula (I-A) wherein R3 is trifluoromethyl-, R4 is 3,5-dichlorophenyl-, Y1-Y2-Y3 is —C=N—O—, A2 is CH, A3 is CH, A4 is CH, R5b, n and R2 have the values listed in the Table Y.

Table 3
Table 3 provides 3507 compounds of formula (I-A) wherein R3 is trifluoromethyl-, R4 is 3,5-dichlorophenyl-, Y1-Y2-Y3 is —C=N—O—, A2 is CH, A3 is CH, A4 is CH, R5b, n and R2 have the values listed in the Table Y.

Table 4
Table 4 provides 3507 compounds of formula (I-A) wherein R3 is trifluoromethyl-, R4 is 3,5-dichlorophenyl-, Y1-Y2-Y3 is —C=N—O—, A2 is CH, A3 is N, A4 is CH, R5b, n and R2 have the values listed in the Table Y.

Table 5
Table 5 provides 3507 compounds of formula (I-A) wherein R3 is trifluoromethyl-, R4 is 3,5-dichlorophenyl-, Y1-Y2-Y3 is —C=N—CH2-, A2 is CH, A3 is CH, A4 is CH, R5b, n and R2 have the values listed in the Table Y.

Table 6
Table 6 provides 3507 compounds of formula (I-A) wherein R3 is trifluoromethyl-, R4 is 3,5-dichlorophenyl-, Y1-Y2-Y3 is —C=N—CH2-, A2 is CH, A3 is CH, A4 is N, R5b, n and R2 have the values listed in the Table Y.

Table 7
Table 7 provides 3507 compounds of formula (I-A) wherein R3 is trifluoromethyl-, R4 is 3,5-dichlorophenyl-, Y1-Y2-Y3 is —C=N—CH2-, A2 is N, A3 is N, A4 is CH, R5b, n and R2 have the values listed in the Table Y.

Table 8
Table 8 provides 3507 compounds of formula (I-A) wherein R3 is trifluoromethyl-, R4 is 3,5-dichlorophenyl-, Y1-Y2-Y3 is —N—CH2-CH2-, A2 is CH, A3 is CH, A4 is N, R5b, n and R2 have the values listed in the Table Y.

Table 9
Table 9 provides 3507 compounds of formula (I-A) wherein R3 is trifluoromethyl-, R4 is 3,5-dichlorophenyl-, Y1-Y2-Y3 is —N—CH2-CH2-, A2 is CH, A3 is CH, A4 is N, R5b, n and R2 have the values listed in the Table Y.

Table 10
Table 10 provides 3507 compounds of formula (I-A) wherein R3 is trifluoromethyl-, R4 is 3,5-dichlorophenyl-, Y1-Y2-Y3 is —N—CH2-CH2-, A2 is CH, A3 is CH, A4 is N, R5b, n and R2 have the values listed in the Table Y.

Table 11
Table 11 provides 3507 compounds of formula (I-A) wherein R3 is trifluoromethyl-, R4 is 3,5-dichlorophenyl-, Y1-Y2-Y3 is —N—CH2-CH2-, A2 is N, A3 is N, A4 is CH, R5b, n and R2 have the values listed in the Table Y.

Table 12
Table 12 provides 3507 compounds of formula (I-A) wherein R3 is trifluoromethyl-, R4 is 3,5-dichlorophenyl-, Y1-Y2-Y3 is —N—CH2-CH2-, A2 is N, A3 is N, A4 is CH, R5b, n and R2 have the values listed in the Table Y.

Table 13
Table 13 provides 3507 compounds of formula (I-A) wherein R3 is trifluoromethyl-, R4 is 3,5-dichlorophenyl-, Y1-Y2-Y3 is —C=CH—O—, A2 is CH, A3 is CH, A4 is CH, R5b, n and R2 have the values listed in the Table Y.

Table 14
Table 14 provides 3507 compounds of formula (I-A) wherein R3 is trifluoromethyl-, R4 is 3,5-dichlorophenyl-, Y1-Y2-Y3 is —C=CH—O—, A2 is CH, A3 is N, A4 is CH, R5b, n and R2 have the values listed in the Table Y.

Table 15
Table 15 provides 3507 compounds of formula (I-A) wherein R3 is trifluoromethyl-, R4 is 3,5-dichlorophenyl-, Y1-Y2-Y3 is —C=CH—O—, A2 is N, A3 is N, A4 is CH, R5b, n and R2 have the values listed in the Table Y.

Table 16
Table 16 provides 3507 compounds of formula (I-A) wherein R3 is trifluoromethyl-, R4 is 3,5-dichlorophenyl-, Y1-Y2-Y3 is —C=CH—O—, A2 is N, A3 is N, A4 is CH, R5b, n and R2 have the values listed in the Table Y.

Table 17
Table 17 provides 3507 compounds of formula (I-A) wherein R3 is trifluoromethyl-, R4 is 2,6-bis(trifluoromethyl)-4-pyridyl-, Y1-Y2-Y3 is —C=N—O—, A2 is CH, A3 is CH, A4 is CH, R5b, n and R2 have the values listed in the Table Y.

Table 18
Table 18 provides 3507 compounds of formula (I-A) wherein R3 is trifluoromethyl-, R4 is 2,6-bis(trifluoromethyl)-4-pyridyl-, Y1-Y2-Y3 is —C=N—O—, A2 is CH, A3 is CH, A4 is CH, R5b, n and R2 have the values listed in the Table Y.

Table 19
Table 19 provides 3507 compounds of formula (I-A) wherein R3 is trifluoromethyl-, R4 is 2,6-bis(trifluoromethyl)-4-pyridyl-, Y1-Y2-Y3 is —C=N—O—, A2 is CH, A3 is N, A4 is CH, R5b, n and R2 have the values listed in the Table Y.

Table 20
Table 20 provides 3507 compounds of formula (I-A) wherein R3 is trifluoromethyl-, R4 is 2,6-bis(trifluoromethyl)-4-pyridyl-, Y1-Y2-Y3 is —C=N—O—, A2 is CH, A3 is CH, A4 is N, R5b, n and R2 have the values listed in the Table Y.

Table 21
Table 21 provides 3507 compounds of formula (I-A) wherein R3 is trifluoromethyl-, R4 is 2,6-bis(trifluoromethyl)-4-pyridyl-, Y1-Y2-Y3 is —C=N—O—, A2 is CH, A3 is CH, A4 is N, R5b, n and R2 have the values listed in the Table Y.

Table 22
Table 22 provides 3507 compounds of formula (I-A) wherein R3 is trifluoromethyl-, R4 is 2,6-bis(trifluoromethyl)-4-pyridyl-, Y1-Y2-Y3 is —C=N—CH2-, A2 is CH, A3 is CH, A4 is N, R5b, n and R2 have the values listed in the Table Y.

Table 23
Table 23 provides 3507 compounds of formula (I-A) wherein R3 is trifluoromethyl-, R4 is 2,6-bis(trifluoromethyl)-4-pyridyl-, Y1-Y2-Y3 is —C=N—CH2-, A2 is CH, A3 is CH, A4 is N, R5b, n and R2 have the values listed in the Table Y.
Table 24
Table 24 provides 3507 compounds of formula (I-A) wherein R3 is trifluoromethyl-, R4 is 2,6-bis(trifluoromethyl)-4-pyridyl-, Y1-Y2-Y3 is —C=N—CH2-, A2 is N, A3 is N, A4 is CH, R5b, n and R2 have the values listed in the Table Y.
Table 25
Table 25 provides 3507 compounds of formula (I-A) wherein R3 is trifluoromethyl-, R4 is 2,6-bis(trifluoromethyl)-4-pyridyl-, Y1-Y2-Y3 is —C=N—CH2-, A2 is N, A3 is N, A4 is CH, R5b, n and R2 have the values listed in the Table Y.
Table 26
Table 26 provides 3507 compounds of formula (I-A) wherein R3 is trifluoromethyl-, R4 is 2,6-bis(trifluoromethyl)-4-pyridyl-, Y1-Y2-Y3 is —N—CH2-CH2-, A2 is CH, A3 is CH, A4 is CH, R5b, n and R2 have the values listed in the Table Y.
Table 27
Table 27 provides 3507 compounds of formula (I-A) wherein R3 is trifluoromethyl-, R4 is 2,6-bis(trifluoromethyl)-4-pyridyl-, Y1-Y2-Y3 is —N—CH2-CH2-, A2 is CH, A3 is CH, A4 is CH, R5b, n and R2 have the values listed in the Table Y.
Table 28
Table 28 provides 3507 compounds of formula (I-A) wherein R3 is trifluoromethyl-, R4 is 2,6-bis(trifluoromethyl)-4-pyridyl-, Y1-Y2-Y3 is —N—CH2-CH2-, A2 is CH, A3 is CH, A4 is N, R5b, n and R2 have the values listed in the Table Y.
Table 29
Table 29 provides 3507 compounds of formula (I-A) wherein R3 is trifluoromethyl-, R4 is 2,6-bis(trifluoromethyl)-4-pyridyl-, Y1-Y2-Y3 is —N—CH2-CH2-, A2 is CH, A3 is CH, A4 is N, R5b, n and R2 have the values listed in the Table Y.
Table 30
Table 30 provides 3507 compounds of formula (I-A) wherein R3 is trifluoromethyl-, R4 is 2,6-bis(trifluoromethyl)-4-pyridyl-, Y1-Y2-Y3 is —N—CH2-CH2-, A2 is N, A3 is N, A4 is CH, R5b, n and R2 have the values listed in the Table Y.
Table 31
Table 31 provides 3507 compounds of formula (I-A) wherein R3 is trifluoromethyl-, R4 is 2,6-bis(trifluoromethyl)-4-pyridyl-, Y1-Y2-Y3 is —C=CH—O—, A2 is CH, A3 is CH, A4 is N, R5b, n and R2 have the values listed in the Table Y.
Table 32
Table 32 provides 3507 compounds of formula (I-A) wherein R3 is trifluoromethyl-, R4 is 2,6-bis(trifluoromethyl)-4-pyridyl-, Y1-Y2-Y3 is —C=CH—O—, A2 is N, A3 is N, A4 is CH, R5b, n and R2 have the values listed in the Table Y.
Table 33
Table 33 provides 3507 compounds of formula (I-A) wherein R3 is trifluoromethyl-, R4 is 3,5-dichloro-4-bromophenyl-, Y1-Y2-Y3 is —C=N—O—, A2 is CH, A3 is CH, A4 is CH, R5b, n and R2 have the values listed in the Table Y.
Table 34
Table 34 provides 3507 compounds of formula (I-A) wherein R3 is trifluoromethyl-, R4 is 3,5-dichloro-4-bromophenyl-, Y1-Y2-Y3 is —C=N—O—, A2 is CH, A3 is CH, A4 is CH, R5b, n and R2 have the values listed in the Table Y.
Table 35
Table 35 provides 3507 compounds of formula (I-A) wherein R3 is trifluoromethyl-, R4 is 3,5-dichloro-4-bromophenyl-, Y1-Y2-Y3 is —C=N—O—, A2 is CH, A3 is CH, A4 is CH, R5b, n and R2 have the values listed in the Table Y.
Table 36
Table 36 provides 3507 compounds of formula (I-A) wherein R3 is trifluoromethyl-, R4 is 3,5-dichloro-4-bromophenyl-, Y1-Y2-Y3 is —C=N—O—, A2 is CH, A3 is CH, A4 is N, R5b, n and R2 have the values listed in the Table Y.
Table 37
Table 37 provides 3507 compounds of formula (I-A) wherein R3 is trifluoromethyl-, R4 is 3,5-dichloro-4-bromophenyl-, Y1-Y2-Y3 is —C=N—O—, A2 is CH, A3 is CH, A4 is N, R5b, n and R2 have the values listed in the Table Y.
Table 38
Table 38 provides 3507 compounds of formula (I-A) wherein R3 is trifluoromethyl-, R4 is 3,5-dichloro-4-bromophenyl-, Y1-Y2-Y3 is —C=N—O—, A2 is N, A3 is N, A4 is CH, R5b, n and R2 have the values listed in the Table Y.
Table 39
Table 39 provides 3507 compounds of formula (I-A) wherein R3 is trifluoromethyl-, R4 is 3,5-dichloro-4-bromophenyl-, Y1-Y2-Y3 is —C=N—CH2-, A2 is CH, A3 is N, A4 is CH, R5b, n and R2 have the values listed in the Table Y.
Table 40
Table 40 provides 3507 compounds of formula (I-A) wherein R3 is trifluoromethyl-, R4 is 3,5-dichloro-4-bromophenyl-, Y1-Y2-Y3 is —C=N—CH2-, A2 is N, A3 is N, A4 is CH, R5b, n and R2 have the values listed in the Table Y.
Table 41
Table 41 provides 3507 compounds of formula (I-A) wherein R3 is trifluoromethyl-, R4 is 3,5-dichloro-4-bromophenyl-, Y1-Y2-Y3 is —N—CH2-CH2-, A2 is CH, A3 is CH, A4 is CH, R5b, n and R2 have the values listed in the Table Y.
Table 42
Table 42 provides 3507 compounds of formula (I-A) wherein R3 is trifluoromethyl-, R4 is 3,5-dichloro-4-bromophenyl-, Y1-Y2-Y3 is —N—CH2-CH2-, A2 is CH, A3 is N, A4 is CH, R5b, n and R2 have the values listed in the Table Y.
Table 43
Table 43 provides 3507 compounds of formula (I-A) wherein R3 is trifluoromethyl-, R4 is 3,5-dichloro-4-bromophenyl-, Y1-Y2-Y3 is —C=CH—O—, A2 is CH, A3 is CH, A4 is CH, R5b, n and R2 have the values listed in the Table Y.
Table 44
Table 44 provides 3507 compounds of formula (I-A) wherein R3 is trifluoromethyl-, R4 is 3,5-dichloro-4-bromophenyl-, Y1-Y2-Y3 is —C=CH—O—, A2 is CH, A3 is N, A4 is CH, R5b, n and R2 have the values listed in the Table Y.
Table 45
Table 45 provides 3507 compounds of formula (I-A) wherein R3 is trifluoromethyl-, R4 is 3,5-dichloro-4-bromophenyl-, Y1-Y2-Y3 is —C=CH—O—, A2 is CH, A3 is N, A4 is CH, R5b, n and R2 have the values listed in the Table Y.
Table 46
Table 46 provides 3507 compounds of formula (I-A) wherein R3 is trifluoromethyl-, R4 is 3,5-dichloro-4-bromophenyl-, Y1-Y2-Y3 is —C=CH—O—, A2 is CH, A3 is N, A4 is CH, R5b, n and R2 have the values listed in the Table Y.
Table 47
Table 47 provides 3507 compounds of formula (I-A) wherein R3 is trifluoromethyl-, R4 is 3,5-dichloro-4-bromophenyl-, Y1-Y2-Y3 is —C=CH—O—, A2 is CH, A3 is CH, A4 is N, R5b, n and R2 have the values listed in the Table Y.
Table 48
Table 48 provides 3507 compounds of formula (I-A) wherein R3 is trifluoromethyl-, R4 is 3,5-dichloro-4-bromophenyl-, Y1-Y2-Y3 is —C=CH—O—, A2 is N, A3 is N, A4 is CH, R5b, n and R2 have the values listed in the Table Y.

Table 49
Table 49 provides 3507 compounds of formula (I-A) wherein R3 is trifluoromethyl-, R4 is 3-bromo-5-(trifluoromethyl)phenyl-, Y1-Y2-Y3 is —C=N—O—, A2 is N, A3 is N, A4 is CH, R5b, n and R2 have the values listed in the Table Y.

Table 50
Table 50 provides 3507 compounds of formula (I-A) wherein R3 is trifluoromethyl-, R4 is 3-bromo-5-(trifluoromethyl)phenyl-, Y1-Y2-Y3 is —C=N—O—, A2 is N, A3 is N, A4 is CH, R5b, n and R2 have the values listed in the Table Y.

Table 51
Table 51 provides 3507 compounds of formula (I-A) wherein R3 is trifluoromethyl-, R4 is 3-bromo-5-(trifluoromethyl)phenyl-, Y1-Y2-Y3 is —C=N—O—, A2 is N, A3 is N, A4 is CH, R5b, n and R2 have the values listed in the Table Y.

Table 52
Table 52 provides 3507 compounds of formula (I-A) wherein R3 is trifluoromethyl-, R4 is 3-bromo-5-(trifluoromethyl)phenyl-, Y1-Y2-Y3 is —C=N—O—, A2 is N, A3 is N, A4 is CH, R5b, n and R2 have the values listed in the Table Y.

Table 53
Table 53 provides 3507 compounds of formula (I-A) wherein R3 is trifluoromethyl-, R4 is 3-bromo-5-(trifluoromethyl)phenyl-, Y1-Y2-Y3 is —C=N—CH2-, A2 is CH, A3 is N, A4 is CH, R5b, n and R2 have the values listed in the Table Y.

Table 54
Table 54 provides 3507 compounds of formula (I-A) wherein R3 is trifluoromethyl-, R4 is 3-bromo-5-(trifluoromethyl)phenyl-, Y1-Y2-Y3 is —C=N—CH2-, A2 is CH, A3 is N, A4 is CH, R5b, n and R2 have the values listed in the Table Y.

Table 55
Table 55 provides 3507 compounds of formula (I-A) wherein R3 is trifluoromethyl-, R4 is 3-bromo-5-(trifluoromethyl)phenyl-, Y1-Y2-Y3 is —C=N—CH2-, A2 is CH, A3 is CH, A4 is N, R5b, n and R2 have the values listed in the Table Y.

Table 56
Table 56 provides 3507 compounds of formula (I-A) wherein R3 is trifluoromethyl-, R4 is 3-bromo-5-(trifluoromethyl)phenyl-, Y1-Y2-Y3 is —N—CH2-CH2-, A2 is CH, A3 is CH, A4 is CH, R5b, n and R2 have the values listed in the Table Y.

Table 57
Table 57 provides 3507 compounds of formula (I-A) wherein R3 is trifluoromethyl-, R4 is 3-bromo-5-(trifluoromethyl)phenyl-, Y1-Y2-Y3 is —N—CH2-CH2-, A2 is CH, A3 is CH, A4 is CH, R5b, n and R2 have the values listed in the Table Y.

Table 58
Table 58 provides 3507 compounds of formula (I-A) wherein R3 is trifluoromethyl-, R4 is 3-bromo-5-(trifluoromethyl)phenyl-, Y1-Y2-Y3 is —N—CH2-CH2-, A2 is CH, A3 is CH, A4 is CH, R5b, n and R2 have the values listed in the Table Y.

Table 59
Table 59 provides 3507 compounds of formula (I-A) wherein R3 is trifluoromethyl-, R4 is 3-bromo-5-(trifluoromethyl)phenyl-, Y1-Y2-Y3 is —N—CH2-CH2-, A2 is CH, A3 is N, A4 is CH, R5b, n and R2 have the values listed in the Table Y.

Table 60
Table 60 provides 3507 compounds of formula (I-A) wherein R3 is trifluoromethyl-, R4 is 3-bromo-5-(trifluoromethyl)phenyl-, Y1-Y2-Y3 is —N—CH2-CH2-, A2 is CH, A3 is N, A4 is CH, R5b, n and R2 have the values listed in the Table Y.

Table 61
Table 61 provides 3507 compounds of formula (I-A) wherein R3 is trifluoromethyl-, R4 is 3-bromo-5-(trifluoromethyl)phenyl-, Y1-Y2-Y3 is —C=CH—O—, A2 is CH, A3 is N, A4 is CH, R5b, n and R2 have the values listed in the Table Y.

Table 62
Table 62 provides 3507 compounds of formula (I-A) wherein R3 is trifluoromethyl-, R4 is 3-bromo-5-(trifluoromethyl)phenyl-, Y1-Y2-Y3 is —C=CH—O—, A2 is CH, A3 is CH, A4 is N, R5b, n and R2 have the values listed in the Table Y.

Table 63
Table 63 provides 3507 compounds of formula (I-A) wherein R3 is trifluoromethyl-, R4 is 3-bromo-5-(trifluoromethyl)phenyl-, Y1-Y2-Y3 is —C=CH—O—, A2 is CH, A3 is CH, A4 is N, R5b, n and R2 have the values listed in the Table Y.

Table 64
Table 64 provides 3507 compounds of formula (I-A) wherein R3 is trifluoromethyl-, R4 is 3-bromo-5-(trifluoromethyl)phenyl-, Y1-Y2-Y3 is —C=CH—O—, A2 is N, A3 is N, A4 is CH, R5b, n and R2 have the values listed in the Table Y.

Table 65
Table 65 provides 3507 compounds of formula (I-A) wherein R3 is trifluoromethyl-, R4 is 3,5-dibromophenyl-, Y1-Y2-Y3 is —C=N—O—, A2 is CH, A3 is CH, A4 is CH, R5b, n and R2 have the values listed in the Table Y.

Table 66
Table 66 provides 3507 compounds of formula (I-A) wherein R3 is trifluoromethyl-, R4 is 3,5-dibromophenyl-, Y1-Y2-Y3 is —C=N—O—, A2 is CH, A3 is CH, A4 is CH, R5b, n and R2 have the values listed in the Table Y.

Table 67
Table 67 provides 3507 compounds of formula (I-A) wherein R3 is trifluoromethyl-, R4 is 3,5-dibromophenyl-, Y1-Y2-Y3 is —C=N—O—, A2 is N, A3 is N, A4 is CH, R5b, n and R2 have the values listed in the Table Y.

Table 68
Table 68 provides 3507 compounds of formula (I-A) wherein R3 is trifluoromethyl-, R4 is 3,5-dibromophenyl-, Y1-Y2-Y3 is —C=N—CH2-, A2 is CH, A3 is CH, A4 is CH, R5b, n and R2 have the values listed in the Table Y.

Table 69
Table 69 provides 3507 compounds of formula (I-A) wherein R3 is trifluoromethyl-, R4 is 3,5-dibromophenyl-, Y1-Y2-Y3 is —C=N—CH2-, A2 is CH, A3 is N, A4 is CH, R5b, n and R2 have the values listed in the Table Y.

Table 70
Table 70 provides 3507 compounds of formula (I-A) wherein R3 is trifluoromethyl-, R4 is 3,5-dibromophenyl-, Y1-Y2-Y3 is —C=N—CH2-, A2 is CH, A3 is CH, A4 is N, R5b, n and R2 have the values listed in the Table Y.

Table 71
Table 71 provides 3507 compounds of formula (I-A) wherein R3 is trifluoromethyl-, R4 is 3,5-dibromophenyl-, Y1-Y2-Y3 is —C=N—CH2-, A2 is CH, A3 is CH, A4 is N, R5b, n and R2 have the values listed in the Table Y.

Table 72
Table 72 provides 3507 compounds of formula (I-A) wherein R3 is trifluoromethyl-, R4 is 3,5-dibromophenyl-, Y1-Y2-Y3 is —C=N—CH2-, A2 is N, A3 is N, A4 is CH, R5b, n and R2 have the values listed in the Table Y.

Table 73
Table 73 provides 3507 compounds of formula (I-A) wherein R3 is trifluoromethyl-, R4 is 3,5-dibromophenyl-, Y1-Y2-Y3 is —N—CH2-CH2-, A2 is CH, A3 is N, A4 is CH, R5b, n and R2 have the values listed in the Table Y.

Table 74
Table 74 provides 3507 compounds of formula (I-A) wherein R3 is trifluoromethyl-, R4 is 3,5-dibromophenyl-, Y1-Y2-Y3 is —N—CH2-CH2-, A2 is CH, A3 is CH, A4 is CH, R5b, n and R2 have the values listed in the Table Y.

Table 75
Table 75 provides 3507 compounds of formula (I-A) wherein R3 is trifluoromethyl-, R4 is 3,5-dibromophenyl-, Y1-Y2-Y3 is —N—CH2-CH2-, A2 is CH, A3 is N, A4 is CH, R5b, n and R2 have the values listed in the Table Y.

Table 76
Table 76 provides 3507 compounds of formula (I-A) wherein R3 is trifluoromethyl-, R4 is 3,5-dibromophenyl-, Y1-Y2-Y3 is —N—CH2-CH2-, A2 is N, A3 is N, A4 is CH, R5b, n and R2 have the values listed in the Table Y.

Table 77
Table 77 provides 3507 compounds of formula (I-A) wherein R3 is trifluoromethyl-, R4 is 3,5-dibromophenyl-, Y1-Y2-Y3 is —C═CH—O—, A2 is CH, A3 is CH, A4 is CH, R5b, n and R2 have the values listed in the Table Y.

Table 78
Table 78 provides 3507 compounds of formula (I-A) wherein R3 is trifluoromethyl-, R4 is 3,5-dibromophenyl-, Y1-Y2-Y3 is —C═CH—O—, A2 is CH, A3 is CH, A4 is N, R5b, n and R2 have the values listed in the Table Y.

Table 79
Table 79 provides 3507 compounds of formula (I-A) wherein R3 is trifluoromethyl-, R4 is 3,5-dibromophenyl-, Y1-Y2-Y3 is —C═CH—O—, A2 is N, A3 is N, A4 is CH, R5b, n and R2 have the values listed in the Table Y.

Table 80
Table 80 provides 3507 compounds of formula (I-A) wherein R3 is trifluoromethyl-, R4 is 3,5-dibromophenyl-, Y1-Y2-Y3 is —C═CH—O—, A2 is N, A3 is N, A4 is CH, R5b, n and R2 have the values listed in the Table Y.

Table 81
Table 81 provides 3507 compounds of formula (I-A) wherein R3 is trifluoromethyl-, R4 is 3,4-dichlorophenyl-, Y1-Y2-Y3 is —C═N—O—, A2 is CH, A3 is CH, A4 is CH, R5b, n and R2 have the values listed in the Table Y.

Table 82
Table 82 provides 3507 compounds of formula (I-A) wherein R3 is trifluoromethyl-, R4 is 3,4-dichlorophenyl-, Y1-Y2-Y3 is —C═N—O—, A2 is CH, A3 is N, A4 is CH, R5b, n and R2 have the values listed in the Table Y.

Table 83
Table 83 provides 3507 compounds of formula (I-A) wherein R3 is trifluoromethyl-, R4 is 3,4-dichlorophenyl-, Y1-Y2-Y3 is —C═N—O—, A2 is CH, A3 is CH, A4 is N, R5b, n and R2 have the values listed in the Table Y.

Table 84
Table 84 provides 3507 compounds of formula (I-A) wherein R3 is trifluoromethyl-, R4 is 3,4-dichlorophenyl-, Y1-Y2-Y3 is —C═N—O—, A2 is N, A3 is N, A4 is CH, R5b, n and R2 have the values listed in the Table Y.

Table 85
Table 85 provides 3507 compounds of formula (I-A) wherein R3 is trifluoromethyl-, R4 is 3,4-dichlorophenyl-, Y1-Y2-Y3 is —C═N—CH2-, A2 is CH, A3 is CH, A4 is CH, R5b, n and R2 have the values listed in the Table Y.

Table 86
Table 86 provides 3507 compounds of formula (I-A) wherein R3 is trifluoromethyl-, R4 is 3,4-dichlorophenyl-, Y1-Y2-Y3 is —C═N—CH2-, A2 is CH, A3 is N, A4 is CH, R5b, n and R2 have the values listed in the Table Y.

Table 87
Table 87 provides 3507 compounds of formula (I-A) wherein R3 is trifluoromethyl-, R4 is 3,4-dichlorophenyl-, Y1-Y2-Y3 is —C═N—CH2-, A2 is CH, A3 is N, A4 is N, R5b, n and R2 have the values listed in the Table Y.

Table 88
Table 88 provides 3507 compounds of formula (I-A) wherein R3 is trifluoromethyl-, R4 is 3,4-dichlorophenyl-, Y1-Y2-Y3 is —C═N—CH2-, A2 is N, A3 is N, A4 is CH, R5b, n and R2 have the values listed in the Table Y.

Table 89
Table 89 provides 3507 compounds of formula (I-A) wherein R3 is trifluoromethyl-, R4 is 3,4-dichlorophenyl-, Y1-Y2-Y3 is —N—CH2-CH2-, A2 is CH, A3 is N, A4 is CH, R5b, n and R2 have the values listed in the Table Y.

Table 90
Table 90 provides 3507 compounds of formula (I-A) wherein R3 is trifluoromethyl-, R4 is 3,4-dichlorophenyl-, Y1-Y2-Y3 is —N—CH2-CH2-, A2 is CH, A3 is N, A4 is CH, R5b, n and R2 have the values listed in the Table Y.

Table 91
Table 91 provides 3507 compounds of formula (I-A) wherein R3 is trifluoromethyl-, R4 is 3,4-dichlorophenyl-, Y1-Y2-Y3 is —N—CH2-CH2-, A2 is CH, A3 is N, A4 is CH, R5b, n and R2 have the values listed in the Table Y.

Table 92
Table 92 provides 3507 compounds of formula (I-A) wherein R3 is trifluoromethyl-, R4 is 3,4-dichlorophenyl-, Y1-Y2-Y3 is —N—CH2-CH2-, A2 is CH, A3 is CH, A4 is N, R5b, n and R2 have the values listed in the Table Y.

Table 93
Table 93 provides 3507 compounds of formula (I-A) wherein R3 is trifluoromethyl-, R4 is 3,4-dichlorophenyl-, Y1-Y2-Y3 is —C═CH—O—, A2 is CH, A3 is CH, A4 is CH, R5b, n and R2 have the values listed in the Table Y.

Table 94
Table 94 provides 3507 compounds of formula (I-A) wherein R3 is trifluoromethyl-, R4 is 3,4-dichlorophenyl-, Y1-Y2-Y3 is —C═CH—O—, A2 is CH, A3 is N, A4 is CH, R5b, n and R2 have the values listed in the Table Y.

Table 95
Table 95 provides 3507 compounds of formula (I-A) wherein R3 is trifluoromethyl-, R4 is 3,4-dichlorophenyl-, Y1-Y2-Y3 is —C═CH—O—, A2 is CH, A3 is CH, A4 is N, R5b, n and R2 have the values listed in the Table Y.

Table 96
Table 96 provides 3507 compounds of formula (I-A) wherein R3 is trifluoromethyl-, R4 is 3,4-dichlorophenyl-, Y1-Y2-Y3 is —C═CH—O—, A2 is N, A3 is N, A4 is CH, R5b, n and R2 have the values listed in the Table Y.

Table 97
Table 97 provides 3507 compounds of formula (I-A) wherein R3 is trifluoromethyl-, R4 is 3-chloro-5-bromophenyl-, Y1-Y2-Y3 is —C═N—O—, A2 is CH, A3 is CH, A4 is CH, R5b, n and R2 have the values listed in the Table Y.

Table 98
Table 98 provides 3507 compounds of formula (I-A) wherein R3 is trifluoromethyl-, R4 is 3-chloro-5-bromophenyl-, Y1-Y2-Y3 is —C═N—O—, A2 is CH, A3 is CH, A4 is N, R5b, n and R2 have the values listed in the Table Y.

Table 99
Table 99 provides 3507 compounds of formula (I-A) wherein R3 is trifluoromethyl-, R4 is 3-chloro-5-bromophenyl-, Y1-Y2-Y3 is —C═N—O—, A2 is N, A3 is N, A4 is CH, R5b, n and R2 have the values listed in the Table Y.

Table 100
Table 100 provides 3507 compounds of formula (I-A) wherein R3 is trifluoromethyl-, R4 is 3-chloro-5-bromophenyl-, Y1-Y2-Y3 is —C═N—CH2-, A2 is CH, A3 is N, A4 is CH, R5b, n and R2 have the values listed in the Table Y.

Table 101
Table 101 provides 3507 compounds of formula (I-A) wherein R3 is trifluoromethyl-, R4 is 3-chloro-5-bromophenyl-, Y1-Y2-Y3 is —C=N—CH2-, A2 is CH, A3 is N, A4 is CH, R5b, n and R2 have the values listed in the Table Y.

Table 102
Table 102 provides 3507 compounds of formula (I-A) wherein R3 is trifluoromethyl-, R4 is 3-chloro-5-bromophenyl-, Y1-Y2-Y3 is —C=N—CH2-, A2 is CH, A3 is N, A4 is CH, R5b, n and R2 have the values listed in the Table Y.

Table 103
Table 103 provides 3507 compounds of formula (I-A) wherein R3 is trifluoromethyl-, R4 is 3-chloro-5-bromophenyl-, Y1-Y2-Y3 is —C=N—CH2-, A2 is CH, A3 is CH, A4 is N, R5b, n and R2 have the values listed in the Table Y.

Table 104
Table 104 provides 3507 compounds of formula (I-A) wherein R3 is trifluoromethyl-, R4 is 3-chloro-5-bromophenyl-, Y1-Y2-Y3 is —C=N—CH2-, A2 is CH, A3 is CH, A4 is N, R5b, n and R2 have the values listed in the Table Y.

Table 105
Table 105 provides 3507 compounds of formula (I-A) wherein R3 is trifluoromethyl-, R4 is 3-chloro-5-bromophenyl-, Y1-Y2-Y3 is —C=N—CH2-, A2 is N, A3 is N, A4 is CH, R5b, n and R2 have the values listed in the Table Y.

Table 106
Table 106 provides 3507 compounds of formula (I-A) wherein R3 is trifluoromethyl-, R4 is 3-chloro-5-bromophenyl-, Y1-Y2-Y3 is —C=N—CH2-, A2 is N, A3 is N, A4 is CH, R5b, n and R2 have the values listed in the Table Y.

Table 107
Table 107 provides 3507 compounds of formula (I-A) wherein R3 is trifluoromethyl-, R4 is 3-chloro-5-bromophenyl-, Y1-Y2-Y3 is —N—CH2-CH2-, A2 is CH, A3 is N, A4 is CH, R5b, n and R2 have the values listed in the Table Y.

Table 108
Table 108 provides 3507 compounds of formula (I-A) wherein R3 is trifluoromethyl-, R4 is 3-chloro-5-bromophenyl-, Y1-Y2-Y3 is —N—CH2-CH2-, A2 is CH, A3 is CH, A4 is N, R5b, n and R2 have the values listed in the Table Y.

Table 109
Table 109 provides 3507 compounds of formula (I-A) wherein R3 is trifluoromethyl-, R4 is 3-chloro-5-bromophenyl-, Y1-Y2-Y3 is —C=CH—O—, A2 is CH, A3 is CH, A4 is CH, R5b, n and R2 have the values listed in the Table Y.

Table 110
Table 110 provides 3507 compounds of formula (I-A) wherein R3 is trifluoromethyl-, R4 is 3-chloro-5-bromophenyl-, Y1-Y2-Y3 is —C=CH—O—, A2 is CH, A3 is CH, A4 is N, R5b, n and R2 have the values listed in the Table Y.

Table 111
Table 111 provides 3507 compounds of formula (I-A) wherein R3 is trifluoromethyl-, R4 is 3-chloro-5-bromophenyl-, Y1-Y2-Y3 is —C=CH—O—, A2 is CH, A3 is CH, A4 is N, R5b, n and R2 have the values listed in the Table Y.

Table 112
Table 112 provides 3507 compounds of formula (I-A) wherein R3 is trifluoromethyl-, R4 is 3-chloro-5-bromophenyl-, Y1-Y2-Y3 is —C=CH—O—, A2 is N, A3 is N, A4 is CH, R5b, n and R2 have the values listed in the Table Y.

Table 113
Table 113 provides 3507 compounds of formula (I-A) wherein R3 is trifluoromethyl-, R4 is 3-chloro-5-fluorophenyl-, Y1-Y2-Y3 is —C=N—O—, A2 is CH, A3 is CH, A4 is CH, R5b, n and R2 have the values listed in the Table Y.

Table 114
Table 114 provides 3507 compounds of formula (I-A) wherein R3 is trifluoromethyl-, R4 is 3-chloro-5-fluorophenyl-, Y1-Y2-Y3 is —C=N—O—, A2 is CH, A3 is N, A4 is CH, R5b, n and R2 have the values listed in the Table Y.

Table 115
Table 115 provides 3507 compounds of formula (I-A) wherein R3 is trifluoromethyl-, R4 is 3-chloro-5-fluorophenyl-, Y1-Y2-Y3 is —C=N—O—, A2 is CH, A3 is CH, A4 is N, R5b, n and R2 have the values listed in the Table Y.

Table 116
Table 116 provides 3507 compounds of formula (I-A) wherein R3 is trifluoromethyl-, R4 is 3-chloro-5-fluorophenyl-, Y1-Y2-Y3 is —C=N—O—, A2 is N, A3 is N, A4 is CH, R5b, n and R2 have the values listed in the Table Y.

Table 117
Table 117 provides 3507 compounds of formula (I-A) wherein R3 is trifluoromethyl-, R4 is 3-chloro-5-fluorophenyl-, Y1-Y2-Y3 is —C=N—O—, A2 is N, A3 is N, A4 is CH, R5b, n and R2 have the values listed in the Table Y.

Table 118
Table 118 provides 3507 compounds of formula (I-A) wherein R3 is trifluoromethyl-, R4 is 3-chloro-5-fluorophenyl-, Y1-Y2-Y3 is —C=N—CH2-, A2 is CH, A3 is CH, A4 is CH, R5b, n and R2 have the values listed in the Table Y.

Table 119
Table 119 provides 3507 compounds of formula (I-A) wherein R3 is trifluoromethyl-, R4 is 3-chloro-5-fluorophenyl-, Y1-Y2-Y3 is —C=N—CH2-, A2 is CH, A3 is CH, A4 is N, R5b, n and R2 have the values listed in the Table Y.

Table 120
Table 120 provides 3507 compounds of formula (I-A) wherein R3 is trifluoromethyl-, R4 is 3-chloro-5-fluorophenyl-, Y1-Y2-Y3 is —N—CH2-CH2-, A2 is CH, A3 is CH, A4 is CH, R5b, n and R2 have the values listed in the Table Y.

Table 121
Table 121 provides 3507 compounds of formula (I-A) wherein R3 is trifluoromethyl-, R4 is 3-chloro-5-fluorophenyl-, Y1-Y2-Y3 is —N—CH2-CH2-, A2 is CH, A3 is N, A4 is CH, R5b, n and R2 have the values listed in the Table Y.

Table 122
Table 122 provides 3507 compounds of formula (I-A) wherein R3 is trifluoromethyl-, R4 is 3-chloro-5-fluorophenyl-, Y1-Y2-Y3 is —N—CH2-CH2-, A2 is N, A3 is N, A4 is CH, R5b, n and R2 have the values listed in the Table Y.

Table 123
Table 123 provides 3507 compounds of formula (I-A) wherein R3 is trifluoromethyl-, R4 is 3-chloro-5-fluorophenyl-, Y1-Y2-Y3 is —N—CH2-CH2-, A2 is N, A3 is N, A4 is CH, R5b, n and R2 have the values listed in the Table Y.

Table 124
Table 124 provides 3507 compounds of formula (I-A) wherein R3 is trifluoromethyl-, R4 is 3-chloro-5-fluorophenyl-, Y1-Y2-Y3 is —C=CH—O—, A2 is CH, A3 is CH, A4 is N, R5b, n and R2 have the values listed in the Table Y.

Table 125
Table 125 provides 3507 compounds of formula (I-A) wherein R3 is trifluoromethyl-, R4 is 3-chloro-5-fluorophenyl-, Y1-Y2-Y3 is —C=CH—O—, A2 is CH, A3 is CH, A4 is N, R5b, n and R2 have the values listed in the Table Y.

Table 126
Table 126 provides 3507 compounds of formula (I-A) wherein R3 is trifluoromethyl-, R4 is 3-chloro-5-fluorophenyl-, Y1-Y2-Y3 is —C=CH—O—, A2 is CH, A3 is CH, A4 is N, R5b, n and R2 have the values listed in the Table Y.

Table 127
Table 127 provides 3507 compounds of formula (I-A) wherein R3 is trifluoromethyl-, R4 is 3-chloro-5-fluorophenyl-, Y1-Y2-Y3 is —C=CH—O—, A2 is N, A3 is N, A4 is CH, R5b, n and R2 have the values listed in the Table Y.

Table 128
Table 128 provides 3507 compounds of formula (I-A) wherein R3 is trifluoromethyl-, R4 is 3-chloro-5-fluorophenyl-, Y1-Y2-Y3 is —C=CH—O—, A2 is N, A3 is N, A4 is CH, R5b, n and R2 have the values listed in the Table Y.

Table 129
Table 129 provides 3507 compounds of formula (I-A) wherein R3 is trifluoromethyl-, R4 is 3-chloro-5-(trifluoromethyl)phenyl-, Y1-Y2-Y3 is —C=N—O—, A2 is CH, A3 is CH, A4 is CH, R5b, n and R2 have the values listed in the Table Y.

Table 130
Table 130 provides 3507 compounds of formula (I-A) wherein R3 is trifluoromethyl-, R4 is 3-chloro-5-(trifluoromethyl)phenyl-, Y1-Y2-Y3 is —C=N—O—, A2 is CH, A3 is CH, A4 is N, R5b, n and R2 have the values listed in the Table Y.

Table 131
Table 131 provides 3507 compounds of formula (I-A) wherein R3 is trifluoromethyl-, R4 is 3-chloro-5-(trifluoromethyl)phenyl-, Y1-Y2-Y3 is —C=N—O—, A2 is CH, A3 is CH, A4 is N, R5b, n and R2 have the values listed in the Table Y.

Table 132
Table 132 provides 3507 compounds of formula (I-A) wherein R3 is trifluoromethyl-, R4 is 3-chloro-5-(trifluoromethyl)phenyl-, Y1-Y2-Y3 is —C=N—O—, A2 is N, A3 is N, A4 is CH, R5b, n and R2 have the values listed in the Table Y.

Table 133
Table 133 provides 3507 compounds of formula (I-A) wherein R3 is trifluoromethyl-, R4 is 3-chloro-5-(trifluoromethyl)phenyl-, Y1-Y2-Y3 is —C=N—CH2-, A2 is CH, A3 is CH, A4 is CH, R5b, n and R2 have the values listed in the Table Y.

Table 134
Table 134 provides 3507 compounds of formula (I-A) wherein R3 is trifluoromethyl-, R4 is 3-chloro-5-(trifluoromethyl)phenyl-, Y1-Y2-Y3 is —C=N—CH2-, A2 is CH, A3 is N, A4 is CH, R5b, n and R2 have the values listed in the Table Y.

Table 135
Table 135 provides 3507 compounds of formula (I-A) wherein R3 is trifluoromethyl-, R4 is 3-chloro-5-(trifluoromethyl)phenyl-, Y1-Y2-Y3 is —C=N—CH2-, A2 is CH, A3 is N, A4 is CH, R5b, n and R2 have the values listed in the Table Y.

Table 136
Table 136 provides 3507 compounds of formula (I-A) wherein R3 is trifluoromethyl-, R4 is 3-chloro-5-(trifluoromethyl)phenyl-, Y1-Y2-Y3 is —C=N—CH2-, A2 is N, A3 is N, A4 is CH, R5b, n and R2 have the values listed in the Table Y.

Table 137
Table 137 provides 3507 compounds of formula (I-A) wherein R3 is trifluoromethyl-, R4 is 3-chloro-5-(trifluoromethyl)phenyl-, Y1-Y2-Y3 is —C=N—CH2-, A2 is N, A3 is N, A4 is CH, R5b, n and R2 have the values listed in the Table Y.

Table 138
Table 138 provides 3507 compounds of formula (I-A) wherein R3 is trifluoromethyl-, R4 is 3-chloro-5-(trifluoromethyl)phenyl-, Y1-Y2-Y3 is —N—CH2-CH2-, A2 is CH, A3 is N, A4 is CH, R5b, n and R2 have the values listed in the Table Y.

Table 139
Table 139 provides 3507 compounds of formula (I-A) wherein R3 is trifluoromethyl-, R4 is 3-chloro-5-(trifluoromethyl)phenyl-, Y1-Y2-Y3 is —N—CH2-CH2-, A2 is CH, A3 is N, A4 is CH, R5b, n and R2 have the values listed in the Table Y.

Table 140
Table 140 provides 3507 compounds of formula (I-A) wherein R3 is trifluoromethyl-, R4 is 3-chloro-5-(trifluoromethyl)phenyl-, Y1-Y2-Y3 is —N—CH2-CH2-, A2 is CH, A3 is N, A4 is CH, R5b, n and R2 have the values listed in the Table Y.

Table 141
Table 141 provides 3507 compounds of formula (I-A) wherein R3 is trifluoromethyl-, R4 is 3-chloro-5-(trifluoromethyl)phenyl-, Y1-Y2-Y3 is —N—CH2-CH2-, A2 is N, A3 is N, A4 is CH, R5b, n and R2 have the values listed in the Table Y.

Table 142
Table 142 provides 3507 compounds of formula (I-A) wherein R3 is trifluoromethyl-, R4 is 3-chloro-5-(trifluoromethyl)phenyl-, Y1-Y2-Y3 is —N—CH2-CH2-, A2 is N, A3 is N, A4 is CH, R5b, n and R2 have the values listed in the Table Y.

Table 143
Table 143 provides 3507 compounds of formula (I-A) wherein R3 is trifluoromethyl-, R4 is 3-chloro-5-(trifluoromethyl)phenyl-, Y1-Y2-Y3 is —C=CH—O—, A2 is CH, A3 is CH, A4 is N, R5b, n and R2 have the values listed in the Table Y.

Table 144
Table 144 provides 3507 compounds of formula (I-A) wherein R3 is trifluoromethyl-, R4 is 3-chloro-5-(trifluoromethyl)phenyl-, Y1-Y2-Y3 is —C=CH—O—, A2 is N, A3 is N, A4 is CH, R5b, n and R2 have the values listed in the Table Y.

Table 145
Table 145 provides 3507 compounds of formula (I-A) wherein R3 is trifluoromethyl-, R4 is 3,5-dichloro-4-fluorophenyl-, Y1-Y2-Y3 is —C=N—O—, A2 is CH, A3 is CH, A4 is CH, R5b, n and R2 have the values listed in the Table Y.

Table 146
Table 146 provides 3507 compounds of formula (I-A) wherein R3 is trifluoromethyl-, R4 is 3,5-dichloro-4-fluorophenyl-, Y1-Y2-Y3 is —C=N—O—, A2 is CH, A3 is N, A4 is CH, R5b, n and R2 have the values listed in the Table Y.

Table 147
Table 147 provides 3507 compounds of formula (I-A) wherein R3 is trifluoromethyl-, R4 is 3,5-dichloro-4-fluorophenyl-, Y1-Y2-Y3 is —C=N—O—, A2 is CH, A3 is N, A4 is CH, R5b, n and R2 have the values listed in the Table Y.

Table 148
Table 148 provides 3507 compounds of formula (I-A) wherein R3 is trifluoromethyl-, R4 is 3,5-dichloro-4-fluorophenyl-, Y1-Y2-Y3 is —C=N—O—, A2 is N, A3 is N, A4 is CH, R5b, n and R2 have the values listed in the Table Y.

Table 149
Table 149 provides 3507 compounds of formula (I-A) wherein R3 is trifluoromethyl-, R4 is 3,5-dichloro-4-fluorophenyl-, Y1-Y2-Y3 is —C=N—CH2-, A2 is CH, A3 is CH, A4 is CH, R5b, n and R2 have the values listed in the Table Y.

Table 150
Table 150 provides 3507 compounds of formula (I-A) wherein R3 is trifluoromethyl-, R4 is 3,5-dichloro-4-fluorophenyl-, Y1-Y2-Y3 is —C=N—CH2-, A2 is CH, A3 is CH, A4 is CH, R5b, n and R2 have the values listed in the Table Y.

Table 151
Table 151 provides 3507 compounds of formula (I-A) wherein R3 is trifluoromethyl-, R4 is 3,5-dichloro-4-fluorophenyl-, Y1-Y2-Y3 is —C=N—CH2-, A2 is CH, A3 is CH, A4 is N, R5b, n and R2 have the values listed in the Table Y.

Table 152
Table 152 provides 3507 compounds of formula (I-A) wherein R3 is trifluoromethyl-, R4 is 3,5-dichloro-4-fluorophenyl-, Y1-Y2-Y3 is —C=N—CH2-, A2 is CH, A3 is CH, A4 is N, R5b, n and R2 have the values listed in the Table Y.

Table 153
Table 153 provides 3507 compounds of formula (I-A) wherein R3 is trifluoromethyl-, R4 is 3,5-dichloro-4-fluorophenyl-, Y1-Y2-Y3 is —C=N—CH2-, A2 is N, A3 is N, A4 is CH, R5b, n and R2 have the values listed in the Table Y.

Table 154
Table 154 provides 3507 compounds of formula (I-A) wherein R3 is trifluoromethyl-, R4 is 3,5-dichloro-4-fluorophenyl-, Y1-Y2-Y3 is —N—CH2-CH2-, A2 is CH, A3 is CH, A4 is CH, R5b, n and R2 have the values listed in the Table Y.

Table 155
Table 155 provides 3507 compounds of formula (I-A) wherein R3 is trifluoromethyl-, R4 is 3,5-dichloro-4-fluorophenyl-, Y1-Y2-Y3 is —N—CH2-CH2-, A2 is CH, A3 is CH, A4 is N, R5b, n and R2 have the values listed in the Table Y.

Table 156
Table 156 provides 3507 compounds of formula (I-A) wherein R3 is trifluoromethyl-, R4 is 3,5-dichloro-4-fluorophenyl-, Y1-Y2-Y3 is —N—CH2-CH2-, A2 is N, A3 is N, A4 is CH, R5b, n and R2 have the values listed in the Table Y.

Table 157
Table 157 provides 3507 compounds of formula (I-A) wherein R3 is trifluoromethyl-, R4 is 3,5-dichloro-4-fluorophenyl-, Y1-Y2-Y3 is —N—CH2-CH2-, A2 is N, A3 is N, A4 is CH, R5b, n and R2 have the values listed in the Table Y.

Table 158
Table 158 provides 3507 compounds of formula (I-A) wherein R3 is trifluoromethyl-, R4 is 3,5-dichloro-4-fluorophenyl-, Y1-Y2-Y3 is —C=CH—O—, A2 is CH, A3 is CH, A4 is CH, R5b, n and R2 have the values listed in the Table Y.

Table 159
Table 159 provides 3507 compounds of formula (I-A) wherein R3 is trifluoromethyl-, R4 is 3,5-dichloro-4-fluorophenyl-, Y1-Y2-Y3 is —C=CH—O—, A2 is CH, A3 is N, A4 is CH, R5b, n and R2 have the values listed in the Table Y.

Table 160
Table 160 provides 3507 compounds of formula (I-A) wherein R3 is trifluoromethyl-, R4 is 3,5-dichloro-4-fluorophenyl-, Y1-Y2-Y3 is —C=CH—O—, A2 is CH, A3 is CH, A4 is N, R5b, n and R2 have the values listed in the Table Y.

Table 161
Table 161 provides 3507 compounds of formula (I-A) wherein R3 is trifluoromethyl-, R4 is 3,4,5-trichlorophenyl-, Y1-Y2-Y3 is —C=N—O—, A2 is CH, A3 is CH, A4 is CH, R5b, n and R2 have the values listed in the Table Y.

Table 162
Table 162 provides 3507 compounds of formula (I-A) wherein R3 is trifluoromethyl-, R4 is 3,4,5-trichlorophenyl-, Y1-Y2-Y3 is —C=N—O—, A2 is CH, A3 is N, A4 is CH, R5b, n and R2 have the values listed in the Table Y.

Table 163
Table 163 provides 3507 compounds of formula (I-A) wherein R3 is trifluoromethyl-, R4 is 3,4,5-trichlorophenyl-, Y1-Y2-Y3 is —C=N—O—, A2 is CH, A3 is CH, A4 is N, R5b, n and R2 have the values listed in the Table Y.

Table 164
Table 164 provides 3507 compounds of formula (I-A) wherein R3 is trifluoromethyl-, R4 is 3,4,5-trichlorophenyl-, Y1-Y2-Y3 is —C=N—CH2-, A2 is CH, A3 is CH, A4 is CH, R5b, n and R2 have the values listed in the Table Y.

Table 165
Table 165 provides 3507 compounds of formula (I-A) wherein R3 is trifluoromethyl-, R4 is 3,4,5-trichlorophenyl-, Y1-Y2-Y3 is —C=N—CH2-, A2 is CH, A3 is CH, A4 is CH, R5b, n and R2 have the values listed in the Table Y.

Table 166
Table 166 provides 3507 compounds of formula (I-A) wherein R3 is trifluoromethyl-, R4 is 3,4,5-trichlorophenyl-, Y1-Y2-Y3 is —C=N—CH2-, A2 is CH, A3 is N, A4 is CH, R5b, n and R2 have the values listed in the Table Y.

Table 167
Table 167 provides 3507 compounds of formula (I-A) wherein R3 is trifluoromethyl-, R4 is 3,4,5-trichlorophenyl-, Y1-Y2-Y3 is —C=N—CH2-, A2 is N, A3 is N, A4 is CH, R5b, n and R2 have the values listed in the Table Y.

Table 168
Table 168 provides 3507 compounds of formula (I-A) wherein R3 is trifluoromethyl-, R4 is 3,4,5-trichlorophenyl-, Y1-Y2-Y3 is —N—CH2-CH2-, A2 is CH, A3 is CH, A4 is CH, R5b, n and R2 have the values listed in the Table Y.

Table 169
Table 169 provides 3507 compounds of formula (I-A) wherein R3 is trifluoromethyl-, R4 is 3,4,5-trichlorophenyl-, Y1-Y2-Y3 is —N—CH2-CH2-, A2 is CH, A3 is N, A4 is CH, R5b, n and R2 have the values listed in the Table Y.

Table 170
Table 170 provides 3507 compounds of formula (I-A) wherein R3 is trifluoromethyl-, R4 is 3,4,5-trichlorophenyl-, Y1-Y2-Y3 is —N—CH2-CH2-, A2 is CH, A3 is CH, A4 is N, R5b, n and R2 have the values listed in the Table Y.

Table 171
Table 171 provides 3507 compounds of formula (I-A) wherein R3 is trifluoromethyl-, R4 is 3,4,5-trichlorophenyl-, Y1-Y2-Y3 is —N—CH2-CH2-, A2 is CH, A3 is CH, A4 is N, R5b, n and R2 have the values listed in the Table Y.

Table 172
Table 172 provides 3507 compounds of formula (I-A) wherein R3 is trifluoromethyl-, R4 is 3,4,5-trichlorophenyl-, Y1-Y2-Y3 is —N—CH2-CH2-, A2 is N, A3 is N, A4 is CH, R5b, n and R2 have the values listed in the Table Y.

Table 173
Table 173 provides 3507 compounds of formula (I-A) wherein R3 is trifluoromethyl-, R4 is 3,4,5-trichlorophenyl-, Y1-Y2-Y3 is —N—CH2-CH2-, A2 is N, A3 is N, A4 is CH, R5b, n and R2 have the values listed in the Table Y.

Table 174
Table 174 provides 3507 compounds of formula (I-A) wherein R3 is trifluoromethyl-, R4 is 3,4,5-trichlorophenyl-, Y1-Y2-Y3 is —C=CH—O—, A2 is CH, A3 is N, A4 is CH, R5b, n and R2 have the values listed in the Table Y.

Table 175
Table 175 provides 3507 compounds of formula (I-A) wherein R3 is trifluoromethyl-, R4 is 3,4,5-trichlorophenyl-, Y1-Y2-Y3 is —C═CH—O—, A2 is CH, A3 is CH, A4 is N, R5b, n and R2 have the values listed in the Table Y.

Table 176
Table 176 provides 3507 compounds of formula (I-A) wherein R3 is trifluoromethyl-, R4 is 3,4,5-trichlorophenyl-, Y1-Y2-Y3 is —C═CH—O—, A2 is CH, A3 is CH, A4 is N, R5b, n and R2 have the values listed in the Table Y.

Table 177
Table 177 provides 3507 compounds of formula (I-A) wherein R3 is trifluoromethyl-, R4 is 3,5-bis(trifluoromethyl)phenyl-, Y1-Y2-Y3 is —C═N—O—, A2 is CH, A3 is CH, A4 is N, R5b, n and R2 have the values listed in the Table Y.

Table 178
Table 178 provides 3507 compounds of formula (I-A) wherein R3 is trifluoromethyl-, R4 is 3,5-bis(trifluoromethyl)phenyl-, Y1-Y2-Y3 is —C═N—O—, A2 is N, A3 is N, A4 is CH, R5b, n and R2 have the values listed in the Table Y.

Table 179
Table 179 provides 3507 compounds of formula (I-A) wherein R3 is trifluoromethyl-, R4 is 3,5-bis(trifluoromethyl)phenyl-, Y1-Y2-Y3 is —C═N—O—, A2 is N, A3 is N, A4 is CH, R5b, n and R2 have the values listed in the Table Y.

Table 180
Table 180 provides 3507 compounds of formula (I-A) wherein R3 is trifluoromethyl-, R4 is 3,5-bis(trifluoromethyl)phenyl-, Y1-Y2-Y3 is —C═N—CH2-, A2 is CH, A3 is CH, A4 is CH, R5b, n and R2 have the values listed in the Table Y.

Table 181
Table 181 provides 3507 compounds of formula (I-A) wherein R3 is trifluoromethyl-, R4 is 3,5-bis(trifluoromethyl)phenyl-, Y1-Y2-Y3 is —C═N—CH2-, A2 is CH, A3 is CH, A4 is CH, R5b, n and R2 have the values listed in the Table Y.

Table 182
Table 182 provides 3507 compounds of formula (I-A) wherein R3 is trifluoromethyl-, R4 is 3,5-bis(trifluoromethyl)phenyl-, Y1-Y2-Y3 is —C═N—CH2-, A2 is CH, A3 is N, A4 is CH, R5b, n and R2 have the values listed in the Table Y.

Table 183
Table 183 provides 3507 compounds of formula (I-A) wherein R3 is trifluoromethyl-, R4 is 3,5-bis(trifluoromethyl)phenyl-, Y1-Y2-Y3 is —N—CH2-CH2-, A2 is CH, A3 is CH, A4 is CH, R5b, n and R2 have the values listed in the Table Y.

Table 184
Table 184 provides 3507 compounds of formula (I-A) wherein R3 is trifluoromethyl-, R4 is 3,5-bis(trifluoromethyl)phenyl-, Y1-Y2-Y3 is —N—CH2-CH2-, A2 is CH, A3 is CH, A4 is CH, R5b, n and R2 have the values listed in the Table Y.

Table 185
Table 185 provides 3507 compounds of formula (I-A) wherein R3 is trifluoromethyl-, R4 is 3,5-bis(trifluoromethyl)phenyl-, Y1-Y2-Y3 is —N—CH2-CH2-, A2 is CH, A3 is N, A4 is CH, R5b, n and R2 have the values listed in the Table Y.

Table 186
Table 186 provides 3507 compounds of formula (I-A) wherein R3 is trifluoromethyl-, R4 is 3,5-bis(trifluoromethyl)phenyl-, Y1-Y2-Y3 is —N—CH2-CH2-, A2 is CH, A3 is N, A4 is CH, R5b, n and R2 have the values listed in the Table Y.

Table 187
Table 187 provides 3507 compounds of formula (I-A) wherein R3 is trifluoromethyl-, R4 is 3,5-bis(trifluoromethyl)phenyl-, Y1-Y2-Y3 is —N—CH2-CH2-, A2 is CH, A3 is CH, A4 is N, R5b, n and R2 have the values listed in the Table Y.

Table 188
Table 188 provides 3507 compounds of formula (I-A) wherein R3 is trifluoromethyl-, R4 is 3,5-bis(trifluoromethyl)phenyl-, Y1-Y2-Y3 is —N—CH2-CH2-, A2 is CH, A3 is CH, A4 is N, R5b, n and R2 have the values listed in the Table Y.

Table 189
Table 189 provides 3507 compounds of formula (I-A) wherein R3 is trifluoromethyl-, R4 is 3,5-bis(trifluoromethyl)phenyl-, Y1-Y2-Y3 is —C═CH—O—, A2 is CH, A3 is CH, A4 is CH, R5b, n and R2 have the values listed in the Table Y.

Table 190
Table 190 provides 3507 compounds of formula (I-A) wherein R3 is trifluoromethyl-, R4 is 3,5-bis(trifluoromethyl)phenyl-, Y1-Y2-Y3 is —C═CH—O—, A2 is CH, A3 is N, A4 is CH, R5b, n and R2 have the values listed in the Table Y.

Table 191
Table 191 provides 3507 compounds of formula (I-A) wherein R3 is trifluoromethyl-, R4 is 3,5-bis(trifluoromethyl)phenyl-, Y1-Y2-Y3 is —C═CH—O—, A2 is CH, A3 is CH, A4 is N, R5b, n and R2 have the values listed in the Table Y.

Table 192
Table 192 provides 3507 compounds of formula (I-A) wherein R3 is trifluoromethyl-, R4 is 3,5-bis(trifluoromethyl)phenyl-, Y1-Y2-Y3 is —C═CH—O—, A2 is N, A3 is N, A4 is CH, R5b, n and R2 have the values listed in the Table Y.

Table 193
Table 193 provides 3507 compounds of formula (I-A) wherein R3 is trifluoromethyl-, R4 is 3-(trifluoromethyl)phenyl-, Y1-Y2-Y3 is —C═N—O—, A2 is CH, A3 is CH, A4 is CH, R5b, n and R2 have the values listed in the Table Y.

Table 194
Table 194 provides 3507 compounds of formula (I-A) wherein R3 is trifluoromethyl-, R4 is 3-(trifluoromethyl)phenyl-, Y1-Y2-Y3 is —C═N—O—, A2 is CH, A3 is N, A4 is CH, R5b, n and R2 have the values listed in the Table Y.

Table 195
Table 195 provides 3507 compounds of formula (I-A) wherein R3 is trifluoromethyl-, R4 is 3-(trifluoromethyl)phenyl-, Y1-Y2-Y3 is —C═N—O—, A2 is N, A3 is N, A4 is CH, R5b, n and R2 have the values listed in the Table Y.

Table 196
Table 196 provides 3507 compounds of formula (I-A) wherein R3 is trifluoromethyl-, R4 is 3-(trifluoromethyl)phenyl-, Y1-Y2-Y3 is —C═N—CH2-, A2 is CH, A3 is CH, A4 is CH, R5b, n and R2 have the values listed in the Table Y.

Table 197
Table 197 provides 3507 compounds of formula (I-A) wherein R3 is trifluoromethyl-, R4 is 3-(trifluoromethyl)phenyl-, Y1-Y2-Y3 is —C═N—CH2-, A2 is CH, A3 is CH, A4 is CH, R5b, n and R2 have the values listed in the Table Y.

Table 198
Table 198 provides 3507 compounds of formula (I-A) wherein R3 is trifluoromethyl-, R4 is 3-(trifluoromethyl)phenyl-, Y1-Y2-Y3 is —C═N—CH2-, A2 is CH, A3 is CH, A4 is N, R5b, n and R2 have the values listed in the Table Y.

Table 199
Table 199 provides 3507 compounds of formula (I-A) wherein R3 is trifluoromethyl-, R4 is 3-(trifluoromethyl)phenyl-, Y1-Y2-Y3 is —C═N—CH2-, A2 is N, A3 is N, A4 is CH, R5b, n and R2 have the values listed in the Table Y.

Table 200
Table 200 provides 3507 compounds of formula (I-A) wherein R3 is trifluoromethyl-, R4 is 3-(trifluoromethyl)phenyl-, Y1-Y2-Y3 is —N—CH2-CH2-, A2 is CH, A3 is N, A4 is CH, R5b, n and R2 have the values listed in the Table Y.

Table 201
Table 201 provides 3507 compounds of formula (I-A) wherein R3 is trifluoromethyl-, R4 is 3-(trifluoromethyl)phenyl-, Y1-Y2-Y3 is —N—CH2-CH2-, A2 is CH, A3 is N, A4 is CH, R5b, n and R2 have the values listed in the Table Y.

Table 202

Table 202 provides 3507 compounds of formula (I-A) wherein R3 is trifluoromethyl-, R4 is 3-(trifluoromethyl)phenyl-, Y1-Y2-Y3 is —C=CH—O—, A2 is CH, A3 is CH, A4 is CH, R5b, n and R2 have the values listed in the Table Y.

Table 203

Table 203 provides 3507 compounds of formula (I-A) wherein R3 is trifluoromethyl-, R4 is 3-(trifluoromethyl)phenyl-, Y1-Y2-Y3 is —C=CH—O—, A2 is CH, A3 is CH, A4 is CH, R5b, n and R2 have the values listed in the Table Y.

Table 204

Table 204 provides 3507 compounds of formula (I-A) wherein R3 is trifluoromethyl-, R4 is 3-(trifluoromethyl)phenyl-, Y1-Y2-Y3 is —C=CH—O—, A2 is CH, A3 is CH, A4 is CH, R5b, n and R2 have the values listed in the Table Y.

Table 205

Table 205 provides 3507 compounds of formula (I-A) wherein R3 is trifluoromethyl-, R4 is 3-(trifluoromethyl)phenyl-, Y1-Y2-Y3 is —C=CH—O—, A2 is CH, A3 is N, A4 is CH, R5b, n and R2 have the values listed in the Table Y.

Table 206

Table 206 provides 3507 compounds of formula (I-A) wherein R3 is trifluoromethyl-, R4 is 3-(trifluoromethyl)phenyl-, Y1-Y2-Y3 is —C=CH—O—, A2 is CH, A3 is N, A4 is CH, R5b, n and R2 have the values listed in the Table Y.

Table 207

Table 207 provides 3507 compounds of formula (I-A) wherein R3 is trifluoromethyl-, R4 is 3-(trifluoromethyl)phenyl-, Y1-Y2-Y3 is —C=CH—O—, A2 is CH, A3 is CH, A4 is N, R5b, n and R2 have the values listed in the Table Y.

Table 208

Table 208 provides 3507 compounds of formula (I-A) wherein R3 is trifluoromethyl-, R4 is 3-(trifluoromethyl)phenyl-, Y1-Y2-Y3 is —C=CH—O—, A2 is N, A3 is N, A4 is CH, R5b, n and R2 have the values listed in the Table Y.

Table 209

Table 209 provides 3507 compounds of formula (I-A) wherein R3 is trifluoromethyl-, R4 is 2,6-dichloro-4-pyridyl-, Y1-Y2-Y3 is —C=N—O—, A2 is CH, A3 is N, A4 is CH, R5b, n and R2 have the values listed in the Table Y.

Table 210

Table 210 provides 3507 compounds of formula (I-A) wherein R3 is trifluoromethyl-, R4 is 2,6-dichloro-4-pyridyl-, Y1-Y2-Y3 is —C=N—O—, A2 is CH, A3 is N, A4 is CH, R5b, n and R2 have the values listed in the Table Y.

Table 211

Table 211 provides 3507 compounds of formula (I-A) wherein R3 is trifluoromethyl-, R4 is 2,6-dichloro-4-pyridyl-, Y1-Y2-Y3 is —C=N—O—, A2 is CH, A3 is CH, A4 is N, R5b, n and R2 have the values listed in the Table Y.

Table 212

Table 212 provides 3507 compounds of formula (I-A) wherein R3 is trifluoromethyl-, R4 is 2,6-dichloro-4-pyridyl-, Y1-Y2-Y3 is —C=N—O—, A2 is N, A3 is N, A4 is CH, R5b, n and R2 have the values listed in the Table Y.

Table 213

Table 213 provides 3507 compounds of formula (I-A) wherein R3 is trifluoromethyl-, R4 is 2,6-dichloro-4-pyridyl-, Y1-Y2-Y3 is —C=N—CH2-, A2 is CH, A3 is CH, A4 is CH, R5b, n and R2 have the values listed in the Table Y.

Table 214

Table 214 provides 3507 compounds of formula (I-A) wherein R3 is trifluoromethyl-, R4 is 2,6-dichloro-4-pyridyl-, Y1-Y2-Y3 is —C=N—CH2-, A2 is CH, A3 is N, A4 is CH, R5b, n and R2 have the values listed in the Table Y.

Table 215

Table 215 provides 3507 compounds of formula (I-A) wherein R3 is trifluoromethyl-, R4 is 2,6-dichloro-4-pyridyl-, Y1-Y2-Y3 is —C=N—CH2-, A2 is CH, A3 is CH, A4 is N, R5b, n and R2 have the values listed in the Table Y.

Table 216

Table 216 provides 3507 compounds of formula (I-A) wherein R3 is trifluoromethyl-, R4 is 2,6-dichloro-4-pyridyl-, Y1-Y2-Y3 is —C=N—CH2-, A2 is N, A3 is N, A4 is CH, R5b, n and R2 have the values listed in the Table Y.

Table 217

Table 217 provides 3507 compounds of formula (I-A) wherein R3 is trifluoromethyl-, R4 is 2,6-dichloro-4-pyridyl-, Y1-Y2-Y3 is —C=N—CH2-, A2 is N, A3 is N, A4 is CH, R5b, n and R2 have the values listed in the Table Y.

Table 218

Table 218 provides 3507 compounds of formula (I-A) wherein R3 is trifluoromethyl-, R4 is 2,6-dichloro-4-pyridyl-, Y1-Y2-Y3 is —N—CH2-CH2-, A2 is CH, A3 is CH, A4 is CH, R5b, n and R2 have the values listed in the Table Y.

Table 219

Table 219 provides 3507 compounds of formula (I-A) wherein R3 is trifluoromethyl-, R4 is 2,6-dichloro-4-pyridyl-, Y1-Y2-Y3 is —N—CH2-CH2-, A2 is CH, A3 is CH, A4 is N, R5b, n and R2 have the values listed in the Table Y.

Table 220

Table 220 provides 3507 compounds of formula (I-A) wherein R3 is trifluoromethyl-, R4 is 2,6-dichloro-4-pyridyl-, Y1-Y2-Y3 is —N—CH2-CH2-, A2 is CH, A3 is CH, A4 is N, R5b, n and R2 have the values listed in the Table Y.

Table 221

Table 221 provides 3507 compounds of formula (I-A) wherein R3 is trifluoromethyl-, R4 is 2,6-dichloro-4-pyridyl-, Y1-Y2-Y3 is —C=CH—O—, A2 is CH, A3 is CH, A4 is CH, R5b, n and R2 have the values listed in the Table Y.

Table 222

Table 222 provides 3507 compounds of formula (I-A) wherein R3 is trifluoromethyl-, R4 is 2,6-dichloro-4-pyridyl-, Y1-Y2-Y3 is —C=CH—O—, A2 is CH, A3 is CH, A4 is CH, R5b, n and R2 have the values listed in the Table Y.

Table 223

Table 223 provides 3507 compounds of formula (I-A) wherein R3 is trifluoromethyl-, R4 is 2,6-dichloro-4-pyridyl-, Y1-Y2-Y3 is —C=CH—O—, A2 is CH, A3 is CH, A4 is CH, R5b, n and R2 have the values listed in the Table Y.

Table 224

Table 224 provides 3507 compounds of formula (I-A) wherein R3 is trifluoromethyl-, R4 is 2,6-dichloro-4-pyridyl-, Y1-Y2-Y3 is —C=CH—O—, A2 is CH, A3 is N, A4 is CH, R5b, n and R2 have the values listed in the Table Y.

Table 225

Table 225 provides 3507 compounds of formula (I-A) wherein R3 is difluorochloromethyl-, R4 is 3,5-dichlorophenyl-, Y1-Y2-Y3 is —C=N—O—, A2 is CH, A3 is CH, A4 is CH, R5b, n and R2 have the values listed in the Table Y.

Table 226

Table 226 provides 3507 compounds of formula (I-A) wherein R3 is difluorochloromethyl-, R4 is 3,5-dichlorophenyl-, Y1-Y2-Y3 is —C=N—O—, A2 is CH, A3 is N, A4 is CH, R5b, n and R2 have the values listed in the Table Y.

Table 227

Table 227 provides 3507 compounds of formula (I-A) wherein R3 is difluorochloromethyl-, R4 is 3,5-dichlorophenyl-, Y1-Y2-Y3 is —C=N—O—, A2 is CH, A3 is N, A4 is CH, R5b, n and R2 have the values listed in the Table Y.

Table 228
Table 228 provides 3507 compounds of formula (I-A) wherein R3 is difluorochloromethyl-, R4 is 3,5-dichlorophenyl-, Y1-Y2-Y3 is —C=N—O—, A2 is CH, A3 is N, A4 is CH, R5b, n and R2 have the values listed in the Table Y.

Table 229
Table 229 provides 3507 compounds of formula (I-A) wherein R3 is difluorochloromethyl-, R4 is 3,5-dichlorophenyl-, Y1-Y2-Y3 is —C=N—O—, A2 is CH, A3 is N, A4 is CH, R5b, n and R2 have the values listed in the Table Y.

Table 230
Table 230 provides 3507 compounds of formula (I-A) wherein R3 is difluorochloromethyl-, R4 is 3,5-dichlorophenyl-, Y1-Y2-Y3 is —C=N—O—, A2 is CH, A3 is CH, A4 is N, R5b, n and R2 have the values listed in the Table Y.

Table 231
Table 231 provides 3507 compounds of formula (I-A) wherein R3 is difluorochloromethyl-, R4 is 3,5-dichlorophenyl-, Y1-Y2-Y3 is —C=N—CH2-, A2 is CH, A3 is CH, A4 is CH, R5b, n and R2 have the values listed in the Table Y.

Table 232
Table 232 provides 3507 compounds of formula (I-A) wherein R3 is difluorochloromethyl-, R4 is 3,5-dichlorophenyl-, Y1-Y2-Y3 is —C=N—CH2-, A2 is CH, A3 is CH, A4 is N, R5b, n and R2 have the values listed in the Table Y.

Table 233
Table 233 provides 3507 compounds of formula (I-A) wherein R3 is difluorochloromethyl-, R4 is 3,5-dichlorophenyl-, Y1-Y2-Y3 is —C=N—CH2-, A2 is N, A3 is N, A4 is CH, R5b, n and R2 have the values listed in the Table Y.

Table 234
Table 234 provides 3507 compounds of formula (I-A) wherein R3 is difluorochloromethyl-, R4 is 3,5-dichlorophenyl-, Y1-Y2-Y3 is —C=N—CH2-, A2 is N, A3 is N, A4 is CH, R5b, n and R2 have the values listed in the Table Y.

Table 235
Table 235 provides 3507 compounds of formula (I-A) wherein R3 is difluorochloromethyl-, R4 is 3,5-dichlorophenyl-, Y1-Y2-Y3 is —N—CH2-CH2-, A2 is CH, A3 is N, A4 is CH, R5b, n and R2 have the values listed in the Table Y.

Table 236
Table 236 provides 3507 compounds of formula (I-A) wherein R3 is difluorochloromethyl-, R4 is 3,5-dichlorophenyl-, Y1-Y2-Y3 is —N—CH2-CH2-, A2 is CH, A3 is CH, A4 is N, R5b, n and R2 have the values listed in the Table Y.

Table 237
Table 237 provides 3507 compounds of formula (I-A) wherein R3 is difluorochloromethyl-, R4 is 3,5-dichlorophenyl-, Y1-Y2-Y3 is —N—CH2-CH2-, A2 is N, A3 is N, A4 is CH, R5b, n and R2 have the values listed in the Table Y.

Table 238
Table 238 provides 3507 compounds of formula (I-A) wherein R3 is difluorochloromethyl-, R4 is 3,5-dichlorophenyl-, Y1-Y2-Y3 is —C=CH—O—, A2 is CH, A3 is CH, A4 is CH, R5b, n and R2 have the values listed in the Table Y.

Table 239
Table 239 provides 3507 compounds of formula (I-A) wherein R3 is difluorochloromethyl-, R4 is 3,5-dichlorophenyl-, Y1-Y2-Y3 is —C=CH—O—, A2 is CH, A3 is N, A4 is CH, R5b, n and R2 have the values listed in the Table Y.

Table 240
Table 240 provides 3507 compounds of formula (I-A) wherein R3 is difluorochloromethyl-, R4 is 3,5-dichlorophenyl-, Y1-Y2-Y3 is —C=CH—O—, A2 is CH, A3 is CH, A4 is N, R5b, n and R2 have the values listed in the Table Y.

Table 241
Table 241 provides 3507 compounds of formula (I-A) wherein R3 is difluorochloromethyl-, R4 is 2,6-bis(trifluoromethyl)-4-pyridyl-, Y1-Y2-Y3 is —C=N—O—, A2 is CH, A3 is CH, A4 is CH, R5b, n and R2 have the values listed in the Table Y.

Table 242
Table 242 provides 3507 compounds of formula (I-A) wherein R3 is difluorochloromethyl-, R4 is 2,6-bis(trifluoromethyl)-4-pyridyl-, Y1-Y2-Y3 is —C=N—O—, A2 is CH, A3 is CH, A4 is CH, R5b, n and R2 have the values listed in the Table Y.

Table 243
Table 243 provides 3507 compounds of formula (I-A) wherein R3 is difluorochloromethyl-, R4 is 2,6-bis(trifluoromethyl)-4-pyridyl-, Y1-Y2-Y3 is —C=N—O—, A2 is N, A3 is N, A4 is CH, R5b, n and R2 have the values listed in the Table Y.

Table 244
Table 244 provides 3507 compounds of formula (I-A) wherein R3 is difluorochloromethyl-, R4 is 2,6-bis(trifluoromethyl)-4-pyridyl-, Y1-Y2-Y3 is —C=N—CH2-, A2 is CH, A3 is CH, A4 is CH, R5b, n and R2 have the values listed in the Table Y.

Table 245
Table 245 provides 3507 compounds of formula (I-A) wherein R3 is difluorochloromethyl-, R4 is 2,6-bis(trifluoromethyl)-4-pyridyl-, Y1-Y2-Y3 is —C=N—CH2-, A2 is CH, A3 is CH, A4 is CH, R5b, n and R2 have the values listed in the Table Y.

Table 246
Table 246 provides 3507 compounds of formula (I-A) wherein R3 is difluorochloromethyl-, R4 is 2,6-bis(trifluoromethyl)-4-pyridyl-, Y1-Y2-Y3 is —C=N—CH2-, A2 is CH, A3 is N, A4 is CH, R5b, n and R2 have the values listed in the Table Y.

Table 247
Table 247 provides 3507 compounds of formula (I-A) wherein R3 is difluorochloromethyl-, R4 is 2,6-bis(trifluoromethyl)-4-pyridyl-, Y1-Y2-Y3 is —C=N—CH2-, A2 is N, A3 is N, A4 is CH, R5b, n and R2 have the values listed in the Table Y.

Table 248
Table 248 provides 3507 compounds of formula (I-A) wherein R3 is difluorochloromethyl-, R4 is 2,6-bis(trifluoromethyl)-4-pyridyl-, Y1-Y2-Y3 is —N—CH2-CH2-, A2 is CH, A3 is CH, A4 is CH, R5b, n and R2 have the values listed in the Table Y.

Table 249
Table 249 provides 3507 compounds of formula (I-A) wherein R3 is difluorochloromethyl-, R4 is 2,6-bis(trifluoromethyl)-4-pyridyl-, Y1-Y2-Y3 is —N—CH2-CH2-, A2 is CH, A3 is CH, A4 is CH, R5b, n and R2 have the values listed in the Table Y.

Table 250
Table 250 provides 3507 compounds of formula (I-A) wherein R3 is difluorochloromethyl-, R4 is 2,6-bis(trifluoromethyl)-4-pyridyl-, Y1-Y2-Y3 is —N—CH2-CH2-, A2 is CH, A3 is N, A4 is CH, R5b, n and R2 have the values listed in the Table Y.

Table 251
Table 251 provides 3507 compounds of formula (I-A) wherein R3 is difluorochloromethyl-, R4 is 2,6-bis(trifluoromethyl)-4-pyridyl-, Y1-Y2-Y3 is —N—CH2-CH2-, A2 is CH, A3 is N, A4 is CH, R5b, n and R2 have the values listed in the Table Y.

Table 252
Table 252 provides 3507 compounds of formula (I-A) wherein R3 is difluorochloromethyl-, R4 is 2,6-bis(trifluoromethyl)-4-pyridyl-, Y1-Y2-Y3 is —C=CH—O—, A2 is CH, A3 is N, A4 is CH, R5b, n and R2 have the values listed in the Table Y.

Table 253
Table 253 provides 3507 compounds of formula (I-A) wherein R3 is difluorochloromethyl-, R4 is 2,6-bis(trifluoromethyl)-4-pyridyl-, Y1-Y2-Y3 is —C=CH—O—, A2 is CH, A3 is N, A4 is CH, R5b, n and R2 have the values listed in the Table Y.

Table 254
Table 254 provides 3507 compounds of formula (I-A) wherein R3 is difluorochloromethyl-, R4 is 2,6-bis(trifluoromethyl)-4-pyridyl-, Y1-Y2-Y3 is —C=CH—O—, A2 is CH, A3 is CH, A4 is N, R5b, n and R2 have the values listed in the Table Y.

Table 255
Table 255 provides 3507 compounds of formula (I-A) wherein R3 is difluorochloromethyl-, R4 is 2,6-bis(trifluoromethyl)-4-pyridyl-, Y1-Y2-Y3 is —C=CH—O—, A2 is N, A3 is N, A4 is CH, R5b, n and R2 have the values listed in the Table Y.

Table 256
Table 256 provides 3507 compounds of formula (I-A) wherein R3 is difluorochloromethyl-, R4 is 2,6-bis(trifluoromethyl)-4-pyridyl-, Y1-Y2-Y3 is —C=CH—O—, A2 is N, A3 is N, A4 is CH, R5b, n and R2 have the values listed in the Table Y.

Table 257
Table 257 provides 3507 compounds of formula (I-A) wherein R3 is difluorochloromethyl-, R4 is 3,5-dichloro-4-bromophenyl-, Y1-Y2-Y3 is —C=N—O—, A2 is CH, A3 is N, A4 is CH, R5b, n and R2 have the values listed in the Table Y.

Table 258
Table 258 provides 3507 compounds of formula (I-A) wherein R3 is difluorochloromethyl-, R4 is 3,5-dichloro-4-bromophenyl-, Y1-Y2-Y3 is —C=N—O—, A2 is CH, A3 is CH, A4 is N, R5b, n and R2 have the values listed in the Table Y.

Table 259
Table 259 provides 3507 compounds of formula (I-A) wherein R3 is difluorochloromethyl-, R4 is 3,5-dichloro-4-bromophenyl-, Y1-Y2-Y3 is —C=N—CH2-, A2 is CH, A3 is CH, A4 is CH, R5b, n and R2 have the values listed in the Table Y.

Table 260
Table 260 provides 3507 compounds of formula (I-A) wherein R3 is difluorochloromethyl-, R4 is 3,5-dichloro-4-bromophenyl-, Y1-Y2-Y3 is —C=N—CH2-, A2 is CH, A3 is N, A4 is CH, R5b, n and R2 have the values listed in the Table Y.

Table 261
Table 261 provides 3507 compounds of formula (I-A) wherein R3 is difluorochloromethyl-, R4 is 3,5-dichloro-4-bromophenyl-, Y1-Y2-Y3 is —C=N—CH2-, A2 is CH, A3 is N, A4 is CH, R5b, n and R2 have the values listed in the Table Y.

Table 262
Table 262 provides 3507 compounds of formula (I-A) wherein R3 is difluorochloromethyl-, R4 is 3,5-dichloro-4-bromophenyl-, Y1-Y2-Y3 is —C=N—CH2-, A2 is N, A3 is N, A4 is CH, R5b, n and R2 have the values listed in the Table Y.

Table 263
Table 263 provides 3507 compounds of formula (I-A) wherein R3 is difluorochloromethyl-, R4 is 3,5-dichloro-4-bromophenyl-, Y1-Y2-Y3 is —N—CH2-CH2-, A2 is CH, A3 is CH, A4 is N, R5b, n and R2 have the values listed in the Table Y.

Table 264
Table 264 provides 3507 compounds of formula (I-A) wherein R3 is difluorochloromethyl-, R4 is 3,5-dichloro-4-bromophenyl-, Y1-Y2-Y3 is —N—CH2-CH2-, A2 is CH, A3 is CH, A4 is N, R5b, n and R2 have the values listed in the Table Y.

Table 265
Table 265 provides 3507 compounds of formula (I-A) wherein R3 is difluorochloromethyl-, R4 is 3,5-dichloro-4-bromophenyl-, Y1-Y2-Y3 is —N—CH2-CH2-, A2 is CH, A3 is CH, A4 is N, R5b, n and R2 have the values listed in the Table Y.

Table 266
Table 266 provides 3507 compounds of formula (I-A) wherein R3 is difluorochloromethyl-, R4 is 3,5-dichloro-4-bromophenyl-, Y1-Y2-Y3 is —N—CH2-CH2-, A2 is CH, A3 is CH, A4 is N, R5b, n and R2 have the values listed in the Table Y.

Table 267
Table 267 provides 3507 compounds of formula (I-A) wherein R3 is difluorochloromethyl-, R4 is 3,5-dichloro-4-bromophenyl-, Y1-Y2-Y3 is —N—CH2-CH2-, A2 is N, A3 is N, A4 is CH, R5b, n and R2 have the values listed in the Table Y.

Table 268
Table 268 provides 3507 compounds of formula (I-A) wherein R3 is difluorochloromethyl-, R4 is 3,5-dichloro-4-bromophenyl-, Y1-Y2-Y3 is —N—CH2-CH2-, A2 is N, A3 is N, A4 is CH, R5b, n and R2 have the values listed in the Table Y.

Table 269
Table 269 provides 3507 compounds of formula (I-A) wherein R3 is difluorochloromethyl-, R4 is 3,5-dichloro-4-bromophenyl-, Y1-Y2-Y3 is —C=CH—O—, A2 is CH, A3 is CH, A4 is CH, R5b, n and R2 have the values listed in the Table Y.

Table 270
Table 270 provides 3507 compounds of formula (I-A) wherein R3 is difluorochloromethyl-, R4 is 3,5-dichloro-4-bromophenyl-, Y1-Y2-Y3 is —C=CH—O—, A2 is CH, A3 is CH, A4 is CH, R5b, n and R2 have the values listed in the Table Y.

Table 271
Table 271 provides 3507 compounds of formula (I-A) wherein R3 is difluorochloromethyl-, R4 is 3,5-dichloro-4-bromophenyl-, Y1-Y2-Y3 is —C=CH—O—, A2 is CH, A3 is CH, A4 is CH, R5b, n and R2 have the values listed in the Table Y.

Table 272
Table 272 provides 3507 compounds of formula (I-A) wherein R3 is difluorochloromethyl-, R4 is 3,5-dichloro-4-bromophenyl-, Y1-Y2-Y3 is —C=CH—O—, A2 is CH, A3 is CH, A4 is N, R5b, n and R2 have the values listed in the Table Y.

Table 273
Table 273 provides 3507 compounds of formula (I-A) wherein R3 is difluorochloromethyl-, R4 is 3-bromo-5-(trifluoromethyl)phenyl-, Y1-Y2-Y3 is —C=N—O—, A2 is CH, A3 is CH, A4 is CH, R5b, n and R2 have the values listed in the Table Y.

Table 274
Table 274 provides 3507 compounds of formula (I-A) wherein R3 is difluorochloromethyl-, R4 is 3-bromo-5-(trifluoromethyl)phenyl-, Y1-Y2-Y3 is —C=N—O—, A2 is CH, A3 is CH, A4 is N, R5b, n and R2 have the values listed in the Table Y.

Table 275
Table 275 provides 3507 compounds of formula (I-A) wherein R3 is difluorochloromethyl-, R4 is 3-bromo-5-(trifluoromethyl)phenyl-, Y1-Y2-Y3 is —C=N—O—, A2 is CH, A3 is CH, A4 is N, R5b, n and R2 have the values listed in the Table Y.

Table 276
Table 276 provides 3507 compounds of formula (I-A) wherein R3 is difluorochloromethyl-, R4 is 3-bromo-5-(trifluoromethyl)phenyl-, Y1-Y2-Y3 is —C=N—O—, A2 is N, A3 is N, A4 is CH, R5b, n and R2 have the values listed in the Table Y.

Table 277
Table 277 provides 3507 compounds of formula (I-A) wherein R3 is difluorochloromethyl-, R4 is 3-bromo-5-(trifluoromethyl)phenyl-, Y1-Y2-Y3 is —C=N—O—, A2 is N, A3 is N, A4 is CH, R5b, n and R2 have the values listed in the Table Y.

Table 278
Table 278 provides 3507 compounds of formula (I-A) wherein R3 is difluorochloromethyl-, R4 is 3-bromo-5-(trifluoromethyl)phenyl-, Y1-Y2-Y3 is —C=N—CH2-, A2 is CH, A3 is N, A4 is CH, R5b, n and R2 have the values listed in the Table Y.

Table 279
Table 279 provides 3507 compounds of formula (I-A) wherein R3 is difluorochloromethyl-, R4 is 3-bromo-5-(trifluoromethyl)phenyl-, Y1-Y2-Y3 is —C=N—CH2-, A2 is CH, A3 is CH, A4 is N, R5b, n and R2 have the values listed in the Table Y.

Table 280
Table 280 provides 3507 compounds of formula (I-A) wherein R3 is difluorochloromethyl-, R4 is 3-bromo-5-(trifluoromethyl)phenyl-, Y1-Y2-Y3 is —C=N—CH2-, A2 is CH, A3 is CH, A4 is N, R5b, n and R2 have the values listed in the Table Y.

Table 281
Table 281 provides 3507 compounds of formula (I-A) wherein R3 is difluorochloromethyl-, R4 is 3-bromo-5-(trifluoromethyl)phenyl-, Y1-Y2-Y3 is —C=N—CH2-, A2 is N, A3 is N, A4 is CH, R5b, n and R2 have the values listed in the Table Y.

Table 282
Table 282 provides 3507 compounds of formula (I-A) wherein R3 is difluorochloromethyl-, R4 is 3-bromo-5-(trifluoromethyl)phenyl-, Y1-Y2-Y3 is —C=N—CH2-, A2 is N, A3 is N, A4 is CH, R5b, n and R2 have the values listed in the Table Y.

Table 283
Table 283 provides 3507 compounds of formula (I-A) wherein R3 is difluorochloromethyl-, R4 is 3-bromo-5-(trifluoromethyl)phenyl-, Y1-Y2-Y3 is —N—CH2-CH2-, A2 is CH, A3 is CH, A4 is CH, R5b, n and R2 have the values listed in the Table Y.

Table 284
Table 284 provides 3507 compounds of formula (I-A) wherein R3 is difluorochloromethyl-, R4 is 3-bromo-5-(trifluoromethyl)phenyl-, Y1-Y2-Y3 is —N—CH2-CH2-, A2 is CH, A3 is N, A4 is CH, R5b, n and R2 have the values listed in the Table Y.

Table 285
Table 285 provides 3507 compounds of formula (I-A) wherein R3 is difluorochloromethyl-, R4 is 3-bromo-5-(trifluoromethyl)phenyl-, Y1-Y2-Y3 is —C=CH—O—, A2 is CH, A3 is CH, A4 is CH, R5b, n and R2 have the values listed in the Table Y.

Table 286
Table 286 provides 3507 compounds of formula (I-A) wherein R3 is difluorochloromethyl-, R4 is 3-bromo-5-(trifluoromethyl)phenyl-, Y1-Y2-Y3 is —C=CH—O—, A2 is CH, A3 is N, A4 is CH, R5b, n and R2 have the values listed in the Table Y.

Table 287
Table 287 provides 3507 compounds of formula (I-A) wherein R3 is difluorochloromethyl-, R4 is 3-bromo-5-(trifluoromethyl)phenyl-, Y1-Y2-Y3 is —C=CH—O—, A2 is CH, A3 is CH, A4 is N, R5b, n and R2 have the values listed in the Table Y.

Table 288
Table 288 provides 3507 compounds of formula (I-A) wherein R3 is difluorochloromethyl-, R4 is 3-bromo-5-(trifluoromethyl)phenyl-, Y1-Y2-Y3 is —C=CH—O—, A2 is N, A3 is N, A4 is CH, R5b, n and R2 have the values listed in the Table Y.

Table 289
Table 289 provides 3507 compounds of formula (I-A) wherein R3 is difluorochloromethyl-, R4 is 3,5-dibromophenyl-, Y1-Y2-Y3 is —C=N—O—, A2 is CH, A3 is CH, A4 is CH, R5b, n and R2 have the values listed in the Table Y.

Table 290
Table 290 provides 3507 compounds of formula (I-A) wherein R3 is difluorochloromethyl-, R4 is 3,5-dibromophenyl-, Y1-Y2-Y3 is —C=N—O—, A2 is CH, A3 is N, A4 is CH, R5b, n and R2 have the values listed in the Table Y.

Table 291
Table 291 provides 3507 compounds of formula (I-A) wherein R3 is difluorochloromethyl-, R4 is 3,5-dibromophenyl-, Y1-Y2-Y3 is —C=N—O—, A2 is CH, A3 is N, A4 is CH, R5b, n and R2 have the values listed in the Table Y.

Table 292
Table 292 provides 3507 compounds of formula (I-A) wherein R3 is difluorochloromethyl-, R4 is 3,5-dibromophenyl-, Y1-Y2-Y3 is —C=N—O—, A2 is CH, A3 is CH, A4 is N, R5b, n and R2 have the values listed in the Table Y.

Table 293
Table 293 provides 3507 compounds of formula (I-A) wherein R3 is difluorochloromethyl-, R4 is 3,5-dibromophenyl-, Y1-Y2-Y3 is —C=N—O—, A2 is N, A3 is N, A4 is CH, R5b, n and R2 have the values listed in the Table Y.

Table 294
Table 294 provides 3507 compounds of formula (I-A) wherein R3 is difluorochloromethyl-, R4 is 3,5-dibromophenyl-, Y1-Y2-Y3 is —C=N—O—, A2 is N, A3 is N, A4 is CH, R5b, n and R2 have the values listed in the Table Y.

Table 295
Table 295 provides 3507 compounds of formula (I-A) wherein R3 is difluorochloromethyl-, R4 is 3,5-dibromophenyl-, Y1-Y2-Y3 is —C=N—CH2-, A2 is CH, A3 is CH, A4 is CH, R5b, n and R2 have the values listed in the Table Y.

Table 296
Table 296 provides 3507 compounds of formula (I-A) wherein R3 is difluorochloromethyl-, R4 is 3,5-dibromophenyl-, Y1-Y2-Y3 is —C=N—CH2-, A2 is CH, A3 is N, A4 is CH, R5b, n and R2 have the values listed in the Table Y.

Table 297
Table 297 provides 3507 compounds of formula (I-A) wherein R3 is difluorochloromethyl-, R4 is 3,5-dibromophenyl-, Y1-Y2-Y3 is —C=N—CH2-, A2 is CH, A3 is CH, A4 is N, R5b, n and R2 have the values listed in the Table Y.

Table 298

Table 298 provides 3507 compounds of formula (I-A) wherein R3 is difluorochloromethyl-, R4 is 3,5-dibromophenyl-, Y1-Y2-Y3 is —N—CH2-CH2-, A2 is CH, A3 is CH, A4 is CH, R5b, n and R2 have the values listed in the Table Y.

Table 299

Table 299 provides 3507 compounds of formula (I-A) wherein R3 is difluorochloromethyl-, R4 is 3,5-dibromophenyl-, Y1-Y2-Y3 is —N—CH2-CH2-, A2 is CH, A3 is CH, A4 is N, R5b, n and R2 have the values listed in the Table Y.

Table 300

Table 300 provides 3507 compounds of formula (I-A) wherein R3 is difluorochloromethyl-, R4 is 3,5-dibromophenyl-, Y1-Y2-Y3 is —N—CH2-CH2-, A2 is CH, A3 is CH, A4 is N, R5b, n and R2 have the values listed in the Table Y.

Table 301

Table 301 provides 3507 compounds of formula (I-A) wherein R3 is difluorochloromethyl-, R4 is 3,5-dibromophenyl-, Y1-Y2-Y3 is —N—CH2-CH2-, A2 is N, A3 is N, A4 is CH, R5b, n and R2 have the values listed in the Table Y.

Table 302

Table 302 provides 3507 compounds of formula (I-A) wherein R3 is difluorochloromethyl-, R4 is 3,5-dibromophenyl-, Y1-Y2-Y3 is —C=CH—O—, A2 is CH, A3 is CH, A4 is CH, R5b, n and R2 have the values listed in the Table Y.

Table 303

Table 303 provides 3507 compounds of formula (I-A) wherein R3 is difluorochloromethyl-, R4 is 3,5-dibromophenyl-, Y1-Y2-Y3 is —C=CH—O—, A2 is CH, A3 is N, A4 is CH, R5b, n and R2 have the values listed in the Table Y.

Table 304

Table 304 provides 3507 compounds of formula (I-A) wherein R3 is difluorochloromethyl-, R4 is 3,5-dibromophenyl-, Y1-Y2-Y3 is —C=CH—O—, A2 is N, A3 is N, A4 is CH, R5b, n and R2 have the values listed in the Table Y.

Table 305

Table 305 provides 3507 compounds of formula (I-A) wherein R3 is difluorochloromethyl-, R4 is 3,4-dichlorophenyl-, Y1-Y2-Y3 is —C=N—O—, A2 is CH, A3 is N, A4 is CH, R5b, n and R2 have the values listed in the Table Y.

Table 306

Table 306 provides 3507 compounds of formula (I-A) wherein R3 is difluorochloromethyl-, R4 is 3,4-dichlorophenyl-, Y1-Y2-Y3 is —C=N—O—, A2 is CH, A3 is CH, A4 is N, R5b, n and R2 have the values listed in the Table Y.

Table 307

Table 307 provides 3507 compounds of formula (I-A) wherein R3 is difluorochloromethyl-, R4 is 3,4-dichlorophenyl-, Y1-Y2-Y3 is —C=N—O—, A2 is N, A3 is N, A4 is CH, R5b, n and R2 have the values listed in the Table Y.

Table 308

Table 308 provides 3507 compounds of formula (I-A) wherein R3 is difluorochloromethyl-, R4 is 3,4-dichlorophenyl-, Y1-Y2-Y3 is —C=N—CH2-, A2 is CH, A3 is CH, A4 is CH, R5b, n and R2 have the values listed in the Table Y.

Table 309

Table 309 provides 3507 compounds of formula (I-A) wherein R3 is difluorochloromethyl-, R4 is 3,4-dichlorophenyl-, Y1-Y2-Y3 is —C=N—CH2-, A2 is CH, A3 is CH, A4 is CH, R5b, n and R2 have the values listed in the Table Y.

Table 310

Table 310 provides 3507 compounds of formula (I-A) wherein R3 is difluorochloromethyl-, R4 is 3,4-dichlorophenyl-, Y1-Y2-Y3 is —C=N—CH2-, A2 is CH, A3 is CH, A4 is CH, R5b, n and R2 have the values listed in the Table Y.

Table 311

Table 311 provides 3507 compounds of formula (I-A) wherein R3 is difluorochloromethyl-, R4 is 3,4-dichlorophenyl-, Y1-Y2-Y3 is —C=N—CH2-, A2 is CH, A3 is N, A4 is CH, R5b, n and R2 have the values listed in the Table Y.

Table 312

Table 312 provides 3507 compounds of formula (I-A) wherein R3 is difluorochloromethyl-, R4 is 3,4-dichlorophenyl-, Y1-Y2-Y3 is —C=N—CH2-, A2 is CH, A3 is CH, A4 is N, R5b, n and R2 have the values listed in the Table Y.

Table 313

Table 313 provides 3507 compounds of formula (I-A) wherein R3 is difluorochloromethyl-, R4 is 3,4-dichlorophenyl-, Y1-Y2-Y3 is —C=N—CH2-, A2 is N, A3 is N, A4 is CH, R5b, n and R2 have the values listed in the Table Y.

Table 314

Table 314 provides 3507 compounds of formula (I-A) wherein R3 is difluorochloromethyl-, R4 is 3,4-dichlorophenyl-, Y1-Y2-Y3 is —N—CH2-CH2-, A2 is CH, A3 is CH, A4 is CH, R5b, n and R2 have the values listed in the Table Y.

Table 315

Table 315 provides 3507 compounds of formula (I-A) wherein R3 is difluorochloromethyl-, R4 is 3,4-dichlorophenyl-, Y1-Y2-Y3 is —N—CH2-CH2-, A2 is N, A3 is N, A4 is CH, R5b, n and R2 have the values listed in the Table Y.

Table 316

Table 316 provides 3507 compounds of formula (I-A) wherein R3 is difluorochloromethyl-, R4 is 3,4-dichlorophenyl-, Y1-Y2-Y3 is —N—CH2-CH2-, A2 is N, A3 is N, A4 is CH, R5b, n and R2 have the values listed in the Table Y.

Table 317

Table 317 provides 3507 compounds of formula (I-A) wherein R3 is difluorochloromethyl-, R4 is 3,4-dichlorophenyl-, Y1-Y2-Y3 is —N—CH2-CH2-, A2 is N, A3 is N, A4 is CH, R5b, n and R2 have the values listed in the Table Y.

Table 318

Table 318 provides 3507 compounds of formula (I-A) wherein R3 is difluorochloromethyl-, R4 is 3,4-dichlorophenyl-, Y1-Y2-Y3 is —C=CH—O—, A2 is CH, A3 is CH, A4 is CH, R5b, n and R2 have the values listed in the Table Y.

Table 319

Table 319 provides 3507 compounds of formula (I-A) wherein R3 is difluorochloromethyl-, R4 is 3,4-dichlorophenyl-, Y1-Y2-Y3 is —C=CH—O—, A2 is CH, A3 is CH, A4 is N, R5b, n and R2 have the values listed in the Table Y.

Table 320

Table 320 provides 3507 compounds of formula (I-A) wherein R3 is difluorochloromethyl-, R4 is 3,4-dichlorophenyl-, Y1-Y2-Y3 is —C=CH—O—, A2 is CH, A3 is CH, A4 is N, R5b, n and R2 have the values listed in the Table Y.

Table 321

Table 321 provides 3507 compounds of formula (I-A) wherein R3 is difluorochloromethyl-, R4 is 3-chloro-5-bromophenyl-, Y1-Y2-Y3 is —C=N—O—, A2 is CH, A3 is CH, A4 is CH, R5b, n and R2 have the values listed in the Table Y.

Table 322

Table 322 provides 3507 compounds of formula (I-A) wherein R3 is difluorochloromethyl-, R4 is 3-chloro-5-bromophenyl-, Y1-Y2-Y3 is —C=N—O—, A2 is CH, A3 is N, A4 is CH, R5b, n and R2 have the values listed in the Table Y.

Table 323

Table 323 provides 3507 compounds of formula (I-A) wherein R3 is difluorochloromethyl-, R4 is 3-chloro-5-bromophenyl-, Y1-Y2-Y3 is —C=N—O—, A2 is CH, A3 is CH, A4 is N, R5b, n and R2 have the values listed in the Table Y.

Table 324
Table 324 provides 3507 compounds of formula (I-A) wherein R3 is difluorochloromethyl-, R4 is 3-chloro-5-bromophenyl-, Y1-Y2-Y3 is —C=N—O—, A2 is CH, A3 is CH, A4 is N, R5b, n and R2 have the values listed in the Table Y.

Table 325
Table 325 provides 3507 compounds of formula (I-A) wherein R3 is difluorochloromethyl-, R4 is 3-chloro-5-bromophenyl-, Y1-Y2-Y3 is —C=N—CH2-, A2 is CH, A3 is CH, A4 is CH, R5b, n and R2 have the values listed in the Table Y.

Table 326
Table 326 provides 3507 compounds of formula (I-A) wherein R3 is difluorochloromethyl-, R4 is 3-chloro-5-bromophenyl-, Y1-Y2-Y3 is —C=N—CH2-, A2 is CH, A3 is N, A4 is CH, R5b, n and R2 have the values listed in the Table Y.

Table 327
Table 327 provides 3507 compounds of formula (I-A) wherein R3 is difluorochloromethyl-, R4 is 3-chloro-5-bromophenyl-, Y1-Y2-Y3 is —C=N—CH2-, A2 is N, A3 is N, A4 is CH, R5b, n and R2 have the values listed in the Table Y.

Table 328
Table 328 provides 3507 compounds of formula (I-A) wherein R3 is difluorochloromethyl-, R4 is 3-chloro-5-bromophenyl-, Y1-Y2-Y3 is —N—CH2-CH2-, A2 is CH, A3 is CH, A4 is CH, R5b, n and R2 have the values listed in the Table Y.

Table 329
Table 329 provides 3507 compounds of formula (I-A) wherein R3 is difluorochloromethyl-, R4 is 3-chloro-5-bromophenyl-, Y1-Y2-Y3 is —N—CH2-CH2-, A2 is CH, A3 is N, A4 is CH, R5b, n and R2 have the values listed in the Table Y.

Table 330
Table 330 provides 3507 compounds of formula (I-A) wherein R3 is difluorochloromethyl-, R4 is 3-chloro-5-bromophenyl-, Y1-Y2-Y3 is —N—CH2-CH2-, A2 is CH, A3 is N, A4 is CH, R5b, n and R2 have the values listed in the Table Y.

Table 331
Table 331 provides 3507 compounds of formula (I-A) wherein R3 is difluorochloromethyl-, R4 is 3-chloro-5-bromophenyl-, Y1-Y2-Y3 is —N—CH2-CH2-, A2 is N, A3 is N, A4 is CH, R5b, n and R2 have the values listed in the Table Y.

Table 332
Table 332 provides 3507 compounds of formula (I-A) wherein R3 is difluorochloromethyl-, R4 is 3-chloro-5-bromophenyl-, Y1-Y2-Y3 is —C=CH—O—, A2 is CH, A3 is CH, A4 is CH, R5b, n and R2 have the values listed in the Table Y.

Table 333
Table 333 provides 3507 compounds of formula (I-A) wherein R3 is difluorochloromethyl-, R4 is 3-chloro-5-bromophenyl-, Y1-Y2-Y3 is —C=CH—O—, A2 is CH, A3 is N, A4 is CH, R5b, n and R2 have the values listed in the Table Y.

Table 334
Table 334 provides 3507 compounds of formula (I-A) wherein R3 is difluorochloromethyl-, R4 is 3-chloro-5-bromophenyl-, Y1-Y2-Y3 is —C=CH—O—, A2 is CH, A3 is N, A4 is CH, R5b, n and R2 have the values listed in the Table Y.

Table 335
Table 335 provides 3507 compounds of formula (I-A) wherein R3 is difluorochloromethyl-, R4 is 3-chloro-5-bromophenyl-, Y1-Y2-Y3 is —C=CH—O—, A2 is CH, A3 is CH, A4 is N, R5b, n and R2 have the values listed in the Table Y.

Table 336
Table 336 provides 3507 compounds of formula (I-A) wherein R3 is difluorochloromethyl-, R4 is 3-chloro-5-bromophenyl-, Y1-Y2-Y3 is —C=CH—O—, A2 is N, A3 is N, A4 is CH, R5b, n and R2 have the values listed in the Table Y.

Table 337
Table 337 provides 3507 compounds of formula (I-A) wherein R3 is difluorochloromethyl-, R4 is 3-chloro-5-fluorophenyl-, Y1-Y2-Y3 is —C=N—O—, A2 is CH, A3 is CH, A4 is CH, R5b, n and R2 have the values listed in the Table Y.

Table 338
Table 338 provides 3507 compounds of formula (I-A) wherein R3 is difluorochloromethyl-, R4 is 3-chloro-5-fluorophenyl-, Y1-Y2-Y3 is —C=N—O—, A2 is CH, A3 is CH, A4 is CH, R5b, n and R2 have the values listed in the Table Y.

Table 339
Table 339 provides 3507 compounds of formula (I-A) wherein R3 is difluorochloromethyl-, R4 is 3-chloro-5-fluorophenyl-, Y1-Y2-Y3 is —C=N—O—, A2 is N, A3 is N, A4 is CH, R5b, n and R2 have the values listed in the Table Y.

Table 340
Table 340 provides 3507 compounds of formula (I-A) wherein R3 is difluorochloromethyl-, R4 is 3-chloro-5-fluorophenyl-, Y1-Y2-Y3 is —C=N—CH2-, A2 is CH, A3 is CH, A4 is CH, R5b, n and R2 have the values listed in the Table Y.

Table 341
Table 341 provides 3507 compounds of formula (I-A) wherein R3 is difluorochloromethyl-, R4 is 3-chloro-5-fluorophenyl-, Y1-Y2-Y3 is —C=N—CH2-, A2 is CH, A3 is CH, A4 is CH, R5b, n and R2 have the values listed in the Table Y.

Table 342
Table 342 provides 3507 compounds of formula (I-A) wherein R3 is difluorochloromethyl-, R4 is 3-chloro-5-fluorophenyl-, Y1-Y2-Y3 is —C=N—CH2-, A2 is CH, A3 is N, A4 is CH, R5b, n and R2 have the values listed in the Table Y.

Table 343
Table 343 provides 3507 compounds of formula (I-A) wherein R3 is difluorochloromethyl-, R4 is 3-chloro-5-fluorophenyl-, Y1-Y2-Y3 is —C=N—CH2-, A2 is CH, A3 is N, A4 is CH, R5b, n and R2 have the values listed in the Table Y.

Table 344
Table 344 provides 3507 compounds of formula (I-A) wherein R3 is difluorochloromethyl-, R4 is 3-chloro-5-fluorophenyl-, Y1-Y2-Y3 is —C=N—CH2-, A2 is CH, A3 is N, A4 is CH, R5b, n and R2 have the values listed in the Table Y.

Table 345
Table 345 provides 3507 compounds of formula (I-A) wherein R3 is difluorochloromethyl-, R4 is 3-chloro-5-fluorophenyl-, Y1-Y2-Y3 is —C=N—CH2-, A2 is CH, A3 is CH, A4 is N, R5b, n and R2 have the values listed in the Table Y.

Table 346
Table 346 provides 3507 compounds of formula (I-A) wherein R3 is difluorochloromethyl-, R4 is 3-chloro-5-fluorophenyl-, Y1-Y2-Y3 is —C=N—CH2-, A2 is CH, A3 is CH, A4 is N, R5b, n and R2 have the values listed in the Table Y.

Table 347
Table 347 provides 3507 compounds of formula (I-A) wherein R3 is difluorochloromethyl-, R4 is 3-chloro-5-fluorophenyl-, Y1-Y2-Y3 is —C═N—CH2-, A2 is CH, A3 is CH, A4 is N, R5b, n and R2 have the values listed in the Table Y.

Table 348

Table 348 provides 3507 compounds of formula (I-A) wherein R3 is difluorochloromethyl-, R4 is 3-chloro-5-fluorophenyl-, Y1-Y2-Y3 is —N—CH2-CH2-, A2 is CH, A3 is CH, A4 is CH, R5b, n and R2 have the values listed in the Table Y.

Table 349

Table 349 provides 3507 compounds of formula (I-A) wherein R3 is difluorochloromethyl-, R4 is 3-chloro-5-fluorophenyl-, Y1-Y2-Y3 is —C═CH—O—, A2 is CH, A3 is CH, A4 is CH, R5b, n and R2 have the values listed in the Table Y.

Table 350

Table 350 provides 3507 compounds of formula (I-A) wherein R3 is difluorochloromethyl-, R4 is 3-chloro-5-fluorophenyl-, Y1-Y2-Y3 is —C═CH—O—, A2 is CH, A3 is CH, A4 is CH, R5b, n and R2 have the values listed in the Table Y.

Table 351

Table 351 provides 3507 compounds of formula (I-A) wherein R3 is difluorochloromethyl-, R4 is 3-chloro-5-fluorophenyl-, Y1-Y2-Y3 is —C═CH—O—, A2 is CH, A3 is CH, A4 is CH, R5b, n and R2 have the values listed in the Table Y.

Table 352

Table 352 provides 3507 compounds of formula (I-A) wherein R3 is difluorochloromethyl-, R4 is 3-chloro-5-fluorophenyl-, Y1-Y2-Y3 is —C═CH—O—, A2 is CH, A3 is CH, A4 is N, R5b, n and R2 have the values listed in the Table Y.

Table 353

Table 353 provides 3507 compounds of formula (I-A) wherein R3 is difluorochloromethyl-, R4 is 3-chloro-5-(trifluoromethyl)phenyl-, Y1-Y2-Y3 is —C═N—O—, A2 is CH, A3 is CH, A4 is CH, R5b, n and R2 have the values listed in the Table Y.

Table 354

Table 354 provides 3507 compounds of formula (I-A) wherein R3 is difluorochloromethyl-, R4 is 3-chloro-5-(trifluoromethyl)phenyl-, Y1-Y2-Y3 is —C═N—O—, A2 is CH, A3 is N, A4 is CH, R5b, n and R2 have the values listed in the Table Y.

Table 355

Table 355 provides 3507 compounds of formula (I-A) wherein R3 is difluorochloromethyl-, R4 is 3-chloro-5-(trifluoromethyl)phenyl-, Y1-Y2-Y3 is —C═N—O—, A2 is CH, A3 is N, A4 is CH, R5b, n and R2 have the values listed in the Table Y.

Table 356

Table 356 provides 3507 compounds of formula (I-A) wherein R3 is difluorochloromethyl-, R4 is 3-chloro-5-(trifluoromethyl)phenyl-, Y1-Y2-Y3 is —C═N—O—, A2 is CH, A3 is CH, A4 is N, R5b, n and R2 have the values listed in the Table Y.

Table 357

Table 357 provides 3507 compounds of formula (I-A) wherein R3 is difluorochloromethyl-, R4 is 3-chloro-5-(trifluoromethyl)phenyl-, Y1-Y2-Y3 is —C═N—O—, A2 is CH, A3 is CH, A4 is N, R5b, n and R2 have the values listed in the Table Y.

Table 358

Table 358 provides 3507 compounds of formula (I-A) wherein R3 is difluorochloromethyl-, R4 is 3-chloro-5-(trifluoromethyl)phenyl-, Y1-Y2-Y3 is —C═N—O—, A2 is N, A3 is N, A4 is CH, R5b, n and R2 have the values listed in the Table Y.

Table 359

Table 359 provides 3507 compounds of formula (I-A) wherein R3 is difluorochloromethyl-, R4 is 3-chloro-5-(trifluoromethyl)phenyl-, Y1-Y2-Y3 is —C═N—CH2-, A2 is CH, A3 is N, A4 is CH, R5b, n and R2 have the values listed in the Table Y.

Table 360

Table 360 provides 3507 compounds of formula (I-A) wherein R3 is difluorochloromethyl-, R4 is 3-chloro-5-(trifluoromethyl)phenyl-, Y1-Y2-Y3 is —C═N—CH2-, A2 is CH, A3 is CH, A4 is N, R5b, n and R2 have the values listed in the Table Y.

Table 361

Table 361 provides 3507 compounds of formula (I-A) wherein R3 is difluorochloromethyl-, R4 is 3-chloro-5-(trifluoromethyl)phenyl-, Y1-Y2-Y3 is —C═N—CH2-, A2 is N, A3 is N, A4 is CH, R5b, n and R2 have the values listed in the Table Y.

Table 362

Table 362 provides 3507 compounds of formula (I-A) wherein R3 is difluorochloromethyl-, R4 is 3-chloro-5-(trifluoromethyl)phenyl-, Y1-Y2-Y3 is —N—CH2-CH2-, A2 is CH, A3 is N, A4 is CH, R5b, n and R2 have the values listed in the Table Y.

Table 363

Table 363 provides 3507 compounds of formula (I-A) wherein R3 is difluorochloromethyl-, R4 is 3-chloro-5-(trifluoromethyl)phenyl-, Y1-Y2-Y3 is —N—CH2-CH2-, A2 is CH, A3 is CH, A4 is N, R5b, n and R2 have the values listed in the Table Y.

Table 364

Table 364 provides 3507 compounds of formula (I-A) wherein R3 is difluorochloromethyl-, R4 is 3-chloro-5-(trifluoromethyl)phenyl-, Y1-Y2-Y3 is —C═CH—O—, A2 is CH, A3 is N, A4 is CH, R5b, n and R2 have the values listed in the Table Y.

Table 365

Table 365 provides 3507 compounds of formula (I-A) wherein R3 is difluorochloromethyl-, R4 is 3-chloro-5-(trifluoromethyl)phenyl-, Y1-Y2-Y3 is —C═CH—O—, A2 is CH, A3 is CH, A4 is N, R5b, n and R2 have the values listed in the Table Y.

Table 366

Table 366 provides 3507 compounds of formula (I-A) wherein R3 is difluorochloromethyl-, R4 is 3-chloro-5-(trifluoromethyl)phenyl-, Y1-Y2-Y3 is —C═CH—O—, A2 is CH, A3 is CH, A4 is N, R5b, n and R2 have the values listed in the Table Y.

Table 367

Table 367 provides 3507 compounds of formula (I-A) wherein R3 is difluorochloromethyl-, R4 is 3-chloro-5-(trifluoromethyl)phenyl-, Y1-Y2-Y3 is —C═CH—O—, A2 is N, A3 is N, A4 is CH, R5b, n and R2 have the values listed in the Table Y.

Table 368

Table 368 provides 3507 compounds of formula (I-A) wherein R3 is difluorochloromethyl-, R4 is 3-chloro-5-(trifluoromethyl)phenyl-, Y1-Y2-Y3 is —C═CH—O—, A2 is N, A3 is N, A4 is CH, R5b, n and R2 have the values listed in the Table Y.

Table 369

Table 369 provides 3507 compounds of formula (I-A) wherein R3 is difluorochloromethyl-, R4 is 3,5-dichloro-4- fluorophenyl-, Y1-Y2-Y3 is —C=N—O—, A2 is CH, A3 is N, A4 is CH, R5b, n and R2 have the values listed in the Table Y.

Table 370

Table 370 provides 3507 compounds of formula (I-A) wherein R3 is difluorochloromethyl-, R4 is 3,5-dichloro-4-fluorophenyl-, Y1-Y2-Y3 is —C=N—O—, A2 is CH, A3 is N, A4 is CH, R5b, n and R2 have the values listed in the Table Y.

Table 371

Table 371 provides 3507 compounds of formula (I-A) wherein R3 is difluorochloromethyl-, R4 is 3,5-dichloro-4-fluorophenyl-, Y1-Y2-Y3 is —C=N—O—, A2 is CH, A3 is CH, A4 is N, R5b, n and R2 have the values listed in the Table Y.

Table 372

Table 372 provides 3507 compounds of formula (I-A) wherein R3 is difluorochloromethyl-, R4 is 3,5-dichloro-4-fluorophenyl-, Y1-Y2-Y3 is —C=N—O—, A2 is CH, A3 is CH, A4 is N, R5b, n and R2 have the values listed in the Table Y.

Table 373

Table 373 provides 3507 compounds of formula (I-A) wherein R3 is difluorochloromethyl-, R4 is 3,5-dichloro-4-fluorophenyl-, Y1-Y2-Y3 is —C=N—CH2-, A2 is CH, A3 is CH, A4 is CH, R5b, n and R2 have the values listed in the Table Y.

Table 374

Table 374 provides 3507 compounds of formula (I-A) wherein R3 is difluorochloromethyl-, R4 is 3,5-dichloro-4-fluorophenyl-, Y1-Y2-Y3 is —C=N—CH2-, A2 is CH, A3 is CH, A4 is CH, R5b, n and R2 have the values listed in the Table Y.

Table 375

Table 375 provides 3507 compounds of formula (I-A) wherein R3 is difluorochloromethyl-, R4 is 3,5-dichloro-4-fluorophenyl-, Y1-Y2-Y3 is —C=N—CH2-, A2 is CH, A3 is N, A4 is CH, R5b, n and R2 have the values listed in the Table Y.

Table 376

Table 376 provides 3507 compounds of formula (I-A) wherein R3 is difluorochloromethyl-, R4 is 3,5-dichloro-4-fluorophenyl-, Y1-Y2-Y3 is —C=N—CH2-, A2 is N, A3 is N, A4 is CH, R5b, n and R2 have the values listed in the Table Y.

Table 377

Table 377 provides 3507 compounds of formula (I-A) wherein R3 is difluorochloromethyl-, R4 is 3,5-dichloro-4-fluorophenyl-, Y1-Y2-Y3 is —N—CH2-CH2-, A2 is CH, A3 is CH, A4 is CH, R5b, n and R2 have the values listed in the Table Y.

Table 378

Table 378 provides 3507 compounds of formula (I-A) wherein R3 is difluorochloromethyl-, R4 is 3,5-dichloro-4-fluorophenyl-, Y1-Y2-Y3 is —N—CH2-CH2-, A2 is CH, A3 is CH, A4 is N, R5b, n and R2 have the values listed in the Table Y.

Table 379

Table 379 provides 3507 compounds of formula (I-A) wherein R3 is difluorochloromethyl-, R4 is 3,5-dichloro-4-fluorophenyl-, Y1-Y2-Y3 is —N—CH2-CH2-, A2 is N, A3 is N, A4 is CH, R5b, n and R2 have the values listed in the Table Y.

Table 380

Table 380 provides 3507 compounds of formula (I-A) wherein R3 is difluorochloromethyl-, R4 is 3,5-dichloro-4-fluorophenyl-, Y1-Y2-Y3 is —C=CH—O—, A2 is CH, A3 is CH, A4 is CH, R5b, n and R2 have the values listed in the Table Y.

Table 381

Table 381 provides 3507 compounds of formula (I-A) wherein R3 is difluorochloromethyl-, R4 is 3,5-dichloro-4-fluorophenyl-, Y1-Y2-Y3 is —C=CH—O—, A2 is CH, A3 is N, A4 is CH, R5b, n and R2 have the values listed in the Table Y.

Table 382

Table 382 provides 3507 compounds of formula (I-A) wherein R3 is difluorochloromethyl-, R4 is 3,5-dichloro-4-fluorophenyl-, Y1-Y2-Y3 is —C=CH—O—, A2 is CH, A3 is N, A4 is CH, R5b, n and R2 have the values listed in the Table Y.

Table 383

Table 383 provides 3507 compounds of formula (I-A) wherein R3 is difluorochloromethyl-, R4 is 3,5-dichloro-4-fluorophenyl-, Y1-Y2-Y3 is —C=CH—O—, A2 is N, A3 is N, A4 is CH, R5b, n and R2 have the values listed in the Table Y.

Table 384

Table 384 provides 3507 compounds of formula (I-A) wherein R3 is difluorochloromethyl-, R4 is 3,5-dichloro-4-fluorophenyl-, Y1-Y2-Y3 is —C=CH—O—, A2 is N, A3 is N, A4 is CH, R5b, n and R2 have the values listed in the Table Y.

Table 385

Table 385 provides 3507 compounds of formula (I-A) wherein R3 is difluorochloromethyl-, R4 is 3,4,5-trichlorophenyl-, Y1-Y2-Y3 is —C=N—O—, A2 is CH, A3 is N, A4 is CH, R5b, n and R2 have the values listed in the Table Y.

Table 386

Table 386 provides 3507 compounds of formula (I-A) wherein R3 is difluorochloromethyl-, R4 is 3,4,5-trichlorophenyl-, Y1-Y2-Y3 is —C=N—O—, A2 is CH, A3 is CH, A4 is N, R5b, n and R2 have the values listed in the Table Y.

Table 387

Table 387 provides 3507 compounds of formula (I-A) wherein R3 is difluorochloromethyl-, R4 is 3,4,5-trichlorophenyl-, Y1-Y2-Y3 is —C=N—O—, A2 is CH, A3 is CH, A4 is N, R5b, n and R2 have the values listed in the Table Y.

Table 388

Table 388 provides 3507 compounds of formula (I-A) wherein R3 is difluorochloromethyl-, R4 is 3,4,5-trichlorophenyl-, Y1-Y2-Y3 is —C=N—CH2-, A2 is CH, A3 is N, A4 is CH, R5b, n and R2 have the values listed in the Table Y.

Table 389

Table 389 provides 3507 compounds of formula (I-A) wherein R3 is difluorochloromethyl-, R4 is 3,4,5-trichlorophenyl-, Y1-Y2-Y3 is —C=N—CH2-, A2 is CH, A3 is CH, A4 is N, R5b, n and R2 have the values listed in the Table Y.

Table 390

Table 390 provides 3507 compounds of formula (I-A) wherein R3 is difluorochloromethyl-, R4 is 3,4,5-trichlorophenyl-, Y1-Y2-Y3 is —C=N—CH2-, A2 is N, A3 is N, A4 is CH, R5b, n and R2 have the values listed in the Table Y.

Table 391

Table 391 provides 3507 compounds of formula (I-A) wherein R3 is difluorochloromethyl-, R4 is 3,4,5-trichlorophenyl-, Y1-Y2-Y3 is —N—CH2-CH2-, A2 is CH, A3 is CH, A4 is CH, R5b, n and R2 have the values listed in the Table Y.

Table 392

Table 392 provides 3507 compounds of formula (I-A) wherein R3 is difluorochloromethyl-, R4 is 3,4,5-trichlorophenyl-, Y1-Y2-Y3 is —N—CH2-CH2-, A2 is CH, A3 is CH, A4 is CH, R5b, n and R2 have the values listed in the Table Y.

Table 393

Table 393 provides 3507 compounds of formula (I-A) wherein R3 is difluorochloromethyl-, R4 is 3,4,5-trichlorophenyl-, Y1-Y2-Y3 is —N—CH2-CH2-, A2 is CH, A3 is CH, A4 is CH, R5b, n and R2 have the values listed in the Table Y.

Table 394

Table 394 provides 3507 compounds of formula (I-A) wherein R3 is difluorochloromethyl-, R4 is 3,4,5-trichlorophenyl-, Y1-Y2-Y3 is —N—CH2-CH2-, A2 is CH, A3 is N, A4 is CH, R5b, n and R2 have the values listed in the Table Y.

Table 395

Table 395 provides 3507 compounds of formula (I-A) wherein R3 is difluorochloromethyl-, R4 is 3,4,5-trichlorophenyl-, Y1-Y2-Y3 is —N—CH2-CH2-, A2 is CH, A3 is CH, A4 is N, R5b, n and R2 have the values listed in the Table Y.

Table 396

Table 396 provides 3507 compounds of formula (I-A) wherein R3 is difluorochloromethyl-, R4 is 3,4,5-trichlorophenyl-, Y1-Y2-Y3 is —C=CH—O—, A2 is CH, A3 is CH, A4 is CH, R5b, n and R2 have the values listed in the Table Y.

Table 397

Table 397 provides 3507 compounds of formula (I-A) wherein R3 is difluorochloromethyl-, R4 is 3,4,5-trichlorophenyl-, Y1-Y2-Y3 is —C=CH—O—, A2 is CH, A3 is CH, A4 is N, R5b, n and R2 have the values listed in the Table Y.

Table 398

Table 398 provides 3507 compounds of formula (I-A) wherein R3 is difluorochloromethyl-, R4 is 3,4,5-trichlorophenyl-, Y1-Y2-Y3 is —C=CH—O—, A2 is N, A3 is N, A4 is CH, R5b, n and R2 have the values listed in the Table Y.

Table 399

Table 399 provides 3507 compounds of formula (I-A) wherein R3 is difluorochloromethyl-, R4 is 3,4,5-trichlorophenyl-, Y1-Y2-Y3 is —C=CH—O—, A2 is N, A3 is N, A4 is CH, R5b, n and R2 have the values listed in the Table Y.

Table 400

Table 400 provides 3507 compounds of formula (I-A) wherein R3 is difluorochloromethyl-, R4 is 3,4,5-trichlorophenyl-, Y1-Y2-Y3 is —C=CH—O—, A2 is N, A3 is N, A4 is CH, R5b, n and R2 have the values listed in the Table Y.

Table 401

Table 401 provides 3507 compounds of formula (I-A) wherein R3 is difluorochloromethyl-, R4 is 3,5-bis(trifluoromethyl)phenyl-, Y1-Y2-Y3 is —C=N—O—, A2 is CH, A3 is N, A4 is CH, R5b, n and R2 have the values listed in the Table Y.

Table 402

Table 402 provides 3507 compounds of formula (I-A) wherein R3 is difluorochloromethyl-, R4 is 3,5-bis(trifluoromethyl)phenyl-, Y1-Y2-Y3 is —C=N—O—, A2 is CH, A3 is CH, A4 is N, R5b, n and R2 have the values listed in the Table Y.

Table 403

Table 403 provides 3507 compounds of formula (I-A) wherein R3 is difluorochloromethyl-, R4 is 3,5-bis(trifluoromethyl)phenyl-, Y1-Y2-Y3 is —C=N—O—, A2 is CH, A3 is CH, A4 is N, R5b, n and R2 have the values listed in the Table Y.

Table 404

Table 404 provides 3507 compounds of formula (I-A) wherein R3 is difluorochloromethyl-, R4 is 3,5-bis(trifluoromethyl)phenyl-, Y1-Y2-Y3 is —C=N—O—, A2 is N, A3 is N, A4 is CH, R5b, n and R2 have the values listed in the Table Y.

Table 405

Table 405 provides 3507 compounds of formula (I-A) wherein R3 is difluorochloromethyl-, R4 is 3,5-bis(trifluoromethyl)phenyl-, Y1-Y2-Y3 is —C=N—CH2-, A2 is CH, A3 is CH, A4 is CH, R5b, n and R2 have the values listed in the Table Y.

Table 406

Table 406 provides 3507 compounds of formula (I-A) wherein R3 is difluorochloromethyl-, R4 is 3,5-bis(trifluoromethyl)phenyl-, Y1-Y2-Y3 is —C=N—CH2-, A2 is CH, A3 is CH, A4 is CH, R5b, n and R2 have the values listed in the Table Y.

Table 407

Table 407 provides 3507 compounds of formula (I-A) wherein R3 is difluorochloromethyl-, R4 is 3,5-bis(trifluoromethyl)phenyl-, Y1-Y2-Y3 is —C=N—CH2-, A2 is CH, A3 is CH, A4 is N, R5b, n and R2 have the values listed in the Table Y.

Table 408

Table 408 provides 3507 compounds of formula (I-A) wherein R3 is difluorochloromethyl-, R4 is 3,5-bis(trifluoromethyl)phenyl-, Y1-Y2-Y3 is —C=N—CH2-, A2 is N, A3 is N, A4 is CH, R5b, n and R2 have the values listed in the Table Y.

Table 409

Table 409 provides 3507 compounds of formula (I-A) wherein R3 is difluorochloromethyl-, R4 is 3,5-bis(trifluoromethyl)phenyl-, Y1-Y2-Y3 is —N—CH2-CH2-, A2 is CH, A3 is CH, A4 is CH, R5b, n and R2 have the values listed in the Table Y.

Table 410

Table 410 provides 3507 compounds of formula (I-A) wherein R3 is difluorochloromethyl-, R4 is 3,5-bis(trifluoromethyl)phenyl-, Y1-Y2-Y3 is —N—CH2-CH2-, A2 is CH, A3 is N, A4 is CH, R5b, n and R2 have the values listed in the Table Y.

Table 411

Table 411 provides 3507 compounds of formula (I-A) wherein R3 is difluorochloromethyl-, R4 is 3,5-bis(trifluoromethyl)phenyl-, Y1-Y2-Y3 is —N—CH2-CH2-, A2 is CH, A3 is N, A4 is CH, R5b, n and R2 have the values listed in the Table Y.

Table 412

Table 412 provides 3507 compounds of formula (I-A) wherein R3 is difluorochloromethyl-, R4 is 3,5-bis(trifluoromethyl)phenyl-, Y1-Y2-Y3 is —N—CH2-CH2-, A2 is CH, A3 is CH, A4 is N, R5b, n and R2 have the values listed in the Table Y.

Table 413

Table 413 provides 3507 compounds of formula (I-A) wherein R3 is difluorochloromethyl-, R4 is 3,5-bis(trifluoromethyl)phenyl-, Y1-Y2-Y3 is —N—CH2-CH2-, A2 is N, A3 is N, A4 is CH, R5b, n and R2 have the values listed in the Table Y.

Table 414

Table 414 provides 3507 compounds of formula (I-A) wherein R3 is difluorochloromethyl-, R4 is 3,5-bis(trifluoromethyl)phenyl-, Y1-Y2-Y3 is —C=CH—O—, A2 is CH, A3 is CH, A4 is N, R5b, n and R2 have the values listed in the Table Y.

Table 415
Table 415 provides 3507 compounds of formula (I-A) wherein R3 is difluorochloromethyl-, R4 is 3,5-bis(trifluoromethyl)phenyl-, Y1-Y2-Y3 is —C=CH—O—, A2 is N, A3 is N, A4 is CH, R5b, n and R2 have the values listed in the Table Y.

Table 416
Table 416 provides 3507 compounds of formula (I-A) wherein R3 is difluorochloromethyl-, R4 is 3,5-bis(trifluoromethyl)phenyl-, Y1-Y2-Y3 is —C=CH—O—, A2 is N, A3 is N, A4 is CH, R5b, n and R2 have the values listed in the Table Y.

Table 417
Table 417 provides 3507 compounds of formula (I-A) wherein R3 is difluorochloromethyl-, R4 is 3-(trifluoromethyl)phenyl-, Y1-Y2-Y3 is —C=N—O—, A2 is CH, A3 is CH, A4 is CH, R5b, n and R2 have the values listed in the Table Y.

Table 418
Table 418 provides 3507 compounds of formula (I-A) wherein R3 is difluorochloromethyl-, R4 is 3-(trifluoromethyl)phenyl-, Y1-Y2-Y3 is —C=N—O—, A2 is CH, A3 is N, A4 is CH, R5b, n and R2 have the values listed in the Table Y.

Table 419
Table 419 provides 3507 compounds of formula (I-A) wherein R3 is difluorochloromethyl-, R4 is 3-(trifluoromethyl)phenyl-, Y1-Y2-Y3 is —C=N—O—, A2 is N, A3 is N, A4 is CH, R5b, n and R2 have the values listed in the Table Y.

Table 420
Table 420 provides 3507 compounds of formula (I-A) wherein R3 is difluorochloromethyl-, R4 is 3-(trifluoromethyl)phenyl-, Y1-Y2-Y3 is —C=N—CH2-, A2 is CH, A3 is CH, A4 is CH, R5b, n and R2 have the values listed in the Table Y.

Table 421
Table 421 provides 3507 compounds of formula (I-A) wherein R3 is difluorochloromethyl-, R4 is 3-(trifluoromethyl)phenyl-, Y1-Y2-Y3 is —C=N—CH2-, A2 is CH, A3 is CH, A4 is CH, R5b, n and R2 have the values listed in the Table Y.

Table 422
Table 422 provides 3507 compounds of formula (I-A) wherein R3 is difluorochloromethyl-, R4 is 3-(trifluoromethyl)phenyl-, Y1-Y2-Y3 is —C=N—CH2-, A2 is N, A3 is N, A4 is CH, R5b, n and R2 have the values listed in the Table Y.

Table 423
Table 423 provides 3507 compounds of formula (I-A) wherein R3 is difluorochloromethyl-, R4 is 3-(trifluoromethyl)phenyl-, Y1-Y2-Y3 is —C=N—CH2-, A2 is N, A3 is N, A4 is CH, R5b, n and R2 have the values listed in the Table Y.

Table 424
Table 424 provides 3507 compounds of formula (I-A) wherein R3 is difluorochloromethyl-, R4 is 3-(trifluoromethyl)phenyl-, Y1-Y2-Y3 is —N—CH2-CH2-, A2 is CH, A3 is CH, A4 is CH, R5b, n and R2 have the values listed in the Table Y.

Table 425
Table 425 provides 3507 compounds of formula (I-A) wherein R3 is difluorochloromethyl-, R4 is 3-(trifluoromethyl)phenyl-, Y1-Y2-Y3 is —N—CH2-CH2-, A2 is CH, A3 is N, A4 is CH, R5b, n and R2 have the values listed in the Table Y.

Table 426
Table 426 provides 3507 compounds of formula (I-A) wherein R3 is difluorochloromethyl-, R4 is 3-(trifluoromethyl)phenyl-, Y1-Y2-Y3 is —N—CH2-CH2-, A2 is CH, A3 is N, A4 is CH, R5b, n and R2 have the values listed in the Table Y.

Table 427
Table 427 provides 3507 compounds of formula (I-A) wherein R3 is difluorochloromethyl-, R4 is 3-(trifluoromethyl)phenyl-, Y1-Y2-Y3 is —N—CH2-CH2-, A2 is CH, A3 is CH, A4 is N, R5b, n and R2 have the values listed in the Table Y.

Table 428
Table 428 provides 3507 compounds of formula (I-A) wherein R3 is difluorochloromethyl-, R4 is 3-(trifluoromethyl)phenyl-, Y1-Y2-Y3 is —N—CH2-CH2-, A2 is N, A3 is N, A4 is CH, R5b, n and R2 have the values listed in the Table Y.

Table 429
Table 429 provides 3507 compounds of formula (I-A) wherein R3 is difluorochloromethyl-, R4 is 3-(trifluoromethyl)phenyl-, Y1-Y2-Y3 is —N—CH2-CH2-, A2 is N, A3 is N, A4 is CH, R5b, n and R2 have the values listed in the Table Y.

Table 430
Table 430 provides 3507 compounds of formula (I-A) wherein R3 is difluorochloromethyl-, R4 is 3-(trifluoromethyl)phenyl-, Y1-Y2-Y3 is —N—CH2-CH2-, A2 is N, A3 is N, A4 is CH, R5b, n and R2 have the values listed in the Table Y.

Table 431
Table 431 provides 3507 compounds of formula (I-A) wherein R3 is difluorochloromethyl-, R4 is 3-(trifluoromethyl)phenyl-, Y1-Y2-Y3 is —C=CH—O—, A2 is CH, A3 is CH, A4 is CH, R5b, n and R2 have the values listed in the Table Y.

Table 432
Table 432 provides 3507 compounds of formula (I-A) wherein R3 is difluorochloromethyl-, R4 is 3-(trifluoromethyl)phenyl-, Y1-Y2-Y3 is —C=CH—O—, A2 is CH, A3 is CH, A4 is N, R5b, n and R2 have the values listed in the Table Y.

Table 433
Table 433 provides 3507 compounds of formula (I-A) wherein R3 is difluorochloromethyl-, R4 is 2,6-dichloro-4-pyridyl-, Y1-Y2-Y3 is —C=N—O—, A2 is CH, A3 is CH, A4 is CH, R5b, n and R2 have the values listed in the Table Y.

Table 434
Table 434 provides 3507 compounds of formula (I-A) wherein R3 is difluorochloromethyl-, R4 is 2,6-dichloro-4-pyridyl-, Y1-Y2-Y3 is —C=N—O—, A2 is CH, A3 is N, A4 is CH, R5b, n and R2 have the values listed in the Table Y.

Table 435
Table 435 provides 3507 compounds of formula (I-A) wherein R3 is difluorochloromethyl-, R4 is 2,6-dichloro-4-pyridyl-, Y1-Y2-Y3 is —C=N—O—, A2 is CH, A3 is N, A4 is CH, R5b, n and R2 have the values listed in the Table Y.

Table 436
Table 436 provides 3507 compounds of formula (I-A) wherein R3 is difluorochloromethyl-, R4 is 2,6-dichloro-4-pyridyl-, Y1-Y2-Y3 is —C=N—O—, A2 is CH, A3 is CH, A4 is N, R5b, n and R2 have the values listed in the Table Y.

Table 437
Table 437 provides 3507 compounds of formula (I-A) wherein R3 is difluorochloromethyl-, R4 is 2,6-dichloro-4-pyridyl-, Y1-Y2-Y3 is —C=N—CH2-, A2 is CH, A3 is N, A4 is CH, R5b, n and R2 have the values listed in the Table Y.

Table 438
Table 438 provides 3507 compounds of formula (I-A) wherein R3 is difluorochloromethyl-, R4 is 2,6-dichloro-4-pyridyl-, Y1-Y2-Y3 is —C=N—CH2-, A2 is N, A3 is N, A4 is CH, R5b, n and R2 have the values listed in the Table Y.

Table 439
Table 439 provides 3507 compounds of formula (I-A) wherein R3 is difluorochloromethyl-, R4 is 2,6-dichloro-4-pyridyl-, Y1-Y2-Y3 is —N—CH2-CH2-, A2 is CH, A3 is CH, A4 is CH, R5b, n and R2 have the values listed in the Table Y.

Table 440
Table 440 provides 3507 compounds of formula (I-A) wherein R3 is difluorochloromethyl-, R4 is 2,6-dichloro-4-pyridyl-, Y1-Y2-Y3 is —N—CH2-CH2-, A2 is CH, A3 is CH, A4 is N, R5b, n and R2 have the values listed in the Table Y.

Table 441
Table 441 provides 3507 compounds of formula (I-A) wherein R3 is difluorochloromethyl-, R4 is 2,6-dichloro-4-pyridyl-, Y1-Y2-Y3 is —N—CH2-CH2-, A2 is CH, A3 is CH, A4 is N, R5b, n and R2 have the values listed in the Table Y.

Table 442
Table 442 provides 3507 compounds of formula (I-A) wherein R3 is difluorochloromethyl-, R4 is 2,6-dichloro-4-pyridyl-, Y1-Y2-Y3 is —N—CH2-CH2-, A2 is N, A3 is N, A4 is CH, R5b, n and R2 have the values listed in the Table Y.

Table 443
Table 443 provides 3507 compounds of formula (I-A) wherein R3 is difluorochloromethyl-, R4 is 2,6-dichloro-4-pyridyl-, Y1-Y2-Y3 is —C=CH—O—, A2 is CH, A3 is N, A4 is CH, R5b, n and R2 have the values listed in the Table Y.

Table 444
Table 444 provides 3507 compounds of formula (I-A) wherein R3 is difluorochloromethyl-, R4 is 2,6-dichloro-4-pyridyl-, Y1-Y2-Y3 is —C=CH—O—, A2 is CH, A3 is N, A4 is CH, R5b, n and R2 have the values listed in the Table Y.

Table 445
Table 445 provides 3507 compounds of formula (I-A) wherein R3 is difluorochloromethyl-, R4 is 2,6-dichloro-4-pyridyl-, Y1-Y2-Y3 is —C=CH—O—, A2 is CH, A3 is N, A4 is CH, R5b, n and R2 have the values listed in the Table Y.

Table 446
Table 446 provides 3507 compounds of formula (I-A) wherein R3 is difluorochloromethyl-, R4 is 2,6-dichloro-4-pyridyl-, Y1-Y2-Y3 is —C=CH—O—, A2 is CH, A3 is CH, A4 is N, R5b, n and R2 have the values listed in the Table Y.

Table 447
Table 447 provides 3507 compounds of formula (I-A) wherein R3 is difluorochloromethyl-, R4 is 2,6-dichloro-4-pyridyl-, Y1-Y2-Y3 is —C=CH—O—, A2 is N, A3 is N, A4 is CH, R5b, n and R2 have the values listed in the Table Y.

Table 448
Table 448 provides 3507 compounds of formula (I-A) wherein R3 is difluorochloromethyl-, R4 is 2,6-dichloro-4-pyridyl-, Y1-Y2-Y3 is —C=CH—O—, A2 is N, A3 is N, A4 is CH, R5b, n and R2 have the values listed in the Table Y.

Table 449
Table 449 provides 3507 compounds of formula (I-A) wherein R3 is difluoromethyl-, R4 is 3,5-dichlorophenyl-, Y1-Y2-Y3 is —C=N—O—, A2 is CH, A3 is CH, A4 is N, R5b, n and R2 have the values listed in the Table Y.

Table 450
Table 450 provides 3507 compounds of formula (I-A) wherein R3 is difluoromethyl-, R4 is 3,5-dichlorophenyl-, Y1-Y2-Y3 is —C=N—O—, A2 is N, A3 is N, A4 is CH, R5b, n and R2 have the values listed in the Table Y.

Table 451
Table 451 provides 3507 compounds of formula (I-A) wherein R3 is difluoromethyl-, R4 is 3,5-dichlorophenyl-, Y1-Y2-Y3 is —C=N—CH2-, A2 is CH, A3 is CH, A4 is CH, R5b, n and R2 have the values listed in the Table Y.

Table 452
Table 452 provides 3507 compounds of formula (I-A) wherein R3 is difluoromethyl-, R4 is 3,5-dichlorophenyl-, Y1-Y2-Y3 is —C=N—CH2-, A2 is CH, A3 is N, A4 is CH, R5b, n and R2 have the values listed in the Table Y.

Table 453
Table 453 provides 3507 compounds of formula (I-A) wherein R3 is difluoromethyl-, R4 is 3,5-dichlorophenyl-, Y1-Y2-Y3 is —C=N—CH2-, A2 is CH, A3 is CH, A4 is N, R5b, n and R2 have the values listed in the Table Y.

Table 454
Table 454 provides 3507 compounds of formula (I-A) wherein R3 is difluoromethyl-, R4 is 3,5-dichlorophenyl-, Y1-Y2-Y3 is —C=N—CH2-, A2 is CH, A3 is CH, A4 is N, R5b, n and R2 have the values listed in the Table Y.

Table 455
Table 455 provides 3507 compounds of formula (I-A) wherein R3 is difluoromethyl-, R4 is 3,5-dichlorophenyl-, Y1-Y2-Y3 is —C=N—CH2-, A2 is N, A3 is N, A4 is CH, R5b, n and R2 have the values listed in the Table Y.

Table 456
Table 456 provides 3507 compounds of formula (I-A) wherein R3 is difluoromethyl-, R4 is 3,5-dichlorophenyl-, Y1-Y2-Y3 is —N—CH2-CH2-, A2 is CH, A3 is CH, A4 is CH, R5b, n and R2 have the values listed in the Table Y.

Table 457
Table 457 provides 3507 compounds of formula (I-A) wherein R3 is difluoromethyl-, R4 is 3,5-dichlorophenyl-, Y1-Y2-Y3 is —N—CH2-CH2-, A2 is CH, A3 is CH, A4 is CH, R5b, n and R2 have the values listed in the Table Y.

Table 458
Table 458 provides 3507 compounds of formula (I-A) wherein R3 is difluoromethyl-, R4 is 3,5-dichlorophenyl-, Y1-Y2-Y3 is —N—CH2-CH2-, A2 is CH, A3 is CH, A4 is CH, R5b, n and R2 have the values listed in the Table Y.

Table 459
Table 459 provides 3507 compounds of formula (I-A) wherein R3 is difluoromethyl-, R4 is 3,5-dichlorophenyl-, Y1-Y2-Y3 is —N—CH2-CH2-, A2 is N, A3 is N, A4 is CH, R5b, n and R2 have the values listed in the Table Y.

Table 460
Table 460 provides 3507 compounds of formula (I-A) wherein R3 is difluoromethyl-, R4 is 3,5-dichlorophenyl-, Y1-Y2-Y3 is —C=CH—O—, A2 is CH, A3 is N, A4 is CH, R5b, n and R2 have the values listed in the Table Y.

Table 461
Table 461 provides 3507 compounds of formula (I-A) wherein R3 is difluoromethyl-, R4 is 3,5-dichlorophenyl-, Y1-Y2-Y3 is —C=CH—O—, A2 is CH, A3 is N, A4 is CH, R5b, n and R2 have the values listed in the Table Y.

Table 462
Table 462 provides 3507 compounds of formula (I-A) wherein R3 is difluoromethyl-, R4 is 3,5-dichlorophenyl-, Y1-Y2-Y3 is —C=CH—O—, A2 is CH, A3 is N, A4 is CH, R5b, n and R2 have the values listed in the Table Y.

Table 463
Table 463 provides 3507 compounds of formula (I-A) wherein R3 is difluoromethyl-, R4 is 3,5-dichlorophenyl-, Y1-Y2-Y3 is —C=CH—O—, A2 is CH, A3 is CH, A4 is N, R5b, n and R2 have the values listed in the Table Y.

Table 464
Table 464 provides 3507 compounds of formula (I-A) wherein R3 is difluoromethyl-, R4 is 3,5-dichlorophenyl-, Y1-Y2-Y3 is —C=CH—O—, A2 is N, A3 is N, A4 is CH, R5b, n and R2 have the values listed in the Table Y.

Table 465
Table 465 provides 3507 compounds of formula (I-A) wherein R3 is difluoromethyl-, R4 is 2,6-bis(trifluoromethyl)-4-pyridyl-, Y1-Y2-Y3 is —C=N—O—, A2 is CH, A3 is N, A4 is CH, R5b, n and R2 have the values listed in the Table Y.

Table 466
Table 466 provides 3507 compounds of formula (I-A) wherein R3 is difluoromethyl-, R4 is 2,6-bis(trifluoromethyl)-4-pyridyl-, Y1-Y2-Y3 is —C=N—O—, A2 is CH, A3 is CH, A4 is N, R5b, n and R2 have the values listed in the Table Y.

Table 467
Table 467 provides 3507 compounds of formula (I-A) wherein R3 is difluoromethyl-, R4 is 2,6-bis(trifluoromethyl)-4-pyridyl-, Y1-Y2-Y3 is —C=N—O—, A2 is CH, A3 is CH, A4 is N, R5b, n and R2 have the values listed in the Table Y.

Table 468
Table 468 provides 3507 compounds of formula (I-A) wherein R3 is difluoromethyl-, R4 is 2,6-bis(trifluoromethyl)-4-pyridyl-, Y1-Y2-Y3 is —C=N—O—, A2 is N, A3 is N, A4 is CH, R5b, n and R2 have the values listed in the Table Y.

Table 469
Table 469 provides 3507 compounds of formula (I-A) wherein R3 is difluoromethyl-, R4 is 2,6-bis(trifluoromethyl)-4-pyridyl-, Y1-Y2-Y3 is —C=N—CH2-, A2 is CH, A3 is N, A4 is CH, R5b, n and R2 have the values listed in the Table Y.

Table 470
Table 470 provides 3507 compounds of formula (I-A) wherein R3 is difluoromethyl-, R4 is 2,6-bis(trifluoromethyl)-4-pyridyl-, Y1-Y2-Y3 is —C=N—CH2-, A2 is CH, A3 is N, A4 is CH, R5b, n and R2 have the values listed in the Table Y.

Table 471
Table 471 provides 3507 compounds of formula (I-A) wherein R3 is difluoromethyl-, R4 is 2,6-bis(trifluoromethyl)-4-pyridyl-, Y1-Y2-Y3 is —C=N—CH2-, A2 is CH, A3 is N, A4 is CH, R5b, n and R2 have the values listed in the Table Y.

Table 472
Table 472 provides 3507 compounds of formula (I-A) wherein R3 is difluoromethyl-, R4 is 2,6-bis(trifluoromethyl)-4-pyridyl-, Y1-Y2-Y3 is —C=N—CH2-, A2 is CH, A3 is CH, A4 is N, R5b, n and R2 have the values listed in the Table Y.

Table 473
Table 473 provides 3507 compounds of formula (I-A) wherein R3 is difluoromethyl-, R4 is 2,6-bis(trifluoromethyl)-4-pyridyl-, Y1-Y2-Y3 is —N—CH2-CH2-, A2 is CH, A3 is CH, A4 is CH, R5b, n and R2 have the values listed in the Table Y.

Table 474
Table 474 provides 3507 compounds of formula (I-A) wherein R3 is difluoromethyl-, R4 is 2,6-bis(trifluoromethyl)-4-pyridyl-, Y1-Y2-Y3 is —N—CH2-CH2-, A2 is CH, A3 is CH, A4 is N, R5b, n and R2 have the values listed in the Table Y.

Table 475
Table 475 provides 3507 compounds of formula (I-A) wherein R3 is difluoromethyl-, R4 is 2,6-bis(trifluoromethyl)-4-pyridyl-, Y1-Y2-Y3 is —N—CH2-CH2-, A2 is N, A3 is N, A4 is CH, R5b, n and R2 have the values listed in the Table Y.

Table 476
Table 476 provides 3507 compounds of formula (I-A) wherein R3 is difluoromethyl-, R4 is 2,6-bis(trifluoromethyl)-4-pyridyl-, Y1-Y2-Y3 is —C=CH—O—, A2 is CH, A3 is CH, A4 is CH, R5b, n and R2 have the values listed in the Table Y.

Table 477
Table 477 provides 3507 compounds of formula (I-A) wherein R3 is difluoromethyl-, R4 is 2,6-bis(trifluoromethyl)-4-pyridyl-, Y1-Y2-Y3 is —C=CH—O—, A2 is CH, A3 is N, A4 is CH, R5b, n and R2 have the values listed in the Table Y.

Table 478
Table 478 provides 3507 compounds of formula (I-A) wherein R3 is difluoromethyl-, R4 is 2,6-bis(trifluoromethyl)-4-pyridyl-, Y1-Y2-Y3 is —C=CH—O—, A2 is CH, A3 is N, A4 is CH, R5b, n and R2 have the values listed in the Table Y.

Table 479
Table 479 provides 3507 compounds of formula (I-A) wherein R3 is difluoromethyl-, R4 is 2,6-bis(trifluoromethyl)-4-pyridyl-, Y1-Y2-Y3 is —C=CH—O—, A2 is N, A3 is N, A4 is CH, R5b, n and R2 have the values listed in the Table Y.

Table 480
Table 480 provides 3507 compounds of formula (I-A) wherein R3 is difluoromethyl-, R4 is 2,6-bis(trifluoromethyl)-4-pyridyl-, Y1-Y2-Y3 is —C=CH—O—, A2 is N, A3 is N, A4 is CH, R5b, n and R2 have the values listed in the Table Y.

Table 481
Table 481 provides 3507 compounds of formula (I-A) wherein R3 is difluoromethyl-, R4 is 3,5-dichloro-4-bromophenyl-, Y1-Y2-Y3 is —C=N—O—, A2 is CH, A3 is N, A4 is CH, R5b, n and R2 have the values listed in the Table Y.

Table 482
Table 482 provides 3507 compounds of formula (I-A) wherein R3 is difluoromethyl-, R4 is 3,5-dichloro-4-bromophenyl-, Y1-Y2-Y3 is —C=N—O—, A2 is N, A3 is N, A4 is CH, R5b, n and R2 have the values listed in the Table Y.

Table 483
Table 483 provides 3507 compounds of formula (I-A) wherein R3 is difluoromethyl-, R4 is 3,5-dichloro-4-bromophenyl-, Y1-Y2-Y3 is —C=N—O—, A2 is N, A3 is N, A4 is CH, R5b, n and R2 have the values listed in the Table Y.

Table 484
Table 484 provides 3507 compounds of formula (I-A) wherein R3 is difluoromethyl-, R4 is 3,5-dichloro-4-bromophenyl-, Y1-Y2-Y3 is —C=N—O—, A2 is N, A3 is N, A4 is CH, R5b, n and R2 have the values listed in the Table Y.

Table 485
Table 485 provides 3507 compounds of formula (I-A) wherein R3 is difluoromethyl-, R4 is 3,5-dichloro-4-bromophenyl-, Y1-Y2-Y3 is —C=N—CH2-, A2 is CH, A3 is CH, A4 is CH, R5b, n and R2 have the values listed in the Table Y.

Table 486
Table 486 provides 3507 compounds of formula (I-A) wherein R3 is difluoromethyl-, R4 is 3,5-dichloro-4-bromophenyl-, Y1-Y2-Y3 is —C=N—CH2-, A2 is CH, A3 is N, A4 is CH, R5b, n and R2 have the values listed in the Table Y.

Table 487
Table 487 provides 3507 compounds of formula (I-A) wherein R3 is difluoromethyl-, R4 is 3,5-dichloro-4-bromophenyl-, Y1-Y2-Y3 is —C=N—CH2-, A2 is CH, A3 is N, A4 is CH, R5b, n and R2 have the values listed in the Table Y.
Table 488
Table 488 provides 3507 compounds of formula (I-A) wherein R3 is difluoromethyl-, R4 is 3,5-dichloro-4-bromophenyl-, Y1-Y2-Y3 is —C=N—CH2-, A2 is CH, A3 is CH, A4 is N, R5b, n and R2 have the values listed in the Table Y.
Table 489
Table 489 provides 3507 compounds of formula (I-A) wherein R3 is difluoromethyl-, R4 is 3,5-dichloro-4-bromophenyl-, Y1-Y2-Y3 is —C=N—CH2-, A2 is CH, A3 is CH, A4 is N, R5b, n and R2 have the values listed in the Table Y.
Table 490
Table 490 provides 3507 compounds of formula (I-A) wherein R3 is difluoromethyl-, R4 is 3,5-dichloro-4-bromophenyl-, Y1-Y2-Y3 is —C=N—CH2-, A2 is N, A3 is N, A4 is CH, R5b, n and R2 have the values listed in the Table Y.
Table 491
Table 491 provides 3507 compounds of formula (I-A) wherein R3 is difluoromethyl-, R4 is 3,5-dichloro-4-bromophenyl-, Y1-Y2-Y3 is —N—CH2-CH2-, A2 is CH, A3 is CH, A4 is CH, R5b, n and R2 have the values listed in the Table Y.
Table 492
Table 492 provides 3507 compounds of formula (I-A) wherein R3 is difluoromethyl-, R4 is 3,5-dichloro-4-bromophenyl-, Y1-Y2-Y3 is —N—CH2-CH2-, A2 is CH, A3 is CH, A4 is CH, R5b, n and R2 have the values listed in the Table Y.
Table 493
Table 493 provides 3507 compounds of formula (I-A) wherein R3 is difluoromethyl-, R4 is 3,5-dichloro-4-bromophenyl-, Y1-Y2-Y3 is —N—CH2-CH2-, A2 is CH, A3 is CH, A4 is N, R5b, n and R2 have the values listed in the Table Y.
Table 494
Table 494 provides 3507 compounds of formula (I-A) wherein R3 is difluoromethyl-, R4 is 3,5-dichloro-4-bromophenyl-, Y1-Y2-Y3 is —N—CH2-CH2-, A2 is N, A3 is N, A4 is CH, R5b, n and R2 have the values listed in the Table Y.
Table 495
Table 495 provides 3507 compounds of formula (I-A) wherein R3 is difluoromethyl-, R4 is 3,5-dichloro-4-bromophenyl-, Y1-Y2-Y3 is —C=CH—O—, A2 is CH, A3 is N, A4 is CH, R5b, n and R2 have the values listed in the Table Y.
Table 496
Table 496 provides 3507 compounds of formula (I-A) wherein R3 is difluoromethyl-, R4 is 3,5-dichloro-4-bromophenyl-, Y1-Y2-Y3 is —C=CH—O—, A2 is N, A3 is N, A4 is CH, R5b, n and R2 have the values listed in the Table Y.
Table 497
Table 497 provides 3507 compounds of formula (I-A) wherein R3 is difluoromethyl-, R4 is 3-bromo-5-(trifluoromethyl)phenyl-, Y1-Y2-Y3 is —C=N—O—, A2 is CH, A3 is CH, A4 is CH, R5b, n and R2 have the values listed in the Table Y.
Table 498
Table 498 provides 3507 compounds of formula (I-A) wherein R3 is difluoromethyl-, R4 is 3-bromo-5-(trifluoromethyl)phenyl-, Y1-Y2-Y3 is —C=N—O—, A2 is CH, A3 is N, A4 is CH, R5b, n and R2 have the values listed in the Table Y.
Table 499
Table 499 provides 3507 compounds of formula (I-A) wherein R3 is difluoromethyl-, R4 is 3-bromo-5-(trifluoromethyl)phenyl-, Y1-Y2-Y3 is —C=N—O—, A2 is CH, A3 is CH, A4 is N, R5b, n and R2 have the values listed in the Table Y.
Table 500
Table 500 provides 3507 compounds of formula (I-A) wherein R3 is difluoromethyl-, R4 is 3-bromo-5-(trifluoromethyl)phenyl-, Y1-Y2-Y3 is —C=N—CH2-, A2 is CH, A3 is CH, A4 is CH, R5b, n and R2 have the values listed in the Table Y.
Table 501
Table 501 provides 3507 compounds of formula (I-A) wherein R3 is difluoromethyl-, R4 is 3-bromo-5-(trifluoromethyl)phenyl-, Y1-Y2-Y3 is —C=N—CH2-, A2 is CH, A3 is CH, A4 is CH, R5b, n and R2 have the values listed in the Table Y.
Table 502
Table 502 provides 3507 compounds of formula (I-A) wherein R3 is difluoromethyl-, R4 is 3-bromo-5-(trifluoromethyl)phenyl-, Y1-Y2-Y3 is —C=N—CH2-, A2 is CH, A3 is CH, A4 is N, R5b, n and R2 have the values listed in the Table Y.
Table 503
Table 503 provides 3507 compounds of formula (I-A) wherein R3 is difluoromethyl-, R4 is 3-bromo-5-(trifluoromethyl)phenyl-, Y1-Y2-Y3 is —C=N—CH2-, A2 is CH, A3 is CH, A4 is N, R5b, n and R2 have the values listed in the Table Y.
Table 504
Table 504 provides 3507 compounds of formula (I-A) wherein R3 is difluoromethyl-, R4 is 3-bromo-5-(trifluoromethyl)phenyl-, Y1-Y2-Y3 is —N—CH2-CH2-, A2 is CH, A3 is CH, A4 is CH, R5b, n and R2 have the values listed in the Table Y.
Table 505
Table 505 provides 3507 compounds of formula (I-A) wherein R3 is difluoromethyl-, R4 is 3-bromo-5-(trifluoromethyl)phenyl-, Y1-Y2-Y3 is —N—CH2-CH2-, A2 is CH, A3 is CH, A4 is CH, R5b, n and R2 have the values listed in the Table Y.
Table 506
Table 506 provides 3507 compounds of formula (I-A) wherein R3 is difluoromethyl-, R4 is 3-bromo-5-(trifluoromethyl)phenyl-, Y1-Y2-Y3 is —N—CH2-CH2-, A2 is CH, A3 is N, A4 is CH, R5b, n and R2 have the values listed in the Table Y.
Table 507
Table 507 provides 3507 compounds of formula (I-A) wherein R3 is difluoromethyl-, R4 is 3-bromo-5-(trifluoromethyl)phenyl-, Y1-Y2-Y3 is —N—CH2-CH2-, A2 is CH, A3 is CH, A4 is N, R5b, n and R2 have the values listed in the Table Y.
Table 508
Table 508 provides 3507 compounds of formula (I-A) wherein R3 is difluoromethyl-, R4 is 3-bromo-5-(trifluoromethyl)phenyl-, Y1-Y2-Y3 is —N—CH2-CH2-, A2 is N, A3 is N, A4 is CH, R5b, n and R2 have the values listed in the Table Y.
Table 509
Table 509 provides 3507 compounds of formula (I-A) wherein R3 is difluoromethyl-, R4 is 3-bromo-5-(trifluoromethyl)phenyl-, Y1-Y2-Y3 is —C=CH—O—, A2 is CH, A3 is CH, A4 is CH, R5b, n and R2 have the values listed in the Table Y.

Table 510
Table 510 provides 3507 compounds of formula (I-A) wherein R3 is difluoromethyl-, R4 is 3-bromo-5-(trifluoromethyl)phenyl-, Y1-Y2-Y3 is —C=CH—O—, A2 is CH, A3 is N, A4 is CH, R5b, n and R2 have the values listed in the Table Y.

Table 511
Table 511 provides 3507 compounds of formula (I-A) wherein R3 is difluoromethyl-, R4 is 3-bromo-5-(trifluoromethyl)phenyl-, Y1-Y2-Y3 is —C=CH—O—, A2 is CH, A3 is N, A4 is CH, R5b, n and R2 have the values listed in the Table Y.

Table 512
Table 512 provides 3507 compounds of formula (I-A) wherein R3 is difluoromethyl-, R4 is 3-bromo-5-(trifluoromethyl)phenyl-, Y1-Y2-Y3 is —C=CH—O—, A2 is N, A3 is N, A4 is CH, R5b, n and R2 have the values listed in the Table Y.

Table 513
Table 513 provides 3507 compounds of formula (I-A) wherein R3 is difluoromethyl-, R4 is 3,5-dibromophenyl-, Y1-Y2-Y3 is —C=N—O—, A2 is CH, A3 is CH, A4 is CH, R5b, n and R2 have the values listed in the Table Y.

Table 514
Table 514 provides 3507 compounds of formula (I-A) wherein R3 is difluoromethyl-, R4 is 3,5-dibromophenyl-, Y1-Y2-Y3 is —C=N—O—, A2 is CH, A3 is N, A4 is CH, R5b, n and R2 have the values listed in the Table Y.

Table 515
Table 515 provides 3507 compounds of formula (I-A) wherein R3 is difluoromethyl-, R4 is 3,5-dibromophenyl-, Y1-Y2-Y3 is —C=N—O—, A2 is CH, A3 is CH, A4 is N, R5b, n and R2 have the values listed in the Table Y.

Table 516
Table 516 provides 3507 compounds of formula (I-A) wherein R3 is difluoromethyl-, R4 is 3,5-dibromophenyl-, Y1-Y2-Y3 is —C=N—CH2-, A2 is CH, A3 is CH, A4 is CH, R5b, n and R2 have the values listed in the Table Y.

Table 517
Table 517 provides 3507 compounds of formula (I-A) wherein R3 is difluoromethyl-, R4 is 3,5-dibromophenyl-, Y1-Y2-Y3 is —C=N—CH2-, A2 is CH, A3 is CH, A4 is N, R5b, n and R2 have the values listed in the Table Y.

Table 518
Table 518 provides 3507 compounds of formula (I-A) wherein R3 is difluoromethyl-, R4 is 3,5-dibromophenyl-, Y1-Y2-Y3 is —C=N—CH2-, A2 is CH, A3 is CH, A4 is CH, R5b, n and R2 have the values listed in the Table Y.

Table 519
Table 519 provides 3507 compounds of formula (I-A) wherein R3 is difluoromethyl-, R4 is 3,5-dibromophenyl-, Y1-Y2-Y3 is —C=N—CH2-, A2 is N, A3 is N, A4 is CH, R5b, n and R2 have the values listed in the Table Y.

Table 520
Table 520 provides 3507 compounds of formula (I-A) wherein R3 is difluoromethyl-, R4 is 3,5-dibromophenyl-, Y1-Y2-Y3 is —N—CH2-CH2-, A2 is CH, A3 is CH, A4 is CH, R5b, n and R2 have the values listed in the Table Y.

Table 521
Table 521 provides 3507 compounds of formula (I-A) wherein R3 is difluoromethyl-, R4 is 3,5-dibromophenyl-, Y1-Y2-Y3 is —N—CH2-CH2-, A2 is CH, A3 is CH, A4 is CH, R5b, n and R2 have the values listed in the Table Y.

Table 522
Table 522 provides 3507 compounds of formula (I-A) wherein R3 is difluoromethyl-, R4 is 3,5-dibromophenyl-, Y1-Y2-Y3 is —N—CH2-CH2-, A2 is CH, A3 is N, A4 is CH, R5b, n and R2 have the values listed in the Table Y.

Table 523
Table 523 provides 3507 compounds of formula (I-A) wherein R3 is difluoromethyl-, R4 is 3,5-dibromophenyl-, Y1-Y2-Y3 is —N—CH2-CH2-, A2 is N, A3 is N, A4 is CH, R5b, n and R2 have the values listed in the Table Y.

Table 524
Table 524 provides 3507 compounds of formula (I-A) wherein R3 is difluoromethyl-, R4 is 3,5-dibromophenyl-, Y1-Y2-Y3 is —C=CH—O—, A2 is CH, A3 is N, A4 is CH, R5b, n and R2 have the values listed in the Table Y.

Table 525
Table 525 provides 3507 compounds of formula (I-A) wherein R3 is difluoromethyl-, R4 is 3,5-dibromophenyl-, Y1-Y2-Y3 is —C=CH—O—, A2 is CH, A3 is N, A4 is CH, R5b, n and R2 have the values listed in the Table Y.

Table 526
Table 526 provides 3507 compounds of formula (I-A) wherein R3 is difluoromethyl-, R4 is 3,5-dibromophenyl-, Y1-Y2-Y3 is —C=CH—O—, A2 is CH, A3 is CH, A4 is N, R5b, n and R2 have the values listed in the Table Y.

Table 527
Table 527 provides 3507 compounds of formula (I-A) wherein R3 is difluoromethyl-, R4 is 3,5-dibromophenyl-, Y1-Y2-Y3 is —C=CH—O—, A2 is CH, A3 is CH, A4 is N, R5b, n and R2 have the values listed in the Table Y.

Table 528
Table 528 provides 3507 compounds of formula (I-A) wherein R3 is difluoromethyl-, R4 is 3,5-dibromophenyl-, Y1-Y2-Y3 is —C=CH—O—, A2 is N, A3 is N, A4 is CH, R5b, n and R2 have the values listed in the Table Y.

Table 529
Table 529 provides 3507 compounds of formula (I-A) wherein R3 is difluoromethyl-, R4 is 3,4-dichlorophenyl-, Y1-Y2-Y3 is —C=N—O—, A2 is CH, A3 is CH, A4 is CH, R5b, n and R2 have the values listed in the Table Y.

Table 530
Table 530 provides 3507 compounds of formula (I-A) wherein R3 is difluoromethyl-, R4 is 3,4-dichlorophenyl-, Y1-Y2-Y3 is —C=N—O—, A2 is CH, A3 is CH, A4 is CH, R5b, n and R2 have the values listed in the Table Y.

Table 531
Table 531 provides 3507 compounds of formula (I-A) wherein R3 is difluoromethyl-, R4 is 3,4-dichlorophenyl-, Y1-Y2-Y3 is —C=N—O—, A2 is CH, A3 is N, A4 is CH, R5b, n and R2 have the values listed in the Table Y.

Table 532
Table 532 provides 3507 compounds of formula (I-A) wherein R3 is difluoromethyl-, R4 is 3,4-dichlorophenyl-, Y1-Y2-Y3 is —C=N—O—, A2 is CH, A3 is CH, A4 is N, R5b, n and R2 have the values listed in the Table Y.

Table 533
Table 533 provides 3507 compounds of formula (I-A) wherein R3 is difluoromethyl-, R4 is 3,4-dichlorophenyl-, Y1-Y2-Y3 is —C=N—O—, A2 is CH, A3 is CH, A4 is N, R5b, n and R2 have the values listed in the Table Y.

Table 534
Table 534 provides 3507 compounds of formula (I-A) wherein R3 is difluoromethyl-, R4 is 3,4-dichlorophenyl-, Y1-Y2-Y3 is —C=N—CH2-, A2 is N, A3 is N, A4 is CH, R5b, n and R2 have the values listed in the Table Y.

Table 535
Table 535 provides 3507 compounds of formula (I-A) wherein R3 is difluoromethyl-, R4 is 3,4-dichlorophenyl-, Y1-Y2-Y3 is —C═N—CH2-, A2 is N, A3 is N, A4 is CH, R5b, n and R2 have the values listed in the Table Y.

Table 536
Table 536 provides 3507 compounds of formula (I-A) wherein R3 is difluoromethyl-, R4 is 3,4-dichlorophenyl-, Y1-Y2-Y3 is —N—CH2-CH2-, A2 is CH, A3 is N, A4 is CH, R5b, n and R2 have the values listed in the Table Y.

Table 537
Table 537 provides 3507 compounds of formula (I-A) wherein R3 is difluoromethyl-, R4 is 3,4-dichlorophenyl-, Y1-Y2-Y3 is —N—CH2-CH2-, A2 is CH, A3 is CH, A4 is N, R5b, n and R2 have the values listed in the Table Y.

Table 538
Table 538 provides 3507 compounds of formula (I-A) wherein R3 is difluoromethyl-, R4 is 3,4-dichlorophenyl-, Y1-Y2-Y3 is —N—CH2-CH2-, A2 is N, A3 is N, A4 is CH, R5b, n and R2 have the values listed in the Table Y.

Table 539
Table 539 provides 3507 compounds of formula (I-A) wherein R3 is difluoromethyl-, R4 is 3,4-dichlorophenyl-, Y1-Y2-Y3 is —N—CH2-CH2-, A2 is N, A3 is N, A4 is CH, R5b, n and R2 have the values listed in the Table Y.

Table 540
Table 540 provides 3507 compounds of formula (I-A) wherein R3 is difluoromethyl-, R4 is 3,4-dichlorophenyl-, Y1-Y2-Y3 is —C═CH—O—, A2 is CH, A3 is CH, A4 is CH, R5b, n and R2 have the values listed in the Table Y.

Table 541
Table 541 provides 3507 compounds of formula (I-A) wherein R3 is difluoromethyl-, R4 is 3,4-dichlorophenyl-, Y1-Y2-Y3 is —C═CH—O—, A2 is CH, A3 is CH, A4 is CH, R5b, n and R2 have the values listed in the Table Y.

Table 542
Table 542 provides 3507 compounds of formula (I-A) wherein R3 is difluoromethyl-, R4 is 3,4-dichlorophenyl-, Y1-Y2-Y3 is —C═CH—O—, A2 is CH, A3 is N, A4 is CH, R5b, n and R2 have the values listed in the Table Y.

Table 543
Table 543 provides 3507 compounds of formula (I-A) wherein R3 is difluoromethyl-, R4 is 3,4-dichlorophenyl-, Y1-Y2-Y3 is —C═CH—O—, A2 is CH, A3 is CH, A4 is N, R5b, n and R2 have the values listed in the Table Y.

Table 544
Table 544 provides 3507 compounds of formula (I-A) wherein R3 is difluoromethyl-, R4 is 3,4-dichlorophenyl-, Y1-Y2-Y3 is —C═CH—O—, A2 is CH, A3 is CH, A4 is N, R5b, n and R2 have the values listed in the Table Y.

Table 545
Table 545 provides 3507 compounds of formula (I-A) wherein R3 is difluoromethyl-, R4 is 3-chloro-5-bromophenyl-, Y1-Y2-Y3 is —C═N—O—, A2 is CH, A3 is CH, A4 is CH, R5b, n and R2 have the values listed in the Table Y.

Table 546
Table 546 provides 3507 compounds of formula (I-A) wherein R3 is difluoromethyl-, R4 is 3-chloro-5-bromophenyl-, Y1-Y2-Y3 is —C═N—O—, A2 is CH, A3 is CH, A4 is CH, R5b, n and R2 have the values listed in the Table Y.

Table 547
Table 547 provides 3507 compounds of formula (I-A) wherein R3 is difluoromethyl-, R4 is 3-chloro-5-bromophenyl-, Y1-Y2-Y3 is —C═N—O—, A2 is CH, A3 is CH, A4 is N, R5b, n and R2 have the values listed in the Table Y.

Table 548
Table 548 provides 3507 compounds of formula (I-A) wherein R3 is difluoromethyl-, R4 is 3-chloro-5-bromophenyl-, Y1-Y2-Y3 is —C═N—O—, A2 is N, A3 is N, A4 is CH, R5b, n and R2 have the values listed in the Table Y.

Table 549
Table 549 provides 3507 compounds of formula (I-A) wherein R3 is difluoromethyl-, R4 is 3-chloro-5-bromophenyl-, Y1-Y2-Y3 is —C═N—O—, A2 is N, A3 is N, A4 is CH, R5b, n and R2 have the values listed in the Table Y.

Table 550
Table 550 provides 3507 compounds of formula (I-A) wherein R3 is difluoromethyl-, R4 is 3-chloro-5-bromophenyl-, Y1-Y2-Y3 is —C═N—CH2-, A2 is CH, A3 is CH, A4 is CH, R5b, n and R2 have the values listed in the Table Y.

Table 551
Table 551 provides 3507 compounds of formula (I-A) wherein R3 is difluoromethyl-, R4 is 3-chloro-5-bromophenyl-, Y1-Y2-Y3 is —C═N—CH2-, A2 is CH, A3 is CH, A4 is CH, R5b, n and R2 have the values listed in the Table Y.

Table 552
Table 552 provides 3507 compounds of formula (I-A) wherein R3 is difluoromethyl-, R4 is 3-chloro-5-bromophenyl-, Y1-Y2-Y3 is —N—CH2-CH2-, A2 is CH, A3 is N, A4 is CH, R5b, n and R2 have the values listed in the Table Y.

Table 553
Table 553 provides 3507 compounds of formula (I-A) wherein R3 is difluoromethyl-, R4 is 3-chloro-5-bromophenyl-, Y1-Y2-Y3 is —N—CH2-CH2-, A2 is CH, A3 is N, A4 is CH, R5b, n and R2 have the values listed in the Table Y.

Table 554
Table 554 provides 3507 compounds of formula (I-A) wherein R3 is difluoromethyl-, R4 is 3-chloro-5-bromophenyl-, Y1-Y2-Y3 is —N—CH2-CH2-, A2 is CH, A3 is CH, A4 is N, R5b, n and R2 have the values listed in the Table Y.

Table 555
Table 555 provides 3507 compounds of formula (I-A) wherein R3 is difluoromethyl-, R4 is 3-chloro-5-bromophenyl-, Y1-Y2-Y3 is —N—CH2-CH2-, A2 is CH, A3 is CH, A4 is N, R5b, n and R2 have the values listed in the Table Y.

Table 556
Table 556 provides 3507 compounds of formula (I-A) wherein R3 is difluoromethyl-, R4 is 3-chloro-5-bromophenyl-, Y1-Y2-Y3 is —N—CH2-CH2-, A2 is N, A3 is N, A4 is CH, R5b, n and R2 have the values listed in the Table Y.

Table 557
Table 557 provides 3507 compounds of formula (I-A) wherein R3 is difluoromethyl-, R4 is 3-chloro-5-bromophenyl-, Y1-Y2-Y3 is —N—CH2-CH2-, A2 is N, A3 is N, A4 is CH, R5b, n and R2 have the values listed in the Table Y.

Table 558
Table 558 provides 3507 compounds of formula (I-A) wherein R3 is difluoromethyl-, R4 is 3-chloro-5-bromophenyl-, Y1-Y2-Y3 is —C═CH—O—, A2 is CH, A3 is CH, A4 is CH, R5b, n and R2 have the values listed in the Table Y.

Table 559
Table 559 provides 3507 compounds of formula (I-A) wherein R3 is difluoromethyl-, R4 is 3-chloro-5-bromophenyl-, Y1-Y2-Y3 is —C═CH—O—, A2 is CH, A3 is CH, A4 is CH, R5b, n and R2 have the values listed in the Table Y.

Table 560
Table 560 provides 3507 compounds of formula (I-A) wherein R3 is difluoromethyl-, R4 is 3-chloro-5-bromophenyl-, Y1-Y2-Y3 is —C═CH—O—, A2 is N, A3 is N, A4 is CH, R5b, n and R2 have the values listed in the Table Y.

Table 561
Table 561 provides 3507 compounds of formula (I-A) wherein R3 is difluoromethyl-, R4 is 3-chloro-5-fluorophenyl-, Y1-Y2-Y3 is —C═N—O—, A2 is CH, A3 is CH, A4 is CH, R5b, n and R2 have the values listed in the Table Y.

Table 562
Table 562 provides 3507 compounds of formula (I-A) wherein R3 is difluoromethyl-, R4 is 3-chloro-5-fluorophenyl-, Y1-Y2-Y3 is —C═N—O—, A2 is CH, A3 is N, A4 is CH, R5b, n and R2 have the values listed in the Table Y.

Table 563
Table 563 provides 3507 compounds of formula (I-A) wherein R3 is difluoromethyl-, R4 is 3-chloro-5-fluorophenyl-, Y1-Y2-Y3 is —C═N—O—, A2 is CH, A3 is N, A4 is CH, R5b, n and R2 have the values listed in the Table Y.

Table 564
Table 564 provides 3507 compounds of formula (I-A) wherein R3 is difluoromethyl-, R4 is 3-chloro-5-fluorophenyl-, Y1-Y2-Y3 is —C═N—O—, A2 is N, A3 is N, A4 is CH, R5b, n and R2 have the values listed in the Table Y.

Table 565
Table 565 provides 3507 compounds of formula (I-A) wherein R3 is difluoromethyl-, R4 is 3-chloro-5-fluorophenyl-, Y1-Y2-Y3 is —C═N—CH2-, A2 is CH, A3 is N, A4 is CH, R5b, n and R2 have the values listed in the Table Y.

Table 566
Table 566 provides 3507 compounds of formula (I-A) wherein R3 is difluoromethyl-, R4 is 3-chloro-5-fluorophenyl-, Y1-Y2-Y3 is —C═N—CH2-, A2 is CH, A3 is CH, A4 is N, R5b, n and R2 have the values listed in the Table Y.

Table 567
Table 567 provides 3507 compounds of formula (I-A) wherein R3 is difluoromethyl-, R4 is 3-chloro-5-fluorophenyl-, Y1-Y2-Y3 is —N—CH2-CH2-, A2 is CH, A3 is N, A4 is CH, R5b, n and R2 have the values listed in the Table Y.

Table 568
Table 568 provides 3507 compounds of formula (I-A) wherein R3 is difluoromethyl-, R4 is 3-chloro-5-fluorophenyl-, Y1-Y2-Y3 is —N—CH2-CH2-, A2 is CH, A3 is N, A4 is CH, R5b, n and R2 have the values listed in the Table Y.

Table 569
Table 569 provides 3507 compounds of formula (I-A) wherein R3 is difluoromethyl-, R4 is 3-chloro-5-fluorophenyl-, Y1-Y2-Y3 is —N—CH2-CH2-, A2 is CH, A3 is CH, A4 is N, R5b, n and R2 have the values listed in the Table Y.

Table 570
Table 570 provides 3507 compounds of formula (I-A) wherein R3 is difluoromethyl-, R4 is 3-chloro-5-fluorophenyl-, Y1-Y2-Y3 is —N—CH2-CH2-, A2 is CH, A3 is CH, A4 is N, R5b, n and R2 have the values listed in the Table Y.

Table 571
Table 571 provides 3507 compounds of formula (I-A) wherein R3 is difluoromethyl-, R4 is 3-chloro-5-fluorophenyl-, Y1-Y2-Y3 is —N—CH2-CH2-, A2 is N, A3 is N, A4 is CH, R5b, n and R2 have the values listed in the Table Y.

Table 572
Table 572 provides 3507 compounds of formula (I-A) wherein R3 is difluoromethyl-, R4 is 3-chloro-5-fluorophenyl-, Y1-Y2-Y3 is —N—CH2-CH2-, A2 is N, A3 is N, A4 is CH, R5b, n and R2 have the values listed in the Table Y.

Table 573
Table 573 provides 3507 compounds of formula (I-A) wherein R3 is difluoromethyl-, R4 is 3-chloro-5-fluorophenyl-, Y1-Y2-Y3 is —N—CH2-CH2-, A2 is N, A3 is N, A4 is CH, R5b, n and R2 have the values listed in the Table Y.

Table 574
Table 574 provides 3507 compounds of formula (I-A) wherein R3 is difluoromethyl-, R4 is 3-chloro-5-fluorophenyl-, Y1-Y2-Y3 is —C═CH—O—, A2 is CH, A3 is N, A4 is CH, R5b, n and R2 have the values listed in the Table Y.

Table 575
Table 575 provides 3507 compounds of formula (I-A) wherein R3 is difluoromethyl-, R4 is 3-chloro-5-fluorophenyl-, Y1-Y2-Y3 is —C═CH—O—, A2 is CH, A3 is N, A4 is CH, R5b, n and R2 have the values listed in the Table Y.

Table 576
Table 576 provides 3507 compounds of formula (I-A) wherein R3 is difluoromethyl-, R4 is 3-chloro-5-fluorophenyl-, Y1-Y2-Y3 is —C═CH—O—, A2 is N, A3 is N, A4 is CH, R5b, n and R2 have the values listed in the Table Y.

Table 577
Table 577 provides 3507 compounds of formula (I-A) wherein R3 is difluoromethyl-, R4 is 3-chloro-5-(trifluoromethyl)phenyl-, Y1-Y2-Y3 is —C═N—O—, A2 is CH, A3 is N, A4 is CH, R5b, n and R2 have the values listed in the Table Y.

Table 578
Table 578 provides 3507 compounds of formula (I-A) wherein R3 is difluoromethyl-, R4 is 3-chloro-5-(trifluoromethyl)phenyl-, Y1-Y2-Y3 is —C═N—O—, A2 is N, A3 is N, A4 is CH, R5b, n and R2 have the values listed in the Table Y.

Table 579
Table 579 provides 3507 compounds of formula (I-A) wherein R3 is difluoromethyl-, R4 is 3-chloro-5-(trifluoromethyl)phenyl-, Y1-Y2-Y3 is —C═N—CH2-, A2 is CH, A3 is CH, A4 is CH, R5b, n and R2 have the values listed in the Table Y.

Table 580
Table 580 provides 3507 compounds of formula (I-A) wherein R3 is difluoromethyl-, R4 is 3-chloro-5-(trifluoromethyl)phenyl-, Y1-Y2-Y3 is —C═N—CH2-, A2 is CH, A3 is N, A4 is CH, R5b, n and R2 have the values listed in the Table Y.

Table 581
Table 581 provides 3507 compounds of formula (I-A) wherein R3 is difluoromethyl-, R4 is 3-chloro-5-(trifluoromethyl)phenyl-, Y1-Y2-Y3 is —C═N—CH2-, A2 is CH, A3 is CH, A4 is N, R5b, n and R2 have the values listed in the Table Y.

Table 582
Table 582 provides 3507 compounds of formula (I-A) wherein R3 is difluoromethyl-, R4 is 3-chloro-5-(trifluoromethyl)phenyl-, Y1-Y2-Y3 is —C═N—CH2-, A2 is N, A3 is N, A4 is CH, R5b, n and R2 have the values listed in the Table Y.

Table 583
Table 583 provides 3507 compounds of formula (I-A) wherein R3 is difluoromethyl-, R4 is 3-chloro-5-(trifluoromethyl)phenyl-, Y1-Y2-Y3 is —N—CH2-CH2-, A2 is CH, A3 is CH, A4 is CH, R5b, n and R2 have the values listed in the Table Y.

Table 584
Table 584 provides 3507 compounds of formula (I-A) wherein R3 is difluoromethyl-, R4 is 3-chloro-5-(trifluoromethyl)phenyl-, Y1-Y2-Y3 is —N—CH2-CH2-, A2 is CH, A3 is CH, A4 is CH, R5b, n and R2 have the values listed in the Table Y.

Table 585
Table 585 provides 3507 compounds of formula (I-A) wherein R3 is difluoromethyl-, R4 is 3-chloro-5-(trifluoromethyl)phenyl-, Y1-Y2-Y3 is —N—CH2-CH2-, A2 is CH, A3 is CH, A4 is CH, R5b, n and R2 have the values listed in the Table Y.

Table 586
Table 586 provides 3507 compounds of formula (I-A) wherein R3 is difluoromethyl-, R4 is 3-chloro-5-(trifluoromethyl)phenyl-, Y1-Y2-Y3 is —N—CH2-CH2-, A2 is CH, A3 is CH, A4 is N, R5b, n and R2 have the values listed in the Table Y.

Table 587
Table 587 provides 3507 compounds of formula (I-A) wherein R3 is difluoromethyl-, R4 is 3-chloro-5-(trifluoromethyl)phenyl-, Y1-Y2-Y3 is —N—CH2-CH2-, A2 is CH, A3 is CH, A4 is N, R5b, n and R2 have the values listed in the Table Y.

Table 588
Table 588 provides 3507 compounds of formula (I-A) wherein R3 is difluoromethyl-, R4 is 3-chloro-5-(trifluoromethyl)phenyl-, Y1-Y2-Y3 is —C=CH—O—, A2 is CH, A3 is CH, A4 is CH, R5b, n and R2 have the values listed in the Table Y.

Table 589
Table 589 provides 3507 compounds of formula (I-A) wherein R3 is difluoromethyl-, R4 is 3-chloro-5-(trifluoromethyl)phenyl-, Y1-Y2-Y3 is —C=CH—O—, A2 is CH, A3 is CH, A4 is CH, R5b, n and R2 have the values listed in the Table Y.

Table 590
Table 590 provides 3507 compounds of formula (I-A) wherein R3 is difluoromethyl-, R4 is 3-chloro-5-(trifluoromethyl)phenyl-, Y1-Y2-Y3 is —C=CH—O—, A2 is CH, A3 is CH, A4 is CH, R5b, n and R2 have the values listed in the Table Y.

Table 591
Table 591 provides 3507 compounds of formula (I-A) wherein R3 is difluoromethyl-, R4 is 3-chloro-5-(trifluoromethyl)phenyl-, Y1-Y2-Y3 is —C=CH—O—, A2 is CH, A3 is CH, A4 is CH, R5b, n and R2 have the values listed in the Table Y.

Table 592
Table 592 provides 3507 compounds of formula (I-A) wherein R3 is difluoromethyl-, R4 is 3-chloro-5-(trifluoromethyl)phenyl-, Y1-Y2-Y3 is —C=CH—O—, A2 is CH, A3 is CH, A4 is CH, R5b, n and R2 have the values listed in the Table Y.

Table 593
Table 593 provides 3507 compounds of formula (I-A) wherein R3 is difluoromethyl-, R4 is 3,5-dichloro-4-fluorophenyl-, Y1-Y2-Y3 is —C=N—O—, A2 is CH, A3 is N, A4 is CH, R5b, n and R2 have the values listed in the Table Y.

Table 594
Table 594 provides 3507 compounds of formula (I-A) wherein R3 is difluoromethyl-, R4 is 3,5-dichloro-4-fluorophenyl-, Y1-Y2-Y3 is —C=N—O—, A2 is CH, A3 is CH, A4 is N, R5b, n and R2 have the values listed in the Table Y.

Table 595
Table 595 provides 3507 compounds of formula (I-A) wherein R3 is difluoromethyl-, R4 is 3,5-dichloro-4-fluorophenyl-, Y1-Y2-Y3 is —C=N—O—, A2 is CH, A3 is CH, A4 is N, R5b, n and R2 have the values listed in the Table Y.

Table 596
Table 596 provides 3507 compounds of formula (I-A) wherein R3 is difluoromethyl-, R4 is 3,5-dichloro-4-fluorophenyl-, Y1-Y2-Y3 is —C=N—O—, A2 is N, A3 is N, A4 is CH, R5b, n and R2 have the values listed in the Table Y.

Table 597
Table 597 provides 3507 compounds of formula (I-A) wherein R3 is difluoromethyl-, R4 is 3,5-dichloro-4-fluorophenyl-, Y1-Y2-Y3 is —C=N—CH2-, A2 is CH, A3 is N, A4 is CH, R5b, n and R2 have the values listed in the Table Y.

Table 598
Table 598 provides 3507 compounds of formula (I-A) wherein R3 is difluoromethyl-, R4 is 3,5-dichloro-4-fluorophenyl-, Y1-Y2-Y3 is —C=N—CH2-, A2 is CH, A3 is CH, A4 is N, R5b, n and R2 have the values listed in the Table Y.

Table 599
Table 599 provides 3507 compounds of formula (I-A) wherein R3 is difluoromethyl-, R4 is 3,5-dichloro-4-fluorophenyl-, Y1-Y2-Y3 is —C=N—CH2-, A2 is N, A3 is N, A4 is CH, R5b, n and R2 have the values listed in the Table Y.

Table 600
Table 600 provides 3507 compounds of formula (I-A) wherein R3 is difluoromethyl-, R4 is 3,5-dichloro-4-fluorophenyl-, Y1-Y2-Y3 is —N—CH2-CH2-, A2 is CH, A3 is CH, A4 is CH, R5b, n and R2 have the values listed in the Table Y.

Table 601
Table 601 provides 3507 compounds of formula (I-A) wherein R3 is difluoromethyl-, R4 is 3,5-dichloro-4-fluorophenyl-, Y1-Y2-Y3 is —N—CH2-CH2-, A2 is CH, A3 is CH, A4 is CH, R5b, n and R2 have the values listed in the Table Y.

Table 602
Table 602 provides 3507 compounds of formula (I-A) wherein R3 is difluoromethyl-, R4 is 3,5-dichloro-4-fluorophenyl-, Y1-Y2-Y3 is —N—CH2-CH2-, A2 is CH, A3 is N, A4 is CH, R5b, n and R2 have the values listed in the Table Y.

Table 603
Table 603 provides 3507 compounds of formula (I-A) wherein R3 is difluoromethyl-, R4 is 3,5-dichloro-4-fluorophenyl-, Y1-Y2-Y3 is —N—CH2-CH2-, A2 is CH, A3 is CH, A4 is N, R5b, n and R2 have the values listed in the Table Y.

Table 604
Table 604 provides 3507 compounds of formula (I-A) wherein R3 is difluoromethyl-, R4 is 3,5-dichloro-4-fluorophenyl-, Y1-Y2-Y3 is —N—CH2-CH2-, A2 is N, A3 is N, A4 is CH, R5b, n and R2 have the values listed in the Table Y.

Table 605
Table 605 provides 3507 compounds of formula (I-A) wherein R3 is difluoromethyl-, R4 is 3,5-dichloro-4-fluorophenyl-, Y1-Y2-Y3 is —C=CH—O—, A2 is CH, A3 is CH, A4 is CH, R5b, n and R2 have the values listed in the Table Y.

Table 606
Table 606 provides 3507 compounds of formula (I-A) wherein R3 is difluoromethyl-, R4 is 3,5-dichloro-4-fluorophenyl-, Y1-Y2-Y3 is —C=CH—O—, A2 is CH, A3 is N, A4 is CH, R5b, n and R2 have the values listed in the Table Y.

Table 607
Table 607 provides 3507 compounds of formula (I-A) wherein R3 is difluoromethyl-, R4 is 3,5-dichloro-4-fluorophenyl-, Y1-Y2-Y3 is —C=CH—O—, A2 is CH, A3 is CH, A4 is N, R5b, n and R2 have the values listed in the Table Y.

Table 608
Table 608 provides 3507 compounds of formula (I-A) wherein R3 is difluoromethyl-, R4 is 3,5-dichloro-4-fluorophenyl-, Y1-Y2-Y3 is —C=CH—O—, A2 is N, A3 is N, A4 is CH, R5b, n and R2 have the values listed in the Table Y.

Table 609
Table 609 provides 3507 compounds of formula (I-A) wherein R3 is difluoromethyl-, R4 is 3,4,5-trichlorophenyl-, Y1-Y2-Y3 is —C=N—O—, A2 is CH, A3 is CH, A4 is CH, R5b, n and R2 have the values listed in the Table Y.

Table 610
Table 610 provides 3507 compounds of formula (I-A) wherein R3 is difluoromethyl-, R4 is 3,4,5-trichlorophenyl-, Y1-Y2-Y3 is —C=N—O—, A2 is CH, A3 is CH, A4 is CH, R5b, n and R2 have the values listed in the Table Y.

Table 611
Table 611 provides 3507 compounds of formula (I-A) wherein R3 is difluoromethyl-, R4 is 3,4,5-trichlorophenyl-, Y1-Y2-Y3 is —C=N—O—, A2 is CH, A3 is CH, A4 is CH, R5b, n and R2 have the values listed in the Table Y.

Table 612
Table 612 provides 3507 compounds of formula (I-A) wherein R3 is difluoromethyl-, R4 is 3,4,5-trichlorophenyl-, Y1-Y2-Y3 is —C=N—O—, A2 is CH, A3 is N, A4 is CH, R5b, n and R2 have the values listed in the Table Y.

Table 613
Table 613 provides 3507 compounds of formula (I-A) wherein R3 is difluoromethyl-, R4 is 3,4,5-trichlorophenyl-, Y1-Y2-Y3 is —C=N—O—, A2 is CH, A3 is N, A4 is CH, R5b, n and R2 have the values listed in the Table Y.

Table 614
Table 614 provides 3507 compounds of formula (I-A) wherein R3 is difluoromethyl-, R4 is 3,4,5-trichlorophenyl-, Y1-Y2-Y3 is —C=N—O—, A2 is N, A3 is N, A4 is CH, R5b, n and R2 have the values listed in the Table Y.

Table 615
Table 615 provides 3507 compounds of formula (I-A) wherein R3 is difluoromethyl-, R4 is 3,4,5-trichlorophenyl-, Y1-Y2-Y3 is —C=N—CH2-, A2 is CH, A3 is CH, A4 is CH, R5b, n and R2 have the values listed in the Table Y.

Table 616
Table 616 provides 3507 compounds of formula (I-A) wherein R3 is difluoromethyl-, R4 is 3,4,5-trichlorophenyl-, Y1-Y2-Y3 is —C=N—CH2-, A2 is CH, A3 is N, A4 is CH, R5b, n and R2 have the values listed in the Table Y.

Table 617
Table 617 provides 3507 compounds of formula (I-A) wherein R3 is difluoromethyl-, R4 is 3,4,5-trichlorophenyl-, Y1-Y2-Y3 is —C=N—CH2-, A2 is CH, A3 is N, A4 is CH, R5b, n and R2 have the values listed in the Table Y.

Table 618
Table 618 provides 3507 compounds of formula (I-A) wherein R3 is difluoromethyl-, R4 is 3,4,5-trichlorophenyl-, Y1-Y2-Y3 is —C=N—CH2-, A2 is CH, A3 is CH, A4 is N, R5b, n and R2 have the values listed in the Table Y.

Table 619
Table 619 provides 3507 compounds of formula (I-A) wherein R3 is difluoromethyl-, R4 is 3,4,5-trichlorophenyl-, Y1-Y2-Y3 is —C=N—CH2-, A2 is N, A3 is N, A4 is CH, R5b, n and R2 have the values listed in the Table Y.

Table 620
Table 620 provides 3507 compounds of formula (I-A) wherein R3 is difluoromethyl-, R4 is 3,4,5-trichlorophenyl-, Y1-Y2-Y3 is —N—CH2-CH2-, A2 is N, A3 is N, A4 is CH, R5b, n and R2 have the values listed in the Table Y.

Table 621
Table 621 provides 3507 compounds of formula (I-A) wherein R3 is difluoromethyl-, R4 is 3,4,5-trichlorophenyl-, Y1-Y2-Y3 is —C=CH—O—, A2 is CH, A3 is N, A4 is CH, R5b, n and R2 have the values listed in the Table Y.

Table 622
Table 622 provides 3507 compounds of formula (I-A) wherein R3 is difluoromethyl-, R4 is 3,4,5-trichlorophenyl-, Y1-Y2-Y3 is —C=CH—O—, A2 is CH, A3 is CH, A4 is N, R5b, n and R2 have the values listed in the Table Y.

Table 623
Table 623 provides 3507 compounds of formula (I-A) wherein R3 is difluoromethyl-, R4 is 3,4,5-trichlorophenyl-, Y1-Y2-Y3 is —C=CH—O—, A2 is N, A3 is N, A4 is CH, R5b, n and R2 have the values listed in the Table Y.

Table 624
Table 624 provides 3507 compounds of formula (I-A) wherein R3 is difluoromethyl-, R4 is 3,4,5-trichlorophenyl-, Y1-Y2-Y3 is —C=CH—O—, A2 is N, A3 is N, A4 is CH, R5b, n and R2 have the values listed in the Table Y.

Table 625
Table 625 provides 3507 compounds of formula (I-A) wherein R3 is difluoromethyl-, R4 is 3,5-bis(trifluoromethyl)phenyl-, Y1-Y2-Y3 is —C=N—O—, A2 is CH, A3 is CH, A4 is CH, R5b, n and R2 have the values listed in the Table Y.

Table 626
Table 626 provides 3507 compounds of formula (I-A) wherein R3 is difluoromethyl-, R4 is 3,5-bis(trifluoromethyl)phenyl-, Y1-Y2-Y3 is —C=N—O—, A2 is CH, A3 is CH, A4 is CH, R5b, n and R2 have the values listed in the Table Y.

Table 627
Table 627 provides 3507 compounds of formula (I-A) wherein R3 is difluoromethyl-, R4 is 3,5-bis(trifluoromethyl)phenyl-, Y1-Y2-Y3 is —C=N—O—, A2 is CH, A3 is N, A4 is CH, R5b, n and R2 have the values listed in the Table Y.

Table 628
Table 628 provides 3507 compounds of formula (I-A) wherein R3 is difluoromethyl-, R4 is 3,5-bis(trifluoromethyl)phenyl-, Y1-Y2-Y3 is —C=N—O—, A2 is N, A3 is N, A4 is CH, R5b, n and R2 have the values listed in the Table Y.

Table 629
Table 629 provides 3507 compounds of formula (I-A) wherein R3 is difluoromethyl-, R4 is 3,5-bis(trifluoromethyl)phenyl-, Y1-Y2-Y3 is —C=N—O—, A2 is N, A3 is N, A4 is CH, R5b, n and R2 have the values listed in the Table Y.

Table 630
Table 630 provides 3507 compounds of formula (I-A) wherein R3 is difluoromethyl-, R4 is 3,5-bis(trifluoromethyl)phenyl-, Y1-Y2-Y3 is —C=N—CH2-, A2 is CH, A3 is CH, A4 is CH, R5b, n and R2 have the values listed in the Table Y.

Table 631
Table 631 provides 3507 compounds of formula (I-A) wherein R3 is difluoromethyl-, R4 is 3,5-bis(trifluoromethyl)phenyl-, Y1-Y2-Y3 is —C=N—CH2-, A2 is CH, A3 is N, A4 is CH, R5b, n and R2 have the values listed in the Table Y.

Table 632
Table 632 provides 3507 compounds of formula (I-A) wherein R3 is difluoromethyl-, R4 is 3,5-bis(trifluoromethyl)phenyl-, Y1-Y2-Y3 is —C=N—CH2-, A2 is CH, A3 is CH, A4 is N, R5b, n and R2 have the values listed in the Table Y.

Table 633
Table 633 provides 3507 compounds of formula (I-A) wherein R3 is difluoromethyl-, R4 is 3,5-bis(trifluoromethyl)phenyl-, Y1-Y2-Y3 is —C=N—CH2-, A2 is N, A3 is N, A4 is CH, R5b, n and R2 have the values listed in the Table Y.

Table 634
Table 634 provides 3507 compounds of formula (I-A) wherein R3 is difluoromethyl-, R4 is 3,5-bis(trifluoromethyl)phenyl-, Y1-Y2-Y3 is —C=N—CH2-, A2 is N, A3 is N, A4 is CH, R5b, n and R2 have the values listed in the Table Y.

Table 635
Table 635 provides 3507 compounds of formula (I-A) wherein R3 is difluoromethyl-, R4 is 3,5-bis(trifluoromethyl)phenyl-, Y1-Y2-Y3 is —N—CH2-CH2-, A2 is CH, A3 is CH, A4 is CH, R5b, n and R2 have the values listed in the Table Y.

Table 636
Table 636 provides 3507 compounds of formula (I-A) wherein R3 is difluoromethyl-, R4 is 3,5-bis(trifluoromethyl)phenyl-, Y1-Y2-Y3 is —C=CH—O—, A2 is CH, A3 is N, A4 is CH, R5b, n and R2 have the values listed in the Table Y.

Table 637
Table 637 provides 3507 compounds of formula (I-A) wherein R3 is difluoromethyl-, R4 is 3,5-bis(trifluoromethyl)phenyl-, Y1-Y2-Y3 is —C═CH—O—, A2 is CH, A3 is N, A4 is CH, R5b, n and R2 have the values listed in the Table Y.
Table 638
Table 638 provides 3507 compounds of formula (I-A) wherein R3 is difluoromethyl-, R4 is 3,5-bis(trifluoromethyl)phenyl-, Y1-Y2-Y3 is —C═CH—O—, A2 is CH, A3 is N, A4 is CH, R5b, n and R2 have the values listed in the Table Y.
Table 639
Table 639 provides 3507 compounds of formula (I-A) wherein R3 is difluoromethyl-, R4 is 3,5-bis(trifluoromethyl)phenyl-, Y1-Y2-Y3 is —C═CH—O—, A2 is CH, A3 is CH, A4 is N, R5b, n and R2 have the values listed in the Table Y.
Table 640
Table 640 provides 3507 compounds of formula (I-A) wherein R3 is difluoromethyl-, R4 is 3,5-bis(trifluoromethyl)phenyl-, Y1-Y2-Y3 is —C═CH—O—, A2 is CH, A3 is CH, A4 is N, R5b, n and R2 have the values listed in the Table Y.
Table 641
Table 641 provides 3507 compounds of formula (I-A) wherein R3 is difluoromethyl-, R4 is 3-(trifluoromethyl)phenyl-, Y1-Y2-Y3 is —C═N—O—, A2 is CH, A3 is N, A4 is CH, R5b, n and R2 have the values listed in the Table Y.
Table 642
Table 642 provides 3507 compounds of formula (I-A) wherein R3 is difluoromethyl-, R4 is 3-(trifluoromethyl)phenyl-, Y1-Y2-Y3 is —C═N—O—, A2 is CH, A3 is N, A4 is CH, R5b, n and R2 have the values listed in the Table Y.
Table 643
Table 643 provides 3507 compounds of formula (I-A) wherein R3 is difluoromethyl-, R4 is 3-(trifluoromethyl)phenyl-, Y1-Y2-Y3 is —C═N—O—, A2 is CH, A3 is CH, A4 is N, R5b, n and R2 have the values listed in the Table Y.
Table 644
Table 644 provides 3507 compounds of formula (I-A) wherein R3 is difluoromethyl-, R4 is 3-(trifluoromethyl)phenyl-, Y1-Y2-Y3 is —C═N—O—, A2 is CH, A3 is CH, A4 is N, R5b, n and R2 have the values listed in the Table Y.
Table 645
Table 645 provides 3507 compounds of formula (I-A) wherein R3 is difluoromethyl-, R4 is 3-(trifluoromethyl)phenyl-, Y1-Y2-Y3 is —C═N—O—, A2 is CH, A3 is CH, A4 is N, R5b, n and R2 have the values listed in the Table Y.
Table 646
Table 646 provides 3507 compounds of formula (I-A) wherein R3 is difluoromethyl-, R4 is 3-(trifluoromethyl)phenyl-, Y1-Y2-Y3 is —C═N—O—, A2 is N, A3 is N, A4 is CH, R5b, n and R2 have the values listed in the Table Y.
Table 647
Table 647 provides 3507 compounds of formula (I-A) wherein R3 is difluoromethyl-, R4 is 3-(trifluoromethyl)phenyl-, Y1-Y2-Y3 is —C═N—CH2-, A2 is CH, A3 is N, A4 is CH, R5b, n and R2 have the values listed in the Table Y.
Table 648
Table 648 provides 3507 compounds of formula (I-A) wherein R3 is difluoromethyl-, R4 is 3-(trifluoromethyl)phenyl-, Y1-Y2-Y3 is —C═N—CH2-, A2 is CH, A3 is CH, A4 is N, R5b, n and R2 have the values listed in the Table Y.
Table 649
Table 649 provides 3507 compounds of formula (I-A) wherein R3 is difluoromethyl-, R4 is 3-(trifluoromethyl)phenyl-, Y1-Y2-Y3 is —C═N—CH2-, A2 is CH, A3 is CH, A4 is N, R5b, n and R2 have the values listed in the Table Y.
Table 650
Table 650 provides 3507 compounds of formula (I-A) wherein R3 is difluoromethyl-, R4 is 3-(trifluoromethyl)phenyl-, Y1-Y2-Y3 is —C═N—CH2-, A2 is CH, A3 is CH, A4 is N, R5b, n and R2 have the values listed in the Table Y.
Table 651
Table 651 provides 3507 compounds of formula (I-A) wherein R3 is difluoromethyl-, R4 is 3-(trifluoromethyl)phenyl-, Y1-Y2-Y3 is —N—CH2-CH2-, A2 is CH, A3 is N, A4 is CH, R5b, n and R2 have the values listed in the Table Y.
Table 652
Table 652 provides 3507 compounds of formula (I-A) wherein R3 is difluoromethyl-, R4 is 3-(trifluoromethyl)phenyl-, Y1-Y2-Y3 is —N—CH2-CH2-, A2 is CH, A3 is CH, A4 is N, R5b, n and R2 have the values listed in the Table Y.
Table 653
Table 653 provides 3507 compounds of formula (I-A) wherein R3 is difluoromethyl-, R4 is 3-(trifluoromethyl)phenyl-, Y1-Y2-Y3 is —N—CH2-CH2-, A2 is N, A3 is N, A4 is CH, R5b, n and R2 have the values listed in the Table Y.
Table 654
Table 654 provides 3507 compounds of formula (I-A) wherein R3 is difluoromethyl-, R4 is 3-(trifluoromethyl)phenyl-, Y1-Y2-Y3 is —C═CH—O—, A2 is CH, A3 is CH, A4 is CH, R5b, n and R2 have the values listed in the Table Y.
Table 655
Table 655 provides 3507 compounds of formula (I-A) wherein R3 is difluoromethyl-, R4 is 3-(trifluoromethyl)phenyl-, Y1-Y2-Y3 is —C═CH—O—, A2 is CH, A3 is CH, A4 is N, R5b, n and R2 have the values listed in the Table Y.
Table 656
Table 656 provides 3507 compounds of formula (I-A) wherein R3 is difluoromethyl-, R4 is 3-(trifluoromethyl)phenyl-, Y1-Y2-Y3 is —C═CH—O—, A2 is N, A3 is N, A4 is CH, R5b, n and R2 have the values listed in the Table Y.
Table 657
Table 657 provides 3507 compounds of formula (I-A) wherein R3 is difluoromethyl-, R4 is 2,6-dichloro-4-pyridyl-, Y1-Y2-Y3 is —C═N—O—, A2 is CH, A3 is CH, A4 is CH, R5b, n and R2 have the values listed in the Table Y.
Table 658
Table 658 provides 3507 compounds of formula (I-A) wherein R3 is difluoromethyl-, R4 is 2,6-dichloro-4-pyridyl-, Y1-Y2-Y3 is —C═N—O—, A2 is CH, A3 is CH, A4 is N, R5b, n and R2 have the values listed in the Table Y.
Table 659
Table 659 provides 3507 compounds of formula (I-A) wherein R3 is difluoromethyl-, R4 is 2,6-dichloro-4-pyridyl-, Y1-Y2-Y3 is —C═N—O—, A2 is N, A3 is N, A4 is CH, R5b, n and R2 have the values listed in the Table Y.
Table 660
Table 660 provides 3507 compounds of formula (I-A) wherein R3 is difluoromethyl-, R4 is 2,6-dichloro-4-pyridyl-, Y1-Y2-Y3 is —C═N—O—, A2 is N, A3 is N, A4 is CH, R5b, n and R2 have the values listed in the Table Y.
Table 661
Table 661 provides 3507 compounds of formula (I-A) wherein R3 is difluoromethyl-, R4 is 2,6-dichloro-4-pyridyl-, Y1-Y2-Y3 is —C═N—CH2-, A2 is CH, A3 is CH, A4 is CH, R5b, n and R2 have the values listed in the Table Y.
Table 662
Table 662 provides 3507 compounds of formula (I-A) wherein R3 is difluoromethyl-, R4 is 2,6-dichloro-4-pyridyl-, Y1-Y2-Y3 is —C═N—CH2-, A2 is CH, A3 is N, A4 is CH, R5b, n and R2 have the values listed in the Table Y.
Table 663
Table 663 provides 3507 compounds of formula (I-A) wherein R3 is difluoromethyl-, R4 is 2,6-dichloro-4-pyridyl-, Y1-Y2-Y3 is —C═N—CH2-, A2 is CH, A3 is CH, A4 is N, R5b, n and R2 have the values listed in the Table Y.

Table 664

Table 664 provides 3507 compounds of formula (I-A) wherein R3 is difluoromethyl-, R4 is 2,6-dichloro-4-pyridyl-, Y1-Y2-Y3 is —C═N—CH2-, A2 is N, A3 is N, A4 is CH, R5b, n and R2 have the values listed in the Table Y.

Table 665

Table 665 provides 3507 compounds of formula (I-A) wherein R3 is difluoromethyl-, R4 is 2,6-dichloro-4-pyridyl-, Y1-Y2-Y3 is —C═N—CH2-, A2 is N, A3 is N, A4 is CH, R5b, n and R2 have the values listed in the Table Y.

Table 666

Table 666 provides 3507 compounds of formula (I-A) wherein R3 is difluoromethyl-, R4 is 2,6-dichloro-4-pyridyl-, Y1-Y2-Y3 is —N—CH2-CH2-, A2 is CH, A3 is CH, A4 is CH, R5b, n and R2 have the values listed in the Table Y.

Table 667

Table 667 provides 3507 compounds of formula (I-A) wherein R3 is difluoromethyl-, R4 is 2,6-dichloro-4-pyridyl-, Y1-Y2-Y3 is —N—CH2-CH2-, A2 is CH, A3 is N, A4 is CH, R5b, n and R2 have the values listed in the Table Y.

Table 668

Table 668 provides 3507 compounds of formula (I-A) wherein R3 is difluoromethyl-, R4 is 2,6-dichloro-4-pyridyl-, Y1-Y2-Y3 is —N—CH2-CH2-, A2 is CH, A3 is CH, A4 is N, R5b, n and R2 have the values listed in the Table Y.

Table 669

Table 669 provides 3507 compounds of formula (I-A) wherein R3 is difluoromethyl-, R4 is 2,6-dichloro-4-pyridyl-, Y1-Y2-Y3 is —N—CH2-CH2-, A2 is CH, A3 is CH, A4 is N, R5b, n and R2 have the values listed in the Table Y.

Table 670

Table 670 provides 3507 compounds of formula (I-A) wherein R3 is difluoromethyl-, R4 is 2,6-dichloro-4-pyridyl-, Y1-Y2-Y3 is —N—CH2-CH2-, A2 is N, A3 is N, A4 is CH, R5b, n and R2 have the values listed in the Table Y.

Table 671

Table 671 provides 3507 compounds of formula (I-A) wherein R3 is difluoromethyl-, R4 is 2,6-dichloro-4-pyridyl-, Y1-Y2-Y3 is —C═CH—O—, A2 is CH, A3 is CH, A4 is CH, R5b, n and R2 have the values listed in the Table Y.

Table 672

Table 672 provides 3507 compounds of formula (I-A) wherein R3 is difluoromethyl-, R4 is 2,6-dichloro-4-pyridyl-, Y1-Y2-Y3 is —C═CH—O—, A2 is CH, A3 is CH, A4 is CH, R5b, n and $R^2$ have the values listed in the Table Y.

Tables 1A to 12A disclose compounds of particular interest.

Table 1A

Table 1A provides 116 compounds of formula Ia, wherein $R^2$ and $R^{5b}$ are as defined in Table X.

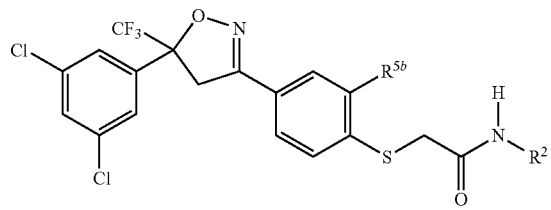

(Ia)

Table 2A

Table 2A provides 116 compounds of formula Ib, wherein $R^2$ and $R^{5b}$ are as defined in Table X.

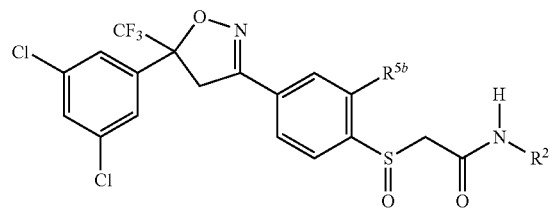

(Ib)

Table 3A

Table 3 provides 116 compounds of formula Ic, wherein $R^2$ and $R^{5b}$ are as defined in Table X.

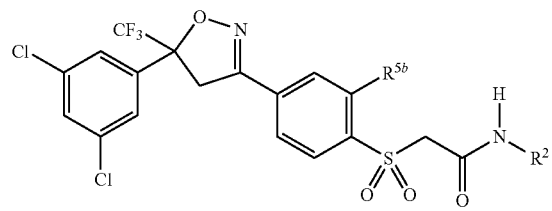

(Ic)

Table 4A

Table 4A provides 116 compounds of formula Id, wherein $R^2$ and $R^{5b}$ are as defined in Table X.

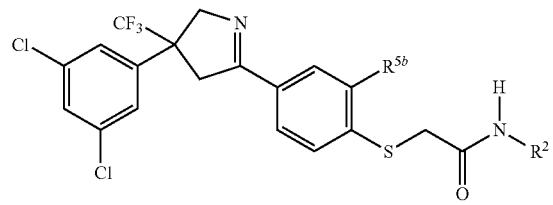

(Id)

Table 5A

Table 5A provides 116 compounds of formula Ie, wherein $R^2$ and $R^{5b}$ are as defined in Table X.

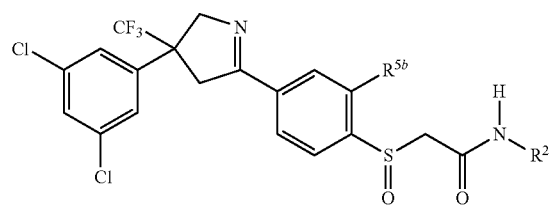

(Ie)

Table 6A

Table 6A provides 116 compounds of formula If, wherein $R^2$ and $R^{5b}$ are as defined in Table X.

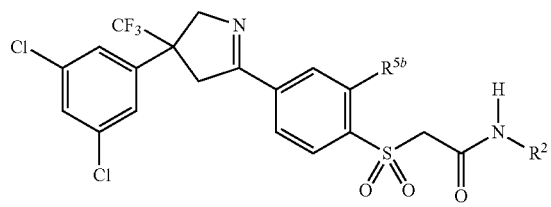
(If)

Table 7A

Table 7A provides 116 compounds of formula Ig, wherein $R^2$ and $R^{5b}$ are as defined in Table X.

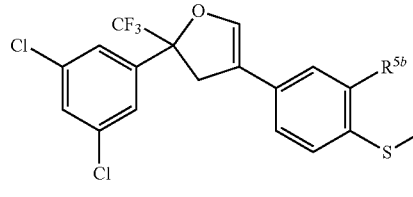
(Ig)

Table 8A

Table 8A provides 116 compounds of formula Ih, wherein $R^2$ and $R^{5b}$ are as defined in Table X.

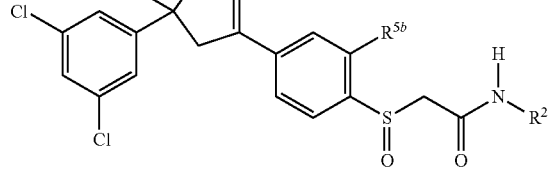
(Ih)

Table 9A

Table 9A provides 116 compounds of formula Ii, wherein $R^2$ and $R^{5b}$ are as defined in Table X.

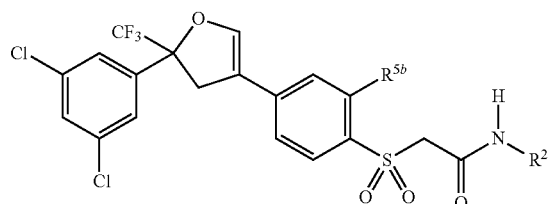
(Ii)

Table 10A

Table 10A provides 116 compounds of formula Ij, wherein $R^2$ and $R^{5b}$ are as defined in Table X.

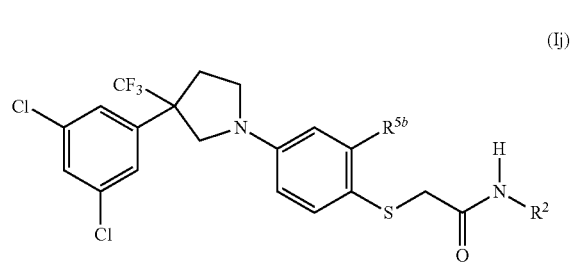
(Ij)

Table 11A

Table 11A provides 116 compounds of formula Ik, wherein $R^2$ and $R^{5b}$ are as defined in Table X.

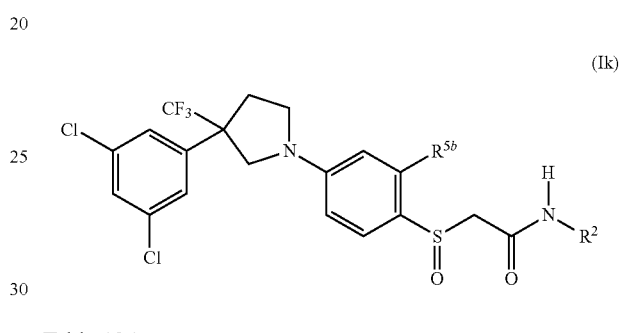
(Ik)

Table 12A

Table 12A provides 116 compounds of formula Il, wherein $R^2$ and $R^{5b}$ are as defined in Table X.

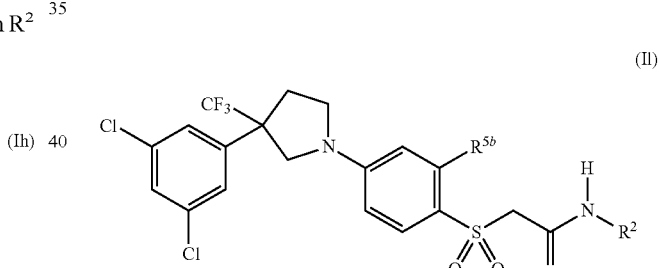
(Il)

TABLE X

|  | $R^{5b}$ | $R^2$ |
|---|---|---|
| X.1 | F | ethyl- |
| X.2 | F | n-butyl- |
| X.3 | F | methyl- |
| X.4 | F | cyclopropyl- |
| X.5 | F | n-propyl |
| X.6 | F | 2,2-difluoroethyl |
| X.7 | F | 1-methoxy-prop-2-yl- |
| X.8 | F | N-(2,2,2-trifluoro-ethyl)-acetamide-2-yl |
| X.9 | F | 2,2,2-trifluoro-ethyl- |
| X.10 | F | 3,3,3-trifluoro-propyl- |
| X.11 | F | but-2-yl- |
| X.12 | F | (tetrahydrofuran-2-yl)-methyl- |
| X.13 | F | phenyl-methyl- |
| X.14 | F | (2-fluoro-phenyl)-methyl- |
| X.15 | F | 1-phenyl-eth-1-yl- |
| X.16 | F | (4-methoxy-phenyl)-methyl- |
| X.17 | F | 1,1-dioxo-thietan-3-yl- |
| X.18 | F | (2-chloro-pyrid-5-yl)-methyl- |
| X.19 | F | 3-fluoro-phenyl- |

TABLE X-continued

| | $R^{5b}$ | $R^2$ |
|---|---|---|
| X.20 | F | (pyrid-2-yl)-methyl- |
| X.21 | F | 1,3-dimethyl-1H-pyrazol-5-yl- |
| X.22 | F | 4-methyl-thiazol-2-yl- |
| X.23 | F | 3-methyl-thietan-3-yl- |
| X.24 | F | 1,1-dimethyl-2-methylsulfanyl-ethyl |
| X.25 | F | 1-oxo-thietan-3-yl- |
| X.26 | F | thietan-3-yl- |
| X.27 | F | bicyclo[2.2.1]hept-2-yl- |
| X.28 | F | cyclobutyl- |
| X.29 | F | 2,2,2-trifluoro-ethyl- |
| X.30 | Cl | ethyl- |
| X.31 | Cl | butyl- |
| X32 | Cl | methyl- |
| X.33 | Cl | cyclopropyl- |
| X.34 | Cl | n-propyl |
| X.35 | Cl | 2,2-difluoroethyl |
| X.36 | Cl | 1-methoxy-prop-2-yl- |
| X.37 | Cl | N-(2,2,2-trifluoro-ethyl)-acetamide-2-yl |
| X.38 | Cl | 2,2,2-trifluoro-ethyl- |
| X.39 | Cl | 3,3,3-trifluoro-propyl- |
| X.40 | Cl | but-2-yl- |
| X.41 | Cl | (tetrahydrofuran-2-yl)-methyl- |
| X.42 | Cl | phenyl-methyl- |
| X.43 | Cl | (2-fluoro-phenyl)-methyl- |
| X.44 | Cl | 1-phenyl-eth-1-yl- |
| X.45 | Cl | (4-methoxy-phenyl)-methyl- |
| X.46 | Cl | 1,1-dioxo-thietan-3-yl- |
| X.47 | Cl | (2-chloro-pyrid-5-yl)-methyl- |
| X.48 | Cl | 3-fluoro-phenyl- |
| X.49 | Cl | (pyrid-2-yl)-methyl- |
| X.50 | Cl | 1,3-dimethyl-1H-pyrazol-5-yl- |
| X.51 | Cl | 4-methyl-thiazol-2-yl- |
| X.52 | Cl | 3-methyl-thietan-3-yl- |
| X.53 | Cl | 1,1-dimethyl-2-methylsulfanyl-ethyl |
| X.54 | Cl | 1-oxo-thietan-3-yl- |
| X.55 | Cl | thietan-3-yl- |
| X.56 | Cl | bicyclo[2.2.1]hept-2-yl- |
| X.57 | Cl | cyclobutyl- |
| X.58 | Cl | 2,2,2-trifluoro-ethyl- |
| X.59 | Br | ethyl- |
| X.60 | Br | butyl- |
| X.61 | Br | methyl- |
| X.62 | Br | cyclopropyl- |
| X.63 | Br | n-propyl |
| X.64 | Br | 2,2-difluoroethyl |
| X.65 | Br | 1-methoxy-prop-2-yl- |
| X.66 | Br | N-(2,2,2-trifluoro-ethyl)-acetamide-2-yl |
| X.67 | Br | 2,2,2-trifluoro-ethyl- |
| X.68 | Br | 3,3,3-trifluoro-propyl- |
| X.69 | Br | but-2-yl |
| X.70 | Br | (tetrahydrofuran-2-yl)-methyl- |
| X.71 | Br | phenyl-methyl- |
| X.72 | Br | (2-fluoro-phenyl)-methyl |
| X.73 | Br | 1-phenyl-eth-1-yl- |
| X.74 | Br | (4-methoxy-phenyl)-methyl- |
| X.75 | Br | 1,1-dioxo-thietan-3-yl- |
| X.76 | Br | (2-chloro-pyrid-5-yl)-methyl- |
| X.77 | Br | 3-fluoro-phenyl- |
| X.78 | Br | (pyrid-2-yl)-methyl- |
| X.79 | Br | 1,3-dimethyl-1H-pyrazol-5-yl- |
| X.80 | Br | 4-methyl-thiazol-2-yl- |
| X.81 | Br | 3-methyl-thietan-3-yl- |
| X.82 | Br | 1,1-dimethyl-2-methylsulfany-ethyl |
| X.83 | Br | 1-oxo-thietan-3-yl- |
| X.84 | Br | thietan-3-yl- |
| X.85 | Br | bicyclo[2.2.1]hept-2-yl- |
| X.86 | Br | cyclobutyl- |
| X.87 | Br | 2,2,2-trifluoro-ethyl- |
| X.88 | $CH_3$ | ehtyl- |
| X.89 | $CH_3$ | butyl- |
| X.90 | $CH_3$ | methyl- |
| X.91 | $CH_3$ | cyclopropyl- |
| X.92 | $CH_3$ | n-propyl |
| X.93 | $CH_3$ | 2,2-difluoroethyl |
| X.94 | $CH_3$ | 1-methoxy-prop-2-yl- |
| X.95 | $CH_3$ | N-(2,2,2-trifluoro-ethyl)-acetamide-2-yl |
| X.96 | $CH_3$ | 2,2,2-trifluoro-ethyl- |
| X.97 | $CH_3$ | 3,3,3-trifluoro-propyl- |
| X.98 | $CH_3$ | but-2-yl- |
| X.99 | $CH_3$ | (tetrahydrofuran-2-yl)-methyl- |
| X.100 | $CH_3$ | phenyl-methyl- |
| X.101 | $CH_3$ | (2-fluoro-phenyl)-methyl- |
| X.102 | $CH_3$ | 1-phenyl-eth-1-yl- |
| X.103 | $CH_3$ | (4-methoxy-phenyl)-methyl- |
| X.104 | $CH_3$ | 1,1-dioxo-thietan-3-yl- |
| X.105 | $CH_3$ | (2-chloro-pyrid-5-yl)-methyl- |
| X.106 | $CH_3$ | 3-fluoro-phenyl- |
| X.107 | $CH_3$ | (pyrid-2-yl)-methyl- |
| X.108 | $CH_3$ | 1,3-dimethyl-1H-pyrazol-5-yl- |
| X.109 | $CH_3$ | 4-methyl-thiazol-2-yl- |
| X.110 | $CH_3$ | 3-methyl-thietan-3-yl- |
| X.111 | $CH_3$ | 1,1-dimethyl-2-methylsulfanyl-ethyl |
| X.112 | $CH_3$ | 1-oxo-thietan-3-yl- |
| X.113 | $CH_3$ | thietan-3-yl- |
| X.114 | $CH_3$ | bicyclo[2.2.1]hept-2-yl- |
| X.115 | $CH_3$ | cyclobutyl- |
| X.116 | $CH_3$ | 2,2,2-trifluoro-ethyl- |

Compounds of formula I include at least one chiral centre and may exist as compounds of formula I* or compounds of formula I**.

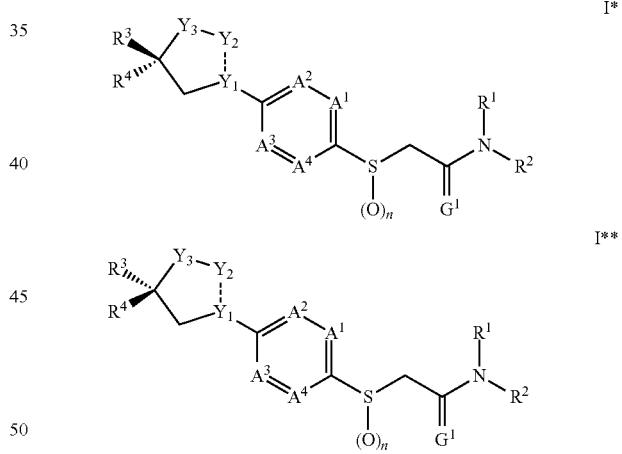

Each compound listed in Tables 1 to 692 and Table 1A to Table 12A represents a specific disclosure corresponding to the compound of formula I* and a specific disclosure corresponding to the compound of formula II. Compounds of formula I are more biologically active than compounds of formula I*. The invention includes mixtures of compounds I* and I in any ratio e.g. in a molar ratio of 1:99 to 99:1, e.g. 10:1 to 1:10, e.g. a substantially 50:50 molar ratio. In an enantiomerically (or epimerically) enriched mixture of formula I, the molar proportion of compound I compared to the total amount of both enantiomers (or epimers) is for example greater than 50%, e.g. at least 55, 60, 65, 70, 75, 80, 85, 90, 95, 96, 97, 98 or at least 99%. Enantiomerically (or epimerically) enriched mixtures of formula I are preferred.

Likewise, the compound of formula Int-I may exist as a compound of formula Int-I* and Int-I**

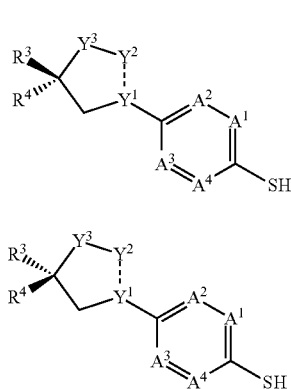

The invention includes mixtures of compounds Int-I* and Int-I in any ratio e.g. in a molar ratio of 1:99 to 99:1, e.g. 10:1 to 1:10, e.g. a substantially 50:50 molar ratio. In an enantiomerically (or epimerically) enriched mixture of formula Int-I, the molar proportion of compound Int-I compared to the total amount of both enantiomers (or epimers) is for example greater than 50%, e.g. at least 55, 60, 65, 70, 75, 80, 85, 90, 95, 96, 97, 98 or at least 99%. Enantiomerically (or epimerically) enriched mixtures of formula Int-I are preferred.

Likewise, the compound of formula Int-II may exist as a compound of formula Int-II* and Int-II**

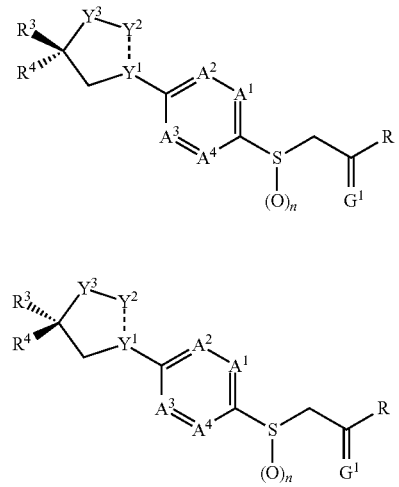

The invention includes mixtures of compounds Int-II* and Int-II in any ratio e.g. in a molar ratio of 1:99 to 99:1, e.g. 10:1 to 1:10, e.g. a substantially 50:50 molar ratio. In an enantiomerically (or epimerically) enriched mixture of formula Int-II, the molar proportion of compound Int-II compared to the total amount of both enantiomers (or epimers) is for example greater than 50%, e.g. at least 55, 60, 65, 70, 75, 80, 85, 90, 95, 96, 97, 98 or at least 99%. Enantiomerically (or epimerically) enriched mixtures of formula Int-II are preferred.

Likewise, the compound of formula Int-IX may exist as a compound of formula Int-IX* and Int-IX**

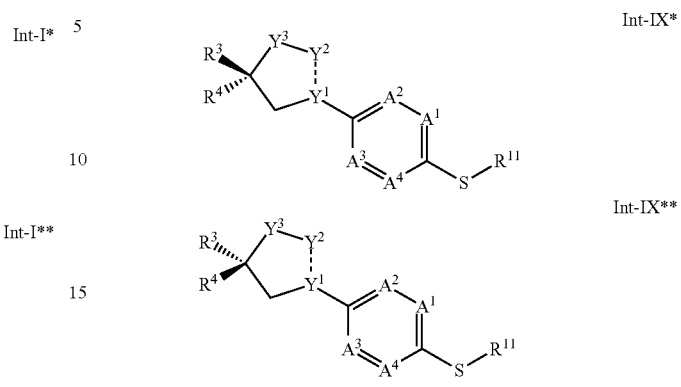

The invention includes mixtures of compounds Int-IX* and Int-IX in any ratio e.g. in a molar ratio of 1:99 to 99:1, e.g. 10:1 to 1:10, e.g. a substantially 50:50 molar ratio. In an enantiomerically (or epimerically) enriched mixture of formula Int-IX, the molar proportion of compound Int-IX compared to the total amount of both enantiomers (or epimers) is for example greater than 50%, e.g. at least 55, 60, 65, 70, 75, 80, 85, 90, 95, 96, 97, 98 or at least 99%. Enantiomerically (or epimerically) enriched mixtures of formula Int-IX are preferred.

The compounds of the invention may be made by a variety of methods as shown in the following Schemes.

Scheme 1

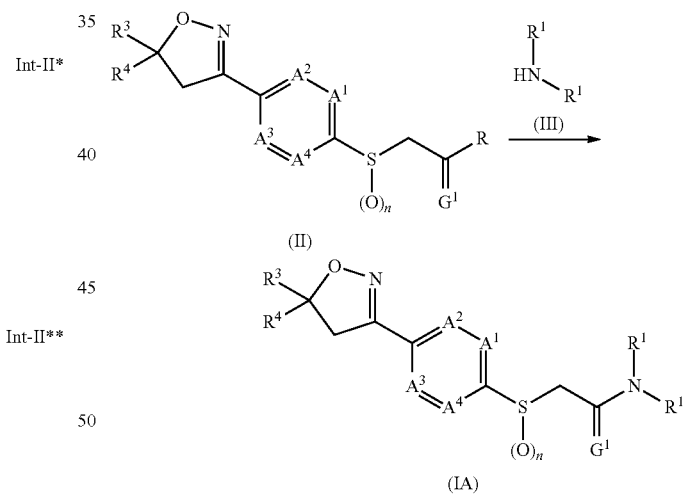

1) Compounds of formula (IA) wherein $G^1$ is oxygen, can be prepared by reacting a compound of formula (II) wherein $G^1$ is oxygen and R is OH, $C_1$-$C_6$alkoxy or Cl, F or Br, with an amine of formula (III) as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)-carbodiimide hydrochloride ("EDC") or bis(2-oxo-3-oxazolidinyl)phosphonic chloride ("BOP—Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature Amines of formula (III) are either known in the literature or can be prepared using methods known to a person skilled in the art. Some of these methods are described in the preparation Examples.

2) Acid halides of formula (II), wherein $G^1$ is oxygen and R is Cl, F or Br, may be made from carboxylic acids of formula (II), wherein $G^1$ is oxygen and R is OH, under standard conditions, as described for example in WO2009/080250.

3) Carboxylic acids of formula (II), wherein $G^1$ is oxygen and R is OH, may be formed from esters of formula (II), wherein $G^1$ is oxygen and R is $C_1$-$C_6$alkoxy as described for example in WO2009/080250.

4) Compounds of formula (IA), wherein $G^1$ is sulfur, may be made by treatment of a compound of formula (II), wherein $G^1$ is oxygen and R is OH, $C_1$-$C_6$alkoxy or Cl, F or Br, with a thio-transfer reagent such as Lawesson's reagent or phosphorus pentasulfide prior to elaborating to compounds of formula (I), as described under 1).

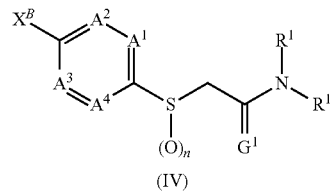

(IV)

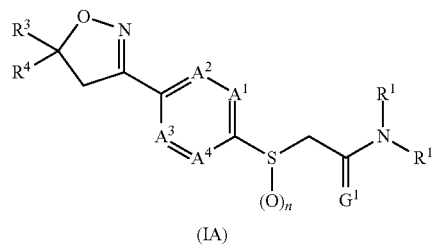

(IA)

5) Alternatively, compounds of formula (IA) wherein $G^1$ is oxygen, can be prepared by various methods from an intermediate of formula (IV) as shown in Scheme 2 wherein $G^1$ is oxygen and $X^B$ is a leaving group, for example a halogen, such as bromo or $X^B$ is cyano, formyl or acetyl according to similar methods to those described in WO2009/080250. An intermediate of formula (IV) can be prepared for example from an intermediate of formula (V) as described in Scheme 1.

Scheme 2

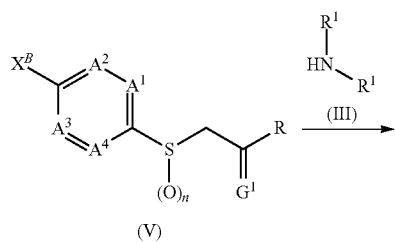

(V)

Scheme 3

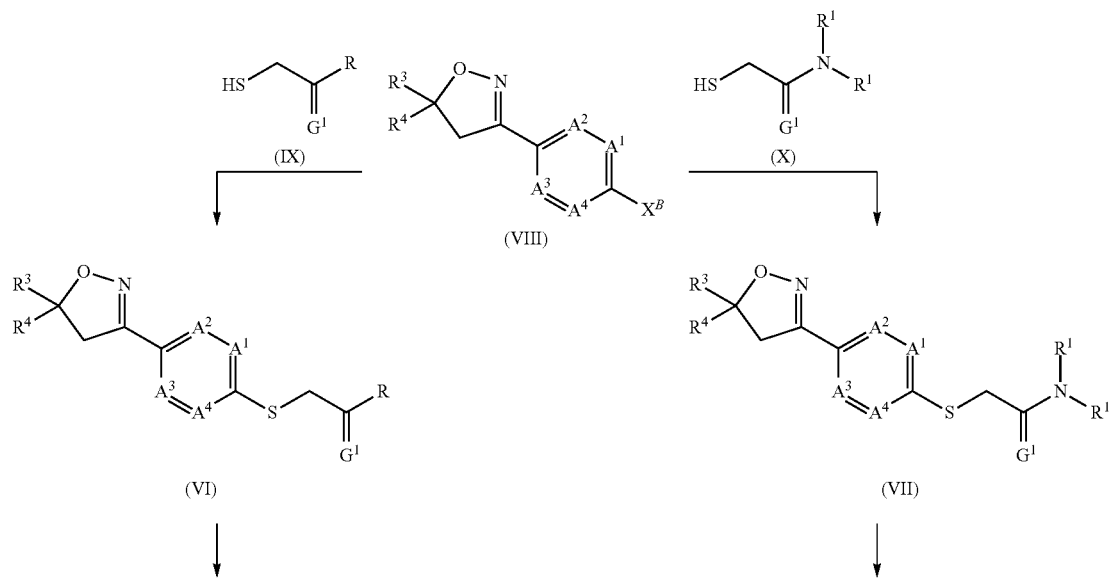

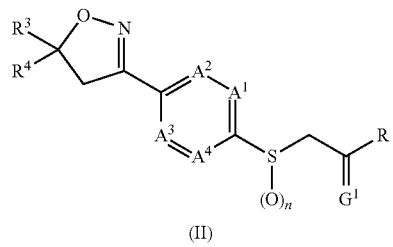
(II)

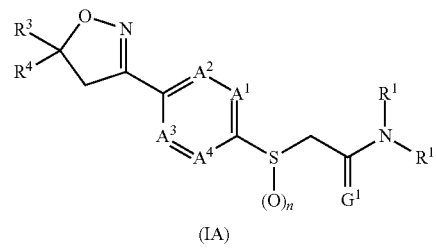
(IA)

6) Compounds of formula (IA) and (II) wherein $G^1$ is oxygen, R is OH or $C_1$-$C_6$alkoxy, and n is 1 or 2, can be prepared respectively by oxidation of compound of formula (VI) and (VII) wherein $G^1$ is oxygen. Such reactions can be carried out by treatment with an oxidising reagent, such as potassium permanganate, 3-chloroperoxybenzoic acid ("MCPBA"), sodium periodate/ruthenium(II) oxide, hydrogen peroxide, oxone and sodium hypochlorite. One equivalent of oxidising reagent is required to convent a sulfide to a sulfoxide, or a sulfoxide to a sulfone. Two equivalents of oxidising reagent are required to convent a sulfide to a sulfone. Preferred solvents are ethanol, methanol, tetrahydrofuran, dioxane, 1,2-dimethoxyethane, ethyl acetate, toluene, dichloromethane and water, or mixtures thereof. The reaction is optionally carried out in the presence of a base, for example a carbonate, such as sodium hydrogen carbonate. The reaction is carried out at a temperature of from 0° C. to 100° C., preferably from 15° C. to 30° C., in particular at ambient temperature.

7) Compounds of formula (VI) wherein $G^1$ is oxygen, R is OH or $C_1$-$C_6$alkoxy, and n is 1 or 2 can be prepared by reacting an intermediate of formula (VIII) wherein $X^B$ is a leaving group, for example a halogen, such as fluoro, chloro or bromo, with a mercaptan of formula (IX) wherein R is OH or $C_1$-$C_6$alkoxy, for example methoxy or tert-butyloxy. Such reactions can be carried out in the presence of a base such as an amine or a carbonate, for example potassium or cesium carbonate in solvents such as acetonitrile, dimethylformamide, dimethylsulfoxide, dimethylacetamide at a temperature of from 0° C. to 150° C., preferably from 25° C. to 100° C. Examples of such reactions can be found in Synlett 2006, 8, 1255-1259, and specific examples are described in the experimental section. Alternatively, the reaction can be carried out in the presence of a catalyst, for a example a palladium catalyst, and a ligand, for example a phosphine ligand in a solvent such as tetrahydrofuran, dioxane, 1,2-dimethoxyethane, ethyl acetate, or toluene at a temperature of from 0° C. to 150° C., preferably from 80° C. to 130° C. This reaction can be carried out under microwave irradiation, as described for example in WO 2007102059, and specific examples are described in the experimental section.

8) Similarly, compounds of formula (VII) wherein $G^1$ is oxygen and n is 1 or 2 can be prepared by reacting an intermediate of formula (VIII) wherein $X^B$ is a leaving group, for example a halogen, such as fluoro, chloro or bromo, with a mercaptan of formula (X).

9) Compounds of formula (IX) and (X) are either known compounds, such a methyl thioglycolate or can be prepared by known methods to a person skilled in the art.

Scheme 4

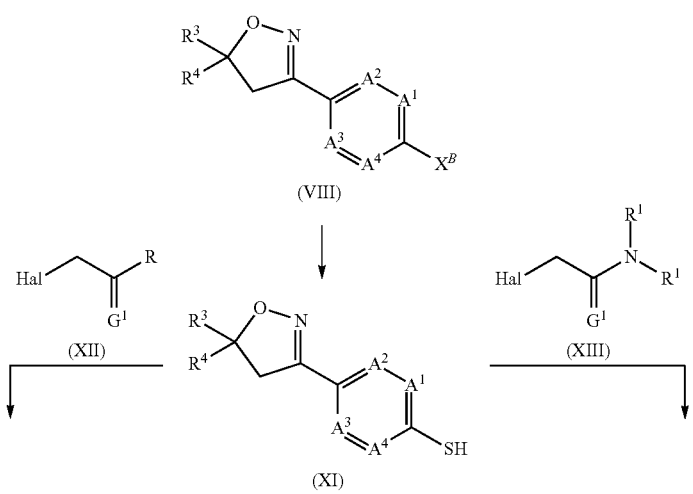

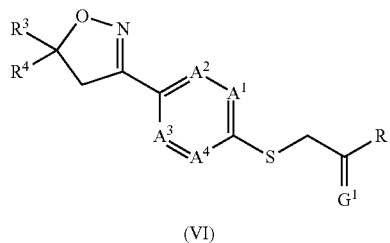

(VI)

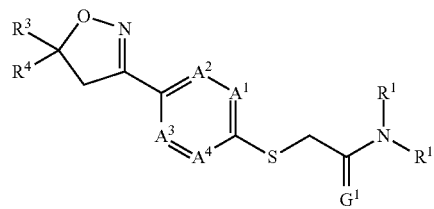

(VII)

10) Alternatively, compounds of formula (VI) wherein $G^1$ is oxygen, R is OH or $C_1$-$C_6$alkoxy can be prepared by alkylation of an intermediate of formula (XI) with a reagent of formula (XII) wherein Hal is chloro or bromo. Such reactions can be carried out under well established methods, described for example in Journal of Organic Chemistry, 45(24), 4961-5; 1980.

11) Similarly, compounds of formula (VII) wherein $G^1$ is oxygen, can be prepared by alkylation of an intermediate of formula (XI) with a reagent of formula (XIII) wherein Hal is chloro or bromo.

12) Compounds of formula (XI) can be prepared by reaction of an intermediate of formula (VIII) wherein $X^B$ is a halogen, such as chloro, bromo, iodo and a transition metal catalyst, such as copper, nickel and palladaium, a sulfur source such as sulfur, thiourea, and alkali thiosulfate. Such reactions can be carried out under well established methods, described for example in U.S. Pat. No. 5,338,886 (Ni and thiourea), Tetrahedron Letters (2011), 52, 205-208 (palladium and thiourea) and Chinese Journal of Chemistry (2010), 28, 1441-1443 (copper and thiorurea). Alternatively compounds of formula (XI) can be prepared by reaction of an intermediate of formula (VIII) wherein $X^B$ is a halogen, such as fluoro and chloro and an excess of alkali alkyl thiolate, such as sodium thiolate at a temperature between 50° C. and a 180° C. This reaction can be carried out, as described for example in Synthesis (1983), (9), 751-5.

Scheme 5

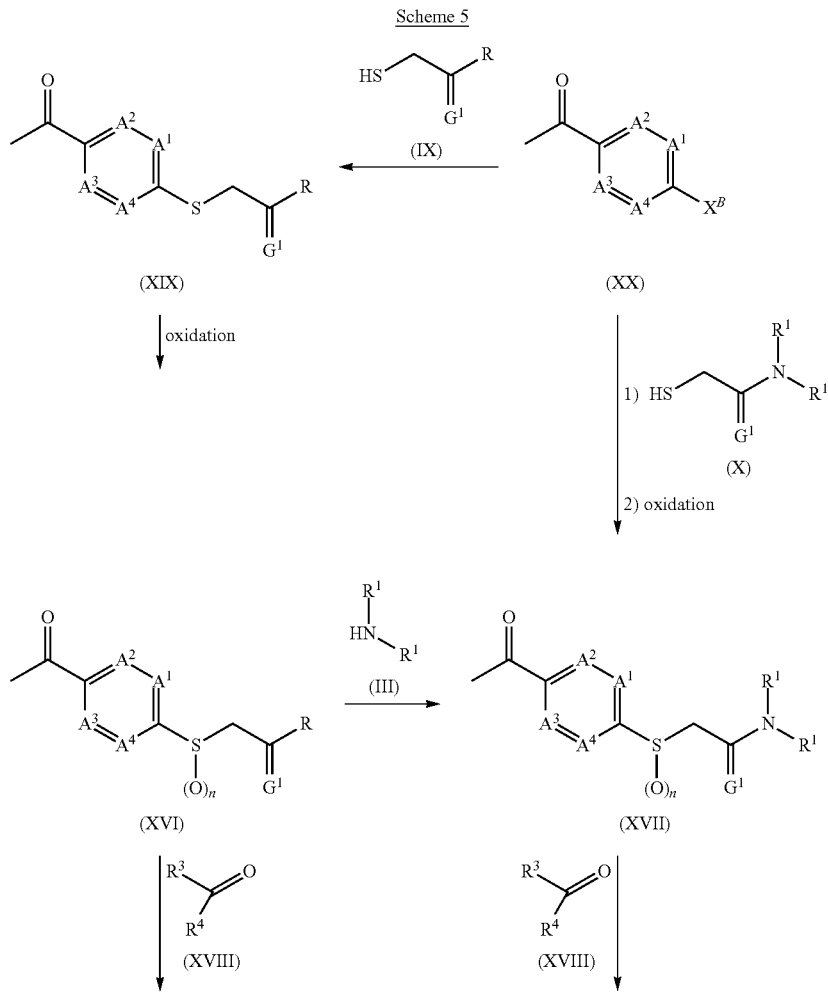

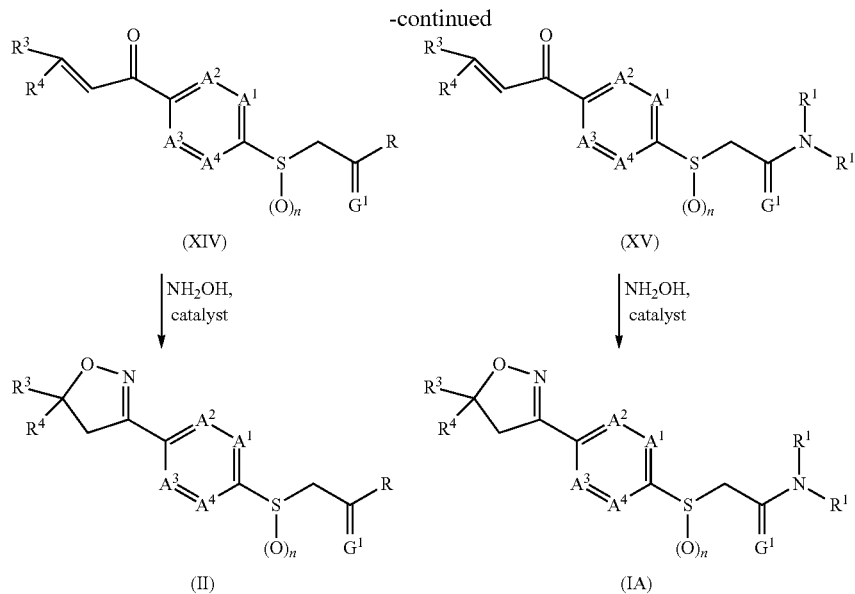

13) Compounds of formula (XVI) wherein $G^1$ is oxygen, R is OH or $C_1$-$C_6$alkoxy, which can be prepared according to the methods described in Schemes 1-4, may be converted to compounds of formula (XIV) wherein $G^1$ is oxygen, R is OH or $C_1$-$C_6$alkoxy by reaction with a ketone of formula (XVIII) according to methods described for example in WO2009/080250.

14) Similarly, Compounds of formula (XV) wherein $G^1$ is oxygen can be obtained from compounds of formula (XVII) wherein $G^1$ is oxygen, which can be obtained according to methods described in Schemes 1-4.

15) Subsequently, compounds of formula (XIV) wherein $G^1$ is oxygen, R is OH or $C_1$-$C_6$alkoxy can be converted into compounds of formula (II) wherein $G^1$ is oxygen, R is OH or $C_1$-$C_6$alkoxy by treatment with hydroxylamine, a base and a phase transfer catalyst, as described for example in WO09080250.

16) Similarly, compounds of formula (XV) wherein $G^1$ is oxygen can be converted into compounds of formula (IA) wherein $G^1$ is oxygen.

Scheme 6

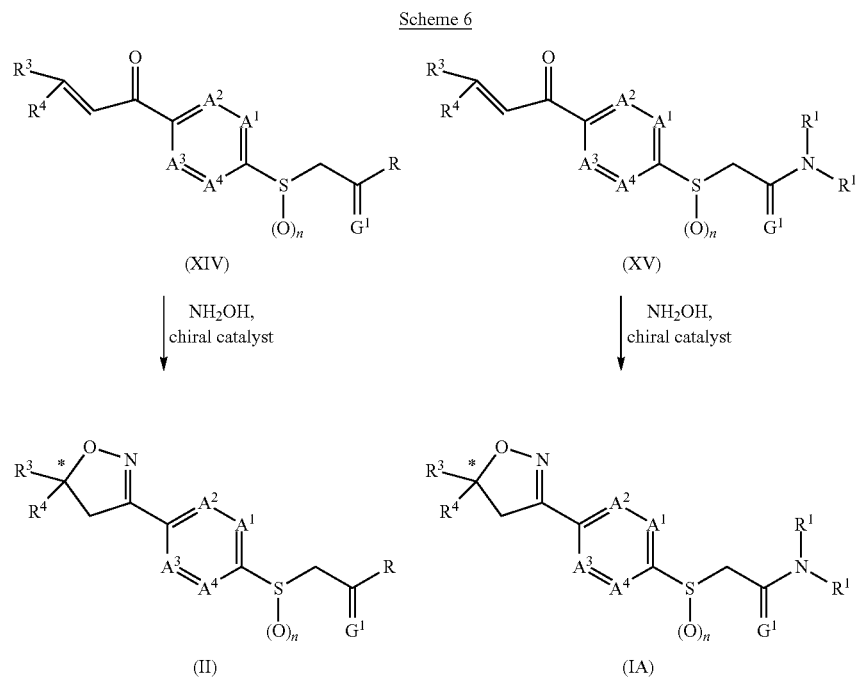

17) Compounds of formula (IA) and (II) can be obtained as an enantiomerically enriched mixture, either by chiral separation of the racemic compound or by use of a chiral catalyst in the as shown on Scheme 6. Such catalysts can for example be a chiral phase transfer catalyst, preferably a quinine derivative, for example a compound of formula XXI

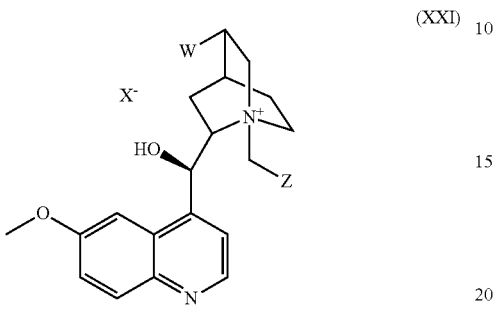

(XXI)

wherein Z is optionally substituted aryl or optionally substituted heteroaryl, W is ethyl or vinyl, and X is an anion, preferably a halogen anion, more preferably chloride or bromide. See for example WO2011/104089.

Scheme 7

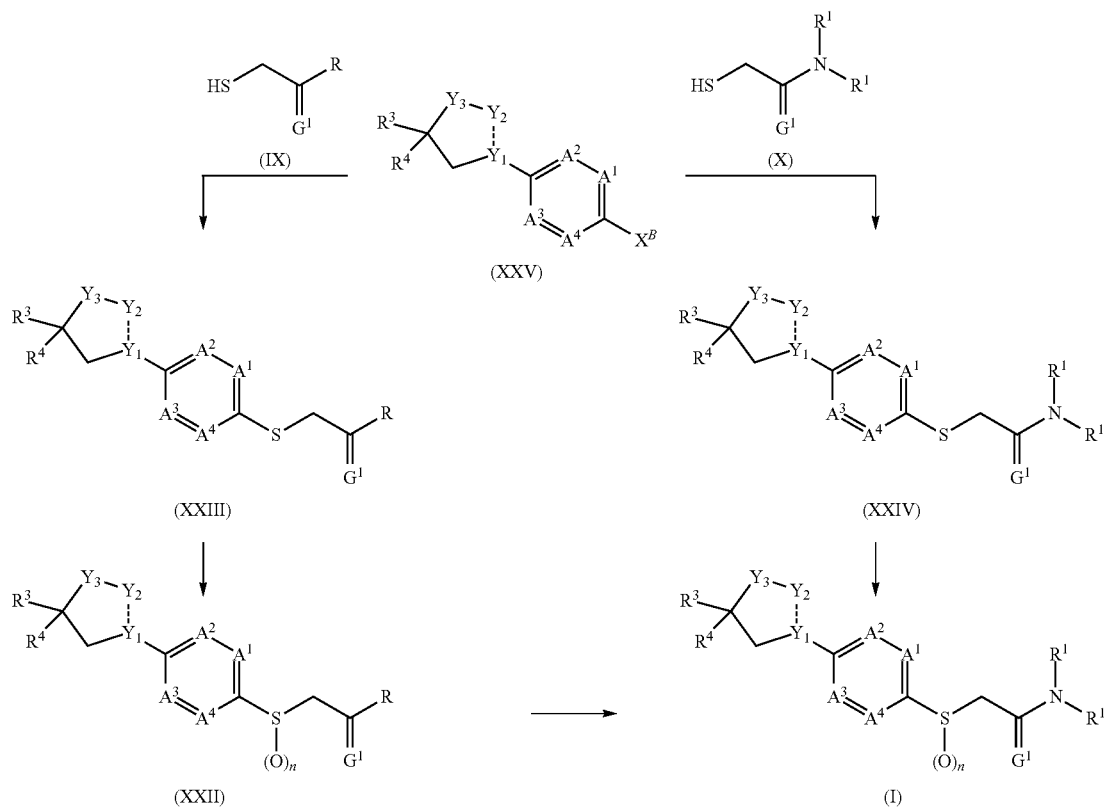

18) Compounds of formula (I) wherein $G^1$ is O and $Y_1$—$Y_2$—$Y_3$ is C=N—$CH_2$, C=CH—O, or N—$CH_2$—$CH_2$ can be similarly obtained as described on Scheme 7, using the same methods as those described under Schemes 1 and 3. See also WO2011/154555. Compounds of formula (XXV) wherein $Y_1$—$Y_2$—$Y_3$ is C=N—$CH_2$ are known in the literature, for example in WO2009/072621. Compounds of formula (XXV) wherein $Y_1$—$Y_2$—$Y_3$ is N—$CH_2$—$CH_2$ are known in the literature, for example in WO2008/128711.

Scheme 8

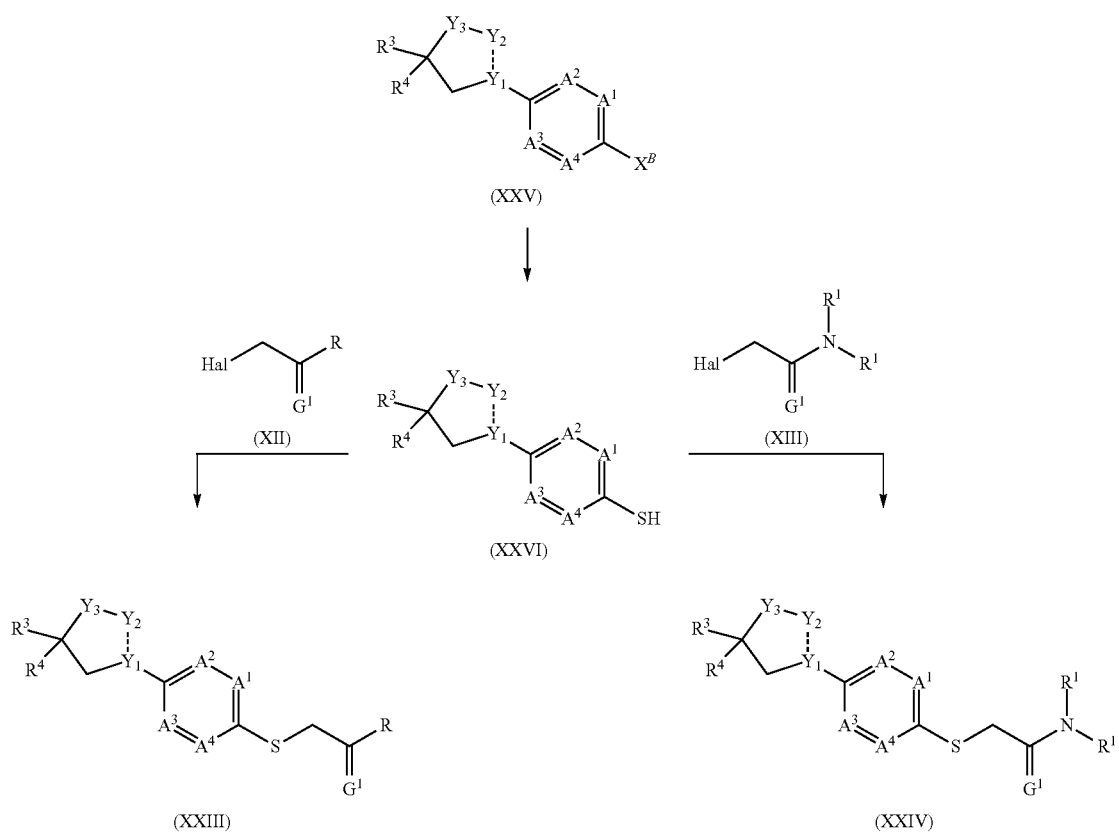

19) Compounds of formula (XXV) wherein $G^1$ is O and $Y_1$—$Y_2$—$Y_3$ is C=N—$CH_2$, C=CH—O, or N—$CH_2$—$CH_2$ may also be similarly converted into compounds of formula (XXIII) and (XXIV) as described on Scheme 8, using the same methods than those described under Scheme 4.

Scheme 9

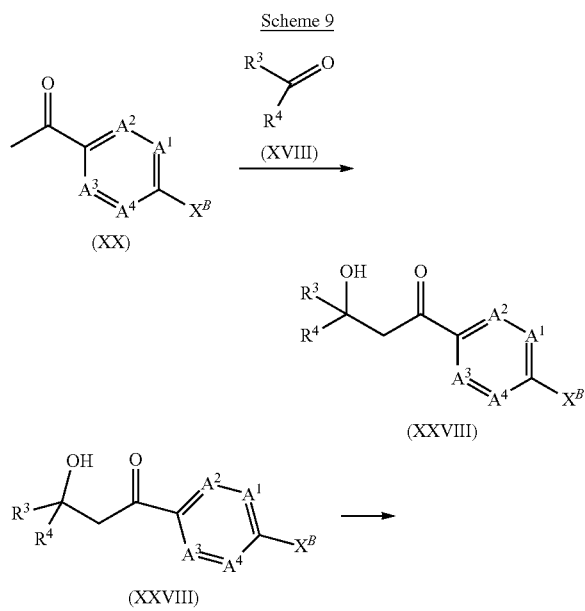

-continued

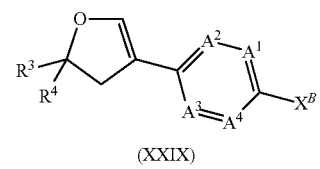

(XXIX)

20) Compounds of formula (XXIX) wherein $X^B$ is a leaving group, for example a halogen, such as bromo, or $C(O)R^x$ wherein $R^x$ is OH or $C_1$-$C_{15}$alkoxy, can be prepared by reacting a compound of formula (XXVIII) wherein $X^B$ is a leaving group, for example a halogen, such as bromo, or $C(O)R^x$ wherein $R^x$ is OH or $C_1$-$C_{15}$alkoxy, with trimethylsilyldiazomethane, in the presence of an organometallic reagent, such as methyl lithium, in a suitable solvent, such as tetrahydrofuran, diethyl ether, N,N-dimethylformamide or dimethoxyethane. The reaction is carried out at a temperature of from −78° C. to 100° C., preferably from −78° C. to ambient temperature. Compounds of formula (XXVIII) are either known compounds or can be prepared using methods described for example in WO2007/074789, preferably by reacting a compound of formula (XX) with a ketone of formula (XVIII).

Scheme 10

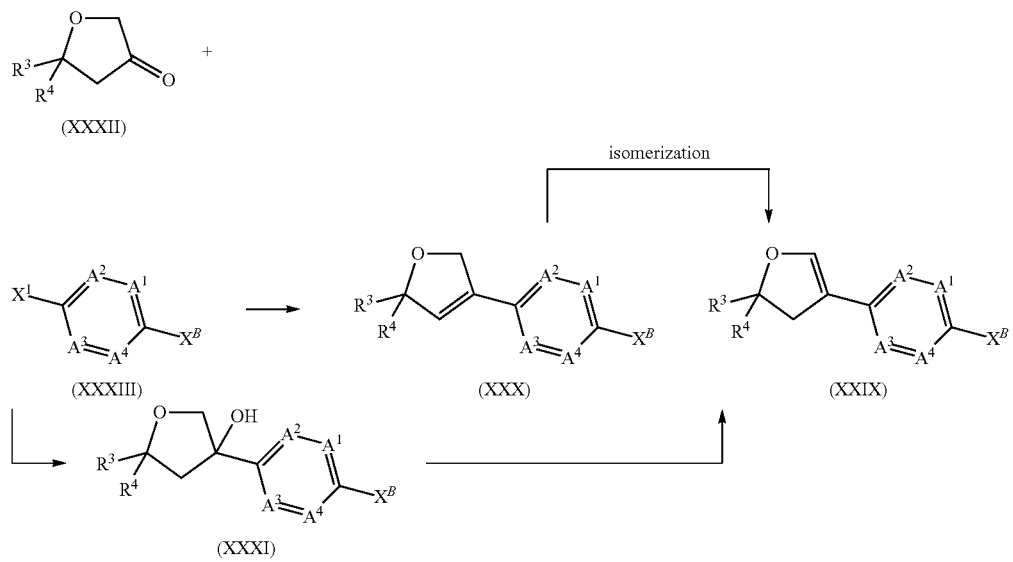

21) Alternatively, 2,3-dihydrofuran compounds of formula (XXIX) wherein $X^B$ is a leaving group for example a halogen may be prepared by isomerisation of 2,5-dihydrofuran of formula (XXX) wherein $X^B$ is a leaving group for example a halogen, using a metal catalyst such as RhCl(PPh$_3$)$_3$, RhH(PPh$_3$)$_4$, H$_2$Ru(CO)(PPh$_3$)$_3$, RuCl$_3$, HClRu(CO)(PPh$_3$)$_3$ or H$_2$Ru(PPh$_3$)$_4$ in a solvent such as toluene or an alcoholic solvent such as ethanol at a temperature of between room temperature and 150° C., preferably between 80° C. and 120° C. Such conditions of isomerisation of 2,5-dihydrofuran compounds have been described in Chem. Eur. J. 2003, 9, 4442-4451 using the general catalytic isomerisation described by M. Mori et al in J. Org. Chem. 2000, 65, 3966-3970 or M. Bartok et al in J. Organomet. Chem. 1985, 297, C37-C40. Alternatively, the isomerisation may be performed in the presence of basic oxide metal catalysts such as MgO, CaO, SrO, or La$_2$O$_3$ as described by K. Tanabe in Chem. Lett. 1981, 341-342 for the isomerisation of 2,5-dihydrofuran.

22) Compounds of formula (XXIX) and (XXX) wherein $X^B$ is a leaving group, for example a halogen, can be prepared by reacting a compound of formula (XXXIII) wherein $X^1$ is a leaving group, for example a halogen, such as iodo or bromo and wherein $X^B$ is a leaving group for example a halogen, with a compound of formula (XXXII), in the presence of a metal, such as catalyst, such as magnesium, lithium, indium, cerium or zinc, in a suitable solvent, such as tetrahydrofuran, diethyl ether or N,N-dimethylformamide. The reaction is carried out at a temperature of from −78° C. to 100° C., preferably from −78° C. to ambient temperature.

23) Compounds of formula (XXXI) can be prepared by reacting a compound of formula (XXXIII) wherein $X^B$ is a leaving group with a compound of formula (XXXII), in the presence of a metal, such as magnesium, indium, cerium, zinc, or an organolithium reagent, such as n-butyl lithium, in a suitable solvent, such as tetrahydrofuran, diethyl ether or N,N-dimethylformamide. The reaction is carried out at a temperature of from −100° C. to 100° C., preferably from −100° C. to ambient temperature.

24) Compounds of formula (XXIX) and (XXX) wherein $X_B$ is a leaving group can be prepared by reacting a compound of formula (XXXI) wherein $X_B$ is a leaving group in the presence of an acid, such as p-toluenesulfonic acid or sulphuric acid, or in the presence of a dehydrating agent, such as POCl$_3$ in a suitable solvent, such as tetrahydrofuran, diethyl ether or dichloromethane. The reaction is carried out at a temperature of from −78° C. to 100° C., preferably from −40° C. to ambient temperature.

25) Alternatively, compounds of formula (XXIX) and (XXX) wherein $X^B$ is a leaving group can be obtained by reacting a compound of formula (XXXI) wherein $X^B$ is a leaving group in the presence of a chlorinating agent, such as thionyl chloride or oxalyl chloride, or an acetylating agent, such as acetic anhydride in the presence of a base, such as triethylamine, potassium carbonate or pyridine, in a suitable solvent, such as tetrahydrofuran, diethyl ether or dichloromethane. The reaction is carried out at a temperature of from −78° C. to 100° C., preferably from −40° C. to ambient temperature.

26) Compounds of formula (XXXIII) are either known compounds or can be prepared by known methods to the person skilled in the art. Compounds of formula (XXXII) can be prepared as described in Scheme 11:

Scheme 11

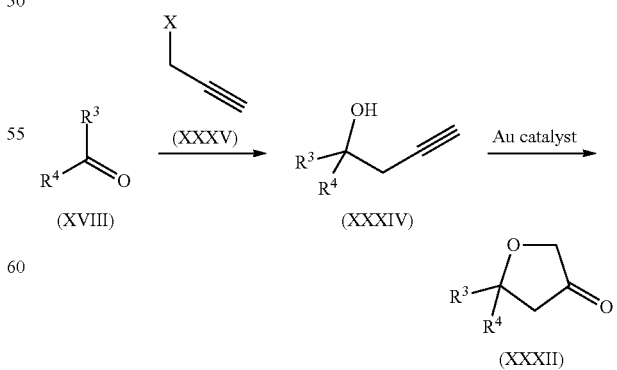

27) Compounds of formula (XXXII) can be prepared by hydrative cyclisation of a compound of formula (XXXIV)

These reactions are usually carried out in the presence of a suitable lewis acid, such as a gold catalyst, as described in *J. Am. Chem. Soc.*, 2010, 132 (10), pp 3258-3259. The reaction is usually carried out using (Triphenylphosphine)gold(I) bis (trifluoromethanesulfonyl)imidate, in the presence of a pyridine N-oxyde, such as 5-Bromo-1-oxy-nicotinic acid methyl ester and an acid, such as methanesulfonic acid, in an aprotic solvent, such as 1,2-dichloroethane. The reaction is carried out at a temperature of from 0° C. to 100° C., preferably from 0° C. to 40° C.

28) Compounds of formula (XXXIV) can be prepared by reacting a ketone of formula (XVIII) with a compound of formula (XXXV), where X is a halogen. These reactions are usually carried out in the presence of a metal, such as magnesium, lithium, indium, cerium or zinc, in a suitable solvent, such as tetrahydrofuran, diethyl ether or N,N-dimethylformamide. The reaction is carried out at a temperature of from −78° C. to 100° C., preferably from −78° C. to ambient temperature. Alternatively, compounds of formula (XXXIV) can be prepared by reacting a compound of formula (XVIII) with a compound of formula (XXXV), where X is a trialkylsilyl group. These reactions are usually carried out in the presence of strong base, such as lithium diisopropylamide, in a suitable solvent, such as tetrahydrofuran, diethyl ether or N,N-dimethylformamide. The reaction is carried out at a temperature of from −78° C. to 100° C., preferably from −78° C. to ambient temperature.

touene, acetonitrile or N,N-dimethylformamide. The reaction is carried out at a temperature of from −20° C. to 150° C., preferably from ambient temperature to 100° C. Alternatively, compounds of formula (XXIX) (and compounds of formula (XXX)) wherein $X_B$ is a leaving group can be prepared by reacting a compound of formula (XXXVI) (and respectively compounds of formula (XXXVII)) wherein X is a leaving group, for example a halogen, such as bromo, or a triflate with a compound of formula (XXXIII) wherein $X^1$ is a trialkylstannane derivative, such as tributyltin, or respectively an organozinc derivative in a Stille or Negishi coupling reaction, in the presence of a palladium catalyst, such as palladium acetate or tetrakis(triphenylphosphine) palladium, in a suitable solvent, such as 1,4-dioxane, touene, acetonitrile or N,N-dimethylformamide 30) Compounds of formula (XXXVI) (and compounds of formula (XXXVII)) wherein X is a halogen, such as bromo, can be prepared by reacting a compound of formula (XXXII) with a brominating agent, such as phosphoric tribromide, in a suitable solvent, such as tetrahydrofuran, or chloroform, dichloromethane. The reaction is carried out at a temperature of from −40° C. to 100° C., preferably from −40° C. to ambient temperature. Alternatively, compounds of formula (XXXVI) (and compounds of formula (XXXVII)) wherein X is a triflate, can be prepared by reacting a compound of formula (XXXII) with a triflating agent, such as triflic anhy- Scheme 12

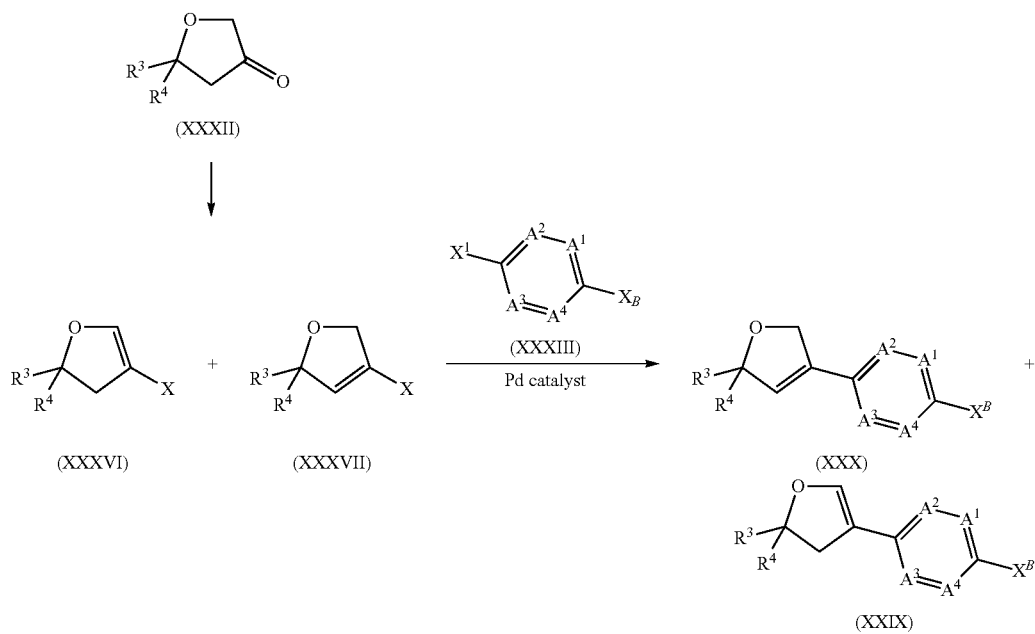

29) Compounds of formula (XXIX) (and compounds of formula (XXX)) wherein $X_B$ is a leaving group can be prepared by reacting a compound of formula (XXXVI) (and respectively compounds of formula (XXXVII)) wherein X is a leaving group, for example a halogen, such as bromo, or a triflate, with a compound of formula (XXXIII) wherein $X_B$ is a leaving group, and wherein $X^1$ is a boron derivative, such as a boronic acid, a pinacolboronate, or a trifluoroborate salt, in a Suzuki coupling reaction, in the presence of a palladium catalyst, such as palladium acetate or tetrakis(triphenylphosphine) palladium, in a suitable solvent, such as 1,4-dioxane, dride or N,N-bis(trifluoromethanesulfonyl)aniline, in the presence of a base, such as 4-picoline, sodium or potassium hexamethyldisilylamide, lithium diisopropylamide, triethylamine or 2,6-lutidine in a suitable solvent, such as tetrahydrofuran, chloroform or dichloromethane. The reaction is carried out at a temperature of from −100° C. to 150° C., preferably from −40° C. to 100° C.

See also WO2011/101229 for additional information relating to preparation of compounds in which $Y_1$—$Y_2$—$Y_3$ is —C═CH—O—.

Scheme 13

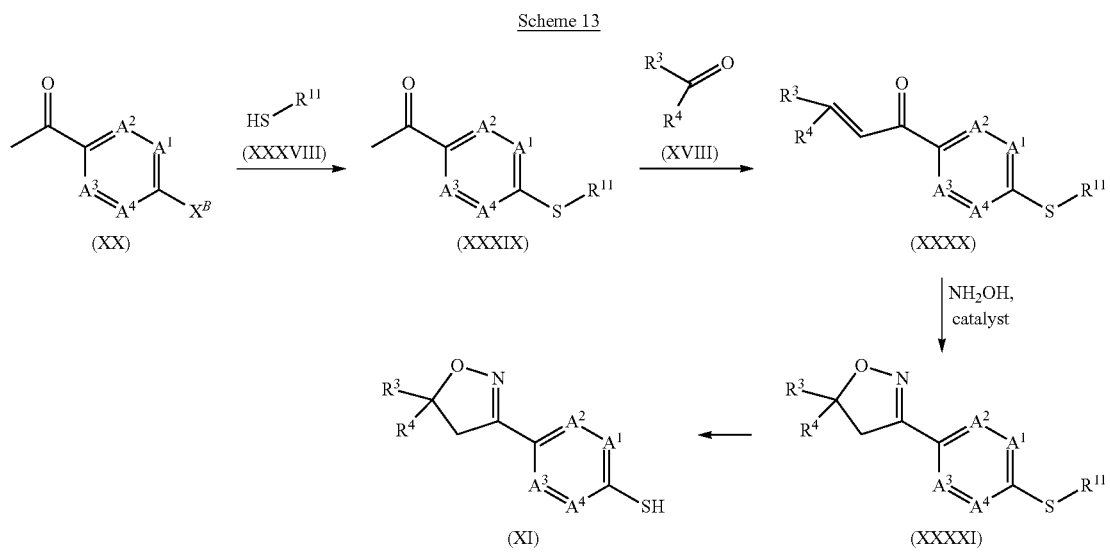

31) Compounds of formula (XXXIX) wherein $R^{11}$ is $C_1$-$C_6$alkyl or $C_1$-$C_6$alkyl optionally substituted by an aryl, can be prepared by reacting an intermediate of formula (XX) wherein $X^B$ is a leaving group, for example a halogen, such as fluoro, chloro or bromo, with a mercaptan of formula (XXXVIII) wherein $R^{11}$ is $C_1$-$C_6$alkyl or $C_1$-$C_6$alkyl optionally substituted by an aryl, for example tert-butyl. Such reactions can be carried out in the presence of a base such as an amine or a carbonate, for example potassium or cesium carbonate in solvents such as acetonitrile, dimethylformamide, dimethylsulfoxide, dimethylacetamide at a temperature of from 0° C. to 150° C., preferably from 25° C. to 100° C. Examples of such reactions can be found in Synlett 2006, 8, 1255-1259, and specific examples are described in the experimental section. Alternatively, the reaction can be carried out in the presence of a catalyst, for a example a palladium catalyst, and a ligand, for example a phosphine ligand in a solvent such as tetrahydrofuran, dioxane, 1,2-dimethoxyethane, ethyl acetate, or toluene at a temperature of from 0° C. to 150° C., preferably from 80° C. to 130° C. This reaction can be carried out under microwave irradiation, as described for example in WO2007/102059, and specific examples are described in the experimental section.

32) Compounds of formula (XXXIX) wherein $R^{11}$ is $C_1$-$C_6$alkyl or $C_1$-$C_6$alkyl optionally substituted by an aryl, may be converted to compounds of formula (XXXX) wherein $R^{11}$ is $C_1$-$C_6$alkyl or $C_1$-$C_6$alkyl optionally substituted by an aryl, by reaction with a ketone of formula (XVIII) according to methods described for example in WO2009/080250.

33) Subsequently, compounds of formula (XXXX) wherein $R^{11}$ is $C_1$-$C_6$alkyl or $C_1$-$C_6$alkyl optionally substituted by an aryl, can be converted into compounds of formula (XXXXI) wherein $R^{11}$ is $C_1$-$C_6$alkyl or $C_1$-$C_6$alkyl optionally substituted by an aryl, by treatment with hydroxylamine, a base and a phase transfer catalyst, as described for example in WO2009/080250.

34) Subsequently, compounds of formula (XXXXI) wherein $R^{11}$ is $C_1$-$C_6$alkyl or $C_1$-$C_6$alkyl optionally substituted by an aryl, can be converted into compounds of formula (XI). Such reactions can be carried out in the presence of an acid or a Lewis acid such as an sulfonic acid, carboxylic acid for example methylsulfonic acid, paratoluenesulfonic acid, trifluoroacetic acid, aluminum trichloride or mercury(II) acetate in solvents such as acetic acid, trifluoroacetic acid, toluene, dichloromethane, water at a temperature of from −78° C. to 150° C., preferably from 0° C. to 110° C. Examples of such reactions can be found in Organometallics, 2007, 26, 897-909 and Chemical Communications 2009, 5236-5238, and specific examples are described in the experimental section.

Scheme 14

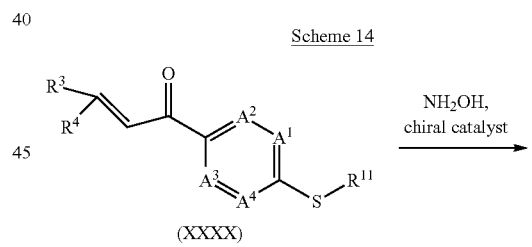

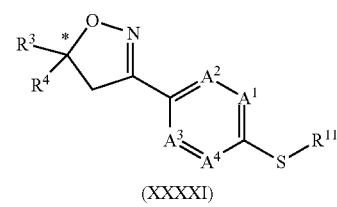

35) Compounds of formula (XXXX) wherein $R^{11}$ is $C_1$-$C_6$alkyl or $C_1$-$C_6$alkyl optionally substituted by an aryl, can be converted into compounds of formula (XXXXI) wherein $R^{11}$ is $C_1$-$C_6$alkyl or $C_1$-$C_6$alkyl optionally substituted by an aryl, by treatment with hydroxylamine, a base and a phase transfer catalyst, as described for example in WO2009/080250.

Scheme 15

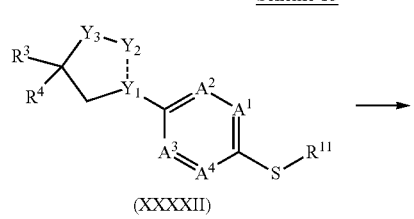

36) Compounds of formula (XXXXII) wherein G $Y_1$—$Y_2$—$Y_3$ is C=N—$CH_2$, C=CH—O, or N—$CH_2$—$CH_2$ may also be similarly converted into compounds of formula (XXVI) as described on Scheme 8, using the same methods than those described under Scheme 4.

Scheme 16

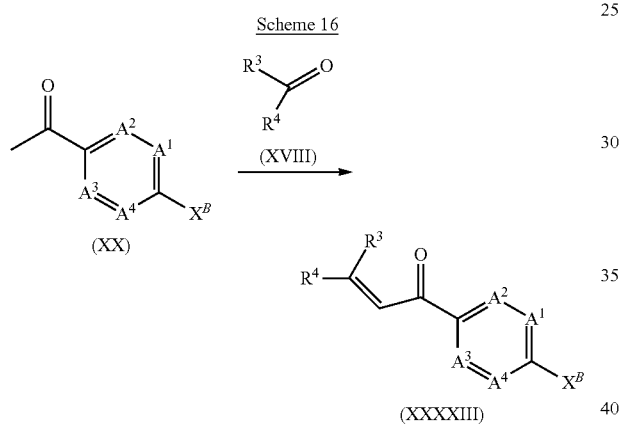

37) Compounds of formula (XX) wherein $X^B$ is a leaving group, for example a halogen, such as fluoro, chloro or bromo, may be converted to compounds of formula (XXXXIII) by reaction with a ketone of formula (XVIII) according to methods described for example in WO2009/080250.

Scheme 17

38) Compounds of formula (XXXXIII) wherein $X^B$ is a leaving group, for example a halogen, such as fluoro, chloro or bromo, can be converted into compounds of formula (VIII) by treatment with hydroxylamine, a base and a phase transfer catalyst, as described for example in WO2009/080250.

Scheme 18:

39) Compounds of formula (XXXXIV) wherein $G^1$ is O may also be similarly converted into compounds of formula (XXXXVII) wherein $X^1$ is a, halogen such as, chloro, bromo, or iodo, or a sulfonate ester such as triflate or mesylate, as described on Scheme 18 by reaction of a pyrrolidine of formula (XXXXVI) in presence of a base, such as alkali metal alkoxide, alkali phosphate or alkali carbonate, and a palladium or copper catalyst. The reaction is carried out at a temperature of from 0° C. to 2000° C., preferably from 20° C. to 160° C. The equivalents of base use can vary from 0.1 to 10 equivalents, preferably from 1 to 4 equivalents.

40) Compounds of formula (XXXXIV) wherein $G^1$ is O may also be similarly converted into compounds of formula (XXXXVIII) wherein $X^1$ is a, halogen such as, chloro, bromo, or iodo, or a sulfonate ester such as triflate or mesylate, as described on Scheme 20 by reaction of a pyrrolidine of formula (XXXXVI) in presence of a base, such as alkali metal alkoxide, alkali phosphate or alkali carbonate, and a palladium or copper catalyst. The reaction is carried out at a temperature of from 0° C. to 2000° C., preferably from 20° C. to 160° C. The equivalents of base use can vary from 0.1 to 10 equivalents, preferably from 1 to 4 equivalents.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the compounds of the invention include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The compounds of the invention may be used for example on turf, ornamentals, such as flowers, shrubs, broad-leaved trees or evergreens, for example conifers, as well as for tree injection, pest management and the like. Compositions comprising the compound of formula I may be used on ornamental garden plants (e.g. flowers, shrubs, broad-leaved trees or evergreens), e.g. to control aphids, whitefly, scales, meelybug, beetles and caterpillars. Compositions comprising the compound of formula I may be used on garden plants (e.g. flowers, shrubs, broad-leaved trees or evergreens), on indoor plants (e.g. flowers and shrubs) and on indoor pest e.g. to control aphids, whitefly, scales, meelybug, beetles and caterpillars.

Furthermore, the compounds of the invention may be effective against harmful insects, without substantially imposing any harmful side effects to cultivated plants. Application of the compounds of the invention may increase the harvest yields, and may improve the quality of the harvested material. The compounds of the invention may have favourable properties with respect to amount appled, residue formulation, selectivity, toxicity, production methodology, high activity, wide spectrum of control, safety, control of resistant organisms, e.g. pests that are resistant to organic phosphorus agents and/or carbamate agents.

Examples of pest species which may be controlled by the compounds of formula (I) include: coleopterans, for example, Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica spp., Monochamus alternatus, Lissorhoptrus oryzophilus, Lyctus bruneus, Aulacophora femoralis; lepidopterans, for example, Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotisfucosa, Galleria mellonella, Plutella maculipennis, Heliothis virescens, Phyllocnistis citrella; hemipterans, for example, Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara spp., Trialeurodes vaporariorm, Psylla spp.; thysanopterans, for example, Thrips palmi, Franklinella occidental; orthopterans, for example, Blatella germanica, Periplaneta americana, Gryllotalpa Africana, Locusta migratoria migratoriodes; isopterans, for example, Reticulitermes speratus, Coptotermes formosanus; dipterans, for example, Musca domestica, Aedes aegypti, Hylemia platura, Culex pipiens, Anopheles sinensis, Culex tritaeniorhynchus, Liriomyza trifolii; acari, for example, Tetranychus cinnabarinus, Tetranychus urticae, Panonychus citri, Aculops pelekassi, Tarsonemus spp.; nematodes, for example, Meloidogyne incognita, Bursaphelenchus lignicolus Mamiya et Kiyohara, Aphelenchoides besseyi, Heterodera glycines, Pratylenchus spp.

Examples of further pest species which may be controlled by the compounds of formula (I) include: from the order of the Anoplura (Phthiraptera), for example, Damalinia spp., Haematopinus spp., Linognathus spp., Pediculus spp., Trichodectes spp.; from the class of the Arachnida, for example, Acarus siro, Aceria sheldoni, Aculops spp., Aculus spp., Amblyomma spp., Argas spp., Boophilus spp., Brevipalpus spp., Bryobia praetiosa, Chorioptes spp., Dermanyssus gallinae, Eotetranychus spp., Epitrimerus pyri, Eutetranychus spp., Eriophyes spp., Hemitarsonemus spp., Hyalomma spp., Ixodes spp., Latrodectus mactans, Metatetranychus spp., Oligonychus spp., Ornithodoros spp., Panonychus spp., Phyllocoptruta oleivora, Polyphagotarsonemus latus, Psoroptes spp., Rhipicephalus spp., Rhizoglyphus spp., Sarcoptes spp., Scorpio maurus, Stenotarsonemus spp., Tarsonemus spp., Tetranychus spp., Vasates lycopersici; from the class of the Bivalva, for example, Dreissena spp.; from the order of the Chilopoda, for example, Geophilus spp., Scutigera spp.; from the order of the Coleoptera, for example, Acanthoscehdes obtectus, Adoretus spp., Agelastica alni, Agriotes spp., Amphimallon solstitialis, Anobium punctatum, Anoplophora spp., Anthonomus spp., Anthrenus spp., Apogonia spp., Atomaria spp., Attagenus spp., Bruchidius obtectus, Bruchus spp., Ceuthorhynchus spp., Cleonus mendicus, Conoderus spp., Cosmopolites spp., Costelytra zealandica, Curculio spp., Cryptorhynchus lapathi, Dermestes spp., Diabrotica spp., Epilachna spp., Faustinus cubae, Gibbium psylloides, Heteronychus arator, Hylamorpha elegans, Hylotrupes bajulus, Hypera postica, Hypothenemus spp., Lachnosterna consanguinea, Leptinotarsa decemlineata, Lissorhoptrus oryzophilus, Lixus spp., Lyctus spp., Meligethes aeneus, Melolontha melolontha, Migdolus spp., Monochamus spp., Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga spp., Popillia japonica, Premnotrypes spp., Psylliodes chrysocephala, Ptinus spp., Rhizobius ventralis, Rhizopertha dominica, Sitophilus spp., Sphenophorus spp., Sternechus spp., Symphyletes spp., Tenebrio molitor, Tribolium spp., Trogoderma spp., Tychius spp., Xylotrechus spp., Zabrus spp.; from the order of the Collembola, for example, Onychiurus armatus; from the order of the Dermaptera, for example, Forficula auricularia; from the order of the Diplopoda, for example, *Blaniulus guttulatus*; from the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.; from the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*; ft may be furthermore possible to control protozoa, such as *Eimeria*; from the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singulanis*, *Scotinophora* spp., *Stephanitis nashi*, *Tibraca* spp., *Triatoma* spp.; from the order of the Homoptena, for example, *Acynthosipon* spp., *Aeneolamia* spp., *Agonoscena* spp., *Aleunodes* spp., *Aleunolobus banodensis*, *Aleunothnixus* spp., *Amnasca* spp., *Anunaphis candui*, *Aonidiella* spp., *Aphanostigma pini*, *Aphis* spp., *Anbonidia apicalis*, *Aspidiella* spp., *Aspidiotus* spp., *Atanus* spp., *Aulaconthum solani*, *Bemisia* spp., *Brachycaudus helichrysii*, *Brachycolus* spp., *Brevicoryne brassicae*, *Calligypona manginata*, *Canneocephala fulgida*, *Cenatovacuna lanigena*, *Cencopidae*, *Cenoplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus nibis*, *Dalbulus* spp., *Dialeunodes* spp., *Diaphonina* spp., *Diaspis* spp., *Dorsalis* spp., *Drosicha* spp., *Dysaphis* spp., *Dysmicoccus* spp., *Empoasca* spp., *Eniosoma* spp., *Erythnoneuna* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax stniatellus*, *Lecanium* spp., *Lepidosaphes* spp., *Lipaphis erysimi*, *Macnosiphum* spp., *Mahanarva fimbriolata*, *Melanaphis sacchani*, *Metcalfiella* spp., *Metopolophium dinhodum*, *Monellia costalis*, *Monelliopsis pecanis*, *Myzus* spp., *Nasonovia nibisnigni*, *Nephotettix* spp., *Nilaparvata lugens*, *Oncometopia* spp., *Onthezia pnaelonga*, *Panabemisia mynicae*, *Panatnioza* spp., *Panlatonia* spp., *Pemphigus* spp., *Penegninus maidis*, *Phenacoccus* spp., *Phloeomyzus passeninii*, *Phonodon humuli*, *Phylloxera* spp., *Pinnaspis aspidistnae*, *Planococcus* spp., *Protopulvinania pyriformis*, *Pseudaulacaspis pentagona*, *Pseudococcus* spp., *Psylla* spp., *Ptenomalus* spp., *Pynilla* spp., *Quadnaspidiotus* spp., *Quesada gigas*, *Rastrococcus* spp., *Rhopalosiphum* spp., *Saissetia* spp., *Scaphoides titanus*, *Schizaphis graminum*, *Selenaspidus anticulatus*, *Sogata* spp., *Sogatella furcifera*, *Sogatodes* spp., *Stictocephala festina*, *Tenalaphana malayensis*, *Tinocallis caryaefoliae*, *Tomaspis* spp., *Toxoptena* spp., *Tnialeunodes vaporariorum*, *Trioza* spp., *Typhlocyba* spp., *Unaspis* spp., *Viteus vitifolii*; from the order of the Hymenoptera, for example, *Diprion* spp., *Hoplocampa* spp., *Lasius* spp., *Mono-morium pharaonic*, *Vespa* spp.; from the order of the Isopoda, for example, *Armadillidium vulgare*, *Oniscus asellus*, *Porcellio scaber*; from the order of the Isoptera, for example, *Reticulitermes* spp., *Odontotermes* spp.; from the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.; from the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*; from the order of the Siphonaptera, for example, *Ceratophyllus* spp., *Xenopsylla cheopis*. From the order of the Symphyla, for example, *Scutigerella immaculata*; from the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.; from the order of the Thysanura, for example, *Lepisma saccharina*. The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

In particular, the compounds of the invention may be used to control the following pest spcies:

*Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta dero*- gata (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus*, *Reticulitermes flavipes*, *R. speratu*, *R. virginicus*, *R. hesperus*, and *R. santonensis*) and the *Termitidae* (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The compounds of the invention may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The compounds of the invention may be used on soybean to control, for example, *Elasmopalpus lignosellus*, *Diloboderus abderus*, *Diabrotica speciosa*, *Sternechus subsignatus*, *Formicidae*, *Agrotis ypsilon*, *Julus* ssp., *Anticarsia gemmatalis*, *Megascelis* ssp., *Procornitermes* ssp., *Gryllotalpidae*, *Nezara viridula*, *Piezodorus* spp., *Acrosternum* spp., *Neomegalotomus* spp., *Cerotoma trifurcata*, *Popillia japonica*, *Edessa* spp., *Liogenys fuscus*, *Euchistus heros*, stalk borer, *Scaptocoris castanea*, *phyllophaga* spp., *Pseudoplusia includens*, *Spodoptera* spp., *Bemisia tabaci*, *Agriotes* spp. The compounds of the invention are preferably used on soybean to control *Diloboderus abderus*, *Diabrotica speciosa*, *Nezara viridula*, *Piezodorus* spp., *Acrosternum* spp., *Cerotoma trifurcata*, *Popillia japonica*, *Euchistus heros*, *phyllophaga* spp., *Agriotes* spp.

The compounds of the invention may be used on corn to control, for example, *Euchistus heros*, *Dichelops furcatus*, *Diloboderus abderus*, *Elasmopalpus lignosellus*, *Spodoptera frugiperda*, *Nezara viridula*, *Cerotoma trifurcata*, *Popillia japonica*, *Agrotis ypsilon*, *Diabrotica speciosa*, *Heteroptera*, *Procornitermes* ssp., *Scaptocoris castanea*, *Formicidae*, *Julus* ssp., *Dalbulus maidis*, *Diabrotica virgifera*, *Mocis latipes*, *Bemisia tabaci*, *heliothis* spp., *Tetranychus* spp., thrips spp., *phyllophaga* spp., *scaptocoris* spp., *Liogenys fuscus*, *Spodoptera* spp., *Ostrinia* spp., *Sesamia* spp., *Agriotes* spp. The compounds of the invention are preferably used on corn to control *Euchistus heros*, *Dichelops furcatus*, *Diloboderus abderus*, *Nezara viridula*, *Cerotoma trifurcata*, *Popillia japonica*, *Diabrotica speciosa*, *Diabrotica virgifera*, *Tetranychus* spp., thrips spp., *phyllophaga* spp., *scaptocoris* spp., *Agriotes* spp.

The compounds of the invention may be used on sugar cane to control, for example, *Sphenophorus* spp., termites, *Mahanarva* spp. The compounds of the invention are preferably used on sugar cane to control termites, *Mahanarva* spp.

The compounds of the invention may be used on alfalfa to control, for example, *Hypera brunneipennis*, *Hypera postica*, *Colias emytheme*, *Collops* spp., *Empoasca solana*, *Epitrix*, *Geocoris* spp., *Lygus hesperus*, *Lygus lineolaris*, *Spissistilus* spp, *Spodoptera* spp., *Trichoplusia ni*. The compounds of the invention are preferably used on alfalfa to control *Hypera brunneipennis*, *Hypera postica*, *Empoasca solana*, *Epitrix*, *Lygus hesperus*, *Lygus lineolaris*, *Trichoplusia ni*.

The compounds of the invention may be used on brassicas to control, for example, *Plutella xylostella*, *Pieris* spp., *Mamestra* spp., *Plusia* spp., *Trichoplusia ni*, *Phyllotreta* spp., *Spodoptera* spp., *Empoasca solana*, thrips spp., *Spodoptera* spp., *Delia* spp. The compounds of the invention are preferably used on brassicas to control *Plutella xylostella* *Pieris* spp., *Plusia* spp., *Trichoplusia ni*, *Phyllotreta* spp., thrips spp.

The compounds of the invention may be used on oil seed rape, e.g. canola, to control, for example, *Meligethes* sp, *Ceutorhynchus napi*, *Psylloides* sp.

The compounds of the invention may be used on potatoes, including sweet potatoes, to control, for example, *Empoasca* sp, *Leptinotarsa* sp, *Diabrotica speciosa*, *Phthorimaea* sp, *Paratrioza* sp, *Maladera matrida*, *Agriotes* sp. The compounds of the invention are preferably used on potatoes, including sweet potatoes, to control *Empoasca* sp, *Leptinotarsa* sp, *Diabrotica speciosa*, *Phthorimaea* sp, *Paratrioza* sp, *Agriotes* sp.

The compounds of the invention may be used on cotton to control, for example, *Anthonomus grandis*, *Pectinophora* sp, *heliothis* sp, *Spodoptera* sp, *Tetranychus* sp, *Empoasca* sp, thrips sp, *Bemisia tabaci*, *Lygus* sp, *phyllophaga* sp, *Scaptocoris* sp. The compounds of the invention are preferably used on cotton to control *Anthonomus grandis*, *Tetranychus* sp, *Empoasca* sp, thrips sp, *Lygus* sp, *phyllophaga* sp, *Scaptocoris* sp.

The compounds of the invention may be used on rice to control, for example, *Leptocorisa* sp, *Cnaphalocrosis* sp, *Chilo* sp, *Scirpophaga* sp, *Lissorhoptrus* sp, *Oebalus pugnax*. The compounds of the invention are preferably used on rice to control *Leptocorisa* sp, *Lissorhoptrus* sp, *Oebalus pugnax*.

The compounds of the invention may be used on coffee to control, for example, *Hypothenemus Hampei*, *Perileucoptera Coffeella*, *Tetranychus* sp. The compounds of the invention are preferably used on coffee to control *Hypothenemus Hampei*, *Perileucoptera Coffeella*.

The compounds of the invention may be used on citrus to control, for example, *Panonychus citri*, *Phyllocoptruta oleivora*, *Brevipalpus* sp, *Diaphorina citri*, *Scirtothrips* sp, thrips sp, *Unaspis* sp, *Ceratitis capitata*, *Phyllocnistis* sp. The compounds of the invention are preferably used on citrus to control *Panonychus citri, Phyllocoptruta oleivora, Brevipalpus* sp, *Diaphorina citri, Scirtothrips* sp, *thrips* sp, *Phyllocnistis* sp.

The compounds of the invention may be used on almonds to control, for example, *Amyelois transitella, Tetranychus* sp.

The compounds of the invention may be used on fruiting vegetable, including tomatoes, pepper, chili, eggplant, cucumber, squash etc, to control *thrips* sp, *Tetranychus* sp, *Polyphagotarsonemus* sp, *Aculops* sp, *Empoasca* sp, *Spodoptera* sp, *heliothis* sp, *Tuta absoluta, Liriomyza* sp, *Bemisia tabaci, Trialeurodes* sp, *Paratrioza* sp, *Frankliniella occidentalis, Frankliniella* sp, *Anthonomus* sp, *Phyllotreta* sp, *Amrasca* sp, *Epilachna* sp, *Halyomorpha* sp, *Scirtothrips* sp, *Leucinodes* sp, *Neoleucinodes* sp. The compounds of the invention are preferably used on fruiting vegetable, including tomatoes, pepper, chili, eggplant, cucumber, squash etc, to control, for example, *thrips* sp, *Tetranychus* sp, *Polyphagotarsonemus* sp, *Aculops* sp, *Empoasca* sp, *Spodoptera* sp, *heliothis* sp, *Tuta absoluta, Liriomyza* sp, *Paratrioza* sp, *Frankliniella occidentalis, Frankliniella* sp, *Amrasca* sp, *Scirtothrips* sp, *Leucinodes* sp, *Neoleucinodes* sp.

The compounds of the invention may be used on tea to control, for example, *Pseudaulacaspis* sp, *Empoasca* sp, *Scirtothrips* sp, *Caloptilia theivora*. The compounds of the invention are preferably used on tea to control *Empoasca* sp, *Scirtothrips* sp.

The compounds of the invention may be used on bulb vegetables, including onion, leek etc to control, for example, *thrips* sp, *Spodoptera* sp, *heliothis* sp. The compounds of the invention are preferably used on bulb vegetables, including onion, leek etc to control *thrips* sp.

The compounds of the invention may be used on grapes to control, for example, *Empoasca* sp, *Lobesia* sp, *Frankliniella* sp, *thrips* sp, *Tetranychus* sp, *Rhipiphorothrips Cruentatus, Eotetranychus Willamettei, Erythroneura Elegantula, Scaphoides* sp. The compounds of the invention are preferably used on grapes to control *Frankliniella* sp, *thrips* sp, *Tetranychus* sp, *Rhipiphorothrips Cruentatus, Scaphoides* sp.

The compounds of the invention may be used on pome fruit, including apples, pairs etc, to control, for example, *Cacopsylla* sp, *Psylla* sp, *Panonychus ulmi, Cydia pomonella*. The compounds of the invention are preferably used on pome fruit, including apples, pairs etc, to control *Cacopsylla* sp, *Psylla* sp, *Panonychus ulmi*.

The compounds of the invention may be used on stone fruit to control, for example, *Grapholita molesta, Scirtothrips* sp, *thrips* sp, *Frankliniella* sp, *Tetranychus* sp. The compounds of the invention are preferably used on stone fruit to control *Scirtothrips* sp, *thrips* sp, *Frankliniella* sp, *Tetranychus* sp.

The compounds of the invention may be used to control animal housing pests including: Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Saw-toothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leafminers (adults), Leaf rollers, Leaf skeletonizers, Midges, Mosquitoes, Oleander moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, Thrips, Tip moths, Tussock moth larvae, Wasps, Broadmites, Brown softscales, California redscales (crawlers), Clover mites, Mealybugs, Pineneedlescales (crawlers), Spider mites, Whiteflies The compounds of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs.

The invention therefore provides a method of combating and/or controlling an animal pest, e.g. an invertebrate animal pest, which comprises applying to the pest, to a locus of the pest, or to a plant susceptible to attack by the pest a pesticidally effective amount of a compound of formula (I). In particular, the invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

The compounds of the invention may be applied to plant parts. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds. Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

Compounds of formula I may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in superadditive ("synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes).

Compounds of formula I may be used on transgenic plants that are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030,295) or Cry1A.105; or vegetative insecticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure® CB (P1) (corn producing Cry1Ab), Agrisure® RW (P2) (corn producing mCry3A), Agrisure® Viptera (P3) (corn hybrids producing Vip3Aa); Agrisure300GT (P4) (corn hybrids producing Cry1Ab and mCry3A); YieldGard® (P5) (corn hybrids producing the Cry1Ab protein), YieldGard® Plus (P6) (corn hybrids producing Cry1Ab and Cry3Bb1), Genuity® SmartStax® (P7) (corn hybrids with Cry1A.105, Cry2Ab2, Cry1F, Cry34/35, Cry3Bb); Herculex® I (P8) (corn hybrids producing Cry1Fa) and Herculex® RW (P9) (corn hybrids producing Cry34Ab1, Cry35Ab1 and the enzyme Phosphinothricin-N-Acetyltransferase [PAT]); NuCOTN® 33B (P10) (cotton cultivars producing Cry1Ac), Bollgard® I (P11) (cotton cultivars producing Cry1Ac), Bollgard® II (P12) (cotton cultivars producing Cry1Ac and Cry2Ab2) and VIPCOT® (P13) (cotton cultivars producing a Vip3Aa). Soybean Cyst Nematode resistance soybean (SCN®—Syngenta (P14)) and soybean with Aphid resistant trait (AMT® (P15)) are also of interest.

Further examples of such transgenic crops are:

1. Bt11 Maize from Syngenta Seeds SAS, Chemin de l'Hobit 27, F-31 790 St. Sauveur, France, registration number C/FR/96/05/10 (P16). Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10 (P17). Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10 (P18). Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9 (P19). MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02. (P20)

6. 1507 Maize from Pioneer Overseas Corporation, Avenue Tedesco, 7 B-1160 Brussels, Belgium, registration number C/NL/00/10. (P21) Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03 (P22). Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Further examples of transgenic plants, and of very high interest, are those carrying traits conferring resistance to 2.4 D (e.g. Enlist®) (e.g. WO 2011066384) (P23), glyphosate (e.g. Roundup Ready®) (P24), Roundup Ready 2 Yield® (P25)), sulfonylurea (e.g. STS®) (P26), glufosinate (e.g. Liberty Link® (P27), Ignite® (P28)), Dicamba (P29) (Monsanto), HPPD tolerance (P30) (e.g. isoxaflutole herbicide) (Bayer CropScience, Syngenta). Double or triple stacks of any of the traits described here are also of interest, including glyphosate and sulfonyl-urea tolerance ((e.g. Optimum GAT®) (P31), plants stacked with STS® and Roundup Ready® (P32) or plants stacked with STS® and Roundup Ready 2 Yield® (P33)), dicamba and glyphosate tolerance (P34) (Monsanto). Of particular interest are soybean plants carrying trains conferring resistance to 2.4 D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonyl-urea tolerance (e.g. Optimum GAT®, plants stacked with STS® and Roundup Ready® or Roundup Ready 2 Yield®), dicamba and glyphosate tolerance (Monsanto). Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is generally used at a rate of 0.0001 g to 10 g (for example 0.001 g or 0.05 g), preferably 0.005 g to 10 g, more preferably 0.005 g to 4 g, per kilogram of seed.

In another aspect the present invention provides a composition comprising a pesticidally effective amount of a compound of formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin and gamma cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E)-(1R,3S)-2,2-dimethyl-3-(2-oxothiolan-3-ylidenemethyl) cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron, diafenthiuron, lufeneron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad, azadirachtin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, thiamethoxam, clothianidin, nithiazine or flonicamid;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Spirotetramat, spirodiclofen or spiromesifen;

s) Diamides, such as flubendiamide, chlorantraniliprole (Rynaxypyr®) or cyantraniliprole;

t) Sulfoxaflor; or u) Metaflumizone;

v) Fipronil and Ethiprole;

w) Pyrifluqinazon;

x) buprofezin; or y) 4-[(6-Chloro-pyridin-3-ylmethyl)-(2,2-difluoro-ethyl)-amino]-5H-furan-2-one (DE 102006015467).

z) flupyradifurone.

aa) CAS: 915972-17-7 (WO 2006129714; WO2011/147953; WO2011/147952)

ab) CAS: 26914-55-8 (WO 2007020986)

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704) (e.g. acibenzolar-5-methyl), alanycarb, aldimorph, anilazine, azaconazole, azoxystrobin, benalaxyl, benomyl, benthiavalicarb, biloxazol, bitertanol, bixafen, blasticidin S, boscalid, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cyclufenamid, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)-N-benzyl-N-([methyl(methyl-thioethylideneamino-oxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluopyram, fluoxastrobin, fluoroimide, fluquinconazole, flusilazole, flutolanil, flutriafol, fluxapyroxad, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, isopyrazam, kasugamycin, kresoxim-methyl, LY186054, LY211795, LY248908, mancozeb, mandipropamid, maneb, mefenoxam, metalaxyl, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, penflufen, penthiopyrad, phenazin oxide, phosetyl-Al, phosphorus acids, phthalide, picoxystrobin (ZA1963), polyoxinD, polyram, probenazole, prochloraz, procymidone, propamocarb, propiconazole, propineb, propionic acid, prothioconazole, pyrazophos, pyrifenox, pyrimethanil, pyraclostrobin, pyroquilon, pyroxyfur, pyrrolnitrin, quaternary ammonium compounds, quinomethionate, quinoxyfen, quintozene, sedaxane, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram, N-[9-(dichloromethylene)-1,2,3,4-tetrahydro-1,4-methanonaphthalen-5-yl]-3-(difluoromethyl)-1-methyl-1H-pyrazole-4-carboxamide [1072957-71-1], 1-methyl-3-difluoromethyl-1H-pyrazole-4-carboxylic acid (2-dichloromethylene-3-ethyl-1-methyl-indan-4-yl)-amide, and 1-methyl-3-difluoromethyl-4H-pyrazole-4-carboxylic acid [2-(2,4-dichloro-phenyl)-2-methoxy-1-methyl-ethyl]-amide.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. No. 5,478,855, U.S. Pat. No. 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp aizawai, kurstaki, *Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with the following: imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide; more preferably, enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone; even more preferably enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

Examples of ratios include 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrates, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool), cultured fish, honeybees. By combating parasites, fatalities and performance reduction (in terms of meat, milk, wool, skins, eggs, etc.) are reduced, so that applying the compounds of the invention allows more economic and simple husbandry of animals.

By controlling these pests it is intended to reduce deaths and improve performance (in the case of meat, milk, wool, hides, eggs, honey and the like) and health of the host animal. Also, controlling parasites may help to prevent the transmittance of infectious agents, the term "controlling" referring to the veterinary field, meaning that the active compounds are effective in reducing the incidence of the respective parasite in an animal infected with such parasites to innocuous levels, e.g. the active compound is effective in killing the respective parasite, inhibiting its growth, or inhibiting its proliferation.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc. and protozoae, such as coccidia).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma*.

Cestodes that are contemplated to be treated by the invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, (6$^{th}$ Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi*.

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites, e.g. insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like. These include e.g. flies such as *Haematobia* (Lyperosia) *irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola* (Damalinia) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Examples of species of animal health pesets include those from the order of the *Anoplurida*, for example *Haematopinus* spp., *Linognathus* spp., *Pediculus* spp., *Phtirus* spp., *Soleno-* potes spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus*; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi*; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca*; from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis*; from the order of the Heteropterida, for example *Cimex* spp., *Triatoma* spp., *Rhodnius* spp., *Panstrongylus* spp; from the order of the Blattarida, for example *Blatta orientalis, Periplaneta americana, Blattela germanica, Supella* spp. (e.g. *Suppella longipalpa*); from the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni*; from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi; Gasterophilus* spp., *Stomoxys* spp., *Trichodectes* spp., *Rhodnius* spp., *Ctenocephalides canis, Cimx lecturius, Ctenocephalides felis, Lucilia cuprina*; examples of acari include *Ornithodoros* spp., *Ixodes* spp., *Boophilus* spp.

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration; or by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection.

The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates.

Such feed concentrate-containing compositions can, in addition to the parasiticidal active ingredients, comprise additives promoting animal health or growth, improving quality of meat from animals for slaughter or otherwise useful to animal husbandry.

These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such asBHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly administration intervals (i.e. administering the compounds to the animal once every month).

The following Examples illustrate, but do not limit, the invention.

The following abbreviations were used in this section: DMF: dimethylformamide; THF: tetrahydrofuran; EtOAc: ethyl acetate; s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; M.p.=melting point; RT=retention time, $[M+H]^+$=molecular mass of the molecular cation, $[M-H]^-$=molecular mass of the molecular anion.

The following LC-MS methods were used to characterize the compounds:

| Method A | |
|---|---|
| MS | ZQ Mass Spectrometer from Waters (single quadrupole mass spectrometer), ionization method: electrospray, polarity: positive ionization, capillary (kV) 3.00, cone (V) 30.00, Extractor: 2.00 V, source temperature (° C.) 100, desolvation temperature (° C.) 250, cone gas flow (L/Hr) 50, desolvation gas flow (L/Hr) 400, mass range: 100 to 900 Da. |
| LC | 1100er Series HPLC from Agilent: quaternary pump, heated column compartment and diode-array detector.<br>Column: Phenomenex Gemini C18, 3 μm, 30 × 3 mm, Temp: 60° C.; DAD Wavelength range (nm): 210 to 500<br>Solvent gradient:<br>A = H2O + 5% MeOH + 0.05% HCOOH<br>B = Acetonitril + 0.05% HCOOH |

| Time (min) | Time (min) | Time (min) | Time (min) |
|---|---|---|---|
| 0.00 | 0.00 | 0.00 | 0.00 |
| 2.00 | 2.00 | 2.00 | 2.00 |
| 2.80 | 2.80 | 2.80 | 2.80 |
| 2.90 | 2.90 | 2.90 | 2.90 |

| Method B | |
|---|---|
| MS | ZMD Mass Spectrometer from Waters (single quadrupole mass spectrometer), ionization method: electrospray, polarity: positive ionization, capillary (kV) 3.80, cone (V) 30.00, extractor (V) 3.00, source temperature (° C.) 150, desolvation temperature (° C.) 350, cone gas flow (L/Hr) off, desolvation gas flow (L/Hr) 600, mass range: 100 to 900 Da. |
| LC | 1100er Series HPLC from Agilent: quaternary pump, heated column compartment and diode-array detector.<br>Column: Phenomenex Gemini C18, 3 μm, 30 × 3 mm, Temp: 60° C.; DAD Wavelength range (nm): 200 to 500<br>Solvent gradient:<br>A = H2O + 5% MeOH + 0.05% HCOOH<br>B = Acetonitril + 0.05% HCOOH |

| Time (min) | A % | B % | Flow (ml/min) |
|---|---|---|---|
| 0.00 | 100 | 0.0 | 1.700 |
| 2.00 | 0 | 100 | 1.700 |
| 2.80 | 0 | 100 | 1.700 |
| 2.90 | 100 | 0 | 1.700 |
| 3.00 | 100 | 0 | 1.700 |

Method C

MS  ACQUITY SQD Mass Spectrometer from Waters (Single quadrupole mass spectrometer)
Ionisation method: Electrospray
Polarity: positive ions
Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 100 to 800 Da
DAD Wavelength range (nm): 210 to 400

LC  Method Waters ACQUITY UPLC with the following HPLC gradient conditions (Solvent A: Water/Methanol 9:1, 0.1% formic acid and Solvent B: Acetonitrile, 0.1% formic acid )

| Time (min) | A % | B % | Flow (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Method D

CHIRAL HPLC  Alliance 2695 HPLC from Waters: solvent degasser, binary pump, heated column compartment and diode-array detector
Column: Chiralpak IB, length (mm) 250, internal diameter (mm) 4.6, particle size (μ) 5, wavelength (nm): 270 nm, temperature (° C.) 30, solvent: Isocratic isopropyl alcohol:heptanes:diethylamine 30:70:0.1, injection volume 50 uL, flow (ml/min) 1.

Method E

MS  ACQUITY SQD Mass Spectrometer from Waters (Single quadrupole mass spectrometer)
Ionisation method: Electrospray
Polarity: positive ions
Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 100 to 800 Da
DAD Wavelength range (nm): 210 to 400

LC  Method Waters ACQUITY UPLC with the following HPLC gradient conditions (Solvent A: Water/Methanol 9:1, 0.1% formic acid and Solvent B: Acetonitrile, 0.1% formic acid )

| Time (min) | A % | B % | Flow (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Method F

CHIRAL HPLC  Alliance 2695 HPLC from Waters: solvent degasser, binary pump, heated column compartment and diode-array detector
Column: Chiralpak IA, length (mm) 250, internal diameter (mm) 4.6, particle size (μ) 5, wavelength (nm): 270 nm, temperature (° C.) 30, solvent: Isocratic isopropyl alcohol:heptanes 10:90, injection volume 50 uL, flow (ml/min) 1.

Method G

MS  LC-20AD Mass Spectrometer from Shimadzu (Single quadrupole mass spectrometer)
Ionisation method: Electrospray
Polarity: positive and negative ions
Capillary (kV) 1.50, Extractor (V) 5.00, Source Temperature (° C.) 200, Desolvation -continued Temperature (° C.) 250, Cone Gas Flow (L/Hr) 90, Desolvation Gas Flow (L/Hr) 90
Mass range: 50 to 1000 Da LC Method Waters ACQUITY UPLC with the following HPLC gradient conditions (Solvent A: Water, 0.1% trifluoroacetic acid and Solvent B: Acetonitrile, 0.1% trifluoroacetic acid)

| Time (min) | A % | B % | Flow (ml/min) |
|---|---|---|---|
| 0 | 90 | 10 | 1.00 |
| 15.00 | 0 | 100 | 1.00 |
| 25.00 | 0 | 100 | 1.00 |
| 27.00 | 90 | 10 | 1.00 |
| 36.00 | 90 | 10 | 1.00 |

EXAMPLE 1

2-{2-Chloro-4-[5-(3,5-Dichloro-phenyl)-5-trifluoromethyl-4,5-dihydro-isoxazol-3-yl]-phenylsulfanyl}-N-(2,2,2-trifluoro-ethyl)-acetamide (compound A29)

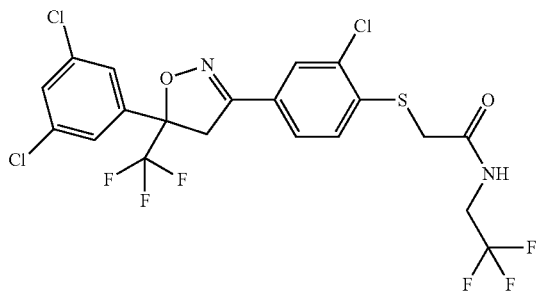 [SMILES: O=C(CSc1ccc(C2=NOC(c3cc(Cl)cc(Cl)c3)(C(F)(F)F)C2)cc1Cl)NCC(F)(F)F]

Step A: 3-Chloro-4-fluoro-benzaldehyde oxime

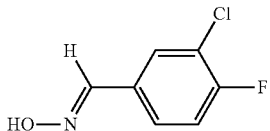

A stirred solution of 3-chloro-4-fluorobenzaldehyde (6 g) in ethanol (80 ml) at room temperature was treated with 50% aqueous hydroxylamine (3.7 g) and the resulting solution was stirred at room temperature for 3 hours. The reaction mixture was concentrated in vacuo and the resulting oily residue was dissolved in ethyl acetate, washed with water, brine then dried over sodium sulphate. The solvent was removed under reduced pressure to afford the crude title compound (6.33 g), which was used as such for the next step. LCMS (Method A) RT 1.49 min, [M+H]$^+$ 174/176.

Step B: 5-(3,5-Dichloro-phenyl)-3-(3-chloro-4-fluoro-phenyl)-5-trifluoromethyl-4,5-dihydro-isoxazole

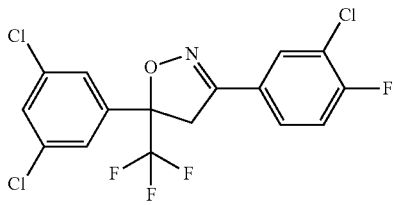

To a solution of 3-chloro-4-fluoro-benzaldehyde oxime (6.2 g) in DMF (80 ml) at 0° C. was added N-chlorosuccinimide (4.8 g) portionwise. The resulting mixture was stirred at room temperature for 3 hours, then cooled to 0° C. and was 1,3-dichloro-5-(1-trifluoromethyl-vinyl)-benzene (13 g, prepared as described in WO 2009/080250) was added followed by triethylamine (7.5 ml). The reaction mixture was allowed to stir at room temperature for 24 hours, diluted with ethyl acetate, the organic layer was washed with water (3×75 ml) and brine solution then dried over sodium sulphate. The solvent was removed under reduced pressure to afford the crude product (18 g), which was purified with the Comb flash Rf200, (column of 220 g), eluted with heptane/ethyl acetate to obtain the title compound as yellow solid (11 g). LCMS (Method A) RT 2.30 min. $^1$H-NMR (CDCl$_3$, 400 MHz): 3.69 (d, 1H), 4.06 (d, 1H), 7.20-7.70 (m, 6H).

Step C: {2-Chloro-4-[5-(3,5-dichloro-phenyl)-5-trifluoromethyl-4,5-dihydro-isoxazol-3-yl]-phenyl-sulfanyl}-acetic acid methyl ester

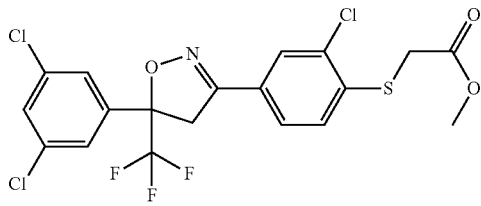 [SMILES: COC(=O)CSc1ccc(C2=NOC(c3cc(Cl)cc(Cl)c3)(C(F)(F)F)C2)cc1Cl]

To a solution of 5-(3,5-dichloro-phenyl)-3-(3-chloro-4-fluoro-phenyl)-5-trifluoromethyl-4,5-dihydro-isoxazole (825 mg) and potassium carbonate (700 mg) in DMF (10 ml) was added methyl thioglycolate (0.20 ml) at room temperature and the reaction mixture was stirred for 1 hour, diluted with ethyl acetate then poured into water. The mixture was extracted with ethyl acetate (3×10 ml), the organic layers were combined, washed with water (5×30 ml), brine solution then dried over sodium sulphate. The solvent was removed under reduced pressure to afford the crude title compound, which was purified by flash chromatography (heptane/EtOAc 80/20) to afford the title compound as a yellow solid (770 mg). LCMS (Method A) RT 2.35 min. [M+H]$^+$ 498/500.

$^1$H-NMR (CDCl$_3$, 400 MHz): 3.69 (1, 2H), 3.70 (s, 2H), 3.75 (s, 3H), 4.05 (d, 1H), 7.35-7.65 (m, 6H).

Step D: {2-Chloro-4-[5-(3,5-dichloro-phenyl)-5-trifluoromethyl-4,5-dihydro-isoxazol-3-yl]-phenyl-sulfanyl}-acetic acid

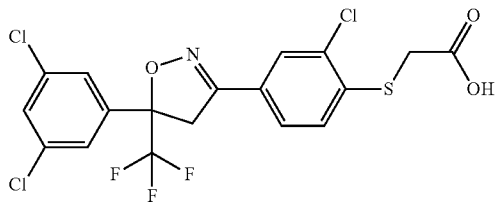

A mixture of {2-chloro-4-[5-(3,5-dichloro-phenyl)-5-trifluoromethyl-4,5-dihydro-isoxazol-3-yl]-phenylsulfanyl}-acetic acid methyl ester (700 mg) and 2N NaOH solution (2.2 ml) in ethanol (15 ml) was stirred at room temperature for 1 hour then the solvent was removed under reduced pressure. The residue was dissolved in ethyl acetate then washed with HCl 1N solution, dried over sodium sulphate and concentrated in vacuo to yield 690 mg of the crude title compound as a solid (690 mg). LCMS (Method A) RT 2.33 min. [M−H]$^-$ 482/484. $^1$H-NMR (DMSO, 400 MHz): 3.45 (s, 2H), 4.30 (d, 1H), 4.35 (d, 1H), 7.40 (d, 1H), 7.6 (d, 1H), 7.62 (m, 2H), 7.7 (s, 1H), 7.80 (t, 1H).

Step E: 2-{2-Chloro-4-[5-(3,5-dichloro-phenyl)-5-trifluoromethyl-4,5-dihydro-isoxazol-3-yl]-phenyl-sulfanyl}-N-(2,2,2-trifluoro-ethyl)-acetamide

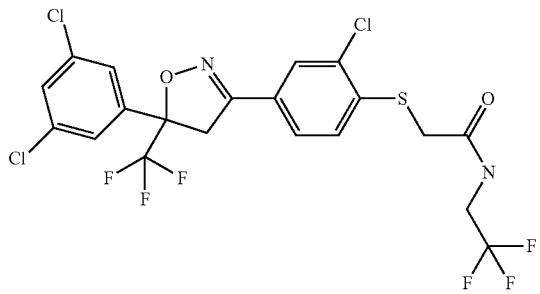 [SMILES: O=C(CSc1ccc(C2=NOC(c3cc(Cl)cc(Cl)c3)(C(F)(F)F)C2)cc1Cl)NCC(F)(F)F]

To a mixture containing 2,2,2-trifluoroethylamine (78 mg), 7-aza-1-hydroxybenzotriazol (AZA.HOBT, 110 mg), O-Benzotriazole-1-yl-N,N,N',N'-tetramethyluronium tetrafluoroborate (TBTU, 257 mg) and triethylamine (0.16 ml) in acetonitrile (7 ml), was added 4-[5-(3,5-dichloro-phenyl)-5-trifluoromethyl-4,5-dihydro-isoxazol-3-yl]-phenylsulfanyl}-acetic acid (320 mg), and triethylamine (0.16 ml) dissolved in acetonitrile (8 ml) over 15 min at room temperature under argon atmosphere. The resulting reaction mixture was stirred overnight at room temperature, quenched with aqueous ammonium chloride solution then extracted with ethyl acetate. The combined organic layers were washed with water, brine, dried over sodium sulphate, filtered and concentrated under reduced pressure to dryness. The product was purified by chromatography, (Isolute Flash, column of 4 g), eluted with dichloromethane and methanol to afford the title product (50 mg). LCMS (Method B) RT 608 min, [M+CH$_3$CN]$^+$606/608; $^1$H-NMR (CDCl$_3$, 400 MHz): 3.65 (d, 1H), 3.78 (s, 2H), 3.90 (m, 2H), 4.05 (d, 1H), 6.95 (br t, NH), 7.20 (d, 1H), 7.42 (s, 1H), 7.50 (m, 3H), 7.71 (s, 1H).

The following compounds were prepared following a similar method to that described in Example 1: 2-{2-bromo-4-[5-(3,5-dichloro-phenyl)-5-trifluoromethyl-4,5-dihydro-isoxazol-3-yl]-phenylsulfanyl}-N-(2,2,2-trifluoro-ethyl)-acetamide (compound A29)

EXAMPLE 2.1

2-{2-Methyl-4-[5-(3,5-Dichloro-phenyl)-5-trifluoromethyl-4,5-dihydro-isoxazol-3-yl]-phenylsulfanyl}-N-(2,2,2-trifluoro-ethyl)-acetamide (compound A49)

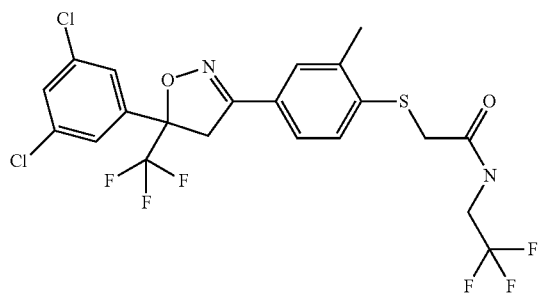 [SMILES: Cc1cc(C2=NOC(c3cc(Cl)cc(Cl)c3)(C(F)(F)F)C2)ccc1SCC(=O)NCC(F)(F)F]

Step A: 1-(4-Fluoro-3-methyl-phenyl)-ethanone

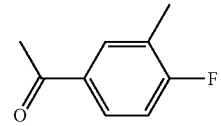

To a solution of 2-fluorotoluene (10.0 g, 90.8 mmol) and acetyl chloride (6.64 ml, 93.4 mmol) in dry CH$_2$Cl$_2$ (50 ml) was added portion-wise AlCl$_3$ (15.3 g, 115 mmol) (caution: vigorous exothermic reaction). The reaction was stirred at room temperature for 24 h. To complete the reaction, the mixture was heated to reflux for 2 h. The reaction mixture was quenched with saturated aqueous Na$_2$CO$_3$, diluted with Et$_2$O and filtered through a pad of Celite®. The organic phase was then separated, washed with saturated aqueous NaCl, dried over Na$_2$SO$_4$ and concentrated in vacuo. Purification by flash chromatography (SiO$_2$, Heptane:Ethylacetate 97:3 to 90:10) gave the title product as a pale brown oil (13.6 g). LCMS (Method B) RT 1.50 min. [M+H]$^+$ 153. $^1$H NMR (400 MHz, CDCl$_3$) 2.32 (d, 3H), 2.58 (s, 3H), 7.06 (t, 1H), 7.77-7.81 (m, 1H), 7.83 (d, 1H).

Step B: 5-(3,5-Dichloro-phenyl)-3-(4-fluoro-3-methyl-phenyl)-5-trifluoromethyl-4,5-dihydro-isoxazole

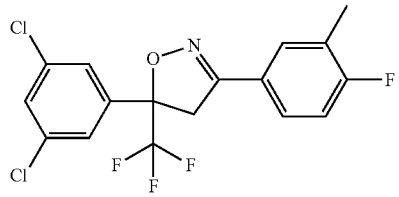 [SMILES: Cc1cc(C2=NOC(c3cc(Cl)cc(Cl)c3)(C(F)(F)F)C2)ccc1F]

A suspension of 1-(4-fluoro-3-methyl-phenyl)-ethanone (4.56 g), 1-(3,5-dichloro-phenyl)-2,2,2-trifluoro-ethanone (7.3 g) and potassium carbonate (4.1 g) in 1,2-dichloroethane (90 ml) was treated with triethylamine (0.4 ml) and the resulting mixture was heated at 100° C. for 12 hours. The reaction mixture was cooled to 0° C. and then tetrabutylammonium bromide (2.9 g), 4N sodium hydroxide aqueous solution (15 ml) and hydroxylamine (50% in water, 4.2 ml) were successively added and the resulting mixture was stirred at 0° C. for 3 hours. The reaction mixture was diluted with dichloromethane and neutralized with 1N hydrochloric acid. The aqueous layer was extracted with dichloromethane (2×50 ml) and then the organic layers were combined, washed with brine, dried over sodium sulphate and the solvent was removed under reduced pressure to afford the title product as a waxy yellow solid. M.p. 72-74° C. LCMS (Method A) RT 2.32 min. $[M+H]^+$ 392/394. $^1$H NMR (400 MHz, CDCl$_3$) 2.31 (s, 3H), 3.70 (d, 1H), 4.10 (d, 1H), 7.05 (m, 1H), 7.40-7.60 (m, 5H).

Step C: {4-[5-(3,5-Dichloro-phenyl)-5-trifluoromethyl-4,5-dihydro-isoxazol-3-yl]-2-methyl-phenylsulfanyl}-acetic acid methyl ester

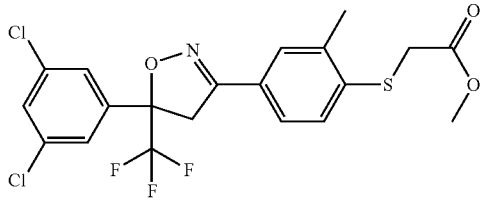 [SMILES: COC(=O)CSc1ccc(C2=NOC(c3cc(Cl)cc(Cl)c3)(C(F)(F)F)C2)cc1C]

A sealed tube is charged with 5-(3,5-dichloro-phenyl)-3-(4-fluoro-3-methyl-phenyl)-5-trifluoromethyl-4,5-dihydro-isoxazole (980 mg), cesium carbonate (900 mg) methyl thioglycolate (0.25 ml) and dimethylformamide (10 ml). The resulting mixture was heated at 130° C. overnight, then cooled to room temperature, and excess water was added. The mixture was extracted with ethyl acetate (3×30 ml) then the organic phase was washed with water (5×15 ml), 2N HCl, brine, then dried over sodium sulfate. The solvent was removed under reduced pressure to afford a crude residue, which was purified with the Comb flash Rf200, (column of 24 g), eluted with heptane/EtOAc. The title product was obtained as a solid (300 mg). LCMS (Method A) RT 1.95 min. $[M+H]^+$ 478/480. $^1$H NMR (400 MHz, CDCl$_3$) 2.39 (s, 3H), 3.70 (d, 1H), 3.71 (s, 2H), 3.73 (s, 3H), 4.08 (d, 1H), 7.30 (d, 1H), 7.41-7.53 (m, 5H).

Step D: {4-[5-(3,5-Dichloro-phenyl)-5-trifluoromethyl-4,5-dihydro-isoxazol-3-yl]-2-methyl-phenylsulfanyl}-acetic acid

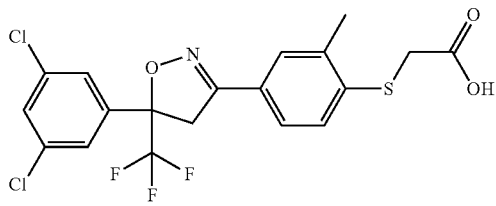 [SMILES: Cc1cc(C2=NOC(c3cc(Cl)cc(Cl)c3)(C(F)(F)F)C2)ccc1SCC(=O)O]

A mixture of {4-[5-(3,5-Dichloro-phenyl)-5-trifluoromethyl-4,5-dihydro-isoxazol-3-yl]-2-methyl-phenylsulfanyl}-acetic acid methyl ester (600 mg) and 2N NaOH solution (2 ml) in ethanol (13 ml) was stirred at room temperature for 1 hour then the solvent was removed under reduced pressure. The residue was dissolved in ethyl acetate then washed with HCl 1N solution, dried over sodium sulphate and concentrated in vacuo to yield 511 mg of the crude title compound as a solid (690 mg). LCMS (Method A) RT 2.14 min. $[M-H]^-$ 462/464. $^1$H NMR (400 MHz, CDCl$_3$) 2.40 (s, 3H), 3.69 (d, 1H), 3.71 (s, 2H), 4.07 (d, 1H), 7.30-7.60 (m, 6H).

Step E: 2-{4-[5-(3,5-Dichloro-phenyl)-5-trifluoromethyl-4,5-dihydro-isoxazol-3-yl]-2-methyl-phenylsulfanyl}-N-(2,2,2-trifluoro-ethyl)-acetamide

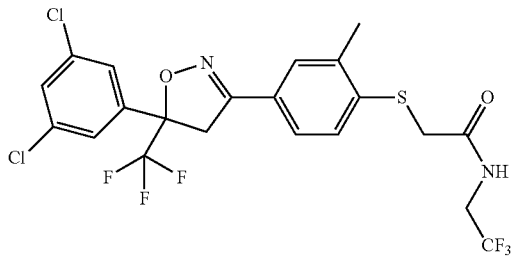 [SMILES: Cc1cc(C2=NOC(c3cc(Cl)cc(Cl)c3)(C(F)(F)F)C2)ccc1SCC(=O)NCC(F)(F)F]

To a mixture containing 2,2,2-trifluoroethylamine (0.036 ml), 7-aza-1-hydroxybenzotriazol (AZA.HOBT, 61 mg), O-Benzotriazole-1-yl-N,N,N',N'-tetramethyluronium tetrafluoroborate (TBTU, 144 mg) and triethylamine (0.185 ml) in acetonitrile (5 ml), was added {4-[5-(3,5-dichloro-phenyl)-5-trifluoromethyl-4,5-dihydro-isoxazol-3-yl]-2-methyl-phenylsulfanyl}-acetic acid (320 mg), and triethylamine (0.09 ml) dissolved in acetonitrile (5 ml) over 15 min at room temperature under argon atmosphere. The resulting reaction mixture was stirred overnight at room temperature, quenched with aqueous ammonium chloride solution then extracted with ethyl acetate. The combined organic layers were washed with water, brine, dried over sodium sulphate, filtered and concentrated under reduced pressure to dryness. The product was purified by chromatography, (Isolute Flash, column of 4 g), eluted with dichloromethane and methanol to afford the title product (122 mg). LCMS (Method A) RT 2.19 min, $[M+H]^+$ 545/547; $^1$H-NMR (CDCl$_3$, 400 MHz): 2.40 (s, 3H), 3.68 (d, 1H), 3.75 (s, 1H), 3.92 (m, 1H), 4.10 (d, 1H), 6.95 (br t, NH), 7.12 (d, 1H), 7.40 (d, 1H), 7.45 (t, 1H), 7.50-7.60 (m, 3H).

EXAMPLE 2.2

2-{2-Methyl-4-[5-(3,5-Dichloro-phenyl)-5-trifluoromethyl-4,5-dihydro-isoxazol-3-yl]-phenylsulfanyl}-N-(2,2,2-trifluoro-ethyl)-acetamide (compound A49)

Step A: (4-Acetyl-2-methyl-phenylsulfanyl)-acetic acid methyl ester

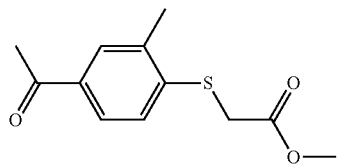 [SMILES: COC(=O)CSc1ccc(C(C)=O)cc1C]

A sealed tube is charged with 1-(4-fluoro-3-methyl-phenyl)-ethanone (760 mg), cesium carbonate (2.4 g) methyl thioglycolate (0.67 ml) and dimethylformamide (15 ml). The resulting mixture was heated at 130° C. overnight, then cooled to room temperature, and excess water was added. The mixture was extracted with ethyl acetate (3×30 ml) then the organic phase was washed with water (5×15 ml), 2N HCl, brine, then dried over sodium sulfate. The solvent was removed under reduced pressure to afford a crude yellow oil, which was purified with the Comb flash Rf200, (column of 24 g), eluted with heptane/EtOAc. The title product was obtained as a solid (800 mg). LCMS (Method A) RT 1.53 min. [M+H]+ 239. 1H NMR (400 MHz, CDCl3) 2.40 (s, 3H), 2.58 (s, 3H), 3.77 (s, 3H), 3.78 (s, 2H), 7.30 (d, 1H), 7.75 (s, 1H), 7.77 (d, 1H).

Step B: {4-[5-(3,5-Dichloro-phenyl)-5-trifluoromethyl-4,5-dihydro-isoxazol-3-yl]-2-methyl-phenylsulfanyl}-acetic acid methyl ester

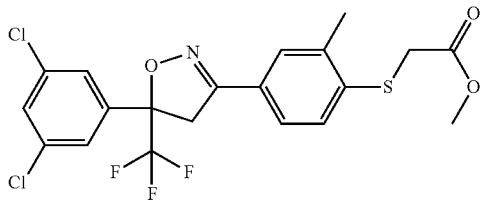 [SMILES: COC(=O)CSc1ccc(C2=NOC(c3cc(Cl)cc(Cl)c3)(C(F)(F)F)C2)cc1C]

A suspension of (4-acetyl-2-methyl-phenylsulfanyl)-acetic acid methyl ester (800 mg), 1-(3,5-dichloro-phenyl)-2,2,2-trifluoro-ethanone (802 mg), potassium carbonate (455 mg), triethylamine (0.05 ml) in 1,2-dichloroethane (10 ml), was heated at 100° C. for 12 hours. The reaction mixture was cooled to 0° C. and then tetrabutylammonium bromide (322 mg), 4N sodium hydroxide aqueous solution (0.82 ml) and hydroxylamine (50% in water, 0.2 ml) were successively added and the resulting mixture was stirred at 0° C. for 3 hours. The reaction mixture was diluted with dichloromethane and neutralized with 1N hydrochloric acid. The aqueous layer was extracted with dichloromethane and then the organic layers were combined, washed with brine, dried over sodium sulphate and the solvent was removed under reduced pressure to afford the title product as a waxy yellow solid. LCMS (Method A) RT 1.95 min. [M+H]+ 479/481. 1H NMR (400 MHz, CDCl3) 2.39 (s, 3H), 3.70 (d, 1H), 3.71 (s, 2H), 3.73 (s, 3H), 4.08 (d, 1H), 7.30 (d, 1H), 7.41-7.53 (m, 5H).

Step C: {4-[5-(3,5-Dichloro-phenyl)-5-trifluoromethyl-4,5-dihydro-isoxazol-3-yl]-2-methyl-phenylsulfanyl}-acetic acid

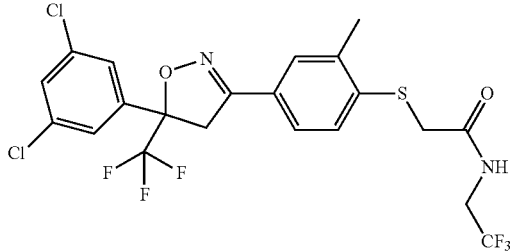 [SMILES: Cc1cc(C2=NOC(c3cc(Cl)cc(Cl)c3)(C(F)(F)F)C2)ccc1SCC(=O)NCC(F)(F)F]

The title product was obtained from {4-[5-(3,5-dichloro-phenyl)-5-trifluoromethyl-4,5-dihydro-isoxazol-3-yl]-2-methyl-phenylsulfanyl}-acetic acid methyl ester as already described in Example 2.1, step D and E.

EXAMPLE 2.3

2-{2-Methyl-4-[5-(3,5-Dichloro-phenyl)-5-trifluoromethyl-4,5-dihydro-isoxazol-3-yl]-phenylsulfanyl}-N-(2,2,2-trifluoro-ethyl)-acetamide (compound A49)

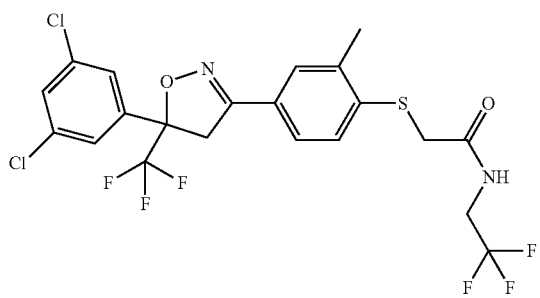 [SMILES: Cc1cc(C2=NOC(c3cc(Cl)cc(Cl)c3)(C(F)(F)F)C2)ccc1SCC(=O)NCC(F)(F)F]

Step A: 5-(3,5-Dichloro-phenyl)-3-(4-bromo-3-methyl-phenyl)-5-trifluoromethyl-4,5-dihydro-isoxazole

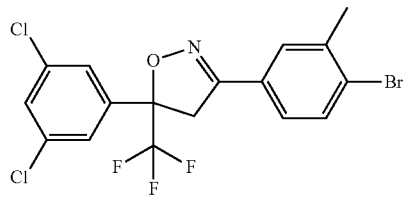 [SMILES: Cc1cc(C2=NOC(c3cc(Cl)cc(Cl)c3)(C(F)(F)F)C2)ccc1Br]

4-Bromo-3-methylbenzaldehyde (25 g) was dissolved in ethanol (285 ml) and water (85 ml) then sodium acetate (11.8 g) and hydroxylamine hydrochloride (10 g) were added. The reaction mixture was stirred at room temperature for 10 min, then ethanol was evaporated in vacuo. The residue was extracted with ethyl acetate, washed with water, then 2N sodium hydroxide, then water and brine. The organic layers were combined, dried over sodium sulfate, filtered and evaporated. The residue (yellow oil) was crystallised from cyclohexane to afford 4-bromo-3-methylbenzaldehyde oxime as white crystals (19.2 g). LCMS (Method A) RT 1.63 min. [M+H]+ 215/216. 1H NMR (400 MHz, CDCl3) 2.45 (s, 3H), 7.30-7.60 (m, 4H), 8.10 (s, 1H). To a solution of 3-chloro-4-bromo-benzaldehyde oxime (15 g) in DMF (1400 ml) at room temperature was added N-chlorosuccinimide (9.4 g). The resulting mixture was stirred at room temperature for 2 hours, then 1,3-dichloro-5-(1-trifluoromethyl-vinyl)-benzene (18.5 g, prepared as described in WO 2009/080250) in DMF (45 ml) was added followed by triethylamine (7.1 ml) in DMF (90 ml) dropwise over 4 hours. The reaction mixture was allowed to stir at room temperature for 24 hours, diluted with ethyl acetate, the organic layer was washed with water (3×75 ml) and brine solution then dried over sodium sulphate. The solvent was removed under reduced pressure to afford the crude product, which was purified with crystallisation from cyclohexane. White crystals (27 g). LCMS (Method A) RT 2.40 min. ¹H-NMR (CDCl₃, 400 MHz): 2.46 (s, 3H), 3.70 (d, 1H), 4.10 (d, 1H), 7.35-7.62 (m, 6H).

Step B: {4-[5-(3,5-Dichloro-phenyl)-5-trifluoromethyl-4,5-dihydro-isoxazol-3-yl]-2-methyl-phenylsulfanyl}-acetic acid tert-butyl ester

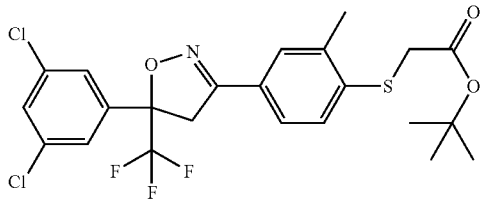 [SMILES: Cc1cc(C2=NOC(c3cc(Cl)cc(Cl)c3)(C(F)(F)F)C2)ccc1SCC(=O)OC(C)(C)C]

In sealed tube were charged 5-(3,5-Dichloro-phenyl)-3-(4-bromo-3-methyl-phenyl)-5-trifluoromethyl-4,5-dihydro-isoxazole (455 mg), N,N-diisopropylethyl amine (0.33 ml), tert-Butyl thioglycolate (148 mg), tris(dibenzylideneacetone)dipalladium (46 mg), Xantphos (58 mg) and 1,4-dioxan (5 ml). The reaction mixture was heated under microwave irradiation at 120° C. for 30 min, then cooled to room temperature and filtered through a pad of celite. The filtrate was concentrated in vacuo to afford 750 mg of a resin which was purified by flash chromatography with ISCO Rf200 machine, column silica 4 g, Heptane/EtOAc to give the title product as a yellow resin (220 mg). LCMS (Method A) RT 2.53 min, [M+H]⁺ 520/522. ¹H-NMR (CDCl₃, 400 MHz): 1.36 (s, 9H), 2.30 (s, 3H), 3.55 (s, 2H), 3.60 (d, 1H), 4.00 (d, 1H), 7.20-7.45 (m, 6H).

Step C: {4-[5-(3,5-Dichloro-phenyl)-5-trifluoromethyl-4,5-dihydro-isoxazol-3-yl]-2-methyl-phenyl-sulfanyl}-acetic acid

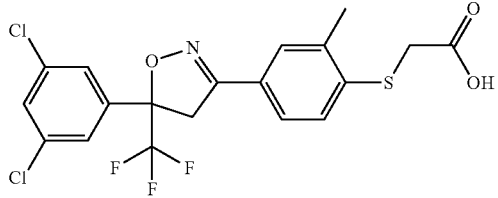 [SMILES: Cc1cc(C2=NOC(c3cc(Cl)cc(Cl)c3)(C(F)(F)F)C2)ccc1SCC(=O)O]

A solution of {4-[5-(3,5-dichloro-phenyl)-5-trifluoromethyl-4,5-dihydro-isoxazol-3-yl]-2-methyl-phenylsulfanyl}-acetic acid tert-butyl ester (200 mg) in dichloromethane (6 ml) was treated with trifluoroacetic acid (0.43 ml) for 1 hour at room temperature then the solution was concentrated in vacuo to afford the crude title acid (180 mg) as a yellow resin. LCMS (Method A) RT 2.26 min, [M+H]⁺464/466.

Step D: 2-{4-[5-(3,5-Dichloro-phenyl)-5-trifluoromethyl-4,5-dihydro-isoxazol-3-yl]-2-methyl-phenyl-sulfanyl}-N-(2,2,2-trifluoro-ethyl)-acetamide

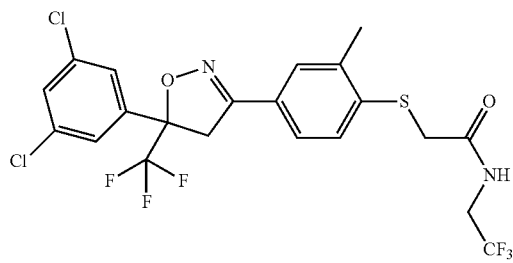 [SMILES: Cc1cc(C2=NOC(c3cc(Cl)cc(Cl)c3)(C(F)(F)F)C2)ccc1SCC(=O)NCC(F)(F)F]

The title product was obtained from {4-[5-(3,5-dichloro-phenyl)-5-trifluoromethyl-4,5-dihydro-isoxazol-3-yl]-2-methyl-phenylsulfanyl}-acetic acid as already described in Example 2.1, step E.

EXAMPLE 3

2-{4-[5-(3,5-Dichloro-phenyl)-5-trifluoromethyl-4,5-dihydro-isoxazol-3-yl]-2-methyl-benzenesulfinyl}-N-(2,2,2-trifluoro-ethyl)-acetamide (compound A50)

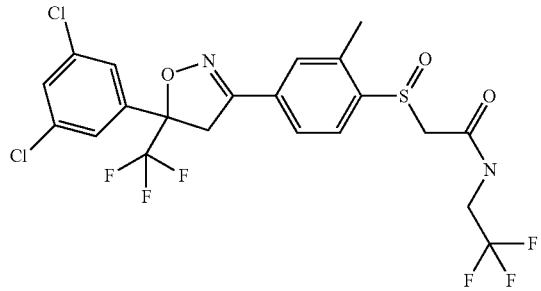 [SMILES: Cc1cc(C2=NOC(c3cc(Cl)cc(Cl)c3)(C(F)(F)F)C2)ccc1S(=O)CC(=O)NCC(F)(F)F]

To a solution of 2-{4-[5-(3,5-dichloro-phenyl)-5-trifluoromethyl-4,5-dihydro-isoxazol-3-yl]-2-methyl-phenylsulfanyl}-N-(2,2,2-trifluoro-ethyl)-acetamide (44 mg) in dichloromethane (4 ml) at 0° C. was added a solution of sodium hydrogenocarbonate (40 mg) in water (1.5 ml) then 3-chloroperbenzoic acid (70% w/w, 22 mg). The resulting mixture was allowed to stir at room temperature for 1 hour. The reaction mixture was then extracted with dichloromethane then the organic phase was washed twice with water, dried over anhydrous sodium sulfate, filtered and evaporated to give the crude product (50 mg) as a solid. Purification by chromatography using the ISCO Rf machine (dichloromethane then 5% methanol) afforded the title product (41 mg) as a white solid and a mixture of diastereomers. M.p. 80-83° C. LCMS (Method B) RT 2.11 min, [M+H]⁺ 561/563. ¹H-NMR (CDCl₃, 400 MHz): 2.35 (s, 3H), 3.40 (d, 1H), 3.65 (d, 1H), 3.70-3.90 (m, 2H), 3.75 (d, 1H), 4.05 (d, 1H), 7.20-7.80 (m, 6H).

The following compounds were prepared following a similar method to that described in Example 3: 2-{2-Bromo-4-[5-(3,5-dichloro-phenyl)-5-trifluoromethyl-4,5-dihydro-isoxazol-3-yl]-benzenesulfinyl}-N-(2,2,2-trifluoro-ethyl)-acetamide (compound A78); 2-{2-Chloro-4-[4-(3,5-dichloro-phenyl)-4-trifluoromethyl-4,5-dihydro-3H-pyrrol-2-yl]-benzenesulfinyl}-N-(2,2,2-trifluoro-ethyl)-acetamide (compound B2).

EXAMPLE 4

2-{4-[5-(3,5-Dichloro-phenyl)-5-trifluoromethyl-4,5-dihydro-isoxazol-3-yl]-2-methyl-benzenesulfonyl}-N-(2,2,2-trifluoro-ethyl)-acetamide (compound A51)

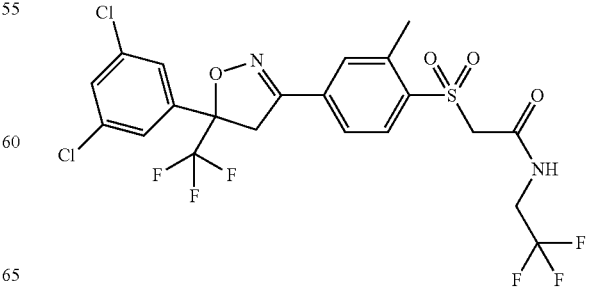

To a solution of 2-{4-[5-(3,5-dichloro-phenyl)-5-trifluoromethyl-4,5-dihydro-isoxazol-3-yl]-2-methyl-phenylsulfanyl}-N-(2,2,2-trifluoro-ethyl)-acetamide (55 mg) in dichloromethane (4 ml) at 0° C. was added a solution of sodium hydrogenocarbonate (50 mg) in water (1.5 ml) then 3-chloroperbenzoic acid (70% w/w, 62 mg). The resulting mixture was allowed to stir at room temperature for 1 hour. The reaction mixture was then extracted with dichloromethane then the organic phase was washed twice with water, dried over anhydrous sodium sulfate, filtered and evaporated to give the crude product (70 mg) as a solid. Purification by chromatography using the ISCO Rf machine (dichloromethane then 5% methanol) afforded the title product (56 mg) as a white solid. M.p. 68-70° C. LCMS (Method B) RT 2.16 min, [M+H]$^+$ 577/579. $^1$H-NMR (CDCl$_3$, 400 MHz): 2.80 (s, 3H), 3.70 (d, 1H), 3.92 (m, 2H), 4.10 (d, 1H), 4.17 (s, 2H), 7.40-8.00 (m, 6H).

The following compounds were prepared following a similar method to that described in Example 4:; 2-{2-Bromo-4-[5-(3,5-dichloro-phenyl)-5-trifluoromethyl-4,5-dihydro-isoxazol-3-yl]-benzenesulfonyl}-N-(2,2,2-trifluoro-ethyl)-acetamide (compound A53); 2-{2-chloro-4-[4-(3,5-Dichloro-phenyl)-4-trifluoromethyl-4,5-dihydro-3H-pyrrol-2-yl]-benzenesulfonyl}-N-(2,2,2-trifluoro-ethyl)-acetamide (compound B3).

EXAMPLE 5

2-{2-Chloro-4-[4-(3,5-dichloro-phenyl)-4-trifluoromethyl-4,5-dihydro-3H-pyrrol-2-yl]-phenylsulfanyl}-N-(2,2,2-trifluoro-ethyl)-acetamide (compound B1)

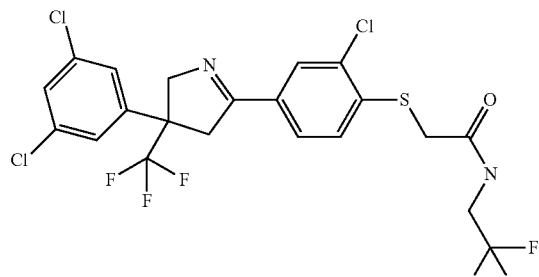

Step A: 3-Chloro-4-fluoro-N-trimethylsilanylmethyl-benzamide

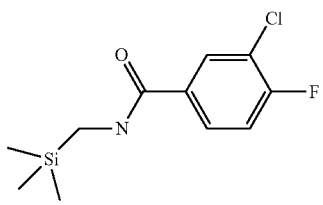 [SMILES: C[Si](C)(C)CNC(=O)c1ccc(F)c(Cl)c1]

To a solution of 3-chloro-4-fluorobenzoic acid (4.6 g) in dichloromethane (100 ml) was added oxalyl chloride (2.5 ml). A drop of DMF (0.01 ml) was added and the reaction mixture was stirred at room temperature during 18 hours. The solution was then concentrated to give a colorless oil, which was diluted in toluene (20 ml). This solution was added dropwise (in approximately 20 minutes) to a mixture of trimethylsilylmethylamine (4 ml) and triethylamine (10 ml) in toluene (40 ml). The solution was stirred at room temperature during 1 hour, then 200 ml of ethyl acetate were added, and the resulting solution was washed twice with water (2×100 ml) and brine (50 ml). The organic phase was then dried over anhydrous sodium sulfate, filtered and evaporated to give the crudetitle compound as a solid (6.4 g). LCMS (Method C)RT 0.98 min, [M+H]$^+$ 258/260. $^1$H-NMR (CDCl$_3$, 400 MHz): 0.00 (s, 9H), 2.81 (s, 2H), 5.90 (m, 1H), 7.05 (m, 1H), 7.49 (m, 1H), 7.70 (m, 1H).

Step B: 3-Chloro-4-fluoro-N-trimethylsilanylmethyl-thiobenzamide

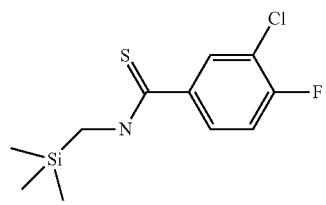 [SMILES: C[Si](C)(C)CNC(=S)c1ccc(F)c(Cl)c1]

To a solution of 3-chloro-4-fluoro-N-trimethylsilanylmethyl-benzamide (6.5 g) in toluene (70 ml) was added Lawerson's reagent (11 g) and the reaction mixture was stirred at reflux during 1 hour. The reaction mixture was concentrated to afford a yellow oil, which was with the Comb flash Rf200 (column of 220 g), eluted with-heptane/ethyl acetate to obtain the title compound as a yellow solid (5.5 g). LCMS (Method A) RT 1.98 min, [M+H]$^+$ 276/278. $^1$H-NMR (CDCl$_3$, 400 MHz): 0.00 (s, 9H), 3.32 (d, 2H), 6.93 (t, 1H), 7.38 (m, 1H), 7.40 (br m, 1H), 7.56 (m, 1H).

Step C: 3-Chloro-4-fluoro-N-trimethylsilanylmethyl-thiobenzimidic acid methyl ester

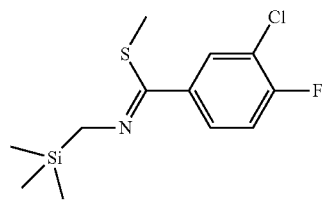 [SMILES: CS/C(=N\C[Si](C)(C)C)c1ccc(F)c(Cl)c1]

Under an argon atmosphere, 3-chloro-4-fluoro-N-trimethylsilanylmethyl-thiobenzamide (5.5 g) was dissolved in butanone (100 ml), followed by the addition of potassium carbonate (5 g). The reaction mixture was then allowed to stir at reflux for 1 hour, whereupon the solution was cooled to room temperature. Methyl iodide (1.9 ml) was then added dropwise, and the reaction mixture was stirred at room temperature for 16 hours. The solvent was evaporated, then 100 ml of water was added to the mixture. The organic layer was extracted twice with ethyl acetate, dried over anhydrous sodium sulphate, filtered and evaporated to give of a yellow liquid, which was purified with the Comb flash Rf200 (column of 220 g), eluted with heptane/ethyl acetate to give the title compound as a yellow solid (4.6 g). LCMS (Method B)

RT 1.81 min, [M+H]+ 290/292. ¹H-NMR (CDCl₃, 400 MHz): 0.00 (s, 9H), 2.00 (s, 3H), 3.52 (s, 2H), 7.00-7.50 (m, 3H).

Step D: 3-(3,5-Dichloro-phenyl)-5-(3-chloro-4-fluoro-phenyl)-3-trifluoromethyl-3,4-dihydro-2H-pyrrole

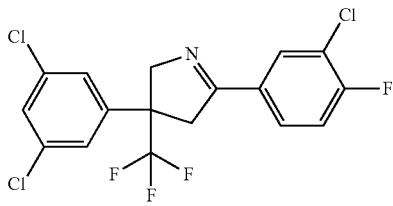 [SMILES: Fc1ccc(C2=NCC(c3cc(Cl)cc(Cl)c3)(C(F)(F)F)C2)cc1Cl]

To a solution of 3-chloro-4-fluoro-N-trimethylsilanylmethyl-thiobenzimidic acid methyl ester (4.6 g) and 1,3-dichloro-5-(1-trifluoromethyl-vinyl)-benzene (4.0 g, prepared as described in WO 2009/080250) in THF (250 ml) at −5° C. was added dropwise a solution of tetrabutylammonium fluoride (1M in THF, 0.75 ml) solution. The solution turned from yellow to orange during the addition, and then turned slowly to black color. The resulting mixture was stirred at 0° C. for 4 hours and the solvent was removed in vacuo. The residue (8 g) was purified with the Comb flash Rf200 (column of 220 g), eluted with heptane/ethyl acetate to give the title compound as a yellow solid (4.5 g). LCMS (Method A) RT 2.22 min, [M+H]+ 410/412. ¹H-NMR (CDCl₃, 400 MHz): 3.45 (d, 2H), 3.80 (d, 2H), 4.45 (d, 2H), 4.95 (d, 2H), 7.20-8.00 (m, 6H).

Step E: {2-Chloro-4-[4-(3,5-dichloro-phenyl)-4-trifluoromethyl-4,5-dihydro-3H-pyrrol-2-yl]-phenylsulfanyl}-acetic acid tert-butyl ester

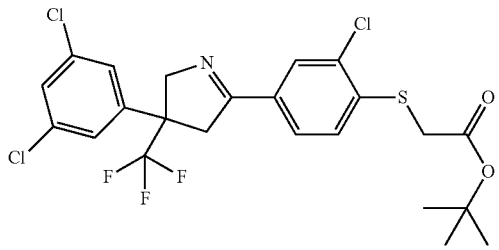 [SMILES: CC(C)(C)OC(=O)CSc1ccc(C2=NCC(c3cc(Cl)cc(Cl)c3)(C(F)(F)F)C2)cc1Cl]

A sealed tube is charged with 3-(3,5-dichloro-phenyl)-5-(3-chloro-4-fluoro-phenyl)-3-trifluoromethyl-3,4-dihydro-2H-pyrrole (410 mg), cesium carbonate (490 mg), tert-butyl thioglycolate (148 mg) and DMF (5 ml). The resulting mixture is heated at 130° C. overnight then the reaction mixture was cooled to rt and excess water was added. The mixture was extracted with EtOAc (3×30 ml) then the organic phase was washed with water (5×15 ml), 2N HCl, brine solution and then dried over sodium sulphate. The solvent was removed under reduced pressure to dryness and the residue was purified with the Comb flash Rf200, (column of 12 g), eluted with-heptanes/EtOAc then EtOAc to afford the title compound as a yellow oil. LCMS (Method B) RT 2.27 min, [M+H]+ 538/540; ¹H-NMR (d-DMSO, 400 MHz): 1.50 (s, 9H), 3.45 (d, 2H), 3.70 (s, 2H), 3.76 (d, 2H), 4.46 (d, 1H), 4.90 (d, 1H), 7.20-7.90 (m, 6H).

Step F: {2-Chloro-4-[4-(3,5-dichloro-phenyl)-4-trifluoromethyl-4,5-dihydro-3H-pyrrol-2-yl]-phenylsulfanyl}-acetic acid

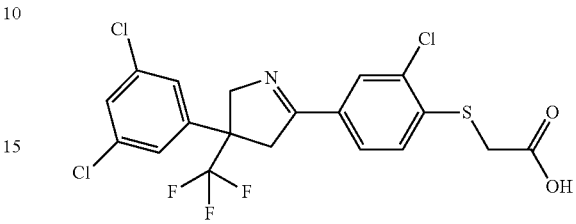

A solution of {2-chloro-4-[4-(3,5-dichloro-phenyl)-4-trifluoromethyl-4,5-dihydro-3H-pyrrol-2-yl]-phenylsulfanyl}-acetic acid tert-butyl ester (600 mg) in dichloromethane (15 ml) was treated with trifluoroacetic acid (2.2 ml) for 1 hour at room temperature then the solution was concentrated in vacuo to afford a yellow resin, which was triturated in diethyl ether to afford the title compound as a solid (300 mg). LCMS (Method A) RT 2.12 min, [M+H]+ 482/484. ¹H-NMR (d-DMSO, 400 MHz): 3.75 (d, 1H), 3.90 (d, 1H), 4.05 (s, 2H), 4.42 (d, 1H), 4.85 (d, 1H), 7.45 (d, 1H), 7.60 (s, 2H), 7.70 (s, 1H), 7.85 (d, 1H), 7.95 (s, 1H).

Step G: 2-{2-Chloro-4-[4-(3,5-dichloro-phenyl)-4-trifluoromethyl-4,5-dihydro-3H-pyrrol-2-yl]-phenyl-sulfanyl}-N-(2,2,2-trifluoro-ethyl)-acetamide

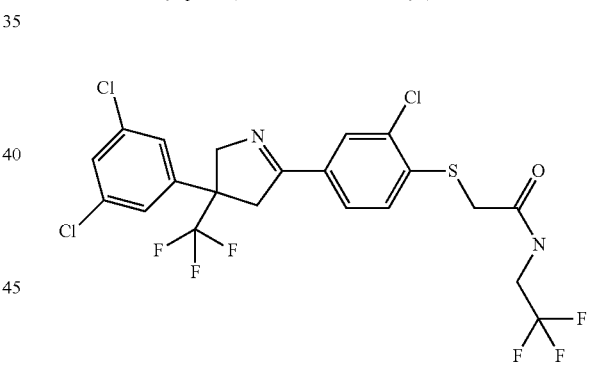

A solution of, 2,2,2-trifluoroethylamine (0.095 ml), 7-aza-1-hydroxybenzotriazol (AZA.HOBT, 163 mg), O-Benzotriazole-1-yl-N,N,N',N'-tetramethyluronium tetrafluoroborate (TBTU, 385 mg) and triethylamine (0.45 ml) in acetonitrile (10 ml), was added {2-chloro-4-[4-(3,5-dichloro-phenyl)-4-trifluoromethyl-4,5-dihydro-3H-pyrrol-2-yl]-phenylsulfanyl}-acetic acid (472 mg) and triethylamine (0.45 ml) dissolved in acetonitrile (10 ml) over 15 min at room temperature under argon atmosphere. The resulting reaction mixture was stirred overnight at room temperature, quenched with aqueous ammonium chloride solution then extracted with ethyl acetate. The combined organic layers were washed with water, brine, dried over sodium sulphate, filtered and concentrated under reduced pressure to dryness. The product was purified by with the Combiflash Rf200, (column of 12 g), eluted with heptane/EtOAc to afford the title product (95 mg) as solid. M.p. 189° C.; LCMS (Method A) RT 2.12 min, [M+H]+ 565/567; ¹H-NMR (CDCl₃, 400 MHz): 3.45 (d, 1H), 3.78 (d, 1H), 3.80 (s, 2H), 4.48 (d, 1H), 4.91 (d, 1H), 7.00 (br t, NH), 7.20-7.40 (m, 4H), 7.71 (d, 1H), 7.95 (s, 1H).

EXAMPLE 6

General Method for Preparing the Compounds of the Invention in Parallel

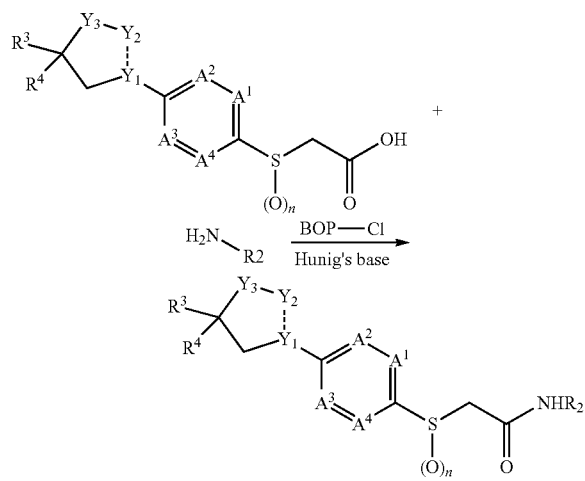

To a solution of carboxylic acid (20 µmol) in N,N-dimethylacetamide ("DMA") (0.4 ml) was added successively a solution of an amine (26 µmol) in N,N-dimethylacetamide ("DMA") (0.4 ml), diisopropylethylamine (Hunig's Base) (0.03 ml), and a solution of bis(2-oxo-3-oxazolidinyl)phosphonic chloride ("BOP—Cl") (10.2 mg) in N,N-dimethylacetamide ("DMA") (0.2 ml). The reaction mixture was stirred at 90° C. for 16 hours. The reaction mixture was concentrated and the crude mixture was redissolved in acetonitrile/N,N-dimethylacetamide (4:1) (0.8 ml) and purified by HPLC. This method was used to prepare a number of compounds (Compound Nos. A1-A49) in parallel.

EXAMPLE 7.1

2-{4-[(S)-5-(3,5-Dichloro-phenyl)-5-trifluoromethyl-4,5-dihydro-isoxazol-3-yl]-2-methyl-phenylsulfanyl}-N-(2,2,2-trifluoro-ethyl)-acetamide (Compound C1)

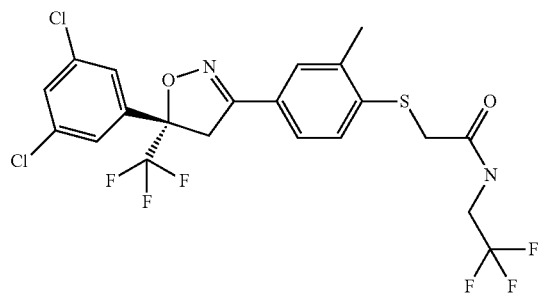 [SMILES: Cc1cc(C2=NO[C@@](c3cc(Cl)cc(Cl)c3)(C(F)(F)F)C2)ccc1SCC(=O)NCC(F)(F)F]

Step A: (4-Acetyl-2-methyl-phenylsulfanyl)-acetic acid

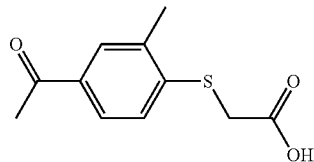

A mixture of (4-acetyl-2-methyl-phenylsulfanyl)-acetic acid methyl ester (4.3 g, Example 2.2, Step A), 2N sodium hydroxide (55 ml) and ethanol (180 ml) was stirred at room temperature for 1 hour and the solvent was removed in vacuo. The residue was dissolved in ethyl acetate, washed with 1N HCl, dried over sodium sulphate and concentrated in vacuo to afford the title compound as a yellow solid (3.7 g). LCMS (Method A) RT 1.34 min, [M–H]+ 223; 1H-NMR (CDCl3, 400 MHz): 2.31 (s, 3H), 2.50 (s, 3H), 3.72 (s, 2H), 7.21 (d, 1H), 7.68 (s, 1H), 7.70 (m, 1H), 8.0-9.0 (br m, 1H).

Step B: 2-(4-Acetyl-2-methyl-phenylsulfanyl)-N-(2,2,2-trifluoro-ethyl)-acetamide

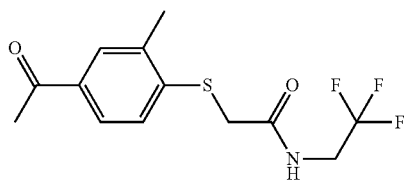 [SMILES: CC(=O)c1ccc(SCC(=O)NCC(F)(F)F)c(C)c1]

A solution of, 2,2,2-trifluoroethylamine (2 ml), 7-aza-1-hydroxybenzotriazol (AZA.HOBT, 3.54 g), O-Benzotriazole-1-yl-N,N,N',N'-tetramethyluronium tetrafluoroborate (TBTU, 8.4 g) and triethylamine (4 ml) in acetonitrile (165 ml), was added (4-Acetyl-2-methyl-phenylsulfanyl)-acetic acid (3.7 g) and triethylamine (4 ml) dissolved in acetonitrile (165 ml) over 15 min at room temperature under argon atmosphere. The resulting reaction mixture was stirred overnight at room temperature, quenched with aqueous ammonium chloride solution then extracted with ethyl acetate. The combined organic layers were washed with water, brine, dried over sodium sulphate, filtered and concentrated under reduced pressure to dryness. The product was purified by with the Combiflash Rf200, (column of 120 g), eluted with heptane/EtOAc to afford the title product (2.5 g) as solid. LCMS (Method A) RT 1.47 min, [M+H]+ 306; 1H-NMR (CDCl3, 400 MHz): 2.31 (s, 3H), 2.50 (s, 3H), 3.70 (s, 2H), 3.72 (m, 2H), 6.90 (br t, NH), 7.03 (d, 1H), 7.67 (d, 1H), 7.70 (s, 1H). 19F-NMR (CDCl3, 400 MHz): –72.4

Step C: 2-{4-[(E)-3-(3,5-Dichloro-phenyl)-4,4,4-trifluoro-but-2-enoyl]-2-methyl-phenylsulfanyl}-N-(2,2,2-trifluoro-ethyl)-acetamide

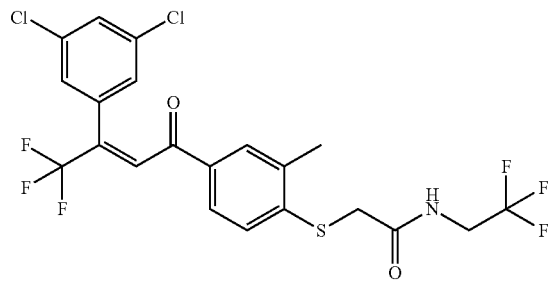 [SMILES: Cc1cc(C(=O)/C=C(\c2cc(Cl)cc(Cl)c2)C(F)(F)F)ccc1SCC(=O)NCC(F)(F)F]

A suspension of 2-(4-acetyl-2-methyl-phenylsulfanyl)-N-(2,2,2-trifluoro-ethyl)-acetamide (3.5 g), 1-(3,5-dichloro-phenyl)-2,2,2-trifluoro-ethanone (2.1 g), potassium carbonate (1.2 g), and triethylamine (0.11 ml) in 1,2-dichloroethane (20 ml), was heated at 100° C. for 12 hours. The reaction mixture was cooled to room temperature, partitioned between dichloromethane and water. The aqueous layer was separated, extracted with dichloromethane and the combined organic layers were dried over sodium sulphate and the solvent removed in vacuo. The residue was purified by with the Combiflash Rf200, (column of 120 g), eluted with heptane/EtOAc to afford the title product (2.8 g) as a yellow oil. LCMS (Method A) RT 2.10 min, [M+H]$^+$ 530/532; $^1$H-NMR (CDCl$_3$, 400 MHz): 2.31 (s, 3H), 3.70 (s, 2H), 3.82 (m, 2H), 6.80 (br t, NH), 7.01 (d, 1H), 7.09 (d, 2H), 7.25 (t, 1H), 7.28 (s, 1H), 7.55-7.58 (m, 2H). $^{19}$F-NMR (CDCl$_3$, 400 MHz): -72.4, -66.4.

Step D: Catalyst Preparation:
1-Anthracen-9-ylmethyl quininium chloride

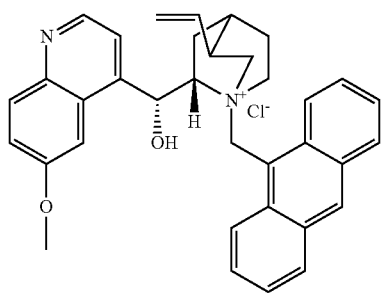 [SMILES: C=CC1C[N+]2(Cc3c4ccccc4cc4ccccc34)CCC1C[C@H]2[C@H](O)c1ccnc2ccc(OC)cc12 ; [Cl-]]

A solution of 9-chloromethylanthracene (25 g) and quinine (36 g) in toluene (650 ml) was heated at 80° C. for 18 hours. The yellow suspension was cooled to room temperature, poured into diethyl ether and the solid collected by filtration. Yellow solid (52.9 g). LCMS (method A) 1.31 min, M$^+$ 515; M.p. 150-152° C. (decomposed). LCMS (method H) 1.31 min, M$^+$ 515; $^1$H NMR (400 MHz, CDCl$_3$) 9.15 (d, 1H), 8.65 (d, 1H), 8.53 (d, 1H), 8.40 (s, 1H), 8.00 (m, 3H), 7.88 (d, 1H), 7.71 (s, 1H), 7.68 (t, 1H), 7.53 (t, 1H), 7.45 (m, 2H), 7.33 (dd, 1H), 7.11 (d, 1H), 7.02 (d, 1H), 6.22 (d, 1H), 5.51 (m, 1H), 5.15 (m, 1H), 4.98 (m, 2H), 4.38 (m, 1H), 3.98 (s, 3H), 3.48 (m, 1H), 2.90 (m, 1H), 2.63 (t, 1H), 2.20 (m, 2H), 1.85 (m, 2H), 1.45 (m, 2H).

Step E: 2-{4-[(S)-5-(3,5-Dichloro-phenyl)-5-trifluoromethyl-4,5-dihydro-isoxazol-3-yl]-2-methyl-phenylsulfanyl}-N-(2,2,2-trifluoro-ethyl)-acetamide

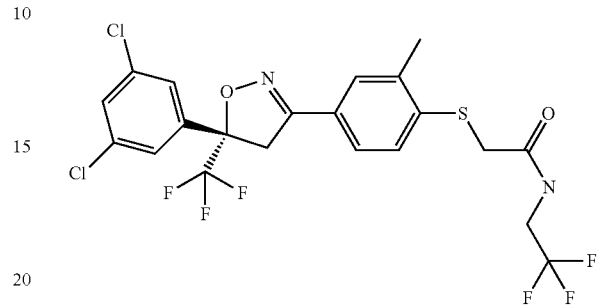

To a solution of 2-{4-[(E)-3-(3,5-Dichloro-phenyl)-4,4,4-trifluoro-but-2-enoyl]-2-methyl-phenylsulfanyl}-N-(2,2,2-trifluoro-ethyl)-acetamide (530 mg) in chloroform (5 ml) was added 1-anthracen-9-ylmethyl quininium chloride (110 mg). The reaction mixture was cooled at -15° C. then hydroxylamine (50% in water, 0.2 ml) and cesium hydroxide (10 N in water, 0.27 ml) were added. The reaction was stirred at -15° C. for 3 hour then at room temperature overnight. The mixture was diluted with water and extracted with dichloromethane several times; the combined organic layers were dried over sodium sulphate and the solvent evaporated under reduced pressure to obtain a brown gum. The residue was treated with saturated aqueous ammonium chloride solution, then extracted with ethyl acetate. The combined organic layers were washed with water, brine, dried over sodium sulphate, filtered and concentrated under reduced pressure to afford a residue (600 mg), which was purified by with the Combiflash Rf200, (column of 24 g), eluted with heptane/EtOAc to afford the title product (470 mg g) as a yellow solid. LCMS (Method A) RT 2.13 min, [M+H]$^+$ 545/547; $^1$H-NMR (CDCl$_3$, 400 MHz): 2.40 (s, 3H), 3.68 (d, 1H), 3.75 (s, 1H), 3.92 (m, 1H), 4.10 (d, 1H), 6.95 (br t, NH), 7.12 (d, 1H), 7.40 (d, 1H), 7.45 (t, 1H), 7.50-7.60 (m, 3H). $^{19}$F-NMR (CDCl$_3$, 400 MHz): -79.5, -72.4. The product was analysed by chiral HPLC (method D): 5.53 min (88.1%), 7.24 min (10.5%).

Step F: enantiomeric enrichment of 2-{4-[(S)-5-(3,5-dichloro-phenyl)-5-trifluoromethyl-4,5-dihydro-isoxazol-3-yl]-2-methyl-phenylsulfanyl}-N-(2,2,2-trifluoro-ethyl)-acetamide (compound C1)

2-{4-[(S)-5-(3,5-Dichloro-phenyl)-5-trifluoromethyl-4,5-dihydro-isoxazol-3-yl]-2-methyl-phenylsulfanyl}-N-(2,2,2-trifluoro-ethyl)-acetamide obtained in Step E (200 mg, ee 78%) was dissolved in diethyl ether (7 ml) and stored at 0° C. for 24 hours. The precipitated solid was filtered off and the solution was concentrated in vacuo to afford 2-{4-[(S)-5-(3,5-dichloro-phenyl)-5-trifluoromethyl-4,5-dihydro-isoxazol-3-yl]-2-methyl-phenylsulfanyl}-N-(2,2,2-trifluoro-ethyl)-acetamide as a white solid (190 mg). The product was analysed by chiral HPLC (method D): 5.99 min (96%).

The following compound was prepared following a similar method to that described in Example 7.1: 2-{4-[(S)-5-(3,5-Dichloro-phenyl)-5-trifluoromethyl-4,5-dihydro-isoxazol-3-yl]-2-methyl-phenylsulfanyl}-N-(2,2,2-trifluoro-ethyl)- acetamide (compound C4). The product was analysed by chiral HPLC (method D): 5.23 min (100%).

2-{4-(S)-[5-(3,5-Dichloro-phenyl)-5-trifluoromethyl-4,5-dihydro-isoxazol-3-yl]-2-methyl-benzenesulfinyl}-N-(2,2,2-trifluoro-ethyl)-acetamide (Compound C2) was obtained from 2-{4-[(S)-5-(3,5-dichloro-phenyl)-5-trifluoromethyl-4,5-dihydro-isoxazol-3-yl]-2-methyl-phenylsulfanyl}-N-(2,2,2-trifluoro-ethyl)-acetamide prepared in Step F following the oxidation procedure described in Example 3. Similarly, 2-{4-(S)-[5-(3,5-dichloro-phenyl)-5-trifluoromethyl-4,5-dihydro-isoxazol-3-yl]-2-chloro-benzenesulfinyl}-N-(2,2,2-trifluoro-ethyl)-acetamide (Compound C5) was obtained as a mixture of diastereoisomers.

2-{4-(S)-[5-(3,5-Dichloro-phenyl)-5-trifluoromethyl-4,5-dihydro-isoxazol-3-yl]-2-methyl-benzenesulfonyl}-N-(2,2,2-trifluoro-ethyl)-acetamide (Compound C3) was obtained from 2-{4-[(S)-5-(3,5-dichloro-phenyl)-5-trifluoromethyl-4,5-dihydro-isoxazol-3-yl]-2-methyl-phenylsulfanyl}-N-(2,2,2-trifluoro-ethyl)-acetamide prepared in Step F following the oxidation procedure described in Example 3. Similarly, 2-{4-(S)-[5-(3,5-dichloro-phenyl)-5-trifluoromethyl-4,5-dihydro-isoxazol-3-yl]-2-chloro-benzenesulfonyl}-N-(2,2,2-trifluoro-ethyl)-acetamide (Compound C6) was obtained.

EXAMPLE 7.2

2-{4-[(S)-5-(3,5-Dichloro-phenyl)-5-trifluoromethyl-4,5-dihydro-isoxazol-3-yl]-2-methyl-phenylsulfanyl}-N-(2,2,2-trifluoro-ethyl)-acetamide

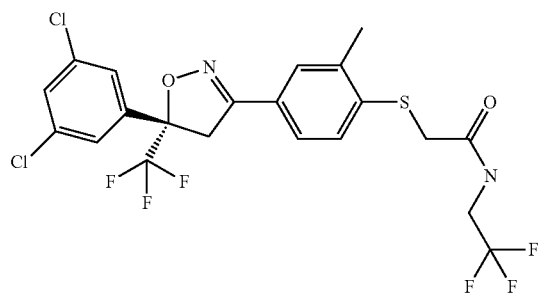 [SMILES: Cc1cc(C2=NO[C@@](c3cc(Cl)cc(Cl)c3)(C(F)(F)F)C2)ccc1SCC(=O)NCC(F)(F)F]

Step A: {4-[3-(3,5-Dichloro-phenyl)-4,4,4-trifluoro-but-2-enoyl]-2-methyl-phenylsulfanyl}-acetic acid methyl ester

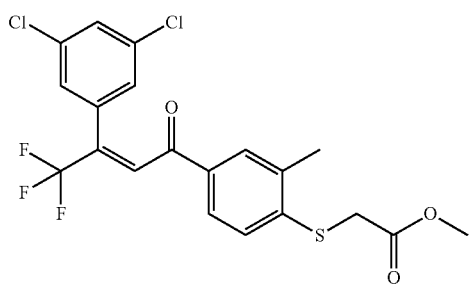 [SMILES: COC(=O)CSc1ccc(C(=O)/C=C(\c2cc(Cl)cc(Cl)c2)C(F)(F)F)cc1C]

A suspension of (4-acetyl-2-methyl-phenylsulfanyl)-acetic acid methyl ester (Example 2.2, Step A, 4.8 g), 1-(3,5-dichloro-phenyl)-2,2,2-trifluoro-ethanone (5 g), potassium carbonate (2.8 g), and triethylamine (0.03 ml) in 1,2-dichloroethane (25 ml), was heated at 100° C. for 12 hours. The reaction mixture was cooled to room temperature, partitioned between dichloromethane and water. The aqueous layer was separated, extracted with dichloromethane and the combined organic layers were dried over sodium sulphate and the solvent removed in vacuo. The residue (11 g) was purified by with the Combiflash Rf200, (column of 125 g), eluted with heptane/EtOAc to afford the title product (6.0 g) as a yellow oil. LCMS (Method A) RT 2.17 min, [M+H]$^+$ 463/465; $^1$H-NMR (CDCl$_3$, 400 MHz): 2.31 (s, 3H), 3.70 (s, 3H), 3.71 (s, 2H), 7.00-7.60 (m, 7H). $^{19}$F-NMR (CDCl$_3$, 400 MHz): −66.4.

Step B: Catalyst Preparation: 2,3,4,5,6-pentafluorophenyl-methyl quininium bromide

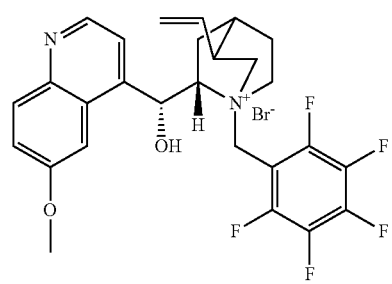 [SMILES: C=CC1C[N+]2(Cc3c(F)c(F)c(F)c(F)c3F)CCC1C[C@H]2[C@H](O)c1ccnc2ccc(OC)cc12 ; [Br-]]

A solution of 1-bromomethyl-2,3,4,5,6-pentafluorobenzene (0.52 g) and quinine (0.5 g) in toluene (9 ml) was heated at 80° C. for 18 hours. The reaction mixture was poured in diethyl ether and then filtrate to afford the title product as a white solid (0.90 g). M.p. 162-165° C. (decomposed). LCMS (method G) 1.08 min, M$^+$ 505; $^1$H NMR (400 MHz, CDCl$_3$) 8.78 (d, 1H), 8.05 (d, 1H), 7.78 (d, 1H), 7.39 (dd, 1H), 7.18 (d, 1H), 6.73 (m, 1H), 6.41 (d, 1H), 6.09 (d, 1H), 5.50 (m, 1H), 5.04 (d, 1H), 4.98 (d, 1H), 4.70 (m, 1H), 4.63 (d, 1H), 3.98 (s, 3H), 3.97 (m, 1H), 3.74 (m, 2H), 3.10 (m, 1H), 2.81 (m, 1H), 2.30 (m, 2H), 2.05 (m, 2H), 1.41 (m, 1H). $^{19}$F NMR (376 MHz, CDCl$_3$)-132.67 (s, 1F), −146.60 (s, 2F), −158.28 (s, 2F).

Step C.1: {4-[(S)-5-(3,5-Dichloro-phenyl)-5-trifluoromethyl-4,5-dihydro-isoxazol-3-yl]-2-methyl-phenylsulfanyl}-acetic acid

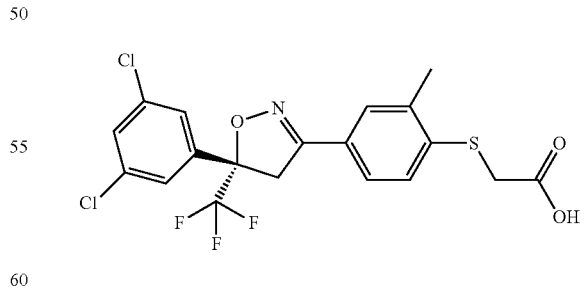

To a solution of 2,3,4,5,6-pentafluorophenyl-methyl quininium bromide (Example 7.2, Step B, 300 mg) in chloroform (5 ml) was added {4-[3-(3,5-dichloro-phenyl)-4,4,4-trifluoro-but-2-enoyl]-2-methyl-phenylsulfanyl}-acetic acid methyl ester (1.15 g) in chloroform (5 ml) and the resulting solution was cooled to −15° C. Aqueous sodium hydroxide (5M, 1 ml) diluted in water (2 ml) was added, followed by hydroxylamine (50% in water, 0.31 ml) diluted in water (2 ml). The reaction was stirred at −15° C. for 3 hour then at room temperature overnight. The mixture was diluted with water and extracted with dichloromethane several times; the combined organic layers were dried over sodium sulphate and the solvent evaporated under reduced pressure to obtain a brown gum. The residue was purified by with the a RediSep machine to afford the title product (430 mg) as a yellow solid. LCMS (Method A) RT 2.13 min, [M+H]+ 464/466 [M−H]+ 462/464; $^1$H-NMR (CDCl$_3$, 400 MHz): 2.31 (s, 3H), 3.60 (d, 1H), 3.69 (s, 2H), 3.98 (d, 1H), 4.10 (d, 1H), 7.20-7.45 (m, 6H).

Step C.2: {4-[(S)-5-(3,5-Dichloro-phenyl)-5-trifluoromethyl-4,5-dihydro-isoxazol-3-yl]-2-methyl-phenylsulfanyl}-acetic acid

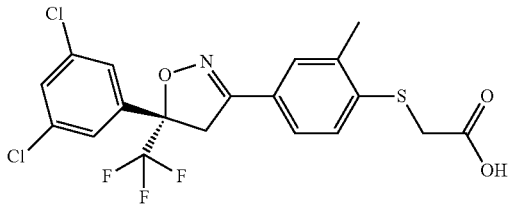 [SMILES: Cc1cc(C2=NO[C@@](c3cc(Cl)cc(Cl)c3)(C(F)(F)F)C2)ccc1SCC(=O)O]

To a solution of 1-anthracen-9-ylmethyl quininium chloride (Example 7.1, Step D, 315 mg) in chloroform (5 ml) was added {4-[3-(3,5-dichloro-phenyl)-4,4,4-trifluoro-but-2-enoyl]-2-methyl-phenylsulfanyl}-acetic acid methyl ester (1.15 g) in chloroform (5 ml) and the resulting solution was cooled to −15° C. Aqueous sodium hydroxide (5M, 1 ml) diluted in water (2 ml) was added, followed by hydroxylamine (50% in water, 0.31 ml) diluted in water (2 ml). The reaction was stirred at −15° C. for 3 hour then at room temperature overnight. The mixture was diluted with water and extracted with dichloromethane several times; the combined organic layers were dried over sodium sulphate and the solvent evaporated under reduced pressure to obtain a brown gum. The residue was purified by with a RediSep machine to afford the title product (480 mg) as a yellow solid.

Step C.3: {4-[(S)-5-(3,5-Dichloro-phenyl)-5-trifluoromethyl-4,5-dihydro-isoxazol-3-yl]-2-methyl-phenylsulfanyl}-acetic acid

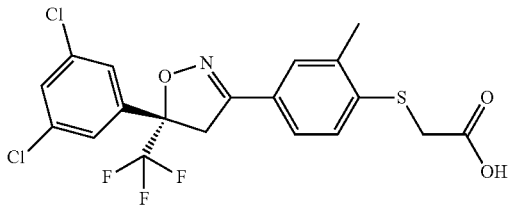 [SMILES: Cc1cc(C2=NO[C@@](c3cc(Cl)cc(Cl)c3)(C(F)(F)F)C2)ccc1SCC(=O)O]

To a solution of 2,3,4,5,6-pentafluorophenyl-methyl quininium bromide (Example 7.2, Step B, 300 mg) in chloroform (5 ml) was added {4-[3-(3,5-dichloro-phenyl)-4,4,4-trifluoro-but-2-enoyl]-2-methyl-phenylsulfanyl}-acetic acid methyl ester (1.15 g) in chloroform (5 ml) and the resulting solution was cooled to −15° C. Cesium hydroxide (1.12 g) diluted in water (4 ml) was added, followed by hydroxylamine (50% in water, 0.31 ml) diluted in water (1 ml). The reaction was stirred at −15° C. for 3 hour then at room temperature overnight. The mixture was diluted with water and extracted with dichloromethane several times; the combined organic layers were dried over sodium sulphate and the solvent evaporated under reduced pressure to obtain a brown gum. The residue was purified by with a RediSep machine to afford the title product (500 mg) as a yellow solid.

Step C.4: {4-[(S)-5-(3,5-Dichloro-phenyl)-5-trifluoromethyl-4,5-dihydro-isoxazol-3-yl]-2-methyl-phenylsulfanyl}-acetic acid

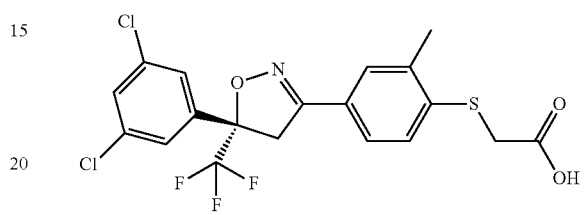

To a solution of 1-anthracen-9-ylmethyl quininium chloride (Example 7.1, Step D, 315 mg) in chloroform (5 ml) was added {4-[3-(3,5-dichloro-phenyl)-4,4,4-trifluoro-but-2-enoyl]-2-methyl-phenylsulfanyl}-acetic acid methyl ester (1.15 g) in chloroform (5 ml) and the resulting solution was cooled to −15° C. Cesium hydroxide (1.12 g) diluted in water (4 ml) was added, followed by hydroxylamine (50% in water, 0.31 ml) diluted in water (1 ml). The reaction was stirred at −15° C. for 3 hour then at room temperature overnight. The mixture was diluted with water and extracted with dichloromethane several times; the combined organic layers were dried over sodium sulphate and the solvent evaporated under reduced pressure to obtain a brown gum. The residue was purified by with a RediSep machine to afford the title product (220 mg) as a yellow solid.

Step D.1: 2-{4-[(S)-5-(3,5-Dichloro-phenyl)-5-trifluoromethyl-4,5-dihydro-isoxazol-3-yl]-2-methyl-phenylsulfanyl}-N-(2,2,2-trifluoro-ethyl)-acetamide

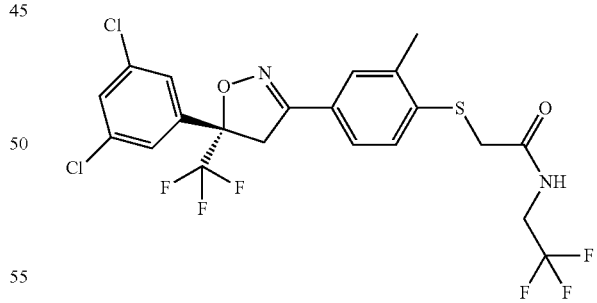

The title compound was obtained from {4-[(S)-5-(3,5-dichloro-phenyl)-5-trifluoromethyl-4,5-dihydro-isoxazol-3-yl]-2-methyl-phenylsulfanyl}-acetic acid (Step C.1, 450 mg) as described in Example 2.1, Step E. The product was purified by with the Combiflash Rf200, (column of 24 g), eluted with heptane/EtOAc to afford the title product (380 mg) as a yellow solid. LCMS (Method A) RT 2.13 min, [M+H]+ 545/547; $^1$H-NMR (CDCl$_3$, 400 MHz): 2.40 (s, 3H), 3.68 (d, 1H), 3.75 (s, 1H), 3.92 (m, 1H), 4.10 (d, 1H), 6.95 (br t, NH), 7.12 (d, 1H), 7.40 (d, 1H), 7.45 (t, 1H), 7.50-7.60 (m, 3H). $^{19}$F-NMR (CDCl₃, 400 MHz): −79.5, −72.4. The product was analysed by chiral HPLC (method D): 5.18 min (69.3%), 6.47 min (30.7%).

Step D.2: 2-{4-[(S)-5-(3,5-Dichloro-phenyl)-5-trifluoromethyl-4,5-dihydro-isoxazol-3-yl]-2-methylphenylsulfanyl}-N-(2,2,2-trifluoro-ethyl)-acetamide

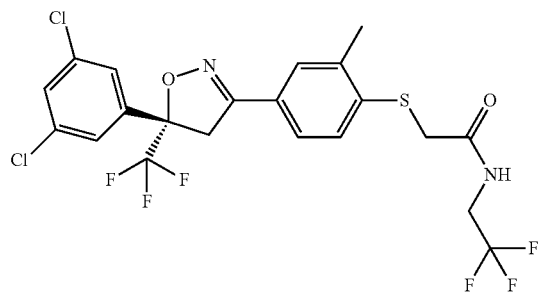 [SMILES: Cc1cc(C2=NO[C@@](c3cc(Cl)cc(Cl)c3)(C(F)(F)F)C2)ccc1SCC(=O)NCC(F)(F)F]

The title compound was obtained from {4-[(S)-5-(3,5-dichloro-phenyl)-5-trifluoromethyl-4,5-dihydro-isoxazol-3-yl]-2-methyl-phenylsulfanyl}-acetic acid (Step C.2, 350 mg) as described in Example 2.1, Step E. The product was purified by with the Combiflash Rf200, (column of 24 g), eluted with heptane/EtOAc to afford the title product (400 mg) as a yellow solid. LCMS (Method A) RT 2.13 min, [M+H]⁺ 545/547; ¹H-NMR (CDCl₃, 400 MHz): 2.40 (s, 3H), 3.68 (d, 1H), 3.75 (s, 1H), 3.92 (m, 1H), 4.10 (d, 1H), 6.95 (br t, NH), 7.12 (d, 1H), 7.40 (d, 1H), 7.45 (t, 1H), 7.50-7.60 (m, 3H). ¹⁹F-NMR (CDCl₃, 400 MHz): −79.5, −72.4. The product was analysed by chiral HPLC (method D): 5.11 min (86.5%), 6.38 min (13.5%).

Step D.3: 2-{4-[(S)-5-(3,5-Dichloro-phenyl)-5-trifluoromethyl-4,5-dihydro-isoxazol-3-yl]-2-methylphenylsulfanyl}-N-(2,2,2-trifluoro-ethyl)-acetamide

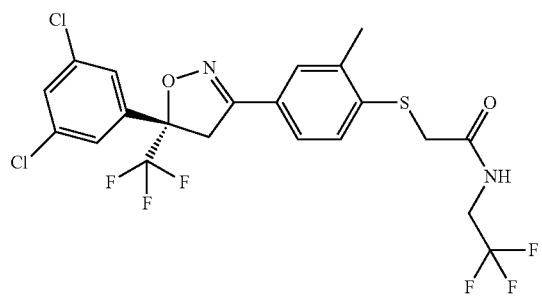 [SMILES: Cc1cc(C2=NO[C@@](c3cc(Cl)cc(Cl)c3)(C(F)(F)F)C2)ccc1SCC(=O)NCC(F)(F)F]

The title compound was obtained from {4-[(S)-5-(3,5-dichloro-phenyl)-5-trifluoromethyl-4,5-dihydro-isoxazol-3-yl]-2-methyl-phenylsulfanyl}-acetic acid (Step C.3, 470 mg) as described in Example 2.1, Step E. The product was purified by with the Combiflash Rf200, (column of 24 g), eluted with heptane/EtOAc to afford the title product (450 mg) as a yellow solid. LCMS (Method A) RT 2.13 min, [M+H]⁺ 545/547; ¹H-NMR (CDCl₃, 400 MHz): 2.40 (s, 3H), 3.68 (d, 1H), 3.75 (s, 1H), 3.92 (m, 1H), 4.10 (d, 1H), 6.95 (br t, NH), 7.12 (d, 1H), 7.40 (d, 1H), 7.45 (t, 1H), 7.50-7.60 (m, 3H). ¹⁹F-NMR (CDCl₃, 400 MHz): −79.5, −72.4. The product was analysed by chiral HPLC (method D): 5.01 min (87.1%), 6.22 min (12.9%).

Step D.4: 2-{4-[(S)-5-(3,5-Dichloro-phenyl)-5-trifluoromethyl-4,5-dihydro-isoxazol-3-yl]-2-methylphenylsulfanyl}-N-(2,2,2-trifluoro-ethyl)-acetamide

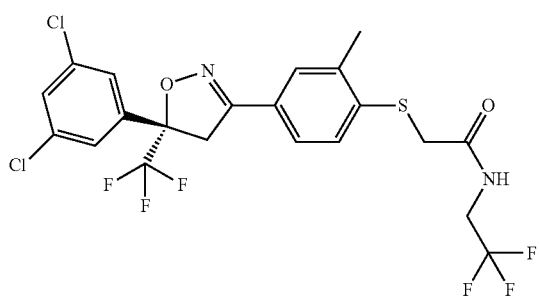 [SMILES: Cc1cc(C2=NO[C@@](c3cc(Cl)cc(Cl)c3)(C(F)(F)F)C2)ccc1SCC(=O)NCC(F)(F)F]

The title compound was obtained from {4-[(S)-5-(3,5-dichloro-phenyl)-5-trifluoromethyl-4,5-dihydro-isoxazol-3-yl]-2-methyl-phenylsulfanyl}-acetic acid (Step C.4, 200 mg) as described in Example 2.1, Step E. The product was purified by with the Combiflash Rf200, (column of 24 g), eluted with heptane/EtOAc to afford the title product (180 mg) as a yellow solid. LCMS (Method A) RT 2.13 min, [M+H]⁺ 545/547; ¹H-NMR (CDCl₃, 400 MHz): 2.40 (s, 3H), 3.68 (d, 1H), 3.75 (s, 1H), 3.92 (m, 1H), 4.10 (d, 1H), 6.95 (br t, NH), 7.12 (d, 1H), 7.40 (d, 1H), 7.45 (t, 1H), 7.50-7.60 (m, 3H). ¹⁹F-NMR (CDCl₃, 400 MHz): −79.5, −72.4. The product was analysed by chiral HPLC (method D): 5.02 min (87.1%), 6.23 min (12.9%).

EXAMPLE 8

2-[2-bromo-4-[(5S)-5-(3,5-dichlorophenyl)-5-(trifluoromethyl)-4H-isoxazol-3-yl]phenyl]sulfanyl-N-cyclopropyl-acetamide

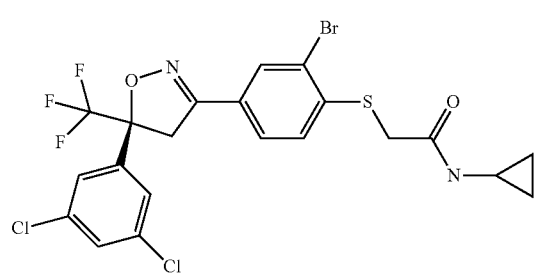 [SMILES: O=C(CSc1ccc(C2=NO[C@@](c3cc(Cl)cc(Cl)c3)(C(F)(F)F)C2)cc1Br)NC1CC1]

Step A:
1-(3-bromo-4-tert-butylsulfanyl-phenyl)ethanone

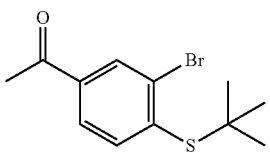

In a mechanically stirred reactor was charged dimethylformamide (350 mL), 1-(4-fluoro-3-bromo-phenyl)-ethanone (30 g), potassium carbonate (29 g) followed by tert-butylthiol (18.7 g). The resulting suspension was heated to 50° C. for 4 hours. The mixture was then cooled to room temperature and poured in brine (1 L), and the aqueous phase was extracted three times with ethyl acetate. The combined organic phases were washed with brine and dried over MgSO$_4$. The solvents were removed to leave the desired compound (40 g). LCMS (Method E) RT 1.11 min. [M+H]$^+$ 277-279. $^1$H NMR (400 MHz, CDCl$_3$) 1.40 (s, 9H), 2.59 (s, 3H), 7.70 (d, 1H), 7.71 (dd, 1H), 8.19 (d, 1H).

Step B: (E)-1-(3-bromo-4-tert-butylsulfanyl-phenyl)-3-(3,5-dichlorophenyl)-4,4,4-trifluoro-but-2-en-1-one

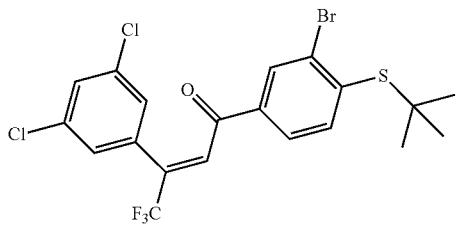 [SMILES: CC(C)(C)Sc1ccc(C(=O)/C=C(\c2cc(Cl)cc(Cl)c2)C(F)(F)F)cc1Br]

A suspension of 1-(3-bromo-4-tert-butylsulfanyl-phenyl) ethanone (Step A, 25.0 g), 1-(3,5-dichloro-phenyl)-2,2,2-trifluoro-ethanone (23.3 g), potassium carbonate (13.5 g), and triethylamine (1.2 ml) in 1,2-dichloroethane (500 ml), was heated at 85° C. for 16 hours. The reaction mixture was cooled to room temperature, partitioned between dichloromethane and water. The aqueous layer was separated, extracted with dichloromethane and the combined organic layers were dried over MgSO$_4$ and the solvent removed in vacuo. The residue (52.5 g) was purified by column chromatography on SiO2 with heptane/EtOAc (95:5) to afford the title product (22.8 g) as a yellow solid. LCMS (Method E) RT 1.37 min, [M+OH]$^+$ 527/529/531; $^1$H-NMR (CDCl$_3$, 400 MHz): 1.39 (s, 9H), 7.10 (s, 2H), 7.37 (m, 2H), 7.64 (m, 2H), 8.01 (s, 1H). $^{19}$F-NMR (CDCl$_3$, 400 MHz): −67.2.

Step D: (5S)-3-(3-bromo-4-tert-butylsulfanyl-phenyl)-5-(3,5-dichlorophenyl)-5-(trifluoromethyl)-4H-isoxazole

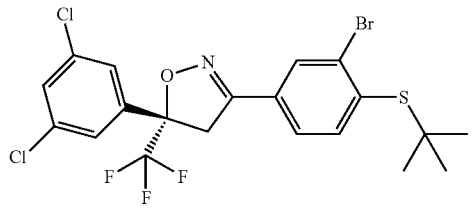 [SMILES: CC(C)(C)Sc1ccc(C2=NO[C@@](c3cc(Cl)cc(Cl)c3)(C(F)(F)F)C2)cc1Br]

To a solution of (E)-1-(3-bromo-4-tert-butylsulfanyl-phenyl)-3-(3,5-dichlorophenyl)-4,4,4-trifluoro-but-2-en-1-one (Step C, 1.0 g) in chloroform (50 ml) was added 1-anthracen-9-ylmethyl quininium chloride (220 mg). The reaction mixture was cooled at −20° C. then hydroxylamine (50% in water, 0.24 ml) and cesium hydroxide (10 N in water, 0.46 ml) were added simultaneously. The reaction was stirred at −20° C. for 2 hour and then brought back to room temperature. The mixture was diluted with water and extracted with dichloromethane several times; the combined organic layers were dried over MgSO$_4$ and the solvent evaporated under reduced pressure to obtain a brown gum (1 g) which was purified by with the Combiflash Rf200, (column of 48 g), eluted with heptane/EtOAc to afford the title product (834 mg) as a yellow solid. LCMS (Method E) RT 1.42 min, [M+Na]$^+$ 544/546/548; $^1$H-NMR (CDCl$_3$, 400 MHz): 1.38 (s, 9H), 3.68 (d, 1H), 4.07 (d, 1H), 7.43 (t, 1H), 7.50 (s, 2H), 7.59 (dd, 1H), 7.68 (d, 1H), 7.91 (d, 1H). $^{19}$F-NMR (CDCl$_3$, 400 MHz): −79.4. The product was analysed by chiral HPLC (method F): 2.39 min (85.2%), 3.21 min (14.8%).

Step E: 2-bromo-4-[(5S)-5-(3,5-dichlorophenyl)-5-(trifluoromethyl)-4H-isoxazol-3-yl]benzenethiol

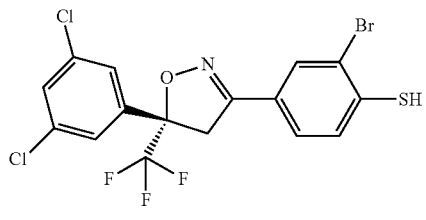 [SMILES: FC(F)(F)[C@@]1(c2cc(Cl)cc(Cl)c2)CC(c2ccc(S)c(Br)c2)=NO1]

To a solution of (5S)-3-(3-bromo-4-tert-butylsulfanyl-phenyl)-5-(3,5-dichlorophenyl)-5-(trifluoromethyl)-4H-isoxazole (5.0 g) in toluene (50 mL) was added toluene-4-sulfonic acid (3.33 g) and the reaction was heated at a 110° C. overnight. The reaction was cooled back down to room temperature and diluted in dichloromethane and washed with an aqueous saturated NaHCO$_3$ solution. The organic phase was dried over MgSO$_4$ and the solvents removed in vacuo to yield the crude product (5.3 g). The crude product was passed through a pad of silica and eluting with heptanes/ethyl acetate (8:1). The product obtained was then triturated with heptanes to yield the title compound as an off-white solide (3.5 g). LCMS (Method E) RT 1.33 min, [M−H]$^-$ 468/470/472; $^1$H-NMR (CDCl$_3$, 400 MHz): 3.64 (d, 1H), 4.03 (d, 1H), 4.17 (s, 1H, SH), 7.39 (d, 1H), 7.41 (m, 2H), 7.49 (m, 3H), 7.78 (d, 1H). $^{19}$F-NMR (CDCl$_3$, 400 MHz): −79.5.

Step F: 2-[2-bromo-4-[(5S)-5-(3,5-dichlorophenyl)-5-(trifluoromethyl)-4H-isoxazol-3-yl]phenyl]sulfanylacetic acid

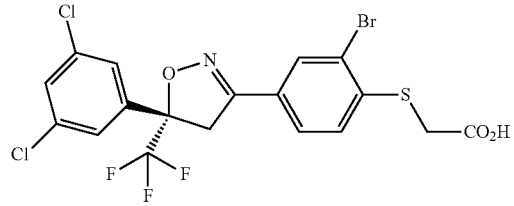 [SMILES: O=C(O)CSc1ccc(C2=NO[C@@](c3cc(Cl)cc(Cl)c3)(C(F)(F)F)C2)cc1Br]

To a solution of 2-bromo-4-[(5S)-5-(3,5-dichlorophenyl)-5-(trifluoromethyl)-4H-isoxazol-3-yl]benzenethiol (810 mg)

in THF (1 mL) was added water (3.5 mL) and chloroacetic acid (166 mg). To this biphasic mixture was added a NaOH solution (4 M, 0.86 mL) over 8 minutes during which time the mixture became homogeneous. The reaction was stited overnight at room temperature and was then acidified to pH 4 with HCl (4 M). The reaction was taken up with ethyl acetate. The reaction was extracted twice with ethyl acetate and the combined organic phases were dried $MgSO_4$ and the solvents evaporated in vacuo to yield the compound as an off-white solid (893 mg). LCMS (Method E) RT 1.25 min, [M−H]⁻ 526/528/530; ¹H-NMR (CDCl₃, 400 MHz): 3.65 (d, 1H), 3.76 (s, 2H), 4.02 (d, 1H), 7.32 (d, 1H), 7.41 (m, 1H), 7.49 (m, 2H), 7.58 (dd, 1H), 7.80 (d, 1H), 12.1 (bs, 1H, CO₂H). ¹⁹F-NMR (CDCl₃, 400 MHz): −79.4.

Step G: 2-[2-bromo-4-[(5S)-5-(3,5-dichlorophenyl)-5-(trifluoromethyl)-4H-isoxazol-3-yl]phenyl]sulfanyl-N-cyclopropyl-acetamide

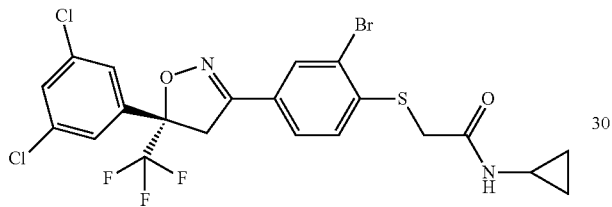

The title compound was obtained from 2-[2-bromo-4-[(5S)-5-(3,5-dichlorophenyl)-5-(trifluoromethyl)-4H-isoxazol-3-yl]phenyl]sulfanylacetic acid as described in Example 2.1, Step E. LCMS (Method E) RT 1.19 min, [M+H]⁺ 567/569/571; ¹H-NMR (CDCl₃, 400 MHz): 0.41 (m, 2H), 0.75 (m, 2H), 2.76 (m, 2H), 3.63 (d, 1H), 3.65 (s, 2H), 4.02 (d, 1H), 6.65 (s, 1H, NH), 7.17 (d, 1H), 7.41 (m, 1H), 7.52 (m, 2H), 7.54 (dd, 1H), 7.85 (d, 1H). ¹⁹F-NMR (CDCl₃, 400 MHz): −79.4.

EXAMPLE 9

Synthesis of N-cyclopropyl-2-[[6-[5-(3,5-dichlorophenyl)-5-(trifluoromethyl)-4H-isoxazol-3-yl]-4-methyl-3-pyridyl]sulfanyl]acetamide

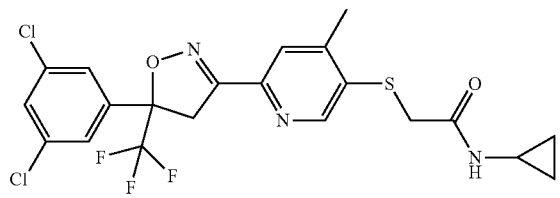 [SMILES: Cc1cc(C2=NOC(c3cc(Cl)cc(Cl)c3)(C(F)(F)F)C2)ncc1SCC(=O)NC1CC1]

Step A: Synthesis of 1-(5-bromo-4-methyl-2-pyridyl)ethanone

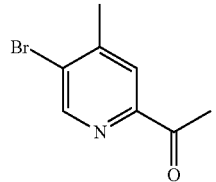

Compound 5-bromo-4-methyl-pyridine-2-carbonitrile (450 mg) dissolved in 5 ml of THF was added to a solution of CH₃MgBr (2 ml, 2.8 mol/L in THF) in 5 ml of THF at 0° C. After stirring for 1 h, the reaction mixture was poured into aqueous NH₄Cl, and extracted with ethyl acetate three times. The combined organic layers were washed with brine, dried over anhydrous Na₂SO₄ and concentrated under reduced pressure. The residue was purified by flash chromatography on silica gel to give the title compound (356 mg). ¹H NMR (300 Mz, CDCl₃): δ 2.47 (s, 3H), 2.70 (s, 3H), 7.91 (s, 1H), 8.69 (s, 1H).

Step B: Synthesis of 3-(5-bromo-4-methyl-2-pyridyl)-5-(3,5-dichlorophenyl)-5-(trifluoromethyl)-4H-isoxazole

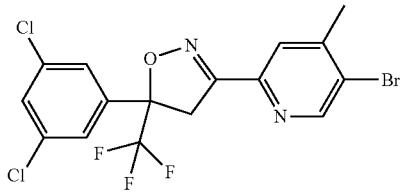 [SMILES: Cc1cc(C2=NOC(c3cc(Cl)cc(Cl)c3)(C(F)(F)F)C2)ncc1Br]

To a mixture of compound 1-(5-bromo-4-methyl-2-pyridyl)ethanone (428 mg), compound 1-(3,5-dichloro-phenyl)-2,2,2-trifluoro-ethanone (726 mg) and K₂CO₃ (345 mg) in 8 mL of dichlorethane was added Et₃N (20 mg). The mixture was refluxed for 20 h. After cooling to 0° C., Bu₄N⁺ Br⁻ (129 mg), NH₂OH.HCl ((276 mg) and NaOH (320 mg, 8 mmol, 4N) was added and the reaction mixture was stirred at room temperature for 16 h. Then, the reaction mixture was poured into diluted hydrochloric acid and extracted with ethyl acetate three times. The combined organic layers were dried over MgSO₄ and concentrated under reduced pressure. The residue was purified by flash column chromatography on silica gel to give the title compound (594 mg two-step yield). ¹H NMR (300 Mz, DMSO-d₆): δ 2.43 (s, 3H), 4.22 (d, 1H), 4.30 (d, 1H), 7.71 (s, 2H), 7.81 (s, 1H), 7.98 (s, 1H), 8.77 (s, 1H); ESI-MS: 453/455 (M+H⁺), 475/477 (M+Na⁺).

Step C: ethyl 2-[[6-[5-(3,5-dichlorophenyl)-5-(trifluoromethyl)-4H-isoxazol-3-yl]-4-methyl-3-pyridyl]sulfanyl]acetate

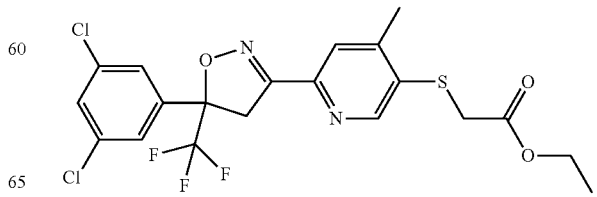

A mixture of compound Synthesis of 3-(5-bromo-4-methyl-2-pyridyl)-5-(3,5-dichlorophenyl)-5-(trifluoromethyl)-4H-isoxazole (453 mg), ethyl mercaptoacetate (180 mg) Pd(dba)₂ (288 mg), xantphos (289 mg) and DIPEA (194 mg) in 30 ml of dry 1,4-dioxane under nitrogen was refluxed for 8 h. The resulting mixture was poured into water and extracted with ethyl acetate three times. The organic phase was dried over anhydrous Na₂SO₄ and concentrated under reduced pressure. The residue was purified by flash column chromatography on silica gel to give the title compound (320 mg). $^1$H NMR (300 Mz, CDCl₃): δ 1.26 (t, 3H), 2.45 (s, 3H), 3.71 (s, 2H), 3.92 (d, 1H), 4.20 (q, 2H), 4.28 (d, 1H), 7.42 (s, 1H), 7.51 (s, 2H), 7.86 (s, 1H), 8.46 (s, 1H); E1-MS: 491 (M−1).

Step D: 2-[[6-[5-(3,5-dichlorophenyl)-5-(trifluoromethyl)-4H-isoxazol-3-yl]-4-methyl-3-pyridyl]sulfanyl]acetic acid

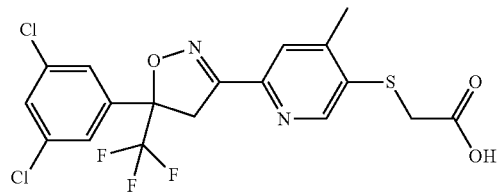 [SMILES: Cc1cc(C2=NOC(c3cc(Cl)cc(Cl)c3)(C(F)(F)F)C2)ncc1SCC(=O)O]

A mixture of compound ethyl 2-[[6-[5-(3,5-dichlorophenyl)-5-(trifluoromethyl)-4H-isoxazol-3-yl]-4-methyl-3-pyridyl]sulfanyl]acetate (380 mg) and LiOH.H₂O (42 mg) in 20 ml of THF and 10 ml of H₂O was stirred at room temperature for 20 min. Then, the reaction mixture was acidified with diluted hydrochloric acid and extracted with ethyl acetate three times. The combined organic layers were dried over anhydrous Na₂SO₄, filtered and concentrated under reduced pressure to give the title compound (357 mg). $^1$H NMR (300 Mz, DMSO-d₆): δ 2.35 (s, 3H), 4.04 (s, 2H), 4.20 (d, 1H), 4.29 (d, 1H), 7.70 (s, 2H), 7.81 (s, 2H), 8.48 (s, 1H).

Step E

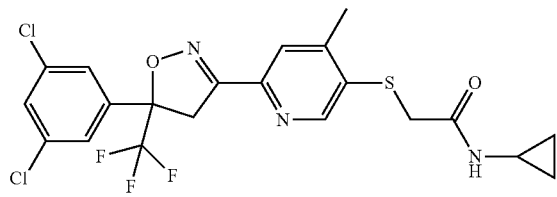

The title compound was obtained from 2-[[6-[5-(3,5-dichlorophenyl)-5-(trifluoromethyl)-4H-isoxazol-3-yl]-4-methyl-3-pyridyl]sulfanyl]acetic acid as described in Example 2.1, Step E. $^1$H NMR (300 Mz, DMSO-d₆): δ 0.35-0.39 (m, 2H), 0.58-0.65 (m, 2H), 2.35 (s, 3H), 2.58-2.64 (m, 1H), 3.74 (s, 2H), 4.20 (d, 1H), 4.29 (d, 1H), 7.71 (s, 2H), 7.80 (s, 2H), 8.30 (s, 1H), 8.49 (s, 1H); $^{19}$F NMR (282 Mz, DMSO-d₆): δ −69.31 (s, 3F); ESI-MS: 504 (M+H⁺), 526 (M+Na⁺), 558 (M+MeOH+Na⁺); m.p.: 134-135° C.

EXAMPLE 10

Synthesis of N-cyclopropyl-2-[[5-[5-(3,5-dichlorophenyl)-5-(trifluoromethyl)-4H-isoxazol-3-yl]-3-methyl-2-pyridyl]sulfanyl]acetamide

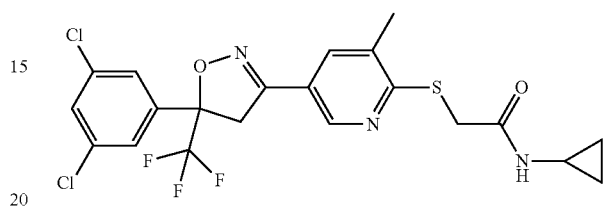

Step A: 6-chloro-5-methyl-pyridine-3-carbaldehyde

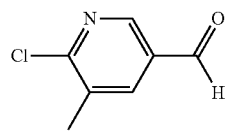

A solution of compound (E)-2-methylbut-2-enenitrile (21.87 g) in DMF (43.8 g) was added dropwise to POCl₃ (91.8 g) at 90° C. After the addition, the mixture was stirred at 100° C. for 15 h. Then, the reaction mixture was poured into water and extracted with ethyl ether three times. The combined organic layers were dried over sodium sulfate, filtered and concentrated under vacuum. The residue was purified by chromatography on silica gel to give the title compound (11.6 g). $^1$H NMR (300 Mz, CDCl₃): δ 2.49 (s, 3H), 8.04 (s, 1H), 8.71 (s, 1H), 10.08 (s, 1H).

Step B: 1-(6-chloro-5-methyl-3-pyridyl)ethanol

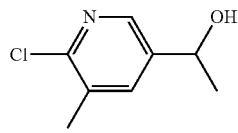

Compound 6-chloro-5-methyl-pyridine-3-carbaldehyde (1.55 g) dissolved in 10 ml of THF was added to a solution of CH₃MgBr (10 ml, 3 mol/L in ether) in 10 ml of THF at 0° C. After stirring for 2 h, the reaction mixture was poured into aqueous NH₄Cl, and extracted with CH₂Cl₂ three times. The combined organic layers were washed with brine, dried over anhydrous Na₂SO₄ and concentrated under reduced pressure. The residue was purified by flash column chromatography on silica gel to give the title compound (1.52 g). $^1$H NMR (300

Mz, CDCl$_3$): δ 1.33 (d, 3H), 2.33 (s, 3H), 4.74-4.80 (m, 1H), 5.39 (br s, 1H), 7.75 (s, 1H), 8.20 (s, 1H); ESI-MS: 172 (M+H$^+$).

Step C: 1-(6-chloro-5-methyl-3-pyridyl)ethanone

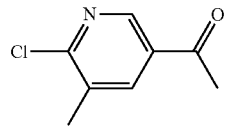

A mixture of PCC (4.26 g) and compound 1-(6-chloro-5-methyl-3-pyridyl)ethanol (1.11 g) in 50 ml of DCM was stirred at room temperature for 5 h. Then the reaction mixture was filtered and the filtrate was concentrated under reduced pressure. The residue was purified by column chromatography on silica gel to the title compound (854 mg). $^1$H NMR (300 Mz, CDCl$_3$): δ 2.46 (s, 3H), 2.64 (s, 3H), 8.09 (s, 1H), 8.77 (s, 1H); ESI-MS: 170 (M+H$^+$).

Step D: 3-(6-chloro-5-methyl-3-pyridyl)-5-(3,5-dichlorophenyl)-5-(trifluoromethyl)-4H-isoxazole

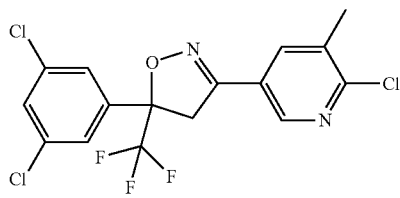 [SMILES: Cc1cc(C2=NOC(c3cc(Cl)cc(Cl)c3)(C(F)(F)F)C2)cnc1Cl]

To a mixture of compound 1-(6-chloro-5-methyl-3-pyridyl)ethanone (850 mg), compound 1-(3,5-dichloro-phenyl)-2,2,2-trifluoro-ethanone (1.82 g) and K$_2$CO$_3$ (862 mg) in 20 ml of dichloroethane was added Et$_3$N (50 mg). The mixture was refluxed for 16 h. After cooling to 0° C., Bu$_4$N$^+$Br$^-$ (322 mg), NH$_2$OH.HCl (690 mg, 10 mmol) and NaOH (800 mg, 4 N) was added and the reaction mixture was stirred at room temperature for 16 h. Then, the reaction mixture was poured into diluted hydrochloric acid and extracted with ethyl acetate three times. The combined organic layers were dried over MgSO$_4$ and concentrated under reduced pressure. The residue was purified by flash column chromatography on silica gel to give the title compound (1.6 g). $^1$H NMR (300 Mz, DMSO-d$_6$): δ 2.39 (s, 3H), 4.37 (d, 1H), 4.43 (d, 1H), 7.62 (s, 2H), 7.83 (s, 1H), 8.17 (s, 1H), 8.55 (s, 1H).

Step E: ethyl 2-[[5-[5-(3,5-dichlorophenyl)-5-(trifluoromethyl)-4H-isoxazol-3-yl]-3-methyl-2-pyridyl]sulfanyl]acetate

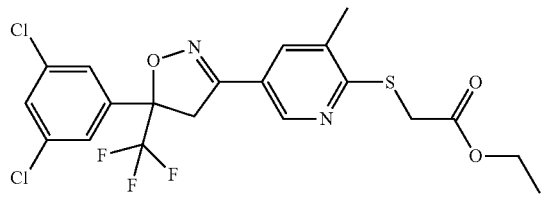 [SMILES: CCOC(=O)CSc1ncc(C2=NOC(c3cc(Cl)cc(Cl)c3)(C(F)(F)F)C2)cc1C]

A mixture of compound 3-(6-chloro-5-methyl-3-pyridyl)-5-(3,5-dichlorophenyl)-5-(trifluoromethyl)-4H-isoxazole (1.6 g), ethyl mercaptoacetate (560 mg) Pd(dba)$_2$ (23 mg, 0.04 mmol), xantphos (23 mg) and Cs$_2$CO$_3$ (1.4 g) in 60 ml of dry toluene under nitrogen was refluxed for 16 h. The resulting mixture was poured into water and extracted with ethyl acetate three times. The organic phase was dried over anhydrous Na$_2$SO$_4$ and concentrated under reduced pressure. The residue was purified by flash column chromatography on silica gel to give the title compound (810 mg, 42% yield). $^1$H NMR (300 Mz, DMSO-d$_6$): δ 1.20 (t, 3H), 2.27 (s, 3H), 4.07 (s, 2H), 4.14 (q, 2H), 4.38 (q, 2H), 7.61 (s, 2H), 7.82 (s, 1H), 7.89 (s, 1H), 8.51 (s, 1H); ESI-MS: 515 (M+Na$^+$).

Step F: 2-[[5-[5-(3,5-dichlorophenyl)-5-(trifluoromethyl)-4H-isoxazol-3-yl]-3-methyl-2-pyridyl]sulfanyl]acetic acid

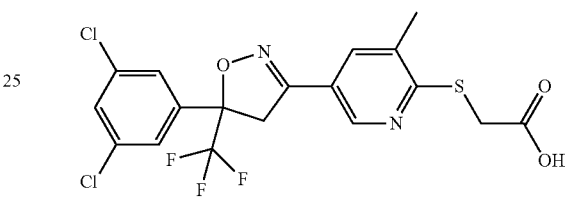

The title compound was obtained from ethyl 2-[[5-[5-(3,5-dichlorophenyl)-5-(trifluoromethyl)-4H-isoxazol-3-yl]-3-methyl-2-pyridyl]sulfanyl]acetate as described in Example 9, Step D. $^1$H NMR (300 Mz, CDCl$_3$): δ 2.37 (s, 3H), 3.74 (d, 1H), 3.88 (s, 2H), 4.05 (d, 1H), 7.44 (s, 1H), 7.50 (s, 2H), 7.91 (s, 1H), 8.47 (s, 1H); ESI-MS: 463 (M−1).

Step G: N-cyclopropyl-2-[[5-[5-(3,5-dichlorophenyl)-5-(trifluoromethyl)-4H-isoxazol-3-yl]-3-methyl-2-pyridyl]sulfanyl]acetamide

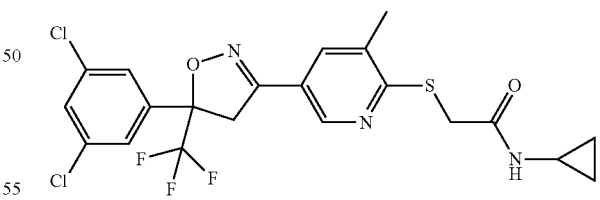

The title compound was obtained from 2-[[5-[5-(3,5-dichlorophenyl)-5-(trifluoromethyl)-4H-isoxazol-3-yl]-3-methyl-2-pyridyl]sulfanyl]acetic acid as described in Example 2.1, Step E. $^1$H NMR (300 Mz, DMSO-d$_6$): δ 0.41-0.43 (m, 2H), 0.62-0.64 (m, 2H), 2.26 (s, 3H), 2.62-2.63 (m, 1H), 3.89 (s, 2H), 4.33 (d, 1H), 4.39 (d, 1H), 7.62 (s, 2H), 7.83 (s, 1H), 7.88 (s, 1H), 8.26 (s, 1H), 8.53 (s, 1H); $^{19}$F NMR (282 Mz, DMSO-d$_6$): δ −69.05 (s, 3F); ESI-MS: 504 (M+H$^+$), 526 (M+Na$^+$); m.p.: 120-121° C.

EXAMPLE 11

2-[[4-[5-(3,5-dichlorophenyl)-5-(trifluoromethyl)-4H-isoxazol-3-yl]-1-naphthyl]sulfanyl]-N-(2,2,2-trifluoroethyl)acetamide. Compound G1

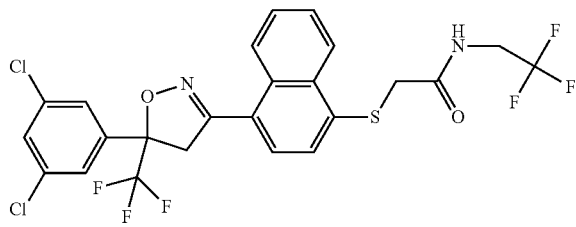 [SMILES: O=C(CSc1ccc(C2=NOC(c3cc(Cl)cc(Cl)c3)(C(F)(F)F)C2)c2ccccc12)NCC(F)(F)F]

Step 1: 2-chloro-N-(2,2,2-trifluoroethyl)acetamide

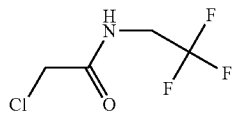

2,2,2-Trifluoroethylamine (4 ml) was dissolved in chloroform (50 ml); the solution was cooled to 0° C. then triethylamine (6 ml) was added, followed by chloroacetyl chloride (6 ml). The ice bath was removed after 30 min, and the solution was stirred at room temperature for 2 hours, then the solvent was removed in vacuo. The residue was purified by flash column chromatography (ethyl acetate/heptanes) on silica gel to give the title product as a white solid (5 g). $^1$H NMR (400 Mz, CDCl$_3$): δ 4.00 (m, 2H), 4.15 (s, 2H), 6.95 (br s, 1H).

Step 2: S-[2-oxo-2-(2,2,2-trifluoroethylamino)ethyl]ethanethioate

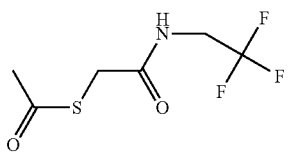

A solution of triethylamine (150 ml) and thioacetic acid (75 ml) in dichloromethane (600 ml) was cooled to 0° C. under argon. 2-Sulfanyl-N-(2,2,2-trifluoroethyl)acetamide (155 g, prepared following the procedure described in step 1) was dissolved in dichlormethane (400 ml) and added slowly to the previous solution. The resulting solution was stirred for another 40 min during which a beige solid precipitated out slowly. 500 ml of dichloromethane was added to dissolve the solid then the solution was washed twice with water (500 ml) then twice with brine (200 ml). The organic layer was dried over sodium sulfate, and the solvent was removed in vacuo to give the title product as a beige solid (195 g). $^1$H NMR (400 Mz, CDCl$_3$): δ 2.40 (s, 3H), 3.60 (s, 2H), 3.85 (m, 2H), 6.75 (br s, 1H).

Step 3: 2-sulfanyl-N-(2,2,2-trifluoroethyl)acetamide

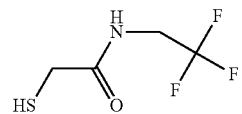

A solution of S-[2-oxo-2-(2,2,2-trifluoroethylamino)ethyl]ethanethioate (195 g) in methanol (1800 ml) was treated with concentrated hydrochloric acid solution (270 ml) for 12 hours at room temperature, at which the solvent was removed in vacuo. The resulting oil was dissolved in dichlormethane (800 ml) then the precipitate removed by filtration. The organic solution was washed with water, then brine, dried over magnesium sulfate and the solvents removed in vacuo to afford the title product as a beige solid (63 g). $^1$H NMR (400 Mz, CDCl$_3$): δ 3.30 (d, 2H), 3.95 (m, 2H), 7.15 (br s, 1H). ESI-MS: 174/176 (M+1)

Step 4: 1-(4-chloro-1-naphthyl)ethanone

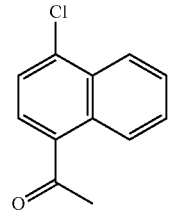

To a suspension of aluminium chloride (22 g) in dichloromethane (150 ml) were added acetyl chloride (7.9 ml), then 1-chloronaphtalene (14 ml) dropwise (exothermic). The resulting solution was refluxed for 30 min, cooled to 10° C., poured into 1n hydrochloric acid solution (30 ml), then extrated with dichloromethane. The organic layer was washed with brine, dried over sodium sulfate then the solvent removed in vacuo. The residue was purified by flash column chromatography (ethyl acetate/heptanes) on silica gel to give the title product as a yellow oil (18 g). $^1$H NMR (400 Mz, CDCl$_3$): δ 1.75 (s, 3H), 7.61 (d, 1H), 7.69 (m, 1H), 7.85 (d, 1H), 8.48 (m, 1H), 8.80 (m, 1H). LCMS (Method A) RT 1.81 min, [M+H]$^+$ 205.

Step 5: 2-[(4-acetyl-1-naphthyl)sulfanyl]-N-(2,2,2-trifluoroethyl)acetamide

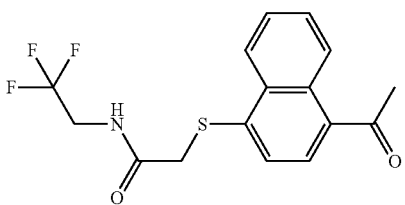 [SMILES: CC(=O)c1ccc(SCC(=O)NCC(F)(F)F)c2ccccc12]

A round bottom flask is charged with 2-sulfanyl-N-(2,2,2-trifluoroethyl)acetamide (1.3 g), cesium carbonate (3.3 g), and dimethylformamide (50 ml). The suspension is stirred for 30 min at room temperature, then 1-(4-chloro-1-naphthyl)ethanone (1 g) was added and the resulting solution stirred at room temperature for 12 hours. The mixture was diluted with ethyl acetate (100 ml) then washed with water (5*50 ml), 2N hydrochloric acid solution, brine, then dried over sodium sulphate. The solvent was removed under reduced pressure to afford the crude residue as yellow solid (2 g). Flash column chromatography (ethyl acetate/heptanes) afforded the title product as a beige solid (1.1 g). $^1$H NMR (400 Mz, CDCl$_3$): δ 1.75 (s, 3H), 2.75 (s, 2H), 3.90 (m, 2H), 7.00 (br s, 1H), 7.45 (d, 1H), 7.70 (m, 1H), 7.90 (d, 1H), 8.30 (d, 1H), 8.72 (d, 1H). LCMS (Method A) RT 0.86 min, [M+H]$^+$ 342.

Step 6: 2-[[4-[3-(3,5-dichlorophenyl)-4,4,4-trifluoro-but-2-enoyl]-1-naphthyl]sulfanyl]-N-(2,2,2-trifluoroethyl)acetamide

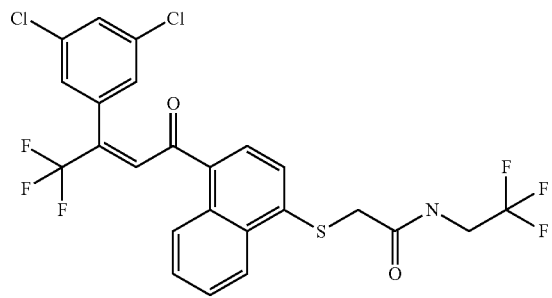 [SMILES: O=C(CSc1ccc(C(=O)/C=C(\c2cc(Cl)cc(Cl)c2)C(F)(F)F)c2ccccc12)NCC(F)(F)F]

A round bottom flask was charged with 2-[(4-acetyl-1-naphthyl)sulfanyl]-N-(2,2,2-trifluoroethyl)acetamide (2.2 g), 1-(3,5-dichloro-phenyl)-2,2,2-trifluoro-ethanone (1.8 g), potassium carbonate (1 g), triethylamine (0.1 ml) and dichloroethane (22 ml). The resulting solution was refluxed for 12 hr. The reaction mixture was cooled to room temperature, partitioned between dichloromethane and water. The aqueous layer was separated, extracted with dichloromethane and the combined organic layers were dried over sodium sulphate and the solvent removed in vacuo. Flash column chromatography of the residue (ethyl acetate/heptanes) afforded the title product as a yellow solid (2 g). $^1$H NMR (400 Mz, CDCl$_3$): δ 3.90 (s, 2H), 3.95 (m, 2H), 6.90 (br s, 1H), 7.05-7.75 (m, 8H), 8.25 (d, 1H), 8.65 (d, 1H). LCMS (Method E) RT 2.51 min, [M+H]$^+$ 582/584.

Step 7: 2-[[4-[5-(3,5-dichlorophenyl)-5-(trifluoromethyl)-4H-isoxazol-3-yl]-1-naphthyl]sulfanyl]-N-(2,2,2-trifluoroethyl)acetamide. Compound G1

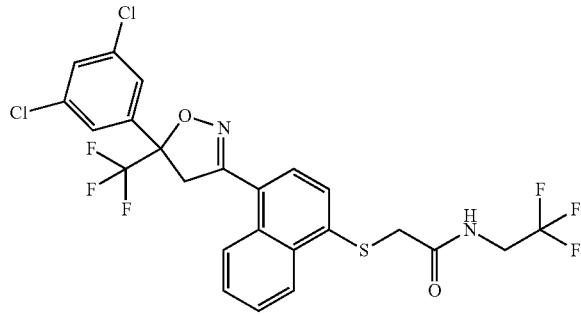 [SMILES: O=C(CSc1ccc(C2=NOC(c3cc(Cl)cc(Cl)c3)(C(F)(F)F)C2)c2ccccc12)NCC(F)(F)F]

To a solution of 2-[[4-[3-(3,5-dichlorophenyl)-4,4,4-trifluoro-but-2-enoyl]-1-naphthyl]sulfanyl]-N-(2,2,2-trifluoroethyl)acetamide (200 mg) in chloroform (3.5 ml) was added tetrabutyl ammonium bromide (34 mg). The reaction mixture was cooled at −15° C. then hydroxylamine (50% in water, 0.05 ml) and sodium hydroxide (10 N in water, 0.14 ml) were added. The reaction was stirred at −15° C. for 3 hour then at room temperature overnight. The mixture was diluted with water and extracted with dichloromethane several times; the combined organic layers were dried over sodium sulphate and the solvent evaporated under reduced pressure to obtain a brown gum. The residue was purified by flash column chromatography of the residue (ethyl acetate/heptanes) afforded the title product as a yellow solid (190 mg). $^1$H NMR (400 Mz, CDCl$_3$): δ 3.80-4.00 (m, 5H), 4.30 (d, 1H), 6.95 (br s, 1H), 7.30-7.80 (m, 7H), 8.35 (d, 1H), 9.00 (d, 1H). LCMS (Method E) RT 2.25 min, [M+H]$^+$ 581/583. The product was analysed by chiral HPLC (method F): 10.54 min (49.2%), 12.40 min (50.8%).

EXAMPLE 12

2-[[4-[5-(S)-(3,5-dichlorophenyl)-5-(trifluoromethyl)-4H-isoxazol-3-yl]-1-naphthyl]sulfanyl]-N-(2,2,2-trifluoroethyl)acetamide. Compound G2

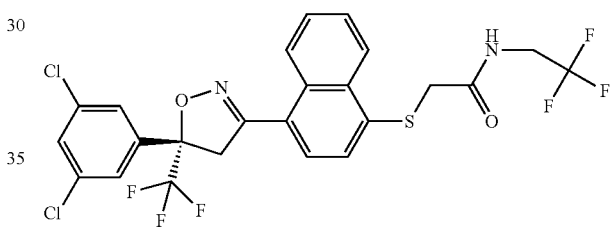

To a solution of 2-[[4-[3-(3,5-dichlorophenyl)-4,4,4-trifluoro-but-2-enoyl]-1-naphthyl]sulfanyl]-N-(2,2,2-trifluoroethyl)acetamide (1.1 g) in chloroform (20 ml) was added 1-anthracen-9-ylmethyl quininium chloride (0.22 g, Example 7, Step D). The reaction mixture was cooled at −15° C. then hydroxylamine (50% in water, 0.25 ml) and cesium hydroxide (0.91 g in 1.5 ml water) were added. The reaction was stirred at −15° C. for 3 hour then at room temperature overnight. The mixture was diluted with water and extracted with dichloromethane several times; the combined organic layers were dried over sodium sulphate and the solvent evaporated under reduced pressure to obtain a brown gum. The residue was purified by flash column chromatography of the residue (ethyl acetate/heptanes) afforded the title product as a yellow solid (900 mg). $^1$H NMR (400 Mz, CDCl$_3$): δ 3.80-4.00 (m, 5H), 4.30 (d, 1H), 6.95 (br s, 1H), 7.30-7.80 (m, 7H), 8.35 (d, 1H), 9.00 (d, 1H). LCMS (Method E) RT 2.25 min, [M+H]$^+$ 581/583. The product was analysed by chiral HPLC (method F): 14.31 min (84.7%), 16.79 min (15.3%). The compound obtained (900 mg) was dissolved in ether (30 ml) then the suspension was stored at 0° C. for 3 days. The solid (200 mg) was separated by filtration and the mother liquor was concentrated to give the title product (600 mg) with higher enantiomeric excess: HPLC (method F): 13.94 min (91.2%), 16.51 min (8.8%).

Similarly, 2-[[4-[5-(S)-(3,5-dichlorophenyl)-5-(trifluoromethyl)-4H-isoxazol-3-yl]-1-naphthyl]sulfanyl]-N-cyclopropylamide was obtained following a similar sequence.

2-[[4-[5-(S)-(3,5-dichlorophenyl)-5-(trifluoromethyl)-4H-isoxazol-3-yl]-1-naphthyl]sulfinyl]-N-(2,2,2-trifluoroethyl)acetamide was obtained by oxidation of 2-[[4-[5-(S)-(3,5-dichlorophenyl)-5-(trifluoromethyl)-4H-isoxazol-3-yl]-1-naphthyl]sulfanyl]-N-(2,2,2-trifluoroethyl)acetamide as described in Example 4.

2-[[4-[5-(S)-(3,5-dichlorophenyl)-5-(trifluoromethyl)-4H-isoxazol-3-yl]-1-naphthyl]sulfonyl]-N-(2,2,2-trifluoroethyl)acetamide was obtained by oxidation of 2-[[4-[5-(S)-(3,5-dichlorophenyl)-5-(trifluoromethyl)-4H-isoxazol-3-yl]-1-naphthyl]sulfanyl]-N-(2,2,2-trifluoroethyl)acetamide as described in Example 5.

EXAMPLE 13

2-[4-[3-(3,5-dichlorophenyl)-3-(trifluoromethyl) pyrrolidin-1-yl]-2-methyl-phenyl]sulfanyl-N-(2,2,2-trifluoroethyl)acetamide. Compound H1

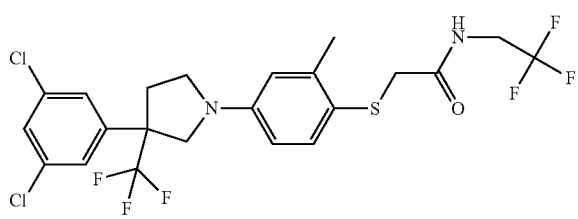 [SMILES: Cc1cc(N2CCC(c3cc(Cl)cc(Cl)c3)(C(F)(F)F)C2)ccc1SCC(=O)NCC(F)(F)F]

Step 1: 2-(2-chloro-4-iodo-phenyl)sulfanyl-N-(2,2,2-trifluoroethyl)acetamide

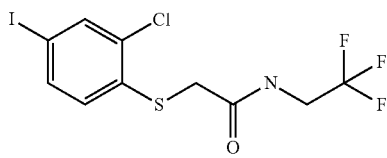 [SMILES: O=C(CSc1ccc(I)cc1Cl)NCC(F)(F)F]

A round bottom flask is charged with 2-sulfanyl-N-(2,2,2-trifluoroethyl)acetamide (example 14, Step 3, 7.69 g), cesium carbonate (19.7 g), dimethylformamide (100 ml) then the suspension is stirred for 30 min at rt. A solution of 3-chloro-4-fluoroiodobenzene (7.69 g) in dimethylformamide (50 ml) was added and the mixture is stirred at room temperature for 12 hours then 1 hour at 70° C. The mixture was diluted with ethyl acetate (100 ml) then washed with water (5*100 ml), 2N hydrochloric acid solution, brine, then dried over sodium sulphate. The solvent was removed under reduced pressure to dryness to afford the crude as yellow solid (13 g). The residue was purified by flash column chromatography of the residue (ethyl acetate/heptanes) afforded the title product as a yellow solid (900 mg). $^1$H NMR (400 Mz, CDCl$_3$): δ 3.70 (s, 2H), 4.40 (m, 2H), 6.90 (d, 2H), 6.95 (br s, 1H), 7.48 (d, 2H), 7.76 (d, 2H). LCMS (Method E) RT 1.03 min, [M+H]$^+$ 408/410.

Step 2: 2-[4-[3-(3,5-dichlorophenyl)-3-(trifluoromethyl)pyrrolidin-1-yl]-2-methyl-phenyl]sulfanyl-N-(2,2,2-trifluoroethyl)acetamide. Compound H1

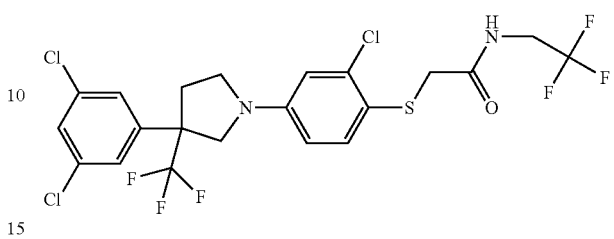

Tris(dibenzylideneacetone)dipalladium chloroform complex (43 mg), Xantphos (73 mg), sodium tertbutoxide (206 mg), was added to a degassed solution of 2-(2-chloro-4-iodo-phenyl)sulfanyl-N-(2,2,2-trifluoroethyl)acetamide (868 mg) and 4-[3-(3,5-dichloro-phenyl)-3-trifluoromethyl-pyrrolidin-1-yl]-2-methyl-benzoic acid (568 mg, preparation described in JP 2008110971) in toluene (8 ml) under argon atmosphere. The mixture was heated in the microwave at 130° C. for 30 min. The mixture was diluted with ethyl acetate (20 ml) then washed twice with water then brine. The organic layer was dried over anhydrous sodium sulfate filtered and concentrated under reduced pressure. The residue was purified by flash chromatography (heptane/EtOAc) to afford the title product as a yellow solid (50 mg). $^1$H NMR (400 Mz, CDCl$_3$): δ 2.55 (m, 1H), 2.90 (m, 1H), 3.50-4.10 (m, 8H), 6.45 (m, 1H), 6.70 (s, 1H), 7.19 (br t, 1H), 7.35 (d, 1H), 7.40 (s, 1H). LCMS (Method E) RT 2.20 min, [M+H]$^+$ 563/565.

TABLE A

Compounds of formula (I-a):

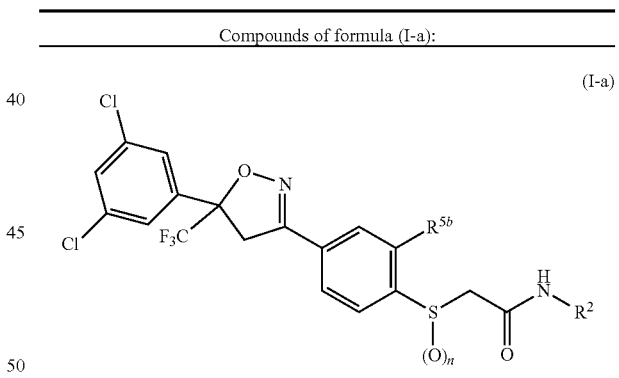

(I-a)

| Comp No. | n | R$^{5b}$ | R$^2$ | LCMS Method | RT (min) | mass spectrum [M + H]$^+$ |
|---|---|---|---|---|---|---|
| A1 | 0 | Cl | ethyl- | C | 2.05 | 511.18 |
| A2 | 0 | Cl | butyl- | C | 2.19 | 539.21 |
| A3 | 0 | Cl | 1-methoxy-prop-2-yl- | C | 2.09 | 555.21 |
| A4 | 0 | Cl | N-(2,2,2-trifluoro-ethyl)-acetamide-2-yl | C | 1.99 | 622.19 |
| A5 | 0 | Cl | 2,2,2-trifluoro-ethyl- | B | 2.27 | 606/608 (M + CH$_3$CN) |
| A6 | 0 | Cl | 3,3,3-trifluoro-propyl- | C | 2.19 | 539.23 |
| A7 | 0 | Cl | but-2-yl- | C | 2.07 | 567.2 |
| A8 | 0 | Cl | (tetrahydrofuran-2-yl)-methyl- | C | 2.18 | 573.21 |
| A9 | 0 | Cl | phenyl-methyl- | C | 2.2 | 591.2 |

TABLE A-continued

Compounds of formula (I-a):

| Comp No. | n | R5b | R2 | LCMS Method | RT (min) | mass spectrum [M + H]+ |
|---|---|---|---|---|---|---|
| A10 | 0 | Cl | (2-fluoro-phenyl)-methyl- | C | 2.13 | 579.19 |
| A11 | 0 | Cl | 1-phenyl-eth-1-yl- | C | 2.24 | 587.21 |
| A12 | 0 | Cl | (4-methoxy-phenyl)-methyl- | C | 2.17 | 603.23 |
| A13 | 0 | Cl | 1,1-dioxo-thietan-3-yl- | C | 1.94 | 587.15 |
| A14 | 0 | Cl | (2-chloro-pyrid-5-yl)-methyl- | C | 2.1 | 608.16 |
| A15 | 0 | Cl | 3-fluoro-phenyl- | C | 2.25 | 577.1 |
| A16 | 0 | Cl | (pyrid-2-yl)-methyl- | C | 1.94 | 574.2 |
| A17 | 0 | Cl | 1,3-dimethyl-1H-pyrazol-5-yl- | C | 2.02 | 577.21 |
| A18 | 0 | Cl | 4-methyl-thiazol-2-yl- | C | 2.01 | 579.63 |
| A19 | 0 | Cl | 3-methyl-thietan-3-yl- | C | 2.19 | 569.22 |
| A20 | 0 | Cl | 1,1-dimethyl-2-methylsulfanyl-ethyl | C | 2.28 | 585.21 |
| A21 | 0 | Cl | 1-oxo-thietan-3-yl- | C | 1.86 | 571.15 |
| A22 | 0 | Cl | thietan-3-yl- | C | 2.11 | 555.22 |
| A23 | 0 | Cl | bicyclo[2.2.1]hept-2-yl- | C | 2.3 | 577.22 |
| A24 | 0 | Cl | cyclobutyl- | C | 2.16 | 537.24 |
| A25 | 0 | Br | ethyl- | C | 2.07 | 555.14 |
| A26 | 0 | Br | butyl- | C | 2.21 | 583.17 |
| A27 | 0 | Br | 1-methoxy-prop-2-yl- | C | 2.11 | 599.18 |
| A28 | 0 | Br | N-(2,2,2-trifluoro-ethyl)-acetamide-2-yl | C | 2.01 | 666.17 |
| A29 | 0 | Br | 2,2,2-trifluoro-ethyl- | A | 2.27 | 609/611 |
| A30 | 0 | Br | 3,3,3-trifluoro-propyl- | C | 2.15 | 623.14 |
| A31 | 0 | Br | but-2-yl- | C | 2.2 | 583.16 |
| A32 | 0 | Br | (tetrahydrofuran-2-yl)-methyl- | C | 2.09 | 611.15 |
| A33 | 0 | Br | phenyl-methyl- | C | 2.2 | 617.13 |
| A34 | 0 | Br | (2-fluoro-phenyl)-methyl- | C | 2.21 | 635.21 |
| A35 | 0 | Br | 1-phenyl-eth-1-yl- | C | 2.26 | 631.16 |
| A36 | 0 | Br | (4-methoxy-phenyl)-methyl- | C | 2.19 | 647.18 |
| A37 | 0 | Br | 1,1-dioxo-thietan-3-yl- | C | 1.96 | 631.05 |
| A38 | 0 | Br | (2-chloro-pyrid-5-yl)-methyl- | C | 2.12 | 652.15 |
| A39 | 0 | Br | 3-fluoro-phenyl- | C | 2.26 | 621.06 |
| A40 | 0 | Br | (pyrid-2-yl)-methyl- | C | 1.95 | 618.17 |
| A41 | 0 | Br | 1,3-dimethyl-1H-pyrazol-5-yl- | C | 2.04 | 621.16 |
| A42 | 0 | Br | 4-methyl-thiazol-2-yl- | C | 2.19 | 624.15 |
| A43 | 0 | Br | 3-methyl-thietan-3-yl- | C | 2.21 | 612.43 |
| A44 | 0 | Br | 1,1-dimethyl-2-methylsulfanyl-ethyl | C | 2.29 | 629.17 |
| A45 | 0 | Br | 1-oxo-thietan-3-yl- | C | 1.88 | 615.09 |
| A46 | 0 | Br | thietan-3-yl- | C | 2.13 | 599.12 |
| A47 | 0 | Br | bicyclo[2.2.1]hept-2-yl- | C | 2.32 | 621.23 |
| A48 | 0 | Br | cyclobutyl- | C | 2.17 | 581.15 |
| A49 | 0 | CH3 | 2,2,2-trifluoro-ethyl- | A | 2.16 | 545/547 |
| A50 | 1 | CH3 | 2,2,2-trifluoro-ethyl- | B | 1.98 | 561/563 |
| A51 | 2 | CH3 | 2,2,2-trifluoro-ethyl- | A | 2.16 | 577/579 |
| A52 | 1 | Br | 2,2,2-trifluoro-ethyl- | A | 2.29 | 627/629 |
| A53 | 2 | Br | 2,2,2-trifluoro-ethyl- | A | 2.16 | 641/643 |
| A54 | 1 | Cl | 2,2,2-trifluoro-ethyl- | A | 2.05 | 581/583 |
| A55 | 2 | Cl | 2,2,2-trifluoro-ethyl- | A | 2.06 | 598/600 |
| A57 | 0 | NO2 | 2,2,2-trifluoro-ethyl- | E | 1.18 | 577.3 |
| A58 | 0 | Cl | 2-ethoxy-2-oxo-ethyl | A | 2.16 | 569/572 |
| A59 | 0 | Br | H | A | 2.04 | 570/572 |
| A62 | 0 | Br | methylsulfonyl- | A | 2.28 | 605/607 |
| A63 | 0 | Br | (1-methyl-2-phenyl-ethyl)- | C | 2.36 | 645.2 |
| A64 | 0 | Br | 2-cyanoethyl- | C | 2.02 | 580.1 |
| A65 | 0 | Br | 1,1,3,3-tetramethylbutyl- | C | 2.52 | 639.2 |
| A66 | 0 | Br | cyclohexylmethyl- | C | 2.40 | 623.1 |
| A67 | 0 | Br | (2-oxopyrrolidin-1-yl)methyl- | C | 1.97 | 624.2 |
| A68 | 0 | Br | [(1S,2S)-1-(hydroxymethyl)-2-methyl-butyl]- | C | 2.13 | 627.2 |
| A69 | 0 | Br | methyl- | C | 2.02 | 541.2 |
| A70 | 0 | Br | 1,2-dimethylpropyl- | C | 2.30 | 597.3 |
| A71 | 0 | Br | 1,1-dimethylprop-2-ynyl- | C | 2.20 | 593.3 |
| A72 | 0 | Br | 2-methylbutyl- | C | 2.30 | 597.3 |
| A73 | 0 | Br | cyclopropyl- | C | 2.10 | 567.2 |
| A74 | 0 | Br | 2-chloroallyl- | C | 2.19 | 601.2 |
| A75 | 0 | Br | 1-cyanoethyl- | C | 2.07 | 580.2 |
| A76 | 0 | Br | 2-methylallyl- | C | 2.19 | 581.2 |
| A77 | 0 | Br | 1-cyano-1-methylethyl- | C | 2.11 | 594.3 |
| A78 | 0 | Br | 2-fluoroethyl- | C | 2.06 | 573.2 |
| A79 | 0 | Br | cyanomethyl- | C | 2.02 | 566.2 |
| A80 | 0 | Br | [(2E)-2-methoxyimino-1,1-dimethyl-ethyl]- | C | 2.25 | 626.3 |
| A81 | 0 | Br | (E)-3-chloroallyl- | C | 2.18 | 601.2 |
| A82 | 0 | Br | but-2-ynyl- | C | 2.14 | 579.3 |
| A83 | 0 | Br | 2-fluoro-1-methylethyl- | C | 2.12 | 587.2 |

TABLE A-continued

Compounds of formula (I-a):

(I-a)

| Comp No. | n | R⁵ᵇ | R² | LCMS Method | RT (min) | mass spectrum [M + H]⁺ |
|---|---|---|---|---|---|---|
| A84 | 0 | Br | 2-fluoropropyl- | C | 2.12 | 587.3 |
| A85 | 0 | Br | n-propyl- | C | 2.17 | 569.2 |
| A86 | 0 | Br | isopropyl- | C | 2.17 | 569.3 |
| A87 | 0 | Br | isobutyl- | C | 2.24 | 583.3 |
| A88 | 0 | Br | propargyl- | C | 2.07 | 565.2 |
| A89 | 0 | Br | 2,2-difluoroethyl- | C | 2.10 | 591.2 |
| A90 | 0 | Br | allyl- | C | 2.13 | 567.2 |
| A91 | 0 | Br | cyclopropylmethyl- | C | 2.18 | 581.2 |

Experimental Details for Compounds A56, A60 and A61

A56: 2-[2-chloro-4-[5-(3,5-dichlorophenyl)-5-(trifluoromethyl)-4H-isoxazol-3-yl]phenyl]sulfinyl-N-(1-cyanocyclopropyl)acetamide (Mixture of Diastereoisomers)

¹H NMR (CHLOROFORM-d, 400 MHz): δ=7.86-7.94 (m, 2H), 7.76 (ddd, J=9.9, 8.3, 1.7 Hz, 1H), 7.48-7.52 (m, 2H), 7.44-7.45 (m, 1H), 7.34 (m, 1H), 4.07 (d, J=17.2 Hz, 1H), 3.67-3.87 (m, 3H), 1.47-1.60 (m, 2H), 1.12-1.28 ppm (m, 2H)

A60: 2-[2-chloro-4-[5-(3,5-dichlorophenyl)-5-(trifluoromethyl)-4H-isoxazol-3-yl]phenyl]sulfanyl-N-(1-cyanocyclopropyl)acetamide ¹H NMR (CHLOROFORM-d, 400 MHz): δ=7.77 (d, J=1.5 Hz, 1H), 7.40-7.53 (m, 4H), 7.21 (d, J=8.4 Hz, 1H), 7.08 (s, 1H), 4.04 (d, J=16.9 Hz, 1H), 3.71 (s, 2H), 3.66 (d, J=17.2 Hz, 1H), 1.52-1.58 (m, 2H), 1.10-1.22 ppm (m, 2H)

A61: 2-[2-chloro-4-[5-(3,5-dichlorophenyl)-5-(trifluoromethyl)-4H-isoxazol-3-yl]phenyl]sulfonyl-N-(1-cyanocyclopropyl)acetamide ¹H NMR (CHLOROFORM-d, 400 MHz): δ=8.14 (d, J=8.1 Hz, 1H), 7.95 (d, J=1.5 Hz, 1H), 7.74 (dd, J=8.3, 1.7 Hz, 1H), 7.49-7.53 (m, 2H), 7.42-7.49 (m, 1H), 7.00 (s, 1H), 4.32 (s, 2H), 4.08 (d, J=17.2 Hz, 1H), 3.71 (d, J=17.2 Hz, 1H), 1.54-1.57 (m, 2H), 1.23-1.29 (m, 2H)

TABLE B

Compounds of formula (I-b):

(I-b)

| Comp No. | n | R⁵ᵇ | R² | LCMS Method | RT (min) | mass spectrum |
|---|---|---|---|---|---|---|
| B1 | 0 | Cl | CH₂CF₃ | A | 2.12 | 563/565 |
| B2 | 1 | Cl | CH₂CF₃ | A | 2 | 579/581 |
| B3 | 2 | Cl | CH₂CF₃ | A | 2.01 | 595/597 |

TABLE C

Compounds of formula (I-c):

(I-c)

| Comp No. | n | R⁵ᵇ | R² | LCMS Method | RT (min): mass spectrum | Chiral HPLC (method D) |
|---|---|---|---|---|---|---|
| C1 | 0 | CH₃ | CH₂CF₃ | B | 2.14 min: 545/547 | 5.99 min (95.5%) |
| C2 | 1 | CH₃ | CH₂CF₃ | B | 1.99 min: 561/563 | |
| C3 | 2 | CH₃ | CH₂CF₃ | B | 2.05 min | |
| C4 | 0 | Cl | CH₂CF₃ | A | 2.17 min: 565/567 | 5.23 min (100%) |
| C5 | 1 | Cl | CH₂CF₃ | A | 2.05 min: 581/583 | 10.11 min (47.65%), 11.68 (51.43%) |
| C6 | 2 | Cl | CH₂CF₃ | A | 2.08 min: 597/599 | 5.27 min (97.91%) |
| C7 | 0 | Br | cyclopropyl- | E | 1.19 min: 567/569/571 | |
| C9 | 0 | Cl | 2-fluorophenyl- | C | 2.25 min: 577.33 | |
| C10 | 0 | Cl | 4-fluorophenyl- | C | 2.22 min: 577.33 | |
| C11 | 0 | Cl | allyl | C | 2.08 min: 523.32 | |
| C12 | 0 | Cl | 2-chlorophenyl- | C | 2.34 min: 593.4 | |
| C13 | 0 | Cl | 2-ethoxy-2-oxo-ethyl- | C | 2.07 min: 569.36 | |
| C14 | 0 | Cl | 2-methoxyethyl- | C | 2.02 min: 541.32 | |
| C15 | 0 | Cl | 2-methylsulfanylethyl- | C | 2.1 min: 557.36 | |

TABLE C-continued

Compounds of formula (I-c):

| Comp No. | n | R5b | R2 | LCMS Method | RT (min): mass spectrum | Chiral HPLC (method D) |
|---|---|---|---|---|---|---|
| C16 | 0 | Cl | 4-methyl-2-pyridyl- | C | 2.17 min: 574.35 | |
| C17 | 0 | Cl | 2,5-difluorophenyl- | C | 2.28 min: 595.31 | |
| C18 | 0 | Cl | o-tolylmethyl- | C | 2.24 min: 587.35 | |
| C19 | 0 | Cl | 2-(3,4-dimethoxyphenyl)ethyl- | C | 2.15 min: 647.38 | |
| C20 | 0 | Cl | p-tolylmethyl- | C | 2.25 min: 587.36 | |
| C21 | 0 | Cl | 3,3-dichloroallyl- | C | 2.22 min: 591.24 | |
| C22 | 0 | Cl | 3,4-dichlorophenyl- | C | 2.4 min: 626.94 | |
| C23 | 0 | Cl | 6-methyl-3-nitrophenyl- | C | 2.24 min: 618.47 | |
| C24 | 0 | Cl | 3,5-dichlorophenyl- | C | 2.44 min: 626.72 | |
| C25 | 0 | Cl | 4-bromophenyl- | C | 2.33 min: 637.51 | |
| C26 | 0 | Cl | 2,6-diisopropylphenyl- | C | 2.43 min: 643.4 | |
| C27 | 0 | Cl | 2-ethoxy-1-ethoxycarbonyl-2-oxo-ethyl- | C | 2.19 min: 641.35 | |
| C28 | 0 | Cl | 3-bromophenyl- | C | 2.34 min: 637.68 | |
| C29 | 0 | Cl | 2,4-dimethylphenyl- | C | 2.31 min: 587.29 | |
| C30 | 0 | Cl | 2,5-dimethylphenyl- | C | 2.32 min: 587.35 | |
| C31 | 0 | Cl | 1,1-dimethylpropyl- | C | 2.3 min: 553.43 | |
| C32 | 0 | Cl | 2-ethylphenyl- | C | 2.3 min: 587.36 | |
| C33 | 0 | Cl | cyclopropylmethyl- | C | 2.13 min: 537.33 | |
| C34 | 0 | Cl | 4-ethylphenyl- | C | 2.34 min: 587.32 | |
| C35 | 0 | Cl | 2-bromophenyl- | C | 2.36 min: 637.21 | |
| C36 | 0 | Cl | 2,4-dichlorophenyl- | C | 2.44 min: 627.12 | |
| C37 | 0 | Cl | 3-chlorophenyl- | C | 2.32 min: 593.39 | |
| C38 | 0 | Cl | 4-(trifluoromethoxy)phenyl- | C | 2.35 min: 643.25 | |
| C39 | 0 | Cl | 2-bromo-4-fluorophenyl- | C | 2.35 min: 655.33 | |
| C40 | 0 | Cl | 2,3-dichlorophenyl- | C | 2.43 min: 627.01 | |
| C41 | 0 | Cl | m-tolylmethyl- | C | 2.25 min: 586.6 | |
| C42 | 0 | Cl | 3,5-dimethylphenyl- | C | 2.35 min: 587.4 | |
| C43 | 0 | Cl | p-tolyl- | C | 2.28 min: 573.37 | |
| C44 | 0 | Cl | propargyl- | C | 2.03 min: 521.3 | |
| C45 | 0 | Cl | 3-nitrophenyl- | C | 2.22 min: 603.57 | |
| C46 | 0 | Cl | 2,6-diethyl-4-methylphenyl- | C | 2.41 min: 629.39 | |
| C47 | 0 | Cl | 4H-1,2,4-triazol-3-yl- | C | 1.86 min: 550.11 | |
| C48 | 0 | Cl | 5-methylthiazol-2-yl- | C | 2.17 min: 580.3 | |
| C49 | 0 | Cl | 5-methyl-2-pyridyl- | C | 2.2 min: 574.4 | |
| C50 | 0 | Cl | 2-hydroxyphenyl- | C | 2.12 min: 575.32 | |
| C51 | 0 | Cl | o-tolyl- | C | 2.25 min: 573.36 | |
| C52 | 0 | Cl | 3-pyridyl- | C | 1.91 min: 560.32 | |
| C53 | 0 | Cl | 2,2-difluoroethyl- | C | 2.06 min: 546.67 | |
| C54 | 0 | Cl | isobutyl- | C | 2.19 min: 539.34 | |
| C55 | 0 | Cl | 2,4-difluorophenyl- | C | 2.24 min: 595.3 | |
| C56 | 0 | Cl | 2-methyl-3-pyridyl- | C | 2.2 min: 594.49 | |
| C57 | 0 | Cl | 2-furylmethyl- | C | 2.11 min: 563.33 | |
| C58 | 0 | Cl | cyclopropyl- | C | 2.05 min: 523.32 | |
| C59 | 0 | Cl | isopropyl- | C | 2.12 min: 525.32 | |
| C60 | 0 | Cl | n-butyl- | C | 2.12 min: 525.1 | |
| C61 | 0 | Cl | phenyl- | C | 2.22 min: 559.33 | |
| C62 | 0 | Cl | tert-butyl- | C | 2.24 min: 539.34 | |
| C65 | 2 | Cl | propargyl- | A | 2.04 min: 555/557 | |
| C66 | 0 | Cl | 2-methylbutyl- | C | 2.29 min: 553.32 | |
| C68 | 0 | Cl | 2-chloroallyl- | C | 2.17 min: 557.14 | |
| C69 | 0 | Cl | 1-cyanoethyl- | C | 2.05 min: 536.32 | |
| C70 | 0 | Cl | 2-methylallyl- | C | 2.17 min: 537.31 | |
| C71 | 0 | Cl | 1-cyano-1-methylethyl- | C | 2.09 min: 550.28 | |
| C72 | 0 | Cl | 2-fluoroethyl- | C | 2.04 min: 529.29 | |
| C73 | 0 | Cl | cyanomethyl- | C | 2 min: 522.25 | |

TABLE C-continued

Compounds of formula (I-c):

(I-c)

| Comp No. | n | R$^{5b}$ | R$^2$ | LCMS Method | RT (min): mass spectrum | Chiral HPLC (method D) |
|---|---|---|---|---|---|---|
| C74 | 0 | Cl | [(2E)-2-methoxyimino-1,1-dimethyl-ethyl]- | C | 2.24 min: 582.33 | |
| C75 | 0 | Cl | (E)-3-chloroallyl- | C | 2.16 min: 557.28 | |
| C76 | 0 | Cl | but-2-ynyl- | C | 2.12 min: 535.26 | |
| C77 | 0 | Cl | 2-fluoro-1-methylethyl- | C | 2.11 min: 543.29 | |
| C78 | 0 | Cl | 2-fluoropropyl- | C | 2.1 min: 543.28 | |
| C79 | 0 | Me | methyl- | C | 1.96 min: 477.33 | |
| C80 | 0 | Me | 1,2-dimethylpropyl- | C | 2.25 min: 533.35 | |
| C81 | 0 | Me | 1,1-dimethylprop-2-ynyl- | C | 2.15 min: 529.35 | |
| C82 | 0 | Me | 2-methylbutyl- | C | 2.25 min: 533.39 | |
| C83 | 0 | Me | cyclopropyl- | C | 2.04 min: 503.33 | |
| C84 | 0 | Me | 2-chloroallyl- | C | 2.14 min: 537.32 | |
| C85 | 0 | Me | 1-cyanoethyl- | C | 2.01 min: 515.71 | |
| C86 | 0 | Me | 2-methylallyl- | C | 2.14 min: 517.35 | |
| C87 | 0 | Me | 1-cyano-1-methylethyl- | C | 2.05 min: 530.34 | |
| C88 | 0 | Me | 2-fluoroethyl- | C | 2 min: 509.39 | |
| C89 | 0 | Me | cyanomethyl- | C | 1.96 min: 502.33 | |
| C90 | 0 | Me | isopropyl- | C | 2.11 min: 505.35 | |
| C91 | 0 | Me | isobutyl- | C | 2.18 min: 519.37 | |
| C92 | 0 | Me | propargyl- | C | 2.02 min: 501.28 | |
| C93 | 0 | Me | 2,2-difluoroethyl- | C | 2.05 min: 527.29 | |
| C94 | 0 | Me | allyl- | C | 2.07 min: 503.35 | |
| C95 | 0 | Me | cyclopropylmethyl- | C | 2.12 min: 517.36 | |
| C96 | 0 | Cl | methyl- | C | 2 min: 497.24 | |
| C97 | 0 | Cl | 1,2-dimethylpropyl- | C | 2.28 min: 553.33 | |
| C98 | 0 | Cl | 1,1-dimethylprop-2-ynyl- | C | 2.18 min: 549.23 | |
| C99 | 0 | Me | [(2E)-2-methoxyimino-1,1-dimethyl-ethyl]- | C | 2.21 min: 562.39 | |
| C100 | 0 | Me | (E)-3-chloroallyl- | C | 2.13 min: 537.41 | |
| C101 | 0 | Me | but-2-ynyl- | C | 2.08 min: 515.29 | |
| C102 | 0 | Me | 2-fluoro-1-methylethyl- | C | 2.07 min: 523.35 | |
| C103 | 0 | Me | 2-fluoropropyl- | C | 2.07 min: 523.35 | |
| C104 | 0 | Me | propyl- | C | 2.11 min: 505.35 | |

Experimental Details for Compound C63 and C64

C63: 2-[4-[(5S)-5-(3,5-dichlorophenyl)-5-(trifluoromethyl)-4H-isoxazol-3-yl]-2-fluoro-phenyl]sulfanyl-N-(2,2,2-trifluoroethyl)acetamide $^1$H NMR (CHLOROFORM-d, 400 MHz): δ=7.50 (d, J=1.5 Hz, 2H), 7.42-7.48 (m, 2H), 7.31-7.37 (m, 2H), 6.94 (m, 1H), 4.04 (d, J=17.2 Hz, 1H), 3.91 (qd, J=8.9, 6.6 Hz, 2H), 3.73 (s, 2H), 3.60-3.69 ppm (m, 1H)

C64: 2-[4-[(5S)-5-(3,5-dichlorophenyl)-5-(trifluoromethyl)-4H-isoxazol-3-yl]-2-fluoro-phenyl]sulfinyl-N-(2,2,2-trifluoroethyl)acetamide (Mixture of Diastereoisomers)

$^1$H NMR (CHLOROFORM-d, 400 MHz): δ=7.74-7.85 (m, 1H), 7.62 (m, 1H), 7.55 (m, 1H), 7.50 (s, 2H), 7.46-7.48 (m, 1H), 7.17 (m, 1H), 3.86-4.14 (m, 3H), 3.55-3.76 ppm (m, 3H)

Experimental Details for Compounds D

D1: 2-[2-chloro-4-[(5S)-5-(3,4,5-trichlorophenyl)-5-(trifluoromethyl)-4H-isoxazol-3-yl]phenyl]sulfanyl-N-(2,2,2-trifluoroethyl)acetamide $^1$H NMR (CHLOROFORM-d, 400 MHz): δ=7.72 (d, J=1.8 Hz, 1H), 7.64 (s, 2H), 7.50 (dd, J=8.4, 1.8 Hz, 1H), 7.21 (d, J=8.4 Hz, 1H), 6.86-6.97 (m, 1H), 4.05 (d, J=17.2 Hz, 1H), 3.90 (m, 2H), 3.78 (s, 2H), 3.65 ppm (d, J=17.2 Hz, 1H)

D2: 2-[2-chloro-4-[(5S)-5-(3,4,5-trichlorophenyl)-5-(trifluoromethyl)-4H-isoxazol-3-yl]phenyl]sulfinyl-N-(2,2,2-trifluoroethyl)acetamide (Mixture of Diastereoisomers)

$^1$H NMR (CHLOROFORM-d, 400 MHz): δ=7.88 (d, J=8.1 Hz, 1H), 7.72-7.81 (m, 2H), 7.64 (s, 2H), 7.09-7.23 (m, 1H), 3.91-4.19 (m, 3H), 3.81 (d, J=14.7 Hz, 1H), 3.58-3.76 ppm (m, 2H)

D3: 2-[2-chloro-4-[(5S)-5-(3,4,5-trichlorophenyl)-5-(trifluoromethyl)-4H-isoxazol-3-yl]phenyl]sulfonyl-N-(2,2,2-trifluoroethyl)acetamide $^1$H NMR (CHLOROFORM-d, 400 MHz): δ=8.13 (d, J=8.1 Hz, 1H), 7.90 (d, J=1.5 Hz, 1H), 7.74 (dd, J=8.3, 1.7 Hz, 1H), 7.63 (s, 2H), 6.79 (m, 1H), 4.40 (s, 2H), 4.04-4.13 (m, 1H), 3.89 (qd, J=8.9, 6.4 Hz, 2H), 3.70 ppm (d, J=17.2 Hz, 1H)

D4: 2-[2-chloro-4-[(5S)-5-(3,4,5-trichlorophenyl)-5-(trifluoromethyl)-4H-isoxazol-3-yl]phenyl]sulfanyl-N-cyclopropyl-acetamide $^1$H NMR (CHLOROFORM-d, 400 MHz): δ=7.71 (d, J=1.8 Hz, 1H), 7.64 (s, 2H), 7.49 (dd, J=8.4, 1.8 Hz, 1H), 7.21 (d, J=8.4 Hz, 1H), 6.65-6.66 (m, 1H), 4.05 (d, J=17.2 Hz, 1H), 3.63-3.67 (m, 3H), 2.68 (m, 1H), 0.75-0.78 (m, 2H), 0.41-0.43 ppm (m, 2H)

D5: 2-[2-chloro-4-[(5S)-5-(3,4,5-trichlorophenyl)-5-(trifluoromethyl)-4H-isoxazol-3-yl]phenyl]sulfinyl-N-cyclopropyl-acetamide (Mixture of Diastereoisomers)

$^1$H NMR (CHLOROFORM-d, 400 MHz): δ=7.86 (d, J=8.1 Hz, 1H), 7.80 (dt, J=8.2, 1.6 Hz, 1H), 7.74 (t, J=1.5 Hz, 1H), 7.64 (s, 2H), 6.73 (m, 1H), 4.09 (d, J=17.2 Hz, 1H), 3.82 (d, J=14.3 Hz, 1H), 3.61-3.74 (m, 2H), 2.62 (m, 1H), 0.74-0.79 (m, 2H), 0.41-0.60 ppm (m, 2H)

D6: 2-[2-chloro-4-[(5S)-5-(3,4,5-trichlorophenyl)-5-(trifluoromethyl)-4H-isoxazol-3-yl]phenyl]sulfonyl-N-cyclopropyl-acetamide $^1$H NMR (CHLOROFORM-d, 400 MHz): δ=8.11 (d, J=8.4 Hz, 1H), 7.87 (d, J=1.5 Hz, 1H), 7.75 (dd, J=8.3, 1.7 Hz, 1H), 7.63 (s, 2H), 6.45 (m, 1H), 4.26 (s, 2H), 4.06-4.11 (m, 1H), 3.70 (d, J=17.2 Hz, 1H), 2.63-2.66 (m, 1H), 0.71-0.82 (m, 2H), 0.39-0.54 ppm (m, 2H)

TABLE E

Compounds of formula (I-e):

| Comp No. | n | LCMS Method | RT (min): mass spectrum | MW | Chiral HPLC (method D) |
|---|---|---|---|---|---|
| E1 | 0 | A | 2.22 | 559/561 | |
| E2 | 1 | A | 2.09 | 575/577 | |
| E3 | 2 | A | 2.17 | 591/592 | |

TABLE F

Compounds of formula (I-f):

| Comp No. | $A^1$ | $A^2$ | $A^3$ | $A^4$ | $R^2$ | n | LCMS Method | RT (min): | mass |
|---|---|---|---|---|---|---|---|---|---|
| F1 | CCH3 | CH | CH | N | cyclopropyl- | 0 | G | 17.18 | 502 [M − H]− |
| F2 | CCH3 | CH | N | CH | cyclopropyl- | 0 | G | 17.02 | 504 [M + H]+ |

BIOLOGICAL EXAMPLES

These Examples illustrate the pesticidal/insecticidal properties of compounds of formula (I).

Tests were performed as follows:

*Spodoptera littoralis* (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compounds gave at least 80% control of *Spodoptera littoralis*:

A1, A10, A11, A12, A13, A14, A15, A16, A19, A2, A21, A22, A24, A25, A26, A27, A28, A29, A3, A30, A31, A32, A33, A34, A35, A36, A37, A38, A39, A4, A40, A42, A43, A45, A46, A48, A49, A5, A50, A51, A52, A53, A54, A55, A56, A57, A58, A59, A6, A60, A61, A62, A63, A64, A67, A69, A7, A70, A71, A72, A73, A74, A75, A76, A77, A78, A79, A8, A80, A81, A82, A83, A84, A85, A86, A87, A88, A89, A9, A90, A91, B1, B2, B3, C1, C10, C100, C101, C102, C103, C104, C11, C12, C12, C13, C14, C14, C15, C16, C17, C18, C19, C2, C20, C21, C3, C33, C4, C44, C5, C53, C54, C55, C56, C57, C58, C59, C6, C60, C62, C63, C64, C65, C66, C68, C69, C7, C70, C72, C73, C74, C75, C76, C77, C78, C79, C80, C81, C82, C83, C84, C86, C87, C88, C89, C9, C90, C91, C92, C93, C94, C95, C96, C97, C98, C99, D1, D2, D3, D4, E1, E2, E3, F1, F2, G1, G2, G3, G4, H1

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compounds gave at least 80% control of *Heliothis virescens*:

A1, A11, A12, A13, A14, A15, A16, A17, A19, A2, A21, A22, A23, A24, A25, A26, A27, A28, A29, A3, A30, A31, A32, A33, A34, A35, A36, A37, A38, A39, A4, A40, A41, A42, A43, A44, A45, A46, A47, A48, A49, A5, A50, A51, A52, A53, A54, A55, A56, A57, A58, A59, A6, A60, A61, A63,

A64, A66, A67, A68, A69, A7, A70, A71, A72, A73, A74, A75, A76, A77, A78, A79, A8, A80, A81, A82, A83, A84, A85, A86, A87, A88, A89, A9, A90, A91, B1, B2, B3, C1, C10, C100, C101, C102, C103, C104, C11, C12, C12, C13, C14, C14, C15, C16, C17, C19, C2, C20, C21, C23, C26, C28, C3, C32, C33, C35, C36, C37, C39, C40, C42, C43, C44, C45, C46, C47, C48, C49, C5, C51, C52, C53, C54, C55, C56, C57, C58, C59, C6, C60, C62, C63, C64, C65, C66, C68, C69, C7, C70, C71, C72, C73, C74, C75, C76, C77, C78, C79, C80, C81, C82, C83, C84, C85, C86, C87, C88, C89, C9, C90, C91, C92, C93, C94, C95, C96, C97, C98, C99, D1, D2, D3, D4, E1, E2, E3, F1, F2, G1, G2, G3, G4, H1,

*Plutella xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compounds gave at least 80% control of *Plutella xylostella*: A1, A10, A12, A13, A14, A16, A17, A19, A2, A21, A22, A23, A24, A25, A26, A27, A28, A29, A3, A30, A31, A32, A33, A34, A35, A36, A37, A38, A4, A40, A41, A42, A45, A46, A48, A49, A5, A50, A51, A52, A53, A54, A55, A56, A57, A58, A59, A6, A60, A61, A63, A64, A67, A69, A7, A71, A72, A73, A74, A75, A76, A78, A79, A8, A81, A82, A83, A84, A85, A86, A87, A88, A89, A9, A90, A91, B1, B2, B3, C1, C100, C101, C102, C103, C104, C11, C12, C13, C14, C14, C15, C2, C3, C33, C4, C44, C47, C5, C53, C54, C56, C58, C59, C6, C60, C62, C63, C64, C65, C66, C68, C69, C7, C70, C71, C72, C73, C74, C75, C76, C77, C78, C79, C80, C81, C82, C83, C84, C85, C86, C87, C88, C89, C90, C91, C92, C93, C94, C95, C96, C98, C99, D1, D2, D3, D4, E1, E2, E3, F1, F2, G1, G2, G3, G4, H1

*Diabrotica balteata* (Corn Root Worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compounds gave at least 80% control of *Diabrotica balteata*:

A1, A10, A11, A12, A13, A14, A15, A16, A17, A19, A2, A20, A21, A22, A23, A24, A25, A26, A27, A28, A29, A3, A30, A31, A32, A33, A34, A35, A36, A37, A38, A39, A4, A40, A41, A42, A43, A44, A45, A46, A47, A48, A49, A5, A50, A51, A52, A53, A54, A55, A56, A57, A58, A59, A6, A60, A61, A63, A64, A66, A69, A7, A70, A71, A72, A73, A74, A75, A76, A77, A78, A79, A8, A80, A81, A82, A83, A84, A85, A86, A87, A88, A89, A9, A90, A91, B1, B2, B3, C1, C10, C100, C101, C102, C103, C104, C11, C12, C12, C13, C14, C14, C15, C16, C17, C18, C19, C2, C20, C21, C25, C27, C28, C29, C3, C30, C31, C32, C33, C35, C4, C40, C41, C43, C44, C47, C48, C49, C5, C50, C51, C52, C53, C54, C55, C56, C57, C58, C59, C6, C60, C61, C62, C63, C64, C65, C66, C68, C69, C7, C70, C71, C72, C73, C75, C76, C77, C78, C79, C80, C81, C82, C83, C84, C85, C86, C87, C88, C89, C9, C90, C91, C92, C93, C94, C95, C96, C97, C98, C99, D1, D2, D3, D4, E1, E2, E3, F1, F2, G1, G2, G3, G4, H1

*Myzus persicae* (Green peach aphid), systemic test: Roots of pea seedlings, infested with an aphid population of mixed ages, are placed directly in the test solutions at an application rate of 12.5 ppm. 6 days after introduction, samples are checked for mortality and special effects on the plant. The following compounds gave at least 80% control of *Myzus persicae*:

A1, A10, A24, A25, A27, A28, A29, A30, A31, A33, A34, A36, A38, A40, A41, A42, A45, A46, A48, A49, A5, A50, A51, A52, A53, A54, A55, A56, A59, A6, A60, A64, A69, A70, A72, A73, A74, A76, A78, A82, A83, A84, A85, A86, A87, A89, A90, A91, B1, B2, B3, C1, C10, C100, C101, C102, C103, C104, C12, C14, C15, C17, C2, C21, C3, C33, C4, C44, C47, C5, C53, C54, C55, C58, C59, C6, C61, C62, C63, C64, C65, C66, C68, C7, C70, C76, C78, C79, C80, C82, C83, C84, C86, C88, C89, C9, C91, C92, C93, C94, C95, C97, D1, D2, D3, D4, D5, D6, F2, G1, G2, G4, H1.

*Thrips tabaci* (Onion Thrips):

Sunflower leaf discs were placed on agar in a 24-well microtiter plate and sprayed with test solutions at an application rate of 200 ppm. After drying, the leaf discs were infested with a thrips population of mixed ages. After an incubation period of 7 days, samples were checked for mortality.

The following compounds gave at least 80% control of *Thrips tabaci*:

A1, A10, A11, A12, A14, A16, A2, A21, A23, A24, A25, A26, A27, A28, A29, A3, A30, A31, A32, A33, A34, A35, A38, A40, A44, A45, A48, A49, A5, A50, A51, A52, A53, A54, A55, A56, A58, A59, A6, A60, A61, A64, A66, A69, A7, A70, A71, A72, A73, A74, A75, A76, A78, A79, A8, A81, A82, A83, A84, A85, A86, A87, A88, A89, A90, A91, B1, B2, B3, C1, C100, C101, C102, C103, C104, C11, C12, C13, C14, C14, C15, C18, C2, C21, C3, C33, C4, C44, C5, C53, C58, C59, C6, C62, C63, C64, C65, C66, C68, C69, C7, C70, C72, C73, C75, C76, C77, C78, C79, C80, C81, C82, C83, C84, C85, C86, C88, C89, C9, C90, C91, C92, C93, C94, C95, C96, C97, C98, D1, D2, D3, D4, F5, G1, G2, G4, H1.

*Tetranychus urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compounds gave at least 80% control of *Tetranychus urticae*:

A1, A10, A11, A12, A13, A14, A16, A17, A18, A2, A21, A22, A23, A24, A25, A26, A27, A28, A29, A3, A30, A31, A32, A33, A34, A36, A37, A38, A39, A4, A40, A43, A45, A46, A47, A48, A49, A5, A50, A51, A52, A53, A54, A55, A56, A57, A59, A6, A60, A61, A62, A64, A66, A67, A69, A7, A70, A71, A72, A73, A74, A75, A76, A78, A79, A8, A81, A82, A83, A84, A85, A86, A87, A88, A89, A9, A90, A91, B1, B2, B3, C1, C100, C101, C102, C103, C104, C11, C12, C14, C15, C18, C2, C20, C21, C3, C33, C4, C41, C42, C44, C47, C5, C53, C54, C57, C58, C59, C6, C60, C62, C63, C64, C65, C66, C68, C69, C7, C70, C72, C73, C74, C75, C76, C77, C78, C79, C80, C81, C82, C83, C84, C86, C87, C88, C89, C90, C91, C92, C93, C94, C95, C96, C97, C98, C99, D1, D2, D3, D4, F1, G1, G2, G3, G4, H1.

COMPARATIVE EXAMPLES

In the comparative test Tables the tests were performed as described above with the application rates indicated in the Tables.

Comparative test Table 1

In this Example compound A49 of the present invention is compared with compound 1-020 of JP2007106756. It can be seen that the structures are identical apart from the substituent on the sulfur atom.

Compound A49 of the present invention

Compound 1-020 of JP2007106756

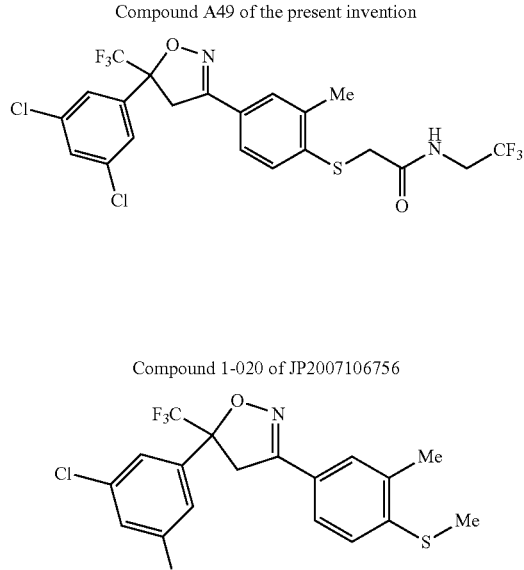

| Compound | Test | Application rate/ppm | Control/% |
|---|---|---|---|
| Compound A49 of the present invention | Heliothis virescens Tobacco budworm | 3 0.8 | 100 80 |
| Compound 1-020 of JP2007106756 | Heliothis virescens Tobacco budworm | 3 0.8 | 0 0 |
| Compound A49 of the present invention | Plutella xylostella Diamond back moth | 3 0.8 | 100 80 |
| Compound 1-020 of JP2007106756 | Plutella xylostella Diamond back moth | 3 0.8 | 0 0 |
| Compound A49 of the present invention | Diabrotica balteata Corn rootworm | 12 3 | 100 100 |
| Compound 1-020 of JP2007106756 | Diabrotica balteata Corn rootworm | 12 3 | 20 not tested |

Comparative test Table 2

In this Example compound A50 of the present invention is compared with the sulfoxide analogues of compound 1-020 of JP2007106756. It can be seen that the structures are identical apart from the substituent on the sulfur atom.

Compound A50 of the present invention

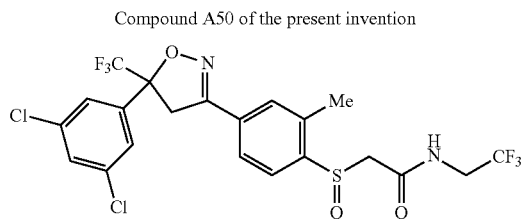 [SMILES: Cc1cc(C2=NOC(c3cc(Cl)cc(Cl)c3)(C(F)(F)F)C2)ccc1S(=O)CC(=O)NCC(F)(F)F]

Sulfoxide analogue of compound 1-020 of JP2007106756

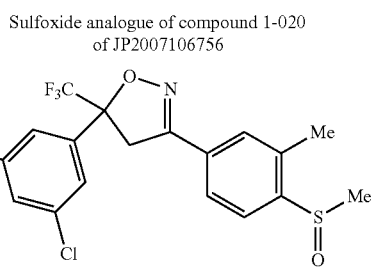

| Compound | Test | Application rate/ppm | Control/% |
|---|---|---|---|
| Compound A50 of the present invention | Heliothis virescens Tobacco budworm | 3 0.8 | 80 80 |
| Sulfoxide analogue of compound 1-020 of JP2007106756 | Heliothis virescens Tobacco budworm | 3 0.8 | 0 0 |
| Compound A50 of the present invention | Plutella xylostella Diamond back moth | 3 0.8 | 100 80 |
| Sulfoxide analogue of compound 1-020 of JP2007106756 | Plutella xylostella Diamond back moth | 3 0.8 | 0 0 |
| Compound A50 of the present invention | Diabrotica balteata Corn rootworm | 12 3 | 100 75 |
| Sulfoxide analogue of compound 1-020 of JP2007106756 | Diabrotica balteata Corn rootworm | 12 3 | 0 0 |

Comparative test Table 3

In this Example compound A51 of the present invention is compared with compound 1-021 of JP2007106756. It can be seen that the structures are identical apart from the substituent on the sulfur atom.

Compound A51 of the present invention

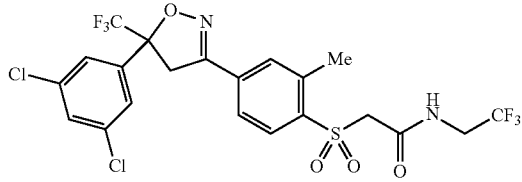

Compound 1-021 of JP2007106756

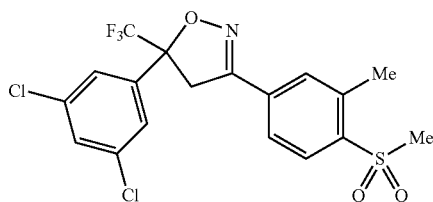

| Compound | Test | Application rate/ppm | Control/% |
|---|---|---|---|
| Compound A51 of the present invention | Heliothis virescens Tobacco budworm | 3 0.8 | 80 80 |
| Compound 1-021 of JP2007106756 | Heliothis virescens Tobacco budworm | 3 0.8 | 0 0 |
| Compound A51 of the present invention | Plutella xylostella Diamond back moth | 3 0.8 | 100 80 |
| Compound 1-021 of JP2007106756 | Plutella xylostella Diamond back moth | 3 0.8 | 0 0 |
| Compound A51 of the present invention | Diabrotica balteata Corn rootworm | 50 12 | 100 100 |
| Compound 1-021 of JP2007106756 | Diabrotica balteata Corn rootworm | 50 12 | 90 0 |

Comparative test Table 4

In this Example compound A49 of the present invention is compared with compound 1-028 of JP2007106756. It can be seen that the structures are identical apart from the presence of an ortho methyl substituent.

Compound A49 of the present invention

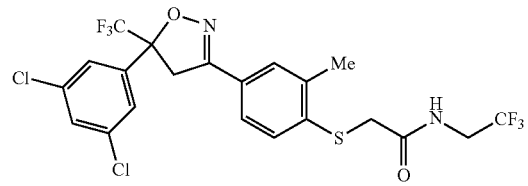

Compound 1-028 of JP2007106756

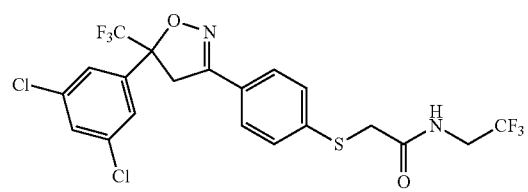

| Compound | Test | Application rate/ppm | Control/% |
|---|---|---|---|
| Compound A49 of the present invention | Heliothis virescens Tobacco budworm | 3 0.8 | 100 80 |
| Compound 1-028 of JP2007106756 | Heliothis virescens Tobacco budworm | 3 0.8 | 90 0 |
| Compound A49 of the present invention | Plutella xylostella Diamond back moth | 3 0.8 | 100 80 |
| Compound 1-028 of JP2007106756 | Plutella xylostella Diamond back moth | 3 0.8 | 50 0 |
| Compound A49 of the present invention | Diabrotica balteata Corn rootworm | 12 3 | 100 100 |
| Compound 1-028 of JP2007106756 | Diabrotica balteata Corn rootworm | 12 3 | 100 20 |

Comparative test Table 5

In this Example compound A50 of the present invention is compared with compound 1-029 of JP2007106756. It can be seen that the structures are identical apart from the presence of an ortho methyl substituent.

Compound A50 of the present invention

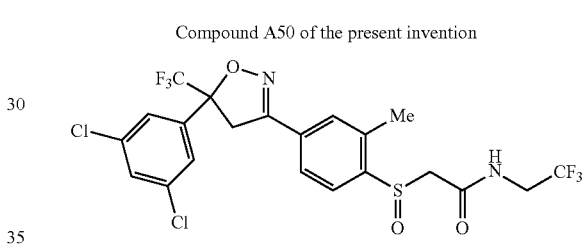

Compound 1-029 of JP2007106756

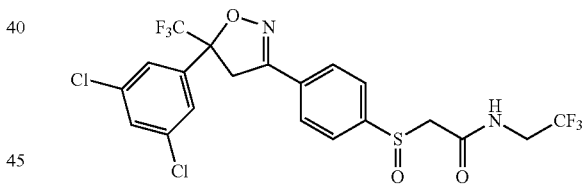

| Compound | Test | Application rate/ppm | Control/% |
|---|---|---|---|
| Compound A50 of the present invention | Heliothis virescens Tobacco budworm | 3 0.8 | 80 80 |
| Compound 1-029 of JP2007106756 | Heliothis virescens Tobacco budworm | 3 0.8 | 80 0 |
| Compound A50 of the present invention | Plutella xylostella Diamond back moth | 3 0.8 | 100 80 |
| Compound 1-029 of JP2007106756 | Plutella xylostella Diamond back moth | 3 0.8 | 80 0 |
| Compound A50 of the present invention | Diabrotica balteata Corn rootworm | 50 12 | 100 100 |
| Compound 1-029 of JP2007106756 | Diabrotica balteata Corn rootworm | 50 12 | 100 50 |

Comparative test Table 6
In this Example compound A51 of the present invention is compared with compound 1-030 of JP2007106756. It can be seen that the structures are identical apart from the presence of an ortho methyl substituent.

Compound A51 of the present invention

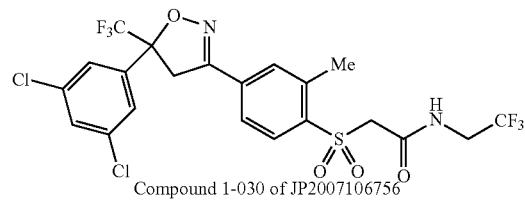

Compound 1-030 of JP2007106756

| Compound | Test | Application rate/ppm | Control/% |
|---|---|---|---|
| Compound A51 of the present invention | Heliothis virescens Tobacco budworm | 3 0.8 | 80 80 |
| Compound 1-030 of JP2007106756 | Heliothis virescens Tobacco budworm | 3 0.8 | 80 0 |
| Compound A51 of the present invention | Plutella xylostella Diamond back moth | 3 0.8 | 100 80 |
| Compound 1-030 of JP2007106756 | Plutella xylostella Diamond back moth | 3 0.8 | 0 0 |
| Compound A51 of the present invention | Diabrotica balteata Corn rootworm | 50 12 | 100 100 |
| Compound 1-030 of JP2007106756 | Diabrotica balteata Corn rootworm | 50 12 | 100 50 |

Comparative test Table 7
In this Example compound C1 of the present invention is compared with compound 1-028 of JP2007106756. It can be seen that the structures are identical apart from the presence of an ortho methyl substituent and the stereocentre configuration (the ratio of the isomer shown compared to the isomer with the opposite stereochemistry was at least 85:15 in favour of the isomer shown)

Compound C1 of the present invention

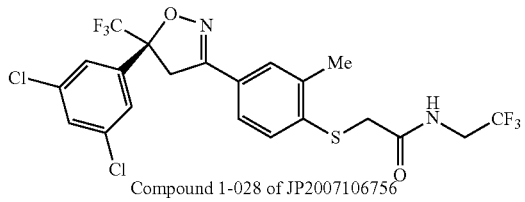

Compound 1-028 of JP2007106756

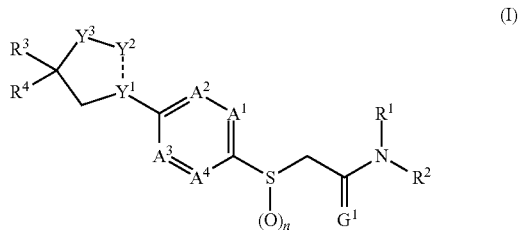

| Compound | Test | Application rate/ppm | Control/% |
|---|---|---|---|
| Compound C1 of the present invention | Heliothis virescens Tobacco budworm | 3 0.8 0.2 | 100 80 80 |
| Compound 1-028 of JP2007106756 | Heliothis virescens Tobacco budworm | 3 0.8 0.2 | 90 0 0 |
| Compound C1 of the present invention | Plutella xylostella Diamond back moth | 3 0.8 0.2 | 100 100 80 |
| Compound 1-028 of JP2007106756 | Plutella xylostella Diamond back moth | 3 0.8 0.2 | 50 0 0 |
| Compound C1 of the present invention | Diabrotica balteata Corn rootworm | 12 3 0.8 | 100 100 80 |
| Compound 1-028 of JP2007106756 | Diabrotica balteata Corn rootworm | 12 3 0.8 | 100 20 0 |

From the results above it can be derived that the insecticidal activity of the compounds of the invention is clearly superior to the structurally closest prior art compounds at low application rates. In many cases the compounds of the present invention provide complete or almost complete control of important pests, whilst at the same rate the compounds of JP2007106756 provide zero control.

This superior performance is important because it allows a more efficient disease control of the pests at significantly lower application rates. In the light of the structural similarities of the tested compounds, this surprising improvement in the insecticidal properties is completely unexpected and cannot be derived from what is known from the prior art.

The invention claimed is:
1. A compound of formula I

(I)

wherein
$A^1$ is C—$R^{5b}$;
$A^2$, $A^3$ and $A^4$ are independently of one another C—H, C—$R^{5a}$ or nitrogen;
$G^1$ is oxygen or sulfur;
$Y_1$—$Y_2$—$Y_3$ is —C=N—O—, —C=N—$CH_2$—, —C=CH—O— or —N—$CH_2$—$CH_2$—;
n is 0, 1 or 2;
$R^1$ is hydrogen, $C_1$-$C_8$alkyl, $C_1$-$C_8$alkyl substituted by one to five $R^6$, $C_1$-$C_8$alkoxy, $C_1$-$C_8$alkylcarbonyl or $C_1$-$C_8$alkoxycarbonyl;
$R^2$ is $C_1$-$C_8$alkyl or $C_1$-$C_8$alkyl substituted by one to five $R^6$, $C_2$-$C_8$alkenyl or $C_2$-$C_8$alkenyl substituted by one to five $R^6$, $C_2$-$C_8$alkynyl or $C_2$-$C_8$alkynyl substituted by one to five $R^6$, $C_3$-$C_{10}$cycloalkyl or $C_3$-$C_{10}$cycloalkyl substituted by one to five $R^7$, $C_3$-$C_{10}$cycloalkyl-$C_1$-$C_4$alkylene or $C_3$-$C_{10}$cycloalkyl-$C_1$-$C_4$alkylene substituted by one to five $R^7$, aryl-$C_1$-$C_4$alkylene or aryl-$C_1$-$C_4$alkylene wherein the aryl moiety is substituted by one to five $R^8$, heterocyclyl-$C_1$-$C_4$alkylene or heterocyclyl-$C_1$-$C_4$alkylene wherein the heterocyclyl moiety is substituted by one to five $R^8$, aryl or aryl substituted by one to five $R^8$, heterocyclyl or heterocyclyl substituted by one to five $R^8$, $C_1$-$C_8$alkylaminocarbonyl-$C_1$-

$C_4$alkylene, $C_1$-$C_8$haloalkylaminocarbonyl-$C_1$-$C_4$alkylene, $C_3$-$C_8$cycloalkyl-aminocarbonyl-$C_1$-$C_4$alkylene, $C_1$-$C_6$alkyl-O—N=CH— or $C_1$-$C_6$haloalkyl-O—N=CH—, $C_1$-$C_6$alkyl-O—N=CH—$C_1$-$C_4$alkylene or $C_1$-$C_6$haloalkyl-O—N=CH—$C_1$-$C_4$alkylene, cyano or $C_1$-$C_8$alkylsulfonyl;

$R^3$ is $C_1$-$C_8$haloalkyl;

$R^4$ is aryl or aryl substituted by one to five $R^9$, or heteroaryl or heteroaryl substituted by one to five $R^9$;

each $R^{5a}$ is independently halogen, cyano, nitro, $C_1$-$C_8$alkyl, $C_1$-$C_8$haloalkyl, $C_2$-$C_8$alkenyl, $C_1$-$C_8$haloalkenyl, $C_2$-$C_8$alkynyl, $C_2$-$C_8$haloalkynyl, $C_3$-$C_{10}$cycloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl-, $C_1$-$C_8$haloalkylsulfinyl-, $C_1$-$C_8$alkylsulfonyl- or $C_1$-$C_8$haloalkylsulfonyl-;

$R^{5b}$ is halogen, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl or $C_3$-$C_{10}$cycloalkyl substituted by one to five $R^7$, or $R^{5a}$ and $R^{5b}$, together form a —CH=CH—CH=CH— bridge or a —N=CH—CH=CH— bridge;

each $R^6$ is independently halogen, cyano, nitro, hydroxy, $C_3$-$C_{10}$cycloalkyl, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl or $C_1$-$C_8$haloalkylsulfonyl;

each $R^7$ is independently halogen, cyano, $C_1$-$C_8$alkyl or $C_1$-$C_8$haloalkyl;

each $R^8$ and $R^9$ is independently halogen, cyano, nitro, $C_1$-$C_8$alkyl, $C_1$-$C_8$haloalkyl, $C_3$— $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{10}$ or heterocyclyl or heterocyclyl substituted by one to five $R^{10}$;

each $R^{10}$ is independently halogen, cyano, nitro, $C_1$-$C_4$alkyl, $C_1$-$C_4$haloalkyl, $C_1$-$C_4$alkoxy or $C_1$-$C_4$haloalkoxy;

or a salt or N-oxide thereof.

2. A compound according to claim 1, wherein $Y_1$—$Y_2$—$Y_3$ is —C=N—O—.

3. A compound according to claim 1, wherein $Y_1$—$Y_2$—$Y_3$ is —C=N—$CH_2$—.

4. A compound according to claim 1, wherein $Y_1$—$Y_2$—$Y_3$ is —C=CH—O—.

5. A compound according to claim 1, wherein $Y_1$—$Y_2$—$Y_3$ is —N—$CH_2$—$CH_2$—.

6. A compound according to claim 1, wherein $R^{5b}$ is bromo, chloro, or methyl.

7. A compound according to claim 1, wherein $R^2$ is $C_1$-$C_4$alkyl or $C_1$-$C_4$alkyl substituted by one to five $R^6$, $C_2$-$C_4$alkenyl or $C_2$-$C_4$alkenyl substituted by one to five $R^6$, $C_2$-$C_4$alkynyl or $C_2$-$C_4$alkynyl substituted by one to five $R^6$, $C_3$-$C_6$cycloalkyl or $C_3$-$C_6$cycloalkyl substituted by one to five $R^7$, $C_3$-$C_6$cycloalkyl-methylene or $C_3$-$C_6$cycloalkyl-methylene substituted by one to five $R^7$, phenyl-$C_1$-$C_2$alkylene or phenyl-$C_1$-$C_2$alkylene wherein the phenyl moiety is substituted by one to five $R^8$, pyridyl-$C_1$-$C_2$alkylene or pyridyl-$C_1$-$C_2$alkylene wherein the pyridyl moiety is substituted by one to four $R^8$, thietanyl or thietanyl substituted by one to five $R^8$, oxo-thietanyl or oxo-thietanyl substituted by one to five $R^8$, dioxo-thietanyl or dioxo-thietanyl substituted by one to five $R^8$.

8. A compound according to claim 1, wherein $R^2$ is $C_1$-$C_4$alkyl or $C_1$-$C_4$alkyl substituted by one to five halogen, $C_3$-$C_6$cycloalkyl or $C_3$-$C_6$cycloalkyl substituted by one to five groups independently selected from halogen, methyl and halomethyl, $C_3$-$C_6$cyclo-alkyl-methylene or $C_3$-$C_6$cycloalkyl-methylene substituted by one to five groups independently selected from halogen, methyl and halomethyl, $C_2$-$C_4$alkenyl or $C_2$-$C_4$alkenyl substituted by one to five $R^6$, $C_2$-$C_4$alkynyl or $C_2$-$C_4$alkynyl substituted by one to five $R^6$.

9. A compound according to claim 1, wherein $R^3$ is chlorodifluoromethyl or trifluoromethyl.

10. A compound according to claim 1, wherein $R^4$ is group A1

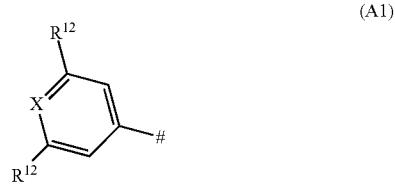

(A1)

wherein X is C—$R^{12}$ or nitrogen and each $R^{12}$ is independently hydrogen, halogen or trihalomethyl, wherein at least two $R^{12}$ are not hydrogen.

11. A compound according to claim 1, wherein $A^1$ is C—$R^{5b}$; $A^2$, $A^3$ and $A^4$ are C—H; $G^1$ is oxygen; $Y_1$—$Y_2$—$Y_3$ is —C=N—O—, —C=N—$CH_2$—, —C=CH—O— or —N—$CH_2$—$CH_2$—; $R^1$ is hydrogen; $R^2$ is $C_1$-$C_4$alkyl or $C_1$-$C_4$alkyl substituted by one to five halogen, $C_3$-$C_6$cycloalkyl or $C_3$-$C_6$cycloalkyl substituted by one to five groups independently selected from halogen, methyl and halomethyl, $C_3$-$C_6$cycloalkyl-methylene or $C_3$-$C_6$cycloalkyl-methylene substituted by one to five groups independently selected from halogen, methyl and halomethyl $C_2$-$C_4$alkenyl or $C_2$-$C_4$alkenyl substituted by one to five halogen, $C_2$-$C_4$alkynyl or $C_2$-$C_4$alkynyl substituted by one to five halogen; $R^3$ is chlorodifluoromethyl or trifluoromethyl; $R^4$ is group A1

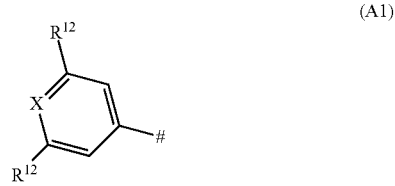

(A1)

wherein X is C—$R^{12}$ or nitrogen and each $R^{12}$ is independently hydrogen, halogen or trihalomethyl, wherein at least two $R^{12}$ are not hydrogen; $R^{5b}$ is chloro, bromo or methyl.

12. A compound according to claim 11, wherein $A^1$ is C—$R^{5b}$; $A^2$, $A^3$ and $A^4$ are C—H; $G^1$ is oxygen; $Y_1$—$Y_2$—$Y_3$ is —C=N—O—, —C=N—$CH_2$—, —C=CH—O— or —N—$CH_2$—$CH_2$—; $R^1$ is hydrogen; $R^2$ is ethyl, propyl, butyl, fluoroethyl, fluoropropyl, fluorobutyl, difluoroethyl, difluoropropyl, difluorobutyl, trifluoroethyl, trifluoropropyl, trifluorobutyl, cyclopropyl, cyclobutyl, cyclopropylmethylene, cyclobutylmethylene, allyl or propargyl; $R^3$ is chlorodifluoromethyl or trifluoromethyl; $R^4$ is group A1, wherein X is C—$R^{12}$ and each $R^{12}$ is independently hydrogen, halogen or trihalomethyl, wherein at least two $R^{12}$ are not hydrogen; $R^{5b}$ is chloro, bromo or methyl.

13. A mixture comprising a compound of formula I* and a compound of formula II*

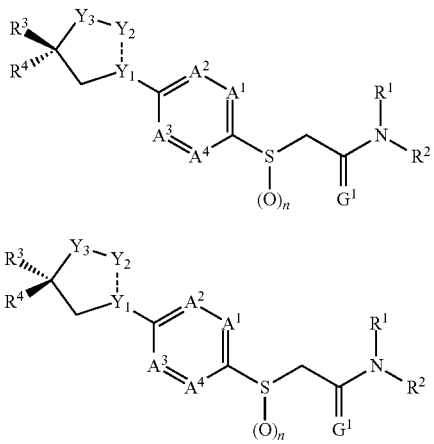

wherein $Y_1$—$Y_2$—$Y_3$ is —C=N—O—, —C=N—CH$_2$—, —C=CH—O— or —N—CH$_2$—CH$_2$— and $A^1, A^2, A^3, A^4, R^1, R^2, R^3, R^4, G^1$ and n are as defined in claim 1, and wherein the molar proportion of the compound of formula I** compared to the total amount of both the compound of formula I* and II* is greater than 50%.

14. A compound according to claim 13, wherein $A^1$ is C—$R^{5b}$; $A^2, A^3$ and $A^4$ are C—H; $G^1$ is oxygen; $Y_1$—$Y_2$—$Y_3$ is —C=N—O—, —C=N—CH$_2$—, —C=CH—O— or —N—CH$_2$—CH$_2$—; $R^1$ is hydrogen; $R^2$ is ethyl, propyl, butyl, fluoroethyl, fluoropropyl, fluorobutyl, difluoroethyl, difluoropropyl, difluorobutyl, trifluoroethyl, trifluoropropyl, trifluorobutyl, cyclopropyl, cyclobutyl, cyclopropylmethylene, cyclobutylmethylene, allyl or propargyl; $R^3$ is chlorodifluoromethyl or trifluoromethyl; $R^4$ is group A1,

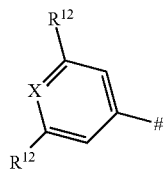

(A1)

wherein X is C—$R^{12}$ and each $R^{12}$ is independently hydrogen, halogen or trihalomethyl, wherein at least two $R^{12}$ are not hydrogen; $R^{5b}$ is chloro, bromo or methyl, and wherein the molar proportion of the compound of formula I** compared to the total amount of both the compound of formula I* and I** is greater than 70%.

15. An insecticidal, acaricidal, nematicidal or molluscicidal composition comprising an insecticidally, acaricidally, nematicidally or molluscicidally effective amount of a compound of formula (I) as defined in claim 1 and optionally at least one additional compound having biological activity.

16. A combination product comprising a pesticidally effective amount of a component A and a pesticidally effective amount of component B, wherein component A is a compound of formula (I) as defined in claim 1, and component B is at least one compound selected from the group consisting of imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone and tebufenozide.

* * * * *